(12) United States Patent
Ba-Maung et al.

(10) Patent No.: US 8,067,409 B2
(45) Date of Patent: Nov. 29, 2011

(54) PROTEIN KINASE INHIBITORS

(75) Inventors: Nwe Y. Ba-Maung, Niles, IL (US);
Randy L. Bell, Lindenhurst, IL (US);
Richard F. Clark, Gurnee, IL (US);
Scott A. Erickson, Zion, IL (US); Steve D. Fidanze, Grayslake, IL (US); Robert D. Hubbard, Lindenhurst, IL (US);
Robert A. Mantei, Franklin, WI (US);
George S. Sheppard, Wilmette, IL (US);
Bryan K. Sorensen, Antioch, IL (US);
Gary T. Wang, Libertyville, IL (US);
Jieyi Wang, Lake Bluff, IL (US)

(73) Assignee: Abbott Laboratories, Abbott Park, IL (US)

( * ) Notice: Subject to any disclaimer, the term of this patent is extended or adjusted under 35 U.S.C. 154(b) by 359 days.

(21) Appl. No.: 12/274,834

(22) Filed: Nov. 20, 2008

(65) Prior Publication Data

US 2009/0253723 A1    Oct. 8, 2009

Related U.S. Application Data

(60) Provisional application No. 60/990,330, filed on Nov. 27, 2007.

(51) Int. Cl.
*C07D 513/04*    (2006.01)
*A61K 31/425*    (2006.01)

(52) U.S. Cl. ............ 514/228.5; 514/235.8; 514/252.14; 514/252.19; 514/275; 544/58.2; 544/60; 544/61; 544/122; 544/295; 544/331

(58) Field of Classification Search ................ 544/58.2, 544/60, 61, 122, 295, 331; 514/228.5, 235.8, 514/252.14, 252.19, 275
See application file for complete search history.

(56) References Cited

FOREIGN PATENT DOCUMENTS

| WO | 0114375 A1 | 3/2001 |
|---|---|---|
| WO | 02066480 A2 | 8/2002 |
| WO | 02066481 A1 | 8/2002 |
| WO | 03000682 A1 | 1/2003 |
| WO | 2004110990 A2 | 12/2004 |
| WO | WO2005068452 A1 | 7/2005 |
| WO | WO2006044869 A1 | 4/2006 |
| WO | WO2006068826 A2 | 6/2006 |
| WO | 2006094236 A1 | 9/2006 |
| WO | 2007123892 A2 | 11/2007 |
| WO | 2008029152 A2 | 3/2008 |

OTHER PUBLICATIONS

Simone, Oncology: Introduction, Cecil Textbook of Medicine, 20th Edition, vol. 1, pp. 1004-1010, 1996.*
Catrina S-B et al., "Insulin-like growth factor-I receptor activity is essential for Kaposi's sarcoma growth and survival", Br. J. Cancer, vol. 92, pp. 1467-147, 2005.
Davies, D., "Targeting the Epidermal Growth Factor Receptor for Therapy of Carcinomas", Biochem. Pharm. vol. 51 (9), pp. 1101-1110, 1996.
Druker, B., "Activity of a Specific Inhibitor of the BCR-ABL Tyrosine Kinase in the Blast Crisis of Chronic Myeloid Leukemia and Acute Lymphoblastic Leukemia with the Philadelphia Chromosome", New England J of Medicine, vol. 344, p. 1038, 2001.
Hirota, S., "Gain of function Mutations of C-kit in Human Gastrointestinal Stromal Tumors", Science, vol. 279, p. 577-580, 1998.
Hynes, N., "The biology of erbB-2/neu/HER-2 and its role in cancer", Biochem. Biophys. Acta. vol. 1198, pp. 165-184, 1994.
Khandwala, H., "The Effects of Insulin-Like Growth Factors on Tumorigenesis and Neoplastic Growth", Endocrine Reviews, vol. 21, (3), pp. 215-244, 2000.
Loewe, et al., "Ein nener Typ der 4-Amino-chinolin-Reihe", Zrzeneim. Forsch, vol. 16,p. 1306-1310, 1966.
Lutz, M.P., "Overexpression and Activation of the Tyrosine Kinase Src in Human Pancreatic Carcinoma", Biochemical & Biophysical Research Commun., vol. 243, pp. 503-508, 1998.
Mathis, G., "HTRF(R) Technology", J. Biomol. Screen, vol. 4(6), pp. 309-314, 1999.
Pure Appl. Chem, "Rules for the Nomenclature of Organic Chemistry, Section E: Stereochemistry", IUPAC Commission on Nomenclature of Organic Chemistry, Pergamon Press,vol. 45, pp. 13-20, 1976.
Rusch, V., "The Epidermal Growth Factor Receptor and Its Ligands as Therapeutic Targets in Human Tumors", Cytokine & Growth Factor Rev. vol. 7, pp. 133-141, 1996.
Slamon, D., "Use of Chemotherapy plus a Monoclonal Antibody against HER2 for Metastatic Breast Cancer that Overexpresses HER2", New England J. Med. vol. 344(11), pp. 783-792, 2001.
Summy, J., "Src family kinases in tumor progression and metastasis", Cancer & Metastasis Rev. vol. 22, p. 337-358, 2003.
Talamonti, M., "Increase in Activity and Level of pp60 c-src in Progressive Stages of Human Colorectal Cancer", J. Clin. Invest. vol. 91, pp. 53-60, 1993.
PCT Search Report for PCT/US2008/084469 mailed on Mar. 18, 2009.

* cited by examiner

*Primary Examiner* — Deepak Rao
(74) *Attorney, Agent, or Firm* — Susan L. Steele; Gregory W. Steele

(57) ABSTRACT

Compounds that inhibit protein kinases, compositions containing the compounds and methods of treating diseases using the compounds are disclosed.

12 Claims, No Drawings

PROTEIN KINASE INHIBITORS

This application claims priority to U.S. Provisional Application Ser. No. 60/990,330, filed Nov. 27, 2007.

FIELD OF THE INVENTION

This invention pertains to compounds that inhibit protein kinases, compositions containing the compounds and methods of treating diseases using the compounds.

BACKGROUND OF THE INVENTION

Numerous human diseases are characterized by increased and uncontrolled cell growth. This biology is driven, in many cases, by increased growth factor signaling. In addition, these pathologies often require an expanding blood supply and new vessel growth. Protein kinases are key components of both cell proliferation and endothelial cell expansion. Kinases are thus important targets for therapeutic intervention in pathologies characterized by uncontrolled cell growth.

SUMMARY OF THE INVENTION

One embodiment of this invention, therefore, pertains to compounds that inhibit protein kinases and have Formula I (I)

and therapeutically acceptable salts, prodrugs and salts of prodrugs thereof, wherein X is CH or N;

$A^1$ is $R^1$, $OR^1$, $NHR^1$, $N(R^1)_2$, $NHC(O)R^1$, $NHC(O)NHR^1$, $NHC(O)N(R^1)_2$, $NHC(O)OR^1$, $C(O)NHR^1$, $C(O)N(R^1)_2$, $C=NOR^1$, or $C(NH_2)NOC(O)R^1$;

$B^1$, $C^1$, $D^1$, $E^1$, $G^1$, and $H^1$ are each independently H, $R^1$, $OR^1$, $NHR^1$, $N(R^1)_2$, $NHC(O)R^1$, $NHC(O)NHR^1$, $NHC(O)N(R^1)_2$, $NHC(O)OR^1$, $C(O)NHR^1$, $C(O)N(R^1)_2$, OH, (O), CN, $N_3$, $NO_2$, $CF_3$, $CF_2CF_3$, $OCF_3$, $OCF_2CF_3$, F, Cl, Br, or I;

$R^1$ is $R^2$, $R^3$, $R^4$ or $R^5$;

$R^2$ is phenyl which is unfused or fused with benzene, heteroarene or $R^{2A}$; $R^{2A}$ is cycloalkane, cycloalkene, heterocycloalkane or heterocycloalkene;

$R^3$ is heteroaryl which is unfused or fused with benzene, heteroarene or $R^{3A}$; $R^{3A}$ is cycloalkane, cycloalkene, heterocycloalkane or heterocycloalkene;

$R^4$ is cycloalkyl, cycloalkenyl, heterocycloalkyl or heterocycloalkenyl, each of which is unfused or fused with benzene, heteroarene or $R^{4A}$; $R^{4A}$ is cycloalkane, cycloalkene, heterocycloalkane or heterocycloalkene;

$R^5$ is alkyl, alkenyl, or alkynyl, each of which is unsubstituted or substituted with one, two, three, four or five of independently selected spiroalkyl, $R^6$, $OR^6$, $NHR^6$, $N(R^6)_2$, $NHC(O)R^6$, $NHC(O)NHR^6$, $NHC(O)OR^6$, $C(O)NHR^6$, $C(O)N(R^6)_2$, $C(O)R^6$, or $CO(O)R^6$;

$R^6$ is $R^7$, $R^8$, $R^9$, or $R^{9B}$;

$R^7$ is phenyl which is unfused or fused with benzene, heteroarene or $R^{7A}$; $R^{7A}$ is cycloalkane, cycloalkene, heterocycloalkane or heterocycloalkene;

$R^8$ is heteroaryl which is unfused or fused with benzene, heteroarene or $R^{8A}$; $R^{8A}$ is cycloalkane, cycloalkene, heterocycloalkane or heterocycloalkene;

$R^9$ is cycloalkyl, cycloalkenyl, heterocycloalkyl or heterocycloalkenyl, each of which is unfused or fused with benzene, heteroarene or $R^{9A}$; $R^{9A}$ is cycloalkane, cycloalkene, heterocycloalkane or heterocycloalkene;

$R^{9B}$ is alkyl, alkenyl, or alkynyl;

$F^1$ is H, $R^{10}$, $C(O)R^{10}$, $R^{11}$ or $R^{110}$;

$R^{10}$ is phenyl which is unfused or fused with $R^{10A}$; $R^{10A}$ is benzene, heteroarene, cycloalkane, cycloalkene, heterocycloalkane, or heterocycloalkene;

$R^{11}$ is heteroaryl which is unfused or fused with $R^{11A}$; $R^{11A}$ is benzene, heteroarene, cycloalkane, cycloalkene, heterocycloalkane, or heterocycloalkene;

$R^{110}$ is alkyl which is unsubstituted or substituted with $R^{111}$;

$R^{112}$ is $R^{112}$, $R^{113}$ or $R^{114}$; $R^{112}$ is phenyl which is unfused or fused with benzene or heteroarene;

$R^8$ is heteroaryl which is unfused or fused with benzene or heteroarene;

$R^9$ is cycloalkyl, cycloalkenyl, heterocycloalkyl or heterocycloalkenyl, each of which is unfused or fused with benzene or heteroarene;

wherein each foregoing variable cyclic moiety is independently unsubstituted or substituted with one or two or three or four or five of independently selected $R^{12}$, $OR^{12}$, $SR^{12}$, $S(O)R^{12}$, $SO_2R^{12}$, $C(O)R^{12}$, $CO(O)R^{12}$, $OC(O)R^{12}$, $OC(O)OR^{12}$, $NH_2$, $NHR^{12}$, $N(R^{12})_2$, $NHC(O)R^{12}$, $NR^{12}C(O)R^{12}$, $NHS(O)_2R^{12}$, $NR^{12}S(O)_2R^{12}$, $NHC(O)OR^{12}$, $NR^{12}C(O)OR^{12}$, $NHC(O)NH_2$, $NHC(O)NHR^{12}$, $NHC(O)N(R^{12})_2$, $NR^{12}C(O)NHR^{12}$, $NR^{12}C(O)N(R^{12})_2$, $NHSO_2R^{12}$, $C(O)NH_2$, $C(O)NHR^{12}$, $C(O)N(R^{12})_2$, $C(O)NHOH$, $C(O)NHOR^{12}$, $C(O)NHSO_2R^{12}$, $C(O)NR^{12}SO_2R^{12}$, $SO_2NH_2$, $SO_2NHR^{12}$, $SO_2N(R^{12})_2$, $C(O)H$, $C(O)OH$, $C(N)NH_2$, $C(N)NHR^{12}$, $C(N)N(R^{12})_2$, CNOH, $CNOCH_3$, OH, (O), CN, $N_3$, $NO_2$, $CF_3$, $CF_2CF_3$, $OCF_3$, $OCF_2CF_3$, F, Cl, Br or I;

$R^{12}$ is $R^{13}$, $R^{14}R^{15}$, or $R^{16}$;

$R^{13}$ is phenyl which is unfused or fused with benzene, heteroarene or $R^{13A}$; $R^{13A}$ is cycloalkane, cycloalkene, heterocycloalkane or heterocycloalkene;

$R^{14}$ is heteroaryl which is unfused or fused with benzene, heteroarene or $R^{14A}$; $R^{14A}$ is cycloalkane, cycloalkene, heterocycloalkane or heterocycloalkene;

$R^{15}$ is cycloalkyl, cycloalkenyl, heterocycloalkyl or heterocycloalkenyl, each of which is unfused or fused with benzene, heteroarene or $R^{15A}$; $R^{15A}$ is cycloalkane, cycloalkene, heterocycloalkane or heterocycloalkene;

$R^{16}$ is alkyl, alkenyl, or alkenyl, each of which is unsubstituted or substituted with one, two, three, four or five of independently selected $R^{17}$, $OR^{17}$, $SR^{17}$, $S(O)R^{17}$, $SO_2R^{17}$, $C(O)R^{17}$, $CO(O)R^{17}$, $OC(O)R^{17}$, $OC(O)OR^{17}$, $NH_2$, $NHR^{17}$, $N(R^{17})_2$, $NHC(O)R^{17}$, $NR^{17}C(O)R^{17}$, $NHS(O)_2R^{17}$, $NR^{17}S(O)_2R^{17}$, $NHC(O)OR^{17}$, $NR^{17}C(O)OR^{17}$, $NHC(O)NH_2$, $NHC(O)NHR^{17}$, $NHC(O)N(R^{17})_2$, $NR^{17}C(O)NHR^{17}$, $NR^{17}C(O)N(R^{17})_2$, $C(O)NH_2$, $C(O)NHR^{17}$, $C(O)N(R^{17})_2$, $C(O)NHOH$, $C(O)NHOR^{17}$, $C(O)NHSO_2R^{17}$, $C(O)NR^{17}SO_2R^{17}$, $SO_2NH_2$, $SO_2NHR^{17}$, $SO_2N(R^{17})_2$, $C(O)H$, C(O)OH, C(N)NH$_2$, C(N)NHR$^{17}$, C(N)N(R$^{17}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I;

R$^{17}$ is R$^{18}$, R$^{19}$, R$^{20}$ or R$^{21}$;

R$^{18}$ is phenyl which is unfused or fused with benzene, heteroarene or R$^{18A}$; R$^{18A}$ is cycloalkane, cycloalkene, heterocycloalkane or heterocycloalkene;

R$^{19}$ is heteroaryl which is unfused or fused with benzene, heteroarene or R$^{19A}$; R$^{19A}$ is cycloalkane, cycloalkene, heterocycloalkane or heterocycloalkene;

R$^{20}$ is cycloalkyl, cycloalkenyl, heterocycloalkyl or heterocycloalkenyl, each of which is unfused or fused with benzene, heteroarene or R$^{20A}$; R$^{20A}$ is cycloalkane, cycloalkene, heterocycloalkane or heterocycloalkene;

R$^{21}$ is alkyl, alkenyl, or alkenyl, each of which is unsubstituted or substituted with one, two, three, four or five of independently selected R$^{22}$, OR$^{22}$, SR$^{22}$, S(O)R$^{22}$, SO$_2$R$^{22}$, C(O)R$^{22}$, CO(O)R$^{22}$, OC(O)R$^{22}$, OC(O)OR$^{22}$, NH$_2$, NHR$^{22}$, N(R$^{22}$)$_2$, NHC(O)R$^{22}$, NR$^{22}$C(O)R$^{22}$, NHS(O)$_2$R$^{22}$, NR$^{22}$S(O)$_2$R$^{22}$, NHC(O)OR$^{22}$, NR$^{22}$C(O)OR$^{22}$, NHC(O)NH$_2$, NHC(O)NHR$^{22}$, NHC(O)N(R$^{22}$)$_2$, NR$^{22}$C(O)NHR$^{22}$, NR$^{22}$C(O)N(R$^{22}$)$_2$, C(O)NH$_2$, C(O)NHR$^{22}$, C(O)N(R$^{22}$)$_2$, C(O)NHOH, C(O)NHOR$^{22}$, C(O)NHSO$_2$R$^{22}$, C(O)NR$^{22}$SO$_2$R$^{22}$, SO$_2$NH$_2$, SO$_2$NHR$^{22}$, SO$_2$N(R$^{22}$)$_2$, C(O)H, C(O)OH, C(N)NH$_2$, C(N)NHR$^{22}$, C(N)N(R$^{22}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I;

R$^{22}$ is alkyl, alkenyl, alkenyl, phenyl, heteroaryl, cycloalkyl, cycloalkenyl or heterocycloalkyl;

wherein the moieties represented by R$^{13}$, R$^{14}$, R$^{15}$, R$^{18}$, R$^{19}$, R$^{20}$, and R$^{22}$ are independently unsubstituted or substituted with one or two or three or four or five of independently selected R$^{23}$, OR$^{23}$, SR$^{23}$, S(O)R$^{23}$, SO$_2$R$^{23}$, C(O)R$^{23}$, CO(O)R$^{23}$, OC(O)R$^{23}$, OC(O)OR$^{23}$, NH$_2$, NHR$^{23}$, N(R$^{23}$)$_2$, NHC(O)R$^{23}$, NR$^{23}$C(O)R$^{23}$, NHS(O)$_2$R$^{23}$, NR$^{23}$S(O)$_2$R$^{23}$, NHC(O)OR$^{23}$, NR$^{23}$C(O)OR$^{23}$, NHC(O)NH$_2$, NHC(O)NHR$^{23}$, NHC(O)N(R$^{23}$)$_2$, NR$^{23}$C(O)NHR$^{23}$, NR$^{23}$C(O)N(R$^{23}$)$_2$, C(O)NH$_2$, C(O)NHR$^{23}$, C(O)N(R$^{23}$)$_2$, C(O)NHOH, C(O)NHOR$^{23}$, C(O)NHSO$_2$R$^{23}$, C(O)NR$^{23}$SO$_2$R$^{23}$, SO$_2$NH$_2$, SO$_2$NHR$^{23}$, SO$_2$N(R$^{23}$)$_2$, C(O)H, C(O)OH, C(N)NH$_2$, C(N)NHR$^{23}$, C(N)N(R$^{23}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I;

R$^{23}$ is alkyl which is unsubstituted or substituted with one or two of independently selected OR$^{24}$; and R$^{24}$ is hydrogen or alkyl which is unsubstituted or substituted with OH.

Another embodiment pertains to compounds having Formula I, wherein

X is N;

A$^1$ is R$^1$, OR$^1$, NHR$^1$, N(R$^1$)$_2$, NHC(O)R$^1$, NHC(O)NHR$^1$, NHC(O)N(R$^1$)$_2$, NHC(O)OR$^1$, C(O)NHR$^1$, C(O)N(R$^1$)$_2$, C=NOR$^1$, or C(NH$_2$)NOC(O)R$^1$;

B$^1$ is H, OR$^1$, NHR$^1$ or N(R$^1$)$_2$;

C$^1$, D$^1$, E$^1$, G$^1$, and H$^1$ are H;

R$^1$ is R$^2$, R$^3$, R$^4$ or R$^5$;

R$^2$ is phenyl which is unfused or fused with benzene or heteroarene;

R$^3$ is heteroaryl which is unfused or fused with benzene, heteroarene or R$^{3A}$; R$^{3A}$ is cycloalkane;

R$^4$ is cycloalkyl, cycloalkenyl, heterocycloalkyl or heterocycloalkyl;

R$^5$ is alkyl, alkenyl, or alkynyl, each of which is unsubstituted or substituted with one, two, three, four or five of independently selected spiroalkyl, R$^6$, OR$^6$, NHR$^6$ or N(R$^6$)$_2$;

R$^6$ is R$^7$, R$^8$, R$^9$, or R$^{9B}$;

R$^7$ is phenyl which is unfused or fused with benzene, heteroarene or R$^{7A}$; R$^{7A}$ is cycloalkane, cycloalkene, heterocycloalkane or heterocycloalkene;

R$^8$ is heteroaryl which is unfused or fused with benzene, heteroarene or R$^{8A}$; R$^{8A}$ is cycloalkane, cycloalkene, heterocycloalkane or heterocycloalkene;

R$^9$ is cycloalkyl, cycloalkenyl, heterocycloalkyl or heterocycloalkenyl, each of which is unfused or fused with benzene, heteroarene or R$^{9A}$; R$^{9A}$ is cycloalkane, cycloalkene, heterocycloalkane or heterocycloalkene;

R$^{9B}$ is alkyl, alkenyl, or alkynyl;

F$^1$ is H, R$^{10}$, C(O)R$^{11}$, R$^{11}$ or R$^{110}$;

R$^{10}$ is phenyl which is unfused or fused with R$^{10A}$; R$^{10A}$ is benzene, heteroarene, cycloalkane, cycloalkene, heterocycloalkane, or heterocycloalkene;

R$^{11}$ is heteroaryl which is unfused or fused with benzene;

R$^{110}$ is alkyl which is unsubstituted or substituted with R$^{111}$;

R$^{111}$ is R$^{112}$, R$^{113}$ or R$^{114}$;

R$^{112}$ is phenyl which is unfused or fused with benzene or heteroarene;

R$^8$ is heteroaryl which is unfused or fused with benzene or heteroarene;

R$^9$ is cycloalkyl, cycloalkenyl, heterocycloalkyl or heterocycloalkenyl, each of which is unfused or fused with benzene or heteroarene;

wherein each foregoing variable cyclic moiety is independently unsubstituted or substituted with one or two or three or four or five of independently selected R$^{12}$, OR$^{12}$, C(O)R$^{12}$, CO(O)R$^{12}$, N(R$^{12}$)$_2$, NHS(O)$_2$R$^{12}$, C(O)NHR$^{12}$, C(O)N(R$^{12}$)$_2$, SO$_2$NH$_2$, SO$_2$N(R$^{12}$)$_2$, C(O)OH, (O), CN, NO$_2$, CF$_3$, OCF$_3$, F, Cl, Br or I;

R$^{12}$ is R$^{13}$, R$^{14}$, R$^{15}$, or R$^{16}$;

R$^{13}$ is phenyl which is unfused or fused with benzene, or R$^{13A}$; R$^{13A}$ is cycloalkane or heterocycloalkane;

R$^{14}$ is heteroaryl which is unfused or fused with benzene;

R$^{15}$ is cycloalkyl, cycloalkenyl, heterocycloalkyl or heterocycloalkyl;

R$^{16}$ is alkyl, alkenyl, or alkenyl, each of which is unsubstituted or substituted with one, two, three, four or five of independently selected R$^{17}$, OR$^{17}$, NH$_2$, NHR$^{17}$, N(R$^{17}$)$_2$;

R$^{17}$ is R$^{18}$, R$^{19}$, R$^{20}$ or R$^{21}$;

R$^{18}$ is phenyl which is unfused or fused with benzene;

R$^{19}$ is heteroaryl which is unfused or fused with benzene;

R$^{20}$ is cycloalkyl, cycloalkenyl, heterocycloalkyl or heterocycloalkenyl, each of which is unfused or fused with benzene, heteroarene or R$^{20A}$; R$^{20A}$ is cycloalkane, cycloalkene, heterocycloalkane or heterocycloalkene;

R$^{21}$ is alkyl, alkenyl, or alkenyl, each of which is unsubstituted or substituted with SO$_2$R$^{22}$;

R$^{22}$ is alkyl, alkenyl, alkenyl, phenyl, heteroaryl, cycloalkyl, cycloalkenyl or heterocycloalkyl;

wherein the moieties represented by R$^{13}$, R$^{14}$, R$^{15}$, R$^{18}$, R$^{19}$, R$^{20}$, and R$^{22}$ are independently unsubstituted or substituted with one or two or three or four or five of independently selected R$^{23}$, OR$^{23}$, SR$^{23}$, S(O)R$^{23}$, SO$_2$R$^{23}$, C(O)R$^{23}$, CO(O)R$^{23}$, OC(O)R$^{23}$, OC(O)OR$^{23}$, NH$_2$, NHR$^{23}$, N(R$^{23}$)$_2$, NHC(O)R$^{23}$, NR$^{23}$C(O)R$^{23}$, NHS(O)$_2$R$^3$, NR$^{23}$S(O)$_2$R$^{23}$, NHC(O)OR$^{23}$, NR$^{23}$C(O)OR$^{23}$, NHC(O)NH$_2$, NHC(O)NHR$^{23}$, NHC(O)N(R$^{23}$)$_2$, NR$^{23}$C(O)NHR$^{23}$, NR$^{23}$C(O)N(R$^{23}$)$_2$, C(O)NH$_2$, C(O)NHR$^{23}$, C(O)N(R$^{23}$)$_2$, C(O)NHOH, C(O)NHOR$^{23}$, C(O)NHSO$_2$R$^{23}$, C(O)NR$^{23}$SO$_2$R$^{23}$, SO$_2$NH$_2$, SO$_2$NHR$^{23}$, SO$_2$N(R$^{23}$)$_2$, C(O)H, C(O)OH, C(N)NH$_2$, C(N)NHR$^{23}$, C(N)N(R$^{23}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I;

$R^{23}$ is alkyl which is unsubstituted or substituted with one or two of independently selected $OR^{24}$; and $R^{24}$ is hydrogen or alkyl which is unsubstituted or substituted with OH.

Still another embodiment pertains to compounds having Formula I, wherein

X is N;

$A^1$ is $R^1$, $OR^1$, $NHR^1$, $N(R^1)_2$, $NHC(O)R^1$, $NHC(O)NHR^1$, $NHC(O)N(R^1)_2$, $NHC(O)OR^1$, $C(O)NHR^1$, $C(O)N(R^1)_2$, $C=NOR^1$, or $C(NH_2)NOC(O)R^1$;

$B^1$ is H, $OR^1$, $NHR^1$ or $N(R^1)_2$;

$C^1$, $D^1$, $E^1$, $G^1$, and $H^1$ are H;

$R^1$ is $R^2$, $R^3$, $R^4$ or $R^5$;

$R^2$ is phenyl;

$R^3$ is heteroaryl which is unfused or fused with benzene or cycloalkane;

$R^4$ is cycloalkyl;

$R^5$ is alkyl, alkenyl, or alkynyl, each of which is unsubstituted or substituted with one or two of independently selected spiroalkyl, $R^6$, $OR^6$, $NHR^6$ or $N(R^6)_2$;

$R^6$ is $R^7$, $R^8$ or $R^9$;

$R^7$ is phenyl which is unfused or fused with benzene or heterocycloalkane;

$R^8$ is heteroaryl;

$R^9$ is cycloalkyl or heterocycloalkyl;

$F^1$ is H, $R^{10}$, $C(O)R^{10}$ or $R^{110}$;

$R^{10}$ is phenyl which is unfused or fused with $R^{10A}$ or heterocycloalkene;

$R^{110}$ is alkyl which is unsubstituted or substituted with phenyl;

wherein each foregoing variable cyclic moiety is independently unsubstituted or substituted with one or two or three or four or five of independently selected $R^{12}$, $OR^{12}$, $C(O)R^{12}$, $CO(O)R^{12}$, $N(R^{12})_2$, $NHS(O)_2R^{12}$, $C(O)NHR^{12}$, $C(O)N(R^{12})_2$, $SO_2NH_2$, $SO_2N(R^{12})_2$, $C(O)OH$, (O), CN, $NO_2$, $CF_3$, $OCF_3$, F, Cl, Br or I;

$R^{12}$ is $R^{13}$, $R^{14}$, $R^{15}$, or $R^{16}$;

$R^{13}$ is phenyl which is unfused or fused with heterocycloalkane;

$R^{14}$ is heteroaryl;

$R^{15}$ is heterocycloalkyl;

$R^{16}$ is alkyl, alkenyl, or alkynyl, each of which is unsubstituted or substituted with one, two, three, four or five of independently selected $R^{17}$, $OR^{17}$, $NH_2$, $NHR^{17}$, $N(R^{17})_2$;

$R^{17}$ is $R^{18}$, $R^{19}$, $R^{20}$ or $R^{21}$;

$R^{18}$ is phenyl;

$R^{19}$ is heteroaryl;

$R^{20}$ is cycloalkyl, cycloalkenyl, heterocycloalkyl or heterocycloalkenyl;

$R^{21}$ is alkyl, alkenyl, or alkenyl, each of which is unsubstituted or substituted with $SO_2R^{22}$;

$R^{22}$ is alkyl, alkenyl, alkenyl, phenyl, heteroaryl, cycloalkyl, cycloalkenyl or heterocycloalkyl;

wherein the moieties represented by $R^{13}$, $R^{14}$, $R^{15}$, $R^{18}$, $R^{19}$, $R^{20}$, and $R^{22}$ are independently unsubstituted or substituted with one or two or three or four or five of independently selected $R^{23}$, $OR^{23}$, $SR^{23}$, $S(O)R^{23}$, $SO_2R^{23}$, $C(O)R^{23}$, (O);

$R^{23}$ is alkyl which is unsubstituted or substituted with one or two of independently selected $OR^{24}$; and $R^{24}$ alkyl which is unsubstituted or substituted with OH.

Still another embodiment pertains to compounds having Formula I, wherein

X is N;

$A^1$ is $R^1$, $OR^1$, $NHR^1$, $NHC(O)R^1$, $NHC(O)NHR^1$, $NHC(O)OR^1$, $C=NOR^1$, or $C(NH_2)NOC(O)R^1$;

$B^1$ is $OR^1$ or $N(R^1)_2$;

$C^1$, $D^1$, $E^1$, $G^1$, and $H^1$ are H;

$R^1$ is $R^2$, $R^3$ or $R^5$;

$R^2$ is phenyl;

$R^3$ is heteroaryl which is unfused or fused with benzene or cycloalkane;

$R^4$ is cycloalkyl;

$R^5$ is alkyl or alkynyl, each of which is unsubstituted or substituted with one or two of independently selected spiroalkyl, $R^6$, $OR^6$ or $N(R^6)_2$;

$R^6$ is $R^7$, $R^8$ or $R^9$;

$R^7$ is phenyl which is unfused or fused with benzene or heterocycloalkane;

$R^8$ is heteroaryl;

$R^9$ is cycloalkyl or heterocycloalkyl;

$F^1$ is H, $R^{10}$, $C(O)R^{10}$ or $R^{110}$;

$R^{10}$ is phenyl which is unfused or fused with $R^{10A}$ or heterocycloalkene;

$R^{110}$ is alkyl which is unsubstituted or substituted with phenyl;

wherein each foregoing variable cyclic moiety is independently unsubstituted or substituted with one or two or three or four or five of independently selected $R^{12}$, $OR^{12}$, $C(O)R^{12}$, $CO(O)R^{12}$, $N(R^{12})_2$, $NHS(O)_2R^{12}$, $C(O)NHR^{12}$, $C(O)N(R^{12})_2$, $SO_2NH_2$, $SO_2N(R^{12})_2$, $C(O)OH$, (O), CN, $NO_2$, $CF_3$, $OCF_3$, F, Cl, Br or I;

$R^{12}$ is $R^{13}$, $R^{14}$, $R^{15}$, or $R^{16}$;

$R^{13}$ is phenyl which is unfused or fused with heterocycloalkane;

$R^{14}$ is heteroaryl;

$R^{15}$ is heterocycloalkyl;

$R^{16}$ is alkyl which is unsubstituted or substituted with one or two of independently selected $R^{17}$, $OR^{17}$, $NHR^{17}$, $N(R^{17})_2$;

$R^{17}$ is $R^{18}$, $R^{19}$, $R^{20}$ or $R^{21}$;

$R^{18}$ is phenyl;

$R^{19}$ is heteroaryl;

$R^{20}$ is heterocycloalkyl;

$R^{21}$ is alkyl which is unsubstituted or substituted with $SO_2R^{22}$;

$R^{22}$ is alkyl;

wherein the moieties represented by $R^{13}$, $R^{14}$, $R^{15}$, $R^{18}$, $R^{19}$, $R^{20}$, and $R^{22}$ are independently unsubstituted or substituted with one or two of independently selected $R^{23}$, $OR^{23}$, $C(O)R^{23}$ or (O);

$R^{23}$ is alkyl which substituted with $OR^{24}$; and $R^{24}$ alkyl which is unsubstituted or substituted with OH.

Still another embodiment pertains to compositions comprising an excipient and a therapeutically effective amount of a compound having Formula I.

Still another embodiment pertains to compositions comprising an excipient and therapeutically effective amounts of a compound having Formula I and one or more than one additional therapeutic agents.

Still another embodiment pertains to methods of treating a mammal having a disease involving overexpression or unregulation of a protein kinase comprising administering thereto a therapeutically effective amount of a compound having Formula I.

Still another embodiment pertains to methods of treating a mammal having a disease involving overexpression or unregulation of a protein kinase comprising administering thereto radiotherapy and a therapeutically effective amount of a compound having Formula I.

Still another embodiment pertains to methods of treating a mammal having cervical cancer, colon cancer, endometrial cancer, esophageal cancer, lung cancer comprising administering thereto a therapeutically effective amount of a compound having Formula I.

Still another embodiment pertains to methods of treating a mammal having cervical cancer, colon cancer, endometrial cancer, esophageal cancer, lung cancer comprising administering thereto radiotherapy and a therapeutically effective amount of a compound having Formula I.

Still another embodiment pertains to methods of treating diseases involving overexpression or unregulation of a protein kinase in a mammal comprising administering thereto therapeutically effective amounts of a compound having Formula I and one or more than one additional therapeutic agents.

Still another embodiment pertains to methods of treating diseases involving overexpression or unregulation of a protein kinase in a mammal comprising administering thereto radiotherapy and therapeutically effective amounts of a compound having Formula I and one or more than one additional therapeutic agents.

Still another embodiment pertains to methods of treating cervical cancer, colon cancer, endometrial cancer, esophageal cancer, lung cancer in a mammal comprising administering thereto a therapeutically effective amount of a compound having Formula I and one or more than one additional therapeutic agents.

Still another embodiment pertains to methods of treating cervical cancer, colon cancer, endometrial cancer, esophageal cancer, lung cancer in a mammal comprising administering thereto radiotherapy a therapeutically effective amount of a compound having Formula I and one or more than one additional therapeutic agents.

Still another embodiment pertains to the compounds

N-(3-(5-(2-anilinopyrimidin-4-yl)imidazo[2,1-b][1,3]thiazol-6-yl)phenyl)-2-chlorobenzamide,
N-(3-(5-(2-anilinopyrimidin-4-yl)imidazo[2,1-b][1,3]thiazol-6-yl)phenyl)benzamide,
2,6-difluoro-N-(3-(5-(2-((4-morpholin-4-ylphenyl)amino)pyrimidin-4-yl)imidazo[2,1-b][1,3]thiazol-6-yl)phenyl)benzamide,
N-(3-(5-(2-((4-morpholin-4-ylphenyl)amino)pyrimidin-4-yl)imidazo[2,1-b][1,3]thiazol-6-yl)phenyl)benzamide,
N-(3-(5-(2-((4-morpholin-4-ylphenyl)amino)pyrimidin-4-yl)imidazo[2,1-b][1,3]thiazol-6-yl)phenyl)-2-phenylacetamide,
N-(3-(5-(2-((3-fluoro-4-methoxyphenyl)amino)pyrimidin-4-yl)imidazo[2,1-b][1,3]thiazol-6-yl)phenyl)benzamide,
N-(3-(5-(2-((3-fluoro-4-methoxyphenyl)amino)pyrimidin-4-yl)imidazo[2,1-b][1,3]thiazol-6-yl)phenyl)-2-phenylacetamide,
N-(3-(5-(2-anilinopyrimidin-4-yl)imidazo[2,1-b][1,3]thiazol-6-yl)phenyl)-2-phenylacetamide,
N-(3-(5-(2-anilinopyrimidin-4-yl)imidazo[2,1-b][1,3]thiazol-6-yl)phenyl)acetamide,
N-(3-(5-(2-((3-fluorophenyl)amino)pyrimidin-4-yl)imidazo[2,1-b][1,3]thiazol-6-yl)phenyl)-2-phenylacetamide,
N-(3-(5-(2-((3-fluorophenyl)amino)pyrimidin-4-yl)imidazo[2,1-b][1,3]thiazol-6-yl)phenyl)benzamide,
N-(3-(5-(2-((3-morpholin-4-ylphenyl)amino)pyrimidin-4-yl)imidazo[2,1-b][1,3]thiazol-6-yl)phenyl)-2-phenylacetamide,
N-(3-(5-(2-((4-morpholin-4-ylphenyl)amino)pyrimidin-4-yl)imidazo[2,1-b][1,3]thiazol-6-yl)phenyl)-N'-phenylurea,
N-(3-(5-(2-((4-(4-(3-methoxypropyl)piperazin-1-yl)phenyl)amino)pyrimidin-4-yl)imidazo[2,1-b][1,3]thiazol-6-yl)phenyl)-2-phenylacetamide,
2-(2,6-difluorophenyl)-N-(3-(5-(2-((4-(4-(3-methoxypropyl)piperazin-1-yl)phenyl)amino)pyrimidin-4-yl)imidazo[2,1-b][1,3]thiazol-6-yl)phenyl)acetamide,
N-(3-(5-(2-((4-(4-(3-methoxypropyl)piperazin-1-yl)phenyl)amino)pyrimidin-4-yl)imidazo[2,1-b][1,3]thiazol-6-yl)phenyl)acetamide,
2-(2-methoxyphenyl)-N-(3-(5-(2-((4-(4-(3-methoxypropyl)piperazin-1-yl)phenyl)amino)pyrimidin-4-yl)imidazo[2,1-b][1,3]thiazol-6-yl)phenyl)acetamide,
N-(2-methoxyphenyl)-N'-(3-(5-(2-((4-morpholin-4-ylphenyl)amino)pyrimidin-4-yl)imidazo[2,1-b][1,3]thiazol-6-yl)phenyl)urea,
N-(2-methylphenyl)-N'-(3-(5-(2-((4-morpholin-4-ylphenyl)amino)pyrimidin-4-yl)imidazo[2,1-b][1,3]thiazol-6-yl)phenyl)urea,
N-(3-methylphenyl)-N'-(3-(5-(2-((4-morpholin-4-ylphenyl)amino)pyrimidin-4-yl)imidazo[2,1-b][1,3]thiazol-6-yl)phenyl)urea,
N-(4-methylphenyl)-N'-(3-(5-(2-((4-morpholin-4-ylphenyl)amino)pyrimidin-4-yl)imidazo[2,1-b][1,3]thiazol-6-yl)phenyl)urea,
N-(2-fluorophenyl)-N'-(3-(5-(2-((4-morpholin-4-ylphenyl)amino)pyrimidin-4-yl)imidazo[2,1-b][1,3]thiazol-6-yl)phenyl)urea,
N-(3-fluorophenyl)-N'-(3-(5-(2-((4-morpholin-4-ylphenyl)amino)pyrimidin-4-yl)imidazo[2,1-b][1,3]thiazol-6-yl)phenyl)urea,
N-(4-fluorophenyl)-N'-(3-(5-(2-((4-morpholin-4-ylphenyl)amino)pyrimidin-4-yl)imidazo[2,1-b][1,3]thiazol-6-yl)phenyl)urea,
N-(2-chlorophenyl)-N'-(3-(5-(2-((4-morpholin-4-ylphenyl)amino)pyrimidin-4-yl)imidazo[2,1-b][1,3]thiazol-6-yl)phenyl)urea,
N-(3-chlorophenyl)-N'-(3-(5-(2-((4-morpholin-4-ylphenyl)amino)pyrimidin-4-yl)imidazo[2,1-b][1,3]thiazol-6-yl)phenyl)urea,
N-(4-chlorophenyl)-N'-(3-(5-(2-((4-morpholin-4-ylphenyl)amino)pyrimidin-4-yl)imidazo[2,1-b][1,3]thiazol-6-yl)phenyl)urea,
N-(3-methoxyphenyl)-N'-(3-(5-(2-((4-morpholin-4-ylphenyl)amino)pyrimidin-4-yl)imidazo[2,1-b][1,3]thiazol-6-yl)phenyl)urea,
N-(4-methoxyphenyl)-N'-(3-(5-(2-((4-morpholin-4-ylphenyl)amino)pyrimidin-4-yl)imidazo[2,1-b][1,3]thiazol-6-yl)phenyl)urea,
N-(3-(5-(2-((4-morpholin-4-ylphenyl)amino)pyrimidin-4-yl)imidazo[2,1-b][1,3]thiazol-6-yl)phenyl)-N'-(2-(trifluoromethyl)phenyl)urea,
N-(3-(5-(2-((4-morpholin-4-ylphenyl)amino)pyrimidin-4-yl)imidazo[2,1-b][1,3]thiazol-6-yl)phenyl)-N'-(3-(trifluoromethyl)phenyl)urea,
N-(3-(5-(2-((4-morpholin-4-ylphenyl)amino)pyrimidin-4-yl)imidazo[2,1-b][1,3]thiazol-6-yl)phenyl)-N'-(4-(trifluoromethyl)phenyl)urea,
N-(3-(5-(2-aminopyrimidin-4-yl)imidazo[2,1-b][1,3]thiazol-6-yl)phenyl)benzamide,
N-(3-(5-(2-((3-(acetylamino)phenyl)amino)pyrimidin-4-yl)imidazo[2,1-b][1,3]thiazol-6-yl)phenyl)benzamide,
N-(3-(5-(2-((3-(acetylamino)phenyl)amino)pyrimidin-4-yl)imidazo[2,1-b][1,3]thiazol-6-yl)phenyl)-2-phenylacetamide,
N-(3-(5-(2-((4-(4-methylpiperazin-1-yl)phenyl)amino)pyrimidin-4-yl)imidazo[2,1-b][1,3]thiazol-6-yl)phenyl)-2-phenylacetamide,
N-(3-(5-(2-((3-chlorophenyl)amino)pyrimidin-4-yl)imidazo[2,1-b][1,3]thiazol-6-yl)phenyl)-2-phenylacetamide,
N-(3-(5-(2-((3-methylphenyl)amino)pyrimidin-4-yl)imidazo[2,1-b][1,3]thiazol-6-yl)phenyl)-2-phenylacetamide,
N-(3-(5-(2-((3-methoxyphenyl)amino)pyrimidin-4-yl)imidazo[2,1-b][1,3]thiazol-6-yl)phenyl)-2-phenylacetamide, N-(3-(5-(2-((4-(1H-imidazol-1-yl)phenyl)amino)pyrimidin-4-yl)imidazo[2,1-b][1,3]thiazol-6-yl)phenyl)-2-phenylacetamide,
N-(3-(5-(2-((4-(1H-imidazol-1-yl)phenyl)amino)pyrimidin-4-yl)imidazo[2,1-b][1,3]thiazol-6-yl)phenyl)-2-phenylbutanamide,
N-(3-(5-(2-((4-(1,1-dioxidothiomorpholin-4-yl)phenyl)amino)pyrimidin-4-yl)imidazo[2,1-b][1,3]thiazol-6-yl)phenyl)-2-phenylacetamide,
N-(3-(5-(2-((4-(1,1-dioxidothiomorpholin-4-yl)phenyl)amino)pyrimidin-4-yl)imidazo[2,1-b][1,3]thiazol-6-yl)phenyl)-2-(3-methoxyphenyl)acetamide,
N-(3-(5-(2-((4-(1,1-dioxidothiomorpholin-4-yl)phenyl)amino)pyrimidin-4-yl)imidazo[2,1-b][1,3]thiazol-6-yl)phenyl)-2-(4-methoxyphenyl)acetamide,
N-benzyl-N'-(3-(5-(2-((4-morpholin-4-ylphenyl)amino)pyrimidin-4-yl)imidazo[2,1-b][1,3]thiazol-6-yl)phenyl)urea,
N-(3-(5-(2-((4-morpholin-4-ylphenyl)amino)pyrimidin-4-yl)imidazo[2,1-b][1,3]thiazol-6-yl)phenyl)-2-thien-2-ylacetamide,
phenyl 3-(5-(2-((4-morpholin-4-ylphenyl)amino)pyrimidin-4-yl)imidazo[2,1-b][1,3]thiazol-6-yl)phenylcarbamate,
N-(3-(5-(2-((3-((methylsulfonyl)amino)phenyl)amino)pyrimidin-4-yl)imidazo[2,1-b][1,3]thiazol-6-yl)phenyl)-2-phenylacetamide,
3-(1H-imidazol-4-yl)-N-(3-(5-(2-((4-morpholin-4-ylphenyl)amino)pyrimidin-4-yl)imidazo[2,1-b][1,3]thiazol-6-yl)phenyl)propanamide,
ethyl 3-((4-(6-(3-((phenylacetyl)amino)phenyl)imidazo[2,1-b][1,3]thiazol-5-yl)pyrimidin-2-yl)amino)benzoate, benzyl 3-(5-(2-((4-morpholin-4-ylphenyl)amino)pyrimidin-4-yl)imidazo[2,1-b][1,3]thiazol-6-yl)phenylcarbamate,
4-methoxyphenyl 3-(5-(2-((4-morpholin-4-ylphenyl)amino)pyrimidin-4-yl)imidazo[2,1-b][1,3]thiazol-6-yl)phenylcarbamate,
N-(3-(5-(2-((3-methylphenyl)amino)pyrimidin-4-yl)imidazo[2,1-b][1,3]thiazol-6-yl)phenyl)benzamide,
N-(3-(5-(2-((4-methylphenyl)amino)pyrimidin-4-yl)imidazo[2,1-b][1,3]thiazol-6-yl)phenyl)benzamide,
N-(3-(5-(2-((4-methylphenyl)amino)pyrimidin-4-yl)imidazo[2,1-b][1,3]thiazol-6-yl)phenyl)-2-phenylacetamide,
N-(3-(5-(2-((2-methylphenyl)amino)pyrimidin-4-yl)imidazo[2,1-b][1,3]thiazol-6-yl)phenyl)benzamide,
N-(3-(5-(2-((2-chlorophenyl)amino)pyrimidin-4-yl)imidazo[2,1-b][1,3]thiazol-6-yl)phenyl)benzamide,
N-(3-(5-(2-((4-chlorophenyl)amino)pyrimidin-4-yl)imidazo[2,1-b][1,3]thiazol-6-yl)phenyl)benzamide,
N-(3-(5-(2-((4-chlorophenyl)amino)pyrimidin-4-yl)imidazo[2,1-b][1,3]thiazol-6-yl)phenyl)-2-phenylacetamide,
3-((4-(6-(3-((phenylacetyl)amino)phenyl)imidazo[2,1-b][1,3]thiazol-5-yl)pyrimidin-2-yl)amino)benzoic acid,
N-(3-(5-(2-((2-methylphenyl)amino)pyrimidin-4-yl)imidazo[2,1-b][1,3]thiazol-6-yl)phenyl)-2-phenylacetamide,
N-(3-(5-(2-((2-chlorophenyl)amino)pyrimidin-4-yl)imidazo[2,1-b][1,3]thiazol-6-yl)phenyl)-2-phenylacetamide,
N-(3-(5-(2-((4-(4-acetylpiperazin-1-yl)phenyl)amino)pyrimidin-4-yl)imidazo[2,1-b][1,3]thiazol-6-yl)phenyl)-2-phenylacetamide,
benzyl 3-(5-(2-((4-(4-acetylpiperazin-1-yl)phenyl)amino)pyrimidin-4-yl)imidazo[2,1-b][1,3]thiazol-6-yl)phenylcarbamate,
N-(3-(5-(2-((4-(2-oxopyrrolidin-1-yl)phenyl)amino)pyrimidin-4-yl)imidazo[2,1-b][1,3]thiazol-6-yl)phenyl)-2-phenylacetamide,
benzyl 3-(5-(2-((4-(2-oxopyrrolidin-1-yl)phenyl)amino)pyrimidin-4-yl)imidazo[2,1-b][1,3]thiazol-6-yl)phenylcarbamate,
2-(2-methylphenyl)-N-(3-(5-(2-((4-morpholin-4-ylphenyl)amino)pyrimidin-4-yl)imidazo[2,1-b][1,3]thiazol-6-yl)phenyl)acetamide,
2-(3-methylphenyl)-N-(3-(5-(2-((4-morpholin-4-ylphenyl)amino)pyrimidin-4-yl)imidazo[2,1-b][1,3]thiazol-6-yl)phenyl)acetamide,
2-(4-methylphenyl)-N-(3-(5-(2-((4-morpholin-4-ylphenyl)amino)pyrimidin-4-yl)imidazo[2,1-b][1,3]thiazol-6-yl)phenyl)acetamide,
N-(3-(5-(2-((4-morpholin-4-ylphenyl)amino)pyrimidin-4-yl)imidazo[2,1-b][1,3]thiazol-6-yl)phenyl)-2-(2-nitrophenyl)acetamide,
2-(2-fluorophenyl)-N-(3-(5-(2-((4-morpholin-4-ylphenyl)amino)pyrimidin-4-yl)imidazo[2,1-b][1,3]thiazol-6-yl)phenyl)acetamide,
2-(2-chlorophenyl)-N-(3-(5-(2-((4-morpholin-4-ylphenyl)amino)pyrimidin-4-yl)imidazo[2,1-b][1,3]thiazol-6-yl)phenyl)acetamide,
2-(3-chlorophenyl)-N-(3-(5-(2-((4-morpholin-4-ylphenyl)amino)pyrimidin-4-yl)imidazo[2,1-b][1,3]thiazol-6-yl)phenyl)acetamide,
2-(4-chlorophenyl)-N-(3-(5-(2-((4-morpholin-4-ylphenyl)amino)pyrimidin-4-yl)imidazo[2,1-b][1,3]thiazol-6-yl)phenyl)acetamide,
2-(2-bromophenyl)-N-(3-(5-(2-((4-morpholin-4-ylphenyl)amino)pyrimidin-4-yl)imidazo[2,1-b][1,3]thiazol-6-yl)phenyl)acetamide,
2-(3-bromophenyl)-N-(3-(5-(2-((4-morpholin-4-ylphenyl)amino)pyrimidin-4-yl)imidazo[2,1-b][1,3]thiazol-6-yl)phenyl)acetamide,
2-(4-bromophenyl)-N-(3-(5-(2-((4-morpholin-4-ylphenyl)amino)pyrimidin-4-yl)imidazo[2,1-b][1,3]thiazol-6-yl)phenyl)acetamide,
N-(3-(5-(2-((4-morpholin-4-ylphenyl)amino)pyrimidin-4-yl)imidazo[2,1-b][1,3]thiazol-6-yl)phenyl)-2-(3-nitrophenyl)acetamide,
N-(3-(5-(2-((4-morpholin-4-ylphenyl)amino)pyrimidin-4-yl)imidazo[2,1-b][1,3]thiazol-6-yl)phenyl)-2-(4-nitrophenyl)acetamide,
2-(1,1'-biphenyl-4-yl)-N-(3-(5-(2-((4-morpholin-4-ylphenyl)amino)pyrimidin-4-yl)imidazo[2,1-b][1,3]thiazol-6-yl)phenyl)acetamide,
2-(4-(dimethylamino)phenyl)-N-(3-(5-(2-((4-morpholin-4-ylphenyl)amino)pyrimidin-4-yl)imidazo[2,1-b][1,3]thiazol-6-yl)phenyl)acetamide,
N-(3-(5-(2-((4-morpholin-4-ylphenyl)amino)pyrimidin-4-yl)imidazo[2,1-b][1,3]thiazol-6-yl)phenyl)-2-(3-(trifluoromethyl)phenyl)acetamide,
N-(3-(5-(2-((4-morpholin-4-ylphenyl)amino)pyrimidin-4-yl)imidazo[2,1-b][1,3]thiazol-6-yl)phenyl)-2-(4-(trifluoromethyl)phenyl)acetamide,
N-(3-(5-(2-((4-morpholin-4-ylphenyl)amino)pyrimidin-4-yl)imidazo[2,1-b][1,3]thiazol-6-yl)phenyl)-2-(3-(trifluoromethoxy)phenyl)acetamide,
N-(3-(5-(2-((4-morpholin-4-ylphenyl)amino)pyrimidin-4-yl)imidazo[2,1-b][1,3]thiazol-6-yl)phenyl)-2-(4-phenoxyphenyl)acetamide,
2-(4-(benzyloxy)phenyl)-N-(3-(5-(2-((4-morpholin-4-ylphenyl)amino)pyrimidin-4-yl)imidazo[2,1-b][1,3]thiazol-6-yl)phenyl)acetamide,
N-(3-(5-(2-((4-morpholin-4-ylphenyl)amino)pyrimidin-4-yl)imidazo[2,1-b][1,3]thiazol-6-yl)phenyl)-2-(1-naphthyl)acetamide, N-(3-(5-(2-((4-morpholin-4-ylphenyl)amino)pyrimidin-4-yl)imidazo[2,1-b][1,3]thiazol-6-yl)phenyl)-2-(2-naphthyl)acetamide, 2-(2,5-dimethylphenyl)-N-(3-(5-(2-((4-morpholin-4-ylphenyl)amino)pyrimidin-4-yl)imidazo[2,1-b][1,3]thiazol-6-yl)phenyl)acetamide, 2-mesityl-N-(3-(5-(2-((4-morpholin-4-ylphenyl)amino)pyrimidin-4-yl)imidazo[2,1-b][1,3]thiazol-6-yl)phenyl)acetamide, 2-(3,5-dimethylphenyl)-N-(3-(5-(2-((4-morpholin-4-ylphenyl)amino)pyrimidin-4-yl)imidazo[2,1-b][1,3]thiazol-6-yl)phenyl)acetamide, 2-(2,3-dimethoxyphenyl)-N-(3-(5-(2-((4-morpholin-4-ylphenyl)amino)pyrimidin-4-yl)imidazo[2,1-b][1,3]thiazol-6-yl)phenyl)acetamide, 2-(2,4-dimethoxyphenyl)-N-(3-(5-(2-((4-morpholin-4-ylphenyl)amino)pyrimidin-4-yl)imidazo[2,1-b][1,3]thiazol-6-yl)phenyl)acetamide, 2-(2,5-dimethoxyphenyl)-N-(3-(5-(2-((4-morpholin-4-ylphenyl)amino)pyrimidin-4-yl)imidazo[2,1-b][1,3]thiazol-6-yl)phenyl)acetamide, 2-(3,4-dimethoxyphenyl)-N-(3-(5-(2-((4-morpholin-4-ylphenyl)amino)pyrimidin-4-yl)imidazo[2,1-b][1,3]thiazol-6-yl)phenyl)acetamide, 2-(3,5-dimethoxyphenyl)-N-(3-(5-(2-((4-morpholin-4-ylphenyl)amino)pyrimidin-4-yl)imidazo[2,1-b][1,3]thiazol-6-yl)phenyl)acetamide, 2-(1,3-benzodioxol-5-yl)-N-(3-(5-(2-((4-morpholin-4-ylphenyl)amino)pyrimidin-4-yl)imidazo[2,1-b][1,3]thiazol-6-yl)phenyl)acetamide, N-(3-(5-(2-((4-morpholin-4-ylphenyl)amino)pyrimidin-4-yl)imidazo[2,1-b][1,3]thiazol-6-yl)phenyl)-2-(3,4,5-trimethoxyphenyl)acetamide, 2-(2,3-difluorophenyl)-N-(3-(5-(2-((4-morpholin-4-ylphenyl)amino)pyrimidin-4-yl)imidazo[2,1-b][1,3]thiazol-6-yl)phenyl)acetamide, 2-(2,4-dichlorophenyl)-N-(3-(5-(2-((4-morpholin-4-ylphenyl)amino)pyrimidin-4-yl)imidazo[2,1-b][1,3]thiazol-6-yl)phenyl)acetamide, 2-(2,5-difluorophenyl)-N-(3-(5-(2-((4-morpholin-4-ylphenyl)amino)pyrimidin-4-yl)imidazo[2,1-b][1,3]thiazol-6-yl)phenyl)acetamide, 2-(3,4-dichlorophenyl)-N-(3-(5-(2-((4-morpholin-4-ylphenyl)amino)pyrimidin-4-yl)imidazo[2,1-b][1,3]thiazol-6-yl)phenyl)acetamide, 2-(2,6-dichlorophenyl)-N-(3-(5-(2-((4-morpholin-4-ylphenyl)amino)pyrimidin-4-yl)imidazo[2,1-b][1,3]thiazol-6-yl)phenyl)acetamide, N-(3-(5-(2-((4-morpholin-4-ylphenyl)amino)pyrimidin-4-yl)imidazo[2,1-b][1,3]thiazol-6-yl)phenyl)-2-furamide, N-(3-(5-(2-((4-morpholin-4-ylphenyl)amino)pyrimidin-4-yl)imidazo[2,1-b][1,3]thiazol-6-yl)phenyl)-3-furamide, 2,5-dimethyl-N-(3-(5-(2-((4-morpholin-4-ylphenyl)amino)pyrimidin-4-yl)imidazo[2,1-b][1,3]thiazol-6-yl)phenyl)-3-furamide, N-(3-(5-(2-((4-morpholin-4-ylphenyl)amino)pyrimidin-4-yl)imidazo[2,1-b][1,3]thiazol-6-yl)phenyl)thiophene-2-carboxamide, N-(3-(5-(2-((4-morpholin-4-ylphenyl)amino)pyrimidin-4-yl)imidazo[2,1-b][1,3]thiazol-6-yl)phenyl)thiophene-3-carboxamide, 3-methyl-N-(3-(5-(2-((4-morpholin-4-ylphenyl)amino)pyrimidin-4-yl)imidazo[2,1-b][1,3]thiazol-6-yl)phenyl)thiophene-2-carboxamide, 5-methyl-N-(3-(5-(2-((4-morpholin-4-ylphenyl)amino)pyrimidin-4-yl)imidazo[2,1-b][1,3]thiazol-6-yl)phenyl)thiophene-2-carboxamide, N-(3-(5-(2-((4-morpholin-4-ylphenyl)amino)pyrimidin-4-yl)imidazo[2,1-b][1,3]thiazol-6-yl)phenyl)-1H-pyrrole-2-carboxamide, 1-methyl-N-(3-(5-(2-((4-morpholin-4-ylphenyl)amino)pyrimidin-4-yl)imidazo[2,1-b][1,3]thiazol-6-yl)phenyl)-1H-pyrrole-2-carboxamide, N-(3-(5-(2-((4-morpholin-4-ylphenyl)amino)pyrimidin-4-yl)imidazo[2,1-b][1,3]thiazol-6-yl)phenyl)-1,3-thiazole-4-carboxamide, N-(3-(5-(2-((4-morpholin-4-ylphenyl)amino)pyrimidin-4-yl)imidazo[2,1-b][1,3]thiazol-6-yl)phenyl)-1,3-thiazole-5-carboxamide, N-(3-(5-(2-((4-morpholin-4-ylphenyl)amino)pyrimidin-4-yl)imidazo[2,1-b][1,3]thiazol-6-yl)phenyl)-1H-pyrazole-4-carboxamide, 3,5-dimethyl-N-(3-(5-(2-((4-morpholin-4-ylphenyl)amino)pyrimidin-4-yl)imidazo[2,1-b][1,3]thiazol-6-yl)phenyl)isoxazole-4-carboxamide, 5-methyl-N-(3-(5-(2-((4-morpholin-4-ylphenyl)amino)pyrimidin-4-yl)imidazo[2,1-b][1,3]thiazol-6-yl)phenyl)-3-phenylisoxazole-4-carboxamide, N-(3-(5-(2-((4-morpholin-4-ylphenyl)amino)pyrimidin-4-yl)imidazo[2,1-b][1,3]thiazol-6-yl)phenyl)pyridine-2-carboxamide, N-(3-(5-(2-((4-morpholin-4-ylphenyl)amino)pyrimidin-4-yl)imidazo[2,1-b][1,3]thiazol-6-yl)phenyl)nicotinamide, N-(3-(5-(2-((4-morpholin-4-ylphenyl)amino)pyrimidin-4-yl)imidazo[2,1-b][1,3]thiazol-6-yl)phenyl)isonicotinamide, N-(3-(5-(2-((4-morpholin-4-ylphenyl)amino)pyrimidin-4-yl)imidazo[2,1-b][1,3]thiazol-6-yl)phenyl)-2-pyridin-2-ylacetamide, N-(3-(5-(2-((4-morpholin-4-ylphenyl)amino)pyrimidin-4-yl)imidazo[2,1-b][1,3]thiazol-6-yl)phenyl)-2-pyridin-3-ylacetamide, N-(3-(5-(2-((4-morpholin-4-ylphenyl)amino)pyrimidin-4-yl)imidazo[2,1-b][1,3]thiazol-6-yl)phenyl)-2-pyridin-4-ylacetamide, N-(3-(5-(2-((4-morpholin-4-ylphenyl)amino)pyrimidin-4-yl)imidazo[2,1-b][1,3]thiazol-6-yl)phenyl)pyrazine-2-carboxamide, N-(3-(5-(2-((4-morpholin-4-ylphenyl)amino)pyrimidin-4-yl)imidazo[2,1-b][1,3]thiazol-6-yl)phenyl)pyrimidine-4-carboxamide, 5-methyl-N-(3-(5-(2-((4-morpholin-4-ylphenyl)amino)pyrimidin-4-yl)imidazo[2,1-b][1,3]thiazol-6-yl)phenyl)pyrazine-2-carboxamide, N-(3-(5-(2-((4-morpholin-4-ylphenyl)amino)pyrimidin-4-yl)imidazo[2,1-b][1,3]thiazol-6-yl)phenyl)-1H-indole-3-carboxamide, 5-methyl-N-(3-(5-(2-((4-morpholin-4-ylphenyl)amino)pyrimidin-4-yl)imidazo[2,1-b][1,3]thiazol-6-yl)phenyl)-1-phenyl-1H-pyrazole-4-carboxamide, N-(3-(5-(2-((4-morpholin-4-ylphenyl)amino)pyrimidin-4-yl)imidazo[2,1-b][1,3]thiazol-6-yl)phenyl)-4-oxo-4,5,6,7-tetrahydro-1-benzofuran-3-carboxamide, $N^3,N^3$-dimethyl-$N^1$-(3-(5-(2-((4-morpholin-4-ylphenyl)amino)pyrimidin-4-yl)imidazo[2,1-b][1,3]thiazol-6-yl)phenyl)-beta-alaninamide, N-(3-(5-(2-((4-morpholin-4-ylphenyl)amino)pyrimidin-4-yl)imidazo[2,1-b][1,3]thiazol-6-yl)phenyl)-2-pyrrolidin-1-ylacetamide, N-(3-(5-(2-((4-morpholin-4-ylphenyl)amino)pyrimidin-4-yl)imidazo[2,1-b][1,3]thiazol-6-yl)phenyl)-3-piperidin-1-ylpropanamide, 2-(4-methylpiperazin-1-yl)-N-(3-(5-(2-((4-morpholin-4-ylphenyl)amino)pyrimidin-4-yl)imidazo[2,1-b][1,3]thiazol-6-yl)phenyl)acetamide, 2-cyclopentyl-N-(3-(5-(2-((4-morpholin-4-ylphenyl)amino)pyrimidin-4-yl)imidazo[2,1-b][1,3]thiazol-6-yl)phenyl)acetamide, N-(4-(4-acetylpiperazin-1-yl)phenyl)-4-(6-(3-((5-phenyl-1,3,4-oxadiazol-2-yl)amino)phenyl)imidazo[2,1-b][1,3]thiazol-5-yl)pyrimidin-2-amine, N-(3-(5-(2-((4-(4-acetylpiperazin-1-yl)phenyl)amino)pyrimidin-4-yl)imidazo[2,1-b][1,3]thiazol-6-yl)phenyl)benzamide, N-(3-(5-(2-((4-(2-oxopyrrolidin-1-yl)phenyl)amino)pyrimidin-4-yl)imidazo[2,1-b][1,3]thiazol-6-yl)phenyl)benzamide, 2-cyclohexyl-N-(3-(5-(2-((4-morpholin-4-ylphenyl)amino)pyrimidin-4-yl)imidazo[2,1-b][1,3]thiazol-6-yl)phenyl)acetamide, 2-chlorobenzyl 3-(5-(2-((4-morpholin-4-ylphenyl)amino)pyrimidin-4-yl)imidazo[2,1-b][1,3]thiazol-6-yl)phenylcarbamate, N-(3-(5-(2-((4-morpholin-4-ylphenyl)amino)pyrimidin-4-yl)imidazo[2,1-b][1,3]thiazol-6-yl)phenyl)-1,3-benzoxazol-2-amine, 5-methyl-N-(3-(5-(2-((4-morpholin-4-ylphenyl)amino)pyrimidin-4-yl)imidazo[2,1-b][1,3]thiazol-6-yl)phenyl)-1,3-benzoxazol-2-amine, 6-chloro-N-(3-(5-(2-((4-morpholin-4-ylphenyl)amino)pyrimidin-4-yl)imidazo[2,1-b][1,3]thiazol-6-yl)phenyl)-1,3-benzoxazol-2-amine, N-(3-(5-(2-((4-morpholin-4-ylphenyl)amino)pyrimidin-4-yl)imidazo[2,1-b][1,3]thiazol-6-yl)phenyl)-1H-indazol-3-amine, N-(3-(5-(2-((4-((dimethylamino)sulfonyl)phenyl)amino)pyrimidin-4-yl)imidazo[2,1-b][1,3]thiazol-6-yl)phenyl)-2-phenylacetamide, N-(3-(5-(2-((3-(2-morpholin-4-ylethoxy)phenyl)amino)pyrimidin-4-yl)imidazo[2,1-b][1,3]thiazol-6-yl)phenyl)benzamide, N-(3-(5-(2-((3-(2-morpholin-4-ylethoxy)phenyl)amino)pyrimidin-4-yl)imidazo[2,1-b][1,3]thiazol-6-yl)phenyl)-2-phenylacetamide, 2-(2-methoxyphenyl)-N-(3-(5-(2-((4-morpholin-4-ylphenyl)amino)pyrimidin-4-yl)imidazo[2,1-b][1,3]thiazol-6-yl)phenyl)acetamide, N-(3-(5-(2-((4-morpholin-4-ylphenyl)amino)pyrimidin-4-yl)imidazo[2,1-b][1,3]thiazol-6-yl)phenyl)-2-(2-(trifluoromethyl)phenyl)acetamide, N-(3-(5-(2-((4-morpholin-4-ylphenyl)amino)pyrimidin-4-yl)imidazo[2,1-b][1,3]thiazol-6-yl)phenyl)-2-(2-(trifluoromethoxy)phenyl)acetamide, 2-(2-fluoro-3-(trifluoromethyl)phenyl)-N-(3-(5-(2-((4-morpholin-4-ylphenyl)amino)pyrimidin-4-yl)imidazo[2,1-b][1,3]thiazol-6-yl)phenyl)acetamide, 2-(2,6-difluorophenyl)-N-(3-(5-(2-((4-morpholin-4-ylphenyl)amino)pyrimidin-4-yl)imidazo[2,1-b][1,3]thiazol-6-yl)phenyl)acetamide, N-(3-(5-(2-((3-(3-(4-methylpiperazin-1-yl)propoxy)phenyl)amino)pyrimidin-4-yl)imidazo[2,1-b][1,3]thiazol-6-yl)phenyl)benzamide, N-(3-(5-(2-((3-(3-(4-methylpiperazin-1-yl)propoxy)phenyl)amino)pyrimidin-4-yl)imidazo[2,1-b][1,3]thiazol-6-yl)phenyl)-2-phenylacetamide, N-(3-(5-(2-((3-(3-morpholin-4-ylpropoxy)phenyl)amino)pyrimidin-4-yl)imidazo[2,1-b][1,3]thiazol-6-yl)phenyl)benzamide, N-(3-(5-(2-((3-(3-morpholin-4-ylpropoxy)phenyl)amino)pyrimidin-4-yl)imidazo[2,1-b][1,3]thiazol-6-yl)phenyl)-2-phenylacetamide, N-(3-(5-(2-((4-(4-(3-methoxypropyl)piperazin-1-yl)phenyl)amino)pyrimidin-4-yl)imidazo[2,1-b][1,3]thiazol-6-yl)phenyl)benzamide, 2,6-difluoro-N-(3-(5-(2-((4-(4-(3-methoxypropyl)piperazin-1-yl)phenyl)amino)pyrimidin-4-yl)imidazo[2,1-b][1,3]thiazol-6-yl)phenyl)benzamide, N-(2-morpholin-4-ylethyl)-3-((4-(6-(3-((phenylacetyl)amino)phenyl)imidazo[2,1-b][1,3]thiazol-5-yl)pyrimidin-2-yl)amino)benzamide, N-(2-methoxy-1-methylethyl)-3-((4-(6-(3-((phenylacetyl)amino)phenyl)imidazo[2,1-b][1,3]thiazol-5-yl)pyrimidin-2-yl)amino)benzamide, N-(2-ethoxyethyl)-3-((4-(6-(3-((phenylacetyl)amino)phenyl)imidazo[2,1-b][1,3]thiazol-5-yl)pyrimidin-2-yl)amino)benzamide, N-(2-isopropoxyethyl)-3-((4-(6-(3-((phenylacetyl)amino)phenyl)imidazo[2,1-b][1,3]thiazol-5-yl)pyrimidin-2-yl)amino)benzamide, 3-((4-(6-(3-((phenylacetyl)amino)phenyl)imidazo[2,1-b][1,3]thiazol-5-yl)pyrimidin-2-yl)amino)-N-(3-propoxypropyl)benzamide, N-(3-methoxypropyl)-3-((4-(6-(3-((phenylacetyl)amino)phenyl)imidazo[2,1-b][1,3]thiazol-5-yl)pyrimidin-2-yl)amino)benzamide, 3-((4-(6-(3-((phenylacetyl)amino)phenyl)imidazo[2,1-b][1,3]thiazol-5-yl)pyrimidin-2-yl)amino)-N-((2S)-tetrahydrofuran-2-ylmethyl)benzamide, N,N-bis(2-ethoxyethyl)-3-((4-(6-(3-((phenylacetyl)amino)phenyl)imidazo[2,1-b][1,3]thiazol-5-yl)pyrimidin-2-yl)amino)benzamide, N-(2-methoxyethyl)-N-methyl-3-((4-(6-(3-((phenylacetyl)amino)phenyl)imidazo[2,1-b][1,3]thiazol-5-yl)pyrimidin-2-yl)amino)benzamide, N-ethyl-N-(2-methoxyethyl)-3-((4-(6-(3-((phenylacetyl)amino)phenyl)imidazo[2,1-b][1,3]thiazol-5-yl)pyrimidin-2-yl)amino)benzamide, N,N-bis(2-methoxyethyl)-3-((4-(6-(3-((phenylacetyl)amino)phenyl)imidazo[2,1-b][1,3]thiazol-5-yl)pyrimidin-2-yl)amino)benzamide, N-(3-(5-(2-((3-(morpholin-4-ylcarbonyl)phenyl)amino)pyrimidin-4-yl)imidazo[2,1-b][1,3]thiazol-6-yl)phenyl)-2-phenylacetamide, 2-phenyl-N-(3-(5-(2-((3-(thiomorpholin-4-ylcarbonyl)phenyl)amino)pyrimidin-4-yl)imidazo[2,1-b][1,3]thiazol-6-yl)phenyl)acetamide, N-(2-(dimethylamino)ethyl)-3-((4-(6-(3-((phenylacetyl)amino)phenyl)imidazo[2,1-b][1,3]thiazol-5-yl)pyrimidin-2-yl)amino)benzamide, 3-((4-(6-(3-((phenylacetyl)amino)phenyl)imidazo[2,1-b][1,3]thiazol-5-yl)pyrimidin-2-yl)amino)-N-(2-pyrrolidin-1-ylethyl)benzamide, 3-((4-(6-(3-((phenylacetyl)amino)phenyl)imidazo[2,1-b][1,3]thiazol-5-yl)pyrimidin-2-yl)amino)-N-(2-piperidin-1-ylethyl)benzamide, N-(3-morpholin-4-ylpropyl)-3-((4-(6-(3-((phenylacetyl)amino)phenyl)imidazo[2,1-b][1,3]thiazol-5-yl)pyrimidin-2-yl)amino)benzamide, N-(2-(4-methylpiperazin-1-yl)ethyl)-3-((4-(6-(3-((phenylacetyl)amino)phenyl)imidazo[2,1-b][1,3]thiazol-5-yl)pyrimidin-2-yl)amino)benzamide, N-methyl-3-((4-(6-(3-((phenylacetyl)amino)phenyl)imidazo[2,1-b][1,3]thiazol-5-yl)pyrimidin-2-yl)amino)-N-(tetrahydrofuran-2-ylmethyl)benzamide, N-(3-(dimethylamino)propyl)-N-methyl-3-((4-(6-(3-((phenylacetyl)amino)phenyl)imidazo[2,1-b][1,3]thiazol-5-yl)pyrimidin-2-yl)amino)benzamide, N-(2-(dimethylamino)ethyl)-N-ethyl-3-((4-(6-(3-((phenylacetyl)amino)phenyl)imidazo[2,1-b][1,3]thiazol-5-yl)pyrimidin-2-yl)amino)benzamide, N-methyl-3-((4-(6-(3-((phenylacetyl)amino)phenyl)imidazo[2,1-b][1,3]thiazol-5-yl)pyrimidin-2-yl)amino)-N-(2-pyridin-2-ylethyl)benzamide, N-(3-(5-(2-((3-((2,6-dimethylmorpholin-4-yl)carbonyl)phenyl)amino)pyrimidin-4-yl)imidazo[2,1-b][1,3]thiazol-6-yl)phenyl)-2-phenylacetamide, N-(3-(5-(2-((3-((4-methylpiperazin-1-yl)carbonyl)phenyl)amino)pyrimidin-4-yl)imidazo[2,1-b][1,3]thiazol-6-yl)phenyl)-2-phenylacetamide, N-(3-(5-(2-((3-((4-ethylpiperazin-1-yl)carbonyl)phenyl)amino)pyrimidin-4-yl)imidazo[2,1-b][1,3]thiazol-6-yl)phenyl)-2-phenylacetamide, N-(3-(5-(2-((3-((4-(2-hydroxyethyl)piperazin-1-yl)carbonyl)phenyl)amino)pyrimidin-4-yl)imidazo[2,1-b][1,3]thiazol-6-yl)phenyl)-2-phenylacetamide, N-(3-(5-(2-((3-((4-(2-(2-hydroxyethoxy)ethyl)piperazin-1-yl)carbonyl)phenyl)amino)pyrimidin-4-yl)imidazo[2,1-b][1,3]thiazol-6-yl)phenyl)-2-phenylacetamide, N-(4-hydroxybutyl)-3-((4-(6-(3-((phenylacetyl)amino)phenyl)imidazo[2,1-b][1,3]thiazol-5-yl)pyrimidin-2-yl)amino)benzamide, N-(4-(dimethylamino)butyl)-3-((4-(6-(3-((phenylacetyl)amino)phenyl)imidazo[2,1-b][1,3]thiazol-5-yl)pyrimidin-2-yl)amino)benzamide, N-(3-(1H-imidazol-1-yl)propyl)-3-((4-(6-(3-((phenylacetyl)amino)phenyl)imidazo[2,1-b][1,3]thiazol-5-yl)pyrimidin-2-yl)amino)benzamide, 2-fluoro-N-(3-(5-(2-((4-morpholin-4-ylphenyl)amino)pyrimidin-4-yl)imidazo[2,1-b][1,3]thiazol-6-yl)phenyl)benzamide, 2-methyl-N-(3-(5-(2-((4-morpholin-4-ylphenyl)amino)pyrimidin-4-yl)imidazo[2,1-b][1,3]thiazol-6-yl)phenyl)benzamide, 4-(6-(3-((5-(4-methoxyphenyl)-1,3-oxazol-2-yl)amino)phenyl)imidazo[2,1-b][1,3]thiazol-5-yl)-N-(4-morpholin-4-ylphenyl)pyrimidin-2-amine, N-(4-morpholin-4-ylphenyl)-4-(6-(3-((5-phenyl-1,3-oxazol-2-yl)amino)phenyl)imidazo[2,1-b][1,3]thiazol-5-yl)pyrimidin-2-amine, N-(3-(2-bromo-5-(2-((3-morpholin-4-ylphenyl)amino)pyrimidin-4-yl)imidazo[2,1-b][1,3]thiazol-6-yl)phenyl)benzamide, N-(3-(2-bromo-5-(2-((3-morpholin-4-ylphenyl)amino)pyrimidin-4-yl)imidazo[2,1-b][1,3]thiazol-6-yl)phenyl)-2-phenylacetamide, 2-methoxy-N-(3-(5-(2-((4-morpholin-4-ylphenyl)amino)pyrimidin-4-yl)imidazo[2,1-b][1,3]thiazol-6-yl)phenyl)benzamide, 2-chloro-N-(3-(5-(2-((4-morpholin-4-ylphenyl)amino)pyrimidin-4-yl)imidazo[2,1-b][1,3]thiazol-6-yl)phenyl)benzamide, 2,6-dimethoxy-N-(3-(5-(2-((4-morpholin-4-ylphenyl)amino)pyrimidin-4-yl)imidazo[2,1-b][1,3]thiazol-6-yl)phenyl)benzamide, 2-chloro-6-fluoro-N-(3-(5-(2-((4-morpholin-4-ylphenyl)amino)pyrimidin-4-yl)imidazo[2,1-b][1,3]thiazol-6-yl)phenyl)benzamide, 2,6-dichloro-N-(3-(5-(2-((4-morpholin-4-ylphenyl)amino)pyrimidin-4-yl)imidazo[2,1-b][1,3]thiazol-6-yl)phenyl)benzamide, N-(3-(5-(2-((4-morpholin-4-ylphenyl)amino)pyrimidin-4-yl)imidazo[2,1-b][1,3]thiazol-6-yl)phenyl)-2-nitrobenzamide, N-(3-(5-(2-((4-morpholin-4-ylphenyl)amino)pyrimidin-4-yl)imidazo[2,1-b][1,3]thiazol-6-yl)phenyl)-2-(trifluoromethyl)benzamide, 2,5-dichloro-N-(3-(5-(2-((4-morpholin-4-ylphenyl)amino)pyrimidin-4-yl)imidazo[2,1-b][1,3]thiazol-6-yl)phenyl)thiophene-3-carboxamide, N-(3-(5-(2-((4-(4-ethylpiperazin-1-yl)phenyl)amino)pyrimidin-4-yl)imidazo[2,1-b][1,3]thiazol-6-yl)phenyl)-2-phenylacetamide, 2-(2-chlorophenyl)-N-(3-(5-(2-((4-(4-ethylpiperazin-1-yl)phenyl)amino)pyrimidin-4-yl)imidazo[2,1-b][1,3]thiazol-6-yl)phenyl)acetamide, N-(3-(5-(2-((4-(4-ethylpiperazin-1-yl)phenyl)amino)pyrimidin-4-yl)imidazo[2,1-b][1,3]thiazol-6-yl)phenyl)-2-(2-methylphenyl)acetamide, N-(3-(5-(2-((4-(4-ethylpiperazin-1-yl)phenyl)amino)pyrimidin-4-yl)imidazo[2,1-b][1,3]thiazol-6-yl)phenyl)-2-(2-(trifluoromethyl)phenyl)acetamide, N-(3-(5-(2-((4-(4-ethylpiperazin-1-yl)phenyl)amino)pyrimidin-4-yl)imidazo[2,1-b][1,3]thiazol-6-yl)phenyl)benzamide, N-(3-(5-(2-((4-(4-ethylpiperazin-1-yl)phenyl)amino)pyrimidin-4-yl)imidazo[2,1-b][1,3]thiazol-6-yl)phenyl)-2,6-difluorobenzamide, 2-chloro-N-(3-(5-(2-((4-(4-ethylpiperazin-1-yl)phenyl)amino)pyrimidin-4-yl)imidazo[2,1-b][1,3]thiazol-6-yl)phenyl)-6-fluorobenzamide, 2-chloro-N-(3-(5-(2-((4-(4-ethylpiperazin-1-yl)phenyl)amino)pyrimidin-4-yl)imidazo[2,1-b][1,3]thiazol-6-yl)phenyl)benzamide, 2,6-dichloro-N-(3-(5-(2-((4-(4-ethylpiperazin-1-yl)phenyl)amino)pyrimidin-4-yl)imidazo[2,1-b][1,3]thiazol-6-yl)phenyl)benzamide, N-(4-(4-ethylpiperazin-1-yl)phenyl)-4-(6-(3-((5-phenyl-1,3,4-oxadiazol-2-yl)amino)phenyl)imidazo[2,1-b][1,3]thiazol-5-yl)pyrimidin-2-amine, N-(4-(4-ethylpiperazin-1-yl)phenyl)-4-(6-(3-((5-phenyl-1,3-oxazol-2-yl)amino)phenyl)imidazo[2,1-b][1,3]thiazol-5-yl)pyrimidin-2-amine, N-(3-(2-bromo-5-(2-((4-morpholin-4-ylphenyl)amino)pyrimidin-4-yl)imidazo[2,1-b][1,3]thiazol-6-yl)phenyl)benzamide, N-(3-(2-bromo-5-(2-((4-morpholin-4-ylphenyl)amino)pyrimidin-4-yl)imidazo[2,1-b][1,3]thiazol-6-yl)phenyl)-2-phenylacetamide, 2-phenyl-N-(3-(5-(2-((3-(3-pyrrolidin-1-ylpropoxy)phenyl)amino)pyrimidin-4-yl)imidazo[2,1-b][1,3]thiazol-6-yl)phenyl)acetamide, (2R)-2-methoxy-N-(3-(5-(2-((4-morpholin-4-ylphenyl)amino)pyrimidin-4-yl)imidazo[2,1-b][1,3]thiazol-6-yl)phenyl)-2-phenylacetamide, N-(3-(5-(2-((3-(morpholin-4-ylsulfonyl)phenyl)amino)pyrimidin-4-yl)imidazo[2,1-b][1,3]thiazol-6-yl)phenyl)-2-phenylacetamide, N-(3-(5-(2-((4-morpholin-4-ylphenyl)amino)pyrimidin-4-yl)imidazo[2,1-b][1,3]thiazol-6-yl)phenyl)-1-phenylcyclopropanecarboxamide, 2-methyl-N-(3-(5-(2-((4-morpholin-4-ylphenyl)amino)pyrimidin-4-yl)imidazo[2,1-b][1,3]thiazol-6-yl)phenyl)-2-phenylpropanamide, N-(2-morpholin-4-ylethyl)-4-((4-(6-(3-((phenylacetyl)amino)phenyl)imidazo[2,1-b][1,3]thiazol-5-yl)pyrimidin-2-yl)amino)benzamide, 3-cyanobenzyl 3-(5-(2-((4-morpholin-4-ylphenyl)amino)pyrimidin-4-yl)imidazo[2,1-b][1,3]thiazol-6-yl)phenylcarbamate,
3-methylbenzyl 3-(5-(2-((4-morpholin-4-ylphenyl)amino)pyrimidin-4-yl)imidazo[2,1-b][1,3]thiazol-6-yl)phenylcarbamate,
3-chlorobenzyl 3-(5-(2-((4-morpholin-4-ylphenyl)amino)pyrimidin-4-yl)imidazo[2,1-b][1,3]thiazol-6-yl)phenylcarbamate,
3-methoxybenzyl 3-(5-(2-((4-morpholin-4-ylphenyl)amino)pyrimidin-4-yl)imidazo[2,1-b][1,3]thiazol-6-yl)phenylcarbamate,
3-fluorobenzyl 3-(5-(2-((4-morpholin-4-ylphenyl)amino)pyrimidin-4-yl)imidazo[2,1-b][1,3]thiazol-6-yl)phenylcarbamate,
4-fluorobenzyl 3-(5-(2-((4-morpholin-4-ylphenyl)amino)pyrimidin-4-yl)imidazo[2,1-b][1,3]thiazol-6-yl)phenylcarbamate,
4-methylbenzyl 3-(5-(2-((4-morpholin-4-ylphenyl)amino)pyrimidin-4-yl)imidazo[2,1-b][1,3]thiazol-6-yl)phenylcarbamate,
3,5-difluorobenzyl 3-(5-(2-((4-morpholin-4-ylphenyl)amino)pyrimidin-4-yl)imidazo[2,1-b][1,3]thiazol-6-yl)phenylcarbamate,
3-(benzyloxy)benzyl 3-(5-(2-((4-morpholin-4-ylphenyl)amino)pyrimidin-4-yl)imidazo[2,1-b][1,3]thiazol-6-yl)phenylcarbamate,
1,3-benzodioxol-5-ylmethyl 3-(5-(2-((4-morpholin-4-ylphenyl)amino)pyrimidin-4-yl)imidazo[2,1-b][1,3]thiazol-6-yl)phenylcarbamate,
N-(3-(5-(2-((3-((dimethylamino)sulfonyl)phenyl)amino)pyrimidin-4-yl)imidazo[2,1-b][1,3]thiazol-6-yl)phenyl)-2-phenylacetamide,
N-(3-(5-(2-((3-morpholin-4-ylphenyl)amino)pyrimidin-4-yl)imidazo[2,1-b][1,3]thiazol-6-yl)phenyl)-N'-phenylurea,
N-(2-methylphenyl)-N'-(3-(5-(2-((3-morpholin-4-ylphenyl)amino)pyrimidin-4-yl)imidazo[2,1-b][1,3]thiazol-6-yl)phenyl)urea,
N-(2-fluorophenyl)-N'-(3-(5-(2-((3-morpholin-4-ylphenyl)amino)pyrimidin-4-yl)imidazo[2,1-b][1,3]thiazol-6-yl)phenyl)urea,
N-(3-(5-(2-((4-(4-ethylpiperazin-1-yl)phenyl)amino)pyrimidin-4-yl)imidazo[2,1-b][1,3]thiazol-6-yl)phenyl)-1-phenylcyclopropanecarboxamide,
N-(3-(5-(2-((3-(3-morpholin-4-ylpropoxy)phenyl)amino)pyrimidin-4-yl)imidazo[2,1-b][1,3]thiazol-6-yl)phenyl)-N'-phenylurea,
N-(2-methylphenyl)-N'-(3-(5-(2-((3-(3-morpholin-4-ylpropoxy)phenyl)amino)pyrimidin-4-yl)imidazo[2,1-b][1,3]thiazol-6-yl)phenyl)urea,
N-(2-fluorophenyl)-N'-(3-(5-(2-((3-(3-morpholin-4-ylpropoxy)phenyl)amino)pyrimidin-4-yl)imidazo[2,1-b][1,3]thiazol-6-yl)phenyl)urea,
N-(3-(5-(2-((3-(3-(4-methylpiperazin-1-yl)propoxy)phenyl)amino)pyrimidin-4-yl)imidazo[2,1-b][1,3]thiazol-6-yl)phenyl)-N'-phenylurea,
N-(2-methylphenyl)-N'-(3-(5-(2-((3-(3-(4-methylpiperazin-1-yl)propoxy)phenyl)amino)pyrimidin-4-yl)imidazo[2,1-b][1,3]thiazol-6-yl)phenyl)urea,
N-(2-fluorophenyl)-N'-(3-(5-(2-((3-(3-(4-methylpiperazin-1-yl)propoxy)phenyl)amino)pyrimidin-4-yl)imidazo[2,1-b][1,3]thiazol-6-yl)phenyl)urea,
N-(3-(5-(2-((3-(aminosulfonyl)phenyl)amino)pyrimidin-4-yl)imidazo[2,1-b][1,3]thiazol-6-yl)phenyl)-2-phenylacetamide,
N-(3-(5-(2-((4-(aminosulfonyl)phenyl)amino)pyrimidin-4-yl)imidazo[2,1-b][1,3]thiazol-6-yl)phenyl)-2-phenylacetamide,
N-(3-(5-(2-((3-(((2-morpholin-4-ylethyl)amino)sulfonyl)phenyl)amino)pyrimidin-4-yl)imidazo[2,1-b][1,3]thiazol-6-yl)phenyl)-2-phenylacetamide, trans-2-phenyl-N-(3-(5-(2-((4-piperidin-1-ylphenyl)amino)pyrimidin-4-yl)imidazo[2,1-b][1,3]thiazol-6-yl)phenyl)cyclopropanecarboxamide,
3-phenyl-N-(3-(5-(2-((4-piperidin-1-ylphenyl)amino)pyrimidin-4-yl)imidazo[2,1-b][1,3]thiazol-6-yl)phenyl)propanamide,
2-phenyl-N-(3-(5-(2-((4-piperidin-1-ylphenyl)amino)pyrimidin-4-yl)imidazo[2,1-b][1,3]thiazol-6-yl)phenyl)acetamide,
N-(3-(5-(2-((4-piperidin-1-ylphenyl)amino)pyrimidin-4-yl)imidazo[2,1-b][1,3]thiazol-6-yl)phenyl)benzamide,
N-(3-(5-(2-((4-(4-(2-hydroxyethyl)piperazin-1-yl)phenyl)amino)pyrimidin-4-yl)imidazo[2,1-b][1,3]thiazol-6-yl)phenyl)-2-phenylacetamide,
N-(3-(5-(2-((4-(4-(2-hydroxyethyl)piperazin-1-yl)phenyl)amino)pyrimidin-4-yl)imidazo[2,1-b][1,3]thiazol-6-yl)phenyl)benzamide, trans-2-phenyl-N-(3-(5-(2-((4-pyrrolidin-1-ylphenyl)amino)pyrimidin-4-yl)imidazo[2,1-b][1,3]thiazol-6-yl)phenyl)cyclopropanecarboxamide,
N-(3-(5-(2-((4-(4-(2-hydroxyethyl)piperazin-1-yl)phenyl)amino)pyrimidin-4-yl)imidazo[2,1-b][1,3]thiazol-6-yl)phenyl)-3-phenylpropanamide,
3-phenyl-N-(3-(5-(2-((4-pyrrolidin-1-ylphenyl)amino)pyrimidin-4-yl)imidazo[2,1-b][1,3]thiazol-6-yl)phenyl)propanamide, trans-N-(3-(5-(2-((4-(4-(2-hydroxyethyl)piperazin-1-yl)phenyl)amino)pyrimidin-4-yl)imidazo[2,1-b][1,3]thiazol-6-yl)phenyl)-2-phenylcyclopropanecarboxamide,
N-(3-(5-(2-((4-(4-isopropylpiperazin-1-yl)phenyl)amino)pyrimidin-4-yl)imidazo[2,1-b][1,3]thiazol-6-yl)phenyl)-2-phenylacetamide,
2-phenyl-N-(3-(5-(2-((4-pyrrolidin-1-ylphenyl)amino)pyrimidin-4-yl)imidazo[2,1-b][1,3]thiazol-6-yl)phenyl)acetamide,
N-(3-(5-(2-((4-(4-isopropylpiperazin-1-yl)phenyl)amino)pyrimidin-4-yl)imidazo[2,1-b][1,3]thiazol-6-yl)phenyl)benzamide,
N-(3-(5-(2-((4-(4-isopropylpiperazin-1-yl)phenyl)amino)pyrimidin-4-yl)imidazo[2,1-b][1,3]thiazol-6-yl)phenyl)-3-phenylpropanamide,
N-(3-(5-(2-((4-pyrrolidin-1-ylphenyl)amino)pyrimidin-4-yl)imidazo[2,1-b][1,3]thiazol-6-yl)phenyl)benzamide,
trans-N-(3-(5-(2-((4-(4-isopropylpiperazin-1-yl)phenyl)amino)pyrimidin-4-yl)imidazo[2,1-b][1,3]thiazol-6-yl)phenyl)-2-phenylcyclopropanecarboxamide,
2-(2-chlorophenyl)-N-(3-(5-(2-((4-(4-isopropylpiperazin-1-yl)phenyl)amino)pyrimidin-4-yl)imidazo[2,1-b][1,3]thiazol-6-yl)phenyl)acetamide,
2-chloro-N-(3-(5-(2-((4-(4-isopropylpiperazin-1-yl)phenyl)amino)pyrimidin-4-yl)imidazo[2,1-b][1,3]thiazol-6-yl)phenyl)benzamide,
N-(3-(5-(2-((3-(acetylamino)phenyl)amino)pyrimidin-4-yl)imidazo[2,1-b][1,3]thiazol-6-yl)phenyl)-2,6-difluorobenzamide,
N-(3-(5-(2-((4-(4-(3-methoxypropyl)piperazin-1-yl)phenyl)amino)pyrimidin-4-yl)imidazo[2,1-b][1,3]thiazol-6-yl)phenyl)-N'-phenylurea,
N-(2-chlorophenyl)-N'-(3-(5-(2-((4-(4-(3-methoxypropyl)piperazin-1-yl)phenyl)amino)pyrimidin-4-yl)imidazo[2,1-b][1,3]thiazol-6-yl)phenyl)urea, N-(3-((4-(6-(3-((anilinocarbonyl)amino)phenyl)imidazo[2,1-b][1,3]thiazol-5-yl)pyrimidin-2-yl)amino)phenyl)acetamide, N-(3-((4-(6-(3-((((2-chlorophenyl)amino)carbonyl)amino)phenyl)imidazo[2,1-b][1,3]thiazol-5-yl)pyrimidin-2-yl)amino)phenyl)acetamide, N-(3-(5-(2-((3-(acetylamino)phenyl)amino)pyrimidin-4-yl)imidazo[2,1-b][1,3]thiazol-6-yl)phenyl)-2-(2-chlorophenyl)acetamide, 2-(2-chlorophenyl)-N-(3-(5-(2-((4-(4-(3-methoxypropyl)piperazin-1-yl)phenyl)amino)pyrimidin-4-yl)imidazo[2,1-b][1,3]thiazol-6-yl)phenyl)acetamide, N-(3-(5-(2-((4-(4-acetylpiperazin-1-yl)phenyl)amino)pyrimidin-4-yl)imidazo[2,1-b][1,3]thiazol-6-yl)phenyl)-2-(2-chlorophenyl)acetamide, N-(3-(5-(2-((4-(4-acetylpiperazin-1-yl)phenyl)amino)pyrimidin-4-yl)imidazo[2,1-b][1,3]thiazol-6-yl)phenyl)-2,6-difluorobenzamide, N-(3-(5-(2-((4-(4-acetylpiperazin-1-yl)phenyl)amino)pyrimidin-4-yl)imidazo[2,1-b][1,3]thiazol-6-yl)phenyl)-2-chlorobenzamide, N-(3-(5-(2-((4-(4-acetylpiperazin-1-yl)phenyl)amino)pyrimidin-4-yl)imidazo[2,1-b][1,3]thiazol-6-yl)phenyl)-N'-phenylurea, N-(3-(5-(2-((4-(4-acetylpiperazin-1-yl)phenyl)amino)pyrimidin-4-yl)imidazo[2,1-b][1,3]thiazol-6-yl)phenyl)-N'-(2-chlorophenyl)urea, 2,6-difluoro-N-(3-(5-(2-((4-(4-isopropylpiperazin-1-yl)phenyl)amino)pyrimidin-4-yl)imidazo[2,1-b][1,3]thiazol-6-yl)phenyl)benzamide, N-(3-(5-(2-((4-(4-isopropylpiperazin-1-yl)phenyl)amino)pyrimidin-4-yl)imidazo[2,1-b][1,3]thiazol-6-yl)phenyl)-N'-phenylurea, N-(2-chlorophenyl)-N'-(3-(5-(2-((4-(4-isopropylpiperazin-1-yl)phenyl)amino)pyrimidin-4-yl)imidazo[2,1-b][1,3]thiazol-6-yl)phenyl)urea, 2-(5-acetylthien-3-yl)-N-(3-(5-(2-((4-morpholin-4-ylphenyl)amino)pyrimidin-4-yl)imidazo[2,1-b][1,3]thiazol-6-yl)phenyl)acetamide, 2-methyl-N-(3-(5-(2-((3-(2-morpholin-4-ylethyl)phenyl)amino)pyrimidin-4-yl)imidazo[2,1-b][1,3]thiazol-6-yl)phenyl)benzamide, 2-fluoro-N-(3-(5-(2-((3-(2-morpholin-4-ylethyl)phenyl)amino)pyrimidin-4-yl)imidazo[2,1-b][1,3]thiazol-6-yl)phenyl)benzamide, 2,6-difluoro-N-(3-(5-(2-((3-(2-morpholin-4-ylethyl)phenyl)amino)pyrimidin-4-yl)imidazo[2,1-b][1,3]thiazol-6-yl)phenyl)benzamide, N-(3-(5-(2-((3-(2-morpholin-4-ylethyl)phenyl)amino)pyrimidin-4-yl)imidazo[2,1-b][1,3]thiazol-6-yl)phenyl)-N'-phenylurea, N-(3-(5-(2-((3-(2-morpholin-4-ylethyl)phenyl)amino)pyrimidin-4-yl)imidazo[2,1-b][1,3]thiazol-6-yl)phenyl)-2-phenylacetamide, N-(3-(5-(2-((3-(2-oxopyrrolidin-1-yl)phenyl)amino)pyrimidin-4-yl)imidazo[2,1-b][1,3]thiazol-6-yl)phenyl)-2-phenylacetamide, 2-(2-chlorophenyl)-N-(3-(5-(2-((3-(2-oxopyrrolidin-1-yl)phenyl)amino)pyrimidin-4-yl)imidazo[2,1-b][1,3]thiazol-6-yl)phenyl)acetamide, N-(3-(5-(2-((3-(2-oxopyrrolidin-1-yl)phenyl)amino)pyrimidin-4-yl)imidazo[2,1-b][1,3]thiazol-6-yl)phenyl)benzamide, 2-chloro-N-(3-(5-(2-((3-(2-oxopyrrolidin-1-yl)phenyl)amino)pyrimidin-4-yl)imidazo[2,1-b][1,3]thiazol-6-yl)phenyl)benzamide, 2,6-difluoro-N-(3-(5-(2-((3-(2-oxopyrrolidin-1-yl)phenyl)amino)pyrimidin-4-yl)imidazo[2,1-b][1,3]thiazol-6-yl)phenyl)benzamide, 2-(2-chlorophenyl)-N-(3-(5-(2-((3-morpholin-4-ylphenyl)amino)pyrimidin-4-yl)imidazo[2,1-b][1,3]thiazol-6-yl)phenyl)acetamide, N-(3-(5-(2-((3-morpholin-4-ylphenyl)amino)pyrimidin-4-yl)imidazo[2,1-b][1,3]thiazol-6-yl)phenyl)benzamide, 2,6-difluoro-N-(3-(5-(2-((3-morpholin-4-ylphenyl)amino)pyrimidin-4-yl)imidazo[2,1-b][1,3]thiazol-6-yl)phenyl)benzamide, N-(2-chlorophenyl)-N'-(3-(5-(2-((3-morpholin-4-ylphenyl)amino)pyrimidin-4-yl)imidazo[2,1-b][1,3]thiazol-6-yl)phenyl)urea, N-(3-(5-(2-((3-(2-pyrrolidin-1-ylethoxy)phenyl)amino)pyrimidin-4-yl)imidazo[2,1-b][1,3]thiazol-6-yl)phenyl)benzamide, 2-phenyl-N-(3-(5-(2-((3-(2-pyrrolidin-1-ylethoxy)phenyl)amino)pyrimidin-4-yl)imidazo[2,1-b][1,3]thiazol-6-yl)phenyl)acetamide, 2,6-difluoro-N-(3-(5-(2-((3-(3-morpholin-4-ylpropoxy)phenyl)amino)pyrimidin-4-yl)imidazo[2,1-b][1,3]thiazol-6-yl)phenyl)benzamide, N-(2-chlorophenyl)-N'-(3-(5-(2-((3-(3-morpholin-4-ylpropoxy)phenyl)amino)pyrimidin-4-yl)imidazo[2,1-b][1,3]thiazol-6-yl)phenyl)urea, 2-(2-chlorophenyl)-N-(3-(5-(2-((3-(3-morpholin-4-ylpropoxy)phenyl)amino)pyrimidin-4-yl)imidazo[2,1-b][1,3]thiazol-6-yl)phenyl)acetamide, 3-((4-(6-(3-(benzoylamino)phenyl)imidazo[2,1-b][1,3]thiazol-5-yl)pyrimidin-2-yl)amino)-N-(2-(dimethylamino)ethyl)benzamide, N-(3-(5-(2-((3-(((2-(dimethylamino)ethyl)amino)carbonyl)phenyl)amino)pyrimidin-4-yl)imidazo[2,1-b][1,3]thiazol-6-yl)phenyl)-2,6-difluorobenzamide, 3-((4-(6-(3-((anilinocarbonyl)amino)phenyl)imidazo[2,1-b][1,3]thiazol-5-yl)pyrimidin-2-yl)amino)-N-(2-(dimethylamino)ethyl)benzamide, 3-((4-(6-(3-((((2-chlorophenyl)amino)carbonyl)amino)phenyl)imidazo[2,1-b][1,3]thiazol-5-yl)pyrimidin-2-yl)amino)-N-(2-(dimethylamino)ethyl)benzamide, N-(2-chloro-5-(5-(2-((3-morpholin-4-ylphenyl)amino)pyrimidin-4-yl)imidazo[2,1-b][1,3]thiazol-6-yl)phenyl)benzamide, N-(2-(dimethylamino)-5-(5-(2-((3-morpholin-4-ylphenyl)amino)pyrimidin-4-yl)imidazo[2,1-b][1,3]thiazol-6-yl)phenyl)benzamide, N-(2-chloro-5-(5-(2-((3-morpholin-4-ylphenyl)amino)pyrimidin-4-yl)imidazo[2,1-b][1,3]thiazol-6-yl)phenyl)-2-phenylacetamide, N-(2-(dimethylamino)-5-(5-(2-((3-morpholin-4-ylphenyl)amino)pyrimidin-4-yl)imidazo[2,1-b][1,3]thiazol-6-yl)phenyl)-2-phenylacetamide, N-(2-ethoxy-5-(5-(2-((3-morpholin-4-ylphenyl)amino)pyrimidin-4-yl)imidazo[2,1-b][1,3]thiazol-6-yl)phenyl)-2-phenylacetamide, N-(3-(5-(2-((4-(4-(3-hydroxypropyl)piperazin-1-yl)phenyl)amino)pyrimidin-4-yl)imidazo[2,1-b][1,3]thiazol-6-yl)phenyl)benzamide, N-(3-(5-(2-((4-(4-(3-hydroxypropyl)piperazin-1-yl)phenyl)amino)pyrimidin-4-yl)imidazo[2,1-b][1,3]thiazol-6-yl)phenyl)-2-phenylacetamide, 3-((4-(6-(3-(((2-chlorophenyl)acetyl)amino)phenyl)imidazo[2,1-b][1,3]thiazol-5-yl)pyrimidin-2-yl)amino)-N-(2-(dimethylamino)ethyl)benzamide, N-(2-ethoxy-5-(5-(2-((3-morpholin-4-ylphenyl)amino)pyrimidin-4-yl)imidazo[2,1-b][1,3]thiazol-6-yl)phenyl)benzamide, 2,6-difluoro-N-(3-(5-(2-((3-(3-(4-methylpiperazin-1-yl)propoxy)phenyl)amino)pyrimidin-4-yl)imidazo[2,1-b][1,3]thiazol-6-yl)phenyl)benzamide, N-(2-chlorophenyl)-N'-(3-(5-(2-((3-(3-(4-methylpiperazin-1-yl)propoxy)phenyl)amino)pyrimidin-4-yl)imidazo[2,1-b][1,3]thiazol-6-yl)phenyl)urea, 2-(2-chlorophenyl)-N-(3-(5-(2-((3-(3-(4-methylpiperazin-1-yl)propoxy)phenyl)amino)pyrimidin-4-yl)imidazo[2,1-b][1,3]thiazol-6-yl)phenyl)acetamide, N-(3-(5-(2-((3-(4-isopropylpiperazin-1-yl)phenyl)amino)pyrimidin-4-yl)imidazo[2,1-b][1,3]thiazol-6-yl)phenyl)-2-phenylacetamide, N-(3-(5-(2-((3-(4-isopropylpiperazin-1-yl)phenyl)amino)pyrimidin-4-yl)imidazo[2,1-b][1,3]thiazol-6-yl)phenyl)benzamide, 2-(2-chlorophenyl)-N-(3-(5-(2-((3-(4-isopropylpiperazin-1-yl)phenyl)amino)pyrimidin-4-yl)imidazo[2,1-b][1,3]thiazol-6-yl)phenyl)acetamide, 2-chloro-N-(3-(5-(2-((3-(4-isopropylpiperazin-1-yl)phenyl)amino)pyrimidin-4-yl)imidazo[2,1-b][1,3]thiazol-6-yl)phenyl)benzamide, 2,6-difluoro-N-(3-(5-(2-((3-(4-isopropylpiperazin-1-yl)phenyl)amino)pyrimidin-4-yl)imidazo[2,1-b][1,3]thiazol-6-yl)phenyl)benzamide, N-(3-(5-(2-((3-(4-ethylpiperazin-1-yl)phenyl)amino)pyrimidin-4-yl)imidazo[2,1-b][1,3]thiazol-6-yl)phenyl)-2-phenylacetamide, N-(3-(5-(2-((3-(4-ethylpiperazin-1-yl)phenyl)amino)pyrimidin-4-yl)imidazo[2,1-b][1,3]thiazol-6-yl)phenyl)benzamide, N-(3-(5-(2-((3-(4-ethylpiperazin-1-yl)phenyl)amino)pyrimidin-4-yl)imidazo[2,1-b][1,3]thiazol-6-yl)phenyl)-2,6-difluorobenzamide, 2-phenyl-N-(3-(5-(2-(pyridin-4-ylamino)pyrimidin-4-yl)imidazo[2,1-b][1,3]thiazol-6-yl)phenyl)acetamide, N-(3-(5-(2-((4-(4-ethyl-2-oxopiperazin-1-yl)phenyl)amino)pyrimidin-4-yl)imidazo[2,1-b][1,3]thiazol-6-yl)phenyl)-2-phenylacetamide, N-(3-(5-(2-((4-(4-ethyl-2-oxopiperazin-1-yl)phenyl)amino)pyrimidin-4-yl)imidazo[2,1-b][1,3]thiazol-6-yl)phenyl)benzamide, 2-chloro-N-(3-(5-(2-((4-(4-ethyl-2-oxopiperazin-1-yl)phenyl)amino)pyrimidin-4-yl)imidazo[2,1-b][1,3]thiazol-6-yl)phenyl)benzamide, N-(3-(5-(2-((4-(4-ethyl-2-oxopiperazin-1-yl)phenyl)amino)pyrimidin-4-yl)imidazo[2,1-b][1,3]thiazol-6-yl)phenyl)-2,6-difluorobenzamide, 2-chloro-N-(3-(5-(2-((4-(4-ethyl-2-oxopiperazin-1-yl)phenyl)amino)pyrimidin-4-yl)imidazo[2,1-b][1,3]thiazol-6-yl)phenyl)-4-fluorobenzamide, N-(3-(5-(2-((3-(4-ethyl-2-oxopiperazin-1-yl)phenyl)amino)pyrimidin-4-yl)imidazo[2,1-b][1,3]thiazol-6-yl)phenyl)-2-phenylacetamide, N-(3-(5-(2-((3-(4-ethyl-2-oxopiperazin-1-yl)phenyl)amino)pyrimidin-4-yl)imidazo[2,1-b][1,3]thiazol-6-yl)phenyl)benzamide, 2-chloro-N-(3-(5-(2-((3-(4-ethyl-2-oxopiperazin-1-yl)phenyl)amino)pyrimidin-4-yl)imidazo[2,1-b][1,3]thiazol-6-yl)phenyl)benzamide, N-(3-(5-(2-((3-(4-ethyl-2-oxopiperazin-1-yl)phenyl)amino)pyrimidin-4-yl)imidazo[2,1-b][1,3]thiazol-6-yl)phenyl)-2,6-difluorobenzamide, 2-chloro-N-(3-(5-(2-((3-(4-ethyl-2-oxopiperazin-1-yl)phenyl)amino)pyrimidin-4-yl)imidazo[2,1-b][1,3]thiazol-6-yl)phenyl)-4-fluorobenzamide, 2-chloro-4-fluoro-N-(3-(5-(2-((3-(2-oxopyrrolidin-1-yl)phenyl)amino)pyrimidin-4-yl)imidazo[2,1-b][1,3]thiazol-6-yl)phenyl)benzamide, N-(3-(5-(2-((3-methyl-1H-pyrazol-5-yl)amino)pyrimidin-4-yl)imidazo[2,1-b][1,3]thiazol-6-yl)phenyl)-2-phenylacetamide, N-(3-(5-(2-((3-methyl-1H-pyrazol-5-yl)amino)pyrimidin-4-yl)imidazo[2,1-b][1,3]thiazol-6-yl)phenyl)benzamide, N-(3-(2-methyl-5-(2-((3-morpholin-4-ylphenyl)amino)pyrimidin-4-yl)imidazo[2,1-b][1,3]thiazol-6-yl)phenyl)benzamide, N-(3-(2-methyl-5-(2-((3-morpholin-4-ylphenyl)amino)pyrimidin-4-yl)imidazo[2,1-b][1,3]thiazol-6-yl)phenyl)-2-phenylacetamide, N-(3-(2-methyl-5-(2-((4-morpholin-4-ylphenyl)amino)pyrimidin-4-yl)imidazo[2,1-b][1,3]thiazol-6-yl)phenyl)benzamide, 2-phenyl-N-(3-(5-(2-(1H-pyrazol-5-ylamino)pyrimidin-4-yl)imidazo[2,1-b][1,3]thiazol-6-yl)phenyl)acetamide, N-(3-(5-(2-((4-(methylsulfonyl)phenyl)amino)pyrimidin-4-yl)imidazo[2,1-b][1,3]thiazol-6-yl)phenyl)benzamide, 2,6-difluoro-N-(3-(5-(2-((4-(methylsulfonyl)phenyl)amino)pyrimidin-4-yl)imidazo[2,1-b][1,3]thiazol-6-yl)phenyl)benzamide, N-(3-(5-(2-((4-(methylsulfonyl)phenyl)amino)pyrimidin-4-yl)imidazo[2,1-b][1,3]thiazol-6-yl)phenyl)-2-phenylacetamide, N-(3-(5-(2-((3-tert-butyl-1H-pyrazol-5-yl)amino)pyrimidin-4-yl)imidazo[2,1-b][1,3]thiazol-6-yl)phenyl)-N'-phenylurea, N-(3-(5-(2-((3-tert-butyl-1H-pyrazol-5-yl)amino)pyrimidin-4-yl)imidazo[2,1-b][1,3]thiazol-6-yl)phenyl)-2-phenylacetamide, N-(3-(5-(2-((3-(((2-(methylsulfonyl)ethyl)amino)methyl)phenyl)amino)pyrimidin-4-yl)imidazo[2,1-b][1,3]thiazol-6-yl)phenyl)benzamide, 2,6-difluoro-N-(3-(5-(2-((3-(((2-(methylsulfonyl)ethyl)amino)methyl)phenyl)amino)pyrimidin-4-yl)imidazo[2,1-b][1,3]thiazol-6-yl)phenyl)benzamide, N-(3-(5-(2-((3-(((2-(methylsulfonyl)ethyl)amino)methyl)phenyl)amino)pyrimidin-4-yl)imidazo[2,1-b][1,3]thiazol-6-yl)phenyl)-2-phenylacetamide, N-(3-(5-(2-((3-tert-butyl-1H-pyrazol-5-yl)amino)pyrimidin-4-yl)imidazo[2,1-b][1,3]thiazol-6-yl)phenyl)benzamide, 2-phenyl-N-(3-(5-(2-((3-pyridin-3-yl-1H-pyrazol-5-yl)amino)pyrimidin-4-yl)imidazo[2,1-b][1,3]thiazol-6-yl)phenyl)acetamide, N-(3-(5-(2-((3-pyridin-3-yl-1H-pyrazol-5-yl)amino)pyrimidin-4-yl)imidazo[2,1-b][1,3]thiazol-6-yl)phenyl)benzamide, 4-(6-(3-(benzyloxy)phenyl)imidazo[2,1-b][1,3]thiazol-5-yl)-N-(4-morpholin-4-ylphenyl)pyrimidin-2-amine, 4-(6-(3-(benzylamino)phenyl)imidazo[2,1-b][1,3]thiazol-5-yl)-N-(3-(3-morpholin-4-ylpropoxy)phenyl)pyrimidin-2-amine, N-(4-morpholin-4-ylphenyl)-4-(6-(3-((thien-2-ylmethyl)amino)phenyl)imidazo[2,1-b][1,3]thiazol-5-yl)pyrimidin-2-amine, 4-(6-(3-((2-chlorobenzyl)amino)phenyl)imidazo[2,1-b][1,3]thiazol-5-yl)-N-(4-morpholin-4-ylphenyl)pyrimidin-2-amine, 4-(6-(3-((3-methylbenzyl)amino)phenyl)imidazo[2,1-b][1,3]thiazol-5-yl)-N-(4-morpholin-4-ylphenyl)pyrimidin-2-amine, 4-(6-(3-((4-methylbenzyl)amino)phenyl)imidazo[2,1-b][1,3]thiazol-5-yl)-N-(4-morpholin-4-ylphenyl)pyrimidin-2-amine, 4-(6-(3-((4-chlorobenzyl)amino)phenyl)imidazo[2,1-b][1,3]thiazol-5-yl)-N-(4-morpholin-4-ylphenyl)pyrimidin-2-amine, 4-(6-(3-((3-chlorobenzyl)amino)phenyl)imidazo[2,1-b][1,3]thiazol-5-yl)-N-(4-morpholin-4-ylphenyl)pyrimidin-2-amine, 4-(6-(3-((3-methoxybenzyl)amino)phenyl)imidazo[2,1-b][1,3]thiazol-5-yl)-N-(4-morpholin-4-ylphenyl)pyrimidin-2-amine, 2-(((3-(5-(2-((4-morpholin-4-ylphenyl)amino)pyrimidin-4-yl)imidazo[2,1-b][1,3]thiazol-6-yl)phenyl)amino)methyl)benzonitrile, N-(3-(5-(2-((4-morpholin-4-ylphenyl)amino)pyridin-4-yl)imidazo[2,1-b][1,3]thiazol-6-yl)phenyl)-2-phenylacetamide, N-(3-(5-(2-((4-morpholin-4-ylphenyl)amino)pyridin-4-yl)imidazo[2,1-b][1,3]thiazol-6-yl)phenyl)benzamide, N-(3-(4-isopropylpiperazin-1-yl)phenyl)-4-(6-(3-((5-phenyl-1,3,4-oxadiazol-2-yl)amino)phenyl)imidazo[2,1-b][1,3]thiazol-5-yl)pyrimidin-2-amine, N-(3-(5-(2-((1-benzoyl-3-tert-butyl-1H-pyrazol-5-yl)amino)pyrimidin-4-yl)imidazo[2,1-b][1,3]thiazol-6-yl)phenyl)benzamide, N-(3-morpholin-4-ylphenyl)-4-(6-(3-(3-phenoxyprop-1-ynyl)phenyl)imidazo[2,1-b][1,3]thiazol-5-yl)pyrimidin-2-amine, 4-(6-(3-(5-methyl-1,3,4-thiadiazol-2-yl)phenyl)imidazo[2,1-b][1,3]thiazol-5-yl)-N-(3-morpholin-4-ylphenyl)pyrimidin-2-amine, N-(3-morpholin-4-ylphenyl)-4-(6-(3-(1,3-thiazol-2-yl)phenyl)imidazo[2,1-b][1,3]thiazol-5-yl)pyrimidin-2-amine, 4-(6-(3-(1-methyl-1H-imidazol-2-yl)phenyl)imidazo[2,1-b][1,3]thiazol-5-yl)-N-(3-morpholin-4-ylphenyl)pyrimidin-2-amine, N-(2-chloro-3-(5-(2-((3-morpholin-4-ylphenyl)amino)pyrimidin-4-yl)imidazo[2,1-b][1,3]thiazol-6-yl)phenyl)-2,6-difluorobenzamide, N-(2-chloro-3-(5-(2-((3-morpholin-4-ylphenyl)amino)pyrimidin-4-yl)imidazo[2,1-b][1,3]thiazol-6-yl)phenyl)-2-fluorobenzamide, N-(2-chloro-3-(5-(2-((3-morpholin-4-ylphenyl)amino)pyrimidin-4-yl)imidazo[2,1-b][1,3]thiazol-6-yl)phenyl)-2-phenylacetamide, N-(2-(dimethylamino)-3-(5-(2-((3-morpholin-4-ylphenyl)amino)pyrimidin-4-yl)imidazo[2,1-b][1,3]thiazol-6-yl)phenyl)-2,6-difluorobenzamide, N-(2-(dimethylamino)-3-(5-(2-((3-morpholin-4-ylphenyl)amino)pyrimidin-4-yl)imidazo[2,1-b][1,3]thiazol-6-yl)phenyl)-2-phenylacetamide, 2,6-difluoro-N-(3-(5-(2-((3-((4-methylpiperazin-1-yl)methyl)phenyl)amino)pyrimidin-4-yl)imidazo[2,1-b][1,3]thiazol-6-yl)phenyl)benzamide, 2-fluoro-N-(3-(5-(2-((3-((4-methylpiperazin-1-yl)methyl)phenyl)amino)pyrimidin-4-yl)imidazo[2,1-b][1,3]thiazol-6-yl)phenyl)benzamide, N-(3-(5-(2-((3-((4-methylpiperazin-1-yl)methyl)phenyl)amino)pyrimidin-4-yl)imidazo[2,1-b][1,3]thiazol-6-yl)phenyl)-2-phenylacetamide, N-(3-(5-(2-((3-((dimethylamino)methyl)phenyl)amino)pyrimidin-4-yl)imidazo[2,1-b][1,3]thiazol-6-yl)phenyl)-2,6-difluorobenzamide, N-(3-(5-(2-((3-((dimethylamino)methyl)phenyl)amino)pyrimidin-4-yl)imidazo[2,1-b][1,3]thiazol-6-yl)phenyl)-2-fluorobenzamide, N-(3-(5-(2-((3-((dimethylamino)methyl)phenyl)amino)pyrimidin-4-yl)imidazo[2,1-b][1,3]thiazol-6-yl)phenyl)-2-phenylacetamide, 2-chloro-N-(3-(5-(2-((3-((dimethylamino)methyl)phenyl)amino)pyrimidin-4-yl)imidazo[2,1-b][1,3]thiazol-6-yl)phenyl)benzamide, N-(3-(5-(2-((3-((dimethylamino)methyl)phenyl)amino)pyrimidin-4-yl)imidazo[2,1-b][1,3]thiazol-6-yl)phenyl)-N'-phenylurea, 2,6-difluoro-N-(3-(5-(2-((3-(morpholin-4-ylmethyl)phenyl)amino)pyrimidin-4-yl)imidazo[2,1-b][1,3]thiazol-6-yl)phenyl)benzamide, 2-fluoro-N-(3-(5-(2-((3-(morpholin-4-ylmethyl)phenyl)amino)pyrimidin-4-yl)imidazo[2,1-b][1,3]thiazol-6-yl)phenyl)benzamide, N-(3-(5-(2-((3-(morpholin-4-ylmethyl)phenyl)amino)pyrimidin-4-yl)imidazo[2,1-b][1,3]thiazol-6-yl)phenyl)-2-phenylacetamide, 2-chloro-N-(3-(5-(2-((3-(morpholin-4-ylmethyl)phenyl)amino)pyrimidin-4-yl)imidazo[2,1-b][1,3]thiazol-6-yl)phenyl)benzamide, N-(3-(5-(2-((3-(morpholin-4-ylmethyl)phenyl)amino)pyrimidin-4-yl)imidazo[2,1-b][1,3]thiazol-6-yl)phenyl)-N'-phenylurea, methyl 4-((3-(5-(2-((3-morpholin-4-ylphenyl)amino)pyrimidin-4-yl)imidazo[2,1-b][1,3]thiazol-6-yl)phenyl)amino)-2-phenylbutanoate, 4-(6-(3-((5-methyl-1,3,4-thiadiazol-2-yl)amino)phenyl)imidazo[2,1-b][1,3]thiazol-5-yl)-N-(4-morpholin-4-ylphenyl)pyrimidin-2-amine, 4-(6-(3-((5-methyl-1,3,4-thiadiazol-2-yl)amino)phenyl)imidazo[2,1-b][1,3]thiazol-5-yl)-N-(3-morpholin-4-ylphenyl)pyrimidin-2-amine, 4-(6-(3-((5-methyl-1,3,4-thiadiazol-2-yl)amino)phenyl)imidazo[2,1-b][1,3]thiazol-5-yl)-N-(4-pyrrolidin-1-ylphenyl)pyrimidin-2-amine, 3-(5-(2-((3-morpholin-4-ylphenyl)amino)pyrimidin-4-yl)imidazo[2,1-b][1,3]thiazol-6-yl)benzaldehyde O-phenyloxime, 3-(5-(2-((3-morpholin-4-ylphenyl)amino)pyrimidin-4-yl)imidazo[2,1-b][1,3]thiazol-6-yl)benzaldehyde O-benzyloxime, 3-(5-(2-((3-morpholin-4-ylphenyl)amino)pyrimidin-4-yl)imidazo[2,1-b][1,3]thiazol-6-yl)benzaldehyde O-ethyloxime, N'-(benzoyloxy)-3-(5-(2-((3-morpholin-4-ylphenyl)amino)pyrimidin-4-yl)imidazo[2,1-b][1,3]thiazol-6-yl)benzenecarboximidamide, N-(3-(5-(2-((3-(methylsulfonyl)phenyl)amino)pyrimidin-4-yl)imidazo[2,1-b][1,3]thiazol-6-yl)phenyl)benzamide, 2,6-difluoro-N-(3-(5-(2-((3-(methylsulfonyl)phenyl)amino)pyrimidin-4-yl)imidazo[2,1-b][1,3]thiazol-6-yl)phenyl)benzamide, N-(3-(5-(2-((3-(methylsulfonyl)phenyl)amino)pyrimidin-4-yl)imidazo[2,1-b][1,3]thiazol-6-yl)phenyl)-2-phenylacetamide, N-(3-morpholin-4-ylphenyl)-4-(6-(3-(5-phenyl-1,2,4-oxadiazol-3-yl)phenyl)imidazo[2,1-b][1,3]thiazol-5-yl)pyrimidin-2-amine, N-(3-(5-(2-((3-(4-acetylpiperazin-1-yl)phenyl)amino)pyrimidin-4-yl)imidazo[2,1-b][1,3]thiazol-6-yl)phenyl)-2-phenylacetamide, N-(3-(5-(2-((3-(4-acetylpiperazin-1-yl)phenyl)amino)pyrimidin-4-yl)imidazo[2,1-b][1,3]thiazol-6-yl)phenyl)benzamide, N-(3-(5-(2-((3-(4-acetylpiperazin-1-yl)phenyl)amino)pyrimidin-4-yl)imidazo[2,1-b][1,3]thiazol-6-yl)phenyl)-2-chlorobenzamide, N-(3-(5-(2-((3-(4-acetylpiperazin-1-yl)phenyl)amino)pyrimidin-4-yl)imidazo[2,1-b][1,3]thiazol-6-yl)phenyl)-2,6-difluorobenzamide,
4-(6-(3-(5-isobutyl-1,2,4-oxadiazol-3-yl)phenyl)imidazo[2,1-b][1,3]thiazol-5-yl)-N-(3-morpholin-4-ylphenyl)pyrimidin-2-amine,
4-(6-(3-(5-ethyl-1,2,4-oxadiazol-3-yl)phenyl)imidazo[2,1-b][1,3]thiazol-5-yl)-N-(3-morpholin-4-ylphenyl)pyrimidin-2-amine,
(3R)-1-(3-(5-(2-((3-morpholin-4-ylphenyl)amino)pyrimidin-4-yl)imidazo[2,1-b][1,3]thiazol-6-yl)phenyl)-3-phenylpyrrolidin-2-one,
2,6-difluoro-N-(3-(5-(2-((3-((4-(2-hydroxyethyl)piperazin-1-yl)methyl)phenyl)amino)pyrimidin-4-yl)imidazo[2,1-b][1,3]thiazol-6-yl)phenyl)benzamide,
N-(3-(5-(2-((3-((4-(2-hydroxyethyl)piperazin-1-yl)methyl)phenyl)amino)pyrimidin-4-yl)imidazo[2,1-b][1,3]thiazol-6-yl)phenyl)-2-phenylacetamide,
2,6-difluoro-N-(3-(5-(2-((3-((4-(3-methoxypropyl)piperazin-1-yl)methyl)phenyl)amino)pyrimidin-4-yl)imidazo[2,1-b][1,3]thiazol-6-yl)phenyl)benzamide,
2-fluoro-N-(3-(5-(2-((3-((4-(3-methoxypropyl)piperazin-1-yl)methyl)phenyl)amino)pyrimidin-4-yl)imidazo[2,1-b][1,3]thiazol-6-yl)phenyl)benzamide,
2-chloro-N-(3-(5-(2-((3-((4-(3-methoxypropyl)piperazin-1-yl)methyl)phenyl)amino)pyrimidin-4-yl)imidazo[2,1-b][1,3]thiazol-6-yl)phenyl)benzamide,
N-(3-(5-(2-((3-((4-(3-methoxypropyl)piperazin-1-yl)methyl)phenyl)amino)pyrimidin-4-yl)imidazo[2,1-b][1,3]thiazol-6-yl)phenyl)-2-phenylacetamide,
N-(3-(5-(2-((3-((4-(3-methoxypropyl)piperazin-1-yl)methyl)phenyl)amino)pyrimidin-4-yl)imidazo[2,1-b][1,3]thiazol-6-yl)phenyl)-N'-phenylurea,
N-(3-(5-(2-(1H-indazol-5-ylamino)pyrimidin-4-yl)imidazo[2,1-b][1,3]thiazol-6-yl)phenyl)-2-phenylacetamide,
N-(3-(5-(2-(1H-indazol-5-ylamino)pyrimidin-4-yl)imidazo[2,1-b][1,3]thiazol-6-yl)phenyl)benzamide,
2,6-difluoro-N-(3-(5-(2-(1H-indazol-5-ylamino)pyrimidin-4-yl)imidazo[2,1-b][1,3]thiazol-6-yl)phenyl)benzamide,
2-chloro-6-fluoro-N-(3-(5-(2-(1H-indazol-5-ylamino)pyrimidin-4-yl)imidazo[2,1-b][1,3]thiazol-6-yl)phenyl)benzamide,
5-fluoro-N-(3-(5-(2-(1H-indazol-5-ylamino)pyrimidin-4-yl)imidazo[2,1-b][1,3]thiazol-6-yl)phenyl)-2-methylbenzamide,
2-phenyl-N-(3-(5-(2-((2-(trifluoromethyl)-1H-benzimidazol-5-yl)amino)pyrimidin-4-yl)imidazo[2,1-b][1,3]thiazol-6-yl)phenyl)acetamide,
N-(3-(5-(2-((2-(trifluoromethyl)-1H-benzimidazol-5-yl)amino)pyrimidin-4-yl)imidazo[2,1-b][1,3]thiazol-6-yl)phenyl)benzamide,
2,6-difluoro-N-(3-(5-(2-((2-(trifluoromethyl)-1H-benzimidazol-5-yl)amino)pyrimidin-4-yl)imidazo[2,1-b][1,3]thiazol-6-yl)phenyl)benzamide,
2-chloro-6-fluoro-N-(3-(5-(2-((2-(trifluoromethyl)-1H-benzimidazol-5-yl)amino)pyrimidin-4-yl)imidazo[2,1-b][1,3]thiazol-6-yl)phenyl)benzamide,
5-fluoro-2-methyl-N-(3-(5-(2-((2-(trifluoromethyl)-1H-benzimidazol-5-yl)amino)pyrimidin-4-yl)imidazo[2,1-b][1,3]thiazol-6-yl)phenyl)benzamide,
1-(3-(5-(2-((4-morpholin-4-ylphenyl)amino)pyrimidin-4-yl)imidazo[2,1-b][1,3]thiazol-6-yl)phenyl)-3-phenylpyrrolidin-2-one,
3-(5-(2-((3-morpholin-4-ylphenyl)amino)pyrimidin-4-yl)imidazo[2,1-b][1,3]thiazol-6-yl)-N'-(propionyloxy)benzenecarboximidamide,
N'-((3-methylbutanoyl)oxy)-3-(5-(2-((3-morpholin-4-ylphenyl)amino)pyrimidin-4-yl)imidazo[2,1-b][1,3]thiazol-6-yl)benzenecarboximidamide,
3-(5-(2-((3-morpholin-4-ylphenyl)amino)pyrimidin-4-yl)imidazo[2,1-b][1,3]thiazol-6-yl)-N'-((phenylacetyl)oxy)benzenecarboximidamide,
3-methoxy-N-(3-(5-(2-((4-morpholin-4-ylphenyl)amino)pyrimidin-4-yl)imidazo[2,1-b][1,3]thiazol-6-yl)phenyl)benzamide,
2-chloro-6-fluoro-N-(3-(5-(2-((2-pyridin-3-yl-1,3-benzoxazol-5-yl)amino)pyrimidin-4-yl)imidazo[2,1-b][1,3]thiazol-6-yl)phenyl)benzamide,
N-(3-(5-(2-((2-methyl-1,3-benzothiazol-5-yl)amino)pyrimidin-4-yl)imidazo[2,1-b][1,3]thiazol-6-yl)phenyl)-2-phenylacetamide,
N-(3-(5-(2-((2-methyl-1,3-benzothiazol-5-yl)amino)pyrimidin-4-yl)imidazo[2,1-b][1,3]thiazol-6-yl)phenyl)benzamide,
2,6-difluoro-N-(3-(5-(2-((2-methyl-1,3-benzothiazol-5-yl)amino)pyrimidin-4-yl)imidazo[2,1-b][1,3]thiazol-6-yl)phenyl)benzamide,
5-fluoro-2-methyl-N-(3-(5-(2-((2-methyl-1,3-benzothiazol-5-yl)amino)pyrimidin-4-yl)imidazo[2,1-b][1,3]thiazol-6-yl)phenyl)benzamide,
N-(3-(5-(2-((2-oxo-2,3-dihydro-1H-indol-5-yl)amino)pyrimidin-4-yl)imidazo[2,1-b][1,3]thiazol-6-yl)phenyl)benzamide,
2-chloro-6-fluoro-N-(3-(5-(2-((2-oxo-2,3-dihydro-1H-indol-5-yl)amino)pyrimidin-4-yl)imidazo[2,1-b][1,3]thiazol-6-yl)phenyl)benzamide,
N-(3-(5-(2-((3-(3-oxomorpholin-4-yl)phenyl)amino)pyrimidin-4-yl)imidazo[2,1-b][1,3]thiazol-6-yl)phenyl)-2-phenylacetamide,
N-(3-(5-(2-((3-(3-oxomorpholin-4-yl)phenyl)amino)pyrimidin-4-yl)imidazo[2,1-b][1,3]thiazol-6-yl)phenyl)benzamide,
2,6-difluoro-N-(3-(5-(2-((3-(3-oxomorpholin-4-yl)phenyl)amino)pyrimidin-4-yl)imidazo[2,1-b][1,3]thiazol-6-yl)phenyl)benzamide,
2-chloro-6-fluoro-N-(3-(5-(2-((3-(3-oxomorpholin-4-yl)phenyl)amino)pyrimidin-4-yl)imidazo[2,1-b][1,3]thiazol-6-yl)phenyl)benzamide,
2,6-dichloro-N-(3-(5-(2-((3-(3-oxomorpholin-4-yl)phenyl)amino)pyrimidin-4-yl)imidazo[2,1-b][1,3]thiazol-6-yl)phenyl)benzamide,
5-fluoro-2-methyl-N-(3-(5-(2-((3-(3-oxomorpholin-4-yl)phenyl)amino)pyrimidin-4-yl)imidazo[2,1-b][1,3]thiazol-6-yl)phenyl)benzamide,
2-fluoro-N-(3-(5-(2-((3-(3-oxomorpholin-4-yl)phenyl)amino)pyrimidin-4-yl)imidazo[2,1-b][1,3]thiazol-6-yl)phenyl)benzamide,
N-(3-(5-(2-((4-(3-oxomorpholin-4-yl)phenyl)amino)pyrimidin-4-yl)imidazo[2,1-b][1,3]thiazol-6-yl)phenyl)-2-phenylacetamide,
2,6-difluoro-N-(3-(5-(2-((4-(3-oxomorpholin-4-yl)phenyl)amino)pyrimidin-4-yl)imidazo[2,1-b][1,3]thiazol-6-yl)phenyl)benzamide,
2-chloro-6-fluoro-N-(3-(5-(2-((4-(3-oxomorpholin-4-yl)phenyl)amino)pyrimidin-4-yl)imidazo[2,1-b][1,3]thiazol-6-yl)phenyl)benzamide,
2,6-dichloro-N-(3-(5-(2-((4-(3-oxomorpholin-4-yl)phenyl)amino)pyrimidin-4-yl)imidazo[2,1-b][1,3]thiazol-6-yl)phenyl)benzamide,
5-fluoro-2-methyl-N-(3-(5-(2-((4-(3-oxomorpholin-4-yl)phenyl)amino)pyrimidin-4-yl)imidazo[2,1-b][1,3]thiazol-6-yl)phenyl)benzamide, 2-fluoro-N-(3-(5-(2-((4-(3-oxomorpholin-4-yl)phenyl)amino)pyrimidin-4-yl)imidazo[2,1-b][1,3]thiazol-6-yl)phenyl)benzamide,
N-(3-(5-(2-((3-fluoro-5-morpholin-4-ylphenyl)amino)pyrimidin-4-yl)imidazo[2,1-b][1,3]thiazol-6-yl)phenyl)-2-phenylacetamide,
2,6-difluoro-N-(3-(5-(2-((3-fluoro-5-morpholin-4-ylphenyl)amino)pyrimidin-4-yl)imidazo[2,1-b][1,3]thiazol-6-yl)phenyl)benzamide,
N-(3-(5-(2-((3-fluoro-5-morpholin-4-ylphenyl)amino)pyrimidin-4-yl)imidazo[2,1-b][1,3]thiazol-6-yl)phenyl)-N'-phenylurea,
2-chloro-N-(3-(5-(2-((3-fluoro-5-morpholin-4-ylphenyl)amino)pyrimidin-4-yl)imidazo[2,1-b][1,3]thiazol-6-yl)phenyl)benzamide,
N-(3-(5-(2-((3-fluoro-4-morpholin-4-ylphenyl)amino)pyrimidin-4-yl)imidazo[2,1-b][1,3]thiazol-6-yl)phenyl)-2-phenylacetamide,
2,6-difluoro-N-(3-(5-(2-((3-fluoro-4-morpholin-4-ylphenyl)amino)pyrimidin-4-yl)imidazo[2,1-b][1,3]thiazol-6-yl)phenyl)benzamide,
2-chloro-N-(3-(5-(2-((3-fluoro-4-morpholin-4-ylphenyl)amino)pyrimidin-4-yl)imidazo[2,1-b][1,3]thiazol-6-yl)phenyl)benzamide,
N-(3-(5-(2-((3-fluoro-4-morpholin-4-ylphenyl)amino)pyrimidin-4-yl)imidazo[2,1-b][1,3]thiazol-6-yl)phenyl)-N'-phenylurea,
N-(3-(5-(2-((3-fluoro-5-(2-oxopyrrolidin-1-yl)phenyl)amino)pyrimidin-4-yl)imidazo[2,1-b][1,3]thiazol-6-yl)phenyl)-2-phenylacetamide,
2,6-difluoro-N-(3-(5-(2-((3-fluoro-5-(2-oxopyrrolidin-1-yl)phenyl)amino)pyrimidin-4-yl)imidazo[2,1-b][1,3]thiazol-6-yl)phenyl)benzamide,
2-chloro-N-(3-(5-(2-((3-fluoro-5-(2-oxopyrrolidin-1-yl)phenyl)amino)pyrimidin-4-yl)imidazo[2,1-b][1,3]thiazol-6-yl)phenyl)benzamide,
N-(3-(5-(2-((4-fluoro-3-(2-oxopyrrolidin-1-yl)phenyl)amino)pyrimidin-4-yl)imidazo[2,1-b][1,3]thiazol-6-yl)phenyl)-2-phenylacetamide,
2,6-difluoro-N-(3-(5-(2-((4-fluoro-3-(2-oxopyrrolidin-1-yl)phenyl)amino)pyrimidin-4-yl)imidazo[2,1-b][1,3]thiazol-6-yl)phenyl)benzamide,
2-chloro-N-(3-(5-(2-((4-fluoro-3-(2-oxopyrrolidin-1-yl)phenyl)amino)pyrimidin-4-yl)imidazo[2,1-b][1,3]thiazol-6-yl)phenyl)benzamide,
N-(3-(5-(2-((6-morpholin-4-ylpyridin-3-yl)amino)pyrimidin-4-yl)imidazo[2,1-b][1,3]thiazol-6-yl)phenyl)-2-phenylacetamide,
2,6-difluoro-N-(3-(5-(2-((6-morpholin-4-ylpyridin-3-yl)amino)pyrimidin-4-yl)imidazo[2,1-b][1,3]thiazol-6-yl)phenyl)benzamide,
2-chloro-N-(3-(5-(2-((6-morpholin-4-ylpyridin-3-yl)amino)pyrimidin-4-yl)imidazo[2,1-b][1,3]thiazol-6-yl)phenyl)benzamide,
N-(3-(5-(2-((6-morpholin-4-ylpyridin-3-yl)amino)pyrimidin-4-yl)imidazo[2,1-b][1,3]thiazol-6-yl)phenyl)-N'-phenylurea,
4-(6-(3-(benzylamino)phenyl)imidazo[2,1-b][1,3]thiazol-5-yl)-N-(4-morpholin-4-ylphenyl)pyrimidin-2-amine,
N-(4-morpholin-4-ylphenyl)-4-(6-(3-((2-phenylethyl)amino)phenyl)imidazo[2,1-b][1,3]thiazol-5-yl)pyrimidin-2-amine,
2-((3-(5-(2-((4-morpholin-4-ylphenyl)amino)pyrimidin-4-yl)imidazo[2,1-b][1,3]thiazol-6-yl)phenyl)amino)-1-phenylethanone,
2-((3-(5-(2-((4-morpholin-4-ylphenyl)amino)pyrimidin-4-yl)imidazo[2,1-b][1,3]thiazol-6-yl)phenyl)amino)-1-phenylethanol,
N-(4-(4-isopropylpiperazin-1-yl)phenyl)-4-(6-(3-((5-phenyl-1,3,4-oxadiazol-2-yl)amino)phenyl)imidazo[2,1-b][1,3]thiazol-5-yl)pyrimidin-2-amine,
N-(4-morpholin-4-ylphenyl)-4-(6-(3-((pyridin-2-ylmethyl)amino)phenyl)imidazo[2,1-b][1,3]thiazol-5-yl)pyrimidin-2-amine,
4-(6-(3-((2,6-difluorobenzyl)amino)phenyl)imidazo[2,1-b][1,3]thiazol-5-yl)-N-(4-morpholin-4-ylphenyl)pyrimidin-2-amine,
4-(6-(3-((2-methoxybenzyl)amino)phenyl)imidazo[2,1-b][1,3]thiazol-5-yl)-N-(4-morpholin-4-ylphenyl)pyrimidin-2-amine, and salts, esters, amides, prodrugs and salts of esters, amides and prodrugs thereof.

DETAILED DESCRIPTION OF THE INVENTION

Variable moieties of compounds herein are represented by identifiers (capital letters with numerical and/or alphabetical superscripts) and may be specifically embodied.

It is meant to be understood that proper valences are maintained for all moieties and combinations thereof, that monovalent moieties having more than one atom are attached through their left ends.

It is also meant to be understood that a specific embodiment of a variable moiety may be the same or different as another specific embodiment having the same identifier.

The term "cyclic moiety," as used herein, means benzene, cycloalkane, cycloalkyl, cycloalkene, cycloalkenyl, heteroarene, heteroaryl, heterocycloalkane, heterocycloalkyl, heterocycloalkene, heterocycloalkenyl, phenyl, spiroalkyl, spiroalkenyl, spiroheteroalkyl and spiroheteroalkenyl.

The term "cycloalkane," as used herein, means $C_3$-cycloalkane, $C_4$-cycloalkane, $C_5$-cycloalkane and $C_6$-cycloalkane.

The term "cycloalkyl," as used herein, means C3-cycloalkyl, C4-cycloalkyl, $C_5$-cycloalkyl and $C_6$-cycloalkyl.

The term "cycloalkene," as used herein, means $C_4$-cycloalkene, $C_5$-cycloalkene and $C_6$-cycloalkene.

The term "cycloalkenyl," as used herein, means $C_4$-cycloalkenyl, $C_5$-cycloalkenyl and $C_6$-cycloalkenyl.

The term "heteroarene," as used herein, means furan, imidazole, isothiazole, isoxazole, 1,2,3-oxadiazole, 1,2,5-oxadiazole, oxazole, pyrazine, pyrazole, pyridazine, pyridine, pyrimidine, pyrrole, thiazole, thiophene, triazine and 1,2,3-triazole.

The term "heteroaryl," as used herein, means furanyl, imidazolyl, isothiazolyl, isoxazolyl, 1,2,3-oxadiazolyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thiophenyl, triazinyl and 1,2,3-triazolyl.

The term "heterocycloalkane," as used herein, means cycloalkane having one or two or three $CH_2$ moieties replaced with independently selected O, S, S(O), $SO_2$ or NH and one or two CH moieties unreplaced or replaced with N and also means cycloalkane having one or two or three $CH_2$ moieties unreplaced or replaced with independently selected O, S, S(O), $SO_2$ or NH and one or two CH moieties replaced with N.

The term "heterocycloalkyl," as used herein, means cycloalkyl having one or two or three $CH_2$ moieties replaced with independently selected O, S, S(O), $SO_2$ or NH and one or two CH moieties unreplaced or replaced with N and also means cycloalkyl having one or two or three $CH_2$ moieties unreplaced or replaced with independently selected O, S, S(O), SO$_2$ or NH and one or two CH moieties replaced with N.

The term "heterocycloalkene," as used herein, means cycloalkene having one or two or three CH$_2$ moieties replaced with independently selected O, S, S(O), SO$_2$ or NH and one or two CH moieties unreplaced or replaced with N and also means cycloalkene having one or two or three CH$_2$ moieties unreplaced or replaced with independently selected O, S, S(O), SO$_2$ or NH and one or two CH moieties replaced with N.

The term "heterocycloalkenyl," as used herein, means cycloalkenyl having one or two or three CH$_2$ moieties replaced with independently selected O, S, S(O), SO$_2$ or NH and one or two CH moieties unreplaced or replaced with N and also means cycloalkenyl having one or two or three CH$_2$ moieties unreplaced or replaced with independently selected O, S, S(O), SO$_2$ or NH and one or two CH moieties replaced with N.

The term "alkenyl," as used herein, means C$_2$-alkenyl, C$_3$-alkenyl, C$_4$-alkenyl, C$_5$-alkenyl and C$_6$-alkenyl.

The term "alkyl," as used herein, means C$_1$-alkyl, C$_2$-alkyl, C$_3$-alkyl, C$_4$-alkyl, C$_5$-alkyl and C$_6$-alkyl.

The term "alkynyl," as used herein, means C$_2$-alkynyl, C$_3$-alkynyl, C$_4$-alkynyl, C$_5$-alkynyl and C$_6$-alkynyl.

The term "C$_2$-alkenyl," as used herein, means ethenyl (vinyl).

The term "C$_3$-alkenyl," as used herein, means 1-propen-1-yl, 1-propen-2-yl
(isopropenyl) and 1-propen-3-yl (allyl).

The term "C$_4$-alkenyl," as used herein, means 1-buten-1-yl, 1-buten-2-yl, 1,3-butadien-1-yl, 1,3-butadien-2-yl, 2-buten-1-yl, 2-buten-2-yl, 3-buten-1-yl, 3-buten-2-yl, 2-methyl-1-propen-1-yl and 2-methyl-2-propen-1-yl.

The term "C$_5$-alkenyl," as used herein, means 2-methylene-3-buten-1-yl, 2-methylenebut-1-yl, 2-methyl-1-buten-1-yl, 2-methyl-1,3-butadien-1-yl, 2-methyl-2-buten-1-yl, 2-methyl-3-buten-1-yl, 2-methyl-3-buten-2-yl, 3-methyl-1-buten-1-yl, 3-methyl-1-buten-2-yl, 3-methyl-1,3-butadien-1-yl, 3-methyl-1,3-butadien-2-yl, 3-methyl-2-buten-1-yl, 3-methyl-2-buten-2-yl, 3-methyl-3-buten-1-yl, 3-methyl-3-buten-2-yl, 1-penten-1-yl, 1-penten-2-yl, 1-penten-3-yl, 1,3-pentadien-1-yl, 1,3-penta-dien-2-yl, 1,3-pentadien-3-yl, 1,4-pentadien-1-yl, 1,4-pentadien-2-yl, 1,4-pentadien-3-yl, 2-penten-1-yl, 2-penten-2-yl, 2-penten-3-yl, 2,4-pentadien-1-yl, 2,4-pentadien-2-yl, 3-penten-1-yl, 3-penten-2-yl, 4-penten-1-yl and 4-penten-2-yl.

The term "C$_6$-alkenyl," as used herein, means 2,2-dimethyl-3-buten-1-yl, 2,3-dimethyl-1-buten-1-yl, 2,3-dimethyl-1,3-butadien-1-yl, 2,3-dimethyl-2-buten-1-yl, 2,3-dimethyl-3-buten-1-yl, 2,3-dimethyl-3-buten-2-yl, 3,3-dimethyl-1-buten-1-yl, 3,3-dimethyl-1-buten-2-yl, 2-ethenyl-1,3-butadien-1-yl, 2-ethenyl-2-buten-1-yl, 2-ethyl-1-buten-1-yl, 2-ethyl-1,3-butadien-1-yl, 2-ethyl-2-buten-1-yl, 2-ethyl-3-buten-1-yl, 1-hexen-1-yl, 1-hexen-2-yl, 1-hexen-3-yl, 1,3-hexadien-1-yl, 1,3-hexadien-2-yl, 1,3-hexadien-3-yl, 1,3,5-hexatrien-1-yl, 1,3,5-hexatrien-2-yl, 1,3,5-hexatrien-3-yl, 1,4-hexadien-1-yl, 1,4-hexadien-2-yl, 1,4-hexadien-3-yl, 1,5-hexadien-1-yl, 1,5-hexadien-2-yl, 1,5-hexadien-3-yl, 2-hexen-1-yl, 2-hexen-2-yl, 2-hexen-3-yl, 2,4-hexadien-1-yl, 2,4-hexadien-2-yl, 2,4-hexadien-3-yl, 2,5-hexadien-1-yl, 2,5-hexadien-2-yl, 2,5-hexadien-3-yl, 3-hexen-1-yl, 3-hexen-2-yl, 3-hexen-3-yl, 3,5-hexadien-1-yl, 3,5-hexadien-2-yl, 3,5-hexadien-3-yl, 4-hexen-1-yl, 4-hexen-2-yl, 4-hexen-3-yl, 5-hexen-1-yl, 5-hexen-2-yl, 5-hexen-3-yl, 2-methylene-3-methyl-3-buten-1-yl, 2-methylene-3-methylbut-1-yl, 2-methylene-3-penten-1-yl, 2-methylene-4-penten-1-yl, 2-methylenepent-1-yl, 2-methylenepent-3-yl, 3-methylene-1-penten-1-yl, 3-methylene-1-penten-2-yl, 3-methylenepent-1-yl, 3-methylene-1,4-pentadien-1-yl, 3-methylene-1,4-pentadien-2-yl, 3-methylene-pent-2-yl, 2-methyl-1-penten-1-yl, 2-methyl-1-penten-3-yl, 2-methyl-1,3-pentadien-1-yl, 2-methyl-1,3-pentadien-3-yl, 2-methyl-1,4-pentadien-1-yl, 2-methyl-1,4-pentadien-3-yl, 2-methyl-2-penten-1-yl, 2-methyl-2-penten-3-yl, 2-methyl-2,4-pentadien-1-yl, 2-methyl-2,4-pentadien-3-yl, 2-methyl-3-penten-1-yl, 2-methyl-3-penten-2-yl, 2-methyl-3-penten-3-yl, 2-methyl-4-penten-1-yl, 2-methyl-4-penten-2-yl, 2-methyl-4-penten-3-yl, 3-methyl-1-penten-1-yl, 3-methyl-1-penten-2-yl, 3-methyl-1,3-pentadien-1-yl, 3-methyl-1,3-pentadien-2-yl, 3-methyl-1,4-pentadien-1-yl, 3-methyl-1,4-pentadien-2-yl, 3-methyl-2-penten-1-yl, 3-methyl-2-penten-2-yl, 3-methyl-2,4-pentadien-1-yl, 3-methyl-3-penten-1-yl, 3-methyl-3-penten-2-yl, 3-methyl-4-penten-1-yl, 3-methyl-4-penten-2-yl, 3-methyl-4-penten-3-yl, 4-methyl-1-penten-1-yl, 4-methyl-1-penten-2-yl, 4-methyl-1-penten-3-yl, 4-methyl-1,3-pentadien-1-yl, 4-methyl-1,3-pentadien-2-yl, 4-methyl-1,3-pentadien-3-yl, 4-methyl-1,4-pentadien-1-yl, 4-methyl-1,4-pentadien-2-yl, 4-methyl-1,4-pentadien-3-yl, 4-methylene-2-penten-3-yl, 4-methyl-2-penten-1-yl, 4-methyl-2-penten-2-yl, 4-methyl-2-penten-3-yl, 4-methyl-2,4-pentadien-1-yl, 4-methyl-2,4-pentadien-2-yl, 4-methyl-3-penten-1-yl, 4-methyl-3-penten-2-yl, 4-methyl-3-penten-3-yl, 4-methyl-4-penten-1-yl and 4-methyl-4-penten-2-yl.

The term "C$_1$-alkyl," as used herein, means methyl.

The term "C$_2$-alkyl," as used herein, means ethyl.

The term "C$_3$-alkyl," as used herein, means prop-1-yl and prop-2-yl (isopropyl).

The term "C$_4$-alkyl," as used herein, means but-1-yl, but-2-yl, 2-methylprop-1-yl and 2-methylprop-2-yl (tert-butyl).

The term "C$_5$-alkyl," as used herein, means 2,2-dimethylprop-1-yl (neo-pentyl), 2-methylbut-1-yl, 2-methylbut-2-yl, 3-methylbut-1-yl, 3-methylbut-2-yl, pent-1-yl, pent-2-yl and pent-3-yl.

The term "C$_6$-alkyl," as used herein, means 2,2-dimethylbut-1-yl, 2,3-dimethylbut-1-yl, 2,3-dimethylbut-2-yl, 3,3-dimethylbut-1-yl, 3,3-dimethylbut-2-yl, 2-ethylbut-1-yl, hex-1-yl, hex-2-yl, hex-3-yl, 2-methylpent-1-yl, 2-methylpent-2-yl, 2-methylpent-3-yl, 3-methylpent-1-yl, 3-methylpent-2-yl, 3-methylpent-3-yl, 4-methylpent-1-yl and 4-methylpent-2-yl.

The term "alkylene," as used herein, means a divalent radical formed by removal of a hydrogen atom from an alkyl.

The term "C$_2$-alkynyl," as used herein, means ethynyl (acetylenyl).

The term "C$_3$-alkynyl," as used herein, means 1-propyn-1-yl and 2-propyn-1-yl (propargyl).

The term "C$_4$-alkynyl," as used herein, means 1-butyn-1-yl, 1,3-butadiyn-1-yl, 2-butyn-1-yl, 3-butyn-1-yl and 3-butyn-2-yl.

The term "C$_5$-alkynyl," as used herein, means 2-methyl-3-butyn-1-yl, 2-methyl-3-butyn-2-yl, 3-methyl-1-butyn-1-yl, 1,3-pentadiyn-1-yl, 1,4-pentadiyn-1-yl, 1,4-pentadiyn-3-yl, 2,4-pentadiyn-1-yl, 1-pentyn-1-yl, 1-pentyn-3-yl, 2-pentyn-1-yl, 3-pentyn-1-yl, 3-pentyn-2-yl, 4-pentyn-1-yl and 4-pentyn-2-yl.

The term "C$_6$-alkynyl," as used herein, means 2,2-dimethyl-3-butyn-1-yl, 3,3-dimethyl-1-butyn-1-yl, 2-ethyl-3-butyn-1-yl, 2-ethynyl-3-butyn-1-yl, 1-hexyn-1-yl, 1-hexyn-3-yl, 1,3-hexadiyn-1-yl, 1,3,5-hexatriyn-1-yl, 1,4-hexadiyn-1-yl, 1,4-hexadiyn-3-yl, 1,5-hexadiyn-1-yl, 1,5-hexadiyn-3-yl, 2-hexyn-1-yl, 2,5-hexadiyn-1-yl, 3-hexyn-1-yl, 3-hexyn-2-yl, 3,5-hexadiyn-2-yl, 4-hexyn-1-yl, 4-hexyn-2-yl, 4-hexyn- 3-yl, 5-hexyn-1-yl, 5-hexyn-2-yl, 5-hexyn-3-yl, 2-methyl-3-pentyn-1-yl, 2-methyl-3-pentyn-2-yl, 2-methyl-4-pentyn-1-yl, 2-methyl-4-pentyn-2-yl, 2-methyl-4-pentyn-3-yl, 3-methyl-1-pentyn-1-yl, 3-methyl-4-pentyn-1-yl, 3-methyl-4-pentyn-2-yl, 3-methyl-1,4-pentadiyn-1-yl, 3-methyl-1,4-pentadiyn-3-yl, 3-methyl-4-pentyn-1-yl, 3-methyl-4-pentyn-3-yl, 4-methyl-1-pentyn-1-yl and 4-methyl-2-pentyn-1-yl.

The term "$C_4$-cycloalkane," as used herein, means cyclobutane.

The term "$C_5$-cycloalkane," as used herein, means cyclopentane.

The term "$C_6$-cycloalkane," as used herein, means cyclohexane.

The term "$C_4$-cycloalkene," as used herein, means cyclobutene and 1,3-cyclobutadiene.

The term "$C_5$-cycloalkene," as used herein, means cyclopentene and 1,3-cyclopentadiene.

The term "$C_6$-cycloalkene," as used herein, means cyclohexene, 1,3-cyclohexadiene and 1,4-cyclohexadiene.

The term "$C_3$-cycloalkenyl," as used herein, means cycloprop-1-en-1-yl and cycloprop-2-en-1-yl.

The term "$C_4$-cycloalkenyl," as used herein, means cyclobut-1-en-1-yl and cyclobut-2-en-1-yl.

The term "$C_5$-cycloalkenyl," as used herein, means cyclopent-1-en-1-yl, cyclopent-2-en-1-yl, cyclopent-3-en-1-yl and cyclopenta-1,3-dien-1-yl.

The term "$C_6$-cycloalkenyl," as used herein, means cyclohex-1-en-1-yl, cyclohex-2-en-1-yl, cyclohex-3-en-1-yl, cyclohexa-1,3-dien-1-yl, cyclohexa-1,4-dien-1-yl, cyclohexa-1,5-dien-1-yl, cyclohexa-2,4-dien-1-yl and cyclohexa-2,5-dien-1-yl.

The term "$C_3$-cycloalkyl," as used herein, means cycloprop-1-yl.

The term "$C_4$-cycloalkyl," as used herein, means cyclobut-1-yl.

The term "$C_5$-cycloalkyl," as used herein, means cyclopent-1-yl.

The term "$C_6$-cycloalkyl," as used herein, means cyclohex-1-yl.

The term "spiroalkyl," as used herein, means alkylene, both ends of which are attached to the same carbon atom and is exemplified by $C_2$-spiroalkyl, $C_3$-spiroalkyl, $C_4$-spiroalkyl, $C_5$-spiroalkyl, $C_6$-spiroalkyl, $C_7$-spiroalkyl, $C_8$-spiroalkyl, $C_9$-spiroalkyl and the like.

Compounds of this invention may contain asymmetrically substituted carbon atoms in the R or S configuration, wherein the terms "R" and "S" are as defined in Pure Appl. Chem. (1976) 45, 13-10. Compounds having asymmetrically substituted carbon atoms with equal amounts of R and S configurations are racemic at those atoms. Atoms having excess of one configuration over the other are assigned the configuration in excess, preferably an excess of about 85%-90%, more preferably an excess of about 95%-99%, and still more preferably an excess greater than about 99%. Accordingly, this invention is meant to embrace racemic mixtures and relative and absolute diastereoisomers of the compounds thereof.

Compounds of this invention may also contain carbon-carbon double bonds or carbon-nitrogen double bonds in the Z or E configuration, in which the term "Z" represents the larger two substituents on the same side of a carbon-carbon or carbon-nitrogen double bond and the term "E" represents the larger two substituents on opposite sides of a carbon-carbon or carbon-nitrogen double bond. The compounds of this invention may also exist as a mixture of "Z" and "E" isomers.

Compounds of this invention may also exist as tautomers or equilibrium mixtures thereof wherein a proton of a compound shifts from one atom to another. Examples of tautomers include, but are not limited to, keto-enol, phenol-keto, oxime-nitroso, nitro-aci, imine-enamine and the like.

Compounds of this invention containing NH, C(O)OH, OH or SH moieties may have attached thereto prodrug-forming moieties. The prodrug-forming moieties are removed by metabolic processes and release the compounds having the freed NH, C(O)OH, OH or SH in vivo. Prodrugs are useful for adjusting such pharmacokinetic properties of the compounds as solubility and/or hydrophobicity, absorption in the gastrointestinal tract, bioavailability, tissue penetration, and rate of clearance.

Metabolites of compounds having Formula I produced by in vitro or in vivo metabolic processes, may also have utility for treating diseases associated with overexpression or unregulation of a kinase.

Certain precursor compounds which may be metabolized in vitro or in vivo to form compounds having Formula I may also have utility for treating diseases associated with overexpression or unregulation of a kinase.

Compounds having Formula I may exist as acid addition salts, basic addition salts or zwitterions. Salts of compounds having Formula I are prepared during their isolation or following their purification. Acid addition salts are those derived from the reaction of a compound having Formula I with acid. Accordingly, salts including the acetate, adipate, alginate, bicarbonate, citrate, aspartate, benzoate, benzenesulfonate (besylate), bisulfate, butyrate, camphorate, camphorsulfonate, digluconate, formate, fumarate, glycerophosphate, glutamate, hemisulfate, heptanoate, hexanoate, hydrochloride, hydrobromide, hydroiodide, lactobionate, lactate, maleate, mesitylenesulfonate, methanesulfonate, naphthylenesulfonate, nicotinate, oxalate, pamoate, pectinate, persulfate, phosphate, picrate, propionate, succinate, tartrate, thiocyanate, trichloroacetic, trifluoroacetic, para-toluenesulfonate and undecanoate salts of the compounds having Formula I are meant to be embraced by this invention. Basic addition salts of compounds are those derived from the reaction of the compounds having Formula I with the bicarbonate, carbonate, hydroxide or phosphate of cations such as lithium, sodium, potassium, calcium and magnesium.

Compounds having Formula I may be administered, for example, bucally, ophthalmically, orally, osmotically, parenterally (intramuscularly, intraperitoneally intrasternally, intravenously, subcutaneously), rectally, topically, transdermally, vaginally and intraarterially as well as by intraarticular injection, infusion, and placement in the body, such as, for example, the vasculature.

Therapeutically effective amounts of a compound having Formula I depend on recipient of treatment, disease treated and severity thereof, composition comprising it, time of administration, route of administration, duration of treatment, potency, rate of clearance and whether or not another drug is co-administered. The amount of a compound having Formula I used to make a composition to be administered daily to a mammal in a single dose or in divided doses is from about 0.001 to about 200 mg/kg body weight. Single dose compositions contain these amounts or a combination of submultiples thereof.

Compounds having Formula I may be administered with or without an excipient. Excipients include, but are not limited to, encapsulators and additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents, mixtures thereof and the like.

Excipients for preparation of compositions comprising a compound having Formula I to be administered orally include, but are not limited to, agar, alginic acid, aluminum hydroxide, benzyl alcohol, benzyl benzoate, 1,3-butylene glycol, carbomers, castor oil, cellulose, cellulose acetate, cocoa butter, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl celluose, isopropanol, isotonic saline, lactose, magnesium hydroxide, magnesium stearate, malt, mannitol, monoglycerides, olive oil, peanut oil, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, soybean oil, stearic acids, stearyl fumarate, sucrose, surfactants, talc, tragacanth, tetrahydrofurfuryl alcohol, triglycerides, water, mixtures thereof and the like. Excipients for preparation of compositions comprising a compound having Formula I to be administered ophthalmically or orally include, but are not limited to, 1,3-butylene glycol, castor oil, corn oil, cottonseed oil, ethanol, fatty acid esters of sorbitan, germ oil, groundnut oil, glycerol, isopropanol, olive oil, polyethylene glycols, propylene glycol, sesame oil, water, mixtures thereof and the like. Excipients for preparation of compositions comprising a compound having Formula I to be administered osmotically include, but are not limited to, chlorofluorohydrocarbons, ethanol, water, mixtures thereof and the like. Excipients for preparation of compositions comprising a compound having Formula I to be administered parenterally include, but are not limited to, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water, mixtures thereof and the like. Excipients for preparation of compositions comprising a compound having Formula I to be administered rectally or vaginally include, but are not limited to, cocoa butter, polyethylene glycol, wax, mixtures thereof and the like.

Compounds having Formula I are also expected to be useful as chemotherapeutic agents in combination with actinomycins, alkylating agents, anthracyclines, antifolates, antiestrogen agents, anti-metabolites, anti-androgens, antimicrotubule agents, aromatase inhibitors, bleomycins, $Ca^{2+}$ adenosine triphosphate (ATP)ase inhibitors, cytosine analogs, deltoids/retinoids, dihydrofolate reductase inhibitors, deoxyribonucleic acid (DNA) topoisomerase inhibitors, dopaminergic neurotoxins, glucocorticoids, histone deacetylase (HDAC) inhibitors, hormonal therapies, immunotherapeutic agents, inosine monophosphate (IMP) dehydrogenase inhibitors, isoprenylation inhibitors, luteinizing hormone-releasing hormone agonists, mammalian target of rapamycin (mtor) inhibitors, multi-drug resistance (MDR) inhibitors, mitomycins, photodyamic therapies, proteasome inhibitors, platinum containing compounds, radiation, receptor tyrosine kinase inhibitors, ribonucleotide reductase inhibitors, thrombospondin mimetics, uracil analogs, vinca alkaloids, and vitamin D3 analogs such as, but not limited to, γ-radiation or an additional chemotherapeutic agent or additional chemotherapeutic agents such as N—Ac-Sar-Gly-Val-D-alloIle-Thr-Nva-Ile-Arg-Pro-NHCH$_2$CH$_3$ or a salt thereof, actinomycin D, AG13736, 17-allylamino-17-demethoxygeldanamycin, 9-aminocamptothecin, N-(4-(3-amino-1H-indazol-4-yl)phenyl)-N'-(2-fluoro-5-methylphenyl)urea or a salt thereof, N-(4-(4-aminothieno(2,3-d)pyrimidin-5-yl)phenyl)-N'-(2-fluoro-5-(trifluoromethyl)phenyl)urea or a salt thereof, anastozole, AP-23573, asparaginase, azacitidine, bevacizumab, bicalutamide, bleomycin a2, bleomycin b2, bortezamib, busulfan, campathecins, carboplatin, carmustine (BCNU), CB1093, cetuximab, CHOP (C: Cytoxan® (cyclophosphamide); H: Adriamycin® (hydroxydoxorubicin); O: Vincristine (Oncovin®); P: prednisone), chlorambucil, CHIR258, cisplatin, CNF-101, CNF-1001, CNF-2024, CP547632, crisnatol, cytarabine, cyclophosphamide, cytosine arabinoside, daunorubicin, dacarbazine, dactinomycin, dasatinib, daunorubicin, deferoxamine, demethoxyhypocrellin A, depsipeptide, dexamethasone, 17-dimethylaminoethylamino-17-demethoxygeldanamycin, docetaxel, doxifluridine, doxorubicin, EB1089, epothilone D, epirubicin, 5-ethynyl-1-β-D-ribofuranosylimidazole-4-carboxamide (EICAR), erlotinib, etoposide, everolimus, 5-fluorouracil (5-FU), floxuridine, fludarabine, flutamide, gefitinib, geldanamycin, gemcitabine, goserelin, N-(2-(4-hydroxyanilino)-3-pyridinyl)-4-methoxybenzenesulfonamide or a salt thereof, hydroxyurea, idarubicin, ifosfamide, imatinab, interferon-α, interferon-γ, IPI-504, irinotecan, KH 1060, lapatanib, leucovorin calcium, LAQ824, leuprolide acetate, letrozole, lomustine (CCNU), lovastatin, megestrol, melphalan, mercaptopurine, methotrexate, 1-methyl-4-phyenylpyridinium, MG132, mitomycin, mitoxantrone, MLN-518, MS-275, mycophenolic acid, mitomycin C, nitrosoureas, oprelvekin, oxaliplatin, paclitaxel, PD98059, peplomycin, photosensitizer Pc4, phtalocyanine, pirarubicin, plicamycin, prednisone, procarbizine, PTK787, PU24FC1, PU3, radicicol, raloxifene, rapamycin, ratitrexed, retinoids such as pheuretinide, ribavirin, rituximab (Rituxin®), sorafenib, staurosporine, steroids such as dexamethasone and prednisone, suberoylanilide hydroxamic acid, sunitinib, tamoxifen, taxol, temozolamide, temsirolimus, teniposide, thapsigargin, thioguanine, thrombospondin-1, tiazofurin, topotecan, trapoxin, trastuzumab, treosulfan, trichostatin A, trimetrexate, trofosfamide, tumor necrosis factor, valproic acid, VER49009, verapamil, vertoporfin, vinblastine, vincristine, vindesine, vinorelbine vitamin D3, VX-680, zactima, ZK-EPO, zorubicin or combinations thereof.

To determine the binding of compounds having Formula I to a representative protein kinase, protein tyrosine kinase, the following assay was used:

EGFR(L858R) kinase activity was assayed by a homogenous time-resolved fluorescence (HTRF) in vitro kinase assay (Mathis, G., *HTRF® Technolog.* J Biomol Screen, 1999. 4(6): p. 309-314). Specifically, 10 µL C-terminal GST-tagged, recombinant, human EGFR, amino acids 696-end containing the mutation L858R expressed by baculovirus in Sf21 cells (Millipore) was mixed with 10 ul inhibitor (various concentrations, 2% final DMSO) and 10 ul of ATP (50 µM final concentration) in reaction buffer (50 mM HEPES, pH 7.5, 10 mM MgCl$_2$, 2 mM MnCl$_2$, 0.1% BSA and 1 mM DTT, 40 µL final volume). The reaction was initiated by addition of 10 ul of biotinylated peptide substrate (Biotin-Ahx-AEEEY-FFLFA, 0.5 µM final concentration) in a black 384-well plate (Packard). After 60 minutes incubation at room temperature, the reaction was quenched by addition 60 µL stop/revelation buffer to give 30 mM EDTA, 1 µg/ml streptavidin-APC (Prozyme), 50 ng/ml anti-phosphotyrosine mAb PT66-K Europium Cryptate, 30 mM HEPES, pH 7.5, 120 mM KF, 0.005% Tween-20, 0.05% BSA). The quenched reaction was allowed to stand at room temperature for 1 hour and then read in a time-resolved fluorescence detector (Envision, Perkin Elmer) at 615 nm and 665 nm simultaneously. The ratio between the signal of 615 nm and 665 nm was used in the calculation of the $IC_{50}$. Results are shown in TABLE 1.

| Inhibition (μM) | | | | |
|---|---|---|---|---|
| 12500 | 12500 | 12500 | 12500 | 12500 |
| 12500 | 12500 | 12500 | 12500 | 11100 |
| 10200 | 7730 | 6550 | 6490 | 6030 |
| 4880 | 4850 | 4780 | 4600 | 4380 |
| 4270 | 3920 | 3460 | 3200 | 3130 |
| 2840 | 2830 | 2540 | 2400 | 2380 |
| 2340 | 2220 | 2070 | 2030 | 1960 |
| 1920 | 1730 | 1700 | 1680 | 1670 |
| 1610 | 1570 | 1470 | 1320 | 1310 |
| 1280 | 1280 | 1250 | 1250 | 1220 |
| 1200 | 1170 | 1130 | 1100 | 1090 |
| 1070 | 1040 | 965 | 952 | 951 |
| 938 | 923 | 874 | 857 | 846 |
| 761 | 736 | 717 | 714 | 686 |
| 686 | 673 | 662 | 656 | 636 |
| 623 | 617 | 614 | 575 | 562 |
| 546 | 546 | 540 | 509 | 494 |
| 490 | 487 | 468 | 462 | 461 |
| 441 | 439 | 412 | 406 | 402 |
| 401 | 398 | 394 | 386 | 378 |
| 377 | 376 | 373 | 371 | 370 |
| 365 | 359 | 358 | 358 | 349 |
| 344 | 339 | 331 | 325 | 320 |
| 316 | 312 | 305 | 301 | 301 |
| 301 | 300 | 297 | 291 | 286 |
| 283 | 282 | 280 | 275 | 273 |
| 269 | 260 | 260 | 259 | 257 |
| 256 | 250 | 238 | 230 | 230 |
| 229 | 227 | 224 | 220 | 218 |
| 217 | 206 | 206 | 204 | 203 |
| 201 | 201 | 200 | 197 | 196 |
| 187 | 187 | 186 | 186 | 183 |
| 182 | 181 | 179 | 177 | 173 |
| 170 | 168 | 167 | 165 | 164 |
| 156 | 156 | 153 | 152 | 152 |
| 152 | 152 | 152 | 150 | 150 |
| 149 | 145 | 142 | 140 | 139 |
| 137 | 136 | 132 | 131 | 130 |
| 127 | 127 | 126 | 126 | 125 |
| 122 | 121 | 119 | 118 | 117 |
| 117 | 116 | 113 | 113 | 112 |
| 112 | 109 | 109 | 109 | 108 |
| 106 | 106 | 105 | 104 | 104 |
| 102 | 102 | 100 | 99 | 98 |
| 98 | 96 | 96 | 94 | 94 |
| 94 | 93 | 91 | 90 | 90 |
| 88 | 88 | 87 | 87 | 86 |
| 85 | 85 | 83 | 83 | 81 |
| 81 | 81 | 80 | 80 | 79 |
| 78 | 78 | 77 | 76 | 74 |
| 74 | 73 | 73 | 73 | 72 |
| 72 | 70 | 69 | 69 | 68 |
| 67 | 67 | 66 | 66 | 66 |
| 66 | 65 | 64 | 64 | 64 |
| 63 | 62 | 62 | 61 | 61 |
| 58 | 58 | 56 | 55 | 55 |
| 55 | 55 | 54 | 54 | 54 |
| 53 | 53 | 52 | 52 | 52 |
| 52 | 51 | 50 | 49 | 49 |
| 49 | 46 | 46 | 46 | 45 |
| 45 | 43 | 42 | 41 | 40 |
| 39 | 39 | 37 | 36 | 33 |
| 33 | 33 | 33 | 33 | 31 |
| 31 | 29 | 29 | 28 | 27 |
| 27 | 26 | 26 | 25 | 25 |
| 25 | 25 | 24 | 24 | 24 |
| 24 | 23 | 23 | 23 | 22 |
| 22 | 20 | 18 | 18 | 18 |
| 17 | 17 | 16 | 16 | 16 |
| 16 | 16 | 16 | 15 | 15 |
| 15 | 15 | 15 | 15 | 15 |
| 14 | 14 | 14 | 14 | 14 |
| 14 | 13 | 13 | 13 | 13 |
| 12 | 12 | 11 | 11 | 10 |
| 10 | 10 | 10 | 10 | 10 |
| 10 | 10 | 10 | 9 | 9 |
| 9 | 9 | 9 | 9 | 8 |
| 8 | 8 | 8 | 8 | 8 |
| 8 | 8 | 8 | 7 | 7 |
| 7 | 7 | 7 | 7 | 7 |
| 6 | 6 | 6 | 6 | 6 |
| 6 | 6 | 6 | 6 | 6 |
| 6 | 5 | 5 | 5 | 5 |
| 5 | 5 | 5 | 5 | 5 |
| 5 | 5 | 5 | 4 | 4 |
| 4 | 4 | 4 | 3 | 3 |
| 3 | 3 | 3 | 3 | 3 |
| 3 | 3 | 3 | 3 | 3 |
| 2 | 2 | 2 | 2 | 2 |
| 2 | 2 | 2 | 2 | 1 |
| 1 | 1 | 1 | | |

These data demonstrate the utility of compounds having Formula I as protein kinase inhibitors and are therefore expected to have utility in treatment of diseases during which any kinase family member is expressed.

Diseases involving overexpression or unregulation of a protein kinase family member include, but are not limited to, acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myleogeneous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, heavy chain disease, hemangioblastoma, hepatoma, hepatocellular cancer, hormone insensitive prostate cancer, leiomyosarcoma, liposarcoma, lung cancer, lymphagioendothelio-sarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma, meningioma, mesothelioma, multiple myeloma, myelogenous leukemia, myeloma, myxosarcoma, neuroblastoma, non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor.

It is also expected that compounds having Formula I would inhibit the growth of cells derived from a cancer or neoplasm such as breast cancer (including estrogen-receptor positive breast cancer), colorectal cancer, endometrial cancer, lung cancer (including small cell lung cancer), lymphoma (including follicular or Diffuse Large B-cell), lymphoma (including non-Hodgkin's lymphoma), neuroblastoma, ovarian cancer, prostate cancer (including hormone-insensitive prostate cancer) and testicular cancer (including germ cell testicular cancer).

It is also expected that compounds having Formula I would inhibit the growth of cells derived from a pediatric cancer or neoplasm such as embryonal rhabdomyosarcoma, pediatric acute lymphoblastic leukemia, pediatric acute myelogenous leukemia, pediatric alveolar rhabdomyosarcoma, pediatric anaplastic ependymoma, pediatric anaplastic large cell lymphoma, pediatric anaplastic medulloblastoma, pediatric atypical teratoid/rhabdoid tumor of the central nervous system, pediatric biphenotypic acute leukemia, pediatric Burkitts lymphoma, pediatric cancers of Ewing's family of tumors such as primitive neuroectodermal rumors, pediatric diffuse anaplastic Wilm's tumor, pediatric favorable histology Wilm's tumor, pediatric glioblastoma, pediatric medulloblastoma, pediatric neuroblastoma, pediatric neuroblastoma-derived myelocytomatosis, pediatric pre-B-cell cancers (such as leukemia), pediatric psteosarcoma, pediatric rhabdoid kidney tumor, pediatric rhabdomyosarcoma, and pediatric T-cell cancers such as lymphoma and skin cancer.

For example, involvement of protein kinases in in bladder cancer, breast cancer, cervical cancer, colon cancer, endometrial cancer, esophageal cancer, lung cancer, ovarian cancer, pancreatic cancer, prostate cancer, rectal cancer, skin cancer, stomach cancer and thyroid cancer are reported in Endocrine Rev. 21, 215 (2000), Br. J. Cancer 92, 1467 (2005), Cytokine Growth Factor Rev. 7, 133 (1996) and Biochem. Pharm. 51, 1101 (1996) (IGF1R-1); Biochem. Biophys. Acta 1198, 165 (1994), New Eng. J. Med. 344,783 (2001) (ErbB2); Cancer Metastasis Rev. 22, 337 (2003), J. Clin. Invest. 91, 53 (1993) and BBRC 243,503 (1998) (SRC-1); Science 279, 577 (1998) and NELM 344, 1038 (2001).

Still another embodiment comprises methods of treating a mammal having a disease characterized by unregulated protein kinase activity comprising administering thereto therapeutically effective amounts of a compound having formula (J) and one or more than one additional therapeutic agents, with or without administering radiation.

Compounds having formula (J) are also expected to be useful when used with alkylating agents, angiogenesis inhibitors, antibodies, antimetabolites, antimitotics, antiproliferatives, aurora kinase inhibitors, Bcr-Abl kinase inhibitors, biologic response modifiers, cyclin-dependent kinase inhibitors, cell cycle inhibitors, cyclooxygenase-2 inhibitors, leukemia viral oncogene homolog (ErbB2) receptor inhibitors, growth factor inhibitors, heat shock protein (HSP)-90 inhibitors, histone deacetylase (HDAC) inhibitors inhibitors, hormonal therapies, immunologicals, intercalating antibiotics, kinase inhibitors, mammalian target of rapomycin inhibitors, mitogen-activated extracellular signal-regulated kinase inhibitors, non-steroidal anti-inflammatory drugs (NSAID's), platinum chemotherapeutics, polo-like kinase inhibitors, proteasome inhibitors, purine analogs, pyrimidine analogs, receptor tyrosine kinase inhibitors, retinoids/deltoids plant alkaloids, topoisomerase inhibitors and the like.

Alkylating agents include altretamine, AMD-473, AP-5280, apaziquone, bendamustine, brostallicin, busulfan, carboquone, carmustine (BCNU), chlorambucil, Cloretazine™ (VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, treosulfan, trofosfamide and the like.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs vascular endothelial growth factor receptor tyrosine kinase (VEGFR) inhibitors and the like.

Aurora kinase inhibitors include AZD-1152, MLN-8054, VX-680 and the like.

Bcr-Abl kinase inhibitors include DASATINIB® (BMS-354825), GLEEVEC® (imatinib) and the like.

CDK inhibitors include AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709 and the like.

COX-2 inhibitors include ABT-963, ARCOXIA® (etoricoxib), BEXTRA® (valdecoxib), BMS347070, CELEBREX™ (celecoxib), COX-189 (lumiracoxib), CT-3, DERAMAXX® (deracoxib), JTE-522, 4-methyl-2-(3,4-dimethylphenyl)-1-(4-sulfamoylphenyl-1H-pyrrole), MK-663 (etoricoxib), NS-398, parecoxib, RS-57067, SC-58125, SD-8381, SVT-2016, S-2474, T-614, VIOXX® (rofecoxib) and the like.

EGFR inhibitors include ABX-EGF, anti-EGFr immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib) and the like.

ErbB2 receptor inhibitors include CP-724-714, CI-1033 (canertinib), Herceptin® (trastuzumab), TYKERB® (lapatinib), OMNITARG® (2C4, petuzumab), TAK-165, GW-572016 (ionafamib), GW-282974, EKB-569, PI-166, dHER2 (HER2 vaccine), APC-8024 (HER-2 vaccine), anti-HER/2neu bispecific antibody, B7.her2IgG3, AS HER2 trifunctional bispecfic antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17-AAG-nab, 17-AAG, CNF-101, CNF-1010, CNF-2024, 17-DMAG, geldanamycin, IPI-504, KOS-953, MYCOGRAB®, NCS-683664, PU24FCl, PU-3, radicicol, SNX-2112, STA-9090 VER49009 and the like.

MEK inhibitors include ARRY-142886, ARRY-438162 PD-325901, PD-98059 and the like.

mTOR inhibitors include AP-23573, CCI-779, everolimus, RAD-001, rapamycin, temsirolimus and the like.

Non-steroidal anti-inflammatory drugs include AMIGESIC® (salsalate), DOLOBID® (diflunisal), MOTRIN® (ibuprofen), ORUDIS® (ketoprofen), RELAFEN® (nabumetone), FELDENE (piroxicam) ibuprofin cream, ALEVE and NAPROSYN® (naproxen), VOLTAREN® (diclofenac), INDOCIN® (indomethacin), CLINORIL® (sulindac), TOLECTIN® (tolmetin), LODINE (etodolac), TORADOL® (ketorolac), DAYPRO® (oxaprozin) and the like.

PDGFR inhibitors include C-451, CP-673, CP-868596 and the like.

Platinum chemotherapeutics include cisplatin, ELOXATIN® (oxaliplatin) eptaplatin, lobaplatin, nedaplatin, PARAPLATIN® (carboplatin), satraplatin and the like.

Polo-like kinase inhibitors include BI-2536 and the like.

Thrombospondin analogs include ABT-510, ABT-567, ABT-898, TSP-1 and the like.

VEGFR inhibitors include AVASTIN® (bevacizumab), ABT-869, AEE-788, ANGIOZYME™, axitinib (AG-13736), AZD-2171, CP-547,632, IM-862, Macugen (pegaptamib), NEXAVAR® (sorafenib, BAY43-9006), pazopanib (GW-786034), (PTK-787, ZK-222584), SUTENT (sunitinib, SU-11248), VEGF trap, vatalanib, ZACTIMA™ (vandetanib, ZD-6474) and the like.

Antimetabolites include ALIMTA (premetrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflomithine, EICAR, enocitabine, ethnylcytidine, fludarabine, hydroxyurea, 5-fluorouracil (5-FU) alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosate, pelitrexol, pentostatin, raltitrexed, Ribavirin, triapine, trimetrexate, S-1, tiazofurin, tegafur, TS-1, vidarabine, UFT and the like.

Antibiotics include intercalating antibiotics aclarubicin, actinomycin D, amrubicin, annamycin, adriamycin, BLENOXANE® (bleomycin), daunorubicin, CAELYX® or MYOCET® (doxorubicin), elsamitrucin, epirbucin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Topoisomerase inhibitors include aclarubicin, 9-aminocamptothecin, amonafide, amsacrine, becatecarin, belotecan, BN-80915, CAMPTOSAR® (irinotecan hydrochloride), camptothecin, CARDIOXANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include AVASTIN® (bevacizumab), CD40-specific antibodies, chTNT-1/B, denosumab, ERBITUX® (cetuximab), HUMAX-CD4® (zanolimumab), IGF1R-specific antibodies, lintuzumab, PANOREX® (edrecolomab), RENCAREX® (WX G250), RITUXAN® (rituximab), ticilimumab, trastuzimab and the like.

Hormonal therapies include ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL®, (flutamide), EVISTA® (raloxifene), fadrozole, FARESTON® (toremifene), FASLODEX® (fulvestrant), FEMARA®, (letrozole), formestane, glucocorticoids, HECTOROL® or RENAGEL® (doxercalciferol), lasofoxifene, leuprolide acetate, MEGACE (megesterol), MIFEPREX® (mifepristone), NILANDRON™ (nilutamide), NOLVADEX® (tamoxifen citrate), PLENAXIS™ (abarelix), predisone, PROPECIA® (finasteride), rilostane, SUPREFACT® (buserelin), TRELSTAR® (luteinizing hormone releasing hormone (LHRH)), vantas, VETORYL®, (trilostane or modrastane), ZOLADEX® (fosrelin, goserelin) and the like. Deltoids and retinoids include seocalcitol (EB1089, CB1093), lexacalcitrol (KH1060), fenretinide, PANRETIN® (aliretinoin), ATRAGEN (liposomal tretinoin), TARGRETIN® (bexarotene), LGD-1550 and the like.

Plant alkaloids include, but are not limited to, vincristine, vinblastine, vindesine, vinorelbine and the like.

Proteasome inhibitors include VELCADE (bortezomib), MG132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, ACTIMMUNE (interferon gamma-1b), or interferon gamma-nl, combinations thereof and the like. Other agents include ALFAFERONE, BAM-002, BEROMUN® (tasonermin), BEXXAR® (tositumomab), CamPath® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010, melanoma vaccine, mitumomab, molgramostim, MYLOTARG™ (gemtuzumab ozogamicin), NEUPOGEN® (filgrastim), OncoVAC-CL, OvaRex® (oregovomab), pemtumomab (Y-muHMFG1), PROVENGE®, sargaramostim, sizofilan, teceleukin, TheraCys®, ubenimex, VIRULIZIN®, Z-100, WF-10, PROLEUKIN® (aldesleukin), ZADAXIN® (thymalfasin), ZENAPAX® (daclizumab), ZEVALIN® (90Y-Ibritumomab tiuxetan) and the like.

Biological response modifiers are agents that modify defense mechanisms of living organisms or biological responses, such as survival, growth, or differentiation of tissue cells to direct them to have anti-tumor activity and include include krestin, lentinan, sizofuran, picibanil PF-3512676 (CpG-8954), ubenimex and the like.

Pyrimidine analogs include cytarabine (ara C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Purine analogs include LANVIS® (thioguanine) and PURI-NETHOL® (mercaptopurine).

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881, vinflunine, ZK-EPO and the like.

Compounds of this invention are also intended to be used as a radiosensitizer that enhances the efficacy of radiotherapy. Examples of radiotherapy include, but are not limited to, external beam radiotherapy, teletherapy, brachtherapy and sealed and unsealed source radiotherapy.

Additionally, compounds having formula (J) may be combined with other chemptherapeutic agents such as ABRAXANE™ (ABI-007), ABT-100 (farnesyl transferase inhibitor), ADVEXIN®, ALTOCOR® or MEVACOR® (lovastatin), AMPLIGEN® (poly I:poly C12U, a synthetic RNA), APTOSYN™ (exisulind), AREDIA® (pamidronic acid), arglabin, L-asparaginase, atamestane (1-methyl-3,17-dione-androsta-1,4-diene), AVAGE® (tazarotne), AVE-8062, BEC2 (mitumomab), cachectin or cachexin (tumor necrosis factor), canvaxin (vaccine), CeaVac™ (cancer vaccine), CELEUK® (celmoleukin), CEPLENE® (histamine dihydrochloride), CERVARIX™ (human papillomavirus vaccine), CHOP® (C: CYTOXAN® (cyclophosphamide); H: ADRIAMYCIN® (hydroxydoxorubicin); O: Vincristine (ONCOVIN®); P: prednisone), CyPat™, combrestatin A4P, DAB(389)EGF or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE (T4N5 liposome lotion), discodermolide, DX-8951f (exatecan mesylate), enzastaurin, EP0906, GARDASIL (quadrivalent human papillomavirus (Types 6, 11, 16, 18) recombinant vaccine), gastrimmune, genasense, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-pseudomonas exotoxin, interferon-α, interferon-γ, JUNOVAN™ or MEPACT™ (mifamurtide), lonafarnib, 5,10-methylenetetrahydrofolate, miltefosine (hexadecylphosphocholine), NEOVASTAT (AE-941), NEUTREXIN® (trimetrexate glucuronate), NIPENT (pentostatin), ONCONASE (a ribonuclease enzyme), ONCOPHAGE® (melanoma vaccine treatment), OncoVAX (IL-2 Vaccine), ORATHECIN™ (rubitecan), OSIDEM® (antibody-based cell drug), OvaRex® MAb (murine monoclonal antibody), paditaxel, PANDIMEX™ (aglycone saponins from ginseng comprising 20(S)protopanaxadiol (aPPD) and 20(S)protopanaxatriol (aPPT)), panitumumab, PANVAC®-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE LA (lanreotide), SORIATANE (acitretin), staurosporine (*Streptomyces* staurospores), talabostat (PT 100), TARGRETIN® (bexarotene), Taxoprexin® (DHA-paclitaxel), TELCYTA™ (TLK286), temilifene, TEMODAR® (temozolomide), tesmilifene, thalidomide, THERATOPE (STn-KLH), thymitaq (2-amino-3,4-dihydro-6-methyl-4-oxo-5-(4-pyridylthio)quinazoline dihydrochloride), TNFerade™ (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS™ (trabectedin), ZD-6126, ZINECARD® (dexrazoxane), zometa (zolendronic acid), zorubicin and the like.

It is also expected that compounds having formula (I) would inhibit growth of cells derived from a pediatric cancer or neoplasm including embryonal rhabdomyosarcoma, pediatric acute lymphoblastic leukemia, pediatric acute myelogenous leukemia, pediatric alveolar rhabdomyosarcoma, pediatric anaplastic ependymoma, pediatric anaplastic large cell lymphoma, pediatric anaplastic medulloblastoma, pediatric atypical teratoid/rhabdoid tumor of the central nervous system, pediatric biphenotypic acute leukemia, pediatric Burkitts lymphoma, pediatric cancers of Ewing's family of tumors such as primitive neuroectodermal rumors, pediatric diffuse anaplastic Wilm's tumor, pediatric favorable histology Wilm's tumor, pediatric glioblastoma, pediatric medulloblastoma, pediatric neuroblastoma, pediatric neuroblastoma-derived myelocytomatosis, pediatric pre-B-cell cancers (such as leukemia), pediatric psteosarcoma, pediatric rhabdoid kidney tumor, pediatric rhabdomyosarcoma, and pediatric T-cell cancers such as lymphoma and skin cancer and the like.

Compounds having Formula I may be made by synthetic chemical processes, examples of which are shown hereinbelow. It is meant to be understood that the order of the steps in the processes may be varied, that reagents, solvents and reaction conditions may be substituted for those specifically mentioned, and that vulnerable moieties may be protected and deprotected, as necessary.

Protecting groups for C(O)OH moieties include, but are not limited to, acetoxymethyl, allyl, benzoylmethyl, benzyl, benzyloxymethyl, tert-butyl, tert-butyldiphenylsilyl, diphenylmethyl, cyclobutyl, cyclohexyl, cyclopentyl, cyclopropyl, diphenylmethylsilyl, ethyl, para-methoxybenzyl, methoxymethyl, methoxyethoxymethyl, methyl, methylthioethyl, naphthyl, para-nitrobenzyl, phenyl, n-propyl, 2,2,2-trichloroethyl, triethylsilyl, 2-(trimethylsilyl)ethyl, 2-(trimethylsilyl)ethoxymethyl, triphenylmethyl and the like.

Protecting groups for C(O) and C(O)H moieties include, but are not limited to, 1,3-dioxylketal, diethylketal, dimethylketal, 1,3-dithianylketal, O-methyloxime, O-phenyloxime and the like.

Protecting groups for NH moieties include, but are not limited to, acetyl, alanyl, benzoyl, benzyl (phenylmethyl), benzylidene, benzyloxycarbonyl (Cbz), tert-butoxycarbonyl (Boc), 3,4-dimethoxybenzyloxycarbonyl, diphenylmethyl, diphenylphosphoryl, formyl, methanesulfonyl, para-methoxybenzyloxycarbonyl, phenylacetyl, phthaloyl, succinyl, trichloroethoxycarbonyl, triethylsilyl, trifluoroacetyl, trimethylsilyl, triphenylmethyl, triphenylsilyl, para-toluenesulfonyl and the like.

Protecting groups for OH and SH moieties include, but are not limited to, acetyl, allyl, allyloxycarbonyl, benzyloxycarbonyl (Cbz), benzoyl, benzyl, tert-butyl, tert-butyldimethylsilyl, tert-butyldiphenylsilyl, 3,4-dimethoxybenzyl, 3,4-dimethoxybenzyloxycarbonyl, 1,1-dimethyl-2-propenyl, diphenylmethyl, formyl, methanesulfonyl, methoxyacetyl, 4-methoxybenzyloxycarbonyl, para-methoxybenzyl, methoxycarbonyl, methyl, para-toluenesulfonyl, 2,2,2-trichloroethoxycarbonyl, 2,2,2-trichloroethyl, triethylsilyl, trifluoroacetyl, 2-(trimethylsilyl)ethoxycarbonyl, 2-trimethylsilylethyl, triphenylmethyl, 2-(triphenylphosphonio)ethoxycarbonyl and the like.

The following abbreviations have the meanings indicated. ADDP means 1,1'-(azodicarbonyl)dipiperidine; AD-mix-β means a mixture of $(DHQD)_2PHAL$, $K_3Fe(CN)_6$, $K_2CO_3$ and $K_2SO_4$); AIBN means 2,2'-azobis(2-methylpropionitrile); 9-BBN means 9-borabicyclo(3.3.1)nonane; Cp means cyclopentadiene; $(DHQD)_2PHAL$ means hydroquinidine 1,4-phthalazinediyl diethyl ether; DBU means 1,8-diazabicyclo (5.4.0)undec-7-ene; DCC means dicyclohexylcarbodiimide; DIBAL means diisobutylaluminum hydride; DIEA means diisopropylethylamine; DMAP means N,N-dimethylaminopyridine; DME means 1,2-dimethoxyethane; DMF means N,N-dimethylformamide; dmpe means 1,2-bis(dimethylphosphino)ethane; DMSO means dimethylsulfoxide; dppa means diphenylphosphoryl azide; dppb means 1,4-bis(diphenylphosphino)butane; dppe means 1,2-bis(diphenylphosphino)ethane; dppf means 1,1'-bis(diphenylphosphino)ferrocene; dppm means 1,1-bis(diphenylphosphino)methane; EDAC means 1-(3-dimethylaminopropyl)-3-ethylcarbodiimide; Fmoc means fluorenylmethoxycarbonyl; HATU means O-(7-azabenzotriazol-1-yl)-N,N'NN'-tetramethyluronium hexafluorophosphate; HMPA means hexamethylphosphoramide; IPA means isopropyl alcohol; LDA means lithium diisopropylamide; LHMDS means lithium bis(hexamethyldisilylamide); MP-$BH_3$ means macroporus triethylammonium methylpolystyrene cyanoborohydride; LAH means lithium aluminum hydride; NCS means N-chlorosuccinimide; PyBOP means benzotriazol-1-yloxytripyrrolidinophosphonium hexafluorophosphate; TDA-1 means tris(2-(2-methoxyethoxy)ethyl)amine; TEA means triethylamine; TFA means trifluoroacetic acid; THF means tetrahydrofuran; NCS means N-chlorosuccinimide; NMM means N-methylmorpholine; NMP means N-methylpyrrolidine; $PPh_3$ means triphenylphosphine.

SCHEME 1

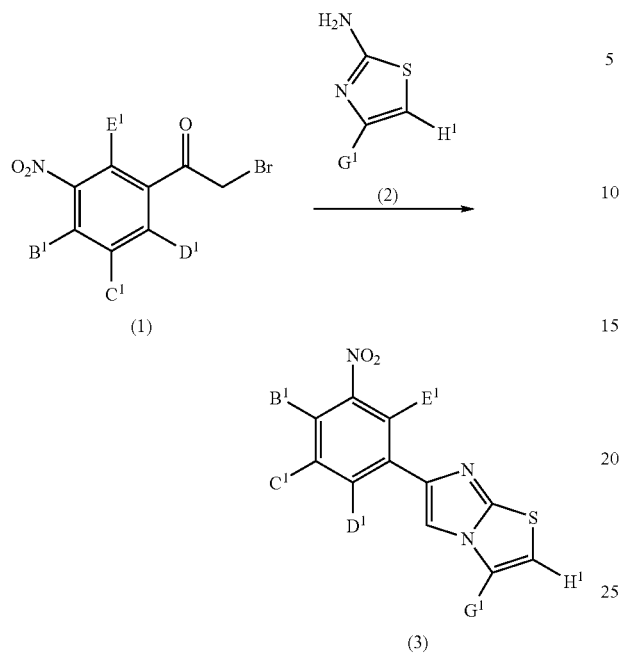

As shown in SCHEME 1, compounds of Formula (1), when treated with compounds of Formula (2), will provide compounds of Formula (3). The reaction may require heating, and is typically performed in a solvent such as but not limited to N-methylpyrrolidone.

SCHEME 2

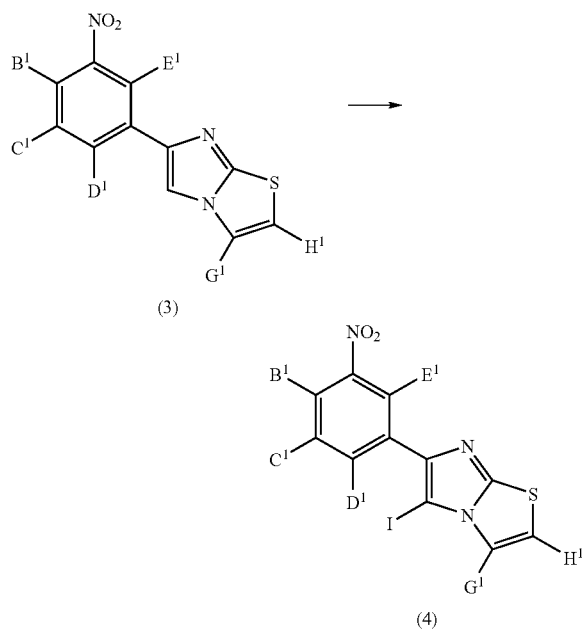

As shown in SCHEME 2, compounds of Formula (3), when treated with an iodination reagent, can be converted to compounds of Formula (4). Examples of iodination reagents include N-iodosuccinimide and the like. The reaction is typically performed at ambient temperature in a solvent such as but not limited to N,N-dimethylformamide.

SCHEME 3

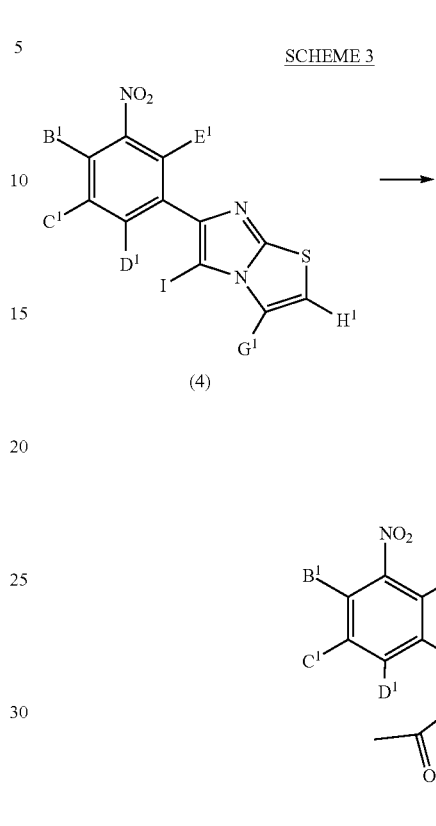

Compounds of Formula (4) can be converted to compounds of Formula (5) when treated with a catalyst, tributyl(1-ethoxyvinyl)stannane, and an optional salt additive, followed by treatment with an acid. Examples of catalysts include bis(triphenylphosphine)palladium(II) dichloride, palladium on carbon, tetrakis(triphenylphosphine)palladium (0), and tris(dibenzylideneacetone)dipalladium(0). Examples of optional salt additives include LiCl, and Cu(I) or Mn(II) salts. Examples of acids include hydrochloric acid and the like. The first step is typically performed under an inert atmosphere at increased temperatures in a solvent such as but not limited to N,N-dimethylformamide, dioxane, and acetonitrile. The second step is typically performed at ambient temperature in a solvent such as but not limited to methanol.

SCHEME 4

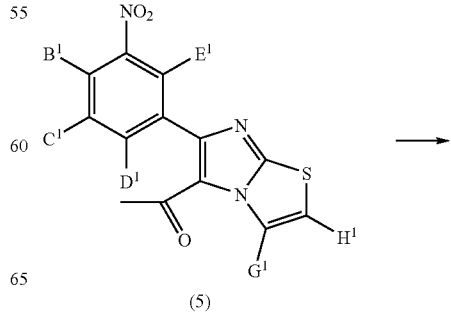

SCHEME 6

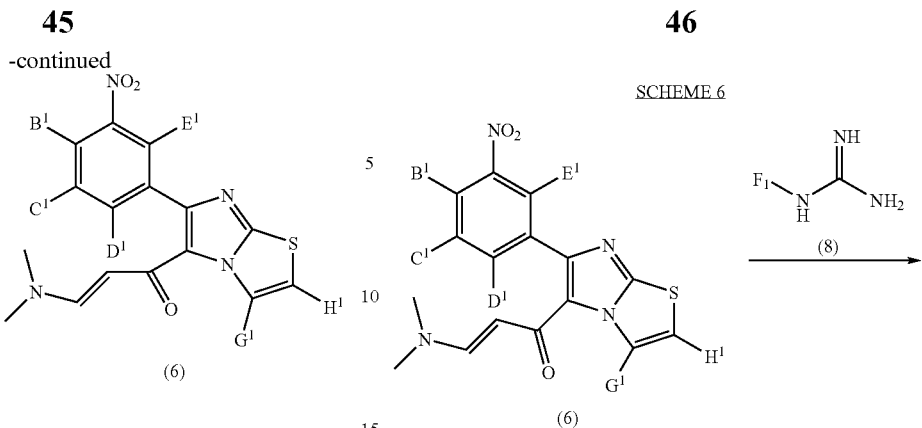

As shown in Scheme 4, compounds of Formula (5), when treated with 1,1-di-tert-butoxy-N,N-dimethylmethanamine, will provide compounds of Formula (6). The reaction typically requires the use of heat and may be performed in a solvent such as but not limited to N-methylpyrrolidone.

SCHEME 5

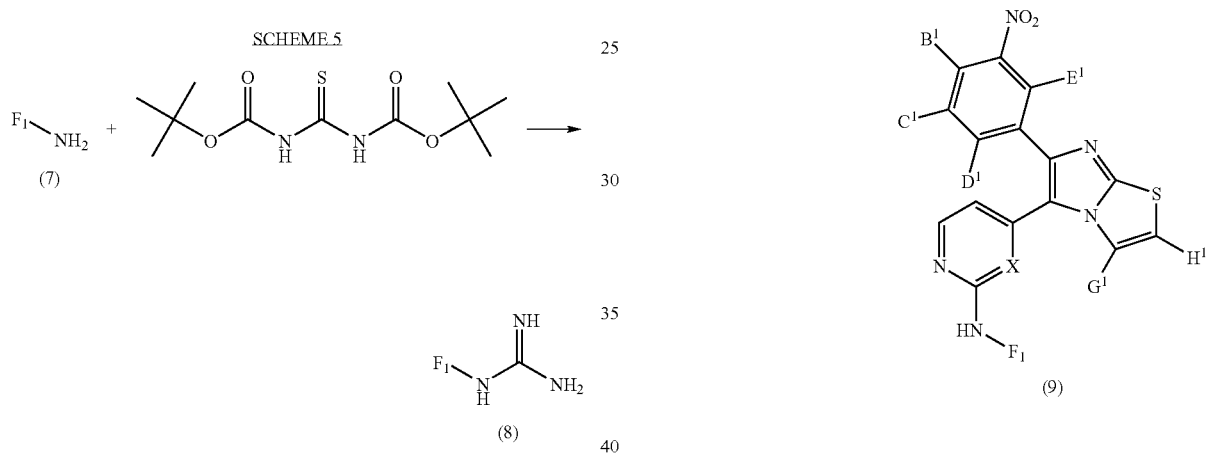

Compounds of Formula (8) may be prepared by treating compounds of Formula (7) with 2,2,10,10-tetramethyl-6-thioxo-3,9-dioxa-5,7-diazaundecane-4,8-dione and a coupling reagent such as but not limited to 1-(3-dimethylaminopropyl)-3-ethylcarbodiimide hydrochloride (EDCI), 1,3-dicyclohexylcarbodiimide (DCC), bis(2-oxo-3-oxazolidinyl) phosphinic chloride (BOPCl), O-(7-azabenzotriazol-1-yl)-N,N,N',N'-tetramethyluronium hexafluorophosphate (HATU), or O-benzotriazol-1-yl-N,N,N',N'-tetramethyluronium tetrafluoroborate (TBTU); followed by deprotection of the BOC groups. The coupling reagents may be added as a solid, a solution or as the reagent bound to a solid support resin. In addition to the coupling reagents, auxiliary-coupling reagents may facilitate the coupling reaction. Auxiliary coupling reagents that are often used in the coupling reactions include but are not limited to 4-dimethylaminopyridine (DMAP), 1-hydroxy-7-azabenzotriazole (HOAT) and 1-hydroxybenzotriazole hydrate (HOBT). The coupling reaction may be carried out in solvents such as but not limited to tetrahydrofuran, N,N,-dimethylformamide, dichloromethane, and ethyl acetate. The reaction is generally conducted at ambient or elevated temperatures. The deprotection of the BOC groups may be performed by treating the bis-BOC intermediate with an acid such as but not limited to trifluoroacetic acid or hydrochloric acid in a solvent such as but not limited to methylene chloride or dioxane.

As shown in Scheme 6, compounds of Formula (6), when treated with a base and compounds of Formula (8), which can be prepared as shown in SCHEME 5 or purchased from commercial sources, will provide compounds of Formula (9) wherein X is N. The reaction typically requires the use of heat and may be performed in a solvent such as but not limited to ethanol.

SCHEME 7

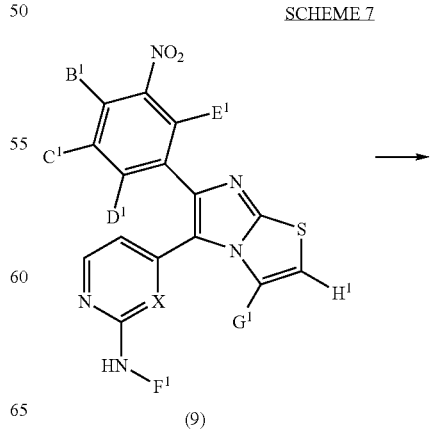

-continued

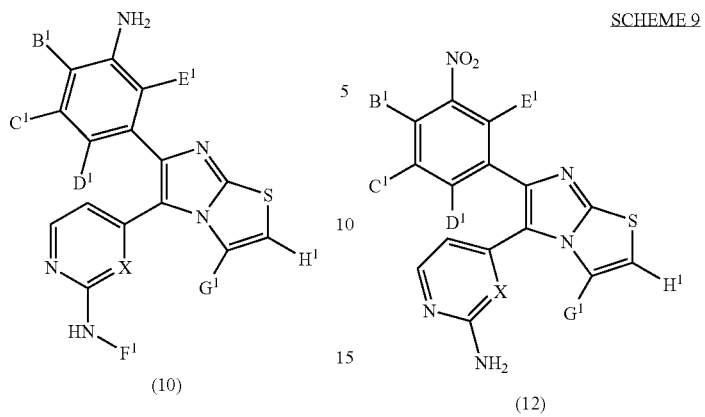

Compounds of Formula (10) may be prepared by reduction of the nitro group of compounds of Formula (9). Reduction of the nitro group may be accomplished using iron and ammonium chloride, SnCl$_2$ and hydrochloric acid, or other methods known in the literature and to those skilled in the art. The reaction may require heat and may be performed in a solvent such as but not limited to ethanol, N-methylpyrrolidone and the like.

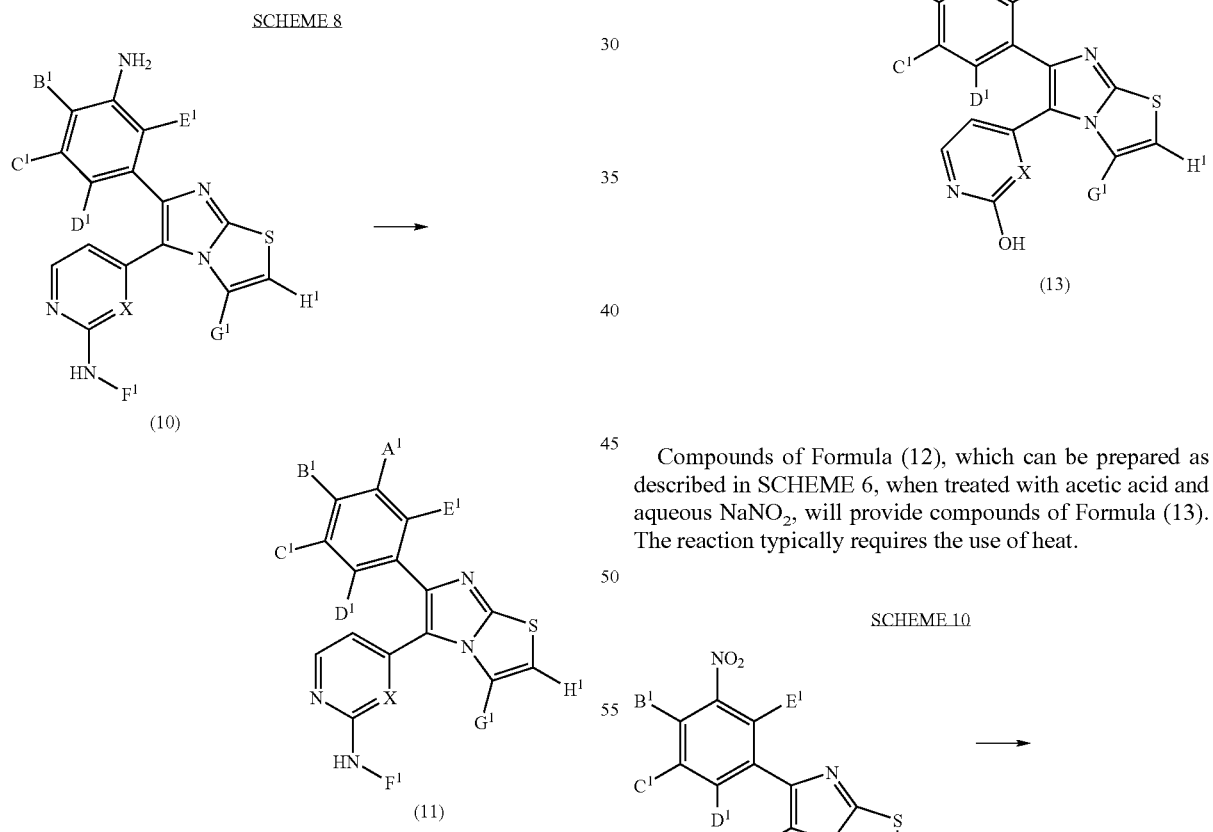

Compounds of Formula (12), which can be prepared as described in SCHEME 6, when treated with acetic acid and aqueous NaNO$_2$, will provide compounds of Formula (13). The reaction typically requires the use of heat.

As shown in Scheme 8, compounds of Formula (11), wherein A$^1$ is NHR$^1$, N(R$^1$)$_2$, NHC(O)R$^1$, NHC(O)NHR$^1$, NHC(O)N(R$^1$)$_2$, or NHC(O)OR$^1$, and which are representative of the compounds of this invention; may be prepared by methods widely known to those skilled in the art and available in the literature.

49

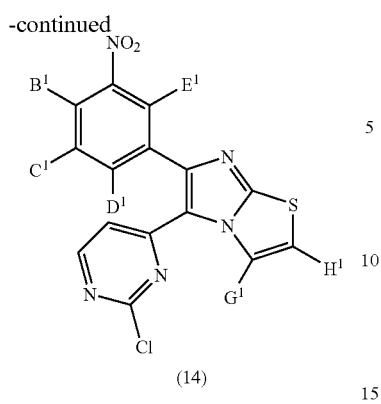

(14)

As shown in SCHEME 10, compounds of Formula (13), when treated with POCl$_3$, will provide compounds of Formula (14). The reaction typically requires the use of heat, and may be performed without an additional solvent.

SCHEME 11

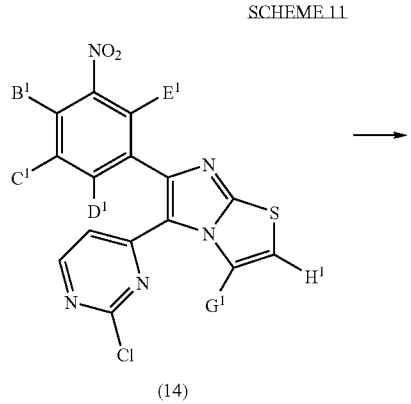

(14)

50

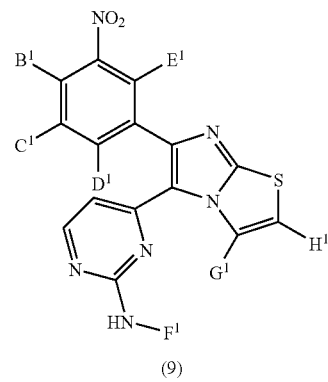

(9)

Compounds of Formula (9) can be prepared by treating compounds of Formula (14) with an amine of Formula NH$_2$F$^1$. The reaction typically requires the use of heat, and may be performed in a solvent such as but not limited to isopropyl alcohol, N-methylpyrrolidone, N,N,-dimethylformamide, and the like.

SCHEME 12

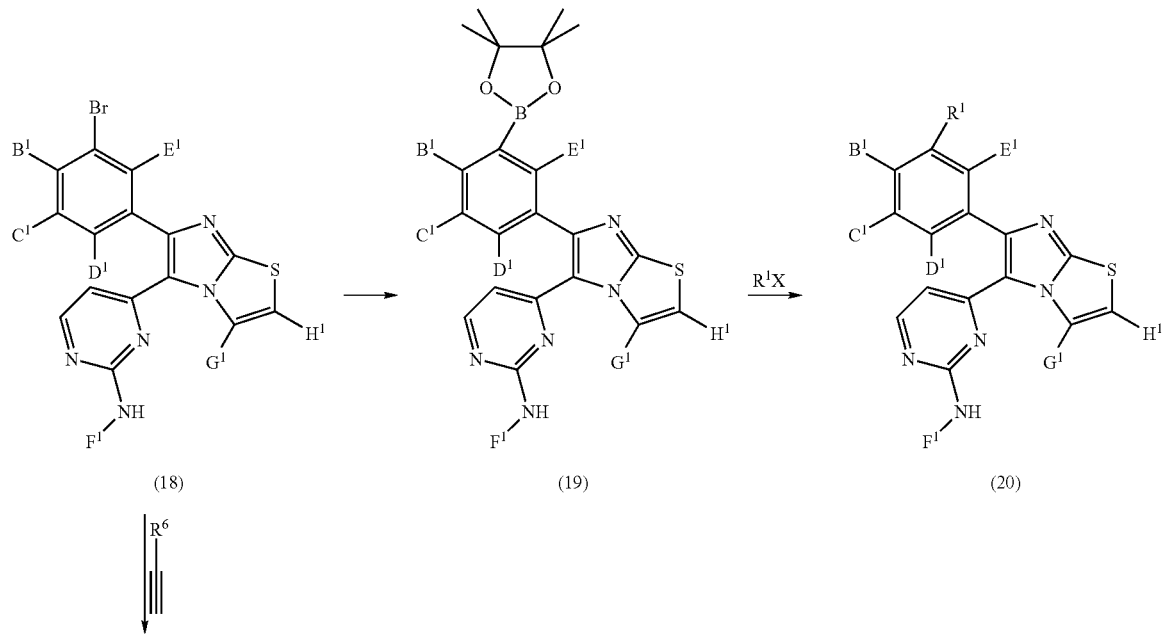

(18)     (19)     (20)

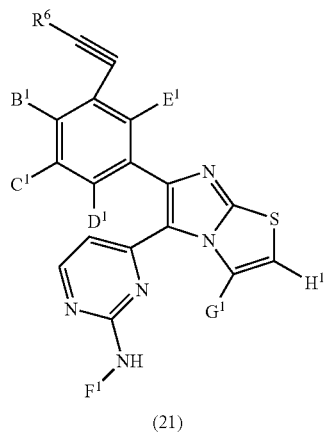

(21)

As shown in SCHEME 12, compounds of Formula (18) which can be prepared as shown in SCHEME 1-6, when treated with bis(pinacolato)diboron, a base, and a catalyst, will provide compounds of Formula (19). Examples of bases often employed include potassium acetate and the like. Examples of catalysts often employed include bis(triphenylphosphine)palladium(II) dichloride and (1,1'-bis(diphenylphosphino)ferrocene)dichloropalladium(II) dichloromethane. The reaction typically requires the use of heat and a solvent such as but not limited to dimethylsulfoxide, dioxane, or toluene.

Compounds of Formula (20) can be prepared by treating compounds of Formula (19) with compounds of Formula $R^1X$, wherein X is I, Br, Cl or triflate. The reaction typically requires the use of a base and a catalyst. Examples of bases include but are not limited to $K_2CO_3$, KOtBu, $Na_2CO_3$, $CsCO_3$, and CsF. Examples of catalysts include but are not limited to $Pd(PPh_3)_4$, $PdCl_2(dppf)_n CH_2Cl_2$, $Pd_2(dba)_3$, $Pd(OAc)_2$, and $PdCl_2(PPh_3)_2$. The reaction may be conducted in a solvent such as but not limited to water, dioxane, DME, DMF, toluene, ethanol, THF and the like or mixtures thereof. The reaction may be conducted at ambient or elevated temperatures.

Alternatively, compounds of Formula 18, when treated with a substituted or unsubstituted terminal alkyne, palladium catalyst, Cu(I) halide salt, and base will provide compounds of Formula (21). Examples of palladium catalysts include tetrakis(triphenylphosphine)palladium(0), dichlorobis(triphenylphosphine)palladium(II), and the like. Bases often employed include triethylamine, diethylamine and the like. The reaction is typically performed under an inert atmosphere in a solvent such as but not limited to N,N-dimethylformamide, toluene, and the like.

SCHEME 13

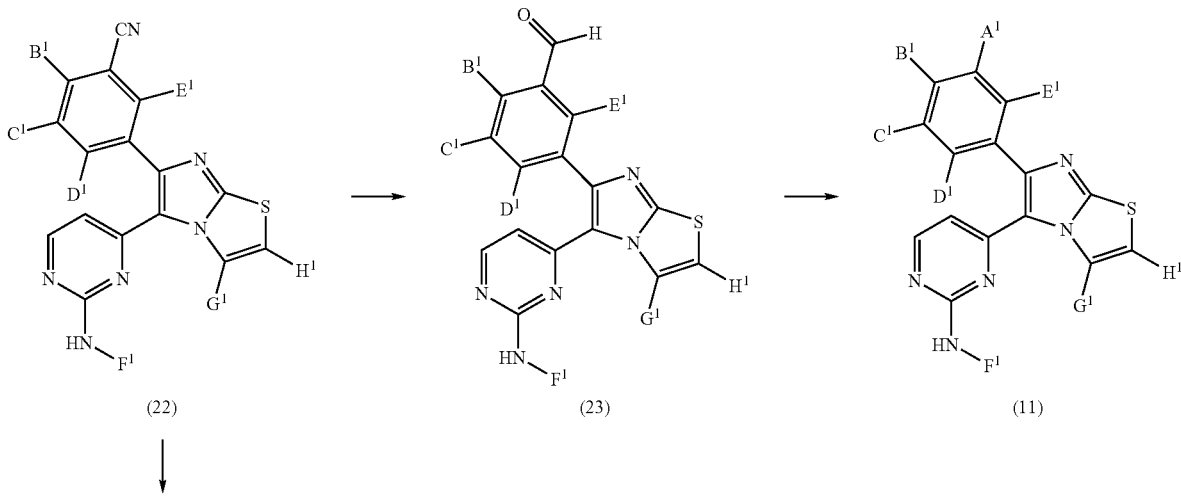

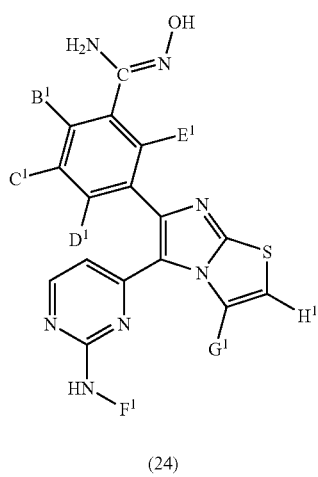 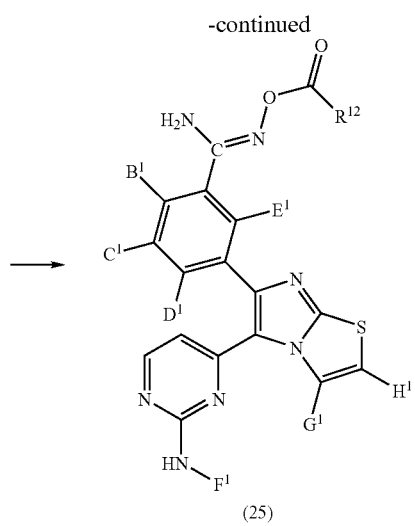 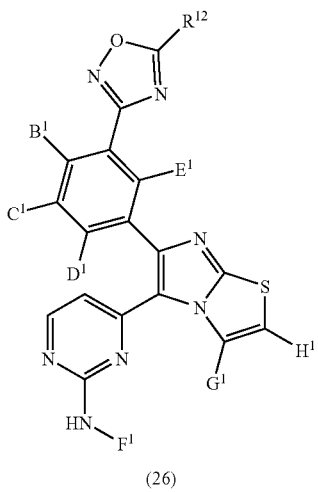

(24) (25) (26)

Compounds of Formula (22), which can be prepared as shown in SCHEME 1-6, can be converted to compounds of Formula (23) using a reducing agent such as but not limited to diisobutylaluminium hydride in a solvent such as but not limited to tetrahydrofuran and the like. Compounds of Formula (23) can be converted to compounds of Formula (11), wherein $A^1$ is $R^1$, $OR^1$, $NHR^1$, $N(R^1)_2$, $NHC(O)R^1$, $NHC(O)NHR^1$, $NHC(O)N(R^1)_2$, $NHC(O)OR^1$, $C(O)NHR^1$, or $C(O)N(R^1)_2$, which are representative of the compounds of this invention; and which may be prepared by methods widely known to those skilled in the art and available in the literature.

Alternatively, compounds of Formula (22) can be converted to compounds of Formula (24) by reacting the former with hydroxylamine. The reaction may be performed in a solvent such as but not limited to ethyl alcohol, N-methylpyrrolidone, N,N,-dimethylformamide, and the like or mixtures thereof. Compounds of Formula (25) can be prepared from compounds of Formula (24) by reacting the latter with an acid chloride of Formula $R^{12}COCl$. The reaction may be performed in a solvent such as but not limited to tetrahydrofuran, N-methylpyrrolidone, N,N,-dimethylformamide, and the like or mixtures thereof. Compounds of Formula (25), when heated in a solvent such as but not limited to N-methylpyrrolidone, will provide compounds of Formula (26) which are representative of the compounds of the invention.

SCHEME 14

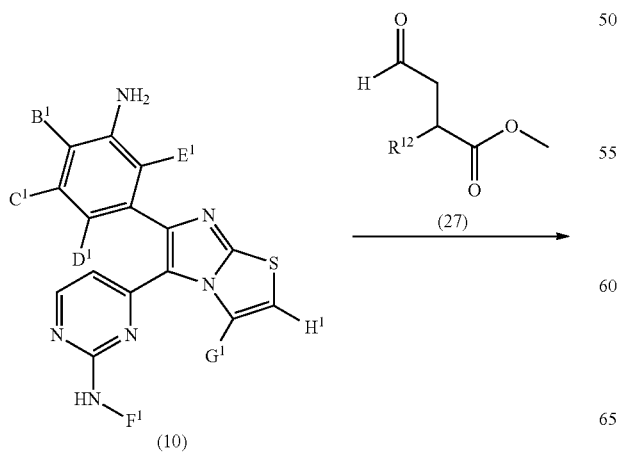

(10) (27)

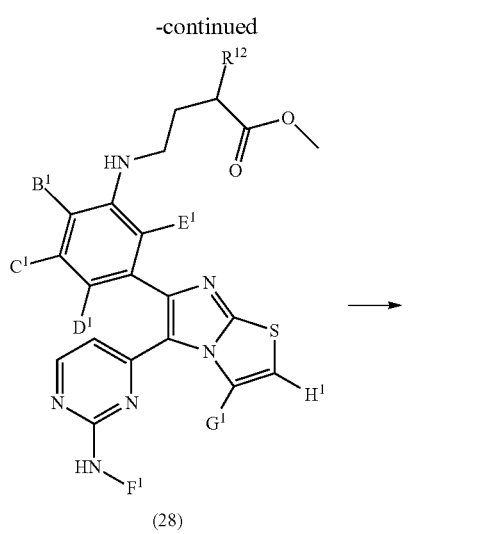

(28)

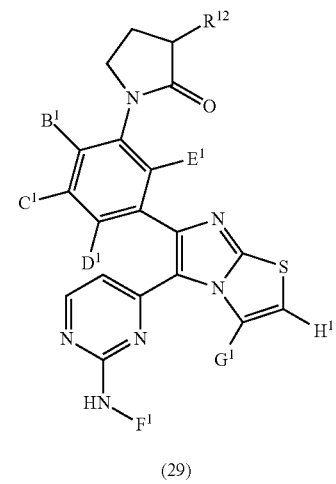

(29)

As shown in SCHEME 14, compounds of Formula (10) can be converted to compounds of Formula (28), by reacting the former, compounds of Formula (27) (prepared as described in J. Org. Chem.; 43; 21; 1978; 4115-4120), a reducing agent such as but not limited to sodium cyanoborohydride, and acetic acid. The reaction may be performed in a solvent such as but not limited to tetrahydrofuran, or N,N,-dimethylformamide.

Compounds of Formula (28) can be converted to compounds of Formula (29) with an aqueous acid such as but not limited to trifluoroacetic acid in a solvent such as but not limited to acetonitrile.

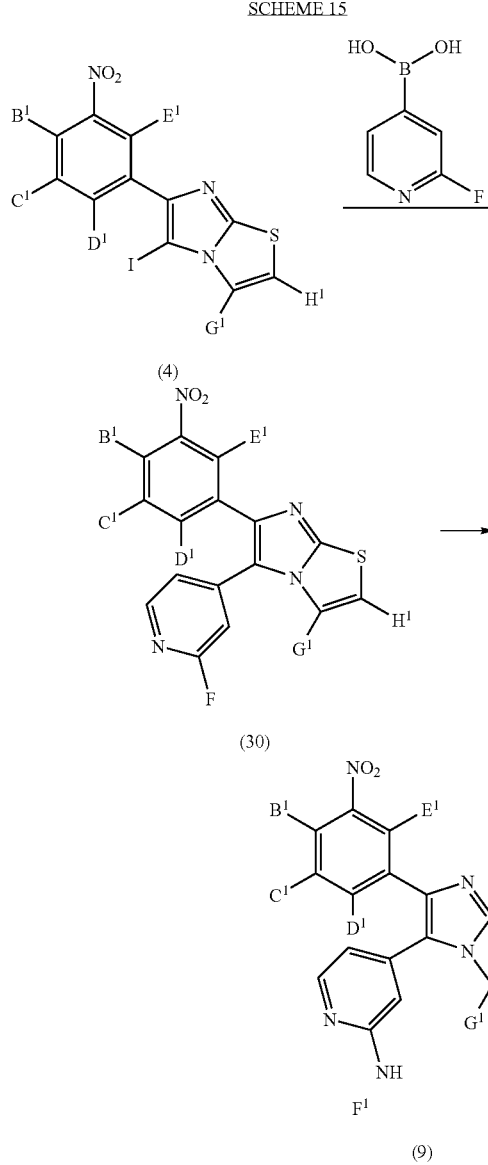

Compounds of Formula (4), when treated with 2-fluoropyridin-4-ylboronic acid, will provide compounds of Formula (30). The reaction typically requires the use of a base and a catalyst. Examples of bases include but are not limited to $K_2CO_3$, potassium t-butoxide, $Na_2CO_3$, $CsCO_3$, and CsF. Examples of catalysts include but are not limited to tetrakis (triphenylphosphine)palladium(0), (1,1'-bis(diphenylphosphino)ferrocene)dichloropalladium(II) dichloromethane, tris (dibenzylideneacetone)dipalladium(0), palladium(II) acetate, and bis(triphenylphosphine)palladium(II) dichloride. The reaction may be conducted in a solvent such as but not limited to water, dioxane, 1-methyl-2-pyrrolidinone, dimethoxyethane, N,N-dimethylformamide, toluene, ethanol, tetrahydrofuran and the like or mixtures thereof. The reaction may be conducted at ambient or elevated temperatures.

Compounds of Formula (9) can be prepared from compounds of Formula (30) by reacting the former and compounds of Formula $NH_2F^1$. The reaction typically requires the use of heat, and may be performed in a solvent such as but not limited to isopropyl alcohol, N-methylpyrrolidone, N,N,-dimethylformamide, and the like.

The following examples are presented to provide what is believed to be the most useful and readily understood description of procedures and conceptual aspects of this invention.

EXAMPLE 1

N-(3-(5-(2-anilinopyrimidin-4-yl)imidazo[2,1-b][1,3]thiazol-6-yl)phenyl)-2-chlorobenzamide

EXAMPLE 1A

Into a 1 L round-bottomed flask was charged 2-bromo-1-(3-nitrophenyl)ethanone (10 g) and thiazol-2-amine (4.10 g) in N-methylpyrrolidone (82 ml). The mixture was heated at 85-90° C. overnight. To the cooled mixture was added diethyl ether (275 ml) and the suspension was stirred at room temperature for 4 hours. The mixture was filtered and the solid was washed with diethyl ether and transferred to 4 L erlenmeyer flask. To the flask was added methanol (50 ml), ethyl acetate (400 ml), and saturated sodium carbonate (220 ml). The mixture was stirred at room temperature overnight. The mixture was separated and the aqueous layer was extracted with ethyl acetate (3×200 mL). The organic layers were combined, and dried over magnesium sulfate and concentrated in vacuo. The resulting solid was dried in vacuo. MS (ESI(+)) m/e 245 (M+H)$^+$.

EXAMPLE 1B

Into a 1 L round-bottomed flask was placed EXAMPLE 1A (15.5 g) in N,N-dimethylformamide (316 ml). After 10 minutes N-iodosuccinimide (14.93 g) was added. The mixture was allowed to stir at room temperature. The mixture became heterogenous upon stirring. After 2.5 hours, water (500 mL) was added, and the mixture stirred at room temperature for 2 hours. The mixture was filtered, and washed with water (300 mL) and diethyl ether (200 mL). The resulting solid was dried in vacuo overnight to afford the title compound. MS (ESI(+)) m/e 372 (M+H)$^+$; (ESI(−)) m/e 370 (M−H)$^−$.

EXAMPLE 1C

Into a 1 L round-bottomed flask was placed EXAMPLE 1B (22.2 g), and tributyl(1-ethoxyvinyl)stannane (23.14 ml), and bis(triphenylphosphine)palladium(II) dichloride (2.099 g) were added to the mixture, which was diluted with toluene (374 ml). The mixture was heated under $N_2$ to 110° C. After 18 hours, the mixture was cooled to room temperature, filtered, and concentrated in vacuo to afford the crude enolether. The mixture was diluted with methanol (97 ml) at room temperature, and HCl (100 ml) was added. The mixture stirred for 1 hour. The mixture formed a precipitate that was filtered. The material was dissolved in $CH_2Cl_2$/methanol, and treated with 10% NaOH for 30 minutes. The layers were separated, and the aqueous layer was extracted with $CH_2Cl_2$ (3×100 mL). The combined organic layers were dried over MgSO$_4$, and concentrated in vacuo to afford a solid. The solid was dried in vacuo at 40° C. for 3 hours. MS (ESI(+)) m/e 288 (M+H)$^+$.

EXAMPLE 1D

Into a 250 mL round-bottomed flask was added EXAMPLE 1C (3.8 g) and 1,1-di-tert-butoxy-N,N-dimethylmethanamine (15.82 ml) in N-methylpyrrolidone (5.29 ml) to give a suspension, and the mixture was heated to 90° C. After 1 hour, the mixture was cooled to room temperature. The mixture was diluted with 200 mL of diethyl ether, and cooled at 0° C. for 2 hours. The mixture was filtered and washed with diethyl ether to afford a solid. MS (ESI(+)) m/e 343 (M+H)$^+$.

EXAMPLE 1E

A slurry of EXAMPLE 1D (2.5 mmol), phenyl guanidine (0.4 g), and K$_2$CO$_3$ (0.86 g) in ethanol (5 mL) was heated to 80° C. After 12 hours, additional phenyl guanidine (0.2 g) and K$_2$CO$_3$ (0.43 g) was added and the mixture was heated for another 24 hours. The mixture was cooled to room temperature, diluted with CH$_2$Cl$_2$ and water, and the layers were separated. The aqueous layer was extracted with CH$_2$Cl$_2$ (3×25 mL). The organics were combined, dried over MgSO$_4$, filtered and concentrated in vacuo onto silica. The residue was purified via an Intelliflash-280 purification system (hexanes: ethyl acetate). MS (ESI(+)) m/e 415 (M+H)$^+$; (ESI(−)) m/e 413 (M−H)$^−$.

EXAMPLE 1F

To a slurry of EXAMPLE 1E (0.22 g), iron powder (0.22 g) and NH$_4$Cl (0.022 g) was added a 0.1 M solution of ethanol/water (80/20, v/v). The mixture was heated to 90° C. for 2 hours. The mixture was filtered through a pad of Celite®, and the pad was washed with ethyl acetate. The organics were collected, washed with brine, and dried over MgSO$_4$. The organics were concentrated in vacuo, and the material was used in the next step without further purification.

EXAMPLE 1G

EXAMPLE 1F (0.084 g) was slurried into a 0.05 M solution of tetrahydrofuran/N-methylpyrrolidone (1/1, v/v), and 2-chlorobenzyol chloride (0.042 g) was added. The mixture stirred for 15 minutes and (polystyryl)trisamine resin (Argonaut Technologies, 3.41 mmol/g, 3 equivalents) was added to quench the excess acid chloride. The resin was stirred in the mixture overnight, and the mixture was treated with 1 mL of triethylamine. The resin was filtered, and washed with CH$_2$Cl$_2$. The filtrate was washed with saturated aqueous NaHCO$_3$ and brine. The resulting organics were dried over MgSO$_4$, filtered, and concentrated in vacuo onto silica. The material was purified on an Intelliflash-280 purification system (hexanes:ethyl acetate) to afford the desired product. MS (ESI(+)) m/e 523 (M+H)$^+$; (ESI(−)) m/e 521 (M−H)$^−$; $^1$H-NMR (300 MHz, DMSO-d$_6$) ☐ 10.62 (s, 1H); 9.68 (s, 1H); 8.63 (d, 1H); 8.29 (d, 1H); 8.02 (s, 1H); 7.81 (d, 1H); 7.73 (d, 2H); 7.59-7.48 (m, 6H); 7.38-7.29 (m, 3H); 6.99 (t, 1H); 6.64 (d, 1H).

EXAMPLE 2

N-(3-(5-(2-anilinopyrimidin-4-yl)imidazo[2,1-b][1,3]thiazol-6-yl)phenyl)benzamide

EXAMPLE 2A

To a solution of EXAMPLE 1A (3 g) in a 0.2 M solution of 90/10 N-methylpyrrolidone/concentrated HCl (v/v), was added SnCl$_2$ (13.7 g). The mixture was heated to 85° C., and after 10 minutes the mixture was cooled to room temperature. 100 mL of 1 M NaOH was added to the mixture, and the resulting slurry was diluted with 100 mL of CH$_2$Cl$_2$/isopropyl alcohol (4/1, v/v). After 1 hour, the mixture was filtered. The filtrate was washed with brine, dried over MgSO$_4$, and concentrated in vacuo directly onto silica. The mixture was purified via an Intelliflash-280 purification system (hexanes: ethyl acetate) to afford the title compound.

EXAMPLE 2B

EXAMPLE 2A (1.8 g) was dissolved in 20 mL of N-methylpyrrolidone and benzoyl chloride (1.26 g) was added. The mixture stirred for 30 minutes, and (polystyryl)trisamine resin (Argonaut Technologies, 3.41 mmol/g, 3 equivalents) was added before stirring an additional 10 hours. The mixture was treated with 5 mL of triethylamine. The mixture was filtered, and the resin was rinsed with CH$_2$Cl$_2$. The filtrate was washed with brine (3×100 mL), and dried over MgSO$_4$, filtered, and concentrated in vacuo onto silica. The mixture was purified via an Intelliflash-280 purification system (hexanes:ethyl acetate) to afford the desired product, which contained trace amounts of N-methylpyrrolidone. The material was used in the next step without further purification.

EXAMPLE 2C

EXAMPLE 2B (8.3 mmol) was dissolved in 30 mL of N,N-dimethylformamide, N-iodosuccinimide (1.86 g) was added, and the resulting solution was stirred for 30 minutes. An additional amount of N-iodosuccinimide (0.2 g) was added, and the mixture stirred for 30 minutes before it was treated with 100 mL of water. The resulting thick slurry was stirred for 1 hour, filtered, and washed with water and diethyl ether. The solid was dried in vacuo at 60° C. overnight, to afford the desired product.

EXAMPLE 2D

Into a 100 mL round-bottomed flask was added EXAMPLE 2C (1 g), tributyl(1-ethoxyvinyl)stannane (0.83 mL), and bis(triphenylphosphine)palladium(II) dichloride (0.078 g), and the mixture was diluted with toluene (14 ml). The mixture was heated to 110° C. for 24 hours, N-methylpyrrolidone (3 mL) was added and the mixture was heated for an additional 8 hours. The mixture was cooled to room temperature and concentrated in vacuo. The residue was redissolved into 20 ml methanol/3 M HCl (1/1, v/v), and heated to 85° C. for 2 hours. The residue was cooled and diluted with ethyl acetate. The organics were washed with water and brine. The organics were dried over MgSO$_4$, filtered, and concentrated in vacuo onto silica. The residue was purified via an Intelliflash-280 purification system (hexanes: ethyl acetate) to afford the desired product, which was contaminated with N-methylpyrrolidone. The crude material was used in the next step without further purification.

EXAMPLE 2E

Into a 20 mL vial was added EXAMPLE 2D (2.25 mmol) in N-methylpyrrolidone (1 ml), followed by N,N-dimethylformamide di-tert-butyl acetal (2.5 ml). The mixture was allowed to stir at 90° C. After 2 hours, the mixture was cooled to room temperature, and concentrated in vacuo. The material containing some residual N-methylpyrrolidone was used in the next step without further purification.

EXAMPLE 2F

EXAMPLE 2D was dissolved in ethanol (2 mL); phenylguanidine (0.33 g) and K$_2$CO$_3$ (0.4 g) were added; and the mixture stirred at 80° C. for 12 hours. Additional phenylguanidine (0.16 g) and K$_2$CO$_3$ (0.2 g) were added and the mixture stirred for an additional 24 hours. The mixture was cooled to room temperature and diluted with 30 mL of ethyl acetate/isopropyl alcohol (4/1, v/v) and water (30 mL). The layers were separated. The resulting organic layer was washed with water and brine, dried over MgSO$_4$, filtered, and concentrated in vacuo onto silica. The material was purified via an Intelliflash-280 purification system (hexanes:ethyl acetate) to afford the desired product. MS (ESI(+)) m/e 489 (M+H)$^+$; $^1$H-NMR (300 MHz, DMSO-d$_6$) ☐ 10.37 (s, 1H); 9.69 (s, 1H); 8.85 (d, 1H); 8.30 (d, 1H); 8.09 (m, 1H); 7.95 (m, 3H); 7.74 (d, 1H); 7.60-7.44 (m, 5H); 7.37-7.29 (m, 3H); 6.99 (t, 1H); 6.66 (d, 1H).

EXAMPLE 3

2,6-difluoro-N-(3-(5-(2-((4-morpholin-4-ylphenyl)amino)pyrimidin-4-yl)imidazo[2,1-b][1,3]thiazol-6-yl)phenyl)benzamide

EXAMPLE 3A

A solution of 4-morpholinoaniline (1 g) in ethanol (6 mL) was treated with HNO$_3$ (0.35 mL) and 50% aqueous cyanamide (0.75 mL). The mixture was heated at 75° C. for 18 hours. The mixture was cooled to room temperature, and concentrated in vacuo. The resulting solid was filtered, and washed with diethyl ether to afford the product, which was used without further purification.

EXAMPLE 3B

EXAMPLE 1D (0.39 g) and EXAMPLE 3A (0.49 g) were added to a 5 mL solution of ethanol/N-methylpyrrolidone (4/1, v/v). K$_2$CO$_3$ (0.4 g) was added and the mixture was heated at 80° C. for 16 hours. Additional guanidine (0.25 g) and K$_2$CO$_3$ (0.2 g) were added and heating was continued for an additional 8 hours. The mixture was cooled to room temperature, and was treated with water (25 mL). The solid was filtered and washed with water and diethyl ether. The solid was dissolved in ethyl acetate, concentrated in vacuo onto silica and purified via an Intelliflash-280 purification system (hexanes:ethyl acetate) to afford the desired product.

EXAMPLE 3C

To a slurry of EXAMPLE 3B (0.26 g) in 0.1 M ethanol/water (1/1, v/v), was added iron powder (0.26 g), followed by NH$_4$Cl (0.026 g). The mixture was heated to 90° C. After 5 hours, the mixture was cooled to room temperature. The mixture was partitioned between CH$_2$Cl$_2$/water. The layers were separated. The aqueous layer was extracted with CH$_2$Cl$_2$ (3×50 mL). The organics were combined, dried over MgSO$_4$, filtered, and concentrated in vacuo onto silica. The material was purified via an Intelliflash-280 purification system (ethyl acetate:methanol) to afford the desired product.

EXAMPLE 3D

A slurry of EXAMPLE 3C (0.2 g) in tetrahydrofuran (2 mL) was treated with 2,6-difluorobenzoyl chloride (75 ☐L) at room temperature. The mixture was allowed to stir at room temperature for 2 hours. The slurry was treated with (polystyryl)trisamine resin (Argonaut Technologies, 3.41 mmol/g, 0.15 equivalents). After stirring for 12 hours, 2 mL of triethylamine was added, and the mixture was filtered, and the resin was washed with CH$_2$Cl$_2$. The organics were concentrated in vacuo onto silica. The material was purified via an Intelliflash-280 purification system (ethyl acetate:methanol) to afford the desired product. MS (ESI(+)) m/e 610 (M+H)$^+$; (ESI(−)) m/e 609 (M−H)$^−$; $^1$H-NMR (300 MHz, DMSO-d$_6$) ☐ 10.91 (s, 1H); 9.44 (s, 1H); 8.74 (bs, 1H); 8.23 (d, 1H); 7.97 (bs, 1H); 7.77 (d, 1H); 7.65-7.45 (m, 6H); 7.38 (d, 1H); 7.26 (t, 2H); 6.92 (d, 2H); 6.56 (d, 1H); 3.75 (m, 4H); 3.06 (m, 4H).

EXAMPLE 4

N-(3-(5-(2-((4-morpholin-4-ylphenyl)amino)pyrimidin-4-yl)imidazo[2,1-b][1,3]thiazol-6-yl)phenyl)benzamide To a solution of EXAMPLE 2E (0.77 mmol) and EXAMPLE 3A (0.33 g) in 5 mL of methanol/N-methylpyrrolidone (4/1, v/v), was added K$_2$CO$_3$ (0.27 g). The mixture was heated to 80° C. After 18 hours, additional guanidine (0.16 g) and K$_2$CO$_3$ (0.14 g) were added and the mixture stirred for an additional 8 hours. The mixture was cooled to room temperature. The mixture was partitioned between ethyl acetate and water. The layers were separated, and the aqueous layer was extracted with ethyl acetate (3×50 mL). The organics were combined, dried over MgSO$_4$, filtered, and concentrated in vacuo onto silica. The material was purified via an Intelliflash-280 purification system (hexanes:ethyl acetate) to afford the title compound. MS (ESI(+)) m/e 574 (M+H)$^+$; (ESI(−)) m/e 572 (M−H)$^−$; $^1$H-NMR (300 MHz, DMSO-d$_6$) ☐ 10.37 (s, 1H); 9.44 (s, 1H); 8.76 (bs, 1H); 8.23 (d, 1H); 8.09 (bs, 1H); 7.98-7.91 (m, 3H); 7.62-7.43 (m, 7H); 7.33 (d, 1H); 6.93 (d, 2H); 6.58 (d, 1H); 3.74 (m, 4H); 3.05 (m, 4H).

EXAMPLE 5

N-(3-(5-(2-((4-morpholin-4-ylphenyl)amino)pyrimidin-4-yl)imidazo[2,1-b][1,3]thiazol-6-yl)phenyl)-2-phenylacetamide To a slurry of EXAMPLE 3C (0.075 g) in tetrahydrofuran (2 mL) at room temperature, was added phenylacetyl chloride (0.027 g). The mixture stirred for 20 minutes and (polystyryl) trisamine resin (Argonaut Technologies, 3.41 mmol/g, 0.15 equivalents) was added and the mixture stirred overnight. The mixture was treated with triethylamine (1 mL), filtered, and the resin was washed with CH$_2$Cl$_2$. The organics were concentrated in vacuo onto silica. The material was purified via an Intelliflash-280 purification system (hexanes:ethyl acetate) to afford the title compound. MS (ESI(+)) m/e 588 (M+H)$^+$; $^1$H-NMR (300 MHz, DMSO-d$_6$) ☐ 10.28 (s, 1H); 9.43 (s, 1H); 8.74 (bs, 1H); 8.20 (d, 1H); 7.86 (bs, 1H); 7.71 (bd, 1H); 7.54 (d, 2H); 7.46 (d, 1H); 7.40 (t, 1H); 7.33 (m, 4H); 7.29-7.21 (m, 2H); 6.92 (d, 2H); 6.52 (d, 1H); 3.75 (m, 4H); 3.65 (s, 2H); 3.06 (m, 4H).

EXAMPLE 6

N-(3-(5-(2-((3-fluoro-4-methoxyphenyl)amino)pyrimidin-4-yl)imidazo[2,1-b][1,3]thiazol-6-yl)phenyl)benzamide The title compound was prepared as described in EXAMPLE 3, substituting 1-(3-fluoro-4-methoxyphenyl)

guanidine nitrate for 1-(4-morpholinophenyl)guanidine nitrate and benzoyl chloride for 2,6-difluorobenzoyl chloride. $^1$H-NMR (300 MHz, DMSO-d$_6$) ☐ 10.36 (s, 1H); 9.68 (s, 1H); 8.81 (bs, 1H); 8.29 (d, 1H); 8.09 (s, 1H); 7.97-7.91 (m, 3H); 7.74 (d, 1H); 7.60-7.51 (m, 5H); 7.36 (t, 2H); 6.65 (d, 1H); 3.81 (s, 3H).

EXAMPLE 7

N-(3-(5-(2-((3-fluoro-4-methoxyphenyl)amino)pyrimidin-4-yl)imidazo[2,1-b][1,3]thiazol-6-yl)phenyl)-2-phenylacetamide The title compound was prepared as described in EXAMPLE 3, substituting 1-(3-fluoro-4-methoxyphenyl)guanidine nitrate for 1-(4-morpholinophenyl)guanidine nitrate and phenacteyl chloride for 2,6-difluorobenzoyl chloride. MS SI(+) m/e 551 (M+H)$^+$; $^1$H-NMR (300 MHz, DMSO-d$_6$) ☐ 10.27 (s, 1H); 9.67 (s, 1H); 8.78 (bs, 1H); 8.26 (d, 1H); 7.87 (s, 1H); 7.77-7.70 (m, 2H); 7.51 (d, 1H); 7.42-7.24 (m, 8H); 7.12 (t, 1H); 6.59 (d, 1H); 3.81 (s, 3H); 3.64 (s, 2H).

EXAMPLE 8

N-(3-(5-(2-anilinopyrimidin-4-yl)imidazo[2,1-b][1,3]thiazol-6-yl)phenyl)-2-phenylacetamide The title compound was prepared as described in EXAMPLE 1, substituting phenylacetyl chloride for 2-chlorobenzoyl chloride in EXAMPLE 1G. MS (ESI(+)) m/e 503 (M+H)$^+$; $^1$H-NMR (300 MHz, DMSO-d$_6$) ☐ 10.29 (s, 1H); 9.69 (s, 1H); 8.82 (d, 1H); 8.27 (d, 1H); 7.88 (s, 1H); 7.73 (d, 2H); 7.51 (d, 1H); 7.41 (t, 1H); 7.35-7.22 (m, 9H); 6.99 (t, 1H); 6.60 (d, 1H).

EXAMPLE 9

N-(3-(5-(2-anilinopyrimidin-4-yl)imidazo[2,1-b][1,3]thiazol-6-yl)phenyl)acetamide The title compound was prepared as described in EXAMPLE 1E, substituting EXAMPLE 39F for EXAMPLE 1D. MS (ESI(+)) m/e 427 (M+H)$^+$; $^1$H-NMR (300 MHz, DMSO-d$_6$) ☐ 10.05 (s, 1H); 9.70 (s, 1H); 8.84 (d, 1H); 8.28 (d, 1H); 7.86 (s, 1H); 7.73 (d, 1H); 7.69 (d, 2H); 7.51 (d, 1H); 7.40 (t, 1H); 7.35-7.26 (m, 3H); 6.99 (t, 1H); 6.59 (d, 1H); 2.05 (s, 3H).

EXAMPLE 10

N-(3-(5-(2-((3-fluorophenyl)amino)pyrimidin-4-yl)imidazo[2,1-b][1,3]thiazol-6-yl)phenyl)-2-phenylacetamide The title compound was prepared as described in EXAMPLE 3, substituting 3-fluoro-phenylguanidine nitrate for 1-(4-morpholinophenyl)guanidine nitrate and phenylacetyl chloride for 2,6-difluorobenzoyl chloride. MS (ESI(+)) m/e 521 (M+H)$^+$; $^1$H-NMR (300 MHz, DMSO-d$_6$) ☐ 10.29 (s, 1H); 9.92 (s, 1H); 8.54 (d, 1H); 8.32 (d, 1H); 7.88 (bs, 1H); 7.80 (dd, 1H); 7.53 (d, 1H); 7.45 (m, 1H); 7.40-7.37 (m, 1H); 7.34-7.30 (m, 6H); 7.26-7.24 (m, 1H); 6.78 (m, 1H); 6.65 (d, 1H); 2.64 (s, 2H).

EXAMPLE 11

N-(3-(5-(2-((3-fluorophenyl)amino)pyrimidin-4-yl)imidazo[2,1-b][1,3]thiazol-6-yl)phenyl)benzamide The title compound was prepared as described in EXAMPLE 3, substituting 3-fluoro-phenylguanidine nitrate for 1-(4-morpholinophenyl)guanidine nitrate and benzoyl chloride for 2,6-difluorobenzoyl chloride. MS (ESI(+)) m/e 507 (M+H)$^+$; $^1$H-NMR (300 MHz, DMSO-d$_6$) ☐ 10.37 (s, 1H); 9.92 (s, 1H); 8.87 (d, 1H); 8.35 (d, 1H); 8.10 (m, 1H); 7.97-7.91 (m, 3H); 7.83-7.79 (m, 1H); 7.60-7.57 (m, 1H); 7.56-7.53 (m, 3H); 7.51-7.47 (m, 1H); 7.46-7.45 (m, 1H); 7.37-7.30 (m, 2H); 6.81-6.75 (m, 1H); 6.71 (d, 1H).

EXAMPLE 12

N-(3-(5-(2-((3-morpholin-4-ylphenyl)amino)pyrimidin-4-yl)imidazo[2,1-b][1,3]thiazol-6-yl)phenyl)-2-phenylacetamide

EXAMPLE 12A

EXAMPLE 1D (5 g), K$_2$CO$_3$ (4.04 g), and guanidine•HCl (2.093 g) in N-methylpyrrolidone (48.7 ml) were added to a round bottom flask and the mixture was heated to 100° C. After stirring for 12 hours, the mixture was cooled to room temperature and diluted with 100 mL of water. The mixture stirred for 30 minutes at room temperature and was filtered. The resulting solid was dissolved into CH$_2$Cl$_2$/methanol and washed with brine. The organics were separated, dried over MgSO$_4$, filtered, and concentrated in vacuo to afford the desired product. The material was used in the next step without further purification.

EXAMPLE 12B

Into a 500 mL round-bottomed flask was added EXAMPLE 12A (14.99 g) in acetic acid (130 ml), and the slurry was heated to 60° C. To the mixture was added NaNO$_2$ (9.17 g) in water (25 ml), dropwise via an addition funnel over 20 minutes. During the addition, a solid formed. After stirring for 1 hour, the mixture was cooled to 0° C., and quenched with 10% NaOH, until pH 7-8. The resulting solid was stirred for an additional 30 minutes at 0° C., filtered, and washed with water and diethyl ether. The product was dried in vacuo at 50° C. for 12 hours.

EXAMPLE 12C

Into a 500 mL round-bottomed flask was added EXAMPLE 12B (4.25 g) and POCl$_3$ (23.35 ml), and the mixture was heated at 80° C. for 2 hours. The mixture was concentrated in vacuo to afford an oil. The oil was added slowly to ice water, in an ice water bath, so the internal temperature did not rise above 20° C. The mixture was allowed to stir for an additional 20 minutes. While maintaining cooling, 10% NaOH was added to the mixture, until pH of 8-10. The resulting solid was filtered, washed with water, and dried in vacuo overnight at 30-50° C. The product was used in the next step without further purification.

EXAMPLE 12D

A slurry of EXAMPLE 12C (0.28 g), 3-morpholinoaniline (0.15 g), and HCl (1 drop) in isopropyl alcohol (2 mL) was heated to 90° C. for 12 hours. The mixture was cooled to room temperature, diluted with CH$_2$Cl$_2$/isopropyl alcohol (4/1, v/v), and washed with saturated aqueous NaHCO$_3$. The layers were separated. The resulting aqueous layer was washed with water and brine, dried over MgSO$_4$, filtered, and concentrated in vacuo onto silica. The material was purified via an Intelliflash-280 purification system (hexanes:ethyl acetate) to afford the desired product.

EXAMPLE 12E

Into a 200 mL round-bottomed flask was added EXAMPLE 12D (0.85 g) and SnCl$_2$ (1 g) in N-methylpyrrolidone (8 ml) and HCl (37%, 2 ml). The mixture was warmed to 90° C. and allowed to stir at 90° C. for 20 minutes. The mixture was cooled to room temperature, treated with 10% NaOH, and diluted with CH$_2$Cl$_2$. The mixture stirred at room temperature for 20 minutes or until the layers became homogenous, and the layers were separated. The aqueous layer was extracted with 3×50 mL CH$_2$Cl$_2$. The organics were combined, dried over MgSO$_4$, filtered, and concentrated in vacuo. The resulting oil was dissolved in ethyl acetate, and washed with 3×50 mL of water. The resulting organics were dried over MgSO$_4$, filtered, and concentrated in vacuo to afford a solid. The solid was used in the next step without further purification.

EXAMPLE 12F

EXAMPLE 12E was dissolved into 1 mL of N-methylpyrrolidone, at room temperature, and phenylacetyl chloride was added. The mixture stirred for 15 minutes, and trisamine resin (polystyryl)trisamine resin (Argonaut Technologies, 3.41 mmol/g, 15 mg) was added. After 4 hours, the mixture was treated with 1 mL of triethylamine and filtered. The resin was washed with tetrahydrofuran and ethyl acetate. The organics were washed with water (3×15 mL), dried over MgSO$_4$, filtered and concentrated in vacuo to afford a solid. The material was dissolved in minimal CH$_2$Cl$_2$, and triturated with diethyl ether. The solid was filtered, and dried in vacuo at 40° C. overnight, to afford the desired product. MS (ESI(+)) m/e 588 (M+H)$^+$; $^1$H-NMR (300 MHz, DMSO-d$_6$) □ 10.28 (s, 1H); 9.55 (s, 1H); 8.81 (bs, 1H); 8.25 (d, 1H); 7.88 (bs, 1H); 7.71 (d, 1H); 7.49 (d, 1H); 7.40 (t, 1H); 7.35-7.32 (m, 5H); 7.30-7.22 (m, 3H); 7.16 (t, 1H); 6.62-6.57 (m, 2H); 3.75-3.72 (m, 4H); 3.64 (s, 2H); 3.10-3.07 (m, 4H).

EXAMPLE 13

N-(3-(5-(2-((4-morpholin-4-ylphenyl)amino)pyrimidin-4-yl)imidazo[2,1-b][1,3]thiazol-6-yl)phenyl)-N'-phenylurea EXAMPLE 3C (62.6 mg) was dissolved in N-methylpyrrolidone (1.0 mL), and phenylisocyanate (1.0 eq) was added. The mixture was stirred at room temperature 18 hours, and diluted with ethyl acetate and water. The layers were separated, and the organic layer was washed with water (3×) and brine. The organic layer was dried over MgSO$_4$, filtered, and concentrated onto silica gel. The material was purified by flash chromatography using a Flashmaster Solo system (hexanes:ethyl acetate) to afford the desired product. MS (ESI) m/e 589 (M+H)$^+$; $^1$H NMR (300 MHz, DMSO-d$_6$) δ 9.42 (s, 1H), 8.84 (s, 1H), 8.70 (s, 1H), 8.22 (d, 1H), 7.72 (t, 1H), 7.53 (m, 3H), 7.46 (m, 3H), 7.38 (t, 1H), 7.27 (m, 2H), 7.19 (m, 1H), 6.97 (d, 1H), 6.92 (m, 2H), 6.57 (d, 1H), 3.74 (m, 4H), 3.06 (m, 4H).

EXAMPLE 14

N-(3-(5-(2-((4-(4-(3-methoxypropyl)piperazin-1-yl)phenyl)amino)pyrimidin-4-yl)imidazo[2,1-b][1,3]thiazol-6-yl)phenyl)-2-phenylacetamide

EXAMPLE 14A 1-(4-Nitrophenyl)-piperazine (1.03 g), 1-bromo-3-methoxypropane (1.53 g) and potassium carbonate (1.7 g) in acetonitrile 10 ml were stirred at room temperature overnight. The mixture was diluted with ethyl acetate and water. The ethyl acetate layer was separated and washed with brine. The organic layer was passed through a silica gel plug eluting with 5% methanol in ethyl acetate to afford the title compound.

EXAMPLE 14B

The title compound was prepared as described in EXAMPLE 1F, substituting EXAMPLE 14A for EXAMPLE 1E.

EXAMPLE 14C

The title compound was prepared as described in EXAMPLE 12 by substituting EXAMPLE 14B for 3-morpholinoaniline in EXAMPLE 12D. MS (ESI(+)) m/e 659 (M+H)$^+$; $^1$H-NMR (300 MHz, DMSO-d$_6$) □ 10.30 (s, 1H); 9.53 (s, 1H); 8.77 (bs, 1H); 8.21 (d, 1H); 7.89 (s, 1H); 7.69 (d, 1H); 7.60 (d, 2H); 7.48 (d, 1H); 7.40 (t, 1H); 7.35-7.24 (m, 6H); 7.00 (d, 2H); 6.54 (d, 1H); 3.75 (m, 4H); 3.65 (s, 2H); 3.42 (t, 2H); 3.27 (s, 3H); 3.19 (m, 4H); 2.95 (t, 2H); 1.95 (m, 2H).

EXAMPLE 15

2-(2,6-difluorophenyl)-N-(3-(5-(2-((4-(4-(3-methoxypropyl)piperazin-1-yl)phenyl)amino)pyrimidin-4-yl)imidazo[2,1-b][1,3]thiazol-6-yl)phenyl)acetamide The title compound was prepared as described in EXAMPLE 12, substituting EXAMPLE 14B for 3-morpholinoaniline in EXAMPLE 12D and 2,6-difluorobenzoyl chloride for phenylacetyl chloride in EXAMPLE 12F. MS (ESI (+)) m/e 695 (M+H)$^+$; $^1$H-NMR (300 MHz, DMSO-d$_6$) □ 10.42 (s, 1H); 9.52 (s, 1H); 8.77 (bs, 1H); 8.22 (d, 1H); 7.87 (s, 1H); 7.68 (d, 1H); 7.60 (d, 2H); 7.48 (d, 1H); 7.44-7.27 (m, 3H); 7.10 (m, 2H); 7.00 (d, 2H); 6.55 (d, 1H); 3.75 (m, 4H); 3.63 (s, 2H); 3.42 (t, 2H); 3.27 (s, 3H); 3.20 (m, 4H); 2.95 (t, 2H); 1.95 (m, 2H).

EXAMPLE 16

N-(3-(5-(2-((4-(4-(3-methoxypropyl)piperazin-1-yl)phenyl)amino)pyrimidin-4-yl)imidazo[2,1-b][1,3]thiazol-6-yl)phenyl)acetamide The title compound was prepared as described in EXAMPLE 12, substituting EXAMPLE 14B for 3-morpholinoaniline in EXAMPLE 12D and acetyl chloride for phenylacetyl chloride in EXAMPLE 12F. MS (ESI(+)) m/e 583 (M+H)$^+$; $^1$H-NMR (300 MHz, DMSO-d$_6$) □ 10.05 (s, 1H); 9.52 (s, 1H); 8.78 (bs, 1H); 8.22 (d, 1H); 7.87 (s, 1H); 7.66 (d, 1H); 7.60 (d, 2H); 7.48 (d, 1H); 7.39 (t, 1H); 7.25 (d, 1H); 7.00 (d, 2H); 6.54 (d, 1H); 3.76 (m, 4H); 3.61 (m, 4H); 3.27 (s, 3H); 3.20 (m, 2H); 2.95 (t, 2H); 2.05 (s, 3H); 1.95 (m, 2H).

EXAMPLE 17

2-(2-methoxyphenyl)-N-(3-(5-(2-((4-(4-(3-methoxypropyl)piperazin-1-yl)phenyl)amino)pyrimidin-4-yl)imidazo[2,1-b][1,3]thiazol-6-yl)phenyl)acetamide The title compound was prepared as described in EXAMPLE 12 by substituting EXAMPLE 14B for 3-morpholinoaniline in EXAMPLE 12D and 2-methoxyphenylacetyl chloride for phenylacetyl chloride in EXAMPLE 12F. MS (ESI(+)) m/e 689 (M+H)$^+$; $^1$H-NMR (300 MHz, DMSO-d$_6$) ☐ 10.18 (s, 1H); 9.53 (s, 1H); 8.77 (bs, 1H); 8.22 (d, 1H); 7.89 (s, 1H); 7.70 (d, 1H); 7.59 (d, 2H); 7.48 (d, 1H); 7.40 (t, 1H); 7.28-7.20 (m, 3H); 6.99 (m, 3H); 6.90 (t, 1H); 6.56 (d, 1H); 3.76 (s, 3H); 3.72 (m, 4H); 3.63 (s, 2H); 3.42 (t, 2H); 3.27 (s, 3H); 3.20 (m, 4H); 2.95 (t, 2H); 1.94 (m, 2H).

EXAMPLE 18

N-(2-methoxyphenyl)-N'-(3-(5-(2-((4-morpholin-4-ylphenyl)amino)pyrimidin-4-yl)imidazo[2,1-b][1,3]thiazol-6-yl)phenyl)urea The title compound was prepared as described in EXAMPLE 13, substituting 2-methoxyphenylisocyanate for phenylisocyanate. MS (ESI) m/e 619 (M+H)$^+$; $^1$H NMR (300 MHz, DMSO-d$_6$) δ 9.44 (s, 2H), 8.23 (d, 1H), 8.22 (s, 1H), 8.11 (dd, 1H), 7.72 (t, 1H), 7.53 (m, 3H), 7.47 (d, 1H), 7.39 (t, 1H), 7.19 (dt, 1H), 7.02 (dd, 1H), 6.91 (m, 4H), 6.57 (d, 1H), 3.88 (s, 3H), 3.74 (m, 4H), 3.05 (m, 4H).

EXAMPLE 19

N-(2-methylphenyl)-N'-(3-(5-(2-((4-morpholin-4-ylphenyl)amino)pyrimidin-4-yl)imidazo[2,1-b][1,3]thiazol-6-yl)phenyl)urea The title compound was prepared as described in EXAMPLE 13, substituting 2-methylphenylisocyanate for phenylisocyanate. MS (ESI) m/e 603 (M+H)$^+$; $^1$H NMR (300 MHz, DMSO-d$_6$) δ 9.42 (s, 1H), 9.16 (s, 1H), 8.23 (d, 1H), 7.93 (s, 1H), 7.81 (dd, 1H), 7.74 (t, 1H), 7.54 (m, 3H), 7.46 (d, 1H), 7.39 (t, 1H), 7.16 (m, 3H), 6.92 (m, 3H), 6.57 (d, 1H), 3.74 (m, 4H), 3.06 (m, 4H), 2.24 (s, 3H).

EXAMPLE 20

N-(3-methylphenyl)-N'-(3-(5-(2-((4-morpholin-4-ylphenyl)amino)pyrimidin-4-yl)imidazo[2,1-b][1,3]thiazol-6-yl)phenyl)urea The title compound was prepared as described in EXAMPLE 13, substituting 3-methylphenylisocyanate for phenylisocyanate. MS (ESI) m/e 603 (M+H)$^+$; $^1$H NMR (300 MHz, DMSO-d$_6$) δ 9.43 (s, 1H), 8.81 (s, 1H), 8.54 (s, 1H), 8.61 (s, 1H), 8.22 (d, 1H), 7.73 (m, 1H), 7.53 (m, 3H), 7.47 (d, 1H), 7.38 (t, 1H), 7.29 (m, 1H), 7.17 (m, 3H), 6.92 (d, 2H), 6.78 (d, 1H), 6.56 (d, 1H), 3.74 (m, 4H), 3.06 (m, 4H), 2.27 (s, 3H).

EXAMPLE 21

N-(4-methylphenyl)-N'-(3-(5-(2-((4-morpholin-4-ylphenyl)amino)pyrimidin-4-yl)imidazo[2,1-b][1,3]thiazol-6-yl)phenyl)urea The title compound was prepared as described in EXAMPLE 13, substituting 4-methylphenylisocyanate for phenylisocyanate. MS (ESI) m/e 603 (M+H)$^+$; $^1$H NMR (300 MHz, DMSO-d$_6$) δ 9.43 (s, 1H), 8.78 (s, 2H), 8.57 (s, 1H), 8.22 (dd, 1H), 7.71 (m, 1H), 7.53 (m, 3H), 7.47 (dd, 1H), 7.38 (td, 1H), 7.32 (dt, 2H), 7.18 (d, 1H), 7.07 (dd, 2H), 6.92 (dd, 2H), 6.56 (dd, 1H), 3.74 (m, 4H), 3.06 (m, 4H), 2.24 (s, 3H).

EXAMPLE 22

N-(2-fluorophenyl)-N'-(3-(5-(2-((4-morpholin-4-ylphenyl)amino)pyrimidin-4-yl)imidazo[2,1-b][1,3]thiazol-6-yl)phenyl)urea The title compound was prepared as described in EXAMPLE 13, substituting 2-fluorophenylisocyanate for phenylisocyanate. MS (ESI) m/e 607 (M+H)$^+$; $^1$H NMR (300 MHz, DMSO-d$_6$) δ 9.44 (s, 1H), 9.21 (s, 1H), 8.75 (br s, 1H), 8.55 (d, 1H), 8.23 (d, 1H), 8.13 (td, 1H), 7.74 (m, 1H), 7.54 (m, 3H), 7.47 (d, 1H), 7.40 (t, 1H), 7.24 (m, 2H), 7.13 (m, 1H), 7.01 (m, 1H), 6.93 (d, 2H), 6.57 (d, 1H), 3.74 (m, 4H), 3.06 (m, 4H).

EXAMPLE 23

N-(3-fluorophenyl)-N'-(3-(5-(2-((4-morpholin-4-ylphenyl)amino)pyrimidin-4-yl)imidazo[2,1-b][1,3]thiazol-6-yl)phenyl)urea The title compound was prepared as described in EXAMPLE 13, substituting 3-fluorophenylisocyanate for phenylisocyanate. MS (ESI) m/e 607 (M+H)$^+$; $^1$H NMR (300 MHz, DMSO-d$_6$) δ 9.42 (s, 1H), 8.91 (s, 1H), 8.89 (s, 1H), 8.76 (br s, 1H), 8.22 (d, 1H), 7.72 (m, 1H), 7.54 (m, 3H), 7.47 (m, 2H), 7.39 (t, 1H), 7.30 (m, 1H), 7.22 (m, 1H), 7.13 (m, 1H), 6.92 (d, 2H), 6.77 (td, 1H), 6.56 (d, 1H), 3.74 (m, 4H), 3.06 (m, 4H).

EXAMPLE 24

N-(4-fluorophenyl)-N'-(3-(5-(2-((4-morpholin-4-ylphenyl)amino)pyrimidin-4-yl)imidazo[2,1-b][1,3]thiazol-6-yl)phenyl)urea The title compound was prepared as described in EXAMPLE 13, substituting 4-fluorophenylisocyanate for phenylisocyanate. MS (ESI) m/e 607 (M+H)$^+$; $^1$H NMR (300 MHz, DMSO-d$_6$) δ 9.43 (s, 1H), 8.81 (s, 1H), 8.77 (br s, 1H), 8.71 (s, 1H), 8.22 (d, 1H), 7.71 (m, 1H), 7.53 (m, 3H), 7.45 (m, 3H), 7.38 (t, 1H), 7.19 (m, 1H), 7.11 (m, 2H), 6.93 (m, 2H), 6.56 (d, 1H), 3.74 (m, 4H), 3.06 (m, 4H).

EXAMPLE 25

N-(2-chlorophenyl)-N'-(3-(5-(2-((4-morpholin-4-ylphenyl)amino)pyrimidin-4-yl)imidazo[2,1-b][1,3]thiazol-6-yl)phenyl)urea The title compound was prepared as described in EXAMPLE 13, substituting 2-chlorophenylisocyanate for phenylisocyanate. MS (ESI) m/e 623 (M+H)$^+$; $^1$H NMR (300 MHz, DMSO-d$_6$) δ 9.55 (s, 1H), 9.43 (s, 1H), 8.76 (br s, 1H), 8.31 (s, 1H), 8.23 (d, 1H), 8.15 (dd, 1H), 7.75 (m, 1H), 7.53 (m, 3H), 7.46 (m, 2H), 7.41 (t, 1H), 7.29 (m, 1H), 7.23 (m, 1H), 7.03 (m, 1H), 6.93 (d, 2H), 6.57 (d, 1H), 3.74 (m, 4H), 3.06 (m, 4H).

EXAMPLE 26

N-(3-chlorophenyl)-N'-(3-(5-(2-((4-morpholin-4-ylphenyl)amino)pyrimidin-4-yl)imidazo[2,1-b][1,3]thiazol-6-yl)phenyl)urea The title compound was prepared as described in EXAMPLE 13, substituting 3-chlorophenylisocyanate for phenylisocyanate. MS (ESI) m/e 623 (M+H)$^+$; $^1$H NMR (300 MHz, DMSO-d$_6$) δ 9.44 (s, 1H), 8.90 (2s, 2H), 8.76 (br s, 1H), 8.22 (d, 1H), 7.71 (m, 2H), 7.53 (m, 3H), 7.47 (d, 1H), 7.39 (t, 1H), 7.29 (m, 2H), 7.21 (m, 1H), 7.01 (m, 1H), 6.92 (d, 2H), 6.57 (d, 1H), 3.74 (m, 4H), 3.06 (m, 4H).

EXAMPLE 27

N-(4-chlorophenyl)-N'-(3-(5-(2-((4-morpholin-4-ylphenyl)amino)pyrimidin-4-yl)imidazo[2,1-b][1,3]thiazol-6-yl)phenyl)urea The title compound was prepared as described in EXAMPLE 13, substituting 4-chlorophenylisocyanate for phenylisocyanate. MS (ESI) m/e 623 (M+H)$^+$; $^1$H NMR (300 MHz, DMSO-d$_6$) δ 9.44 (s, 1H), 8.86 (s, 1H), 8.83 (s, 1H), 8.76 (br s, 1H), 8.22 (d, 1H), 7.72 (m, 1H), 7.53 (m, 3H), 7.47 (m, 3H), 7.39 (t, 1H), 7.31 (m, 2H), 7.21 (m, 1H), 6.93 (d, 2H), 6.56 (d, 1H), 3.74 (m, 4H), 3.06 (m, 4H).

EXAMPLE 28

N-(3-methoxyphenyl)-N'-(3-(5-(2-((4-morpholin-4-ylphenyl)amino)pyrimidin-4-yl)imidazo[2,1-b][1,3]thiazol-6-yl)phenyl)urea The title compound was prepared as described in EXAMPLE 13, substituting 3-methoxyphenylisocyanate for phenylisocyanate. MS (ESI) m/e 619 (M+H)$^+$; $^1$H NMR (300 MHz, DMSO-d$_6$) δ 9.43 (s, 1H), 8.82 (s, 1H), 8.76 (br s, 1H), 8.71 (s, 1H), 8.22 (d, 1H), 7.73 (m, 1H), 7.53 (m, 3H), 7.47 (d, 1H), 7.38 (t, 1H), 7.29 (m, 1H), 7.18 (m, 3H), 6.93 (m, 3H), 6.55 (m, 2H), 3.74 (m, 4H), 3.72 (s, 3H), 3.06 (m, 4H).

EXAMPLE 29

N-(4-methoxyphenyl)-N'-(3-(5-(2-((4-morpholin-4-ylphenyl)amino)pyrimidin-4-yl)imidazo[2,1-b][1,3]thiazol-6-yl)phenyl)urea The title compound was prepared as described in EXAMPLE 13, substituting 4-methoxyphenylisocyanate for phenylisocyanate. MS (ESI) m/e 619 (M+H)$^+$; $^1$H NMR (300 MHz, DMSO-d$_6$) δ 9.42 (s, 1H), 8.76 (br s, 1H), 8.73 (s, 1H), 8.48 (s, 1H), 8.22 (d, 1H), 7.71 (m, 1H), 7.53 (m, 3H), 7.46 (d, 1H), 7.35 (m, 3H), 7.17 (m, 1H), 6.92 (d, 2H), 6.85 (d, 2H), 6.56 (d, 1H), 3.74 (m, 4H), 3.71 (s, 3H), 3.06 (m, 4H).

EXAMPLE 30

N-(3-(5-(2-((4-morpholin-4-ylphenyl)amino)pyrimidin-4-yl)imidazo[2,1-b][1,3]thiazol-6-yl)phenyl)-N'-(2-(trifluoromethyl)phenyl)urea The title compound was prepared as described in EXAMPLE 13, substituting 2-(trifluoromethyl)phenylisocyanate for phenylisocyanate. MS (ESI) m/e 657 (M+H)$^+$; $^1$H NMR (300 MHz, DMSO-d$_6$) δ 9.51 (s, 1H), 9.43 (s, 1H), 8.75 (br s, 1H), 8.23 (d, 1H), 8.08 (s, 1H), 7.94 (d, 1H), 7.75 (m, 1H), 7.64 (m, 2H), 7.54 (m, 3H), 7.46 (d, 1H), 7.40 (t, 1H), 7.26 (m, 2H), 6.93 (d, 2H), 6.57 (m, 2H), 3.75 (m, 4H), 3.06 (m, 4H).

EXAMPLE 31

N-(3-(5-(2-((4-morpholin-4-ylphenyl)amino)pyrimidin-4-yl)imidazo[2,1-b][1,3]thiazol-6-yl)phenyl)-N'-(3-(trifluoromethyl)phenyl)urea The title compound was prepared as described in EXAMPLE 13, substituting 3-(trifluoromethyl)phenylisocyanate for phenylisocyanate. MS (ESI) m/e 657 (M+H)$^+$; $^1$H NMR (300 MHz, DMSO-d$_6$) δ 9.44 (s, 1H), 9.08 (s, 1H), 8.97 (s, 1H), 8.76 (br s, 1H), 8.22 (d, 1H), 8.01 (m, 1H), 7.75 (m, 1H), 7.52 (m, 6H), 7.40 (t, 1H), 7.31 (m, 1H), 7.22 (dt, 1H), 6.93 (d, 2H), 6.56 (d, 1H), 3.74 (m, 4H), 3.06 (m, 4H).

EXAMPLE 32

N-(3-(5-(2-((4-morpholin-4-ylphenyl)amino)pyrimidin-4-yl)imidazo[2,1-b][1,3]thiazol-6-yl)phenyl)-N'-(4-(trifluoromethyl)phenyl)urea The title compound was prepared as described in EXAMPLE 13, substituting 4-(trifluoromethyl)phenylisocyanate for phenylisocyanate. MS (ESI) m/e 657 (M+H)$^+$; $^1$H NMR (300 MHz, DMSO-d$_6$) δ 9.44 (s, 1H), 9.13 (s, 1H), 8.97 (s, 1H), 8.76 (br s, 1H), 8.23 (d, 1H), 7.74 (m, 1H), 7.64 (m, 4H), 7.55 (m, 3H), 7.47 (d, 1H), 7.40 (t, 1H), 7.23 (dt, 1H), 6.93 (d, 2H), 6.56 (d, 1H), 3.74 (m, 4H), 3.06 (m, 4H).

EXAMPLE 33

N-(3-(5-(2-aminopyrimidin-4-yl)imidazo[2,1-b][1,3]thiazol-6-yl)phenyl)benzamide

EXAMPLE 33A

Into a 100 mL round-bottomed flask was added EXAMPLE 1C (1 g), iron (1 g), and NH$_4$Cl (0.1 g) in ethanol (27.8 ml) and water (6.96 ml). The mixture was allowed to stir at 85-90° C. for 0.5 hours. The mixture was cooled to room temperature, and diluted with ethyl acetate, and brine. The aqueous layer was extracted with ethyl acetate (3×25 mL). The combined organics were dried over MgSO$_4$, filtered and concentrated in vacuo to afford the title compound which was used without further purification.

EXAMPLE 33B

Into a 100 mL round-bottomed flask was added EXAMPLE 33A (0.48 g) and benzoyl chloride (0.238 ml) in tetrahydrofuran (9.33 ml). After the mixture had stirred at room temperature for 30 minutes, (polystyryl)trisamine resin (Argonaut Technologies, 3.41 mmol/g, 0.207 g, 0.725 mmol) was added. The mixture stirred overnight. The mixture was treated with triethylamine (4 mL), filtered and washed with CH$_2$Cl$_2$. The organics were concentrated in vacuo. The resulting solid was filtered, and washed with diethyl ether. The product was used in the next step without further purification.

EXAMPLE 33C

Into a 20 mL vial was added EXAMPLE 33B (0.76 g) in N-methylpyrrolidone (1 ml), followed by N,N-dimethylformamide di-tert-butyl acetal (2.52 ml). The mixture was allowed to stir at 90° C. for 2 hours. The mixture was cooled to room temperature, and concentrated in vacuo. The desired product containing some residual N-methylpyrrolidone was used in the next step without further purification.

EXAMPLE 33D

Into a 20 mL vial was added EXAMPLE 33C (0.875 g) in N-methylpyrrolidone (1 ml) followed by potassium carbonate (0.726 g) and guanidine hydrochloride (0.401 g). The mixture was allowed to stir at 90° C. overnight. Because a LC/MS of the crude mixture indicated that starting material remained, an additional 1 equivalent of $K_2CO_3$ and guanidine were added. After an additional 6 hours, the mixture was cooled to room temperature, diluted with water and extracted with $CH_2Cl_2$/methanol. The aqueous layer was extracted with $CH_2Cl_2$/methanol (3×10 mL). The combined the organic layers were dried over $MgSO_4$, filtered and concentrated. The residue was purified via reverse phase HPLC ($CH_3CN$/0.1% $NH_4OH$ in water) to afford the title compound. MS (ESI(+)) m/e 413 (M+H)$^+$; (ESI(−)) m/e 411 (M−H)$^−$; $^1$H-NMR (300 MHz, DMSO-$d_6$) ☐ 10.36 (s, 1H); 8.89 (d, 1H); 8.06 (d, 1H); 7.95 (dd, 2H); 7.92-7.89 (m, 1H); 7.62-7.51 (m, 3H); 7.48-7.42 (m, 2H); 7.33-7.31 (m, 1H); 6.81 (bs, 2H); 6.42 (d, 1H).

EXAMPLE 34

N-(3-(5-(2-((3-(acetylamino)phenyl)amino)pyrimidin-4-yl)imidazo[2,1-b][1,3]thiazol-6-yl)phenyl) benzamide

EXAMPLE 34A

Into a 100 mL round-bottomed flask were added EXAMPLE 12C (1 g), N-(3-aminophenyl)acetamide (0.840 g), and 12 N HCl (0.425 ml) in 2-propanol (13.98 ml) and the mixture was heated to 90° C. After 18 hours, the mixture was cooled to room temperature and diluted with 10 mL of cold isopropyl alcohol. The solid was filtered, and washed with diethyl ether. The solid was used in the next step without further purification.

EXAMPLE 34B

Into a 100 mL round-bottomed flask was added EXAMPLE 34A (1.7 g) and iron (1.7 g) in ethanol (26.8 ml). $NH_4Cl$ (0.179 g) in water (6.69 ml) was added and the mixture was heated to 90° C. After 30 minutes, the mixture was cooled to room temperature and diluted with $CH_2Cl_2$, and washed with saturated aqueous $NaHCO_3$. The organics were dried over $MgSO_4$, filtered, and concentrated in vacuo onto silica. The material was purified via an Intelliflash-280 purification system (hexanes:ethyl acetate) to afford the title compound.

EXAMPLE 34C

The title compound was prepared as described in EXAMPLE 12F, substituting benzoyl chloride for phenylacetyl chloride, and EXAMPLE 34B for EXAMPLE 12E. (ESI(+)) m/e 546 (M+H)$^+$; (ESI(−)) m/e 544 (M−H)$^−$; $^1$H-NMR (300 MHz, DMSO-$d_6$) ☐ 10.36 (s, 1H); 9.88 (s, 1H); 9.69 (s, 1H); 8.91 (bs, 1H); 8.28 (d, 1H); 8.09 (m, 1H); 8.01-7.92 (m, 4H); 7.62-7.53 (m, 2H); 7.52-7.47 (m, 2H); 7.45-7.41 (m, 1H); 7.37-7.34 (m, 1H); 7.22-7.20 (m, 2H); 6.64 (d, 1H); 2.04 (s, 3H).

EXAMPLE 35

N-(3-(5-(2-((3-(acetylamino)phenyl)amino)pyrimidin-4-yl)imidazo[2,1-b][1,3]thiazol-6-yl)phenyl)-2-phenylacetamide The title compound was prepared as described in EXAMPLE 12F, substituting EXAMPLE 34B for EXAMPLE 12E. MS (ESI(+)) m/e 560 (M+H)$^+$; $^1$H-NMR (300 MHz, DMSO-$d_6$) ☐ 10.28 (s, 1H); 9.88 (bs, 1H); 9.68 (s, 1H); 8.88 (d, 1H); 8.25 (d, 1H); 8.00 (bs, 1H); 7.86 (m, 1H); 7.74-7.71 (m, 1H); 7.47 (d, 1H); 7.43-7.38 (m, 2H); 7.34-7.32 (m, 4H); 7.29-7.24 (m, 2H); 7.22-7.20 (m, 2H); 6.58 (d, 1H); 3.65 (s, 2H); 2.04 (m, 3H).

EXAMPLE 36

N-(3-(5-(2-((4-(4-methylpiperazin-1-yl)phenyl) amino)pyrimidin-4-yl)imidazo[2,1-b][1,3]thiazol-6-yl)phenyl)-2-phenylacetamide

EXAMPLE 36A

The title compound was prepared as described in EXAMPLE 3A, substituting 4-(4-methylpiperazin-1-yl) aniline for 4-morpholinoaniline.

EXAMPLE 36B

The title compound was prepared as described in EXAMPLE 1E, substituting EXAMPLE 36A for phenyl guanidine.

EXAMPLE 36C

The title compound was prepared as described in EXAMPLE 1F, substituting EXAMPLE 36B for EXAMPLE 1E.

EXAMPLE 36D

N-(3-(5-(2-((4-(4-methylpiperazin-1-yl)phenyl) amino)pyrimidin-4-yl)imidazo[2,1-b][1,3]thiazol-6-yl)phenyl)-2-phenylacetamide A solution of EXAMPLE 36C (60 mg), phenylacetyl chloride (0.024 mL) and pyridine (0.020 mL) in $CH_2Cl_2$ (3 mL) and N-methylpyrrolidone (1 mL) was stirred for 8 hours. The mixture was concentrated and the residue was purified by HPLC using a reverse phase column eluting with a water and acetonitrile gradient containing 0.1% trifluoroacetic acid to afford the title compound as a trifluoroacetic acid salt. MS (ESI), m/e 601.3; (ESI), m/e 599.1 (M−H)$^−$; $^1$H-NMR (300 MHz, DMSO-$d_6$) ☐ ppm 10.30 (s, 1 H), 9.71 (bs, 1 H), 9.54 (s, 1 H), 8.76 (bs, 1 H), 8.21 (d, 1 H), 7.89 (s, 1 H), 7.70 (d, 1 H), 7.59 (d, 2 H), 7.48 (d, 1 H), 7.40 (t, 1 H), 7.23-7.35 (m, 5 H), 7.00 (d, 2 H), 6.54 (d, 1 H), 3.76-3.77 (m, 2 H), 3.65 (s, 2H), 3.54-3.56 (m, 2 H), 3.15-3.25 (m, 2 H), 2.85-2.95 (m, 2H), 2.88 (s, 3 H).

EXAMPLE 37

N-(3-(5-(2-((3-chlorophenyl)amino)pyrimidin-4-yl) imidazo[2,1-b][1,3]thiazol-6-yl)phenyl)-2-phenylacetamide

EXAMPLE 37A

The title compound was prepared as described in EXAMPLE 42A, substituting 3-chloroaniline for 4-(1H-imidazol-1-yl)aniline.

EXAMPLE 37B

The title compound was prepared as described in EXAMPLE 1, substituting EXAMPLE 37A for phenylguanidine in EXAMPLE 1E and phenylacetyl chloride for 2-chlorobenzoyl chloride in EXAMPLE 1G. MS (ESI(+)) m/e 537 (M+H)$^+$; $^1$H-NMR (300 MHz, DMSO-d$_6$) ☐ 10.29 (s, 1H); 9.90 (s, 1H); 8.83 (d, 1H); 8.33 (d, 1H); 8.01 (s, 1H); 7.88 (s, 1H); 7.71 (d, 1H); 7.61 (d, 1H); 7.53 (d, 1H); 7.41 (t, 1H); 7.35-7.22 (m, 7H); 7.02 (d, 1H); 6.65 (d, 1H).

EXAMPLE 38

N-(3-(5-(2-((3-methylphenyl)amino)pyrimidin-4-yl) imidazo[2,1-b][1,3]thiazol-6-yl)phenyl)-2-phenylacetamide

EXAMPLE 38A

The title compound was prepared as described in EXAMPLE 42A, substituting 3-methylaniline for 4-(1H-imidazol-1-yl)aniline.

EXAMPLE 38B

The title compound was prepared as described in EXAMPLE 1, substituting EXAMPLE 38A for phenylguanidine in EXAMPLE 1E and phenylacetyl chloride for 2-chlorobenzoyl chloride in EXAMPLE 1G. (ESI(+)) m/e 517 (M+H)$^+$; $^1$H-NMR (300 MHz, DMSO-d$_6$) ☐ 10.28 (s, 1H); 9.63 (s, 1H); 8.80 (d, 1H); 8.26 (d, 1H); 7.88 (s, 1H); 7.71 (d, 1H); 7.58 (s, 1H); 7.51 (d, 1H); 7.48 (d, 1H); 7.41 (t, 1H); 7.35-7.17 (m, 7H); 6.82 (d, 1H); 6.59 (d, 1H).

EXAMPLE 41

N-(3-(5-(2-((3-methoxyphenyl)amino)pyrimidin-4-yl)imidazo[2,1-b][1,3]thiazol-6-yl)phenyl)-2-phenylacetamide

EXAMPLE 41A

Into a 20 mL vial was added 1-(3-methoxyphenyl)guanidine nitrate (0.400 g) and EXAMPLE 1D (0.5 g) in N-methylpyrrolidone (5 ml), followed by K$_2$CO$_3$ (0.303 g). The mixture was allowed to stir at 85° C. After 24 hours, the mixture was cooled to room temperature, and diluted with water. The resulting solid was filtered, and washed with diethyl ether. The material was dissolved in CH$_2$Cl$_2$/methanol, and washed with water and brine. The resulting organics were dried over MgSO$_4$, filtered, and concentrated in vacuo onto silica. The material was purified via an Intelliflash-280 purification system (hexanes:ethyl acetate) to afford the title compound.

EXAMPLE 41B

Into a 100 mL round-bottomed flask was added EXAMPLE 41A (0.275 g) to a mixed solvent system of 9/1 N-methylpyrrolidone (2.025 ml)/hydrochloric acid, 37% (0.405 ml). The solution was heated to 90° C. for 5 minutes. SnCl$_2$ (0.553 g) was added, and the resulting mixture was allowed to stir at 90° C. After 1 hour, the mixture was cooled to room temperature, quenched with 10% NaOH, and stirred at room temperature for 20 minutes. The mixture was diluted with CH$_2$Cl$_2$ and water. The aqueous layer was extracted three times with CH$_2$Cl$_2$. The organics were combined, dried over MgSO$_4$, filtered, and concentrated in vacuo to afford the title compound, which was used in the next step without further purification.

EXAMPLE 41C

Into a 20 mL vial was added EXAMPLE 41B (1.5 ml) as a 0.2 M solution in CH$_2$Cl$_2$ and phenylacetyl chloride (0.038 ml). The mixture was allowed to stir at room temperature. After 30 minutes, the mixture was treated with (polystyryl) trisamine resin (Argonaut Technologies, 3.41 mmol/g, 3 equivalents) and stirred at room temperature overnight. The mixture was quenched with triethylamine, diluted with CH$_2$Cl$_2$, filtered, and the resin was washed with CH$_2$Cl$_2$. The organics were concentrated in vacuo onto silica. The residue was purified via an Analogix Intelliflash-280 purification system using a gradient elution (90% to 20% hexane/ethyl acetate; SF25-34 g column). MS (ESI(+)) m/e 533 (M+H)$^+$; (ESI(−)) m/e 531 (M−H)$^-$; $^1$H-NMR (300 MHz, DMSO-d$_6$) ☐ 10.29 (s, 1H); 9.68 (s, 1H); 8.86 (d, 1H); 8.27 (d, 1H); 7.88 (bs, 1H); 7.72 (d, 1H); 7.51 (d, 1H); 7.44-7.38 (m, 2H); 7.34-7.30 (m, 6H); 7.27-7.18 (m, 2H); 6.61-6.55 (m, 2H); 3.74 (s, 3H); 3.64 (m, 2H).

EXAMPLE 42

N-(3-(5-(2-((4-(1H-imidazol-1-yl)phenyl)amino) pyrimidin-4-yl)imidazo[2,1-b][1,3]thiazol-6-yl)phenyl)-2-phenylacetamide

EXAMPLE 42A 4-(1H-imidazol-1-yl)aniline (0.98 g), 2,2,10,10-tetramethyl-6-thioxo-3,9-dioxa-5,7-diazaundecane-4,8-dione (2.49 g) and polystryen-carbodiimide (Argonaut P/N 800371, 1.42 mmole/g, 6.3 g) were mixed with CH$_2$Cl$_2$ (60 mL) in a peptide flask and shaken at room temperature overnight. The solution was filtered and the resin was washed with CH$_2$Cl$_2$ (4×50 mL). The combined solution was concentrated and dissolved in 4N HCl in dioxane (50 mL) and stirred at room temperature overnight. The resulting solid was collected and washed with ether, then vacuum dried to afford the title compound.

EXAMPLE 42B

The title compound was prepared as described in EXAMPLE 1E, substituting EXAMPLE 42A for phenyl guanidine.

EXAMPLE 42C

The title compound was prepared as described in EXAMPLE 1F, substituting EXAMPLE 42B for EXAMPLE 1E.

EXAMPLE 42D

N-(3-(5-(2-((4-(1H-imidazol-1-yl)phenyl)amino)
pyrimidin-4-yl)imidazo[2,1-b][1,3]thiazol-6-yl)phenyl)-2-phenylacetamide The title compound was prepared as a trifluoroacetic acid salt as described in EXAMPLE 36, substituting EXAMPLE 42C for EXAMPLE 36C. MS (ESI), m/e 569.2; (ESI), m/e 567.1 (M−H)−; $^1$H-NMR (300 MHz, DMSO-$d_6$) ☐ ppm 10.31 (s, 1 H), 10.06 (s, 1 H), 9.60 (s, 1 H), 8.85 (bs, 1 H), 8.34 (d, 1 H), 8.23 (s, 1 H), 7.99 (d, 2 H), 7.91 (d, 2 H), 7.73 (d, 2 H), 7.69 (d, 1 H), 7.54 (d, 1 H), 7.41 (t, 1 H), 7.23-7.35 (m, 6 H), 6.69 (d, 1 H), 3.65 (s, 3 H).

EXAMPLE 43

N-(3-(5-(2-((4-(1H-imidazol-1-yl)phenyl)amino)
pyrimidin-4-yl)imidazo[2,1-b][1,3]thiazol-6-yl)phenyl)-2-phenylbutanamide The title compound was prepared as described in EXAMPLE 36, substituting EXAMPLE 42C for EXAMPLE 36C and 2-phenylbutanoyl chloride for phenylacetyl chloride. MS (ESI), m/e 597.3; (ESI), m/e 595.1 (M−H)−; $^1$H-NMR (300 MHz, DMSO-$d_6$) ☐ ppm 10.23 (s, 1 H), 10.04 (s, 1 H), 9.47 (s, 1 H), 8.84 (bs, 1 H), 8.32 (d, 1 H), 8.18 (s, 1 H), 7.98 (d, 2 H), 7.95 (s, 1 H), 7.84 (s, 1 H), 7.72 (d, 2 H), 7.67 (d, 1 H), 7.53 (d, 1 H), 7.23-7.40 (m, 7 H), 6.69 (d, 1 H), 3.59 (t, 1 H), 1.70 (m, 2H), 0.87 (t, 3 H).

EXAMPLE 44

N-(3-(5-(2-((4-(1,1-dioxidothiomorpholin-4-yl)phenyl)amino)pyrimidin-4-yl)imidazo[2,1-b][1,3]thiazol-6-yl)phenyl)-2-phenylacetamide

EXAMPLE 44A

The title compound was prepared as described in EXAMPLE 42A, substituting (4-aminophenyl)thiomorpholine-1,1-dioxide for 4-(1H-imidazol-1-yl)aniline.

EXAMPLE 44B

The title compound was prepared as described in EXAMPLE 1E, substituting EXAMPLE 44A for phenyl guanidine.

EXAMPLE 44C

The title compound was prepared as described in EXAMPLE 1F, substituting EXAMPLE 44B for EXAMPLE 1E.

EXAMPLE 44D

N-(3-(5-(2-((4-(1,1-dioxidothiomorpholin-4-yl)phenyl)amino)pyrimidin-4-yl)imidazo[2,1-b][1,3]thiazol-6-yl)phenyl)-2-phenylacetamide The title compound was prepared as a trifluoroacetic acid salt as described in EXAMPLE 36D, substituting EXAMPLE 44C for EXAMPLE 36C. MS (ESI), m/e 636.2; (ESI), m/e 634.0 (M−H)−; $^1$H-NMR (300 MHz, DMSO-$d_6$) ☐ ppm 10.29 (s, 1 H), 9.53 (s, 1 H), 8.76 (bs, 1 H), 8.21 (d, 1 H), 7.88 (s, 1 H), 7.71 (d, 1 H), 7.57 (d, 2 H), 7.48 (d, 1 H), 7.40 (t, 1 H), 7.23-7.35 (m, 6 H), 7.02 (d, 2 H), 6.54 (d, 1 H), 3.67-3.70 (m, 4 H), 3.65 (s, 2H), 3.16-3.17 (m, 4 H).

EXAMPLE 45

N-(3-(5-(2-((4-(1,1-dioxidothiomorpholin-4-yl)phenyl)amino)pyrimidin-4-yl)imidazo[2,1-b][1,3]thiazol-6-yl)phenyl)-2-(3-methoxyphenyl)acetamide The title compound was prepared as described in EXAMPLE 36D, substituting EXAMPLE 44C for EXAMPLE 36C and 2-(3-methoxyphenyl)acetyl chloride for phenylacetyl chloride. MS (ESI), m/e 666.2; (ESI), m/e 663.9 (M−H)−; $^1$H-NMR (300 MHz, DMSO-$d_6$) ☐ ppm 10.27 (s, 1 H), 9.56 (s, 1 H), 8.76 (bs, 1 H), 8.21 (d, 1 H), 7.88 (s, 1 H), 7.71 (d, 1 H), 7.57 (d, 2 H), 7.49 (d, 1 H), 7.40 (t, 1 H), 7.28 (d, 1 H), 7.21-7.25 (m, 2 H), 7.03 (d, 2 H), 6.90-6.91 (m, 2 H), 6.81-6.83 (m, 2 H), 6.54 (d, 1 H), 3.74 (s, 3 H), 3.70-3.73 (m, 4 H), 3.61 (s, 2H), 3.14-3.17 (m, 4 H).

EXAMPLE 46

N-(3-(5-(2-((4-(1,1-dioxidothiomorpholin-4-yl)phenyl)amino)pyrimidin-4-yl)imidazo[2,1-b][1,3]thiazol-6-yl)phenyl)-2-(4-methoxyphenyl)acetamide The title compound was prepared as described in EXAMPLE 36, substituting EXAMPLE 44C for EXAMPLE 36C and 2-(4-methoxyphenyl)acetyl chloride for phenylacetyl chloride. MS (ESI), m/e 666.2; (ESI), m/e 664.0 (M−H)−; $^1$H-NMR (300 MHz, DMSO-$d_6$) ☐ ppm 10.23 (s, 1 H), 9.57 (s, 1 H), 8.76 (bs, 1 H), 8.21 (d, 1 H), 7.87 (s, 1 H), 7.70 (d, 1 H), 7.56 (d, 2 H), 7.49 (d, 1 H), 7.40 (t, 1 H), 7.25 (d, 2 H), 7.17 (d, 1 H), 7.03 (d, 2H), 6.88 (d, 2 H), 6.54 (d, 1 H), 3.72 (s, 3 H), 3.70-3.73 (m, 4 H), 3.56 (s, 2 H), 3.14-3.17 (m, 4 H).

EXAMPLE 47

N-benzyl-N'-(3-(5-(2-((4-morpholin-4-ylphenyl)amino)pyrimidin-4-yl)imidazo[2,1-b][1,3]thiazol-6-yl)phenyl)urea Into a 4 mL vial was added EXAMPLE 3C (100 mg), (isocyanatomethyl)benzene (0.026 ml) and N-methylpyrrolidone (1.065 ml). The mixture was allowed to stir at room temperature for 72 hours. The mixture was diluted with methanol, filtered, and purified by reverse phase HPLC with acetonitrile and water as the solvent. The sample was freeze-dried to afford the title compound. MS (ESI(+)) m/e 603 (M+H)+; (ESI(−)) m/e 601 (M−H)−; $^1$H-NMR (300 MHz, DMSO-$d_6$) ☐ 9.41 (s, 1H), 8.74 (s, 1H), 8.20 (d, 1H), 7.68 (t, 1H), 7.47-7.57 (m, 3H), 7.46 (d, 1H), 7.27-7.38 (m, 5H), 7.20-7.27 (m, 1H), 7.12 (dt, 1H), 6.88-6.97 (m, 2H), 6.67 (t, 1H), 6.54 (d, 1H), 4.29 (d, 2H), 3.72-3.78 (m, 4H), 3.03-3.09 (m, 4H).

EXAMPLE 48

N-(3-(5-(2-((4-morpholin-4-ylphenyl)amino)pyrimidin-4-yl)imidazo[2,1-b][1,3]thiazol-6-yl)phenyl)-2-thien-2-ylacetamide The title compound was prepared as described in EXAMPLE 47, substituting 2-(thiophen-2-yl)acetyl chloride for (isocyanatomethyl)benzene. MS (ESI(+)) m/e 594 (M+H)+; (ESI(−)) m/e 592 (M−H)−; $^1$H-NMR (300 MHz, DMSO-d$_6$) □ 10.32 (s, 1H), 9.43 (s, 1H), 8.74 (s, 1H), 8.20 (d, 1H), 7.86 (t, 1H), 7.70 (ddd, 1H), 7.54 (d, 2H), 7.47 (d, 1H), 7.37-7.44 (m, 2H), 7.29 (dt, 1H), 6.90-7.01 (m, 4H), 6.52 (d, 1H), 3.88 (s, 2H), 3.72-3.77 (m, 4H), 3.03-3.09 (m, 4H).

EXAMPLE 49 phenyl 3-(5-(2-((4-morpholin-4-ylphenyl)amino) pyrimidin-4-yl)imidazo[2,1-b][1,3]thiazol-6-yl)phenylcarbamate The title compound was prepared as described in EXAMPLE 47, substituting phenyl carbonochloridate for (isocyanatomethyl)benzene. MS (ESI(+)) m/e 590 (M+H)$^+$; $^1$H-NMR (300 MHz, DMSO-d$_6$) □ 10.35 (s, 1H), 9.42 (s, 1H), 8.74 (bs, 1H), 8.22 (d, 1H), 7.76 (t, 1H), 7.64 (d, 1H), 7.54 (d, 2H), 7.39-7.48 (m, 4H), 7.19-7.31 (m, 4H), 6.52 (d, 1H), 3.72-3.78 (m, 4H), 3.03-3.09 (m, 4H).

EXAMPLE 50

N-(3-(5-(2-((3-((methylsulfonyl)amino)phenyl) amino)pyrimidin-4-yl)imidazo[2,1-b][1,3]thiazol-6-yl)phenyl)-2-phenylacetamide The title compound was prepared as described in EXAMPLE 12, substituting N-(3-aminophenyl)methanesulfonamide for 4-morpholinoaniline, and phenylacetyl chloride for 2,6-difluorobenzoyl chloride. MS (ESI(+)) m/e 596 (M+H)$^+$; (ESI(−)) m/e 594 (M−H)$^-$; $^1$H-NMR (300 MHz, DMSO-d$_6$) □ 10.28 (s, 1H); 9.74-9.70 (m, 2H); 8.88 (d, 1H); 8.26 (m, 1H); 7.87 (bs, 1H); 7.72 (d, 1H); 7.63 (m, 1H); 7.54-7.48 (m, 2H); 7.41 (t, 1H); 7.34-7.30 (m, 5H); 7.27-7.22 (m, 2H); 6.85 (m, 1H); 6.60 (d, 1H); 3.65 (s, 2H); 2.99 (s, 3H).

EXAMPLE 51

3-(1H-imidazol-4-yl)-N-(3-(5-(2-((4-morpholin-4-ylphenyl)amino)pyrimidin-4-yl)imidazo[2,1-b][1,3]thiazol-6-yl)phenyl)propanamide Into a 4 mL vial was added EXAMPLE 3C (69.8 mg), 1-ethyl-3-(3-(dimethylamino)propyl)-carbodiimide hydrochloride (31.3 mg), 1-hydroxybenzotriazole hydrate (34.1 mg) and N,N-dimethylformamide (1.486 mL). The mixture was allowed to stir for 10 minutes and 3-(1H-imidazol-4-yl) propanoic acid (25 mg) was added. The mixture was allowed to stir at room temperature for 72 hours. The mixture was diluted with methanol, filtered, and purified by reverse phase HPLC with acetonitrile and water as the solvent. The sample was freeze-dried to afford the title compound. MS (ESI(+)) m/e 592 (M+H)$^+$; (ESI(−)) m/e 590 (M−H)$^-$; $^1$H-NMR (300 MHz, DMSO-d$_6$) □ 10.12 (s, 1H), 9.43 (s, 1H), 8.75 (bs, 1H), 8.37 (s, 1H), 8.20 (d, 1H), 7.87 (t, 1H), 7.68 (ddd, 1H), 7.54 (d, 2H), 7.47 (d, 1H), 7.40 (t, 2H), 7.26 (dt, 1H), 6.89-6.96 (m, 2H), 6.51 (d, 1H), 4.08 (d, 1H), 3.71-3.78 (m, 4H), 3.17 (d, 3H), 3.02-3.09 (m, 4H), 2.90 (t, 2H), 2.69 (t, 2H).

EXAMPLE 52 ethyl 3-((4-(6-(3-((phenylacetyl)amino)phenyl)imidazo[2,1-b][1,3]thiazol-5-yl)pyrimidin-2-yl)amino) benzoate

EXAMPLE 52A

The title compound was prepared as described in EXAMPLE 3A, substituting ethyl 3-aminobenzoate for 4-morpholinoaniline.

EXAMPLE 52B

The title compound was prepared as described in EXAMPLE 3, substituting EXAMPLE 52A for 1-(4-morpholinophenyl)guanidine nitrate and phenylacetyl chloride for 2,6-difluorobenzoyl chloride. MS (ESI) m/e 575 (M+H)$^+$; $^1$H NMR (300 MHz, DMSO-d$_6$) δ 10.29 (s, 1H), 9.93 (s, 1H), 8.85 (d, 1H), 8.35 (m, 1H), 8.31 (d, 1H), 8.08 (m, 1H), 7.88 (m, 1H), 7.71 (m, 1H), 7.57 (m, 1H), 7.50 (d, 1H), 7.46 (t, 1H), 7.41 (t, 1H), 7.20-7.35 (m, 6H), 6.64 (d, 1H), 4.31 (q, 2H), 3.65 (s, 2H), 1.30 (t, 3H).

EXAMPLE 53 benzyl 3-(5-(2-((4-morpholin-4-ylphenyl)amino) pyrimidin-4-yl)imidazo[2,1-b][1,3]thiazol-6-yl)phenylcarbamate The title compound was prepared as described in EXAMPLE 47, substituting benzyl carbonochloridate for (isocyanatomethyl)benzene. MS (ESI(+)) m/e 604 (M+H)$^+$; $^1$H-NMR (300 MHz, DMSO-d$_6$) □ 9.90 (s, 1H), 9.43 (s, 1H), 8.75 (bs, 1H), 8.20 (d, 1H), 7.50-7.63 (m, 3H), 7.28-7.50 (m, 7H), 7.22 (dt, 1H), 6.87-6.98 (m, 2H), 6.50 (d, 1H), 5.15 (s, 2H), 3.72-3.79 (m, 4H), 2.99-3.10 (m, 4H).

EXAMPLE 54

4-methoxyphenyl 3-(5-(2-((4-morpholin-4-ylphenyl) amino)pyrimidin-4-yl)imidazo[2,1-b][1,3]thiazol-6-yl)phenylcarbamate The title compound was prepared as described in EXAMPLE 47, substituting 4-methoxyphenyl carbonochloridate for (isocyanatomethyl)benzene. MS (ESI(+)) m/e 620 (M+H)$^+$; $^1$H-NMR (300 MHz, DMSO-d$_6$) □ 10.28 (s, 1H), 9.43 (s, 1H), 8.75 (bs, 1H), 8.22 (d, 1H), 7.75 (s, 1H), 7.63 (s, 1H), 7.54 (d, 2H), 7.47 (d, 1H), 7.43 (t, 1H), 7.27 (d, 1H), 7.10-7.17 (m, 2H), 6.89-6.99 (m, 5H), 6.52 (d, 1H), 3.71-3.78 (m, 7H), 3.03-3.09 (m, 4H).

EXAMPLE 55

N-(3-(5-(2-((3-methylphenyl)amino)pyrimidin-4-yl) imidazo[2,1-b][1,3]thiazol-6-yl)phenyl)benzamide The title compound was prepared as described in EXAMPLE 1, substituting EXAMPLE 38A for phenylguanidine in EXAMPLE 1E and benzoyl chloride for 2-chlorobenzoyl chloride in EXAMPLE 1G. MS (ESI(+)) m/e 503 (M+H)$^+$; $^1$H-NMR (300 MHz, DMSO-d$_6$) □ 10.37 (s, 1H); 9.63 (s, 1H); 8.85 (d, 1H); 8.29 (d, 1H); 8.10 (s, 1H); 7.98-7.91 (m, 3H); 7.63-7.45 (m, 7H); 7.36 (d, 1H); 7.20 (t, 1H); 6.82 (d, 1H); 6.65 (d, 1H); 2.30 (s, 3H).

EXAMPLE 56

N-(3-(5-(2-((4-methylphenyl)amino)pyrimidin-4-yl) imidazo[2,1-b][1,3]thiazol-6-yl)phenyl)benzamide

EXAMPLE 56A

The title compound was prepared as described in EXAMPLE 42A, substituting 4-methylaniline for 4-(1H-imidazol-1-yl)aniline.

EXAMPLE 56B

The title compound was prepared as described in EXAMPLE 1 by substituting EXAMPLE 56A for phenylguanidine in EXAMPLE 1E and benzoyl chloride for 2-chlorobenzoyl chloride in EXAMPLE 1G. MS (ESI(+)) m/e 503 (M+H)$^+$; $^1$H-NMR (300 MHz, DMSO-d$_6$) □ 10.36 (s, 1H); 9.59 (s, 1H); 8.82 (d, 1H); 8.27 (d, 1H); 8.09 (s, 1H); 7.98-7.91 (m, 3H); 7.62-7.44 (m, 7H); 7.35 (d, 1H); 7.13 (d, 2H); 6.62 (d, 1H); 2.27 (s, 3H).

EXAMPLE 57

N-(3-(5-(2-((4-methylphenyl)amino)pyrimidin-4-yl)imidazo[2,1-b][1,3]thiazol-6-yl)phenyl)-2-phenylacetamide The title compound was prepared as described in EXAMPLE 1, substituting EXAMPLE 56A for phenylguanidine in EXAMPLE 1E and phenylacetyl chloride for 2-chlorobenzoyl chloride in EXAMPLE 1G. MS (ESI(+)) m/e 517 (M+H)$^+$; $^1$H-NMR (300 MHz, DMSO-d$_6$) □ 10.28 (s, 1H); 9.60 (s, 1H); 8.78 (d, 1H); 8.24 (d, 1H); 7.87 (s, 1H); 7.72 (d, 1H); 7.60 (d, 2H); 7.50 (d, 1H); 7.40 (t, 1H); 7.34-7.23 (m, 6H); 7.12 (d, 2H); 6.56 (d, 1H); 3.64 (s, 2H); 2.27 (s, 3H).

EXAMPLE 58

N-(3-(5-(2-((2-methylphenyl)amino)pyrimidin-4-yl)imidazo[2,1-b][1,3]thiazol-6-yl)phenyl)benzamide

EXAMPLE 58A

The title compound was prepared as described in EXAMPLE 42A, substituting 2-methylaniline for 4-(1H-imidazol-1-yl)aniline.

EXAMPLE 58B

The title compound was prepared as described in EXAMPLE 1, substituting EXAMPLE 58A for phenylguanidine in EXAMPLE 1E and benzoyl chloride for 2-chlorobenzoyl chloride in EXAMPLE 1G. MS (ESI(+)) m/e 503 (M+H)$^+$; $^1$H-NMR (300 MHz, DMSO-d$_6$) □ 10.38 (s, 1H); 9.14 (s, 1H); 8.30 (bs, 1H); 8.17 (d, 1H); 8.07 (s, 1H); 7.97-7.91 (m, 3H); 7.63-7.43 (m, 5H); 7.33 (m, 3H); 7.26 (t, 1H); 7.18 (t, 1H); 6.58 (d, 1H); 2.25 (s, 3H).

EXAMPLE 59

N-(3-(5-(2-((2-chlorophenyl)amino)pyrimidin-4-yl)imidazo[2,1-b][1,3]thiazol-6-yl)phenyl)benzamide

EXAMPLE 59A

The title compound was prepared as described in EXAMPLE 42A, substituting 2-chlororaniline for 4-(1H-imidazol-1-yl)aniline.

EXAMPLE 59B

The title compound was prepared as described in EXAMPLE 1, substituting EXAMPLE 59A for phenylguanidine in EXAMPLE 1E and benzoyl chloride for 2-chlorobenzoyl chloride in EXAMPLE 1G. MS (ESI(+)) m/e 523 (M+H)$^+$; $^1$H-NMR (300 MHz, DMSO-d$_6$) □ 10.37 (s, 1H); 9.21 (s, 1H); 8.47 (d, 1H); 8.22 (d, 1H); 8.07 (s, 1H); 7.97-7.91 (m, 3H); 7.73 (d, 1H); 7.59-7.44 (m, 5H); 7.42-7.32 (m, 3H); 7.25 (t, 1H); 6.64 (d, 1H).

EXAMPLE 60

N-(3-(5-(2-((4-chlorophenyl)amino)pyrimidin-4-yl)imidazo[2,1-b][1,3]thiazol-6-yl)phenyl)benzamide

EXAMPLE 60 A

The title compound was prepared as described in EXAMPLE 42A, substituting 4-chlororaniline for 4-(1H-imidazol-1-yl)aniline.

EXAMPLE 60B

The title compound was prepared as described in EXAMPLE 1, substituting EXAMPLE 60 A for phenylguanidine in EXAMPLE 1E and benzoyl chloride for 2-chlorobenzoyl chloride in EXAMPLE 1G. MS (ESI(+)) m/e 523 (M+H)$^+$; $^1$H-NMR (300 MHz, DMSO-d$_6$) □ 10.37 (s, 1H); 9.84 (s, 1H); 8.82 (d, 1H); 8.32 (d, 1H); 8.09 (s, 1H); 7.97-7.91 (m, 3H); 7.79 (d, 2H); 7.60-7.44 (m, 5H); 7.36 (m, 3H); 6.69 (d, 1H).

EXAMPLE 61

N-(3-(5-(2-((4-chlorophenyl)amino)pyrimidin-4-yl)imidazo[2,1-b][1,3]thiazol-6-yl)phenyl)-2-phenylacetamide The title compound was prepared as described in EXAMPLE 1, substituting EXAMPLE 60 A for phenylguanidine in EXAMPLE 1E and phenylacetyl chloride for 2-chlorobenzoyl chloride in EXAMPLE 1G. MS (ESI(+)) m/e 537 (M+H)$^+$; $^1$H-NMR (300 MHz, DMSO-d$_6$) □ 10.29 (s, 1H); 9.84 (s, 1H); 8.80 (d, 1H); 8.29 (d, 1H); 7.88 (s, 1H); 7.78 (d, 2H); 7.71 (d, 1H); 7.53 (d, 1H); 7.43-7.22 (m, 9H); 6.63 (d, 1H); 3.64 (s, 2H).

EXAMPLE 62

3-((4-(6-(3-((phenylacetyl)amino)phenyl)imidazo[2,1-b][1,3]thiazol-5-yl)pyrimidin-2-yl)amino)benzoic acid EXAMPLE 52 (1.14 g) was dissolved in tetrahydrofuran:methanol:water (12:4:4 mL). Lithium hydroxide hydrate (0.250 g) was added, and the resulting solution stirred 4 hours at room temperature. The mixture was acidified with 1N HCl and filtered. The solid was washed with water and ether and collected. MS (ESI) m/e 547 (M+H)$^+$; $^1$H NMR (300 MHz, DMSO-d$_6$) δ 10.35 (s, 1H), 9.94 (s, 1H), 8.86 (d, 1H), 8.34 (m, 1H), 8.30 (d, 1H), 8.03 (m, 1H), 7.89 (m, 1H), 7.73 (m, 1H), 7.57 (m, 1H), 7.50 (d, 1H), 7.42 (m, 2H), 7.20-7.35 (m, 6H), 6.61 (d, 1H), 3.66 (s, 2H).

EXAMPLE 63

N-(3-(5-(2-((2-methylphenyl)amino)pyrimidin-4-yl)imidazo[2,1-b][1,3]thiazol-6-yl)phenyl)-2-phenylacetamide The title compound was prepared as described in EXAMPLE 1, substituting EXAMPLE 58A for phenylguanidine in EXAMPLE 1E and phenylacetyl chloride for 2-chlorobenzoyl chloride in EXAMPLE 1G. MS (ESI(+)) m/e 517 (M+H)$^+$; $^1$H-NMR (300 MHz, DMSO-d$_6$) □ 10.28 (s, 1H); 8.98 (s, 1H); 8.28 (bs, 1H); 8.15 (d, 1H); 7.84 (s, 1H); 7.71 (d, 1H); 7.44-7.37 (m, 2H); 7.34-7.21 (m, 9H); 7.15 (t, 1H); 6.50 (d, 1H); 3.65 (s, 2H); 2.25 (s, 3H).

EXAMPLE 64

N-(3-(5-(2-((2-chlorophenyl)amino)pyrimidin-4-yl) imidazo[2,1-b][1,3]thiazol-6-yl)phenyl)-2-phenylacetamide The title compound was prepared as described in EXAMPLE 1, substituting EXAMPLE 59A for phenylguanidine in EXAMPLE 1E and phenylacetyl chloride for 2-chlorobenzoyl chloride in EXAMPLE 1G. MS (ESI(+)) m/e 537 (M+H)$^+$; $^1$H-NMR (300 MHz, DMSO-$d_6$) □ 10.29 (s, 1H); 9.20 (s, 1H); 8.44 (d, 1H); 8.19 (d, 1H); 7.85 (s, 1H); 7.72 (d, 2H); 7.57 (d, 1H); 7.43-7.22 (m, 10H); 6.58 (d, 1H); 3.65 (s, 2H).

EXAMPLE 65

N-(3-(5-(2-((4-(4-acetylpiperazin-1-yl)phenyl) amino)pyrimidin-4-yl)imidazo[2,1-b][1,3]thiazol-6-yl)phenyl)-2-phenylacetamide

EXAMPLE 65A

The title compound was prepared as described in EXAMPLE 42A, substituting 1-(4-(4-aminophenyl)piperazin-1-yl)ethanone for 4-(1H-imidazol-1-yl)aniline.

EXAMPLE 65B

The title compound was prepared as described in EXAMPLE 1E, substituting EXAMPLE 65A for phenyl guanidine.

EXAMPLE 65C

The title compound was prepared as described in EXAMPLE 1F, substituting EXAMPLE 65B for EXAMPLE 1E.

EXAMPLE 65D

N-(3-(5-(2-((4-(4-acetylpiperazin-1-yl)phenyl) amino)pyrimidin-4-yl)imidazo[2,1-b][1,3]thiazol-6-yl)phenyl)-2-phenylacetamide The title compound was prepared as a TFA salt as described in EXAMPLE 36D, substituting EXAMPLE 65C for EXAMPLE 36C. MS (ESI), m/e 627.1; $^1$H-NMR (300 MHz, DMSO-$d_6$) □ ppm 10.31 (s, 1 H), 9.48 (s, 1 H), 8.75 (bs, 1 H), 8.21 (d, 1 H), 7.87 (s, 1 H), 7.72 (d, 1 H), 7.55 (d, 2 H), 7.47 (d, 1 H), 7.40 (t, 1 H), 7.23-7.32 (m, 6 H), 6.97 (d, 2 H), 6.52 (d, 1 H), 3.65 (s, 2 H), 3.57-3.60 (m, 4 H), 3.08-3.13 (m, 2 H), 3.02-3.07 (m, 2 H), 2.05 (s, 3H).

EXAMPLE 66 benzyl 3-(5-(2-((4-(4-acetylpiperazin-1-yl)phenyl) amino)pyrimidin-4-yl)imidazo[2,1-b][1,3]thiazol-6-yl)phenylcarbamate A solution of EXAMPLE 65C (60 mg), benzyl chloroformate (0.025 mL) and pyridine (0.019 mL) in CH$_2$Cl$_2$ (3 mL) and N-methylpyrrolidone (0.5 mL) was stirred for 3 hours. The mixture was mixed with water. The resulting solid was collected and washed with more water, and vacuum dried to afford the title compound. MS (ESI), m/e 645.3; $^1$H-NMR (300 MHz, DMSO-$d_6$) □ ppm 9.91 (s, 1 H), 9.48 (s, 1 H), 8.75 (bs, 1 H), 8.21 (d, 1 H), 7.74 (s, 1 H), 7.54-7.59 (m, 3 H), 7.37-7.47 (m, 7 H), 7.22 (d, 1 H), 6.97 (d, 2 H), 6.51 (d, 1 H), 5.15 (s, 2 H), 3.58-3.60 (m, 4 H), 3.08-3.11 (m, 2 H), 3.02-3.05 (m, 2 H), 2.05 (s, 3H).

EXAMPLE 67

N-(3-(5-(2-((4-(2-oxopyrrolidin-1-yl)phenyl)amino) pyrimidin-4-yl)imidazo[2,1-b][1,3]thiazol-6-yl)phenyl)-2-phenylacetamide

EXAMPLE 67A

The title compound was prepared as described in EXAMPLE 42A, substituting 1-(4-aminophenyl)pyrrolidin-2-one for 4-(1H-imidazol-1-yl)aniline.

EXAMPLE 67B

The title compound was prepared as described in EXAMPLE 1E, substituting EXAMPLE 67A for phenyl guanidine.

EXAMPLE 67C

The title compound was prepared as described in EXAMPLE 1F, substituting EXAMPLE 67B for EXAMPLE 1E.

EXAMPLE 67D

N-(3-(5-(2-((4-(2-oxopyrrolidin-1-yl)phenyl)amino) pyrimidin-4-yl)imidazo[2,1-b][1,3]thiazol-6-yl)phenyl)-2-phenylacetamide The title compound was prepared as a TFA salt as described in EXAMPLE 36D, substituting EXAMPLE 67C for EXAMPLE 36C. MS (ESI), m/e 586.2; (ESI), m/e 584.1 (M−H)$^-$; $^1$H-NMR (300 MHz, DMSO-$d_6$) □ ppm 10.30 (s, 1 H), 9.70 (s, 1 H), 8.81 (bs, 1 H), 8.25 (d, 1 H), 7.88 (s, 1 H), 7.70-7.73 (m, 3 H), 7.59 (d, 2 H), 7.50 (d, 1 H), 7.40 (t, 1 H), 7.23-7.33 (m, 6 H), 6.58 (d, 1 H), 3.83 (t, 2 H), 3.65 (s, 2 H), 2.48 (t, 2 H), 2.07 (p, 3H).

EXAMPLE 68 benzyl 3-(5-(2-((4-(2-oxopyrrolidin-1-yl)phenyl) amino)pyrimidin-4-yl)imidazo[2,1-b][1,3]thiazol-6-yl)phenylcarbamate This compound was prepared as described in EXAMPLE 66, substituting EXAMPLE 67C for EXAMPLE 65C. MS (ESI), m/e 602.2; $^1$H-NMR (300 MHz, DMSO-$d_6$) □ 9.91 (s, 1 H), 9.68 (s, 1 H), 8.82 (bs, 1 H), 8.25 (d, 1 H), 7.74 (s, 1 H), 7.70 (d, 2 H), 7.58-7.60 (m, 3 H), 7.49 (d, 1 H), 7.35-7.44 (m, 6 H), 7.24 (d, 1 H), 6.56 (d, 1 H), 3.83 (t, 2 H), 2.48 (t, 2 H), 2.06 (p, 3H).

EXAMPLE 69

2-(2-methylphenyl)-N-(3-(5-(2-((4-morpholin-4-ylphenyl)amino)pyrimidin-4-yl)imidazo[2,1-b][1,3] thiazol-6-yl)phenyl)acetamide To a suspension of EXAMPLE 3C (22.5 mg) in N,N-dimethylformamide (0.375 mL) was added 2-o-tolylacetic acid (1.1 eq) in N,N-dimethylformamide (0.26 mL), O-(7-azabenzotriazol-1-yl)-N,N,N',N'-tetramethyluronium hexafluorophosphate (1.0 eq) in N,N-dimethylformamide (0.375 mL), and diisopropylethylamine (2.0 eq) in N,N-dimethylformamide (0.375 mL). The mixture was heated at 80° C. for 18 hours. The resulting solution was filtered through a 2 g Si-Carbonate SPE column and concentrated. The mixture was purified by HPLC on a Waters Nova-Pak® HR C18 6 um 60 Å Prep-Pak® cartridge column (25 mm×100 mm, acetonitrile: 10 mM ammonium acetate) to afford the title compound. MS (ESI) m/e 600 (M−H)$^-$; $^1$H NMR (300 MHz, DMSO-d$_6$) δ 8.71 (br s, 1H), 8.19 (d, 1H), 7.88 (m, 1H), 7.68 (m, 1H), 7.52 (d, 2H), 7.43 (m, 2H), 7.28 (m, 1H), 7.24 (m, 1H), 7.16 (m, 3H), 6.97 (d, 2H), 6.53 (d, 1H), 3.76 (m, 4H), 3.69 (s, 2H), 3.06 (m, 4H), 2.29 (s, 3H).

EXAMPLE 70

2-(3-methylphenyl)-N-(3-(5-(2-((4-morpholin-4-ylphenyl)amino)pyrimidin-4-yl)imidazo[2,1-b][1,3]thiazol-6-yl)phenyl)acetamide The title compound was prepared as described in EXAMPLE 69, substituting 2-m-tolylacetic acid for 2-o-tolylacetic acid. MS (ESI) m/e 600 (M−H)$^-$; $^1$H NMR (300 MHz, DMSO-d$_6$) δ 8.70 (br s, 1H), 8.18 (d, 1H), 7.87 (m, 1H), 7.69 (m, 1H), 7.52 (d, 2H), 7.42 (m, 2H), 7.28 (m, 1H), 7.22 (t, 1H), 7.14 (m, 2H), 7.07 (m, 1H), 6.94 (d, 2H), 6.51 (d, 1H), 3.75 (m, 4H), 3.60 (s, 2H), 3.06 (m, 4H), 2.29 (s, 3H).

EXAMPLE 71

2-(4-methylphenyl)-N-(3-(5-(2-((4-morpholin-4-ylphenyl)amino)pyrimidin-4-yl)imidazo[2,1-b][1,3]thiazol-6-yl)phenyl)acetamide The title compound was prepared as described in EXAMPLE 69, substituting 2-p-tolylacetic acid for 2-o-tolylacetic acid. MS (ESI) m/e 602 (M+H)$^+$; $^1$H NMR (300 MHz, DMSO-d$_6$) δ 8.71 (br s, 1H), 8.18 (d, 1H), 7.86 (m, 1H), 7.68 (m, 1H), 7.52 (d, 2H), 7.42 (m, 2H), 7.27 (m, 1H), 7.22 (d, 2H), 7.14 (d, 2H), 6.94 (d, 2H), 6.51 (d, 1H), 3.76 (m, 4H), 3.59 (s, 2H), 3.06 (m, 4H), 2.27 (s, 3H).

EXAMPLE 72

N-(3-(5-(2-((4-morpholin-4-ylphenyl)amino)pyrimidin-4-yl)imidazo[2,1-b][1,3]thiazol-6-yl)phenyl)-2-(2-nitrophenyl)acetamide The title compound was prepared as described in EXAMPLE 69, substituting 2-(2-nitrophenyl)acetic acid for 2-o-tolylacetic acid. MS (ESI) m/e 633 (M+H)$^+$; $^1$H NMR (300 MHz, DMSO-d$_6$) δ 8.72 (br s, 1H), 8.18 (d, 1H), 8.07 (m, 1H), 7.84 (m, 1H), 7.72 (m, 1H), 7.63 (m, 1H), 7.57 (m, 2H), 7.52 (d, 2H), 7.42 (m, 2H), 7.28 (m, 1H), 6.94 (d, 2H), 6.53 (d, 1H), 4.14 (s, 2H), 3.76 (m, 4H), 3.06 (m, 4H).

EXAMPLE 73

2-(2-fluorophenyl)-N-(3-(5-(2-((4-morpholin-4-ylphenyl)amino)pyrimidin-4-yl)imidazo[2,1-b][1,3]thiazol-6-yl)phenyl)acetamide The title compound was prepared as described in EXAMPLE 69, substituting 2-(2-fluorophenyl)acetic acid for 2-o-tolylacetic acid. MS (ESI) m/e 606 (M+H)$^+$; $^1$H NMR (300 MHz, DMSO-d$_6$) δ 10.33 (s, 1H), 9.43 (s, 1H), 8.74 (br s, 1H), 8.21 (d, 1H), 7.86 (m, 1H), 7.71 (m, 1H), 7.53 (d, 2H), 7.46 (d, 1H), 7.41 (m, 2H), 7.29 (m, 2H), 7.17 (m, 2H), 6.92 (d, 2H), 6.52 (d, 1H), 3.74 (m, 4H), 3.73 (s, 2H), 3.06 (m, 4H).

EXAMPLE 74

2-(2-chlorophenyl)-N-(3-(5-(2-((4-morpholin-4-ylphenyl)amino)pyrimidin-4-yl)imidazo[2,1-b][1,3]thiazol-6-yl)phenyl)acetamide The title compound was prepared as described in EXAMPLE 69, substituting 2-(2-chlorophenyl)acetic acid for 2-o-tolylacetic acid. MS (ESI) m/e 620 (M−H)$^-$; $^1$H NMR (300 MHz, DMSO-d$_6$) δ 8.71 (br s, 1H), 8.18 (d, 1H), 7.86 (m, 1H), 7.69 (m, 1H), 7.52 (d, 2H), 7.43 (m, 3H), 7.37 (m, 1H), 7.31 (m, 3H), 6.94 (d, 2H), 6.52 (d, 1H), 3.76 (m, 4H), 3.68 (s, 2H), 3.06 (m, 4H).

EXAMPLE 75

2-(3-chlorophenyl)-N-(3-(5-(2-((4-morpholin-4-ylphenyl)amino)pyrimidin-4-yl)imidazo[2,1-b][1,3]thiazol-6-yl)phenyl)acetamide The title compound was prepared as described in EXAMPLE 69, substituting 2-(3-chlorophenyl)acetic acid for 2-o-tolylacetic acid. MS (ESI) m/e 620 (M−H)$^-$; $^1$H NMR (300 MHz, DMSO-d$_6$) δ 8.71 (br s, 1H), 8.18 (d, 1H), 7.86 (m, 1H), 7.69 (m, 1H), 7.52 (d, 2H), 7.26-7.45 (m, 7H), 6.94 (d, 2H), 6.51 (d, 1H), 3.76 (m, 4H), 3.68 (s, 2H), 3.06 (m, 4H).

EXAMPLE 76

2-(4-chlorophenyl)-N-(3-(5-(2-((4-morpholin-4-ylphenyl)amino)pyrimidin-4-yl)imidazo[2,1-b][1,3]thiazol-6-yl)phenyl)acetamide The title compound was prepared as described in EXAMPLE 69, substituting 2-(4-chlorophenyl)acetic acid for 2-o-tolylacetic acid. MS (ESI) m/e 620 (M−H)$^-$; $^1$H NMR (300 MHz, DMSO-d$_6$) δ 8.70 (br s, 1H), 8.18 (d, 1H), 7.86 (m, 1H), 7.68 (m, 1H), 7.52 (d, 2H), 7.35-7.44 (m, 6H), 7.28 (d, 1H), 6.94 (d, 2H), 6.51 (d, 1H), 3.76 (m, 4H), 3.66 (s, 2H), 3.06 (m, 4H).

EXAMPLE 77

2-(2-bromophenyl)-N-(3-(5-(2-((4-morpholin-4-ylphenyl)amino)pyrimidin-4-yl)imidazo[2,1-b][1,3]thiazol-6-yl)phenyl)acetamide The title compound was prepared as described in EXAMPLE 69, substituting 2-(2-bromophenyl)acetic acid for 2-o-tolylacetic acid. MS (ESI) m/e 666 (M+H)$^+$; $^1$H NMR (300 MHz, DMSO-d$_6$) δ 8.71 (br s, 1H), 8.19 (d, 1H), 7.88 (m, 1H), 7.68 (m, 1H), 7.61 (d, 1H), 7.52 (d, 2H), 7.42 (m, 3H), 7.37 (td, 1H), 7.29 (d, 1H), 7.23 (td, 1H), 6.94 (d, 2H), 6.54 (d, 1H), 3.86 (s, 2H), 3.76 (m, 4H), 3.06 (m, 4H).

EXAMPLE 78

2-(3-bromophenyl)-N-(3-(5-(2-((4-morpholin-4-ylphenyl)amino)pyrimidin-4-yl)imidazo[2,1-b][1,3]thiazol-6-yl)phenyl)acetamide The title compound was prepared as described in EXAMPLE 69, substituting 2-(3-bromophenyl)acetic acid for 2-o-tolylacetic acid. MS (ESI) m/e 666 (M+H)$^+$; $^1$H NMR (300 MHz, DMSO-d$_6$) δ 8.71 (br s, 1H), 8.19 (d, 1H), 7.86 (m, 1H), 7.68 (m, 1H), 7.53 (m, 3H), 7.46 (m, 1H), 7.42 (m, 2H), 7.27-7.35 (m, 3H), 7.18 (m, 1H), 6.94 (d, 2H), 6.52 (d, 1H), 3.76 (m, 4H), 3.67 (s, 2H), 3.06 (m, 4H).

EXAMPLE 79

2-(4-bromophenyl)-N-(3-(5-(2-((4-morpholin-4-ylphenyl)amino)pyrimidin-4-yl)imidazo[2,1-b][1,3]thiazol-6-yl)phenyl)acetamide The title compound was prepared as described in EXAMPLE 69, substituting 2-(4-bromophenyl)acetic acid for 2-o-tolylacetic acid. MS (ESI) m/e 666 (M+H)$^+$; $^1$H NMR (300 MHz, DMSO-d$_6$) δ 8.71 (br s, 1H), 8.18 (d, 1H), 7.86 (m, 1H), 7.67 (m, 1H), 7.52 (d, 4H), 7.43 (m, 2H), 7.29 (m, 3H), 6.94 (d, 2H), 6.51 (d, 1H), 3.76 (m, 4H), 3.64 (s, 2H), 3.06 (m, 4H).

EXAMPLE 80

N-(3-(5-(2-((4-morpholin-4-ylphenyl)amino)pyrimidin-4-yl)imidazo[2,1-b][1,3]thiazol-6-yl)phenyl)-2-(3-nitrophenyl)acetamide The title compound was prepared as described in EXAMPLE 69, substituting 2-(3-nitrophenyl)acetic acid for 2-o-tolylacetic acid. MS (ESI) m/e 633 (M+H)$^+$; $^1$H NMR (300 MHz, DMSO-d$_6$) δ 8.72 (br s, 1H), 8.23 (m, 1H), 8.18 (d, 1H), 8.14 (dd, 1H), 7.87 (m, 1H), 7.79 (m, 1H), 7.69 (m, 1H), 7.65 (t, 1H), 7.52 (d, 2H), 7.43 (m, 2H), 7.30 (d, 1H), 6.93 (d, 2H), 6.51 (d, 1H), 3.85 (s, 2H), 3.75 (m, 4H), 3.06 (m, 4H).

EXAMPLE 81

N-(3-(5-(2-((4-morpholin-4-ylphenyl)amino)pyrimidin-4-yl)imidazo[2,1-b][1,3]thiazol-6-yl)phenyl)-2-(4-nitrophenyl)acetamide The title compound was prepared as described in EXAMPLE 69, substituting 2-(4-nitrophenyl)acetic acid for 2-o-tolylacetic acid. MS (ESI) m/e 633 (M+H)$^+$; $^1$H NMR (300 MHz, DMSO-d$_6$) δ 8.73 (br s, 1H), 8.20 (m, 3H), 7.86 (m, 1H), 7.79 (m, 1H), 7.68 (m, 1H), 7.62 (d, 2H), 7.52 (d, 2H), 7.43 (m, 2H), 7.30 (d, 1H), 6.93 (d, 2H), 6.51 (d, 1H), 3.76 (m, 4H), 3.75 (s, 2H), 3.06 (m, 4H).

EXAMPLE 82

2-(1,1'-biphenyl-4-yl)-N-(3-(5-(2-((4-morpholin-4-ylphenyl)amino)pyrimidin-4-yl)imidazo[2,1-b][1,3]thiazol-6-yl)phenyl)acetamide The title compound was prepared as described in EXAMPLE 69, substituting 2-(biphenyl-4-yl)acetic acid for 2-o-tolylacetic acid. MS (ESI) m/e 664 (M+H)$^+$; $^1$H NMR (300 MHz, DMSO-d$_6$) δ 8.69 (br s, 1H), 8.19 (d, 1H), 7.89 (m, 1H), 7.69 (m, 1H), 7.64 (m, 4H), 7.52 (d, 2H), 7.45 (m, 6H), 7.37 (t, 1H), 7.29 (d, 1H), 6.93 (d, 2H), 6.52 (d, 1H), 3.76 (m, 4H), 3.70 (s, 2H), 3.06 (m, 4H).

EXAMPLE 83

2-(4-(dimethylamino)phenyl)-N-(3-(5-(2-((4-morpholin-4-ylphenyl)amino)pyrimidin-4-yl)imidazo[2,1-b][1,3]thiazol-6-yl)phenyl)acetamide The title compound was prepared as described in EXAMPLE 69, substituting 2-(4-(dimethylamino)phenyl) acetic acid for 2-o-tolylacetic acid. MS (ESI) m/e 629 (M−H)$^-$; $^1$H NMR (300 MHz, DMSO-d$_6$) δ 8.71 (br s, 1H), 8.18 (d, 1H), 7.85 (m, 1H), 7.68 (m, 1H), 7.52 (d, 2H), 7.41 (m, 2H), 7.26 (d, 1H), 7.16 (d, 2H), 6.94 (d, 2H), 6.89 (d, 2H), 6.51 (d, 1H), 3.76 (m, 4H), 3.49 (s, 2H), 3.06 (m, 4H), 2.85 (s, 6H).

EXAMPLE 84

N-(3-(5-(2-((4-morpholin-4-ylphenyl)amino)pyrimidin-4-yl)imidazo[2,1-b][1,3]thiazol-6-yl)phenyl)-2-(3-(trifluoromethyl)phenyl)acetamide The title compound was prepared as described in EXAMPLE 69, substituting 2-(3-(trifluoromethyl)phenyl) acetic acid for 2-o-tolylacetic acid. MS (ESI) m/e 656 (M+H)$^+$; $^1$H NMR (300 MHz, DMSO-d$_6$) δ 8.71 (br s, 1H), 8.18 (d, 1H), 7.87 (m, 1H), 7.69 (m, 2H), 7.64 (m, 2H), 7.59 (m, 1H), 7.52 (d, 2H), 7.43 (m, 2H), 7.29 (d, 1H), 6.94 (d, 2H), 6.51 (d, 1H), 3.79 (s, 2H), 3.76 (m, 4H), 3.06 (m, 4H).

EXAMPLE 85

N-(3-(5-(2-((4-morpholin-4-ylphenyl)amino)pyrimidin-4-yl)imidazo[2,1-b][1,3]thiazol-6-yl)phenyl)-2-(4-(trifluoromethyl)phenyl)acetamide The title compound was prepared as described in EXAMPLE 69, substituting 2-(4-(trifluoromethyl)phenyl) acetic acid for 2-o-tolylacetic acid. MS (ESI) m/e 656 (M+H)$^+$; $^1$H NMR (300 MHz, DMSO-d$_6$) δ 8.70 (br s, 1H), 8.19 (d, 1H), 7.87 (m, 1H), 7.69 (m, 3H), 7.56 (d, 2H), 7.52 (d, 2H), 7.43 (m, 2H), 7.29 (d, 1H), 6.93 (d, 2H), 6.52 (d, 1H), 3.78 (s, 2H), 3.75 (m, 4H), 3.06 (m, 4H).

EXAMPLE 86

N-(3-(5-(2-((4-morpholin-4-ylphenyl)amino)pyrimidin-4-yl)imidazo[2,1-b][1,3]thiazol-6-yl)phenyl)-2-(3-(trifluoromethoxy)phenyl)acetamide The title compound was prepared as described in EXAMPLE 69, substituting 2-(3-(trifluoromethoxy)phenyl) acetic acid for 2-o-tolylacetic acid. MS (ESI) m/e 670 (M−H)$^-$; $^1$H NMR (300 MHz, DMSO-d$_6$) δ 8.71 (br s, 1H), 8.18 (d, 1H), 7.87 (m, 1H), 7.68 (m, 1H), 7.52 (d, 2H), 7.48 (t, 1H), 7.42 (m, 2H), 7.38 (d, 1H), 7.34 (s, 1H), 7.29 (d, 1H), 7.26 (d, 1H), 6.94 (d, 2H), 6.51 (d, 1H), 3.76 (m, 4H), 3.73 (s, 2H), 3.06 (m, 4H).

EXAMPLE 87

N-(3-(5-(2-((4-morpholin-4-ylphenyl)amino)pyrimidin-4-yl)imidazo[2,1-b][1,3]thiazol-6-yl)phenyl)-2-(4-phenoxyphenyl)acetamide The title compound was prepared as described in EXAMPLE 69, substituting 2-(4-phenoxyphenyl)acetic acid for 2-o-tolylacetic acid. MS (ESI) m/e 680 (M+H)$^+$; $^1$H NMR (300 MHz, DMSO-d$_6$) δ 8.71 (br s, 1H), 8.18 (d, 1H), 7.88 (m, 1H), 7.69 (m, 1H), 7.52 (d, 2H), 7.35-7.44 (m, 6H), 7.28 (d, 1H), 7.14 (t, 1H), 6.98 (m, 4H), 6.93 (d, 2H), 6.52 (d, 1H), 3.76 (m, 4H), 3.64 (s, 2H), 3.06 (m, 4H).

EXAMPLE 88

2-(4-(benzyloxy)phenyl)-N-(3-(5-(2-((4-morpholin-4-ylphenyl)amino)pyrimidin-4-yl)imidazo[2,1-b][1,3]thiazol-6-yl)phenyl)acetamide The title compound was prepared as described in EXAMPLE 69, substituting 2-(4-(benzyloxy)phenyl)acetic acid for 2-o-tolylacetic acid. MS (ESI) m/e 694 (M+H)$^+$; $^1$H NMR (300 MHz, DMSO-d$_6$) δ 8.70 (br s, 1H), 8.19 (m, 1H), 7.86 (m, 1H), 7.68 (m, 1H), 7.52 (d, 2H), 7.40 (m, 5H), 7.32 (m, 1H), 7.27 (m, 1H), 6.94 (m, 3H), 6.51 (d, 1H), 5.08 (s, 2H), 3.76 (s, 2H), 3.75 (m, 4H), 3.06 (m, 4H).

EXAMPLE 89

N-(3-(5-(2-((4-morpholin-4-ylphenyl)amino)pyrimidin-4-yl)imidazo[2,1-b][1,3]thiazol-6-yl)phenyl)-2-(1-naphthyl)acetamide The title compound was prepared as described in EXAMPLE 69, substituting 2-(naphthalen-1-yl)acetic acid for 2-o-tolylacetic acid. $^1$H NMR (300 MHz, DMSO-d$_6$) δ 8.70 (br s, 1H), 8.18 (d, 1H), 8.14 (d, 1H), 7.95 (m, 1H), 7.87 (m, 2H), 7.69 (m, 1H), 7.47-7.58 (m, 6H), 7.43 (m, 2H), 7.29 (d, 1H), 6.93 (d, 2H), 6.53 (d, 1H), 4.16 (s, 2H), 3.75 (m, 4H), 3.06 (m, 4H).

EXAMPLE 90

N-(3-(5-(2-((4-morpholin-4-ylphenyl)amino)pyrimidin-4-yl)imidazo[2,1-b][1,3]thiazol-6-yl)phenyl)-2-(2-naphthyl)acetamide The title compound was prepared as described in EXAMPLE 69, substituting 2-(naphthalen-2-yl)acetic acid for 2-o-tolylacetic acid. MS (ESI) m/e 638 (M+H)$^+$; $^1$H NMR (300 MHz, DMSO-d$_6$) δ 8.70 (br s, 1H), 8.18 (d, 1H), 7.89 (m, 4H), 7.84 (s, 1H), 7.70 (m, 1H), 7.51 (m, 5H), 7.43 (m, 2H), 7.28 (d, 1H), 6.93 (d, 2H), 6.58 (d, 1H), 3.84 (s, 2H), 3.75 (m, 4H), 3.06 (m, 4H).

EXAMPLE 91

2-(2,5-dimethylphenyl)-N-(3-(5-(2-((4-morpholin-4-ylphenyl)amino)pyrimidin-4-yl)imidazo[2,1-b][1,3]thiazol-6-yl)phenyl)acetamide The title compound was prepared as described in EXAMPLE 69, substituting 2-(2,5-dimethylphenyl)acetic acid for 2-o-tolylacetic acid. MS (ESI) m/e 616 (M+H)$^+$; $^1$H NMR (300 MHz, DMSO-d$_6$) δ 8.70 (br s, 1H), 8.18 (d, 1H), 7.88 (m, 1H), 7.69 (m, 1H), 7.52 (d, 2H), 7.43 (m, 2H), 7.28 (d, 1H), 7.06 (m, 2H), 6.97 (m, 1H), 6.93 (d, 2H), 6.53 (d, 1H), 3.75 (m, 4H), 3.64 (s, 2H), 3.06 (m, 4H), 2.24 (s, 6H).

EXAMPLE 92

2-mesityl-N-(3-(5-(2-((4-morpholin-4-ylphenyl)amino)pyrimidin-4-yl)imidazo[2,1-b][1,3]thiazol-6-yl)phenyl)acetamide The title compound was prepared as described in EXAMPLE 69, substituting 2-mesitylacetic acid for 2-o-tolylacetic acid. MS (ESI) m/e 630 (M+H)$^+$; $^1$H NMR (300 MHz, DMSO-d$_6$) δ 8.71 (br s, 1H), 8.18 (d, 1H), 7.86 (m, 1H), 7.67 (m, 1H), 7.52 (d, 2H), 7.42 (m, 2H), 7.27 (d, 1H), 6.93 (d, 2H), 6.83 (s, 2H), 6.53 (d, 1H), 3.75 (m, 4H), 3.70 (s, 2H), 3.06 (m, 4H), 2.23 (s, 6H), 2.20 (s, 3H).

EXAMPLE 93

2-(3,5-dimethylphenyl)-N-(3-(5-(2-((4-morpholin-4-ylphenyl)amino)pyrimidin-4-yl)imidazo[2,1-b][1,3]thiazol-6-yl)phenyl)acetamide The title compound was prepared as described in EXAMPLE 69, substituting 2-(3,5-dimethylphenyl)acetic acid for 2-o-tolylacetic acid. MS (ESI) m/e 614 (M–H)$^-$; $^1$H NMR (300 MHz, DMSO-d$_6$) δ 8.71 (br s, 1H), 8.18 (d, 1H), 7.87 (m, 1H), 7.69 (m, 1H), 7.52 (d, 2H), 7.42 (m, 2H), 7.27 (d, 1H), 6.94 (m, 4H), 6.89 (s, 1H), 6.51 (d, 1H), 3.76 (m, 4H), 3.55 (s, 2H), 3.06 (m, 4H), 2.25 (s, 6H).

EXAMPLE 94

2-(2,3-dimethoxyphenyl)-N-(3-(5-(2-((4-morpholin-4-ylphenyl)amino)pyrimidin-4-yl)imidazo[2,1-b][1,3]thiazol-6-yl)phenyl)acetamide The title compound was prepared as described in EXAMPLE 69, substituting 2-(2,3-dimethoxyphenyl)acetic acid for 2-o-tolylacetic acid. MS (ESI) m/e 646 (M–H)$^-$; $^1$H NMR (300 MHz, DMSO-d$_6$) δ 8.70 (br s, 1H), 8.18 (d, 1H), 7.88 (m, 1H), 7.69 (m, 1H), 7.51 (d, 2H), 7.42 (m, 2H), 7.27 (d, 1H), 7.02 (t, 1H), 6.96 (dd, 1H), 6.93 (d, 2H), 6.85 (dd, 1H), 6.53 (d, 1H), 3.80 (s, 3H), 3.76 (m, 4H), 3.69 (s, 3H), 3.65 (s, 2H), 3.06 (m, 4H).

EXAMPLE 95

2-(2,4-dimethoxyphenyl)-N-(3-(5-(2-((4-morpholin-4-ylphenyl)amino)pyrimidin-4-yl)imidazo[2,1-b][1,3]thiazol-6-yl)phenyl)acetamide The title compound was prepared as described in EXAMPLE 69, substituting 2-(2,4-dimethoxyphenyl)acetic acid for 2-o-tolylacetic acid. MS (ESI) m/e 648 (M+H)$^+$; $^1$H NMR (300 MHz, DMSO-d$_6$) δ 8.71 (br s, 1H), 8.19 (d, 1H), 7.86 (m, 1H), 7.69 (m, 1H), 7.52 (d, 2H), 7.42 (m, 2H), 7.26 (d, 1H), 7.11 (d, 1H), 6.93 (d, 2H), 6.54 (m, 2H), 6.48 (dd, 1H), 3.76 (m, 4H), 3.75 (2s, 6H), 3.55 (s, 2H), 3.06 (m, 4H).

EXAMPLE 96

2-(2,5-dimethoxyphenyl)-N-(3-(5-(2-((4-morpholin-4-ylphenyl)amino)pyrimidin-4-yl)imidazo[2,1-b][1,3]thiazol-6-yl)phenyl)acetamide The title compound was prepared as described in EXAMPLE 69, substituting 2-(2,5-dimethoxyphenyl)acetic acid for 2-o-tolylacetic acid. MS (ESI) m/e 648 (M+H)$^+$; $^1$H NMR (300 MHz, DMSO-d$_6$) δ 8.71 (br s, 1H), 8.19 (d, 1H), 7.86 (m, 1H), 7.68 (m, 1H), 7.52 (d, 2H), 7.42 (m, 2H), 7.27 (d, 1H), 6.94 (d, 2H), 6.91 (d, 1H), 6.82 (m, 2H), 6.53 (d, 1H), 3.76 (m, 4H), 3.71 (s, 3H), 3.69 (s, 3H), 3.61 (s, 2H), 3.06 (m, 4H).

EXAMPLE 97

2-(3,4-dimethoxyphenyl)-N-(3-(5-(2-((4-morpholin-4-ylphenyl)amino)pyrimidin-4-yl)imidazo[2,1-b][1,3]thiazol-6-yl)phenyl)acetamide The title compound was prepared as described in EXAMPLE 69, substituting 2-(3,4-dimethoxyphenyl)acetic acid for 2-o-tolylacetic acid. MS (ESI) m/e 646 (M–H)⁻; ¹H NMR (300 MHz, DMSO-$d_6$) δ 8.71 (br s, 1H), 8.18 (d, 1H), 7.87 (m, 1H), 7.68 (m, 1H), 7.52 (d, 2H), 7.42 (m, 2H), 7.28 (d, 1H), 6.96 (d, 1H), 6.93 (d, 2H), 6.90 (d, 1H), 6.86 (dd, 1H), 6.51 (d, 1H), 3.76 (m, 4H), 3.74 (s, 3H), 3.73 (s, 3H), 3.56 (s, 2H), 3.06 (m, 4H).

EXAMPLE 98

2-(3,5-dimethoxyphenyl)-N-(3-(5-(2-((4-morpholin-4-ylphenyl)amino)pyrimidin-4-yl)imidazo[2,1-b][1,3]thiazol-6-yl)phenyl)acetamide The title compound was prepared as described in EXAMPLE 69, substituting 2-(3,5-dimethoxyphenyl)acetic acid for 2-o-tolylacetic acid. MS (ESI) m/e 648 (M+H)⁺; ¹H NMR (300 MHz, DMSO-$d_6$) δ 8.72 (br s, 1H), 8.18 (d, 1H), 7.86 (m, 1H), 7.68 (d, 1H), 7.52 (d, 2H), 7.42 (m, 2H), 7.28 (d, 1H), 6.94 (d, 2H), 6.52 (d, 2H), 6.51 (d, 1H), 6.39 (t, 1H), 3.76 (m, 4H), 3.73 (s, 6H), 3.57 (s, 2H), 3.06 (m, 4H).

EXAMPLE 99

2-(1,3-benzodioxol-5-yl)-N-(3-(5-(2-((4-morpholin-4-ylphenyl)amino)pyrimidin-4-yl)imidazo[2,1-b][1,3]thiazol-6-yl)phenyl)acetamide The title compound was prepared as described in EXAMPLE 69, substituting 2-(benzo[d][1,3]dioxol-5-yl)acetic acid for 2-o-tolylacetic acid. MS (ESI) m/e 632 (M+H)⁺; ¹H NMR (300 MHz, DMSO-$d_6$) δ 8.70 (br s, 1H), 8.18 (d, 1H), 7.86 (m, 1H), 7.67 (dd, 1H), 7.52 (d, 2H), 7.42 (m, 2H), 7.28 (d, 1H), 6.94 (d, 2H), 6.91 (d, 1H), 6.86 (d, 1H), 6.80 (dd, 1H), 6.51 (d, 1H), 5.97 (s, 2H), 3.76 (m, 4H), 3.55 (s, 2H), 3.06 (m, 4H).

EXAMPLE 100

N-(3-(5-(2-((4-morpholin-4-ylphenyl)amino)pyrimidin-4-yl)imidazo[2,1-b][1,3]thiazol-6-yl)phenyl)-2-(3,4,5-trimethoxyphenyl)acetamide The title compound was prepared as described in EXAMPLE 69, substituting 2-(3,4,5-trimethoxyphenyl)acetic acid for 2-o-tolylacetic acid. MS (ESI) m/e 676 (M–H)⁻; ¹H NMR (300 MHz, DMSO-$d_6$) δ 8.72 (br s, 1H), 8.17 (d, 1H), 7.87 (m, 1H), 7.69 (d, 1H), 7.52 (d, 2H), 7.43 (m, 2H), 7.28 (d, 1H), 6.94 (d, 2H), 6.67 (s, 2H), 6.51 (d, 1H), 3.76 (s, 6H), 3.75 (m, 4H), 3.64 (s, 3H), 3.58 (s, 2H), 3.06 (m, 4H).

EXAMPLE 101

2-(2,3-difluorophenyl)-N-(3-(5-(2-((4-morpholin-4-ylphenyl)amino)pyrimidin-4-yl)imidazo[2,1-b][1,3]thiazol-6-yl)phenyl)acetamide The title compound was prepared as described in EXAMPLE 69, substituting 2-(2,3-difluorophenyl)acetic acid for 2-o-tolylacetic acid. MS (ESI) m/e 624 (M+H)⁺; ¹H NMR (300 MHz, DMSO-$d_6$) δ 8.72 (br s, 1H), 8.18 (d, 1H), 7.86 (m, 1H), 7.68 (d, 1H), 7.52 (d, 2H), 7.43 (m, 2H), 7.28 (d, 1H), 7.25 (m, 2H), 7.17 (m, 1H), 6.94 (d, 2H), 6.52 (d, 1H), 3.76 (m, 6H), 3.06 (m, 4H).

EXAMPLE 102

2-(2,4-dichlorophenyl)-N-(3-(5-(2-((4-morpholin-4-ylphenyl)amino)pyrimidin-4-yl)imidazo[2,1-b][1,3]thiazol-6-yl)phenyl)acetamide The title compound was prepared as described in EXAMPLE 69, substituting 2-(2,4-dichlorophenyl)acetic acid for 2-o-tolylacetic acid. MS (ESI) m/e 654 (M–H)⁻; ¹H NMR (300 MHz, DMSO-$d_6$) δ 8.70 (br s, 1H), 8.19 (d, 1H), 7.86 (m, 1H), 7.67 (d, 1H), 7.54 (dd, 1H), 7.52 (d, 2H), 7.43 (m, 3H), 7.29 (d, 1H), 7.18 (dd, 1H), 6.94 (d, 2H), 6.53 (d, 1H), 3.85 (s, 2H), 3.76 (m, 4H), 3.06 (m, 4H).

EXAMPLE 103

2-(2,5-difluorophenyl)-N-(3-(5-(2-((4-morpholin-4-ylphenyl)amino)pyrimidin-4-yl)imidazo[2,1-b][1,3]thiazol-6-yl)phenyl)acetamide The title compound was prepared as described in EXAMPLE 69, substituting 2-(2,5-difluorophenyl)acetic acid for 2-o-tolylacetic acid. MS (ESI) m/e 622 (M–H)⁻; ¹H NMR (300 MHz, DMSO-$d_6$) δ 8.71 (br s, 1H), 8.19 (d, 1H), 7.85 (m, 1H), 7.65 (d, 1H), 7.52 (d, 2H), 7.43 (m, 2H), 7.29 (d, 1H), 7.24 (m, 2H), 7.17 (m, 1H), 6.94 (d, 2H), 6.52 (d, 1H), 3.76 (m, 4H), 3.06 (m, 4H).

EXAMPLE 104

2-(3,4-dichlorophenyl)-N-(3-(5-(2-((4-morpholin-4-ylphenyl)amino)pyrimidin-4-yl)imidazo[2,1-b][1,3]thiazol-6-yl)phenyl)acetamide The title compound was prepared as described in EXAMPLE 69, substituting 2-(3,4-dichlorophenyl)acetic acid for 2-o-tolylacetic acid. MS (ESI) m/e 654 (M–H)⁻; ¹H NMR (300 MHz, DMSO-$d_6$) δ 8.71 (br s, 1H), 8.19 (d, 1H), 7.86 (m, 1H), 7.67 (d, 1H), 7.60 (s, 1H), 7.58 (d, 1H), 7.52 (d, 2H), 7.42 (m, 2H), 7.29 (d, 1H), 7.31 (m, 1H), 6.94 (d, 2H), 6.51 (d, 1H), 3.76 (m, 4H), 3.69 (s, 2H), 3.06 (m, 4H).

EXAMPLE 105

2-(2,6-dichlorophenyl)-N-(3-(5-(2-((4-morpholin-4-ylphenyl)amino)pyrimidin-4-yl)imidazo[2,1-b][1,3]thiazol-6-yl)phenyl)acetamide The title compound was prepared as described in EXAMPLE 69, substituting 2-(2,6-dichlorophenyl)acetic acid for 2-o-tolylacetic acid. MS (ESI) m/e 656 (M+H)⁺; ¹H NMR (300 MHz, DMSO-$d_6$) δ 8.71 (br s, 1H), 8.19 (d, 1H), 7.86 (m, 1H), 7.66 (d, 1H), 7.52 (d, 2H), 7.49 (d, 2H), 7.43 (m, 2H), 7.35 (t, 1H), 6.94 (d, 2H), 6.53 (d, 1H), 4.07 (s, 2H), 3.76 (m, 4H), 3.06 (m, 4H).

EXAMPLE 106

N-(3-(5-(2-((4-morpholin-4-ylphenyl)amino)pyrimidin-4-yl)imidazo[2,1-b][1,3]thiazol-6-yl)phenyl)-2-furamide The title compound was prepared as described in EXAMPLE 69, substituting furan-2-carboxylic acid for 2-o-tolylacetic acid. MS (ESI) m/e 562 (M–H)⁻; ¹H NMR (300 MHz, DMSO-$d_6$) δ 8.71 (br s, 1H), 8.21 (d, 1H), 8.05 (m, 1H), 7.91 (m, 1H), 7.84 (dd, 1H), 7.52 (d, 2H), 7.48 (t, 1H), 7.43 (d, 1H), 7.35 (t, 2H), 6.95 (d, 2H), 6.71 (dd, 1H), 6.58 (d, 1H), 3.75 (m, 4H), 3.07 (m, 4H).

EXAMPLE 107

N-(3-(5-(2-((4-morpholin-4-ylphenyl)amino)pyrimidin-4-yl)imidazo[2,1-b][1,3]thiazol-6-yl)phenyl)-3-furamide The title compound was prepared as described in EXAMPLE 69, substituting furan-3-carboxylic acid for 2-o-tolylacetic acid. MS (ESI) m/e 562 (M−H)$^-$; $^1$H NMR (300 MHz, DMSO-d$_6$) δ 8.72 (br s, 1H), 8.37 (m, 1H), 8.21 (d, 1H), 8.01 (m, 1H), 7.82 (dd, 1H), 7.78 (m, 1H), 7.51 (d, 2H), 7.47 (t, 1H), 7.42 (d, 1H), 7.33 (d, 1H), 7.00 (m, 1H), 6.94 (d, 2H) 6.58 (d, 1H), 3.75 (m, 4H), 3.06 (m, 4H).

EXAMPLE 108

2,5-dimethyl-N-(3-(5-(2-((4-morpholin-4-ylphenyl)amino)pyrimidin-4-yl)imidazo[2,1-b][1,3]thiazol-6-yl)phenyl)-3-furamide The title compound was prepared as described in EXAMPLE 69, substituting 2,5-dimethylfuran-3-carboxylic acid for 2-o-tolylacetic acid. MS (ESI) m/e 590 (M−H)$^-$; $^1$H NMR (300 MHz, DMSO-d$_6$) δ 8.73 (br s, 1H), 8.20 (d, 1H), 8.01 (m, 1H), 7.81 (dd, 1H), 7.53 (d, 2H), 7.44 (t, 1H), 7.42 (d, 1H), 7.30 (d, 1H), 6.95 (d, 2H), 6.64 (s, 1H), 6.57 (d, 1H), 3.75 (m, 4H), 3.07 (m, 4H), 2.50 (s, 3H), 2.26 (s, 3H).

EXAMPLE 109

N-(3-(5-(2-((4-morpholin-4-ylphenyl)amino)pyrimidin-4-yl)imidazo[2,1-b][1,3]thiazol-6-yl)phenyl)thiophene-2-carboxamide The title compound was prepared as described in EXAMPLE 69, substituting thiophene-2-carboxylic acid for 2-o-tolylacetic acid. MS (ESI) m/e 578 (M−H)$^-$; $^1$H NMR (300 MHz, DMSO-d$_6$) δ 8.73 (br s, 1H), 8.22 (d, 1H), 8.02 (m, 2H), 7.84 (m, 2H), 7.51 (d, 2H), 7.48 (t, 1H), 7.43 (d, 1H), 7.34 (d, 1H), 7.24 (dd, 1H), 6.93 (d, 2H), 6.59 (d, 1H), 3.74 (m, 4H), 3.05 (m, 4H).

EXAMPLE 110

N-(3-(5-(2-((4-morpholin-4-ylphenyl)amino)pyrimidin-4-yl)imidazo[2,1-b][1,3]thiazol-6-yl)phenyl)thiophene-3-carboxamide The title compound was prepared as described in EXAMPLE 69, substituting thiophene-3-carboxylic acid for 2-o-tolylacetic acid. MS (ESI) m/e 578 (M−H)$^-$; $^1$H NMR (300 MHz, DMSO-d$_6$) δ 8.72 (br s, 1H), 8.34 (m, 1H), 8.22 (d, 1H), 8.03 (m, 1H), 7.85 (m, 1H), 7.64 (m, 2H), 7.51 (d, 2H), 7.48 (t, 1H), 7.43 (d, 1H), 7.33 (d, 1H), 6.93 (d, 2H), 6.59 (d, 1H), 3.74 (m, 4H), 3.05 (m, 4H).

EXAMPLE 111

3-methyl-N-(3-(5-(2-((4-morpholin-4-ylphenyl)amino)pyrimidin-4-yl)imidazo[2,1-b][1,3]thiazol-6-yl)phenyl)thiophene-2-carboxamide The title compound was prepared as described in EXAMPLE 69, substituting 3-methylthiophene-2-carboxylic acid for 2-o-tolylacetic acid. MS (ESI) m/e 592 (M−H)$^-$; $^1$H NMR (300 MHz, DMSO-d$_6$) δ 8.71 (br s, 1H), 8.22 (d, 1H), 7.96 (m, 1H), 7.78 (m, 1H), 7.65 (d, 1H), 7.51 (d, 2H), 7.47 (t, 1H), 7.42 (d, 1H), 7.33 (d, 1H), 7.03 (d, 1H), 6.93 (d, 2H), 6.59 (d, 1H), 3.75 (m, 4H), 3.06 (m, 4H), 2.45 (s, 3H).

EXAMPLE 112

5-methyl-N-(3-(5-(2-((4-morpholin-4-ylphenyl)amino)pyrimidin-4-yl)imidazo[2,1-b][1,3]thiazol-6-yl)phenyl)thiophene-2-carboxamide The title compound was prepared as described in EXAMPLE 69, substituting 5-methylthiophene-2-carboxylic acid for 2-o-tolylacetic acid. MS (ESI) m/e 578 (M−H)$^-$; $^1$H NMR (300 MHz, DMSO-d$_6$) δ 8.71 (br s, 1H), 8.22 (d, 1H), 7.96 (m, 2H), 7.78 (m, 1H), 7.65 (d, 1H), 7.51 (d, 2H), 7.47 (t, 1H), 7.42 (d, 1H), 7.33 (d, 1H), 7.03 (d, 1H), 6.93 (d, 2H), 6.59 (d, 1H), 3.75 (m, 4H), 3.06 (m, 4H), 2.45 (s, 3H).

EXAMPLE 113

N-(3-(5-(2-((4-morpholin-4-ylphenyl)amino)pyrimidin-4-yl)imidazo[2,1-b][1,3]thiazol-6-yl)phenyl)-1H-pyrrole-2-carboxamide The title compound was prepared as described in EXAMPLE 69, substituting 1H-pyrrole-2-carboxylic acid for 2-o-tolylacetic acid. MS (ESI) m/e 561 (M−H)$^-$; $^1$H NMR (300 MHz, DMSO-d$_6$) δ 8.72 (br s, 1H), 8.21 (d, 1H), 8.05 (m, 1H), 7.84 (m, 1H), 7.51 (d, 2H), 7.45 (t, 1H), 7.43 (d, 1H), 7.28 (d, 1H), 7.09 (m, 1H), 7.00 (m, 1H), 6.94 (d, 2H), 6.60 (d, 1H), 6.20 (dd, 1H), 3.74 (m, 4H), 3.06 (m, 4H).

EXAMPLE 114

1-methyl-N-(3-(5-(2-((4-morpholin-4-ylphenyl)amino)pyrimidin-4-yl)imidazo[2,1-b][1,3]thiazol-6-yl)phenyl)-1H-pyrrole-2-carboxamide The title compound was prepared as described in EXAMPLE 69, substituting 1-methyl-1H-pyrrole-2-carboxylic acid for 2-o-tolylacetic acid. MS (ESI) m/e 577 (M+H)$^+$; $^1$H NMR (300 MHz, DMSO-d$_6$) δ 8.73 (br s, 1H), 8.21 (d, 1H), 8.02 (m, 1H), 7.81 (m, 1H), 7.51 (d, 2H), 7.43 (m, 2H), 7.27 (d, 1H), 7.04 (m, 1H), 7.01 (m, 1H), 6.93 (d, 2H), 6.58 (d, 1H), 6.11 (dd, 1H), 3.87 (s, 3H), 3.74 (m, 4H), 3.06 (m, 4H).

EXAMPLE 115

N-(3-(5-(2-((4-morpholin-4-ylphenyl)amino)pyrimidin-4-yl)imidazo[2,1-b][1,3]thiazol-6-yl)phenyl)-1,3-thiazole-4-carboxamide The title compound was prepared as described in EXAMPLE 69, substituting thiazole-4-carboxylic acid for 2-o-tolylacetic acid. MS (ESI) m/e 579 (M−H)$^-$; $^1$H NMR (300 MHz, DMSO-d$_6$) δ 9.23 (d, 1H), 8.73 (br s, 1H), 8.49 (d, 1H), 8.21 (d, 1H), 8.16 (m, 1H), 7.90 (m, 1H), 7.51 (d, 2H), 7.49 (t, 1H), 7.43 (d, 1H), 7.35 (d, 1H), 6.93 (d, 2H), 6.58 (d, 1H), 3.74 (m, 4H), 3.06 (m, 4H).

EXAMPLE 116

N-(3-(5-(2-((4-morpholin-4-ylphenyl)amino)pyrimidin-4-yl)imidazo[2,1-b][1,3]thiazol-6-yl)phenyl)-1,3-thiazole-5-carboxamide The title compound was prepared as described in EXAMPLE 69, substituting thiazole-5-carboxylic acid for 2-o-tolylacetic acid. MS (ESI) m/e 579 (M−H)⁻; ¹H NMR (300 MHz, DMSO-d₆) δ 9.29 (s, 1H), 8.72 (br s, 1H), 8.69 (s, 1H), 8.22 (d, 1H), 8.01 (m, 1H), 7.82 (m, 1H), 7.51 (m, 3H) 7.42 (d, 1H), 7.37 (d, 1H), 6.94 (d, 2H), 6.58 (d, 1H), 3.75 (m, 4H), 3.06 (m, 4H).

EXAMPLE 117

N-(3-(5-(2-((4-morpholin-4-ylphenyl)amino)pyrimidin-4-yl)imidazo[2,1-b][1,3]thiazol-6-yl)phenyl)-1H-pyrazole-4-carboxamide The title compound was prepared as described in EXAMPLE 69, substituting 1H-pyrazole-4-carboxylic acid for 2-o-tolylacetic acid. MS (ESI) m/e 562 (M−H)⁻; ¹H NMR (300 MHz, DMSO-d₆) δ 8.73 (br s, 1H), 8.22 (m, 2H), 8.16 (m, 1H), 8.00 (m, 1H), 7.83 (m, 1H), 7.52 (m, 2H), 7.44 (m, 2H), 7.30 (d, 1H), 6.94 (d, 2H), 6.58 (d, 1H), 3.74 (m, 4H), 3.06 (m, 4H).

EXAMPLE 118

3,5-dimethyl-N-(3-(5-(2-((4-morpholin-4-ylphenyl)amino)pyrimidin-4-yl)imidazo[2,1-b][1,3]thiazol-6-yl)phenyl)isoxazole-4-carboxamide The title compound was prepared as described in EXAMPLE 69, substituting 3,5-dimethylisoxazole-4-carboxylic acid for 2-o-tolylacetic acid. MS (ESI) m/e 593 (M+H)⁺; ¹H NMR (300 MHz, DMSO-d₆) δ 8.71 (br s, 1H), 8.22 (d, 1H), 7.94 (m, 1H), 7.77 (dd, 1H), 7.53 (d, 2H), 7.48 (t, 1H), 7.42 (d, 1H), 7.36 (d, 1H), 6.95 (d, 2H), 6.59 (d, 1H), 3.76 (m, 4H), 3.07 (m, 4H), 2.55 (s, 3H), 2.33 (s, 3H).

EXAMPLE 119

5-methyl-N-(3-(5-(2-((4-morpholin-4-ylphenyl)amino)pyrimidin-4-yl)imidazo[2,1-b][1,3]thiazol-6-yl)phenyl)-3-phenylisoxazole-4-carboxamide The title compound was prepared as described in EXAMPLE 69, substituting 5-methyl-3-phenylisoxazole-4-carboxylic acid for 2-o-tolylacetic acid. MS (ESI) m/e 653 (M−H)⁻; ¹H NMR (300 MHz, DMSO-d₆) δ 8.69 (br s, 1H), 8.21 (d, 1H), 7.92 (m, 1H), 7.69 (m, 3H), 7.51 (m, 6H), 7.42 (d, 1H), 7.38 (d, 1H), 6.95 (d, 2H), 6.58 (d, 1H), 3.76 (m, 4H), 3.07 (m, 4H), 2.59 (s, 3H).

EXAMPLE 120

N-(3-(5-(2-((4-morpholin-4-ylphenyl)amino)pyrimidin-4-yl)imidazo[2,1-b][1,3]thiazol-6-yl)phenyl)pyridine-2-carboxamide The title compound was prepared as described in EXAMPLE 69, substituting picolinic acid for 2-o-tolylacetic acid. MS (ESI) m/e 575 (M+H)⁺; ¹H NMR (300 MHz, DMSO-d₆) δ 8.75 (d, 1H), 8.72 (br s, 1H), 8.24 (m, 1H), 8.21 (d, 1H), 8.16 (d, 1H), 8.08 (td, 1H), 7.95 (m, 1H), 7.69 (ddd, 1H), 7.53 (d, 2H), 7.51 (t, 1H), 7.44 (d, 1H), 7.37 (d, 1H), 6.97 (d, 2H), 6.59 (d, 1H), 3.75 (m, 4H), 3.08 (m, 4H).

EXAMPLE 121

N-(3-(5-(2-((4-morpholin-4-ylphenyl)amino)pyrimidin-4-yl)imidazo[2,1-b][1,3]thiazol-6-yl)phenyl)nicotinamide The title compound was prepared as described in EXAMPLE 69, substituting nicotinic acid for 2-o-tolylacetic acid. MS (ESI) m/e 573 (M−H)⁻; ¹H NMR (300 MHz, DMSO-d₆) δ 9.10 (d, 1H), 8.77 (dd, 1H), 8.72 (br s, 1H), 8.31 (dt, 1H), 8.22 (d, 1H), 8.07 (m, 1H), 7.88 (dd, 1H), 7.60 (dd, 1H), 7.5 m (m, 3H), 7.43 (d, 1H), 7.37 (d, 1H), 6.94 (d, 2H), 6.59 (d, 1H), 3.75 (m, 4H), 3.06 (m, 4H).

EXAMPLE 122

N-(3-(5-(2-((4-morpholin-4-ylphenyl)amino)pyrimidin-4-yl)imidazo[2,1-b][1,3]thiazol-6-yl)phenyl)isonicotinamide The title compound was prepared as described in EXAMPLE 69, substituting isonicotinic acid for 2-o-tolylacetic acid. MS (ESI) m/e 575 (M+H)⁺; ¹H NMR (300 MHz, DMSO-d₆) δ 8.78 (d, 2H), 8.73 (br s, 1H), 8.22 (m, 1H), 8.18 (d, 1H), 8.07 (m, 1H), 7.87 (m, 2H), 7.53 (m, 3H), 7.43 (d, 1H), 7.39 (d, 1H), 6.97 (d, 2H), 6.58 (d, 1H), 3.75 (m, 4H), 3.08 (m, 4H).

EXAMPLE 123

N-(3-(5-(2-((4-morpholin-4-ylphenyl)amino)pyrimidin-4-yl)imidazo[2,1-b][1,3]thiazol-6-yl)phenyl)-2-pyridin-2-ylacetamide The title compound was prepared as described in EXAMPLE 69, substituting 2-(pyridin-2-yl)acetic acid for 2-o-tolylacetic acid. MS (ESI) m/e 587 (M−H)⁻; ¹H NMR (300 MHz, DMSO-d₆) δ 8.72 (br s, 1H), 8.51 (d, 1H), 8.19 (d, 1H), 7.88 (m, 1H), 7.80 (td, 1H), 7.70 (m, 1H), 7.53 (m, 3H), 7.44 (m, 3H), 7.32 (dd, 1H), 7.29 (d, 1H), 6.94 (d, 2H), 6.52 (d, 1H), 3.76 (m, 6H), 3.06 (m, 4H).

EXAMPLE 124

N-(3-(5-(2-((4-morpholin-4-ylphenyl)amino)pyrimidin-4-yl)imidazo[2,1-b][1,3]thiazol-6-yl)phenyl)-2-pyridin-3-ylacetamide The title compound was prepared as described in EXAMPLE 69, substituting 2-(pyridin-3-yl)acetic acid for 2-o-tolylacetic acid. MS (ESI) m/e 587 (M−H)⁻; ¹H NMR (300 MHz, DMSO-d₆) δ 8.71 (br s, 1H), 8.56 (m, 1H), 8.50 (d, 1H), 8.18 (d, 1H), 7.86 (m, 2H), 7.68 (m, 1H), 7.52 (d, 2H), 7.43 (m, 3H), 7.29 (d, 1H), 6.94 (d, 2H), 6.51 (d, 1H), 3.75 (m, 6H), 3.07 (m, 4H).

EXAMPLE 125

N-(3-(5-(2-((4-morpholin-4-ylphenyl)amino)pyrimidin-4-yl)imidazo[2,1-b][1,3]thiazol-6-yl)phenyl)-2-pyridin-4-ylacetamide The title compound was prepared as described in EXAMPLE 69, substituting 2-(pyridin-4-yl)acetic acid for 2-o-tolylacetic acid. MS (ESI) m/e 587 (M–H)⁻; ¹H NMR (300 MHz, DMSO-d₆) δ 8.72 (br s, 1H), 8.52 (m, 1H), 8.19 (m, 1H), 7.86 (m, 1H), 7.67 (m, 1H), 7.52 (m, 3H), 7.42 (m, 4H), 7.29 (d, 1H), 6.94 (d, 2H), 6.52 (d, 1H), 3.76 (m, 6H), 3.06 (m, 4H).

EXAMPLE 126

N-(3-(5-(2-((4-morpholin-4-ylphenyl)amino)pyrimidin-4-yl)imidazo[2,1-b][1,3]thiazol-6-yl)phenyl)pyrazine-2-carboxamide The title compound was prepared as described in EXAMPLE 69, substituting 2-(pyrazin-2-yl)acetic acid for 2-o-tolylacetic acid. MS (ESI) m/e 574 (M–H)⁻; ¹H NMR (300 MHz, DMSO-d₆) δ 9.41 (d, 1H), 9.12 (d, 1H), 8.72 (br s, 1H), 8.22 (m, 2H), 8.13 (dd, 1H), 7.96 (m, 1H), 7.52 (m, 3H), 7.43 (d, 1H), 7.41 (d, 1H), 6.95 (d, 2H), 6.58 (d, 1H), 3.75 (m, 6H), 3.07 (m, 4H).

EXAMPLE 127

N-(3-(5-(2-((4-morpholin-4-ylphenyl)amino)pyrimidin-4-yl)imidazo[2,1-b][1,3]thiazol-6-yl)phenyl)pyrimidine-4-carboxamide The title compound was prepared as described in EXAMPLE 69, substituting 2-(pyrimidin-4-yl)acetic acid for 2-o-tolylacetic acid. MS (ESI) m/e 574 (M–H)⁻; ¹H NMR (300 MHz, DMSO-d₆) δ 9.29 (d, 1H), 8.92 (d, 1H), 8.82 (dd, 1H), 8.72 (br s, 1H), 8.21 (m, 2H), 7.96 (m, 1H), 7.54 (m, 3H), 7.44 (d, 1H), 7.40 (d, 1H), 7.00 (d, 2H), 6.60 (d, 1H), 3.77 (m, 6H), 3.11 (m, 4H).

EXAMPLE 128

5-methyl-N-(3-(5-(2-((4-morpholin-4-ylphenyl)amino)pyrimidin-4-yl)imidazo[2,1-b][1,3]thiazol-6-yl)phenyl)pyrazine-2-carboxamide The title compound was prepared as described in EXAMPLE 69, substituting 2-(5-methylpyrazin-2-yl)acetic acid for 2-o-tolylacetic acid. MS (ESI) m/e 588 (M–H)⁻; ¹H NMR (300 MHz, DMSO-d₆) δ 9.14 (d, 1H), 8.72 (br s, 1H), 8.69 (d, 1H), 8.21 (m, 2H), 7.95 (m, 1H), 7.53 (m, 3H), 7.44 (d, 1H), 7.38 (d, 1H), 6.98 (d, 2H), 6.59 (d, 1H), 3.76 (m, 6H), 3.09 (m, 4H), 2.64 (s, 3H).

EXAMPLE 129

N-(3-(5-(2-((4-morpholin-4-ylphenyl)amino)pyrimidin-4-yl)imidazo[2,1-b][1,3]thiazol-6-yl)phenyl)-1H-indole-3-carboxamide The title compound was prepared as described in EXAMPLE 69, substituting 1H-indole-3-carboxylic acid for 2-o-tolylacetic acid. MS (ESI) m/e 613 (M+H)⁺; ¹H NMR (300 MHz, DMSO-d₆) δ 8.73 (br s, 1H), 8.29 (m, 1H), 8.23 (d, 2H), 8.18 (d, 1H), 8.07 (m, 1H), 7.89 (m, 1H), 7.43-7.53 (m, 5H), 7.27 (d, 1H), 7.22 (t, 1H), 7.17 (t, 1H) 6.96 (d, 2H), 6.63 (d, 1H), 3.74 (m, 6H), 3.09 (m, 4H).

EXAMPLE 130

5-methyl-N-(3-(5-(2-((4-morpholin-4-ylphenyl)amino)pyrimidin-4-yl)imidazo[2,1-b][1,3]thiazol-6-yl)phenyl)-1-phenyl-1H-pyrazole-4-carboxamide The title compound was prepared as described in EXAMPLE 69, substituting 5-methyl-1-phenyl-1H-pyrazole-4-carboxylic acid for 2-o-tolylacetic acid. MS (ESI) m/e 652 (M–H)⁻; ¹H NMR (300 MHz, DMSO-d₆) δ 8.72 (br s, 1H), 8.32 (s, 1H), 8.22 (d, 2H), 8.04 (m, 1H), 7.84 (m, 1H), 7.59 (m, 2H), 7.53 (m, 5H), 7.47 (t, 1H), 7.43 (d, 1H), 7.31 (d, 1H), 6.94 (d, 2H), 6.60 (d, 1H), 3.75 (m, 6H), 3.06 (m, 4H), 2.54 (s, 3H).

EXAMPLE 131

N-(3-(5-(2-((4-morpholin-4-ylphenyl)amino)pyrimidin-4-yl)imidazo[2,1-b][1,3]thiazol-6-yl)phenyl)-4-oxo-4,5,6,7-tetrahydro-1-benzofuran-3-carboxamide The title compound was prepared as described in EXAMPLE 69, substituting 4-oxo-4,5,6,7-tetrahydrobenzofuran-3-carboxylic acid for 2-o-tolylacetic acid. MS (ESI) m/e 630 (M–H)⁻; ¹H NMR (300 MHz, DMSO-d₆) δ 8.70 (br s, 1H), 8.37 (s, 1H), 8.22 (d, 2H), 8.00 (m, 1H), 7.77 (m, 1H), 7.52 (m, 3H), 7.43 (d, 1H), 7.36 (d, 1H), 6.95 (d, 2H), 6.59 (d, 1H), 3.76 (m, 6H), 3.08 (m, 4H), 2.99 (t, 2H), 2.66 (t, 2H), 2.16 (quintet, 2H).

EXAMPLE 132

N³,N³-dimethyl-N'-(3-(5-(2-((4-morpholin-4-ylphenyl)amino)pyrimidin-4-yl)imidazo[2,1-b][1,3]thiazol-6-yl)phenyl)-beta-alaninamide The title compound was prepared as described in EXAMPLE 69, substituting 3-(dimethylamino)propanoic acid for 2-o-tolylacetic acid. MS (ESI) m/e 569 (M+H)⁺; ¹H NMR (300 MHz, DMSO-d₆) δ 8.71 (br s, 1H), 8.21 (d, 1H), 7.53 (d, 2H), 7.47 (t, 1H), 7.43 (d, 1H), 7.30 (d, 1H), 7.12 (m, 1H), 6.98 (m, 1H), 6.94 (d, 2H), 6.50 (d, 1H), 3.76 (m, 6H), 3.06 (m, 4H), 2.84 (s, 8H).

EXAMPLE 133

N-(3-(5-(2-((4-morpholin-4-ylphenyl)amino)pyrimidin-4-yl)imidazo[2,1-b][1,3]thiazol-6-yl)phenyl)-2-pyrrolidin-1-ylacetamide The title compound was prepared as described in EXAMPLE 69, substituting 2-(pyrrolidin-1-yl)acetic acid for 2-o-tolylacetic acid. MS (ESI) m/e 579 (M–H)⁻; ¹H NMR (300 MHz, DMSO-d₆) δ 8.72 (br s, 1H), 8.19 (d, 1H), 7.92 (m, 1H), 7.69 (m, 1H), 7.52 (d, 2H), 7.44 (m, 2H), 7.31 (d, 1H), 6.94 (d, 2H), 6.51 (d, 1H), 3.76 (m, 6H), 3.49 (s, 2H), 3.06 (m, 4H), 2.78 (s, 4H), 1.80 (m, 4H).

EXAMPLE 134

N-(3-(5-(2-((4-morpholin-4-ylphenyl)amino)pyrimidin-4-yl)imidazo[2,1-b][1,3]thiazol-6-yl)phenyl)-3-piperidin-1-ylpropanamide The title compound was prepared as described in EXAMPLE 69, substituting 3-(piperidin-1-yl)propanoic acid for 2-o-tolylacetic acid. MS (ESI) m/e 607 (M–H)⁻; ¹H NMR (300 MHz, DMSO-d₆) δ 8.70 (br s, 1H), 8.20 (d, 1H), 7.81 (m, 1H), 7.68 (m, 1H), 7.52 (d, 2H), 7.44 (m, 2H), 7.29 (d, 1H), 6.94 (d, 2H), 6.52 (d, 1H), 3.76 (m, 6H), 3.06 (m, 4H), 2.78 (t, 2H), 2.57 (m, 6H), 1.54 (m, 4H), 1.41 (m, 2H).

EXAMPLE 135

2-(4-methylpiperazin-1-yl)-N-(3-(5-(2-((4-morpholin-4-ylphenyl)amino)pyrimidin-4-yl)imidazo[2,1-b][1,3]thiazol-6-yl)phenyl)acetamide The title compound was prepared as described in EXAMPLE 69, substituting 2-(4-methylpiperazin-1-yl)acetic acid for 2-o-tolylacetic acid. MS (ESI) m/e 608 (M−H)−; $^1$H NMR (300 MHz, DMSO-$d_6$) δ 8.72 (br s, 1H), 8.19 (d, 1H), 7.90 (m, 1H), 7.70 (m, 1H), 7.52 (d, 2H), 7.44 (m, 2H), 7.30 (d, 1H), 6.94 (d, 2H), 6.53 (d, 1H), 3.76 (m, 6H), 3.18 (m, 2H), 3.12 (s, 2H), 3.06 (m, 4H), 2.39 (m, 4H), 2.17 (s, 3H).

EXAMPLE 136

2-cyclopentyl-N-(3-(5-(2-((4-morpholin-4-ylphenyl)amino)pyrimidin-4-yl)imidazo[2,1-b][1,3]thiazol-6-yl)phenyl)acetamide The title compound was prepared as described in EXAMPLE 47, substituting substituting 4-2-cyclopentylacetyl chloride for (isocyanatomethyl)benzene. MS (ESI(+)) m/e 580 (M+H)$^+$; (ESI(−)) m/e 578 (M−H)$^-$; $^1$H-NMR (300 MHz, DMSO-$d_6$) □ 9.94 (s, 1H), 9.42 (s, 1H), 8.74 (bs, 1H), 8.20 (d, 1H), 7.87 (t, 1H), 7.69 (d, 1H), 7.54 (d, 2H), 7.46 (d, 1H), 7.38 (t, 1H), 7.25 (d, 1H), 6.93 (d, 2H), 6.53 (d, 1H), 3.71-3.78 (m, 4H), 3.02-3.10 (m, 4H), 2.14-2.34 (m, 3H), 1.67-1.82 (m, 2H), 1.44-1.66 (m, 4H), 1.09-1.26 (m, 2H).

EXAMPLE 137

N-(4-(4-acetylpiperazin-1-yl)phenyl)-4-(6-(3-((5-phenyl-1,3,4-oxadiazol-2-yl)amino)phenyl)imidazo[2,1-b][1,3]thiazol-5-yl)pyrimidin-2-amine A mixture of EXAMPLE 65C (50 mg) and the 2-bromo-5-phenyl-oxadiazole (66 mg) in acetonitrile (3 mL) and N-methylpyrrolidone (2 mL) was stirred at 100° C. for two days. The mixture was concentrated and the residue was purified on a reverse phase HPLC with a water and acetonitrile gradient containing 0.1% trifluoroacetic acid to afford the title compound as a. trifluoroacetic acid salt. MS (ESI), m/e 655.2; $^1$H-NMR (300 MHz, DMSO-$d_6$) □ 10.86 (s, 1 H), 9.60 (s, 1 H), 8.77 (bs, 1 H), 8.23 (d, 1 H), 7.87-7.90 (m, 3 H), 7.73 (d, 1 H), 7.56-7.58 (m, 5 H), 7.47-7.50 (m, 2 H), 7.25 (d, 1 H), 7.02 (d, 2 H), 6.59 (d, 1 H), 3.59-3.62 (m, 4 H), 3.15-3.17 (m, 2 H), 3.07-3.09 (m, 2 H), 2.05 (s, 3H).

EXAMPLE 138

N-(3-(5-(2-((4-(4-acetylpiperazin-1-yl)phenyl)amino)pyrimidin-4-yl)imidazo[2,1-b][1,3]thiazol-6-yl)phenyl)benzamide The title compound was prepared as described in EXAMPLE 36, substituting EXAMPLE 65C for EXAMPLE 36C and benzoyl chloride for phenylacetyl chloride. MS (ESI), m/e 615.3; (ESI), m/e 613.1 (M−H)$^-$; $^1$H-NMR (300 MHz, DMSO-$d_6$) □ ppm 10.35 (s, 1H), 9.44 (s, 1 H), 8.76 (bs, 1 H), 8.23 (d, 1 H), 8.09 (s, 1 H), 7.96 (d, 2 H), 7.92 (d, 1 H), 7.44-7.60 (m, 7 H), 7.34 (d, 1 H), 6.95 (d, 2 H), 6.59 (d, 1 H), 3.56-3.58 (m, 4 H), 3.08-3.11 (m, 2 H), 3.02-3.05 (m, 2 H), 2.04 (s, 3H).

EXAMPLE 139

N-(3-(5-(2-((4-(2-oxopyrrolidin-1-yl)phenyl)amino)pyrimidin-4-yl)imidazo[2,1-b][1,3]thiazol-6-yl)phenyl)benzamide The title compound was prepared as described in EXAMPLE 36, substituting EXAMPLE 67C for EXAMPLE 36C and benzoyl chloride for phenylacetyl chloride. MS (ESI), m/e 572.2; (ESI), m/e 570.0 (M−H)$^-$; $^1$H-NMR (300 MHz, DMSO-$d_6$) □ ppm 10.35 (s, 1 H), 9.67 (s, 1 H), 8.83 (bs, 1 H), 8.28 (d, 1 H), 8.09 (s, 1 H), 7.91-7.97 (m, 3 H), 7.71 (d, 2 H), 7.45-7.60 (m, 7 H), 7.35 (d, 1 H), 6.64 (d, 1 H), 3.82 (t, 2 H), 2.48 (t, 2 H), 2.06 (p, 3H).

EXAMPLE 140

2-cyclohexyl-N-(3-(5-(2-((4-morpholin-4-ylphenyl)amino)pyrimidin-4-yl)imidazo[2,1-b][1,3]thiazol-6-yl)phenyl)acetamide The title compound was prepared as described in EXAMPLE 47, substituting 2-cyclohexylacetyl chloride for (isocyanatomethyl)benzene. MS (ESI(+)) m/e 594 (M+H)$^+$; (ESI(−)) m/e 592 (M−H)$^-$; $^1$H-NMR (300 MHz, DMSO-$d_6$) □ 9.96 (s, 1H), 9.44 (s, 1H), 8.74 (bs, 1H), 8.20 (d, 1H), 7.88 (t, 1H), 7.68 (ddd, 1H), 7.54 (d, 2H), 7.47 (d, 1H), 7.38 (t, 1H), 7.25 (ddd, 1H), 6.90-6.96 (m, 2H), 6.51-6.54 (m, 1H), 3.71-3.78 (m, 4H), 3.02-3.10 (m, 4H), 2.19 (d, 2H), 1.57-1.85 (m, 6H), 1.07-1.32 (m, 3H), 0.88-1.05 (m, 2H).

EXAMPLE 141

2-chlorobenzyl 3-(5-(2-((4-morpholin-4-ylphenyl)amino)pyrimidin-4-yl)imidazo[2,1-b][1,3]thiazol-6-yl)phenylcarbamate The title compound was prepared as described in EXAMPLE 47, substituting 2-chlorobenzyl carbonochloridate for (isocyanatomethyl)benzene. MS (ESI(+)) m/e 638 (M+H)$^+$; $^1$H-NMR (300 MHz, DMSO-$d_6$) □9.99 (s, 1H), 9.43 (s, 1H), 8.75 (bs, 1H), 8.21 (d, 1H), 7.74 (t, 1H), 7.643-7.62 (m, 6H), 7.35-7.44 (m, 3H), 7.23 (dt, 1H), 6.88-6.97 (m, 2H), 6.50 (d, 1H), 5.23 (s, 2H), 3.71-3.78 (m, 4H), 3.01-3.09 (m, 4H).

EXAMPLE 142

N-(3-(5-(2-((4-morpholin-4-ylphenyl)amino)pyrimidin-4-yl)imidazo[2,1-b][1,3]thiazol-6-yl)phenyl)-1,3-benzoxazol-2-amine A mixture of EXAMPLE 3C (60 mg), 2-chlorobenzo[d]oxazole (21.58 mg) and 2-propanol (2 ml) was sealed in a vial under argon and heated at 80° C. for 18 hours. The mixture was concentrated and the residue was purified by reverse phase preparative HPLC with an acetonitrile (A)-0.1% trifluoroacetic acid in water (B) gradient to afford the title compound as the trifluoroacetic acid salt. MS (ESI(+)) m/e 587 (M+H)$^+$, (ESI(−)) m/e 585 (M−H)$^-$; $^1$H-NMR (300 MHz, DMSO-$d_6$) □ 10.75 (s, 1H), 9.56 (s, 1H), 8.74 (br s, 1H), 8.23 (d, 1H), 8.05 (m, 1H), 7.85 (m, 1H), 7.57-7.41 (m, 6H), 7.25

(m, 1H), 7.20 (m, 1H), 7.13 (m, 1H), 6.98 (d, 2H), 6.59 (d, 1H), 3.76 (m, 4H), 3.10 (m, 4H).

EXAMPLE 143

5-methyl-N-(3-(5-(2-((4-morpholin-4-ylphenyl)amino)pyrimidin-4-yl)imidazo[2,1-b][1,3]thiazol-6-yl)phenyl)-1,3-benzoxazol-2-amine The title compound was prepared as described in EXAMPLE 142, substituting 2-chloro-5-methylbenzo[d]oxazole for 2-chlorobenzo[d]oxazole. MS (ESI(+)) m/e 601 (M+H)⁺, (ESI(−)) m/e 599 (M−H)⁻; ¹H-NMR (300 MHz, DMSO-d₆) □ 10.70 (s, 1H), 9.61 (s, 1H), 8.73 (br s, 1H), 8.22 (d, 1H), 8.04 (m, 1H), 7.83 (m, 1H), 7.57 (d, 2H), 7.48 (m, 2H), 7.34 (d, 1H), 7.26 (d, 1H), 7.22 (s, 1H), 7.02 (d, 2H), 6.93 (d, 1H), 6.60 (d, 1H), 3.76 (m, 4H), 3.12 (m, 4H), 2.34 (s, 3H).

EXAMPLE 144

6-chloro-N-(3-(5-(2-((4-morpholin-4-ylphenyl)amino)pyrimidin-4-yl)imidazo[2,1-b][1,3]thiazol-6-yl)phenyl)-1,3-benzoxazol-2-amine The title compound was prepared as described in EXAMPLE 142, substituting 2,6-dichlorobenzo[d]oxazole for 2-chlorobenzo[d]oxazole. MS (ESI(+)) m/e 621 (M+H)⁺, (ESI(−)) m/e 619 (M−H)⁻; ¹H-NMR (300 MHz, DMSO-d₆) □ 10.90 (s, 1H), 9.55 (s, 1H), 8.74 (br s, 1H), 8.22 (d, 1H), 8.02 (m, 1H), 7.83 (m, 1H), 7.69 (d, 1H), 7.57-7.40 (m, 5H), 7.27 (m, 2H), 6.97 (d, 2H), 6.58 (d, 1H), 3.75 (m, 4H), 3.09 (m, 4H).

EXAMPLE 145

N-(3-(5-(2-((4-morpholin-4-ylphenyl)amino)pyrimidin-4-yl)imidazo[2,1-b][1,3]thiazol-6-yl)phenyl)-1H-indazol-3-amine The title compound was prepared as described in EXAMPLE 142, substituting 3-chloro-1H-indazole for 2-chlorobenzo[d]oxazole, N-methyl-2-pyrrolidinone for 2- and microwave heating in a Biotage Initiator 2 monomode microwave reactor at 210° C. for 20 minutes instead of 80° C. for 18 hours. MS (ESI(+)) m/e 587 (M+H)⁺, (ESI(−)) m/e 584 (M−H)⁻; ¹H-NMR (300 MHz, DMSO-d₆) □ 10.75 (s, 1H), 9.54 (s, 1H), 8.74 (br s, 1H), 8.22 (d, 1H), 8.05 (m, 1H), 7.85 (dd, 1H), 7.57-7.42 (m, 6H), 7.28-7.08 (m, 4H), 6.97 (d, 2H), 6.59 (d, 1H), 3.75 (m, 4H), 3.09 (m, 4H).

EXAMPLE 146

N-(3-(5-(2-((4-((dimethylamino)sulfonyl)phenyl)amino)pyrimidin-4-yl)imidazo[2,1-b][1,3]thiazol-6-yl)phenyl)-2-phenylacetamide The title compound was prepared as described in EXAMPLE 3, substituting 4-amino-N,N-dimethylbenzenesulfonamide for 4-morpholinoaniline, and phenylacetyl chloride for 2,6-difluorobenzoyl chloride. MS (ESI(+)) m/e 610 (M+H)⁺; (ESI(−)) m/e 609 (M−H)⁻; ¹H-NMR (300 MHz, DMSO-d₆) □ 10.28 (s, 1H); 10.19 (s, 1H); 8.86 (d, 1H); 8.37 (d, 1H); 7.99 (d, 2H); 7.90 (bs, 1H); 7.72-7.66 (m, 3H); 7.54 (d, 1H); 7.41 (t, 1H); 7.33-7.24 (m, 6H); 6.73 (d, 1H); 3.65 (s, 2H); 2.59 (s, 6H).

EXAMPLE 147

N-(3-(5-(2-((3-(2-morpholin-4-ylethoxy)phenyl)amino)pyrimidin-4-yl)imidazo[2,1-b][1,3]thiazol-6-yl)phenyl)benzamide The title compound was prepared as described in EXAMPLE 3, substituting 3-(2-morpholinoethoxy)aniline for 4-morpholinoaniline, and benzyol chloride for 2,6-difluorobenzoyl chloride. MS (ESI(+)) m/e 610 (M+H)⁺; (ESI(−)) m/e 616 (M−H)⁻; ¹H-NMR (300 MHz, DMSO-d₆) □ 10.37 (s, 1H); 9.67 (s, 1H); 8.87 (bs, 1H); 8.31 (d, 1H); 8.10 (s, 1H); 7.97-7.91 (m, 3H); 7.60-7.44 (m, 6H); 7.35 (m, 1H); 7.26 (m, 1H); 7.20 (t, 1H); 6.66 (d, 1H); 6.58 (m, 1H); 4.06 (t, 2H); 3.57 (m, 4H); 2.69 (t, 2H); 2.46 (m, 4H).

EXAMPLE 148

N-(3-(5-(2-((3-(2-morpholin-4-ylethoxy)phenyl)amino)pyrimidin-4-yl)imidazo[2,1-b][1,3]thiazol-6-yl)phenyl)-2-phenylacetamide The title compound was prepared as described in EXAMPLE 3, substituting 3-(2-morpholinoethoxy)aniline for 4-morpholinoaniline, and phenylacetyl chloride for 2,6-difluorobenzoyl chloride. MS (ESI(+)) m/e 632 (M+H)⁺; (ESI(−)) m/e 630 (M−H)⁻; ¹H-NMR (300 MHz, DMSO-d₆) □ 10.28 (s, 1H); 9.66 (s, 1H); 8.83 (d, 1H); 8.28 (d, 1H); 7.88 (bs, 1H); 7.72 (d, 1H); 7.51-7.46 (m, 2H); 7.40 (t, 1H); 7.34-7.24 (m, 6H); 7.20 (t, 1H); 6.61-6.56 (m, 2H); 4.06 (t, 2H); 3.65 (s, 2H); 3.59-3.56 (m, 4H); 2.70-2.68 (m, 2H); 2.47-2.44 (m, 4H).

EXAMPLE 149

2-(2-methoxyphenyl)-N-(3-(5-(2-((4-morpholin-4-ylphenyl)amino)pyrimidin-4-yl)imidazo[2,1-b][1,3]thiazol-6-yl)phenyl)acetamide The title compound was prepared as described in EXAMPLE 69, substituting 2-(2-methoxyphenyl)acetic acid for 2-o-tolylacetic acid. MS (ESI) m/e 618 (M+H)⁺; ¹H NMR (300 MHz, DMSO-d₆) δ 10.16 (s, 1H), 9.43 (s, 1H), 8.74 (br s, 1H), 8.21 (d, 1H), 7.86 (m, 1H), 7.72 (m, 1H), 7.53 (d, 2H), 7.46 (d, 1H), 7.40 (t, 1H), 7.23 (m, 3H), 6.87-6.99 (m, 4H), 6.51 (d, 1H), 3.76 (s, 3H), 3.75 (m, 4H), 3.63 (s, 2H), 3.06 (m, 4H).

EXAMPLE 150

N-(3-(5-(2-((4-morpholin-4-ylphenyl)amino)pyrimidin-4-yl)imidazo[2,1-b][1,3]thiazol-6-yl)phenyl)-2-(2-(trifluoromethyl)phenyl)acetamide The title compound was prepared as described in EXAMPLE 69, substituting 2-(2-(trifluoromethyl)phenyl)acetic acid for 2-o-tolylacetic acid. MS (ESI) m/e 656 (M+H)⁺; ¹H NMR (300 MHz, DMSO-d₆) δ 10.32 (s, 1H), 9.43 (s, 1H), 8.74 (br s, 1H), 8.20 (d, 1H), 7.85 (m, 1H), 7.67 (m, 3H), 7.46-7.55 (m, 5H), 7.40 (t, 1H), 7.28 (m, 1H), 6.92 (d, 2H), 6.53 (d, 1H), 3.93 (s, 2H), 3.75 (m, 4H), 3.06 (m, 4H).

EXAMPLE 151

N-(3-(5-(2-((4-morpholin-4-ylphenyl)amino)pyrimidin-4-yl)imidazo[2,1-b][1,3]thiazol-6-yl)phenyl)-2-(2-(trifluoromethoxy)phenyl)acetamide The title compound was prepared as described in EXAMPLE 69, substituting 2-(2-(trifluoromethoxy)phenyl)

acetic acid for 2-o-tolylacetic acid. MS (ESI) m/e 672 (M+H)+; $^1$H NMR (300 MHz, DMSO-$d_6$) δ 10.34 (s, 1H), 9.43 (s, 1H), 8.75 (br s, 1H), 8.19 (d, 1H), 7.85 (m, 1H), 7.70 (m, 1H), 7.32-7.50 (m, 6H), 7.28 (m, 1H), 6.92 (m, 2H), 6.52 (d, 1H), 3.79 (s, 2H), 3.75 (m, 4H), 3.06 (m, 4H).

EXAMPLE 152

2-(2-fluoro-3-(trifluoromethyl)phenyl)-N-(3-(5-(2-((4-morpholin-4-ylphenyl)amino)pyrimidin-4-yl)imidazo[2,1-b][1,3]thiazol-6-yl)phenyl)acetamide The title compound was prepared as described in EXAMPLE 69, substituting 2-(2-fluoro-3-(trifluoromethyl)phenyl)acetic acid for 2-o-tolylacetic acid. MS (ESI) m/e 674 (M+H)+; $^1$H NMR (300 MHz, DMSO-$d_6$) δ 10.41 (s, 1H), 9.43 (s, 1H), 8.74 (br s, 1H), 8.21 (d, 1H), 7.86 (m, 1H), 7.72 (m, 3H), 7.53 (d, 2H), 7.46 (d, 1H), 7.40 (m, 2H), 7.29 (m, 1H), 6.92 (m, 2H), 6.52 (d, 1H), 3.87 (s, 2H), 3.75 (m, 4H), 3.06 (m, 4H).

EXAMPLE 153

2-(2,6-difluorophenyl)-N-(3-(5-(2-((4-morpholin-4-ylphenyl)amino)pyrimidin-4-yl)imidazo[2,1-b][1,3]thiazol-6-yl)phenyl)acetamide The title compound was prepared as described in EXAMPLE 69, substituting 2-(2,6-difluorophenyl)acetic acid for 2-o-tolylacetic acid. MS (ESI) m/e 624 (M+H)+; $^1$H NMR (300 MHz, DMSO-$d_6$) δ 10.41 (s, 1H), 9.43 (s, 1H), 8.74 (br s, 1H), 8.21 (d, 1H), 7.84 (m, 1H), 7.70 (m, 1H), 7.53 (d, 2H), 7.46 (d, 1H), 7.39 (m, 2H), 7.28 (m, 1H), 7.10 (m, 2H), 6.92 (m, 2H), 6.52 (d, 1H), 3.78 (s, 2H), 3.75 (m, 4H), 3.06 (m, 4H).

EXAMPLE 154

N-(3-(5-(2-((3-(3-(4-methylpiperazin-1-yl)propoxy)phenyl)amino)pyrimidin-4-yl)imidazo[2,1-b][1,3]thiazol-6-yl)phenyl)benzamide

EXAMPLE 154A

To a 250 mL round bottom flask was charged 3-nitrophenol (2.78 g), 3-bromopropan-1-ol (3.33 g), and polymer bound triphenylphosphine (Fluka, 3 mmol/g, 1.5 eq, 10 g, 30 mmol) and tetrahydrofuran (75 mL). The resulting mixture was cooled to O C and diisopropyl azodicarboxylate (4.85 g) was added dropwise over 10 minutes The mixture was allowed to stir at room temperature for 14 hours. Additional diisopropyl azodicarboxylate (776 uL) was added and the mixture was stirred for 24 hours longer. The reaction was filtered and the solids were washed with ether. The filtrate was concentrated. The concentrate was dissolved in ethyl acetate, washed with brine, dried over $Na_2SO_4$, filtered, and concentrated. The residue was purified by flash chromatography on silica gel (hexanes:ethyl acetate) to afford the title compound.

EXAMPLE 154B

In a 100 mL round bottom flask, a solution of EXAMPLE 154A (0.910 g) in acetonitrile (18 mL) was treated with N-methylpiperazine (0.701 g) and potassium carbonate (1.209 g). The resulting mixture was stirred at room temperature for 15 hours. The mixture was treated with saturated aqueous NaCl (75 mL) and then extracted with ethyl acetate (2×100 mL). The combined organic layers were dried over $Na_2SO_4$ and concentrated. The concentrate was purified by flash chromatography on silica gel ($CH_2Cl_2$:methanol) to afford the title compound. MS (ESI(+)) m/e 280 (M+H)+.

EXAMPLE 154C

To a 100 mL round bottom flask was charged EXAMPLE 154B (0.978 g) and ethanol (23 mL). The suspension was treated with iron (0.997 g) followed by a solution of ammonium chloride (0.103 g) in water (4.5 mL). The resulting mixture was heated at 90° C. with vigorous stirring for 2 hours. The mixture was cooled to room temperature and the liquid supernatant was decanted into ethyl acetate (100 mL) and was washed with brine (40 mL). The organic layer was dried over $Na_2SO_4$, filtered, and concentrated to afford the title compound. MS (ESI(+)) m/e 250 (M+H)+.

EXAMPLE 154D

The title compound was prepared as described in EXAMPLE 42A, substituting EXAMPLE 154C for 4-(1H-imidazol-1-yl)aniline.

EXAMPLE 154E

The title compound was prepared as described in EXAMPLE 1, substituting EXAMPLE 154D for phenylguanidine in EXAMPLE 1E and benzoyl chloride for 2-chlorobenzoyl chloride in EXAMPLE 1G. MS (ESI(+)) m/e 645 (M+H)+; $^1$H-NMR (300 MHz, DMSO-$d_6$) □ 10.37 (s, 1H); 9.67 (s, 1H); 8.85 (d, 1H); 8.31 (d, 1H); 8.10 (s, 1H); 7.98-7.91 (m, 3H); 7.62-7.44 (m, 6H); 7.37 (d, 1H); 7.28 (d, 1H); 7.19 (t, 1H); 6.66 (d, 1H); 6.56 (d, 1H); 3.97 (t, 2H); 2.45-2.28 (m, 10H); 2.17 (s, 3H); 1.86 (m, 2H).

EXAMPLE 155

N-(3-(5-(2-((3-(3-(4-methylpiperazin-1-yl)propoxy)phenyl)amino)pyrimidin-4-yl)imidazo[2,1-b][1,3]thiazol-6-yl)phenyl)-2-phenylacetamide The title compound was prepared as described in EXAMPLE 1, substituting EXAMPLE 154D for phenylguanidine in EXAMPLE 1E and phenylacetyl chloride for 2-chlorobenzoyl chloride in EXAMPLE 1G. MS (ESI(+)) m/e 659 (M+H)+; $^1$H-NMR (300 MHz, DMSO-$d_6$) □ 10.27 (s, 1H); 9.65 (s, 1H); 8.82 (d, 1H); 8.28 (d, 1H); 7.88 (s, 1H); 7.72 (d, 1H); 7.50 (d, 1H); 7.45 (s, 1H); 7.40 (t, 1H); 7.34-7.26 (m, 7H); 7.19 (t, 1H); 6.60 (d, 1H); 6.56 (d, 1H); 3.97 (t, 2H); 3.64 (s, 2H); 2.45-2.28 (m, 10H); 2.17 (s, 3H); 1.86 (m, 2H).

EXAMPLE 156

N-(3-(5-(2-((3-(3-morpholin-4-ylpropoxy)phenyl)amino)pyrimidin-4-yl)imidazo[2,1-b][1,3]thiazol-6-yl)phenyl)benzamide

EXAMPLE 156A

The title compound was prepared as described in EXAMPLE 154A-D, substituting morpholine for N-methylpiperazine in EXAMPLE 154B.

EXAMPLE 156B

The title compound was prepared as described in EXAMPLE 1, substituting EXAMPLE 156A for phenylguanidine in EXAMPLE 1E and benzoyl chloride for 2-chlorobenzoyl chloride in EXAMPLE 1G. MS (ESI(+)) m/e 632 (M+H)+; 1H-NMR (300 MHz, DMSO-d6) □ 10.36 (s, 1H); 9.00 (s, 1H); 8.86 (d, 1H); 8.31 (d, 1H); 8.10 (s, 1H); 7.98-7.91 (m, 3H); 7.62-7.44 (m, 6H); 7.35 (d, 1H); 7.28 (d, 1H); 7.20 (t, 1H); 6.66 (d, 1H); 6.56 (d, 1H); 3.98 (t, 2H); 3.56 (m, 4H); 2.41 (t, 2H); 2.35 (m, 4H); 1.87 (m, 2H).

EXAMPLE 157

N-(3-(5-(2-((3-(3-morpholin-4-ylpropoxy)phenyl) amino)pyrimidin-4-yl)imidazo[2,1-b][1,3]thiazol-6-yl)phenyl)-2-phenylacetamide The title compound was prepared as described in EXAMPLE 1, substituting EXAMPLE 156A for phenylguanidine in EXAMPLE 1E and phenylacetyl chloride for 2-chlorobenzoyl chloride in EXAMPLE 1G. MS (ESI(+)) m/e 646 (M+H)+; 1H-NMR (300 MHz, DMSO-d6) □ 10.28 (s, 1H); 9.67 (s, 1H); 8.83 (d, 1H); 8.28 (d, 1H); 7.89 (s, 1H); 7.71 (d, 1H); 7.50 (d, 1H); 7.40 (t, 1H); 7.34-7.20 (m, 9H); 6.60 (d, 1H); 6.56 (d, 1H); 3.99 (t, 2H); 3.64 (s, 2H); 3.57 (m, 4H); 2.36 (m, 6H); 1.86 (m, 2H).

EXAMPLE 158

N-(3-(5-(2-((4-(4-(3-methoxypropyl)piperazin-1-yl) phenyl)amino)pyrimidin-4-yl)imidazo[2,1-b][1,3] thiazol-6-yl)phenyl)benzamide The title compound was prepared as described in EXAMPLE 12 by substituting EXAMPLE 14B for 3-morpholinoaniline in EXAMPLE 12D and benzoyl chloride for phenylacetyl chloride in EXAMPLE 12F. MS (ESI(+)) m/e 645 (M+H)+; 1H-NMR (300 MHz, DMSO-d6) □ 10.37 (s, 1H); 9.42 (s, 1H); 8.77 (bs, 1H); 8.23 (d, 1H); 8.09 (s, 1H); 7.98-7.91 (m, 3H); 7.62-7.43 (m, 7H); 7.33 (d, 1H); 6.92 (d, 2H); 6.58 (d, 1H); 3.37 (t, 2H); 3.23 (s, 3H); 3.07 (m, 4H); 2.51 (m, 4H); 2.36 (m, 2H); 1.69 (m, 2H).

EXAMPLE 159

2,6-difluoro-N-(3-(5-(2-((4-(4-(3-methoxypropyl) piperazin-1-yl)phenyl)amino)pyrimidin-4-yl)imidazo [2,1-b][1,3]thiazol-6-yl)phenyl)benzamide The title compound was prepared as described in EXAMPLE 12, substituting EXAMPLE 14B for 3-morpholinoaniline in EXAMPLE 12D and 2,6-difluorobenzoyl chloride for phenylacetyl chloride in EXAMPLE 12F. MS (ESI (+)) m/e 681 (M+H)+; 1H-NMR (300 MHz, DMSO-d6) □ 10.91 (s, 1H); 9.42 (s, 1H); 8.74 (bs, 1H); 8.22 (d, 1H); 7.97 (s, 1H); 7.79 (d, 1H); 7.65-7.45 (m, 5H); 7.38 (d, 1H); 7.26 (t, 2H); 6.91 (d, 2H); 6.56 (d, 1H); 3.37 (t, 2H); 3.23 (s, 3H); 3.07 (m, 4H); 2.51 (m, 4H); 2.36 (m, 2H); 1.70 (m, 2H).

EXAMPLE 160

N-(2-morpholin-4-ylethyl)-3-((4-(6-(3-((phenylacetyl)amino)phenyl)imidazo[2,1-b][1,3]thiazol-5-yl)pyrimidin-2-yl)amino)benzamide To a suspension of EXAMPLE 62 (16.9 mg) in N,N-dimethylformamide (0.375 mL) was added 2-morpholinoethanamine (1.1 eq) in N,N-dimethylformamide (0.17 mL), O-(7-azabenzotriazol-1-yl)-N,N,N',N'-tetramethyluronium hexafluorophosphate (1.0 eq) in N,N-dimethylformamide (0.375 mL), and diisopropylethylamine (2.0 eq) in N,N-dimethylformamide (0.375 mL). The mixture was heated to 80° C. for 18 hours. The resulting solution was filtered through a 2 g Si-Carbonate SPE column and concentrated. The mixture was purified by HPLC on a Waters Nova-Pak® HR C18 6 um 60 Å Prep-Pak® cartridge column (25 mm×100 mm, acetonitrile:0.1% trifluoroacetic acid) to afford the title compound as a trifluoracetic acid salt. MS (ESI) m/e 659 (M+H)+; 1H NMR (300 MHz, DMSO-d6) δ 8.63 (d, 1H), 8.23 (d, 1H), 8.15 (m, 1H), 7.87 (m, 1H), 7.84 (m, 1H), 7.61 (m, 1H), 7.48 (m,1H), 7.34 (m, 9H), 6.67 (d, 1H), 3.86 (m, 4H), 3.67 (t, 2H), 3.65 (s, 2H), 3.31 (m, 6H).

EXAMPLE 161

N-(2-methoxy-1-methylethyl)-3-((4-(6-(3-((phenylacetyl)amino)phenyl)imidazo[2,1-b][1,3]thiazol-5-yl)pyrimidin-2-yl)amino)benzamide The title compound was prepared as described in EXAMPLE 160, substituting 1-methoxypropan-2-amine for 2-morpholinoethanamine. MS (ESI) m/e 730 (M+trifluoroacetic acid —H)−; 1H NMR (300 MHz, DMSO-d6) δ 8.62 (d, 1H), 8.22 (d, 1H), 8.07 (m, 1H), 7.84 (m, 1H), 7.79 (m, 1H), 7.63 (m, 1H), 7.34 (m, 10H), 6.65 (d, 1H), 3.65 (s, 2H), 3.44 (m, 2H), 3.34 (m, 2H), 2.96 (s, 3H), 2.55 (m, 1H), 1.17 (d, 3H).

EXAMPLE 162

N-(2-ethoxyethyl)-3-((4-(6-(3-((phenylacetyl)amino) phenyl)imidazo[2,1-b][1,3]thiazol-5-yl)pyrimidin-2-yl)amino)benzamide The title compound was prepared as described in EXAMPLE 160, substituting 2-ethoxyethanamine for 2-morpholinoethanamine. MS (ESI) m/e 616 (M−H)−; 1H NMR (300 MHz, DMSO-d6) δ 8.62 (d, 1H), 8.22 (d, 1H), 7.84 (m, 1H), 7.70 (m, 1H), 7.34 (m, 10H), 6.94 (m, 1H), 6.65 (d, 1H), 3.65 (s, 2H), 3.29 (m, 2H), 1.12 (t, 3H).

EXAMPLE 163

N-(2-isopropoxyethyl)-3-((4-(6-(3-((phenylacetyl) amino)phenyl)imidazo[2,1-b][1,3]thiazol-5-yl)pyrimidin-2-yl)amino)benzamide The title compound was prepared as described in EXAMPLE 160, substituting 2-isopropoxyethanamine for 2-morpholinoethanamine. MS (ESI) m/e 632 (M+H)+.

EXAMPLE 164

3-((4-(6-(3-((phenylacetyl)amino)phenyl)imidazo[2, 1-b][1,3]thiazol-5-yl)pyrimidin-2-yl)amino)-N-(3-propoxypropyl)benzamide The title compound was prepared as described in EXAMPLE 160, substituting 3-propoxypropan-1-amine for 2-morpholinoethanamine. MS (ESI) m/e 646 (M+H)+; 1H NMR (300 MHz, DMSO-d6) δ 8.62 (d, 1H), 8.22 (d, 1H), 8.07 (m, 1H), 7.84 (m, 1H), 7.79 (m, 1H), 7.63 (m, 1H), 7.46

(d, 1H), 7.34 (m, 10H), 6.65 (d, 1H), 3.65 (s, 2H), 3.45 (t, 2H), 3.34 (m, 4H), 1.79 (t, 2H), 1.50 (m, 2H), 0.85 (t, 3H).

EXAMPLE 165

N-(3-methoxypropyl)-3-((4-(6-(3-((phenylacetyl)amino)phenyl)imidazo[2,1-b][1,3]thiazol-5-yl)pyrimidin-2-yl)amino)benzamide The title compound was prepared as described in EXAMPLE 160, substituting 3-methoxypropan-1-amine for 2-morpholinoethanamine. MS (ESI) m/e 616 (M−H)$^-$; $^1$H NMR (300 MHz, DMSO-d$_6$) δ 8.62 (d, 1H), 8.22 (d, 1H), 8.07 (m, 1H), 7.84 (m, 1H), 7.79 (m, 1H), 7.63 (m, 1H), 7.34 (m, 10H), 6.65 (d, 1H), 3.65 (s, 2H), 3.42 (t, 2H), 3.34 (t, 2H), 2.96 (s, 3H), 1.79 (m, 2H).

EXAMPLE 166

3-((4-(6-(3-((phenylacetyl)amino)phenyl)imidazo[2,1-b][1,3]thiazol-5-yl)pyrimidin-2-yl)amino)-N-((2S)-tetrahydrofuran-2-ylmethyl)benzamide The title compound was prepared as described in EXAMPLE 160, substituting (S)-(tetrahydrofuran-2-yl)methanamine for 2-morpholinoethanamine. MS (ESI) m/e 628 (M−H)$^-$; $^1$H NMR (300 MHz, DMSO-d$_6$) δ 8.62 (d, 1H), 8.22 (d, 1H), 8.09 (m, 1H), 7.84 (m, 1H), 7.79 (m, 1H), 7.63 (m, 1H), 7.34 (m, 9H), 6.65 (d, 1H), 4.00 (m, 1H), 3.80 (m, 1H), 3.65 (m, 3H), 3.36 (d, 2H), 1.85 (m, 2H), 1.60 (m, 2H).

EXAMPLE 167

N,N-bis(2-ethoxyethyl)-3-((4-(6-(3-((phenylacetyl)amino)phenyl)imidazo[2,1-b][1,3]thiazol-5-yl)pyrimidin-2-yl)amino)benzamide The title compound was prepared as described in EXAMPLE 160, substituting bis(2-ethoxyethyl)amine for 2-morpholinoethanamine. MS (ESI) m/e 688 (M−H)$^-$; $^1$H NMR (300 MHz, DMSO-d$_6$) δ 8.61 (d, 1H), 8.22 (d, 1H), 7.84 (m, 1H), 7.76 (m, 1H), 7.65 (m, 2H), 7.34 (m, 9H), 6.98 (m, 1H), 6.65 (d, 1H), 3.65 (s, 2H), 3.52 (m, 8H), 3.40 (q, 4H), 1.07 (t, 3H).

EXAMPLE 168

N-(2-methoxyethyl)-N-methyl-3-((4-(6-(3-((phenylacetyl)amino)phenyl)imidazo[2,1-b][1,3]thiazol-5-yl)pyrimidin-2-yl)amino)benzamide The title compound was prepared as described in EXAMPLE 160, substituting 2-methoxy-N-methylethanamine for 2-morpholinoethanamine. MS (ESI) m/e 618 (M+H)$^+$; $^1$H NMR (300 MHz, DMSO-d$_6$) δ 8.61 (d, 1H), 8.23 (d, 1H), 7.84 (m, 1H), 7.74 (m, 1H), 7.69 (m, 1H), 7.64 (M, 1H) 7.34 (m, 9H), 7.02 (m, 1H), 6.65 (d, 1H), 3.65 (s, 2H), 3.51 (s, 3H), 3.24 (s, 3H), 2.97 (d, 4H).

EXAMPLE 169

N-ethyl-N-(2-methoxyethyl)-3-((4-(6-(3-((phenylacetyl)amino)phenyl)imidazo[2,1-b][1,3]thiazol-5-yl)pyrimidin-2-yl)amino)benzamide The title compound was prepared as described in EXAMPLE 160, substituting N-ethyl-2-methoxyethanamine for 2-morpholinoethanamine. MS (ESI) m/e 632 (M+H)$^+$; $^1$H NMR (300 MHz, DMSO-d$_6$) δ 8.61 (d, 1H), 8.22 (d, 1H), 7.84 (m, 1H), 7.73 (m, 1H), 7.69 (m, 1H), 7.63 (m, 1H), 7.34 (m, 9H), 6.97 (m, 1H), 6.65 (d, 1H), 3.65 (s, 2H), 3.42 (s, 4H), 3.39 (q, 4H), 3.23 (s, 3H), 1.09 (t, 3H).

EXAMPLE 170

N,N-bis(2-methoxyethyl)-3-((4-(6-(3-((phenylacetyl)amino)phenyl)imidazo[2,1-b][1,3]thiazol-5-yl)pyrimidin-2-yl)amino)benzamide The title compound was prepared as described in EXAMPLE 160, substituting bis(2-methoxyethyl)amine for 2-morpholinoethanamine. MS (ESI) m/e 774 (M+trifluoroacetic acid-H)$^-$; $^1$H NMR (300 MHz, DMSO-d$_6$) δ 8.61 (d, 1H), 8.23 (d, 1H), 7.84 (m, 1H), 7.74 (m, 1H), 7.68 (m, 1H), 7.64 (m, 1H), 7.34 (m, 9H), 6.98 (m, 1H), 6.65 (d, 1H), 3.65 (s, 2H), 3.51 (m, 8H), 3.22 (s, 6H).

EXAMPLE 171

N-(3-(5-(2-((3-(morpholin-4-ylcarbonyl)phenyl)amino)pyrimidin-4-yl)imidazo[2,1-b][1,3]thiazol-6-yl)phenyl)-2-phenylacetamide The title compound was prepared as described in EXAMPLE 160, substituting morpholine for 2-morpholinoethanamine. MS (ESI) m/e 616 (M+H)$^+$; $^1$H NMR (300 MHz, DMSO-d$_6$) δ 8.61 (d, 1H), 8.23 (d, 1H), 7.85 (m, 1H), 7.78 (m, 1H), 7.72 (m, 1H), 7.63 (m, 1H), 7.34 (m, 9H), 7.03 (m, 1H), 6.66 (d, 1H), 3.65 (s, 2H), 3.60 (m, 4H), 3.50 (m, 4H).

EXAMPLE 172

2-phenyl-N-(3-(5-(2-((3-(thiomorpholin-4-ylcarbonyl)phenyl)amino)pyrimidin-4-yl)imidazo[2,1-b][1,3]thiazol-6-yl)phenyl)acetamide The title compound was prepared as described in EXAMPLE 160, substituting thiomorpholine for 2-morpholinoethanamine. MS (ESI) m/e 632 (M+H)$^+$; $^1$H NMR (300 MHz, DMSO-d$_6$) δ 8.61 (d, 1H), 8.23 (d, 1H), 7.85 (m, 1H), 7.76 (m, 1H), 7.71 (m, 1H), 7.63 (m, 1H), 7.34 (m, 9H), 7.00 (m, 1H), 6.66 (d, 1H), 3.75 (m, 4H), 3.65 (s, 2H), 2.62 (m, 4H).

EXAMPLE 173

N-(2-(dimethylamino)ethyl)-3-((4-(6-(3-((phenylacetyl)amino)phenyl)imidazo[2,1-b][1,3]thiazol-5-yl)pyrimidin-2-yl)amino)benzamide The title compound was prepared as described in EXAMPLE 160, substituting N$^1$,N$^1$-dimethylethane-1,2-diamine for 2-morpholinoethanamine. MS (ESI) m/e 617 (M−H)$^-$; $^1$H NMR (300 MHz, DMSO-d$_6$) δ 8.61 (d, 1H), 8.23 (d, 1H), 7.87 (m, 1H), 7.78 (m, 1H), 7.72 (m, 1H), 7.63 (m, 1H), 7.34 (m, 9H), 7.03 (m, 1H), 6.67 (d, 1H), 3.66 (s, 2H), 3.52 (m, 2H), 3.31 (m, 2H).

EXAMPLE 174

3-((4-(6-(3-((phenylacetyl)amino)phenyl)imidazo[2,1-b][1,3]thiazol-5-yl)pyrimidin-2-yl)amino)-N-(2-pyrrolidin-1-ylethyl)benzamide The title compound was prepared as described in EXAMPLE 160, substituting 2-(pyrrolidin-1-yl)ethanamine for 2-morpholinoethanamine. MS (ESI) m/e 643 (M+H)+; 1H NMR (300 MHz, DMSO-d6) δ 8.63 (d, 1H), 8.23 (d, 1H), 8.15 (m, 1H), 7.87 (m, 1H), 7.83 (m, 1H), 7.61 (m, 1H), 7.47 (m, 1H), 7.34 (m, 9H), 6.67 (d, 1H), 3.91 (m, 2H), 3.65 (m, 4H), 3.37 (t, 2H), 2.21 (m, 2H), 2.01 (m, 2H).

EXAMPLE 175

3-((4-(6-(3-((phenylacetyl)amino)phenyl)imidazo[2,1-b][1,3]thiazol-5-yl)pyrimidin-2-yl)amino)-N-(2-piperidin-1-ylethyl)benzamide The title compound was prepared as described in EXAMPLE 160, substituting 2-(piperidin-1-yl)ethanamine for 2-morpholinoethanamine. MS (ESI) m/e 657 (M+H)+; 1H NMR (300 MHz, DMSO-d6) δ 8.63 (d, 1H), 8.23 (d, 1H), 8.15 (m, 1H), 7.87 (m, 1H), 7.84 (m, 1H), 7.62 (m, 1H), 7.46 (m, 1H), 7.34 (m, 9H), 6.67 (d, 1H), 3.67 (m, 5H), 3.28 (t, 2H), 1.79 (m, 4H), 1.60 (m, 2H).

EXAMPLE 176

N-(3-morpholin-4-ylpropyl)-3-((4-(6-(3-((phenylacetyl)amino)phenyl)imidazo[2,1-b][1,3]thiazol-5-yl)pyrimidin-2-yl)amino)benzamide The title compound was prepared as described in EXAMPLE 160, substituting 3-morpholinopropan-1-amine for 2-morpholinoethanamine. MS (ESI) m/e 673 (M+H)+; 1H NMR (300 MHz, DMSO-d6) δ 8.63 (d, 1H), 8.23 (d, 1H), 8.12 (m, 1H), 7.87 (m, 1H), 7.82 (m, 1H), 7.62 (m, 1H), 7.47 (m, 1H), 7.34 (m, 9H), 6.66 (d, 1H), 3.85 (m, 4H), 3.66 (s, 2H), 3.39 (t, 2H), 3.25 (m, 4H), 3.16 (m, 2H), 1.98 (m, 2H).

EXAMPLE 177

N-(2-(4-methylpiperazin-1-yl)ethyl)-3-((4-(6-(3-((phenylacetyl)amino)phenyl)imidazo[2,1-b][1,3]thiazol-5-yl)pyrimidin-2-yl)amino)benzamide The title compound was prepared as described in EXAMPLE 160, substituting 2-(4-methylpiperazin-1-yl)ethanamine for 2-morpholinoethanamine. MS (ESI) m/e 672 (M+H)+; 1H NMR (300 MHz, DMSO-d6) δ 8.62 (d, 1H), 8.23 (d, 1H), 8.10 (m, 1H), 7.87 (m, 1H), 7.81 (m, 1H), 7.61 (m, 1H), 7.43 (m, 1H), 7.34 (m, 9H), 6.66 (d, 1H), 3.66 (s, 2H), 3.47 (t, 2H), 3.15 (m, 4H), 2.86 (m, 2H), 2.76 (m, 2H), 2.73 (s, 3H).

EXAMPLE 178

N-methyl-3-((4-(6-(3-((phenylacetyl)amino)phenyl)imidazo[2,1-b][1,3]thiazol-5-yl)pyrimidin-2-yl)amino)-N-(tetrahydrofuran-2-ylmethyl)benzamide The title compound was prepared as described in EXAMPLE 160, substituting N-methyl-1-(tetrahydrofuran-2-yl)methanamine for 2-morpholinoethanamine. MS (ESI) m/e 644 (M+H)+; 1H NMR (300 MHz, DMSO-d6) δ 8.61 (d, 1H), 8.23 (d, 1H), 7.84 (m, 1H), 7.74 (m, 1H), 7.69 (m, 1H), 7.64 (m, 1H), 7.34 (m, 9H), 6.99 (m, 1H) 6.65 (d, 1H), 4.05 (m, 1H), 3.65 (m, 4H), 3.43 (m, 2H), 3.00 (s, 3H), 1.77 (m, 4H).

EXAMPLE 179

N-(3-(dimethylamino)propyl)-N-methyl-3-((4-(6-(3-((phenylacetyl)amino)phenyl)imidazo[2,1-b][1,3]thiazol-5-yl)pyrimidin-2-yl)amino)benzamide The title compound was prepared as described in EXAMPLE 160, substituting $N^1,N^1,N^3$-trimethylpropane-1,3-diamine for 2-morpholinoethanamine. MS (ESI) m/e 631 (M–Me)+; 1H NMR (300 MHz, DMSO-d6) δ 8.62 (d, 1H), 8.23 (d, 1H), 7.87 (m, 1H), 7.77 (m, 1H), 7.72 (m, 1H), 7.62 (m, 1H), 7.34 (m, 9H), 7.04 (m, 1H) 6.67 (d, 1H), 3.65 (s, 2H), 3.49 (m, 2H), 3.43 (s, 3H), 2.98 (s, 3H), 2.80 (s, 3H), 2.07 (m, 2H).

EXAMPLE 180

N-(2-(dimethylamino)ethyl)-N-ethyl-3-((4-(6-(3-((phenylacetyl)amino)phenyl)imidazo[2,1-b][1,3]thiazol-5-yl)pyrimidin-2-yl)amino)benzamide The title compound was prepared as described in EXAMPLE 160, substituting $N^1$-ethyl-$N^2,N^2$-dimethylethane-1,2-diamine for 2-morpholinoethanamine. MS (ESI) m/e 616 (M–Et)+; 1H NMR (300 MHz, DMSO-d6) δ 8.61 (d, 1H), 8.23 (d, 1H), 7.87 (m, 1H), 7.81 (m, 1H), 7.71 (m, 1H), 7.61 (m, 1H), 7.34 (m, 9H), 7.03 (m, 1H) 6.67 (d, 1H), 3.89 (m, 1H), 3.74 (m, 1H), 3.65 (s, 2H), 3.35 (m, 4H), 2.87 (s, 3H), 1.10 (m, 3H).

EXAMPLE 181

N-methyl-3-((4-(6-(3-((phenylacetyl)amino)phenyl)imidazo[2,1-b][1,3]thiazol-5-yl)pyrimidin-2-yl)amino)-N-(2-pyridin-2-ylethyl)benzamide The title compound was prepared as described in EXAMPLE 160, substituting N-methyl-2-(pyridin-2-yl)ethanamine for 2-morpholinoethanamine. MS (ESI) m/e 665 (M+H)+; 1H NMR (300 MHz, DMSO-d6) δ 8.60 (d, 1H), 8.53 (m, 1H), 8.23 (d, 1H), 7.97 (m, 1H), 7.86 (m, 1H), 7.65 (m, 3H), 7.47 (m, 2H), 7.34 (m, 9H), 6.87 (m, 1H) 6.66 (d, 1H), 3.79 (t, 2H), 3.65 (s, 2H), 3.15 (t, 2H), 2.94 (s, 3H).

EXAMPLE 182

N-(3-(5-(2-((3-((2,6-dimethylmorpholin-4-yl)carbonyl)phenyl)amino)pyrimidin-4-yl)imidazo[2,1-b][1,3]thiazol-6-yl)phenyl)-2-phenylacetamide The title compound was prepared as described in EXAMPLE 160, substituting 2,6-dimethylmorpholine for 2-morpholinoethanamine. MS (ESI) m/e 644 (M+H)+; 1H NMR (300 MHz, DMSO-d6) δ 8.61 (d, 1H), 8.23 (d, 1H), 7.85 (m, 1H), 7.78 (m, 1H), 7.71 (m, 1H), 7.63 (m, 1H), 7.34 (m, 9H), 7.02 (m, 1H) 6.66 (d, 1H), 3.95 (m, 2H), 3.65 (s, 2H), 3.53 (m, 2H), 2.61 (m, 2H) 1.07 (d, 6H).

EXAMPLE 183

N-(3-(5-(2-((3-((4-methylpiperazin-1-yl)carbonyl)phenyl)amino)pyrimidin-4-yl)imidazo[2,1-b][1,3]thiazol-6-yl)phenyl)-2-phenylacetamide The title compound was prepared as described in EXAMPLE 160, substituting 1-methylpiperazine for 2-morpholinoethanamine. MS (ESI) m/e 625 (M+H)+; 1H NMR (300 MHz, DMSO-d$_6$) δ 8.63 (d, 1H), 8.24 (d, 1H), 7.87 (m, 1H), 7.84 (m, 1H), 7.74 (m, 1H), 7.61 (m, 1H), 7.34 (m, 9H), 7.09 (m, 1H) 6.67 (d, 1H), 3.77 (m, 4H), 3.66 (s, 2H), 3.27 (m, 4H), 2.85 (s, 3H).

EXAMPLE 184

N-(3-(5-(2-((3-((4-ethylpiperazin-1-yl)carbonyl)phenyl)amino)pyrimidin-4-yl)imidazo[2,1-b][1,3]thiazol-6-yl)phenyl)-2-phenylacetamide The title compound was prepared as described in EXAMPLE 160, substituting 1-ethylpiperazine for 2-morpholinoethanamine. MS (ESI) m/e 643 (M+H)$^+$; $^1$H NMR (300 MHz, DMSO-d$_6$) δ 8.62 (d, 1H), 8.24 (d, 1H), 7.87 (m, 1H), 7.85 (m, 1H), 7.73 (m, 1H), 7.61 (m, 1H), 7.34 (m, 9H), 7.09 (m, 1H) 6.67 (d, 1H), 3.77 (m, 4H), 3.65 (s, 2H), 3.26 (m, 4H), 3.18 (q, 2H), 1.26 (t, 3H).

EXAMPLE 185

N-(3-(5-(2-((3-((4-(2-hydroxyethyl)piperazin-1-yl)carbonyl)phenyl)amino)pyrimidin-4-yl)imidazo[2,1-b][1,3]thiazol-6-yl)phenyl)-2-phenylacetamide The title compound was prepared as described in EXAMPLE 160, substituting 2-(piperazin-1-yl)ethanol for 2-morpholinoethanamine. MS (ESI) m/e 771 (M+trifluoroacetic acid-H)$^-$; $^1$H NMR (300 MHz, DMSO-d$_6$) δ 8.63 (d, 1H), 8.24 (d, 1H), 7.87 (m, 1H), 7.85 (m, 1H), 7.73 (m, 1H), 7.61 (m, 1H), 7.34 (m, 9H), 7.09 (m, 1H) 6.67 (d, 1H), 3.80 (m, 6H), 3.65 (s, 2H), 3.33 (m, 4H), 3.24 (m, 2H).

EXAMPLE 186

N-(3-(5-(2-((3-((4-(2-(2-hydroxyethoxy)ethyl)piperazin-1-yl)carbonyl)phenyl)amino)pyrimidin-4-yl)imidazo[2,1-b][1,3]thiazol-6-yl)phenyl)-2-phenylacetamide The title compound was prepared as described in EXAMPLE 160, substituting 2-(2-(piperazin-1-yl)ethoxy)ethanol for 2-morpholinoethanamine. MS (ESI) m/e 703 (M+H)$^+$; $^1$H NMR (300 MHz, DMSO-d$_6$) δ 8.63 (d, 1H), 8.24 (d, 1H), 7.88 (m, 1H), 7.85 (m, 1H), 7.73 (m, 1H), 7.61 (m, 1H), 7.34 (m, 9H), 7.09 (m, 1H) 6.68 (d, 1H), 3.79 (m, 6H), 3.66 (s, 2H), 3.55 (m, 4H), 3.34 (m, 6H).

EXAMPLE 187

N-(4-hydroxybutyl)-3-((4-(6-(3-((phenylacetyl)amino)phenyl)imidazo[2,1-b][1,3]thiazol-5-yl)pyrimidin-2-yl)amino)benzamide The title compound was prepared as described in EXAMPLE 160, substituting 4-aminobutan-1-ol for 2-morpholinoethanamine. MS (ESI) m/e 618 (M+H)$^+$; $^1$H NMR (300 MHz, DMSO-d$_6$) δ 8.62 (d, 1H), 8.22 (d, 1H), 8.07 (m, 1H), 7.84 (m, 1H), 7.80 (m, 1H), 7.64 (m, 1H), 7.34 (m, 10H), 6.64 (d, 1H), 3.65 (s, 2H), 3.46 (t, 2H), 3.30 (t, 2H), 1.56 (m, 4H).

EXAMPLE 188

N-(4-(dimethylamino)butyl)-3-((4-(6-(3-((phenylacetyl)amino)phenyl)imidazo[2,1-b][1,3]thiazol-5-yl)pyrimidin-2-yl)amino)benzamide The title compound was prepared as described in EXAMPLE 160, substituting N$^1$,N$^1$-dimethylbutane-1,4-diamine for 2-morpholinoethanamine. MS (ESI) m/e 645 (M+H)$^+$; $^1$H NMR (300 MHz, DMSO-d$_6$) δ 8.61 (d, 1H), 8.23 (d, 1H), 7.87 (m, 1H), 7.76 (m, 1H), 7.70 (m, 1H), 7.61 (m, 1H), 7.34 (m, 9H), 7.00 (m, 1H) 6.67 (d, 1H), 3.65 (s, 2H), 3.41 (m, 4H), 2.94 (s, 3H), 2.76 (s, 3H).

EXAMPLE 189

N-(3-(1H-imidazol-1-yl)propyl)-3-((4-(6-(3-((phenylacetyl)amino)phenyl)imidazo[2,1-b][1,3]thiazol-5-yl)pyrimidin-2-yl)amino)benzamide The title compound was prepared as described in EXAMPLE 160, substituting 3-(1H-imidazol-1-yl)propan-1-amine for 2-morpholinoethanamine. MS (ESI) m/e 654 (M+H)$^+$; $^1$H NMR (300 MHz, DMSO-d$_6$) δ 8.92 (m, 1H), 8.62 (d, 1H), 8.23 (d, 1H), 8.10 (m, 1H), 7.87 (m, 1H), 7.81 (m, 1H), 7.66 (m, 1H), 7.61 (m, 1H), 7.54 (m, 1H), 7.34 (m, 10H), 6.66 (d, 1H), 4.20 (t, 2H), 3.65 (s, 2H), 3.35 (t, 2H), 2.14 (m, 2H).

EXAMPLE 190

2-fluoro-N-(3-(5-(2-((4-morpholin-4-ylphenyl)amino)pyrimidin-4-yl)imidazo[2,1-b][1,3]thiazol-6-yl)phenyl)benzamide The title compound was prepared as described in EXAMPLE 47, substituting 2-fluorobenzoyl chloride for (isocyanatomethyl)benzene. MS (ESI(+)) m/e 592 (M+H)$^+$; (ESI(−)) m/e 590 (M−H)$^-$; $^1$H-NMR (300 MHz, DMSO-d$_6$) □ 10.54 (s, 1H), 9.44 (s, 1H), 8.75 (bs, 1H), 8.23 (d, 1H), 8.01 (s, 1H), 7.84 (dd, 1H), 7.67 (td, 1H), 7.50-7.63 (m, 3H), 7.42-7.50 (m, 2H), 7.30-7.40 (m, 3H), 6.88-6.96 (m, 2H), 6.56 (d, 1H), 3.71-3.78 (m, 4H), 3.02-3.09 (m, 4H).

EXAMPLE 191

2-methyl-N-(3-(5-(2-((4-morpholin-4-ylphenyl)amino)pyrimidin-4-yl)imidazo[2,1-b][1,3]thiazol-6-yl)phenyl)benzamide The title compound was prepared as described in EXAMPLE 47, substituting 2-methylbenzoyl chloride for (isocyanatomethyl)benzene. MS (ESI(+)) m/e 588 (M+H)$^+$; (ESI(−)) m/e 586 (M−H)$^-$; $^1$H-NMR (300 MHz, DMSO-d$_6$) □ 10.41 (s, 1H), 9.44 (s, 1H), 8.75 (bs, 1H), 8.22 (d, 1H), 8.05 (s, 1H), 7.84 (d, 1H), 7.54 (d, 1H), 7.26-7.50 (m, 7H), 6.88-6.97 (m, 2H), 6.57 (d, 1H), 3.71-3.78 (m, 4H), 3.02-3.09 (m, 4H), 2.39 (s, 3H).

EXAMPLE 192

4-(6-(3-((5-(4-methoxyphenyl)-1,3-oxazol-2-yl)amino)phenyl)imidazo[2,1-b][1,3]thiazol-5-yl)-N-(4-morpholin-4-ylphenyl)pyrimidin-2-amine

EXAMPLE 192A

A 50 ml flask was charged with 2-amino-1-(4-methoxyphenyl)ethanone hydrochloride (2 g), ethanol (15 ml) and carbon disulfide (1.178 ml). To the suspension was slowly added dropwise a solution of sodium carbonate (1.104 g) in water (3.5 ml) and the mixture was heated at 80° C. for 18 hours. After cooling, the mixture was filtered to remove the solid and the filtrate was treated with glacial acetic acid (3.75 ml) and stirred for 30 minutes The resulting solid was collected by filtration, washed with ethanol and ether, and dried to afford the title compound.

EXAMPLE 192B

A 25 ml flask was charged with EXAMPLE 192A (1.3 g), phosphoryl trichloride (3.51 ml) and cooled to 0° C. under nitrogen. Triethylamine (0.962 ml) was added dropwise and the mixture was then heated at 100° C. for 18 hours. The mixture was concentrated, diluted with methylene chloride, cooled below 0° C., and slowly basified with 2N-isopropanolic ammonia. Following an aqueous work-up the crude product was purified on silica gel with an ethyl acetate and hexane gradient to afford the title compound.

EXAMPLE 192C 4-(6-(3-((5-(4-methoxyphenyl)-1,3-oxazol-2-yl) amino)phenyl)imidazo[2,1-b][1,3]thiazol-5-yl)-N-(4-morpholin-4-ylphenyl)pyrimidin-2-amine The title compound was prepared as described in EXAMPLE 142 substituting EXAMPLE 192B for 2-chlorobenzo[d]oxazole, N-methyl-2-pyrrolidinone for 2-propanol and microwave heating in a Biotage Initiator 2 monomode microwave reactor at 210° C. for 2 hours instead of 80° C. for 18 hours. MS (ESI(+)) m/e 643 (M+H)$^+$; $^1$H-NMR (300 MHz, DMSO-d$_6$) □ 10.40 (s, 1H), 9.60 (s, 1H), 8.76 (br s, 1H), 8.21 (d, 1H), 7.93 (m, 1H), 7.71 (m, 1H), 7.57-7.40 (m, 6H), 7.28 (s, 1H), 7.17 (m, 1H), 6.99 (m, 4H), 6.60 (d, 1H), 3.77 (s, 3H), 3.76 (m, 4H), 3.12 (m, 4H).

EXAMPLE 193

N-(4-morpholin-4-ylphenyl)-4-(6-(3-((5-phenyl-1,3-oxazol-2-yl)amino)phenyl)imidazo[2,1-b][1,3]thiazol-5-yl)pyrimidin-2-amine

EXAMPLE 193A

The title compound was prepared as described in EXAMPLE 192A substituting 2-aminoacetophenone hydrochloride for 2-amino-1-(4-methoxyphenyl)ethanone hydrochloride.

EXAMPLE 193B

The title compound was prepared as described in EXAMPLE 192B, substituting EXAMPLE 193A for EXAMPLE 192A.

EXAMPLE 193C

N-(4-morpholin-4-ylphenyl)-4-(6-(3-((5-phenyl-1,3-oxazol-2-yl)amino)phenyl)imidazo[2,1-b][1,3]thiazol-5-yl)pyrimidin-2-amine The title compound was prepared as a trifluoracetic acid salt described in EXAMPLE 142 substituting EXAMPLE 193B for 2-chlorobenzo[d]oxazole, N-methyl-2-pyrrolidinone for 2-propanol and microwave heating in a Biotage Initiator 2 monomode microwave reactor at 210° C. for 1 hour instead of 80° C. for 18 hours. MS (ESI(+)) m/e 613 (M+H)$^+$; $^1$H-NMR (300 MHz, DMSO-d$_6$) □ 10.52 (s, 1H), 9.605 (s, 1H), 8.78 (br s, 1H), 8.22 (d, 1H), 7.95 (m, 1H), 7.73 (m, 1H), 7.59-7.40 (m, 9H), 7.27 (m, 1H), 7.18 (d, 1H), 7.00 (d, 1H), 6.59 (d, 1H), 3.76 (m, 4H), 3.11 (m, 4H).

EXAMPLE 194

N-(3-(2-bromo-5-(2-((3-morpholin-4-ylphenyl) amino)pyrimidin-4-yl)imidazo[2,1-b][1,3]thiazol-6-yl)phenyl)benzamide The title compound was prepared as described in EXAMPLE 1, substituting 2-amino-5-bromothiazole for 2-aminothiazole in EXAMPLE 1A, EXAMPLE 338A for phenylguanidine in EXAMPLE 1E, and benzoyl chloride for 2-chlorobenzoyl chloride in EXAMPLE 1G. MS (ESI(+)) m/e 654 (M+H)$^+$; $^1$H-NMR (300 MHz, DMSO-d$_6$) □ 10.37 (s, 1H); 9.61 (s, 1H); 9.03 (s, 1H); 8.29 (d, 1H); 8.10 (s, 1H); 7.97-7.90 (m, 3H); 7.60-7.45 (m, 4H); 7.35 (m, 2H); 7.20 (m, 2H); 6.64 (m, 2H); 3.74 (m, 4H); 3.09 (m, 4H).

EXAMPLE 195

N-(3-(2-bromo-5-(2-((3-morpholin-4-ylphenyl) amino)pyrimidin-4-yl)imidazo[2,1-b][1,3]thiazol-6-yl)phenyl)-2-phenylacetamide The title compound was prepared as described in EXAMPLE 1, substituting 2-amino-5-bromothiazole for 2-aminothiazole in EXAMPLE 1A, EXAMPLE 338A for phenylguanidine in EXAMPLE 1E, and phenylacetyl chloride for 2-chlorobenzoyl chloride in EXAMPLE 1G. MS (ESI(+)) m/e 668 (M+H)$^+$; $^1$H-NMR (300 MHz, DMSO-d$_6$) □ 10.28 (s, 1H); 9.59 (s, 1H); 9.00 (s, 1H); 8.26 (d, 1H); 7.88 (s, 1H); 7.70 (d, 1H); 7.41 (t, 1H); 7.33-7.18 (m, 9H); 6.62 (d, 1H); 6.58 (d, 1H); 3.74 (m, 4H); 3.64 (s, 2H); 3.09 (m, 4H).

EXAMPLE 196

2-methoxy-N-(3-(5-(2-((4-morpholin-4-ylphenyl) amino)pyrimidin-4-yl)imidazo[2,1-b][1,3]thiazol-6-yl)phenyl)benzamide The title compound was prepared as described in EXAMPLE 47, substituting 2-methoxybenzoyl chloride for (isocyanatomethyl)benzene. MS (ESI(+)) m/e 604 (M+H)$^+$; $^1$H-NMR (300 MHz, DMSO-d$_6$) □ 10.23 (s, 1H), 9.44 (s, 1H), 8.77 (bs, 1H), 8.22 (d, 1H), 8.01 (s, 1H), 7.85 (dd, 1H), 7.62 (dd, 1H), 7.39-7.57 (m, 5H), 7.31 (dt, 1H), 7.18 (d, 1H), 7.06 (td, 1H), 6.88-6.97 (m, 2H), 6.56 (d, 1H), 3.89 (s, 3H), 3.70-3.77 (m, 4H), 3.02-3.09 (m, 4H).

EXAMPLE 197

2-chloro-N-(3-(5-(2-((4-morpholin-4-ylphenyl) amino)pyrimidin-4-yl)imidazo[2,1-b][1,3]thiazol-6-yl)phenyl)benzamide The title compound was prepared as described in EXAMPLE 47, substituting 2-chlorobenzoyl chloride for (isocyanatomethyl)benzene. MS (ESI(+)) m/e 608 (M+H)$^+$; (ESI(−)) m/e 606 (M−H)$^−$; $^1$H-NMR (300 MHz, DMSO-d$_6$) □ 10.41 (s, 1H), 9.44 (s, 1H), 8.75 (bs, 1H), 8.22 (d, 1H), 8.05 (s, 1H), 7.84 (d, 1H), 7.54 (d, 1H), 7.26-7.50 (m, 7H), 6.88-6.97 (m, 2H), 6.57 (d, 1H), 3.71-3.78 (m, 4H), 3.02-3.09 (m, 4H), 2.39 (s, 3H).

EXAMPLE 198

2,6-dimethoxy-N-(3-(5-(2-((4-morpholin-4-ylphenyl)amino)pyrimidin-4-yl)imidazo[2,1-b][1,3]thiazol-6-yl)phenyl)benzamide The title compound was prepared as described in EXAMPLE 47, substituting 2,6-dimethoxybenzoyl chloride for (isocyanatomethyl)benzene. MS (ESI(+)) m/e 634 (M+H)$^+$; (ESI(−)) m/e 632 (M−H)$^−$; $^1$H-NMR (300 MHz, DMSO-d$_6$) ☐ 10.32 (s, 1H), 9.44 (s, 1H), 8.77 (bs, 1H), 8.22 (d, 1H), 7.99 (t, 1H), 7.79 (ddd, 1H), 7.55 (d, 2H), 7.47 (d, 1H), 7.38 (ddd, 2H), 7.27 (dt, 1H), 6.90-6.97 (m, 2H), 6.73 (d, 2H), 6.55 (d, 1H), 3.71-3.80 (m, 4H), 3.02-3.09 (m, 4H).

EXAMPLE 199

2-chloro-6-fluoro-N-(3-(5-(2-((4-morpholin-4-ylphenyl)amino)pyrimidin-4-yl)imidazo[2,1-b][1,3]thiazol-6-yl)phenyl)benzamide The title compound was prepared as described in EXAMPLE 47, substituting 2-chloro-6-fluorobenzoyl chloride for (isocyanatomethyl)benzene. MS (ESI(+)) m/e 626 (M+H)$^+$; (ESI(−)) m/e 624 (M−H)$^−$; $^1$H-NMR (300 MHz, DMSO-d$_6$) ☐ 10.90 (s, 1H), 9.44 (s, 1H), 8.74 (bs, 1H), 8.23 (d, 1H), 7.99 (t, 1H), 7.76 (d, 1H), 7.33-7.62 (m, 8H), 6.88-6.97 (m, 2H), 6.57 (d, 1H), 3.71-3.78 (m, 4H), 3.02-3.09 (m, 4H).

EXAMPLE 200

2,6-dichloro-N-(3-(5-(2-((4-morpholin-4-ylphenyl)amino)pyrimidin-4-yl)imidazo[2,1-b][1,3]thiazol-6-yl)phenyl)benzamide The title compound was prepared as described in EXAMPLE 47, substituting 2,6-dichlorobenzoyl chloride for (isocyanatomethyl)benzene. MS (ESI(+)) m/e 642 (M+H)$^+$; (ESI(−)) m/e 640 (M−H)$^−$; $^1$H-NMR (300 MHz, DMSO-d$_6$) ☐ 10.86 (s, 1H), 9.45 (s, 1H), 8.74 (bs, 1H), 8.22 (d, 1H), 7.99 (s, 1H), 7.74 (d, 1H), 7.43-7.62 (m, 7H), 7.36-7.41 (m, 2H), 6.93 (d, 1H), 6.58 (d, 1H), 3.71-3.78 (m, 4H), 3.02-3.09 (m, 4H).

EXAMPLE 201

N-(3-(5-(2-((4-morpholin-4-ylphenyl)amino)pyrimidin-4-yl)imidazo[2,1-b][1,3]thiazol-6-yl)phenyl)-2-nitrobenzamide The title compound was prepared as described in EXAMPLE 47, substituting 2-nitrobenzoyl chloride for (isocyanatomethyl)benzene. MS (ESI(+)) m/e 619 (M+H)$^+$; (ESI(−)) m/e 617 (M−H)$^−$; $^1$H-NMR (300 MHz, DMSO-d$_6$) ☐ 10.78 (s, 1H), 9.44 (s, 1H), 8.76 (bs, 1H), 8.22 (d, 1H), 8.15 (dd, 1H), 7.97 (t, 1H), 7.83-7.92 (m, 1H), 7.71-7.83 (m, 3H), 7.54 (d, 2H), 7.42-7.50 (m, 2H), 7.33-7.40 (m, 1H), 6.89-6.97 (m, 2H), 6.58 (d, 1H), 3.70-3.80 (m, 4H), 3.02-3.10 (m, 4H).

EXAMPLE 202

N-(3-(5-(2-((4-morpholin-4-ylphenyl)amino)pyrimidin-4-yl)imidazo[2,1-b][1,3]thiazol-6-yl)phenyl)-2-(trifluoromethyl)benzamide The title compound was prepared as described in EXAMPLE 47, substituting 2-(trifluoromethyl)benzoyl chloride for (isocyanatomethyl)benzene. MS (ESI(+)) m/e 642 (M+H)$^+$; (ESI(−)) m/e 640 (M−H)$^−$; $^1$H-NMR (300 MHz, DMSO-d$_6$) ☐ 10.68 (s, 1H), 9.44 (s, 1H), 8.76 (bs, 1H), 8.22 (d, 1H), 7.97 (t, 1H), 7.67-7.89 (m, 5H), 7.54 (d, 2H), 7.42-7.50 (m, 2H), 7.36 (dt, 1H), 6.88-6.97 (m, 2H), 6.57 (d, 1H), 3.71-3.78 (m, 4H), 3.02-3.09 (m, 4H).

EXAMPLE 203

2,5-dichloro-N-(3-(5-(2-((4-morpholin-4-ylphenyl)amino)pyrimidin-4-yl)imidazo[2,1-b][1,3]thiazol-6-yl)phenyl)thiophene-3-carboxamide The title compound was prepared as described in EXAMPLE 47, substituting 2,5-dichlorothiophene-3-carbonyl chloride for (isocyanatomethyl)benzene. MS (ESI(+)) m/e 648 (M+H)$^+$; (ESI(−)) m/e 646 (M−H)$^−$; $^1$H-NMR (300 MHz, DMSO-d$_6$) ☐ 10.42 (s, 1H), 9.44 (s, 1H), 8.75 (bs, 1H), 8.23 (d, 1H), 7.98 (t, 1H), 7.78-7.84 (m, 1H), 7.54 (d, 2H), 7.51 (s, 1H), 7.43-7.49 (m, 2H), 7.36 (dt, 1H), 6.89-6.97 (m, 2H), 6.55 (d, 1H), 3.72-3.78 (m, 4H), 3.02-3.09 (m, 4H).

EXAMPLE 204

N-(3-(5-(2-((4-(4-ethylpiperazin-1-yl)phenyl)amino)pyrimidin-4-yl)imidazo[2,1-b][1,3]thiazol-6-yl)phenyl)-2-phenylacetamide

EXAMPLE 204A

The title compound was prepared as described in EXAMPLE 42A, substituting 4-(4-ethylpiperazin-1-yl)aniline for 4-(1H-imidazol-1-yl)aniline.

EXAMPLE 204B

The title compound was prepared as described in EXAMPLE 1E, substituting EXAMPLE 204A for phenyl guanidine.

EXAMPLE 204C

The title compound was prepared as described in EXAMPLE 1F, substituting EXAMPLE 204B for EXAMPLE 1E.

EXAMPLE 204D

N-(3-(5-(2-((4-(4-ethylpiperazin-1-yl)phenyl)amino)pyrimidin-4-yl)imidazo[2,1-b][1,3]thiazol-6-yl)phenyl)-2-phenylacetamide The title compound was prepared as a trifluoracetic acid salt as described in EXAMPLE 36, substituting EXAMPLE 204C for EXAMPLE 36C. MS (ESI), m/e 615.3; $^1$H-NMR (300 MHz, DMSO-d$_6$) ☐ ppm 10.27 (s, 1 H), 9.51 (s, 1 H), 9.48 (bs, 1 H), 8.75 (bs, 1 H), 8.20 (d, 1 H), 7.88 (s, 1 H), 7.67 (d, 1 H), 7.58 (d, 2 H), 7.46 (d, 1 H), 7.39 (t, 1H), 7.23-7.32 (m, 5 H), 7.00 (d, 2 H), 6.53 (d, 1 H), 3.76-3.78 (m, 2 H), 3.65 (s, 2 H), 3.57-3.61 (m, 2 H), 3.10-3.23 (m, 4 H), 2.93 (q, 2 H), 1.25 (t, 3H).

EXAMPLE 205

2-(2-chlorophenyl)-N-(3-(5-(2-((4-(4-ethylpiperazin-1-yl)phenyl)amino)pyrimidin-4-yl)imidazo[2,1-b][1,3]thiazol-6-yl)phenyl)acetamide A solution of EXAMPLE 204C (50 mg), 2-(2-chlorophenyl)acetic acid. (26 mg) and N$^1$-((ethylimino)methylene)-N$^3$, N³-dimethylpropane-1,3-diamine hydrochloride (29 mg) in CH₂Cl₂ (3 mL) and N-methylpyrrolidone (0.5 mL) was stirred overnight. The mixture was concentrated and the residue was purified on a reverse phase HPLC eluting with a water-acetonitrile gradient containing 0.1% trifluoroacetic acid, to afford the title compound as a trifluoroacetic acid salt. MS (ESI), m/e 649.3; $^1$H-NMR (300 MHz, DMSO-$d_6$) ☐ ppm 10.33 (s, 1 H), 9.52 (s, 1 H), 9.48 (bs, 1 H), 8.77 (bs, 1 H), 8.22 (d, 1 H), 7.89 (s, 1 H), 7.69 (d, 1H), 7.59 (d, 2 H), 7.38-7.46 (m, 4 H), 7.28-7.32 (m, 3 H), 7.00 (d, 2 H), 6.56 (d, 1 H), 3.85 (s, 2 H), 3.76-3.78 (m, 2 H), 3.57-3.61 (m, 2 H), 3.10-3.23 (m, 4 H), 2.94 (q, 2 H), 1.27 (t, 3H).

EXAMPLE 206

N-(3-(5-(2-((4-(4-ethylpiperazin-1-yl)phenyl)amino)pyrimidin-4-yl)imidazo[2,1-b][1,3]thiazol-6-yl)phenyl)-2-(2-methylphenyl)acetamide The title compound was prepared as described in EXAMPLE 205, substituting 2-O—tolylacetic acid for 2-(2-chlorophenyl)acetic acid. MS (ESI), m/e 629.3; $^1$H-NMR (300 MHz, DMSO-$d_6$) ☐ ppm 10.25 (s, 1 H), 9.51 (s, 1 H), 9.41 (bs, 1 H), 8.77 (bs, 1 H), 8.22 (d, 1H), 7.90 (s, 1 H), 7.69 (d, 1 H), 7.59 (d, 2 H), 7.47 (d, 1 H), 7.40 (t, 1 H), 7.24-7.29 (m, 2 H), 7.12-7.18 (m, 4 H), 7.00 (d, 2 H), 6.56 (d, 1H), 3.76-3.78 (m, 2 H), 3.69 (s, 2 H), 3.57-3.61 (m, 2 H), 3.10-3.23 (m, 4 H), 2.93 (q, 2 H), 2.29 (s, 3 H), 1.27 (t, 3H).

EXAMPLE 207

N-(3-(5-(2-((4-(4-ethylpiperazin-1-yl)phenyl)amino)pyrimidin-4-yl)imidazo[2,1-b][1,3]thiazol-6-yl)phenyl)-2-(2-(trifluoromethyl)phenyl)acetamide The title compound was prepared as described in EXAMPLE 205, substituting 2-(2-(trifluoromethyl)phenyl) acetic acid for 2-(2-chlorophenyl)acetic acid. MS (ESI), m/e 683.2; (ESI), m/e 681.0 (M–H)⁻; $^1$H-NMR (300 MHz, DMSO-$d_6$) ☐ ppm 10.32 (s, 1 H), 9.51 (s, 1 H), 9.44 (bs, 1 H), 8.77 (bs, 1 H), 8.22 (d, 1 H), 7.88 (s, 1 H), 7.63-7.72 (m, 3 H), 7.59 (d, 2 H), 7.46-7.53 (m, 3 H), 7.41 (t, 1 H), 7.28 (d, 1 H), 7.00 (d, 2 H), 6.56 (d, 1 H), 3.76-3.78 (m, 2 H), 3.57-3.60 (m, 2 H), 3.10-3.23 (m, 4 H), 2.93 (q, 2 H), 1.27 (t, 3H).

EXAMPLE 208

N-(3-(5-(2-((4-(4-ethylpiperazin-1-yl)phenyl)amino)pyrimidin-4-yl)imidazo[2,1-b][1,3]thiazol-6-yl)phenyl)benzamide The title compound was prepared as described in EXAMPLE 36, substituting EXAMPLE 204C for EXAMPLE 36C and benzoyl chloride for phenylacetyl chloride. MS (ESI), m/e 601.3; (ESI), m/e 599.4 (M–H)⁻; $^1$H-NMR (300 MHz, DMSO-$d_6$) ☐ ppm 10.36 (s, 1 H), 9.54 (s, 1 H), 9.48 (bs, 1 H), 8.79 (bs, 1 H), 8.24 (d, 1 H), 8.11 (s, 1 H), 7.90-7.98 (m, 4H), 7.45-7.62 (m, 6 H), 7.34 (d, 1 H), 7.00 (d, 2 H), 6.62 (d, 1 H), 3.75-3.79 (m, 2 H), 3.57-3.60 (m, 2 H), 3.10-3.23 (m, 4 H), 2.94 (q, 2 H), 1.27 (t, 3H).

EXAMPLE 209

N-(3-(5-(2-((4-(4-ethylpiperazin-1-yl)phenyl)amino)pyrimidin-4-yl)imidazo[2,1-b][1,3]thiazol-6-yl)phenyl)-2,6-difluorobenzamide The title compound was prepared as described in EXAMPLE 36, substituting EXAMPLE 204C for EXAMPLE 36C and 2,4-difluoro-benzoyl chloride for phenylacetyl chloride. MS (ESI), m/e 637.3; (ESI), m/e 635.1 (M–H)⁻; $^1$H-NMR (300 MHz, DMSO-$d_6$) ☐ ppm 10.93 (s, 1 H), 9.50 (s, 1 H), 8.78 (bs, 1 H), 8.23 (d, 1 H), 7.99 (s, 1 H), 7.77 (d, 1 H), 7.54-7.63 (m, 3 H), 7.46-7.50 (m, 2 H), 7.38 (d, 1 H), 7.24-7.28 (m, 2 H), 6.98 (d, 2 H), 6.58 (d, 1 H), 3.10-3.20 (m, 4 H), 2.60-2.75 (m, 4 H), 2.94 (q, 2 H), 1.23 (t, 3H).

EXAMPLE 210

2-chloro-N-(3-(5-(2-((4-(4-ethylpiperazin-1-yl)phenyl)amino)pyrimidin-4-yl)imidazo[2,1-b][1,3]thiazol-6-yl)phenyl)-6-fluorobenzamide The title compound was prepared as described in EXAMPLE 36, substituting EXAMPLE 204C for EXAMPLE 36C and 2-fluoro-6-chloro-benzoyl chloride for phenylacetyl chloride. MS (ESI), m/e 653.2; (ESI), m/e 650.9 (M–H)⁻; $^1$H-NMR (300 MHz, DMSO-$d_6$) ☐ ppm 10.91 (s, 1 H), 9.51 (s, 1 H), 8.77 (bs, 1 H), 8.23 (d, 1 H), 8.01 (s, 1 H), 7.75 (d, 1 H), 7.54-7.60 (m, 3 H), 7.45-7.48 (m, 3 H), 7.38-7.40 (m, 2 H), 6.98 (d, 2 H), 6.60 (d, 1 H), 3.10-3.20 (m, 4 H), 2.60-2.75 (m, 4 H), 2.94 (q, 2 H), 1.23 (t, 3H).

EXAMPLE 211

2-chloro-N-(3-(5-(2-((4-(4-ethylpiperazin-1-yl)phenyl)amino)pyrimidin-4-yl)imidazo[2,1-b][1,3]thiazol-6-yl)phenyl)benzamide The title compound was prepared as described in EXAMPLE 36, substituting EXAMPLE 204C for EXAMPLE 36C and 2-chloro-benzoyl chloride for phenylacetyl chloride. MS (ESI), m/e 635.3; (ESI), m/e 633.0 (M–H)⁻; $^1$H-NMR (300 MHz, DMSO-$d_6$) ☐ ppm 10.62 (s, 1 H), 9.44 (s, 1 H), 8.75 (bs, 1 H), 8.23 (d, 1 H), 8.02 (s, 1 H), 7.82 (d, 1 H), 7.44-7.61 (m, 8 H), 7.36 (d, 1 H), 6.93 (d, 2 H), 6.56 (d, 1 H), 3.10-3.20 (m, 4 H), 2.60-2.75 (m, 4 H), 2.94 (q, 2 H), 1.09 (t, 3H).

EXAMPLE 212

2,6-dichloro-N-(3-(5-(2-((4-(4-ethylpiperazin-1-yl)phenyl)amino)pyrimidin-4-yl)imidazo[2,1-b][1,3]thiazol-6-yl)phenyl)benzamide The title compound was prepared as described in EXAMPLE 36, substituting EXAMPLE 204C for EXAMPLE 36C and 2,6-dichloro-benzoyl chloride for phenylacetyl chloride. MS (ESI), m/e 669.1; $^1$H-NMR (300 MHz, DMSO-$d_6$) ☐ ppm 10.84 (s, 1 H), 9.53 (s, 1 H), 9.47 (bs, 1 H), 8.77 (bs, 1 H), 8.23 (d, 1 H), 8.02 (s, 1 H), 7.73 (d, 1 H), 7.45-7.61 (m, 7 H), 7.39 (d, 1 H), 7.00 (d, 2 H), 6.62 (d, 1 H), 3.76-3.79 (m, 2 H), 3.57-3.60 (m, 2 H), 3.10-3.25 (m, 4 H), 2.94 (q, 2 H), 1.27 (t, 3H).

EXAMPLE 213

N-(4-(4-ethylpiperazin-1-yl)phenyl)-4-(6-(3-((5-phenyl-1,3,4-oxadiazol-2-yl)amino)phenyl)imidazo[2,1-b][1,3]thiazol-5-yl)pyrimidin-2-amine The title compound was prepared as described in EXAMPLE 137, substituting EXAMPLE 204C for EXAMPLE 65C. MS (ESI), m/e 641.2; (ESI), m/e 639.1 (M–H)⁻; $^1$H-NMR (300 MHz, DMSO-$d_6$) ☐ ppm 10.83 (s, 1 H), 9.40 (s, 1 H), 8.76 (bs, 1 H), 8.21 (d, 1 H), 7.87-7.91 (m, 3 H), 7.74 (dd, 1 H), 7.56-7.61 (m, 3 H), 7.46-7.52 (m, 4 H), 7.25 (d, 1 H), 6.91 (d, 2 H), 6.57 (d, 1 H), 3.31 (m, 4 H), 3.09 (m, 4 H), 2.39 (q, 2 H), 1.04 (t, 3H).

EXAMPLE 214

N-(4-(4-ethylpiperazin-1-yl)phenyl)-4-(6-(3-((5-phenyl-1,3-oxazol-2-yl)amino)phenyl)imidazo[2,1-b][1,3]thiazol-5-yl)pyrimidin-2-amine The title compound was prepared as described in EXAMPLE 137, substituting EXAMPLE 204C for EXAMPLE 65C and 2-chloro-5-phenyl oxazole for 2-bromo-5-phenyl-1,3,4-oxadiazole. MS (ESI), m/e 640.3; $^1$H-NMR (300 MHz, DMSO-$d_6$) □ ppm 10.47 (s, 1H), 9.52 (s, 1 H), 9.46 bs, 1 H), 8.80 (bs, 1 H), 8.23 (d, 1 H), 7.95 (s, 1 H), 7.72 (dd, 1 H), 7.55-7.60 (m, 4 H), 7.48 (d, 1 H), 7.40-7.45 (m, 4 H), 7.27 (t, 1 H), 7.18 (d, 1 H), 7.00 (d, 2H), 6.60 (d, 1 H), 3.75 (m, 2 H), 3.57 (m, 2 H), 3.07-3.23 (m, 4 H), 2.93 (q, 2 H), 1.26 (t, 3H).

EXAMPLE 215

N-(3-(2-bromo-5-(2-((4-morpholin-4-ylphenyl)amino)pyrimidin-4-yl)imidazo[2,1-b][1,3]thiazol-6-yl)phenyl)benzamide The title compound was prepared as described in EXAMPLE 1, substituting 2-amino-5-bromothiazole for 2-aminothiazole in EXAMPLE 1A, EXAMPLE 3A for phenylguanidine in EXAMPLE 1E, and benzoyl chloride for 2-chlorobenzoyl chloride in EXAMPLE 1G. MS (ESI(+)) m/e 654 (M+H)$^+$; $^1$H-NMR (300 MHz, DMSO-$d_6$) □ 10.37 (s, 1H); 9.47 (s, 1H); 8.97 (bs, 1H); 8.24 (d, 1H); 8.08 (s, 1H); 7.98-7.91 (m, 3H); 7.60-7.44 (m, 6H); 7.33 (m, 1H); 6.95 (d, 2H); 6.58 (d, 1H); 3.74 (m, 4H); 3.07 (m, 4H).

EXAMPLE 216

N-(3-(2-bromo-5-(2-((4-morpholin-4-ylphenyl)amino)pyrimidin-4-yl)imidazo[2,1-b][1,3]thiazol-6-yl)phenyl)-2-phenylacetamide The title compound was prepared as described in EXAMPLE 1, substituting 2-amino-5-bromothiazole for 2-aminothiazole in EXAMPLE 1A, EXAMPLE 3A for phenylguanidine in EXAMPLE 1E, and phenylacetyl chloride for 2-chlorobenzoyl chloride in EXAMPLE 1G. MS (ESI(+)) m/e 668 (M+H)$^+$; $^1$H-NMR (300 MHz, DMSO-$d_6$) □ 10.29 (s, 1H); 9.46 (s, 1H); 8.94 (bs, 1H); 8.20 (d, 1H); 7.87 (s, 1H); 7.70 (d, 1H); 7.51 (d, 2H); 7.40 (t, 1H); 7.33-7.24 (m, 6H); 6.95 (d, 2H); 6.51 (d, 1H); 3.75 (m, 4H); 3.64 (s, 2H); 3.07 (m, 4H).

EXAMPLE 217

2-phenyl-N-(3-(5-(2-((3-(3-pyrrolidin-1-ylpropoxy)phenyl)amino)pyrimidin-4-yl)imidazo[2,1-b][1,3]thiazol-6-yl)phenyl)acetamide

EXAMPLE 217A

The title compound was prepared as described in EXAMPLE 154A-D, substituting pyrrolidine for N-methylpiperazine in EXAMPLE 154B.

EXAMPLE 217B

The title compound was prepared as described in EXAMPLE 1, substituting EXAMPLE 217A for phenylguanidine in EXAMPLE 1E and benzoyl chloride for 2-chlorobenzoyl chloride in EXAMPLE 1G. MS (ESI(+)) m/e 630 (M+H)$^+$; $^1$H-NMR (300 MHz, DMSO-$d_6$) □ 10.28 (s, 1H); 9.65 (s, 1H); 8.83 (s, 1H); 8.28 (d, 1H); 7.88 (s, 1H); 7.72 (d, 1H); 7.50 (d, 1H); 7.45 (s, 1H); 7.40 (t, 1H); 7.34-7.16 (m, 8H); 6.60 (d, 1H); 6.56 (d, 1H); 3.98 (t, 2H); 3.65 (s, 2H); 2.43 (m, 6H); 1.88 (m, 2H); 1.67 (m, 4H).

EXAMPLE 218

(2R)-2-methoxy-N-(3-(5-(2-((4-morpholin-4-ylphenyl)amino)pyrimidin-4-yl)imidazo[2,1-b][1,3]thiazol-6-yl)phenyl)-2-phenylacetamide The title compound was prepared as described in EXAMPLE 299, substituting (2R)-2-methoxy-2-phenylacetic acid for 2-(2-chlorophenyl)acetic acid and EXAMPLE 3C for EXAMPLE 297E. MS (ESI(+)) m/e 618 (M+H)$^+$; $^1$H-NMR (300 MHz, DMSO-$d_6$) □ 10.17 (s, 1H); 9.58 (bs, 1H); 8.74 (bs, 1H); 8.19 (bs, 1H); 7.99 (s, 1H); 7.77 (d, 1H); 7.56 (bs, 2H); 7.50 (m, 3H); 7.43-7.29 (m, 6H); 7.00 (bs, 2H); 6.54 (bs, 1H); 4.85 (s, 1H); 3.77 (m, 4H); 3.37 (s, 3H); 3.12 (m, 4H).

EXAMPLE 219

N-(3-(5-(2-((3-(morpholin-4-ylsulfonyl)phenyl)amino)pyrimidin-4-yl)imidazo[2,1-b][1,3]thiazol-6-yl)phenyl)-2-phenylacetamide The title compound was prepared as described in EXAMPLE 12, substituting 3-(morpholinosulfonyl)aniline for 4-morpholinoaniline. MS (ESI(+)) m/e 652 (M+H)$^+$; (ESI (−)) m/e 649 (M−H)$^−$; $^1$H-NMR (300 MHz, DMSO-$d_6$) □ 10.28 (bs, 1H); 10.08 (bs, 1H); 8.87 (d, 1H); 8.33 (d, 1H); 8.16-8.14 (m, 2H); 7.89 (t, 1H); 7.73-7.69 (m, 1H); 7.62-7.57 (m, 1H); 7.53 (d, 1H); 7.41 (t, 1H); 7.34-7.24 (m, 7H); 6.68 (d, 1H); 3.65-3.62 (m, 6H); 2.90 (m, 4H).

EXAMPLE 220

N-(3-(5-(2-((4-morpholin-4-ylphenyl)amino)pyrimidin-4-yl)imidazo[2,1-b][1,3]thiazol-6-yl)phenyl)-1-phenylcyclopropanecarboxamide The title compound was prepared as described in EXAMPLE 299, substituting 1-phenylcyclopropylacetic acid for 2-(2-chlorophenyl)acetic acid and EXAMPLE 3C for EXAMPLE 297E. MS (ESI(+)) m/e 614 (M+H)$^+$; $^1$H-NMR (300 MHz, DMSO-$d_6$) □ 9.53 (bs, 1H); 9.21 (s, 1H); 8.74 (bs, 1H); 8.18 (bs, 1H); 7.84 (s, 1H); 7.66 (d, 1H); 7.55 (bs, 1H); 7.47 (d, 1H); 7.42-7.25 (m, 8H); 6.98 (bs, 2H); 6.52 (bs, 1H); 3.77 (m, 4H); 3.11 (m, 4H); 1.45 (m, 2H); 1.12 (m, 2H).

EXAMPLE 221

2-methyl-N-(3-(5-(2-((4-morpholin-4-ylphenyl)amino)pyrimidin-4-yl)imidazo[2,1-b][1,3]thiazol-6-yl)phenyl)-2-phenylpropanamide The title compound was prepared as described in EXAMPLE 299, substituting 2-methyl-2-phenylpropionic acid for 2-(2-chlorophenyl)acetic acid and EXAMPLE 3C for EXAMPLE 297E. MS (ESI(+)) m/e 616 (M+H)$^+$; $^1$H-NMR (300 MHz, DMSO-$d_6$) □ 9.51 (bs, 1H); 9.22 (s, 1H); 8.74 (bs, 1H); 8.18 (bs, 1H); 7.89 (s, 1H); 7.73 (d, 1H); 7.54 (m, 1H);

7.47 (d, 1H); 7.37-7.24 (m, 8H); 6.97 (bs, 2H); 6.54 (bs, 1H); 3.79 (m, 4H); 3.10 (m, 4H); 1.57 (s, 6H).

EXAMPLE 222

N-(2-morpholin-4-ylethyl)-4-((4-(6-(3-((phenylacetyl)amino)phenyl)imidazo[2,1-b][1,3]thiazol-5-yl)pyrimidin-2-yl)amino)benzamide

EXAMPLE 222A

The title compound was prepared as described in EXAMPLE 1E, substituting 4-carboxyphenylguanidine for phenylguanidine.

EXAMPLE 222B

A mixture of EXAMPLE 222A (0.1 g), 2-morpholinoethanamine (0.029 mL) and di-isopropylethylamine (0.011 mL) in N,N-dimethylformamide (3 mL) was treated with 1-ethyl-3-(3-(dimethylamino)propyl)-carbodiimide hydrochloride (0.050 g), and the mixture stirred for 16 hours at ambient temperature. The mixture was partitioned between ethyl acetate and aqueous NaHCO$_3$, and the organic phase was washed with brine, dried (MgSO$_4$), and concentrated. The crude product was chromatographed on silica eluting with 10% methanol in ethyl acetate to afford the title compound.

EXAMPLE 222C

The title compound was prepared as described in EXAMPLE 1F-G, substituting EXAMPLE 222B for EXAMPLE 1E in EXAMPLE 1F. MS (ESI(+)) m/e 659 (M+H)$^+$; $^1$H-NMR (300 MHz, DMSO-d$_6$) □ 10.30 (s, 1H); 10.02 (s, 1H); 9.59 (bs, 1H); 8.87 (d, 1H); 8.57 (t, 1H); 8.34 (d, 1H); 7.92 (s, 1H); 7.86 (m, 3H); 7.69 (d, 1H); 7.53 (d, 1H); 7.41 (t, 1H); 7.34-7.23 (m, 5H); 6.68 (d, 1H); 4.02 (m, 4H); 3.65 (s, 2H); 3.32 (m, 4H); 3.17 (m, 4H).

EXAMPLE 223

3-cyanobenzyl 3-(5-(2-((4-morpholin-4-ylphenyl)amino)pyrimidin-4-yl)imidazo[2,1-b][1,3]thiazol-6-yl)phenylcarbamate Into a 2 ml microwave vial was added EXAMPLE 3C (50 mg), 3,5-difluorophenyl)methanol (30.7 mg), 1,1'-carbonyldiimidazole (34.5 mg), 4-(dimethylamino)pyridine (2 mg), and acetonitrile (1065 µl). The mixture was heated in a Biotage Initiator 2 monomode microwave reactor at 150° C. for 25 minutes. Into the vial was added another portion of 1,1'-carbonyldiimidazole (34.5 mg) and the mixture was diluted with 1-methyl-2-pyrrolidinone (900 µl) then heated in an oil bath at 70° C. for 5 hours. To the vial was added (3,5-difluorophenyl)methanol (30.7 mg) and the mixture was heated at 70° C. for 18 hours. The mixture was cooled and phosgene (112 µl) in toluene was added and reaction was stirred at room temperature for 1 week. The mixture was filtered and purified using reverse phase HPLC with 0.1% ammonium hydroxide dissolved in the acetonitrile/water as the mobile phase. MS (ESI(+)) m/e 629 (M+H)$^+$; $^1$H-NMR (500 MHz, methanol-d$_4$) □ 8.62 (bs, 1H), 7.98 (d, 1H), 7.72-7.76 (m, 1H), 7.67-7.72 (m, 3H), 7.56 (td, 3H), 7.52 (d, 2H), 7.45 (t, 1H), 7.32 (d, 1H), 7.30 (dt, 1H), 7.20 (d, 1H), 6.69 (d, 1H), 5.19 (s, 2H), 3.87-3.94 (m, 4H), 3.33 (s, 4H).

EXAMPLE 224

3-methylbenzyl 3-(5-(2-((4-morpholin-4-ylphenyl)amino)pyrimidin-4-yl)imidazo[2,1-b][1,3]thiazol-6-yl)phenylcarbamate The title compound was prepared as described in EXAMPLE 223, substituting m-tolylmethanol for 3,5-difluorophenyl)methanol. MS (ESI(+)) m/e 618 (M+H)$^+$; $^1$H-NMR (500 MHz, methanol-d$_4$) □ 8.62 (bs, 1H), 7.97 (d, 1H), 7.81 (s, 1H), 7.49-7.59 (m, 3H), 7.45 (t, 1H), 7.34 (d, 1H), 7.29 (d, 1H), 7.20-7.27 (m, 4H), 7.18 (d, 1H), 7.12 (d, 1H), 6.71 (d, 1H), 5.13 (s, 2H), 3.88-3.96 (m, 4H), 3.34 (d, 4H), 2.33 (s, 3H).

EXAMPLE 225

3-chlorobenzyl 3-(5-(2-((4-morpholin-4-ylphenyl)amino)pyrimidin-4-yl)imidazo[2,1-b][1,3]thiazol-6-yl)phenylcarbamate The title compound was prepared as described in EXAMPLE 223, substituting (3-chlorophenyl)methanol for 3,5-difluorophenyl)methanol. MS (ESI(+)) m/e 638 (M+H)$^+$; $^1$H-NMR (500 MHz, methanol-1) □ 8.62 (bs, 1H), 7.99 (d, 1H), 7.79 (s, 1H), 7.57 (dd, 1H), 7.50 (s, 1H), 7.42-7.47 (m, 2H), 7.27-7.37 (m, 5H), 7.17 (s, 2H), 6.67 (s, 1H), 5.17 (s, 2H), 3.90 (s, 4H), 3.32 (s, 4H).

EXAMPLE 226

3-methoxybenzyl 3-(5-(2-((4-morpholin-4-ylphenyl)amino)pyrimidin-4-yl)imidazo[2,1-b][1,3]thiazol-6-yl)phenylcarbamate The title compound was prepared as described in EXAMPLE 223, substituting (3-methoxyphenyl)methanol for 3,5-difluorophenyl)methanol. MS (ESI(+)) m/e 634 (M+H)$^+$; $^1$H-NMR (500 MHz, methanol-d$_4$) □ 8.63 (bs, 1H), 7.97 (d, 1H), 7.80 (s, 1H), 7.56 (d, 1H), 7.51 (d, 2H), 7.45 (t, 1H), 7.33 (d, 1H), 7.29 (d, 1H), 7.26 (t, 1H), 7.21 (d, 1H), 6.95-6.99 (m, 2H), 6.87 (dd, 1H), 6.71 (d, 1H), 5.15 (s, 2H), 3.88-3.94 (m, 4H), 3.78 (s, 3H), 3.33 (s, 4H).

EXAMPLE 227

3-fluorobenzyl 3-(5-(2-((4-morpholin-4-ylphenyl)amino)pyrimidin-4-yl)imidazo[2,1-b][1,3]thiazol-6-yl)phenylcarbamate The title compound was prepared as described in EXAMPLE 223, substituting (3-fluorophenyl)methanol for 3,5-difluorophenyl)methanol. MS (ESI(+)) m/e 622 (M+H)$^+$; $^1$H-NMR (500 MHz, methanol-d$_4$) □ 8.63 (bs, 1H), 7.97 (d, 1H), 7.94-8.00 (m, 1H), 7.81 (s, 1H), 7.57 (d, 1H), 7.53 (d, 2H), 7.46 (t, 1H), 7.33-7.41 (m, 2H), 7.29 (dt, 1H), 7.19-7.27 (m, 3H), 7.16 (dd, 1H), 7.04 (td, 1H), 6.72 (d, 1H), 5.18 (s, 2H), 3.88-3.96 (m, 4H), 3.33-3.39 (m, 4H).

EXAMPLE 228

4-fluorobenzyl 3-(5-(2-((4-morpholin-4-ylphenyl)amino)pyrimidin-4-yl)imidazo[2,1-b][1,3]thiazol-6-yl)phenylcarbamate The title compound was prepared as described in EXAMPLE 223, substituting (4-fluorophenyl)methanol for 3,5-difluorophenyl)methanol. MS (ESI(+)) m/e 622 (M+H)$^+$; $^1$H-NMR (500 MHz, methanol-1) □ 8.63 (bs, 1H), 7.97 (d, 1H), 7.80 (s, 1H), 7.7.50-7.59 (m, 3H), 7.41-7.48 (m, 3H), 7.35 (d, 2H), 7.29 (dt, 1H), 7.24 (d, 2H), 7.05-7.12 (m, 2H), 6.71 (d, 1H), 5.15 (s, 2H), 3.88-3.96 (m, 4H), 3.33-3.38 (m, 4H).

EXAMPLE 229

4-methylbenzyl 3-(5-(2-((4-morpholin-4-ylphenyl)amino)pyrimidin-4-yl)imidazo[2,1-b][1,3]thiazol-6-yl)phenylcarbamate The title compound was prepared as described in EXAMPLE 223, substituting p-tolylmethanol for 3,5-difluorophenyl)methanol. MS (ESI(+)) m/e 618 (M+H)$^+$; $^1$H-NMR (500 MHz, methanol-d$_4$) □ 8.63 (bs, 1H), 7.97 (d, 1H), 7.80 (s, 1H), 7.54 (dd, 3H), 7.45 (t, 1H), 7.34 (d, 1H), 7.26-7.31 (m, 3H), 7.23 (d, 2H), 7.17 (d, 2H), 6.72 (d, 1H), 5.12 (s, 2H), 3.88-3.95 (m, 4H), 3.32-3.37 (s, 4H), 2.32 (s, 3H).

EXAMPLE 230

3,5-difluorobenzyl 3-(5-(2-((4-morpholin-4-ylphenyl)amino)pyrimidin-4-yl)imidazo[2,1-b][1,3]thiazol-6-yl)phenylcarbamate The title compound was prepared as described in EXAMPLE 223, substituting (3,5-difluorophenyl)methanol for 3,5-difluorophenyl)methanol. MS (ESI(+)) m/e 640 (M+H)$^+$; $^1$H-NMR (500 MHz, methanol-d$_4$) □ 8.64 (bs, 1H), 7.97 (s, 1H), 7.81 (s, 1H), 7.52 (d, 2H), 7.46 (t, 1H), 7.34 (d, 1H), 7.31-7.32 (m, 1H), 7.29-7.30 (m, 1H), 7.20-7.24 (m, 2H), 7.03 (dd, 2H), 6.87-6.93 (m, 1H), 6.71 (s, 1H), 5.19 (s, 2H), 3.91 (s, 4H), 3.34 (s, 4H).

EXAMPLE 231

3-(benzyloxy)benzyl 3-(5-(2-((4-morpholin-4-ylphenyl)amino)pyrimidin-4-yl)imidazo[2,1-b][1,3]thiazol-6-yl)phenylcarbamate The title compound was prepared as described in EXAMPLE 223, substituting (3-(benzyloxy)phenyl)methanol for 3,5-difluorophenyl)methanol. MS (ESI(+)) m/e 710 (M+H)$^+$; $^1$H-NMR (500 MHz, methanol-d$_4$) □ 8.62 (bs, 1H), 7.95 (d, 1H), 7.81-7.83 (m, 1H), 7.50-7.57 (m, 3H), 7.46 (t, 1H), 7.40 (d, 2H), 7.21-7.36 (m, 9H), 7.05 (s, 1H), 6.97 (d, 1H), 6.94 (dd, 1H), 6.72 (d, 1H), 5.15 (s, 2H), 5.06 (s, 2H), 3.90-3.94 (m, 4H), 3.33-3.37 (m, 4H).

EXAMPLE 232

1,3-benzodioxol-5-ylmethyl 3-(5-(2-((4-morpholin-4-ylphenyl)amino)pyrimidin-4-yl)imidazo[2,1-b][1,3]thiazol-6-yl)phenylcarbamate The title compound was prepared as described in EXAMPLE 223, substituting benzo(d)(1,3)dioxol-5-ylmethanol for 3,5-difluorophenyl)methanol. MS (ESI(+)) m/e 648 (M+H)$^+$; $^1$H-NMR (500 MHz, methanol-d$_4$) □ 8.62 (bs, 1H), 7.97 (d, 1H), 7.79 (s, 1H), 7.49-7.56 (m, 3H), 7.45 (t, 1H), 7.33 (d, 1H), 7.28 (ddd, 1H), 7.21 (d, 1H), 6.86-6.92 (m, 2H), 6.82-6.86 (m, 1H), 6.76-6.81 (m, 1H), 6.70 (d, 1H), 5.94 (d, 2H), 5.07 (s, 2H), 3.88-3.95 (m, 4H), 3.33 (s, 4H).

EXAMPLE 233

N-(3-(5-(2-((3-((dimethylamino)sulfonyl)phenyl)amino)pyrimidin-4-yl)imidazo[2,1-b][1,3]thiazol-6-yl)phenyl)-2-phenylacetamide The title compound was prepared as described in EXAMPLE 12, substituting 3-amino-N,N-dimethylbenzenesulfonamide for 4-morpholinoaniline. (ESI(+)) m/e 610 (M+H)$^+$; $^1$H-NMR (300 MHz, DMSO-d$_6$) □ 10.28 (bs, 1H); 10.06 (bs, 1H); 8.87 (d, 1H); 8.33 (d, 1H); 8.16-8.14 (m, 2H); 7.89 (m 1H); 7.70 (m, 1H); 7.60-7.58 (m, 1H); 7.55-7.52 (m, 1H); 7.41 (t, 1H); 7.34-7.24 (m, 7H); 6.88 (d, 1H); 3.65 (s, 2H); 2.64 (s, 6H).

EXAMPLE 234

N-(3-(5-(2-((3-morpholin-4-ylphenyl)amino)pyrimidin-4-yl)imidazo[2,1-b][1,3]thiazol-6-yl)phenyl)-N'-phenylurea The title compound was prepared as described in EXAMPLE 13, substituting EXAMPLE 12E for EXAMPLE 3C. MS (ESI(+)) m/e 589 (M+H)$^+$; $^1$H-NMR (300 MHz, DMSO-d$_6$) □ 9.60 (s, 1H); 8.85 (bs, 1H); 8.82 (s, 1H); 8.68 (s, 1H); 8.28 (d, 1H); 7.75 (s, 1H); 7.55-7.36 (m, 6H); 7.30-7.15 (m, 5H); 6.97 (t, 1H); 6.64 (m, 2H); 3.74 (m, 4H); 3.10 (m, 4H).

EXAMPLE 235

N-(2-methylphenyl)-N'-(3-(5-(2-((3-morpholin-4-ylphenyl)amino)pyrimidin-4-yl)imidazo[2,1-b][1,3]thiazol-6-yl)phenyl)urea The title compound was prepared as described in EXAMPLE 13, substituting 2-methylphenylisocyanate for phenylisocyanate and EXAMPLE 12E for EXAMPLE 3C. MS (ESI(+)) m/e 603 (M+H)$^+$; $^1$H-NMR (300 MHz, DMSO-d$_6$) □ 9.61 (s, 1H); 9.16 (s, 1H); 8.83 (d, 1H); 8.28 (d, 1H); 7.92 (s, 1H); 7.80 (d, 1H); 7.78 (s, 1H); 7.54 (d, 1H); 7.51 (d, 1H); 7.40 (t, 1H); 7.30 (s, 1H); 7.25-7.11 (m, 5H); 6.95 (t, 1H); 6.64 (m, 2H); 3.74 (m, 4H); 3.10 (m, 4H); 2.24 (s, 3H).

EXAMPLE 236

N-(2-fluorophenyl)-N'-(3-(5-(2-((3-morpholin-4-ylphenyl)amino)pyrimidin-4-yl)imidazo[2,1-b][1,3]thiazol-6-yl)phenyl)urea The title compound was prepared as described in EXAMPLE 13, substituting 2-fluorophenylisocyanate for phenylisocyanate and EXAMPLE 12E for EXAMPLE 3C. MS (ESI(+)) m/e 607 (M+H)$^+$; $^1$H-NMR (300 MHz, DMSO-d$_6$) □ 9.60 (s, 1H); 9.20 (s, 1H); 8.83 (d, 1H); 8.55 (d, 1H); 8.28 (d, 1H); 8.13 (t, 1H); 7.76 (s, 1H); 7.51 (m, 2H); 7.41 (t, 1H); 7.36 (s, 1H); 7.25-7.11 (m, 5H); 7.00 (m, 2H); 6.63 (m, 2H); 3.74 (m, 4H); 3.10 (m, 4H).

EXAMPLE 237

N-(3-(5-(2-((4-(4-ethylpiperazin-1-yl)phenyl)amino)pyrimidin-4-yl)imidazo[2,1-b][1,3]thiazol-6-yl)phenyl)-1-phenylcyclopropanecarboxamide The title compound was prepared as described in EXAMPLE 205, substituting 1-phenyl-cyclopropane-carboxylic acid for 2-(2-chlorophenyl)acetic acid. MS (ESI), m/e 641.3; $^1$H-NMR (300 MHz, DMSO-d$_6$) □ ppm 9.41 (s, 1 H), 9.22 (s, 1 H), 8.75 (bs, 1 H), 8.18 (d, 1 H), 7.83 (s, 1 H), 7.67 (d, 1 H), 7.52 (d, 2 H), 7.46 (d, 1 H), 7.34-7.41 (m, 5 H), 7.25-7.30 (m, 2 H), 6.91 (d, 2 H), 6.50 (d, 1 H), 3.33 (m, 4 H), 3.07-3.09 (m, 4 H), 2.37 (q, 2 H), 1.45 (dd, 2 H), 1.12 (dd, 2 H), 1.04 (t, 3H).

EXAMPLE 238

N-(3-(5-(2-((3-(3-morpholin-4-ylpropoxy)phenyl) amino)pyrimidin-4-yl)imidazo[2,1-b][1,3]thiazol-6-yl)phenyl)-N'-phenylurea

EXAMPLE 238A

The title compound was prepared as described in EXAMPLE 1A-F, substituting EXAMPLE 156A for phenylguanidine in EXAMPLE 1E.

EXAMPLE 238B

The title compound was prepared as described in EXAMPLE 13, substituting EXAMPLE 238A for EXAMPLE 3C. MS (ESI(+)) m/e 647 (M+H)$^+$; $^1$H-NMR (300 MHz, DMSO-d$_6$) □ 9.71 (s, 1H); 9.54 (bs, 1H); 8.88 (d, 1H); 8.86 (s, 1H); 8.72 (s, 1H); 8.30 (d, 1H); 7.79 (s, 1H); 7.57 (s, 1H); 7.53-7.37 (m, 5H); 7.29-7.15 (m, 4H); 6.97 (t, 1H); 6.66 (d, 1H); 6.59 (m, 1H); 4.04 (m, 4H); 3.49 (m, 4H); 3.29 (m, 2H); 3.10 (m, 2H); 2.12 (m, 2H).

EXAMPLE 239

N-(2-methylphenyl)-N'-(3-(5-(2-((3-(3-morpholin-4-ylpropoxy)phenyl)amino)pyrimidin-4-yl)imidazo[2,1-b][1,3]thiazol-6-yl)phenyl)urea The title compound was prepared as described in EXAMPLE 13, substituting 2-methylphenylisocyanate for phenylisocyanate and EXAMPLE 238A for EXAMPLE 3C. MS (ESI(+)) m/e 661 (M+H)$^+$; $^1$H-NMR (300 MHz, DMSO-d$_6$) □ 9.71 (s, 1H); 9.54 (bs, 1H); 9.17 (s, 1H); 8.88 (d, 1H); 8.31 (d, 1H); 7.94 (s, 1H); 7.81 (m, 2H); 7.57 (s, 1H); 7.53 (d, 1H); 7.49 (d, 1H); 7.40 (t, 1H); 7.25-7.11 (m, 4H); 6.94 (t, 1H); 6.67 (d, 1H); 6.59 (m, 1H); 4.03 (m, 4H); 3.64 (m, 4H); 3.29 (m, 2H); 3.10 (m, 2H); 2.24 (s, 3H); 2.13 (m, 2H).

EXAMPLE 240

N-(2-fluorophenyl)-N'-(3-(5-(2-((3-(3-morpholin-4-ylpropoxy)phenyl)amino)pyrimidin-4-yl)imidazo[2,1-b][1,3]thiazol-6-yl)phenyl)urea The title compound was prepared as described in EXAMPLE 13, substituting 2-fluorophenylisocyanate for phenylisocyanate and EXAMPLE 238A for EXAMPLE 3C. MS (ESI(+)) m/e 665 (M+H)$^+$; $^1$H-NMR (300 MHz, DMSO-d$_6$) □ 9.72 (s, 1H); 9.58 (bs, 1H); 9.22 (s, 1H); 8.88 (d, 1H); 8.56 (d, 1H); 8.31 (d, 1H); 8.12 (t, 1H); 7.80 (s, 1H); 7.57 (s, 1H); 7.52 (d, 1H); 7.49 (d, 1H); 7.41 (t, 1H); 7.27-7.20 (m, 3H); 7.13 (t, 1H); 7.02 (m, 1H); 6.66 (d, 1H); 6.58 (m, 1H); 4.03 (m, 4H); 3.51 (m, 4H); 3.29 (m, 2H); 3.11 (m, 2H); 2.13 (m, 2H).

EXAMPLE 241

N-(3-(5-(2-((3-(3-(4-methylpiperazin-1-yl)propoxy) phenyl)amino)pyrimidin-4-yl)imidazo[2,1-b][1,3] thiazol-6-yl)phenyl)-N'-phenylurea

EXAMPLE 241A

The title compound was prepared as described in EXAMPLE 1A-F, substituting EXAMPLE 154D for phenylguanidine in EXAMPLE 1E.

EXAMPLE 241B

The title compound was prepared as described in EXAMPLE 13, substituting EXAMPLE 241A for EXAMPLE 3C. MS (ESI(+)) m/e 660 (M+H)$^+$; $^1$H-NMR (300 MHz, DMSO-d$_6$) □ 9.69 (s, 1H); 8.87 (d, 1H); 8.85 (s, 1H); 8.71 (s, 1H); 8.30 (d, 1H); 7.79 (s, 1H); 7.54-7.37 (m, 6H); 7.30-7.20 (m, 5H); 6.96 (t, 1H); 6.65 (d, 1H); 6.59 (m, 1H); 4.01 (t, 2H); 3.56 (m, 6H); 2.95 (m, 4H); 2.74 (s, 3H); 2.00 (m, 2H).

EXAMPLE 242

N-(2-methylphenyl)-N'-(3-(5-(2-((3-(3-(4-methylpiperazin-1-yl)propoxy)phenyl)amino)pyrimidin-4-yl) imidazo[2,1-b][1,3]thiazol-6-yl)phenyl)urea The title compound was prepared as described in EXAMPLE 13, substituting 2-methylphenylisocyanate for phenylisocyanate and EXAMPLE 241A for EXAMPLE 3C. MS (ESI(+)) m/e 674 (M+H)$^+$; $^1$H-NMR (300 MHz, DMSO-d$_6$) □ 9.70 (s, 1H); 9.18 (s, 1H); 8.88 (d, 1H); 8.30 (d, 1H); 7.95 (s, 1H); 7.81 (s, 1H); 7.79 (d, 1H); 7.55-7.49 (m, 3H); 7.40 (t, 1H); 7.24-7.11 (m, 5H); 6.95 (t, 1H); 6.66 (d, 1H); 6.59 (m, 1H); 4.02 (t, 2H); 3.42 (m, 6H); 2.97 (m, 4H); 2.77 (s, 3H); 2.24 (s, 3H); 2.01 (m, 2H).

EXAMPLE 243

N-(2-fluorophenyl)-N'-(3-(5-(2-((3-(3-(4-methylpiperazin-1-yl)propoxy)phenyl)amino)pyrimidin-4-yl) imidazo[2,1-b][1,3]thiazol-6-yl)phenyl)urea The title compound was prepared as described in EXAMPLE 13, substituting 2-fluorophenylisocyanate for phenylisocyanate and EXAMPLE 241A for EXAMPLE 3C. MS (ESI(+)) m/e 678 (M+H)$^+$; $^1$H-NMR (300 MHz, DMSO-d$_6$) □ 9.70 (s, 1H); 9.21 (s, 1H); 8.87 (d, 1H); 8.56 (s, 1H); 8.31 (d, 1H); 8.12 (t, 1H); 7.79 (s, 1H); 7.54-7.49 (m, 3H); 7.41 (t, 1H); 7.27-7.20 (m, 4H); 7.13 (t, 1H); 7.02 (m, 1H); 6.65 (d, 1H); 6.58 (m, 1H); 4.01 (t, 2H); 3.46 (m, 6H); 2.97 (m, 4H); 2.73 (s, 3H); 1.98 (m, 2H).

EXAMPLE 244

N-(3-(5-(2-((3-(aminosulfonyl)phenyl)amino)pyrimidin-4-yl)imidazo[2,1-b][1,3]thiazol-6-yl)phenyl)-2-phenylacetamide The title compound was prepared as described in EXAMPLE 12, substituting 3-aminobenzenesulfonamide for 4-morpholinoaniline. MS (ESI(+)) m/e 582 (M+H)$^+$; (ESI (−)) m/e 580 (M−H)$^-$; $^1$H-NMR (300 MHz, DMSO-d$_6$) □ 10.29 (bs, 1H); 10.01 (s, 1H); 8.99 (d, 1H); 8.31 (d, 1H); 8.25 (m, 1H); 7.98 (d, 1H); 7.89 (m, 1H); 7.72 (m, 1H); 7.53-7.48

(m, 1H); 7.45 (m, 1H); 7.41 (m, 1H); 7.34-7.23 (m, 7H); 6.65 (m, 1H); 3.65 (s, 2H); 2.69 (s, 2H).

EXAMPLE 245

N-(3-(5-(2-((4-(aminosulfonyl)phenyl)amino)pyrimidin-4-yl)imidazo[2,1-b][1,3]thiazol-6-yl)phenyl)-2-phenylacetamide The title compound was prepared as described in EXAMPLE 12, substituting 4-aminobenzenesulfonamide for 4-morpholinoaniline. MS (ESI(+)) m/e 582 (M+H)$^+$; (ESI(−)) m/e 580 (M−H)$^−$; $^1$H-NMR (300 MHz, DMSO-d$_6$) ☐ 10.29 (bs, 1H); 10.09 (s, 1H); 8.86 (d, 1H); 8.34 (d, 1H); 7.93-7.88 (m, 3H) 7.77-7.70 (m, 3H); 7.54 (d, 1H); 7.41 (t, 1H); 7.33-7.30 (m, 6H); 7.19 (s, 2H); 6.69 (d, 1H); 3.65 (s, 2H).

EXAMPLE 246

N-(3-(5-(2-((3-(((2-morpholin-4-ylethyl)amino)sulfonyl)phenyl)amino)pyrimidin-4-yl)imidazo[2,1-b][1,3]thiazol-6-yl)phenyl)-2-phenylacetamide The title compound was prepared as described in EXAMPLE 12, substituting 3-amino-N-(2-morpholinoethyl)benzenesulfonamide for 4-morpholinoaniline. MS (ESI(+)) m/e 695 (M+H)$^+$; (ESI(−)) m/e 693 (M−H)$^−$; $^1$H-NMR (300 MHz, DMSO-d$_6$) ☐ 10.28 (s, 1H); 10.01 (s, 1H); 8.87 (d, 1H); 8.31 (d, 1H); 8.24 (m, 1H); 8.01 (m, 1H); 7.89 (m, 1H); 7.71 (m, 1H); 7.55-7.49 (m, 3H); 7.44-7.39 (m, 2H); 7.34-7.23 (m, 6H); 6.66 (m, 1H); 3.65 (s, 2H); 3.48 (m, 4H); 2.90 (m, 2H); 2.33-2.24 (m, 6H).

EXAMPLE 247

(trans)-2-phenyl-N-(3-(5-(2-((4-piperidin-1-ylphenyl)amino)pyrimidin-4-yl)imidazo[2,1-b][1,3]thiazol-6-yl)phenyl)cyclopropanecarboxamide

EXAMPLE 247A

A peptide flask was charged with the 4-(piperidin-1-yl)aniline (0.881 g), 2,2,10,10-tetramethyl-6-thioxo-3,9-dioxa-5,7-diazaundecane-4,8-dione (1.658 g), dichloromethane (60 ml) and the PS-carbodiimide (Argonaut P/N 800371, lot 03424, 1.42 mmole/eq, 5.28 g, 7.5 mmole, 1.5 eq). The mixture was agitated 72 hours on a rotating mixer. The resin was removed by filtration, washed with methylene chloride and the filtrate and washes were concentrated to a solid, which was purified on silica gel with ethyl acetate-hexane. The pure bis-boc guanidine intermediate was dissolved in 3:1 trifluoroacetic acid: methylene chloride and stirred under nitrogen for 18 hours. The title compound was isolated by concentration and drying under high vacuum.

EXAMPLE 247B

The title compound was prepared as described in EXAMPLE 3B, substituting EXAMPLE 247A for EXAMPLE 3A.

EXAMPLE 247C

The title compound was prepared as described in EXAMPLE 3C, substituting EXAMPLE 247B for EXAMPLE 3B.

EXAMPLE 247D (trans)-2-phenyl-N-(3-(5-(2-((4-piperidin-1-ylphenyl)amino)pyrimidin-4-yl)imidazo[2,1-b][1,3]thiazol-6-yl)phenyl)cyclopropanecarboxamide The title compound was prepared as described in EXAMPLE 3D, substituting EXAMPLE 247C for EXAMPLE 3C and (trans)-2-phenylcyclopropanecarbonyl chloride for 2,6-difluorobenzoyl chloride. MS (ESI(+)) m/e 612 (M+H)$^+$; $^1$H-NMR (300 MHz, DMSO-d$_6$) ☐ 10.39 (s, 1H), 9.94 (s, 1H), 8.82 (br s, 1H), 8.31 (d, 1H), 7.90 (s, 1H), 7.85 (m, 2H), 7.71 (d, 1H), 7.53 (m, 3H), 7.41 (t, 1H), 7.30 (m, 3H), 7.01 (m, 3H), 6.66 (d, 1H), 3.60 (m, 4H), 2.37 (m, 1H), 2.09 (m, 1H), 1.88 (m, 4H), 1.66 (br s, 2H), 1.49 (m, 1H), 1.37 (m, 1H).

EXAMPLE 248

3-phenyl-N-(3-(5-(2-((4-piperidin-1-ylphenyl)amino)pyrimidin-4-yl)imidazo[2,1-b][1,3]thiazol-6-yl)phenyl)propanamide The title compound was prepared as described in EXAMPLE 3D, substituting EXAMPLE 247C for EXAMPLE 3C and 3-phenylpropanoyl chloride for 2,6-difluorobenzoyl chloride. MS (ESI(+)) m/e 600 (M+H)$^+$; (ESI(−)) m/e 598 (M−H)$^−$; $^1$H-NMR (300 MHz, DMSO-d$_6$) ☐ 10.05 (s, 1H), 9.94 (s, 1H), 8.82 (br s, 1H), 8.31 (d, 1H), 7.90 (s, 1H), 7.85 (m, 2H), 7.65 (d, 1H), 7.52 (m, 3H), 7.40 (t, 1H), 7.27 (m, 5H), 7.18 (m, 1H), 6.66 (d, 1H), 3.60 (m, 4H), 2.91 (t, 2H), 2.64 (t, 2H), 1.88 (m, 4H), 1.65 (br s, 2H).

EXAMPLE 249

2-phenyl-N-(3-(5-(2-((4-piperidin-1-ylphenyl)amino)pyrimidin-4-yl)imidazo[2,1-b][1,3]thiazol-6-yl)phenyl)acetamide The title compound was prepared as described in EXAMPLE 3D, substituting 2-phenylacetyl chloride for 2,6-difluorobenzoyl chloride. MS (ESI(+)) m/e 586 (M+H)$^+$; (ESI(−)) m/e 584 (M−H)$^−$; $^1$H-NMR (300 MHz, DMSO-d$_6$) ☐ 10.32 (s, 1H), 9.95 (s, 1H), 8.81 (br s, 1H), 8.31 (d, 1H), 7.91 (s, 1H), 7.86 (m, 2H), 7.70 (d, 1H), 7.56 (m, 2H), 7.52 (d, 1H), 7.41 (t, 1H), 7.35-7.23 (m, 6H), 6.66 (d, 1H), 3.60 (m, 4H), 3.49 (m, 2H), 1.88 (m, 4H), 1.66 (br s, 2H).

EXAMPLE 250

N-(3-(5-(2-((4-piperidin-1-ylphenyl)amino)pyrimidin-4-yl)imidazo[2,1-b][1,3]thiazol-6-yl)phenyl)benzamide The title compound was prepared as described in EXAMPLE 3D, substituting EXAMPLE 247C for EXAMPLE 3C and benzoyl chloride for 2,6-difluorobenzoyl chloride. MS (ESI(+)) m/e 572 (M+H)$^+$; (ESI(−)) m/e 570 (M−H)$^−$; $^1$H-NMR (300 MHz, DMSO-d$_6$) ☐ 10.39 (s, 1H), 9.94 (s, 1H), 8.83 (br s, 1H), 8.33 (d, 1H), 8.12 (s, 1H), 7.96 (d, 2H), 7.91 (d, 2H), 7.85 (m, 2H), 7.62-7.46 (m, 6H), 7.35 (d, 1H), 6.73 (d, 1H), 3.60 (m, 4H), 1.87 (m, 4H), 1.65 (br s, 2H).

EXAMPLE 251

N-(3-(5-(2-((4-(4-(2-hydroxyethyl)piperazin-1-yl)
phenyl)amino)pyrimidin-4-yl)imidazo[2,1-b][1,3]
thiazol-6-yl)phenyl)-2-phenylacetamide

EXAMPLE 251A

The title compound was prepared as described in EXAMPLE 42A, substituting 2-(4-(4-aminophenyl)piperazin-1-yl)ethanol for 4-(1H-imidazol-1-yl)aniline.

EXAMPLE 251B

This compound was prepared as described in EXAMPLE 1E, substituting EXAMPLE 251A for phenyl guanidine.

EXAMPLE 251C

The title compound was prepared as described in EXAMPLE 1F, substituting EXAMPLE 251B for EXAMPLE 1E.

EXAMPLE 251D

N-(3-(5-(2-((4-(4-(2-hydroxyethyl)piperazin-1-yl)
phenyl)amino)pyrimidin-4-yl)imidazo[2,1-b][1,3]
thiazol-6-yl)phenyl)-2-phenylacetamide The title compound was prepared as described in EXAMPLE 36, substituting EXAMPLE 251C for EXAMPLE 36C. MS (ESI), m/e 631.3; (ESI), m/e 629.1 (M−H)$^-$; $^1$H-NMR (300 MHz, DMSO-d$_6$) □ ppm 10.31 (s, 1 H), 9.58 (bs, 1 H), 9.53 (s, 1 H), 8.77 (bs, 1H), 8.21 (d, 1 H), 7.89 (s, 1 H), 7.69 (d, 1 H), 7.59 (d, 2 H), 7.48 (d, 1 H), 7.40 (t, 1 H), 7.23-7.35 (m, 6 H), 6.99 (d, 2 H), 6.54 (d, 1 H), 3.79 (t, 2 H), 3.72-3.7 (m, 4 H), 3.65 (s, 2 H), 3.18-3.30 (m, 4 H), 3.03 (t, 2H).

EXAMPLE 252

N-(3-(5-(2-((4-(4-(2-hydroxyethyl)piperazin-1-yl)
phenyl)amino)pyrimidin-4-yl)imidazo[2,1-b][1,3]
thiazol-6-yl)phenyl)benzamide The title compound was prepared as described in EXAMPLE 36, substituting EXAMPLE 251C for EXAMPLE 36C and benzoyl chloride for phenylacetyl chloride. MS (ESI), m/e 617.3; (ESI), m/e 615.1 (M−H)$^-$; $^1$H-NMR (300 MHz, DMSO-d$_6$) □ ppm 10.38 (s, 1 H), 9.56 (bs, 1 H), 9.54 (s, 1 H), 8.79 (bs, 1 H), 8.24 (d, 1 H), 8.11 (s, 1 H), 7.94-7.97 (m, 3H), 7.90 (d, 1 H), 7.45-7.64 (m, 8 H), 7.34 (d, 1 H), 6.99 (d, 2 H), 6.60 (d, 1 H), 3.79 (t, 2 H), 3.72-3.7 (m, 4 H), 3.18-3.30 (m, 4 H), 3.03 (t, 2H).

EXAMPLE 253

(trans)-2-phenyl-N-(3-(5-(2-((4-pyrrolidin-1-ylphenyl)amino)pyrimidin-4-yl)imidazo[2,1-b][1,3]thiazol-6-yl)phenyl)cyclopropanecarboxamide

EXAMPLE 253A

The title compound was prepared as described in EXAMPLE 247A, substituting 4-(pyrrolidin-1-yl)aniline for 4-(piperidin-1-yl)aniline.

EXAMPLE 253B

The title compound was prepared as described in EXAMPLE 3B substituting EXAMPLE 253A for EXAMPLE 3A.

EXAMPLE 253C

The title compound was prepared as described in EXAMPLE 3C, substituting EXAMPLE 253B for EXAMPLE 3B.

EXAMPLE 253D (trans)-2-phenyl-N-(3-(5-(2-((4-pyrrolidin-1-ylphenyl)amino)pyrimidin-4-yl)imidazo[2,1-b][1,3]thiazol-6-yl)phenyl)cyclopropanecarboxamide The title compound was prepared as described in EXAMPLE 3D, substituting EXAMPLE 253C for EXAMPLE 3C and (trans)-2-phenylcyclopropanecarbonyl chloride for 2,6-difluorobenzoyl chloride. MS (ESI(+)) m/e 598 (M+H)$^+$; $^1$H-NMR (300 MHz, DMSO-d$_6$) □ 10.39 (s, 1H), 9.56 (br s, 1H), 8.72 (br s, 1H), 8.16 (br s, 1H), 7.87 (s, 1H), 7.72 (d, 1H), 7.46 (m, 2H), 7.41 (t, 1H), 7.29 (m, 3H), 7.19 (m, 3H), 6.64 (m, 2H), 6.52 (m, 2H), 3.27 (m, 4H), 2.37 (m, 1H), 2.09 (m, 1H), 1.98 (m, 4H), 1.49 (m, 1H), 1.37 (m, 1H).

EXAMPLE 254

N-(3-(5-(2-((4-(4-(2-hydroxyethyl)piperazin-1-yl)
phenyl)amino)pyrimidin-4-yl)imidazo[2,1-b][1,3]
thiazol-6-yl)phenyl)-3-phenylpropanamide The title compound was prepared as described in EXAMPLE 36D, substituting EXAMPLE 251C for EXAMPLE 36C and 3-phenylpropanoyl chloride for phenylacetyl chloride. MS (ESI), m/e 645.3; (ESI), m/e 643.1 (M−H)$^-$; $^1$H-NMR (300 MHz, DMSO-d$_6$) □ ppm 10.05 (s, 1 H), 9.63 (bs, 1 H), 9.56 (s, 1 H), 8.78 (bs, 1 H), 8.22 (d, 1 H), 7.89 (s, 1 H), 7.66 (d, 1 H), 7.59 (d, 2 H), 7.47 (d, 1 H), 7.40 (t, 1 H), 7.17-7.30 (m, 6 H), 7.00 (d, 2 H), 6.54 (d, 1 H), 3.79 (t, 2 H), 3.73-3.78 (m, 4 H), 3.18-3.30 (m, 4 H), 3.03 (t, 2 H), 2.91 (t, 2 H), 2.82 (t, 2H).

EXAMPLE 255

3-phenyl-N-(3-(5-(2-((4-pyrrolidin-1-ylphenyl)amino)pyrimidin-4-yl)imidazo[2,1-b][1,3]thiazol-6-yl)phenyl)propanamide The title compound was prepared as described in EXAMPLE 3D, substituting EXAMPLE 253C for EXAMPLE 3C and 3-phenylpropanoyl chloride for 2,6-difluorobenzoyl chloride. MS (ESI(+)) m/e 586 (M+H)$^+$; (ESI (−)) m/e 584 (M−H)$^-$; $^1$H-NMR (300 MHz, DMSO-d$_6$) □ 10.05 (s, 1H), 9.59 (br s, 1H), 8.72 (br s, 1H), 8.14 (br s, 1H), 7.88 (s, 1H), 7.68 (d, 1H), 7.46 (m, 3H), 7.40 (t, 1H), 7.27 (m, 5H), 7.18 (m, 1H), 6.66 (m, 2H), 6.50 (m, 1H), 3.27 (m, 4H), 2.91 (t, 2H), 2.64 (t, 2H), 1.98 (m, 4H).

EXAMPLE 256

(trans)-N-(3-(5-(2-((4-(4-(2-hydroxyethyl)piperazin-1-yl)phenyl)amino)pyrimidin-4-yl)imidazo[2,1-b][1,3]thiazol-6-yl)phenyl)-2-phenylcyclopropanecarboxamide The title compound was prepared as described in EXAMPLE 36D, substituting EXAMPLE 25° C. for EXAMPLE 36C and trans-2-phenylcyclopropanecarbonyl chloride for phenylacetyl chloride. MS (ESI), m/e 657.3; $^1$H-NMR (300 MHz, DMSO-d$_6$) ☐ ppm 10.38 (s, 1 H), 9.60 (bs, 1 H), 9.55 (s, 1 H), 8.77 (bs, 1 H), 8.22 (d, 1 H), 7.88 (s, 1 H), 7.7.0 (d, 1H), 7.59 (d, 2 H), 7.47 (d, 1 H), 7.41 (t, 1 H), 7.26-7.30 (m, 3 H), 7.18-7.21 (m, 3 H), 7.00 (d, 2 H), 6.54 (d, 1 H), 3.79 (t, 2 H), 3.73-3.78 (m, 4 H), 3.18-3.30 (m, 4 H), 3.03 (t, 2H), 2.35-2.39 (m, 1 H), 2.07-2.10 (m, 1 H), 1.39-1.51 (m, 1 H), 1.35-1.39 (m, 1 H).

EXAMPLE 257

N-(3-(5-(2-((4-(4-isopropylpiperazin-1-yl)phenyl)amino)pyrimidin-4-yl)imidazo[2,1-b][1,3]thiazol-6-yl)phenyl)-2-phenylacetamide

EXAMPLE 257A

This compound was prepared as described in EXAMPLE 42A, substituting 4-(4-iso-propylpiperazin-1-yl)aniline for 4-(1H-imidazol-1-yl)aniline.

EXAMPLE 257B

The title compound was prepared as described in EXAMPLE 1E, substituting EXAMPLE 257A for phenyl guanidine.

EXAMPLE 257C

The title compound was prepared as described in EXAMPLE 1F, substituting EXAMPLE 257B for EXAMPLE 1E.

EXAMPLE 257D

N-(3-(5-(2-((4-(4-isopropylpiperazin-1-yl)phenyl)amino)pyrimidin-4-yl)imidazo[2,1-b][1,3]thiazol-6-yl)phenyl)-2-phenylacetamide This compound was prepared as described in EXAMPLE 36D, substituting EXAMPLE 257C for EXAMPLE 36C. MS (ESI), m/e 629.3; (ESI), m/e 627.1 (M−H)$^−$; $^1$H-NMR (300 MHz, DMSO-d$_6$) ☐ ppm 10.31 (s, 1 H), 9.56 (s, 1 H), 9.40 (bs, 1 H), 8.77 (bs, 1 H), 8.21 (d, 1 H), 7.90 (s, 1 H), 7.7.0 (d, 1 H), 7.59 (d, 2 H), 7.48 (d, 1 H), 7.40 (t, 1 H), 7.24-7.35 (m, 6 H), 7.01 (d, 2 H), 6.54 (d, 1 H), 3.78-3.81 (m, 2 H), 3.58 (s, 2 H), 3.51-3.56 (m, 3 H), 3.15-3.22 (m, 2 H), 2.92-2.97 (m, 2 H), 1.30 (d, 6 H).

EXAMPLE 258

2-phenyl-N-(3-(5-(2-((4-(4-pyrrolidin-1-ylphenyl)amino)pyrimidin-4-yl)imidazo[2,1-b][1,3]thiazol-6-yl)phenyl)acetamide The title compound was prepared as described in EXAMPLE 3D substituting EXAMPLE 253C for EXAMPLE 3C and phenylacetyl chloride for 2,6-difluorobenzoyl chloride. MS (ESI(+)) m/e 572 (M+H)$^+$; $^1$H-NMR (300 MHz, DMSO-d$_6$) ☐ 10.31 (s, 1H), 9.59 (br s, 1H), 8.70 (br s, 1H), 8.14 (br s, 1H), 7.89 (s, 1H), 7.71 (d, 1H), 7.46 (m, 2H), 7.41 (t, 1H), 7.35-7.19 (m, 7H), 6.65 (m, 2H), 6.52 (m, 1H), 3.65 (s, 2H), 3.27 (m, 4H), 1.98 (m, 4H).

EXAMPLE 259

N-(3-(5-(2-((4-(4-isopropylpiperazin-1-yl)phenyl)amino)pyrimidin-4-yl)imidazo[2,1-b][1,3]thiazol-6-yl)phenyl)benzamide This compound was prepared as described in EXAMPLE 36, substituting EXAMPLE 257C for EXAMPLE 36C and benzoyl chloride for phenylacetyl chloride. MS (ESI), m/e 615.3; (ESI), m/e 613.1 (M−H)$^−$; $^1$H-NMR (300 MHz, DMSO-d$_6$) ☐ ppm 10.38 (s, 1 H), 9.55 (s, 1 H), 9.34 (bs, 1H), 8.80 (bs, 1H), 8.24 (d, 1H), 8.11 (s, 1 H), 7.96 (d, 2 H), 7.90 (d, 1 H), 7.43-7.63 (m, 8 H), 7.34 (d, 1 H), 7.00 (d, 2 H), 6.61 (d, 1 H), 3.78-3.81 (m, 2 H), 3.55 (m, 1 H), 3.45-3.50 (m, 2 H), 3.17-3.19 (m, 2 H), 2.90-2.96 (m, 2 H), 1.30 (d, 6 H).

EXAMPLE 260

N-(3-(5-(2-((4-(4-isopropylpiperazin-1-yl)phenyl)amino)pyrimidin-4-yl)imidazo[2,1-b][1,3]thiazol-6-yl)phenyl)-3-phenylpropanamide This compound was prepared as described in EXAMPLE 36, substituting EXAMPLE 257C for EXAMPLE 36C and 3-phenylpropanoyl chloride for phenylacetyl chloride. MS (ESI), m/e 643.3; (ESI), m/e 641.0 (M−H)$^−$; $^1$H-NMR (300 MHz, DMSO-d$_6$) ☐ ppm 10.05 (s, 1 H), 9.55 (s, 1 H), 9.40 (bs, 1 H), 8.78 (bs, 1 H), 8.22 (d, 1 H), 7.89 (s, 1 H), 7.67 (d, 1 H), 7.60 (d, 2 H), 7.48 (d, 1 H), 7.40 (t, 1 H), 7.17-7.30 (m, 5 H), 7.01 (d, 2 H), 6.55 (d, 1H), 3.78-3.81 (m, 2 H), 3.55 (m, 1 H), 3.16-3.22 (m, 2 H), 2.90-2.97 (m, 4 H), 2.82 (t, 2 H), 2.64 (t, 2 H), 1.30 (d, 6 H).

EXAMPLE 261

N-(3-(5-(2-((4-pyrrolidin-1-ylphenyl)amino)pyrimidin-4-yl)imidazo[2,1-b][1,3]thiazol-6-yl)phenyl)benzamide The title compound was prepared as described in EXAMPLE 3D substituting EXAMPLE 253C for EXAMPLE 3C and benzoyl chloride for 2,6-difluorobenzoyl chloride. MS (ESI(+)) m/e 558 (M+H)$^+$; $^1$H-NMR (300 MHz, DMSO-d$_6$) ☐ 10.39 (s, 1H), 9.62 (br s, 1H), 8.73 (br s, 1H), 8.17 (br s, 1H), 8.10 (s, 1H), 7.97 (d, 2H), 7.92 (d, 1H), 7.62-7.30 (m, 7H), 7.35 (d, 1H), 6.66 (m, 2H), 6.56 (m, 1H), 3.29 (m, 4H), 1.98 (m, 4H).

EXAMPLE 262

(trans)-N-(3-(5-(2-((4-(4-isopropylpiperazin-1-yl)phenyl)amino)pyrimidin-4-yl)imidazo[2,1-b][1,3]thiazol-6-yl)phenyl)-2-phenylcyclopropanecarboxamide This compound was prepared as described in EXAMPLE 36, substituting EXAMPLE 257C for EXAMPLE 36C and trans-2-phenylcyclopropanecarbonyl chloride for phenylacetyl chloride. MS (ESI), m/e 655.3; (ESI), m/e 653.0 (M−H)$^−$; $^1$H-NMR (300 MHz, DMSO-d$_6$) ☐ ppm 10.39 (s, 1 H), 9.56 (s, 1 H), 9.44 (bs, 1 H), 8.78 (bs, 1 H), 8.22 (d, 1 H), 7.89 (s, 1 H), 7.70 (d, 1 H), 7.60 (d, 2 H), 7.48 (d, 1 H), 7.41 (t, 1 H), 7.26-7.32 (m, 3 H), 7.18-7.23 (m, 3H), 7.01 (d, 2 H), 6.55 (d, 1 H), 3.78-3.81 (m, 2 H), 3.58-3.60 (m, 1 H), 3.52-

3.54 (m, 2 H), 3.15-3.22 (m, 2 H), 2.93-2.97 (m, 2 H), 2.34-2.40 (m, 1 H), 2.07-2.09 (m, 1 H), 1.47-1.51 (m, 1 H), 1.35-1.40 (m, 1 H), 1.30 (d, 6 H).

EXAMPLE 263

2-(2-chlorophenyl)-N-(3-(5-(2-((4-(4-isopropylpiperazin-1-yl)phenyl)amino)pyrimidin-4-yl)imidazo[2,1-b][1,3]thiazol-6-yl)phenyl)acetamide This compound was prepared as described in EXAMPLE 205, substituting EXAMPLE 257C for EXAMPLE 204C. MS (ESI), m/e 663.2; $^1$H-NMR (300 MHz, DMSO-$d_6$) ☐ ppm 10.38 (s, 1 H), 10.11 (bs, 1 H), 9.51 (s, 1 H), 8.77 (bs, 1 H), 8.22 (d, 1 H), 7.89 (s, 1 H), 7.70 (d, 1H), 7.45 (d, 2 H), 7.41-7.45 (m, 4 H), 7.29-7.33 (m, 3 H), 6.99 (d, 1 H), 6.55 (d, 1 H), 3.85 (s, 2 H), 3.75-3.77 (m, 2 H), 3.49-3.51 (m, 3 H), 3.15-3.22 (m, 2 H), 3.05-3.09 (m, 2 H), 1.30 (d, 6 H).

EXAMPLE 264

2-chloro-N-(3-(5-(2-((4-(4-isopropylpiperazin-1-yl)phenyl)amino)pyrimidin-4-yl)imidazo[2,1-b][1,3]thiazol-6-yl)phenyl)benzamide This compound was prepared as described in EXAMPLE 36D, substituting EXAMPLE 257C for EXAMPLE 36C and 2-chlor-benzoyl chloride for phenylacetyl chloride. MS (ESI), m/e 649.2; $^1$H-NMR (300 MHz, DMSO-$d_6$) ☐ ppm 10.63 (s, 1 H), 9.55 (s, 1 H), 9.38 (bs, 1 H), 8.78 (bs, 1 H), 8.24 (d, 1 H), 8.04 (s, 1 H), 7.77-7.80 (m, 2 H), 7.42-7.61 (m, 8 H), 7.35 (d, 1H), 7.01 (d, 1H), 6.59 (d, 1 H), 3.78-3.81 (m, 2 H), 3.55 (m, 2 H), 3.45 (m, 1 H), 3.16-3.22 (m, 2 H), 2.92-2.97 (m, 2 H), 1.30 (d, 6 H).

EXAMPLE 265

N-(3-(5-(2-((3-(acetylamino)phenyl)amino)pyrimidin-4-yl)imidazo[2,1-b][1,3]thiazol-6-yl)phenyl)-2,6-difluorobenzamide In a 20 mL vial was added EXAMPLE 34B (0.1 g) in dichloromethane (2.265 ml) and N-methylpyrrolidone (0.2 mL), followed by 2,6-difluorobenzoyl chloride (31 μL) and the mixture stirred at room temperature for 15 minutes. The mixture was treated with (polystyryl)trisamine resin (Argonaut Technologies, 3.41 mmol/g, 3 equivalents), and stirred overnight. Triethylamine (1 mL) was added, and filtered the resin which was washed with tetrahydrofuran. The filtrate was dissolved into ethyl acetate (25 mL) and the organics were washed with water (3×50 mL), then dried over MgSO$_4$. The resulting solid was triturated with CH$_2$Cl$_2$ and diethyl ether to afford the title compound. MS (ESI(+)) m/e 582 (M+H)$^+$; (ESI(−)) m/e 580 (M−H)$^−$; $^1$H-NMR (300 MHz, DMSO-$d_6$) ☐ 10.91 (s, 1H); 9.88 (s, 1H); 9.69 (s, 1H); 8.87 (d, 1H); 8.28 (d, 1H); 8.00-7.97 (m, 2H); 7.81-7.79 (m, 1H); 7.65-7.54 (m, 1H); 7.51-7.46 (m, 1H); 7.44-7.38 (m, 2H); 7.28-7.20 (m, 4H); 6.63 (d, 1H); 2.04 (s, 3H).

EXAMPLE 266

N-(3-(5-(2-((4-(4-(3-methoxypropyl)piperazin-1-yl)phenyl)amino)pyrimidin-4-yl)imidazo[2,1-b][1,3]thiazol-6-yl)phenyl)-N'-phenylurea

EXAMPLE 266A

The title compound was prepared as described in EXAMPLE 1A-F, substituting EXAMPLE 14B for phenylguanidine in EXAMPLE 1E.

EXAMPLE 266B

The title compound was prepared as described in EXAMPLE 13, substituting EXAMPLE 266A for EXAMPLE 3C. MS (ESI(+)) m/e 660 (M+H)$^+$; $^1$H-NMR (300 MHz, DMSO-$d_6$) ☐ 9.53 (s, 1H); 9.36 (bs, 1H); 8.86 (s, 1H); 8.80 (bs, 1H); 8.72 (s, 1H); 8.24 (d, 1H); 7.76 (s, 1H); 7.60 (d, 2H); 7.53-7.43 (m, 3H); 7.39 (t, 1H); 7.27 (t, 2H); 7.20 (d, 1H); 7.01-6.94 (m, 3H); 6.59 (d, 1H); 3.76 (d, 2H); 3.61 (d, 2H); 3.42 (t, 2H); 3.27 (s, 3H); 3.20 (m, 4H); 2.92 (t, 2H); 1.94 (m, 2H).

EXAMPLE 267

N-(2-chlorophenyl)-N'-(3-(5-(2-((4-(4-(3-methoxypropyl)piperazin-1-yl)phenyl)amino)pyrimidin-4-yl)imidazo[2,1-b][1,3]thiazol-6-yl)phenyl)urea The title compound was prepared as described in EXAMPLE 13, substituting 2-chlorophenylisocyanate for phenylisocyanate and EXAMPLE 266A for EXAMPLE 3C. (ESI(+)) m/e 694 (M+H)$^+$; $^1$H-NMR (300 MHz, DMSO-$d_6$) ☐ 9.56 (s, 1H); 9.52 (s, 1H); 9.40 (bs, 1H); 8.79 (bs, 1H); 8.31 (s, 1H); 8.24 (d, 1H); 8.15 (d, 1H); 7.78 (s, 1H); 7.59 (d, 2H); 7.54-7.39 (m, 3H); 7.32-7.22 (m, 2H); 7.06-6.98 (m, 3H); 6.60 (d, 1H); 3.76 (d, 2H); 3.61 (d, 2H); 3.42 (t, 2H); 3.27 (s, 3H); 3.20 (m, 4H); 2.93 (t, 2H); 1.94 (m, 2H).

EXAMPLE 268

N-(3-((4-(6-(3-((anilinocarbonyl)amino)phenyl)imidazo[2,1-b][1,3]thiazol-5-yl)pyrimidin-2-yl)amino)phenyl)acetamide The title compound was prepared as described in EXAMPLE 265, substituting phenyl isocyanate for 2,6-difluorobenzoyl chloride. (ESI(+)) m/e 561 (M+H)$^+$; (ESI(−)) m/e 559 (M−H)$^−$; $^1$H-NMR (300 MHz, DMSO-$d_6$) ☐ 9.89 (s, 1H); 9.69 (s, 1H); 8.92 (d, 1H); 8.84 (s, 1H); 8.70 (s, 1H); 8.28 (d, 1H); 8.01 (s, 1H); 7.73 (m, 1H); 7.56 (m, 1H); 7.49-7.37 (m, 5H); 7.30-7.25 (m, 2H); 7.22-7.20 (m, 3H); 6.96 (m, 1H); 6.63 (d, 1H); 2.04 (s, 3H).

EXAMPLE 269

N-(3-((4-(6-(3-((((2-chlorophenyl)amino)carbonyl)amino)phenyl)imidazo[2,1-b][1,3]thiazol-5-yl)pyrimidin-2-yl)amino)phenyl)acetamide The title compound was prepared as described in EXAMPLE 265, substituting 2-chlorophenyl isocyanate for 2,6-difluorobenzoyl chloride. (ESI(+)) m/e 595 (M+H)$^+$; $^1$H-NMR (300 MHz, DMSO-$d_6$) ☐ 9.89 (s, 1H); 9.70 (s, 1H); 9.57 (s, 1H); 8.91 (d, 1H); 8.33 (bs, 1H); 8.28 (d, 1H); 8.15 (m, 1H); 8.01 (m, 1H); 7.77 (m, 1H); 7.58-7.55 (m, 1H); 7.49-7.40 (m, 4H); 7.33-7.20 (m, 4H); 7.05-7.00 (m, 1H); 6.64-6.63 (m, 2H); 2.04 (s, 3H).

EXAMPLE 270

N-(3-(5-(2-((3-(acetylamino)phenyl)amino)pyrimidin-4-yl)imidazo[2,1-b][1,3]thiazol-6-yl)phenyl)-2-(2-chlorophenyl)acetamide The title compound was prepared as described in EXAMPLE 265, substituting 2-chlorophenyl acetic acid for 2,6-difluorobenzoyl chloride. (ESI(+)) m/e 594 (M+H)$^+$; $^1$H-NMR (300 MHz, DMSO-d$_6$) ☐ 10.34 (s, 1H); 9.88 (s, 1H); 9.68 (s, 1H); 8.89 (d, 1H); 8.26 (d, 1H); 8.00 (s, 1H); 7.86 (s, 1H); 7.72 (d, 1H0); 7.45-7.39 (m, 5H); 7.32-7.28 (m, 3H); 7.22-7.20 (m, 2H); 6.60 (d, 1H); 3.85 (s, 2H); 2.04 (s, 3H).

EXAMPLE 271

2-(2-chlorophenyl)-N-(3-(5-(2-((4-(4-(3-methoxypropyl)piperazin-1-yl)phenyl)amino)pyrimidin-4-yl)imidazo[2,1-b][1,3]thiazol-6-yl)phenyl)acetamide The title compound was prepared as described in EXAMPLE 12, substituting EXAMPLE 14B for 3-morpholinoaniline in EXAMPLE 12D and 2-chlorophenylacetyl chloride for phenylacetyl chloride in EXAMPLE 12F. MS (ESI (+)) m/e 693 (M+H)$^+$; $^1$H-NMR (300 MHz, DMSO-d$_6$) ☐ 10.33 (s, 1H); 9.51 (s, 1H); 9.35 (bs, 1H); 8.77 (bs, 1H); 8.22 (d, 1H); 7.89 (s, 1H); 7.69 (d, 1H); 7.60 (d, 2H); 7.48-7.38 (m, 3H); 7.32-7.27 (m, 3H); 7.00 (d, 2H); 6.56 (d, 1H); 3.85 (s, 2H); 3.76 (d, 2H); 3.61 (d, 2H); 3.42 (t, 2H); 3.27 (s, 3H); 3.20 (m, 4H); 2.93 (t, 2H); 1.94 (m, 2H).

EXAMPLE 272

N-(3-(5-(2-((4-(4-acetylpiperazin-1-yl)phenyl)amino)pyrimidin-4-yl)imidazo[2,1-b][1,3]thiazol-6-yl)phenyl)-2-(2-chlorophenyl)acetamide This compound was prepared as described in EXAMPLE 205, substituting EXAMPLE 65C for EXAMPLE 204C. MS (ESI), m/e 663.1 (M+H)$^+$; (ESI), m/e 661.0 (M−H)$^−$; $^1$H-NMR (300 MHz, DMSO-d$_6$) ☐ ppm 10.36 (s, 1 H), 9.59 (s, 1 H), 8.74 (bs, 1 H), 8.22 (d, 1 H), 7.89 (s, 1 H), 7.71 (d, 1 H), 7.56 (d, 2 H), 7.40-7.48 (m, 4 H), 7.28-7.33 (m, 3 H), 7.02 (d, 2 H), 6.56 (d, 1 H), 3.85 (s, 2 H), 3.60-3.62 (m, 4 H), 3.17 (m, 2 H), 3.09 (m, 2 H), 2.05 (s, 3 H).

EXAMPLE 273

N-(3-(5-(2-((4-(4-acetylpiperazin-1-yl)phenyl)amino)pyrimidin-4-yl)imidazo[2,1-b][1,3]thiazol-6-yl)phenyl)-2,6-difluorobenzamide This compound was prepared as described in EXAMPLE 36D, substituting EXAMPLE 65C for EXAMPLE 36C and 2,6-difluoro-benzoyl chloride for phenylacetyl chloride. MS (ESI), m/e 651.1 (M+H)$^+$; (ESI), m/e 628.1 (M−H)$^−$; $^1$H-NMR (300 MHz, DMSO-d$_6$) ☐ ppm 10.94 (s, 1 H), 9.67 (s, 1 H), 8.73 (bs, 1 H), 8.23 (d, 1 H), 8.00 (s, 1 H), 7.78 (d, 1 H), 7.50-7.63 (m, 3 H), 7.47-7.50 (m, 2 H), 7.38 (d, 1 H), 7.26 (t, 2 H), 7.21 (t, 1 H), 7.06 (d, 2 H), 6.60 (d, 1H), 3.55-3.62 (m, 4 H), 3.17 (m, 2 H), 3.12 (m, 2 H), 2.06 (s, 3 H).

EXAMPLE 274

N-(3-(5-(2-((4-(4-acetylpiperazin-1-yl)phenyl)amino)pyrimidin-4-yl)imidazo[2,1-b][1,3]thiazol-6-yl)phenyl)-2-chlorobenzamide This compound was prepared as described in EXAMPLE 36, substituting EXAMPLE 65C for EXAMPLE 36C and 2-chloro-benzoyl chloride for phenylacetyl chloride. MS (ESI), m/e 649.2 (M+H)$^+$; $^1$H-NMR (300 MHz, DMSO-d$_6$) ☐ ppm 10.63 (s, 1H), 9.62 (s, 1 H), 8.74 (bs, 1 H), 8.23 (d, 1 H), 8.03 (s, 1 H), 7.81 (d, 1 H), 7.79 (d, 1 H), 7.40-7.61 (m, 7 H), 7.36 (d, 1H), 7.03 (d, 2 H), 6.59 (d, 1 H), 3.55-3.62 (m, 4 H), 3.17 (m, 2 H), 3.10 (m, 2 H), 2.05 (s, 3H).

EXAMPLE 275

N-(3-(5-(2-((4-(4-acetylpiperazin-1-yl)phenyl)amino)pyrimidin-4-yl)imidazo[2,1-b][1,3]thiazol-6-yl)phenyl)-N'-phenylurea A solution of EXAMPLE 65C (50 mg) and benzene isocyanate (17 µL) in CH$_2$Cl$_2$ (3 mL) was stirred at 50° C. overnight. The solid was collected by filtration and washed with 60% ethyl acetate in hexane, and vacuum dried. MS (ESI), m/e 630.2 (M+H)$^+$; (ESI), m/e 628.1 (M−H)$^−$; $^1$H-NMR (300 MHz, DMSO-d$_6$) ☐ ppm 9.45 (s, 1H), 8.81 (s, 1 H), 8.76 (bs, 1 H), 8.67 (s, 1 H), 8.22 (d, 1 H), 7.73 (s, 1 H), 7.54-7.55 (m, 3 H), 7.44-7.48 (m, 3 H), 7.39 (t, 1H), 7.28 (t, 2 H), 7.20 (d, 1 H), 6.94-6.98 (m, 3 H), 6.57 (d, 1 H), 3.55-3.60 (m, 4 H), 3.11 (m, 2 H), 3.04 (m, 2 H), 2.04 (s, 3 H).

EXAMPLE 276

N-(3-(5-(2-((4-(4-acetylpiperazin-1-yl)phenyl)amino)pyrimidin-4-yl)imidazo[2,1-b][1,3]thiazol-6-yl)phenyl)-N'-(2-chlorophenyl)urea This compound was prepared as described EXAMPLE 275, substituting 2-chloro-benzene isocyanate for benzene isocyanate. MS (ESI), m/e 664.2 (M+H)$^+$; (ESI), m/e 662.0 (M−H)$^−$; $^1$H-NMR (300 MHz, DMSO-d$_6$) ☐ ppm 9.48 (s, 1H), 9.39 (s, 1 H), 8.69 (bs, 1 H), 8.24 (s, 1H), 8.16 (d, 1 H), 8.08 (d, 1 H), 7.69 (s, 1 H), 7.47-7.49 (m, 3 H), 7.35-7.40 (m, 3 H), 7.33 (t, 1 H), 7.16 (d, 1 H), 6.96 (t, 1 H), 6.88 (d, 2 H), 6.51 (d, 1 H), 3.50-3.55 (m, 4 H), 3.04 (m, 2H), 2.96 (m, 2 H), 1.97 (s, 3 H).

EXAMPLE 277

2,6-difluoro-N-(3-(5-(2-((4-(4-isopropylpiperazin-1-yl)phenyl)amino)pyrimidin-4-yl)imidazo[2,1-b][1,3]thiazol-6-yl)phenyl)benzamide This compound was prepared as described in EXAMPLE 36D, substituting EXAMPLE 257C for EXAMPLE 36C and 2,6-difluoro-benzoyl chloride for phenylacetyl chloride. MS (ESI), m/e 651.2 (M+H)$^+$; (ESI), m/e 649.0 (M−H)$^−$; $^1$H-NMR (300 MHz, DMSO-d$_6$) ☐ ppm 10.93 (s, 1H), 9.55 (s, 1 H), 9.34 (bs, 1 H), 8.77 (bs, 1 H), 8.24 (d, 1 H), 8.01 (s, 1 H), 7.76 (d, 1 H), 7.56-7.63 (m, 3 H), 7.47-7.50 (m, 2 H), 7.38 (d, 1 H), 7.26 (t, 1 H), 7.21 (t, 2 H), 7.02 (d, 2H), 6.59 (d, 1 H), 3.78-3.81 (m, 2 H), 3.55 (m, 2 H), 3.50 (m, 1 H), 3.15-3.20 (m, 2 H), 2.94 (m, 2 H), 1.30 (d, 6 H).

EXAMPLE 278

N-(3-(5-(2-((4-(4-isopropylpiperazin-1-yl)phenyl)amino)pyrimidin-4-yl)imidazo[2,1-b][1,3]thiazol-6-yl)phenyl)-N'-phenylurea This compound was prepared as described in EXAMPLE 275, substituting EXAMPLE 257C for EXAMPLE 65C. MS (ESI), m/e 630.2 (M+H)$^+$; (ESI), m/e 628.0 (M−H)$^-$; $^1$H-NMR (300 MHz, DMSO-d$_6$) □ ppm 9.55 (s, 1H), 9.34 (bs, 1 H), 8.92 (s, 1 H), 8.80 (bs, 1 H), 8.79 (s, 1H), 8.24 (d, 1 H), 7.77 (s, 1 H), 7.59 (d, 2 H), 7.52 (d, 1 H), 7.47 (d, 1 H), 7.45 (d, 2 H), 7.39 (t, 1 H), 7.26-7.29 (m, 2 H), 7.19 (d, 1 H), 6.99 (d, 2 H), 6.97 (t, 1 H), 6.59 (d, 1 H), 3.78-3.81 (m, 2 H), 3.55 (m, 2 H), 3.50 (m, 1 H), 3.15-3.18 (m, 2 H), 2.94 (m, 2 H), 1.30 (d, 6 H).

EXAMPLE 279

N-(2-chlorophenyl)-N'-(3-(5-(2-((4-(4-isopropylpiperazin-1-yl)phenyl)amino)pyrimidin-4-yl)imidazo[2,1-b][1,3]thiazol-6-yl)phenyl)urea This compound was prepared as described in EXAMPLE 275, substituting EXAMPLE 257C for EXAMPLE 65C and 2-chloro-benzene isocyanate for benzene isocyanate. MS (ESI), m/e 664.1 (M+H)$^+$; (ESI), m/e 617.8 (M−H)$^-$; $^1$H-NMR (300 MHz, DMSO-d$_6$) □ ppm 9.58 (s, 1 H), 9.56 (s, 1H), 9.36 (bs, 1 H), 8.79 (bs, 1 H), 8.33 (s, 1 H), 8.24 (d, 1 H), 8.13 (d, 1 H), 7.79 (s, 1 H), 7.59 (d, 2 H), 7.52 (d, 1 H), 7.47-7.48 (m, 1 H), 7.45 (s, 1 H), 7.42 (t, 1 H), 7.29 (t, 1H), 7.23 (d, 1 H), 7.00-7.06 (m, 3 H), 6.61 (d, 1 H), 3.78-3.81 (m, 2 H), 3.55 (m, 2 H), 3.50 (m, 1 H), 3.15-3.18 (m, 2 H), 2.92-2.96 (m, 2 H), 1.30 (d, 6 H).

EXAMPLE 280

2-(5-acetylthien-3-yl)-N-(3-(5-(2-((4-morpholin-4-ylphenyl)amino)pyrimidin-4-yl)imidazo[2,1-b][1,3]thiazol-6-yl)phenyl)acetamide The title compound was prepared as described in EXAMPLE 51, substituting 2-(5-acetylthiophen-3-yl)acetic acid for 3-(1H-imidazol-4-yl)propanoic acid. (ESI(+)) m/e 594 (M+H)$^+$; (ESI(−)) m/e 592 (M−H)$^-$; $^1$H-NMR (500 MHz, DMSO-d$_6$) □ 10.31 (s, 1H), 9.53 (s, 1H), 8.74 (bs, 1H), 8.21 (d, 1H), 7.87-7.90 (m, 1H), 7.86 (d, 1H), 7.77 (s, 1H), 7.71 (dd, 1H), 7.55 (d, 2H), 7.47 (d, 1H), 7.42 (t, 1H), 7.29 (d, 1H), 6.98 (d, 2H), 6.53 (d, 1H), 3.74-3.79 (m, 4H), 3.72 (s, 2H), 3.08-3.13 (m, 4H), 2.52 (s, 3H).

EXAMPLE 281

2-methyl-N-(3-(5-(2-((3-(2-morpholin-4-ylethyl)phenyl)amino)pyrimidin-4-yl)imidazo[2,1-b][1,3]thiazol-6-yl)phenyl)benzamide

EXAMPLE 281A

Into a 500 mL round-bottomed flask was added 2-(3-nitrophenyl)ethanol (1.0235 g), dimethylaminopyridine (0.075 g) and p-toluenesulfonyl chloride (1.401 g) in CH$_2$Cl$_2$ (61.2 ml). Triethylamine (1.707 ml) was added, and the reaction was stirred at room temperature for three hours, washed with water and brine, dried over MgSO$_4$, and concentrated onto silica gel. The residue was purified by flash chromatography using an Argonaut Flashmaster Solo system, 25 g column (100% hexanes to 30% ethyl acetate in hexanes over 25 minutes, then to 100% ethyl acetate over 10 minutes) to provide the title compound.

EXAMPLE 281B

Into a 100 mL microwave vessel was added EXAMPLE 281A (1.33 g) in acetonitrile (10.35 ml). Triethylamine (1.731 ml) and morpholine (1.082 ml) were added. The vessel was sealed and heated with a 10 minute ramp time to 150° C. with a 20 minute hold time on a Milestone Microsynth microwave. The resulting solution was then concentrated onto silica gel. The residue was purified by flash chromatography using an Argonaut Flashmaster Solo system, 25 g column (100% CH$_2$Cl$_2$ for 5 minutes, then 100% CH$_2$Cl$_2$ to 90% CH$_2$Cl$_2$ in MeOH with 1% NH$_4$OH over 25 minutes, then 90% CH$_2$Cl$_2$ in methanol with 1% NH$_4$OH for 5 minutes) to afford the title compound.

EXAMPLE 281C

Into a 100 mL flask was added EXAMPLE 281B (0.7196 g), iron (1.871 g), and ammonium chloride (0.196 g) in ethanol (4.87 ml) and water (1.218 ml). The mixture was heated to 90° C. for 1 hour, and cooled to room temperature. The reaction was diluted with ethyl acetate and filtered. The filtrate was washed with water and brine, dried over MgSO$_4$, filtered, and concentrated.

EXAMPLE 281D 2-methyl-N-(3-(5-(2-((3-(2-morpholin-4-ylethyl)phenyl)amino)pyrimidin-4-yl)imidazo[2,1-b][1,3]thiazol-6-yl)phenyl)benzamide The title compound was prepared as described in EXAMPLE 297, with the following substitutions: 4-(6-(3-aminophenyl)imidazo[2,1-b]thiazol-5-yl)-N-(3-(2-morpholinoethyl)phenyl)pyrimidin-2-amine for 4-(6-(3-aminophenyl)imidazo[2,1-b]thiazol-5-yl)-N-(3-(3-morpholinopropoxy)phenyl)pyrimidin-2-amine and 2-methylbenzoyl chloride for 2,6-difluorobenzoyl chloride. (ESI(+)) m/e 616 (M+H)$^+$; (ESI(−)) m/e 614 (M−H)$^-$; $^1$H-NMR (300 MHz, DMSO-d$_6$) □ 10.40 (s, 1H), 9.61 (s, 1H), 8.81 (d, 1H), 8.29 (d, 1H), 8.06 (s, 1H), 7.84 (d, 1H), 7.25-7.64 (m, 9H), 7.21 (t, 1H), 6.86 (d, 1H), 6.65 (d, 1H), 3.53-3.62 (m, 4H), 3.17 (d, 2H), 2.67-2.77 (m, 2H), 2.36-2.44 (m, 7H).

EXAMPLE 282

2-fluoro-N-(3-(5-(2-((3-(2-morpholin-4-ylethyl)phenyl)amino)pyrimidin-4-yl)imidazo[2,1-b][1,3]thiazol-6-yl)phenyl)benzamide The title compound was prepared as described in EXAMPLE 297, with the following substitutions: 4-(6-(3-aminophenyl)imidazo[2,1-b]thiazol-5-yl)-N-(3-(2-morpholinoethyl)phenyl)pyrimidin-2-amine for 4-(6-(3-aminophenyl)imidazo[2,1-b]thiazol-5-yl)-N-(3-(3-morpholinopropoxy)phenyl)pyrimidin-2-amine and 2-fluorobenzoyl chloride for 2,6-difluorobenzoyl chloride. (ESI(+)) m/e 620 (M+H)$^+$; (ESI(−)) m/e 618 (M−H)$^-$; $^1$H-NMR (300 MHz, DMSO-d$_6$) □ 10.54 (s, 1H), 9.62 (s, 1H), 8.81 (d, 1H), 8.29 (d, 1H), 8.03 (s, 1H), 7.84 (d, 1H), 7.67 (td, 1H), 7.53-7.62 (m, 3H), 7.50 (d, 1H), 7.42-7.48 (m, 1H), 7.30-7.40 (m, 3H), 7.22 (t, 1H), 6.87 (d, 1H), 6.63 (d, 1H), 3.52-3.59 (m, 4H), 3.17 (d, 1H), 3.66-3.77 (m, 2H), 2.51-2.55 (m, 1H), 2.37-2.43 (m, 4H).

EXAMPLE 283

2,6-difluoro-N-(3-(5-(2-((3-(2-morpholin-4-ylethyl)phenyl)amino)pyrimidin-4-yl)imidazo[2,1-b][1,3]thiazol-6-yl)phenyl)benzamide The title compound was prepared as described in EXAMPLE 297, with the following substitutions: 4-(6-(3-aminophenyl)imidazo[2,1-b]thiazol-5-yl)-N-(3-(2-morpholinoethyl)phenyl)pyrimidin-2-amine for 4-(6-(3-aminophenyl)imidazo[2,1-b]thiazol-5-yl)-N-(3-(3-morpholinopropoxy)phenyl)pyrimidin-2-amine and. (ESI(+)) m/e 638 (M+H)$^+$; (ESI(−)) m/e 636 (M−H)$^-$; $^1$H-NMR (300 MHz, DMSO-d$_6$) □ 10.91 (s, 1H), 9.63 (s, 1H), 8.80 (d, 1H), 8.29 (d, 1H), 7.99 (m, 1H), 7.86 (d, 1H), 7.77 (s, 1H), 7.71 (dd, 1H), 7.55 (d, 2H), 7.47 (d, 1H), 7.42 (t, 1H), 7.29 (t, 1H), 7.78 (ddd, 1H), 7.44-7.67 (m, 5H), 7.35-7.43 (m, 1H), 7.16-7.31 (m, 3H), 6.86 (d, 1H), 6.63 (d, 1H), 3.53-3.60 (m, 4H), 2.65-2.79 (m, 2H), 2.54 (s, 2H), 2.35-2.44 (m, 4H).

EXAMPLE 284

N-(3-(5-(2-((3-(2-morpholin-4-ylethyl)phenyl)amino)pyrimidin-4-yl)imidazo[2,1-b][1,3]thiazol-6-yl)phenyl)-N'-phenylurea The title compound was prepared as described in EXAMPLE 297, with the following substitutions: 4-(6-(3-aminophenyl)imidazo[2,1-b]thiazol-5-yl)-N-(3-(2-morpholinoethyl)phenyl)pyrimidin-2-amine for 4-(6-(3-aminophenyl)imidazo[2,1-b]thiazol-5-yl)-N-(3-(3-morpholinopropoxy)phenyl)pyrimidin-2-amine and isocyanatobenzene for 2,6-difluorobenzoyl chloride. (ESI(+)) m/e 617 (M+H)$^+$; (ESI(−)) m/e 615 (M−H)$^-$; $^1$H-NMR (300 MHz, DMSO-d$_6$) □9.65 (s, 1H), 8.84 (s, 2H), 8.70 (s, 1H), 8.29 (d, 1H), 7.74 (t, 1H), 7.49-7.63 (m, 4H), 7.43-7.48 (m, 2H), 7.39 (t, 1H), 7.16-7.31 (m, 4H), 6.92-7.01 (m, 1H), 6.87 (d, 1H), 6.63 (d, 1H), 3.52-3.60 (m, 4H), 2.66-2.77 (m, 2H), 2.52-2.57 (m, 2H), 2.36-2.44 (m, 4H).

EXAMPLE 285

N-(3-(5-(2-((3-(2-morpholin-4-ylethyl)phenyl)amino)pyrimidin-4-yl)imidazo[2,1-b][1,3]thiazol-6-yl)phenyl)-2-phenylacetamide The title compound was prepared as described in EXAMPLE 297, with the following substitutions: 4-(6-(3-aminophenyl)imidazo[2,1-b]thiazol-5-yl)-N-(3-(2-morpholinoethyl)phenyl)pyrimidin-2-amine for 4-(6-(3-aminophenyl)imidazo[2,1-b]thiazol-5-yl)-N-(3-(3-morpholinopropoxy)phenyl)pyrimidin-2-amine and 2-phenylacetyl chloride for 2,6-difluorobenzoyl chloride. (ESI(+)) m/e 616 (M+H)$^+$; (ESI(−)) m/e 614 (M−H)$^-$; $^1$H-NMR (300 MHz, DMSO-d$_6$) □ 10.29 (s, 1H), 9.62 (s, 1H), 8.80 (d, 1H), 8.26 (d, 1H), 7.88 (t, 1H), 7.68-7.74 (m, 1H), 7.54-7.61 (m, 2H), 7.49 (d, 1H), 7.40 (t, 1H), 7.18-7.36 (m, 6H), 6.86 (d, 1H), 6.59 (d, 1H), 3.65 (s, 2H), 3.53-3.60 (m, 4H), 3.17 (d, 1H), 2.68-2.76 (m, 2H), 2.52-2.56 (m, 1H), 2.38-2.43 (m, 4H).

EXAMPLE 286

N-(3-(5-(2-((3-(2-oxopyrrolidin-1-yl)phenyl)amino)pyrimidin-4-yl)imidazo[2,1-b][1,3]thiazol-6-yl)phenyl)-2-phenylacetamide

EXAMPLE 286A

This compound was prepared as described in EXAMPLE 42A, substituting 1-(3-aminophenyl)pyrrolidin-2-one for 4-(1H-imidazol-1-yl)aniline.

EXAMPLE 286B

This compound was prepared as described in EXAMPLE 1E, substituting EXAMPLE 286A for phenyl guanidine.

EXAMPLE 286C

This compound was prepared as described in EXAMPLE 1F, substituting EXAMPLE 286B for EXAMPLE 1E.

EXAMPLE 286D

N-(3-(5-(2-((3-(2-oxopyrrolidin-1-yl)phenyl)amino)pyrimidin-4-yl)imidazo[2,1-b][1,3]thiazol-6-yl)phenyl)-2-phenylacetamide This compound was prepared as described in EXAMPLE 36D, substituting EXAMPLE 286C for EXAMPLE 36C. MS (ESI), m/e 586.2 (M+H)$^+$; $^1$H-NMR (300 MHz, DMSO-d$_6$) □ ppm 10.30 (s, 1H), 9.76 (s, 1H), 8.86 (s, 1H), 8.27 (d, 1H), 8.04 (s, 1H), 7.88 (s, 1H), 7.71 (d, 1H), 7.58 (d, 1H), 7.48 (d, 1H), 7.41 (t, 1H), 7.21-7.36 (m, 8H), 6.61 (d, 1H), 3.82 (t, 2H), 3.65 (s, 2H), 2.50 (m, 2H), 2.06 (p, 2H).

EXAMPLE 287

2-(2-chlorophenyl)-N-(3-(5-(2-((3-(2-oxopyrrolidin-1-yl)phenyl)amino)pyrimidin-4-yl)imidazo[2,1-b][1,3]thiazol-6-yl)phenyl)acetamide This compound was prepared as described in EXAMPLE 205, substituting EXAMPLE 286C for EXAMPLE 204C. MS (ESI), m/e 620.2 (M+H)$^+$; (ESI) m/e 617.8 (M−H)$^-$; $^1$H-NMR (300 MHz, DMSO-d$_6$) □ ppm 10.36 (s, 1 H), 9.77 (s, 1H), 8.86 (s, 1 H), 8.27 (d, 1 H), 8.04 (s, 1 H), 7.88 (s, 1 H), 7.71 (d, 1 H), 7.58 (d, 1 H), 7.49 (d, 1 H), 7.40-7.44 (m, 3 H), 7.25-7.32 (m, 5 H), 6.61 (d, 1 H), 3.85 (s, 2 H), 3.82 (t, 2 H), 2.50 (m, 2 H), 2.07 (p, 2 H).

EXAMPLE 288

N-(3-(5-(2-((3-(2-oxopyrrolidin-1-yl)phenyl)amino)pyrimidin-4-yl)imidazo[2,1-b][1,3]thiazol-6-yl)phenyl)benzamide This compound was prepared as described in EXAMPLE 36D, substituting EXAMPLE 286C for EXAMPLE 36C and benzoyl chloride for phenylacetyl chloride. MS (ESI), m/e 572.2 (M+H)$^+$; (ESI), m/e 570.0 (M−H)$^-$; $^1$H-NMR (300 MHz, DMSO-d$_6$) □ ppm 10.38 (s, 1H), 9.78 (s, 1H), 8.89 (s, 1 H), 8.29 (d, 1 H), 8.09 (s, 1 H), 8.05 (s, 1 H), 7.97 (d, 1 H), 7.92 (d, 2H), 7.60-7.61 (m, 2 H), 7.51-7.55 (m, 4 H), 7.48 (d, 1 H), 7.27-7.39 (m, 2 H), 6.66 (d, 1 H), 3.83 (t, 2 H), 2.50 (m, 2 H), 2.07 (p, 2 H).

EXAMPLE 289

2-chloro-N-(3-(5-(2-((3-(2-oxopyrrolidin-1-yl)phenyl)amino)pyrimidin-4-yl)imidazo[2,1-b][1,3]thiazol-6-yl)phenyl)benzamide This compound was prepared as described in EXAMPLE 36D, substituting EXAMPLE 286C for EXAMPLE 36C and 2-chloro-benzoyl chloride for phenylacetyl chloride. MS (ESI), m/e 606.1 (M+H)+; (ESI), m/e 603.9 (M−H)−; 1H-NMR (300 MHz, DMSO-d6) ☐ ppm 10.63 (s, 1H), 9.77 (s, 1H), 8.86 (s, 1 H), 8.29 (d, 1 H), 8.04 (s, 1 H), 8.02 (s, 1 H), 7.82 (d, 1 H), 7.58-7.61 (m, 3 H), 7.47-7.53 (m, 4 H), 7.46 (d, 1 H), 7.27-7.38 (m, 2 H), 6.65 (d, 1 H), 3.83 (t, 2 H), 2.50 (m, 2 H), 2.07 (p, 2 H).

EXAMPLE 290

2,6-difluoro-N-(3-(5-(2-((3-(2-oxopyrrolidin-1-yl)phenyl)amino)pyrimidin-4-yl)imidazo[2,1-b][1,3]thiazol-6-yl)phenyl)benzamide This compound was prepared as described in EXAMPLE 36D, substituting EXAMPLE 286C for EXAMPLE 36C and 2,6-difluoro-benzoyl chloride for phenylacetyl chloride. MS (ESI), m/e 608.1 (M+H)+; (ESI), m/e 606.0 (M−H)−; 1H-NMR (300 MHz, DMSO-d6) ☐ ppm 10.93 (s, 1 H), 9.77 (s, 1 H), 8.86 (s, 1 H), 8.29 (d, 1 H), 8.04 (s, 1 H), 7.99 (s, 1 H), 7.79 (d, 1 H), 7.49-7.58 (m, 2 H), 7.47-7.49 (m, 2 H), 7.30 (d, 1 H), 7.24-7.30 (m, 4 H), 6.65 (d, 1 H), 3.82 (t, 2 H), 2.50 (m, 2 H), 2.07 (p, 2 H).

EXAMPLE 291

2-(2-chlorophenyl)-N-(3-(5-(2-((3-morpholin-4-ylphenyl)amino)pyrimidin-4-yl)imidazo[2,1-b][1,3]thiazol-6-yl)phenyl)acetamide A 20 ml vial was charged with EXAMPLE 12E (60 mg), 2-(3-chlorophenyl)acetic acid (32.7 mg), 1-ethyl-3-(3-(dimethylamino)propyl)-carbodiimide hydrochloride (36.7 mg) and dichloromethane (5 ml) under argon. The vial sealed and stirred 18 hours. The mixture was concentrated and the residue was purified by reverse phase preparative HPLC with an acetonitrile (A)-0.1% trifluoroacetic acid in water (B) gradient to give the title compound. MS (ESI(+)) m/e 622 (M+H)+, (ESI(−)) m/e 620 (M−H)−; 1H-NMR (300 MHz, DMSO-d6) ☐ 10.33 (s, 1H), 9.57 (s, 1H), 8.81 (m, 1H), 8.26 (d, 1H), 7.88 (m, 1H), 7.70 (m, 1H), 7.49 (d, 1H), 7.46-7.14 (m, 9H), 6.62 (m, 1H), 6.60 (d, 1H), 3.85 (s, 2H), 3.74 (m, 4H), 3.09 (m, 4H).

EXAMPLE 292

N-(3-(5-(2-((3-morpholin-4-ylphenyl)amino)pyrimidin-4-yl)imidazo[2,1-b][1,3]thiazol-6-yl)phenyl)benzamide The title compound was prepared as described in EXAMPLE 3D, substituting EXAMPLE 12E for EXAMPLE 3C and benzoyl chloride for 2,6-difluorobenzoyl chloride. MS (ESI(+)) m/e 574 (M+H)+, (ESI(−)) m/e 572 (M−H)−; 1H-NMR (300 MHz, DMSO-d6) ☐ 10.36 (s, 1H), 9.57 (s, 1H), 8.83 (m, 1H), 8.28 (d, 1H), 8.10 (m, 1H), 7.96 (m, 1H), 7.91 (m, 2H), 7.62-7.44 (m, 5H), 7.36 (m, 2H), 7.24 (m, 1H), 7.17 (t, 1H), 6.64 (d, 1H), 6.61 (m, 1H), 3.74 (m, 4H), 3.09 (m, 4H).

EXAMPLE 293

2,6-difluoro-N-(3-(5-(2-((3-morpholin-4-ylphenyl)amino)pyrimidin-4-yl)imidazo[2,1-b][1,3]thiazol-6-yl)phenyl)benzamide The title compound was prepared as described in EXAMPLE 3D substituting EXAMPLE 12E for EXAMPLE 3C. MS (ESI(+)) m/e 610 (M+H)+, (ESI(−)) m/e 608 (M−H)−; 1H-NMR (300 MHz, DMSO-d6) ☐ 10.90 (s, 1H), 9.56 (s, 1H), 8.81 (m, 1H), 8.28 (d, 1H), 7.99 (m, 1H), 7.78 (m, 1H), 7.60 (m, 1H), 7.48 (m, 2H), 7.38 (m, 2H), 7.30-7.03 (m, 4H), 6.63 (d, 1H), 6.62 (m, 1H), 3.74 (m, 4H), 3.08 (m, 4H).

EXAMPLE 294

N-(2-chlorophenyl)-N'-(3-(5-(2-((3-morpholin-4-ylphenyl)amino)pyrimidin-4-yl)imidazo[2,1-b][1,3]thiazol-6-yl)phenyl)urea A 20 ml vial was charged with EXAMPLE 12E (60 mg), tetrahydrofuran (5 ml) and 1-chloro-2-isocyanatobenzene (0.015 ml) under argon. The vial was sealed and stirred 18 hours. The mixture was concentrated and the residue was purified by reverse phase preparative HPLC with an acetonitrile (A)-0.1% trifluoroacetic acid in water (B) gradient to give the title compound as a trifluoracetic acid salt. MS (ESI (+)) m/e 623 (M+H)+, (ESI(−)) m/e 621 (M−H)−; 1H-NMR (300 MHz, DMSO-d6) ☐ 9.59 (s, 1H), 9.55 (s, 1H), 8.83 (m, 1H), 8.33 (m, 2H), 8.15 (dd, 1H), 7.78 (m, 1H), 7.56-7.23 (m, 8H), 7.17 (t, 1H), 7.03 (dt, 1H), 6.62 (m, 2H), 3.74 (m, 4H), 3.09 (m, 4H).

EXAMPLE 295

N-(3-(5-(2-((3-(2-pyrrolidin-1-ylethoxy)phenyl)amino)pyrimidin-4-yl)imidazo[2,1-b][1,3]thiazol-6-yl)phenyl)benzamide The title compound was prepared as described in EXAMPLE 12, substituting 3-(2-(pyrrolidin-1-yl)ethoxy)aniline for 3-morpholinoaniline and benzoyl chloride for phenylacetyl chloride. MS (ESI(+)) m/e 602.2 (M+H)+; 1H NMR (300 MHz, DMSO-d6) ☐ ppm 10.37 (s, 1 H); 9.75 (s, 1 H); 9.64 (bs, 1 H); 8.88 (d, 1 H); 8.31 (d, 1 H); 8.12 (bs, 1 H); 7.92-8.00 (m, 2 H); 7.89 (d, 1 H); 7.52-7.70 (m, 5 H); 7.47 (t, 1 H); 7.35 (d, 1 H); 7.22-7.30 (m, 2 H); 6.68 (d, 1 H); 6.58-6.66 (m, 1 H); 4.22-4.35 (m, 2 H); 3.01-3.23 (m, 2 H); 2.45-2.56 (m, 4 H); 1.79-2.08 (m, 4 H).

EXAMPLE 296

2-phenyl-N-(3-(5-(2-((3-(2-pyrrolidin-1-ylethoxy)phenyl)amino)pyrimidin-4-yl)imidazo[2,1-b][1,3]thiazol-6-yl)phenyl)acetamide The title compound was prepared as described in EXAMPLE 12, substituting 3-(2-(pyrrolidin-1-yl)ethoxy)aniline for 3-morpholinoaniline. MS (ESI(+)) m/e 616.3 (M+H)+; 1H NMR (300 MHz, DMSO-d6) ☐ ppm 10.27 (s, 1 H); 9.65 (s, 1 H); 8.83 (d, 1 H); 8.28 (d, 1 H); 7.88 (bs, 1 H); 7.72 (d, 1 H); 7.50 (d, 1 H); 7.45-7.48 (m, 1 H); 7.40 (t, 1 H); 7.15-7.34 (m, 8 H); 6.60 (d, 1 H); 6.59 (d, 1 H); 4.04 (t, 2 H); 3.64 (s, 2 H); 2.77 (t, 2 H); 2.43-2.55 (m, 4H); 1.61-1.75 (m, 4 H).

EXAMPLE 297

2,6-difluoro-N-(3-(5-(2-((3-(3-morpholin-4-ylpropoxy)phenyl)amino)pyrimidin-4-yl)imidazo[2,1-b][1,3]thiazol-6-yl)phenyl)benzamide

EXAMPLE 297A

To a 250 mL round bottom flask was charged 3-nitrophenol (2.78 g), 3-bromopropan-1-ol (3.33 g), and polymer bound triphenylphosphine (Fluka, 3 mmol/g, 1.5 eq, 10 g, 30 mmol) and tetrahydrofuran (75 mL). The resulting mixture was cooled to 0° C. and diisopropyl azodicarboxylate (4.85 g) was added dropwise over 10 minutes The mixture was allowed to stir at room temperature for 14 hours. Additional diisopropyl azodicarboxylate (776 uL) was added and the mixture was stirred for 24 hours longer. The reaction was filtered and the solids were washed with ether. The filtrate was concentrated. The concentrate was dissolved in ethyl acetate, washed with brine, dried over $Na_2SO_4$, filtered, and concentrated. The residue was purified by flash chromatography on silica gel (hexanes:ethyl acetate) to afford the title compound.

EXAMPLE 297B

In a 100 mL round bottom flask, a solution of EXAMPLE 297A (1.33 g) in acetonitrile (18 mL) was treated with morpholine (0.891 g) and potassium carbonate (1.767 g). The resulting mixture was stirred at room temperature for 5 hours. The mixture was treated with saturated aqueous NaCl (75 mL) and then extracted with ethyl acetate (2×100 mL). The combined organic layers were dried over $Na_2SO_4$ and concentrated. The concentrate was purified by flash chromatography on silica gel ($CH_2Cl_2$:methanol) to afford the title compound. MS (ESI(+)) m/e 267.1 $(M+H)^+$.

EXAMPLE 297C

To a 100 mL round bottom flask was charged EXAMPLE 297B (1.28 g) and ethanol (23 mL). The suspension was treated with iron (1.61 g) followed by a solution of ammonium chloride (0.193 g) in water (4.5 mL). The resulting mixture was heated at 90° C. with vigorous stirring for 2 hours. The mixture was cooled to room temperature and the liquid supernatant was decanted into ethyl acetate (100 mL) and was washed with brine (40 mL). The organic layer was dried over $Na_2SO_4$, filtered, and concentrated to afford the title compound. MS (ESI(+)) m/e 236.91 $(M+H)^+$.

EXAMPLE 297D

A suspension of EXAMPLE 12C (275 mg) and EXAMPLE 297C (182 mg) in N-methyl-2-pyrrolidinone (4 mL) was treated with concentrated HCl (0.256 mL) and the mixture was heated in a in a Biotage Initiator 2 monomode microwave reactor at 150° C. for 60 minutes. The mixture was cooled to ambient temperature, and poured into water (40 mL). Saturated aqueous sodium bicarbonate (15 mL) was added and the resulting suspension filtered. The collected solids were washed with water and air dried on the filter under vacuum. The crude solids were purified by flash chromatography on silica gel ($CH_2Cl_2$:methanol) to afford the title compound. MS (ESI(+)) m/e 558.2 $(M+H)^+$.

EXAMPLE 297E

To a 50 mL round bottom flask was charged EXAMPLE 297D (0.520 g) and ethanol (16 mL). The suspension was treated with iron (0.469 g) followed by a solution of ammonium chloride (0.050 g) in water (4 mL). The resulting mixture was heated at 90° C. with vigorous stirring for 1 hour. The mixture was cooled to room temperature and filtered. The filtrate was diluted with 5% methanol/$CH_2Cl_2$ (90 mL) and washed with aqueous sodium bicarbonate (20 mL) followed by brine (20 mL). The organic layer was dried over $Na_2SO_4$, filtered and concentrated. The concentrate was purified by flash chromatography on silica gel ($CH_2Cl_2$:methanol) to afford the title compound. MS (ESI(+)) m/e 528.2 $(M+H)^+$.

EXAMPLE 297F

To a 4 mL vial was charged EXAMPLE 297E (65 mg) and tetrahydrofuran (1 mL). The resulting solution was treated with 2,6-difluorobenzoyl chloride (22.4 mg) to give a mixture which was stirred at room temperature for 1 hour. The mixture was treated with 70 mL 10% methanol/$CH_2Cl_2$ and the resulting solution was washed with saturated aqueous sodium bicarbonate (30 mL) and brine (30 mL). The organic layer was dried over $Na_2SO_4$, filtered, and concentrated. The concentrate was purified by flash chromatography on silica gel ($CH_2Cl_2$:methanol) to afford the title compound. MS (ESI(+)) m/e 668.2 $(M+H)^+$; $^1H$ NMR (300 MHz, DMSO-$D_6$) □ ppm 10.90 (s, 1 H); 9.66 (s, 1 H); 8.83 (d, 1 H); 8.31 (d, 1 H); 7.99 (bs, 1 H); 7.78 (d, 1 H); 7.54-7.67 (m, 1 H); 7.37-7.53 (m, 4 H); 7.16-7.32 (m, 4 H); 6.65 (d, 1 H); 6.56 (d, 1 H); 3.89-4.10 (m, 2 H); 3.49-3.64 (m, 4 H); 2.31-2.44 (m, 6 H); 1.76-1.98 (m, 2 H).

EXAMPLE 298

N-(2-chlorophenyl)-N'-(3-(5-(2-((3-(3-morpholin-4-ylpropoxy)phenyl)amino)pyrimidin-4-yl)imidazo[2,1-b][1,3]thiazol-6-yl)phenyl)urea To a 4 mL vial was charged EXAMPLE 297E (65 mg) and tetrahydrofuran (1 mL). The resulting solution was treated with 1-chloro-2-isocyanatobenzene (19.86 mg). The mixture was stirred at room temperature for 1 hour, 70 mL 15% methanol/$CH_2Cl_2$ was added, and the resulting solution was washed with saturated aqueous sodium bicarbonate (30 mL) and brine (30 mL). The organic layer was dried over $Na_2SO_4$, filtered, and concentrated. The residue was triturated with ether (4 mL), filtered, and dried under vacuum to afford the title compound. MS (ESI(+)) m/e 681.2 $(M+H)^+$; $^1H$ NMR (300 MHz, DMSO-$D_6$) □ ppm 9.67 (s, 1 H); 9.57 (s, 1 H); 8.85 (d, 1 H); 8.28-8.39 (m, 2 H); 8.14 (d, 1 H); 7.77 (bs, 1 H); 7.56-7.52 (m, 1 H); 7.51 (d, 1 H); 7.37-7.49 (m, 3 H); 7.14-7.35 (m, 4 H); 6.94-7.09 (m, 1 H); 6.65 (d, 1 H); 6.54-6.58 (m, 1 H); 3.98 (t, 2 H); 3.51-3.61 (m, 4 H); 2.30-2.45 (m, 6 H); 1.83-1.91 (m, 2 H).

EXAMPLE 299

2-(2-chlorophenyl)-N-(3-(5-(2-((3-(3-morpholin-4-ylpropoxy)phenyl)amino)pyrimidin-4-yl)imidazo[2,1-b][1,3]thiazol-6-yl)phenyl)acetamide To a 4 mL vial was charged EXAMPLE 297E (65 mg) and N-methyl-2-pyrrolidinone (1.2 mL). 2-(2-chlorophenyl)acetic acid (24.17 mg), 1 hydroxybenzotriazole hydrate (18.87 mg) and (polystyryl)carbodiimide resin (Argonaut Technologies, 1.42 mmol/g, 0.26 g, 0.370 mmol) were added and the resulting suspension was stirred at room temperature overnight. The mixture was filtered and the collected solids were washed with ethyl acetate. The filtrate was diluted with ethyl acetate (80 mL) and washed with saturated aqueous $Na_2CO_3$ (25 mL), water (3×25 mL) and brine (25 mL). The organic layer was dried over $Na_2SO_4$, filtered, and concentrated. The concentrate was purified by flash chromatography on silica gel ($CH_2Cl_2$:methanol) to afford the title compound. MS (ESI(+)) m/e 680.2 (M+H)$^+$; $^1$H NMR (300 MHz, DMSO-$d_6$) □ ppm 10.34 (s, 1 H); 9.66 (s, 1 H); 8.84 (d, 1 H); 8.29 (d, 1 H); 7.88 (bs, 1 H); 7.70-7.73 (m, 1 H); 7.50 (d, 1 H); 7.38-7.46 (m, 4 H); 7.26-7.34 (m, 4 H); 7.19 (t, 1 H); 6.62 (d, 1 H); 6.51-6.58 (m, 1 H); 3.98 (t, 2 H); 3.85 (s, 2 H); 3.49-3.63 (m, 4 H); 2.31-2.45 (m, 6 H); 1.71-2.04 (m, 2 H).

EXAMPLE 300

3-((4-(6-(3-(benzoylamino)phenyl)imidazo[2,1-b][1,3]thiazol-5-yl)pyrimidin-2-yl)amino)-N-(2-(dimethylamino)ethyl)benzamide

EXAMPLE 300A

The title compound was prepared as described in EXAMPLE 3B, substituting EXAMPLE 52A for EXAMPLE 3A.

EXAMPLE 300B

The title compound was prepared as described in EXAMPLE 62, substituting EXAMPLE 300A for EXAMPLE 52.

EXAMPLE 300C

To EXAMPLE 300B (0.534 g) in N,N-dimethylacetamide (11.6 mL) was added PS-carbodiimide resin (2.462 g, 3.50 mmol, 1.42 mmol/g, Argonaut Technologies) and 1-hydroxybenzotriazole hydrate (0.178 g) followed by $N^1,N^1$-dimethylethane-1,2-diamine (0.140 ml). The mixture was stirred at room temperature for 2 days, filtered, and the resin was rinsed with ethyl acetate. The filtrate was washed with water, saturated aqueous sodium bicarbonate, and brine. The organic layer was dried over $MgSO_4$, filtered and concentrated to afford the title compound.

EXAMPLE 300D

The title compound was prepared as described in EXAMPLE 3C, substituting EXAMPLE 300C for EXAMPLE 3B.

EXAMPLE 300E

The title compound was prepared as described in EXAMPLE 3D, substituting EXAMPLE 300D for EXAMPLE 3C, and benzoyl chloride for 2,6-difluorobenzamide. MS (ESI) m/e 603 (M+H)$^+$; $^1$H NMR (300 MHz, DMSO-$d_6$) □ 10.38 (s, 1H), 9.87 (s, 1H), 9.36 (s, 1H), 8.89 (d, 1H), 8.57 (m, 1H), 8.31 (d, 1H), 8.22 (m, 1H), 8.12 (m, 1H), 7.96 (m, 3H), 7.90 (m, 1H), 7.52 (m, 6H), 7.35 (m, 1H), 6.69 (d, 1H), 3.55 (m, 2H), 3.09 (m, 2H).

EXAMPLE 301

N-(3-(5-(2-((3-(((2-(dimethylamino)ethyl)amino)carbonyl)phenyl)amino)pyrimidin-4-yl)imidazo[2,1-b][1,3]thiazol-6-yl)phenyl)-2,6-difluorobenzamide The title compound was prepared as described in EXAMPLE 3D, substituting EXAMPLE 300E for EXAMPLE 3C. MS (ESI) m/e 639 (M+H)$^+$; $^1$H NMR (300 MHz, DMSO-$d_6$) δ 10.92 (s, 1H), 9.86 (s, 1H), 9.30 (s, 1H), 8.86 (d, 1H), 8.49 (m, 1H), 8.31 (d, 1H), 8.19 (m, 1H), 8.01 (m, 1H), 7.94 (m, 1H), 7.76 (m, 1H), 7.60 (m, 1H), 7.45 (m, 5H), 7.26 (m, 2H), 6.67 (d, 1H), 3.50 (m, 2H), 3.11 (m, 2H).

EXAMPLE 302

3-((4-(6-(3-((anilinocarbonyl)amino)phenyl)imidazo[2,1-b][1,3]thiazol-5-yl)pyrimidin-2-yl)amino)-N-(2-(dimethylamino)ethyl)benzamide The title compound was prepared as described in EXAMPLE 13, substituting EXAMPLE 300E for EXAMPLE 3C. MS (ESI) m/e 618 (M+H)$^+$; $^1$H NMR (300 MHz, DMSO-$d_6$) δ 9.83 (s, 1H), 8.90 (m, 1H), 8.88 (d, 1H), 8.29 (m, 2H), 8.13 (m, 1H), 7.94 (m, 1H), 7.74 (m, 1H), 7.54 (m, 1H), 7.44 (m, 5H), 7.24 (m, 3H), 6.66 (d, 1H), 3.36 (m, 2H), 2.39 (m, 2H), 2.17 (s, 6H).

EXAMPLE 303

3-((4-(6-(3-((((2-chlorophenyl)amino)carbonyl)amino)phenyl)imidazo[2,1-b][1,3]thiazol-5-yl)pyrimidin-2-yl)amino)-N-(2-(dimethylamino)ethyl)benzamide The title compound was prepared as described in EXAMPLE 13, substituting EXAMPLE 300E for EXAMPLE 3C, and 2-chlorophenylisocyanate for phenylisocyanate. MS (ESI) m/e 652 (M+H)$^+$; $^1$H NMR (300 MHz, DMSO-$d_6$) δ 9.83 (s, 1H), 9.55 (s, 1H), 8.89 (m, 1H), 8.28 (m, 3H), 8.13 (m, 2H), 7.94 (m, 1H), 7.77 (m, 1H), 7.55 (m, 1H), 7.44 (m, 5H), 7.27 (m, 3H), 6.66 (m, 1H), 3.36 (m, 2H), 2.39 (m, 2H), 2.17 (s, 6H).

EXAMPLE 304

N-(2-chloro-5-(5-(2-((3-morpholin-4-ylphenyl)amino)pyrimidin-4-yl)imidazo[2,1-b][1,3]thiazol-6-yl)phenyl)benzamide

EXAMPLE 304A

The title compound was prepared as described in EXAMPLE 1, substituting 2-bromo-1-(4-chloro-3-nitrophenyl)ethan-1 one for 2-bromo-1-(3-nitrophenyl)ethone in EXAMPLE 1A, and EXAMPLE 338A for phenylguanidine in EXAMPLE 1E.

EXAMPLE 304B

The title compound was prepared as described in EXAMPLE 1G, substituting benzoyl chloride for 2-chlorobenzoyl chloride and EXAMPLE 304A for EXAMPLE 1F. MS (ESI(+)) m/e 608 (M+H)$^+$; $^1$H-NMR (300 MHz, DMSO-$d_6$) □ 10.14 (s, 1H); 9.60 (s, 1H); 8.81 (d, 1H); 8.33 (d, 1H); 8.00 (d, 2H); 7.91 (d, 1H); 7.68-7.52 (m, 6H); 7.36 (s, 1H); 7.25-7.14 (m, 2H); 6.72 (d, 1H); 6.63 (d, 1H); 3.74 (m, 4H); 3.09 (m, 4H).

EXAMPLE 305

N-(2-(dimethylamino)-5-(5-(2-((3-morpholin-4-ylphenyl)amino)pyrimidin-4-yl)imidazo[2,1-b][1,3]thiazol-6-yl)phenyl)benzamide

EXAMPLE 305A

The title compound was isolated as a side product in EXAMPLE 304A. EXAMPLE 305B

The title compound was prepared as described in EXAMPLE 1G, substituting benzoyl chloride for 2-chlorobenzoyl chloride and EXAMPLE 305A for EXAMPLE 1F. MS (ESI(+)) m/e 617 (M+H)+; ¹H-NMR (300 MHz, DMSO-d₆) ☐ 9.68 (s, 1H); 9.58 (s, 1H); 8.84 (d, 1H); 8.29 (d, 1H); 8.16 (s, 1H); 7.98 (d, 2H); 7.64-7.52 (m, 3H); 7.49 (d, 1H); 7.46 (d, 1H); 7.35 (m, 2H); 7.25 (m, 1H); 7.17 (t, 1H); 6.77 (d, 1H); 6.63 (d, 1H); 3.74 (m, 4H); 3.09 (m, 4H); 2.80 (s, 6H).

EXAMPLE 306

N-(2-chloro-5-(5-(2-((3-morpholin-4-ylphenyl) amino)pyrimidin-4-yl)imidazo[2,1-b][1,3]thiazol-6-yl)phenyl)-2-phenylacetamide The title compound was prepared as described in EXAMPLE 1G, substituting phenylacetyl chloride for 2-chlorobenzoyl chloride and EXAMPLE 304A for EXAMPLE 1F. MS (ESI(+)) m/e 622 (M+H)+; ¹H-NMR (300 MHz, DMSO-d₆) ☐ 9.77 (s, 1H); 9.60 (s, 1H); 8.78 (d, 1H); 8.27 (d, 1H); 8.01 (s, 1H); 7.59 (d, 1H); 7.50 (d, 1H); 7.44 (d, 1H); 7.37-7.30 (m, 5H); 7.27-7.14 (m, 3H); 6.65 (d, 1H); 6.63 (d, 1H); 3.75 (s, 2H); 3.74 (m, 4H); 3.09 (m, 4H).

EXAMPLE 307

N-(2-(dimethylamino)-5-(5-(2-((3-morpholin-4-ylphenyl)amino)pyrimidin-4-yl)imidazo[2,1-b][1,3]thiazol-6-yl)phenyl)-2-phenylacetamide The title compound was prepared as described in EXAMPLE 1G, substituting phenylacetyl chloride for 2-chlorobenzoyl chloride and EXAMPLE 305A for EXAMPLE 1F. MS (ESI(+)) m/e 631 (M+H)+; ¹H-NMR (300 MHz, DMSO-d₆) ☐ 9.56 (s, 1H); 9.16 (s, 1H); 8.80 (d, 1H); 8.24 (d, 1H); 8.16 (s, 1H); 7.47 (d, 1H); 7.37-7.16 (m, 10H); 6.68 (d, 1H); 6.62 (d, 1H); 3.77 (s, 2H); 3.74 (m, 4H); 3.09 (m, 4H); 2.59 (s, 6H).

EXAMPLE 308

N-(2-ethoxy-5-(5-(2-((3-morpholin-4-ylphenyl) amino)pyrimidin-4-yl)imidazo[2,1-b][1,3]thiazol-6-yl)phenyl)-2-phenylacetamide

EXAMPLE 308A

The title compound was isolated as side product in EXAMPLE 304A.

EXAMPLE 308B

The title compound was prepared as described in EXAMPLE 1G, substituting phenylacetyl chloride for 2-chlorobenzoyl chloride and EXAMPLE 308A for EXAMPLE 1F. MS (ESI(+)) m/e 632 (M+H)+; ¹H-NMR (300 MHz, DMSO-d₆) ☐ 9.56 (s, 1H); 9.00 (s, 1H); 8.83 (d, 1H); 8.22 (m, 2H); 7.47 (d, 1H); 7.37-7.09 (m, 10H); 6.61 (m, 2H); 4.12 (q, 2H); 3.77 (s, 2H); 3.74 (m, 4H); 3.09 (m, 4H); 1.34 (t, 3H).

EXAMPLE 309

N-(3-(5-(2-((4-(4-(3-hydroxypropyl)piperazin-1-yl) phenyl)amino)pyrimidin-4-yl)imidazo[2,1-b][1,3] thiazol-6-yl)phenyl)benzamide The title compound was prepared as described in EXAMPLE 12, substituting 3-(4-(4-aminophenyl)-piperazin-1-yl)-propan-1-ol (prepared as described in Loewe et al. Arzeneim. Forsch. 1966, 16, 1306) for 3-morpholinoaniline in EXAMPLE 12D and benzoyl chloride for phenylacetyl chloride in EXAMPLE 12F. MS (ESI(+)) m/e 631 (M+H)+; ¹H-NMR (300 MHz, DMSO-d₆) ☐ 10.37 (s, 1H); 9.53 (s, 1H); 9.37 (bs, 1H); 8.80 (bs, 1H); 8.24 (d, 1H); 8.11 (s, 1H); 7.97-7.88 (m, 3H); 7.61-7.44 (m, 6H); 7.34 (d, 1H); 7.00 (d, 2H); 6.61 (d, 1H); 3.76 (d, 2H); 3.61 (d, 2H); 3.51 (t, 2H); 3.22 (m, 4H); 2.93 (t, 2H); 1.86 (m, 2H).

EXAMPLE 310

N-(3-(5-(2-((4-(4-(3-hydroxypropyl)piperazin-1-yl) phenyl)amino)pyrimidin-4-yl)imidazo[2,1-b][1,3] thiazol-6-yl)phenyl)-2-phenylacetamide The title compound was prepared as described in EXAMPLE 12, substituting 3-(4-(4-aminophenyl)-piperazin-1-yl)-propan-1-ol (prepared as described in Loewe et al. Arzeneim. Forsch. 1966, 16, 1306) for 3-morpholinoaniline in EXAMPLE 12D. MS (ESI(+)) m/e 645 (M+H)+; ¹H-NMR (300 MHz, DMSO-d₆) ☐ 10.29 (s, 1H); 9.52 (s, 1H); 9.32 (bs, 1H); 8.77 (bs, 1H); 8.21 (d, 1H); 7.89 (s, 1H); 7.69 (d, 1H); 7.60 (d, 2H); 7.48 (d, 1H); 7.40 (t, 1H); 7.34-7.24 (m, 5H); 7.00 (d, 2H); 6.55 (d, 1H); 3.78 (d, 2H); 3.65 (d, 2H); 3.51 (t, 2H); 3.22 (m, 4H); 2.93 (t, 2H); 1.86 (m, 2H).

EXAMPLE 311

3-((4-(6-(3-(((2-chlorophenyl)acetyl)amino)phenyl) imidazo[2,1-b][1,3]thiazol-5-yl)pyrimidin-2-yl) amino)-N-(2-(dimethylamino)ethyl)benzamide To a suspension of EXAMPLE 300E (0.0475 g) in N-methylpyrrolidone (1.0 ml) was added 2-(2-chlorophenyl)acetic acid (0.020 g), 1-hydroxybenzotriazole hydrate (0.015 g) and (polystyryl)carbodiimide resin (Argonaut Technologies, 1.42 mmol/g, 0.201 g, 0.286 mmol). The mixture was stirred at room temperature 18 hours, filtered, and the resin was rinsed with ethyl acetate. The filtrate was washed with brine, and adsorbed onto silica gel. The material was purified by flash chromatography using a Flashmaster Solo system (CH₂Cl₂: methanol:NH₄OH) to afford the title compound. MS (ESI) m/e 651 (M+H)+; ¹H NMR (300 MHz, DMSO-d₆) δ 10.34 (s, 1H), 9.82 (s, 1H), 8.85 (m, 1H), 8.28 (m, 2H), 8.13 (m, 2H), 7.93 (m, 1H), 7.88 (m, 1H), 7.70 (m, 1H), 7.44 (m, 6H), 7.30 (m, 3H), 6.63 (m, 1H), 3.85 (s, 2H), 3.36 (m, 2H), 2.40 (m, 2H), 2.18 (s, 6H).

EXAMPLE 312

N-(2-ethoxy-5-(5-(2-((3-morpholin-4-ylphenyl) amino)pyrimidin-4-yl)imidazo[2,1-b][1,3]thiazol-6-yl)phenyl)benzamide The title compound was prepared as described in EXAMPLE 1G, substituting benzoyl chloride for 2-chlorobenzoyl chloride and EXAMPLE 308A for EXAMPLE 1F. (ESI(+)) m/e 618 (M+H)+; ¹H-NMR (300 MHz, DMSO-d₆) ☐ 9.54 (s, 1H); 9.44 (s, 1H); 8.86 (d, 1H); 8.27 (d, 1H); 8.16 (d, 1H); 7.95 (d, 2H); 7.60-7.52 (m, 3H); 7.48 (d, 1H); 7.42 (d, 1H); 7.36 (s, 1H); 7.25-7.14 (m, 3H); 6.71 (d, 1H); 6.61 (d, 1H); 4.20 (q, 2H); 3.74 (m, 4H); 3.09 (m, 4H); 1.42 (t, 3H).

EXAMPLE 313

2,6-difluoro-N-(3-(5-(2-((3-(3-(4-methylpiperazin-1-yl)propoxy)phenyl)amino)pyrimidin-4-yl)imidazo[2,1-b][1,3]thiazol-6-yl)phenyl)benzamide The title compound was prepared as described in EXAMPLE 297D-F, substituting EXAMPLE 154C for EXAMPLE 297C in EXAMPLE 297D. MS (ESI(+)) m/e 681 (M+H)$^+$; (ESI(−)) m/e 679 (M−H)$^−$; $^1$H-NMR (300 MHz, DMSO-d$_6$) □ 10.92 (s, 1H), 9.68 (s, 1H), 8.83 (bs, 1H), 8.31 (d, 1H), 7.99 (s, 1H), 7.79 (dd, 1H), 7.60 (ddd, 1H), 7.51 (d, 1H), 7.48 (t, 1H), 7.45 (s, 1H), 7.40 (d, 1H), 7.23-7.30 (m, 3H), 7.19 (t, 1H), 6.65 (d, 1H), 6.55 (d, 1H), 3.96 (t, 2H), 2.25-2.47 (m, 10H), 2.14 (s, 3H), 1.85 (ddd, 2H).

EXAMPLE 314

N-(2-chlorophenyl)-N'-(3-(5-(2-((3-(3-(4-methylpiperazin-1-yl)propoxy)phenyl)amino)pyrimidin-4-yl)imidazo[2,1-b][1,3]thiazol-6-yl)phenyl)urea The title compound was prepared as described in EXAMPLE 297D-F, substituting EXAMPLE 154C for EXAMPLE 297C and 2-chloro-phenylsocyanate for 2,6-difluorobonzoyl chloride in EXAMPLE 297D. MS (ESI(+)) m/e 694 (M+H)$^+$; (ESI(−)) m/e 692 (M−H)$^−$; $^1$H-NMR (300 MHz, DMSO-d$_6$) □ 9.67 (s, 1H), 9.55 (s, 1H), 8.85 (d, 1H), 8.29-8.34 (m, 2H), 8.15 (dd, 1H), 7.77 (t, 1H), 7.55 (ddd, 1H), 7.51 (d, 1H), 7.43-7.48 (m, 2H), 7.38-7.43 (m, 1H), 7.22-7.33 (m, 3H), 7.19 (t, 1H), 7.03 (td, 1H), 6.65 (d, 1H), 6.55 (ddd, 1H), 4.09 (q, 1H), 3.96 (t, 2H), 2.19-2.46 (m, 8H), 2.13 (s, 3H), 1.85 (dt, 2H).

EXAMPLE 315

2-(2-chlorophenyl)-N-(3-(5-(2-((3-(3-(4-methylpiperazin-1-yl)propoxy)phenyl)amino)pyrimidin-4-yl)imidazo[2,1-b][1,3]thiazol-6-yl)phenyl)acetamide The title compound was prepared as described in EXAMPLE 297D-F, substituting EXAMPLE 154C for EXAMPLE 297C and 2-chlorophenylacetyl chloride for 2,6-difluorobenzoyl chloride in EXAMPLE 297D. MS (ESI(+)) m/e 693 (M+H)$^+$; (ESI(−)) m/e 691 (M−H)$^−$; 1H-NMR (300 MHz, DMSO-d$_6$) □ 10.34 (s, 1H), 9.66 (s, 1H), 8.83 (d, 1H), 8.29 (d, 1H), 7.88 (t, 1H), 7.68-7.74 (m, 1H), 7.50 (d, 1H), 7.38-7.47 (m, 4H), 7.25-7.35 (m, 4H), 7.19 (t, 1H), 6.62 (d, 1H), 6.55 (ddd, 1H), 4.09 (q, 2H), 3.96 (t, 2H), 2.22-2.44 (m, 8H), 2.13 (s, 3H), 1.85 (ddd, 2H).

EXAMPLE 316

N-(3-(5-(2-((3-(4-isopropylpiperazin-1-yl)phenyl)amino)pyrimidin-4-yl)imidazo[2,1-b][1,3]thiazol-6-yl)phenyl)-2-phenylacetamide

EXAMPLE 316A

A 100 ml flask was charged with 1-(3-nitrophenyl)piperazine (1 g), sodium carbonate (1.534 g) and N,N-dimethylformamide (25 ml) under nitrogen. 2-Iodopropane (0.603 ml) was added dropwise and the mixture was heated at 60° C. for 18 hours. The mixture was concentrated and after an aqueous workup and the residue was purified on silica gel with a methanol-methylene chloride gradient to afford the title compound.

EXAMPLE 316B

The title compound was prepared as described in EXAMPLE 3C, substituting EXAMPLE 316A for EXAMPLE 3B.

EXAMPLE 316C

The title compound was prepared as described in EXAMPLE 12D, substituting EXAMPLE 316B for 3-morpholinoaniline.

EXAMPLE 316D

The title compound was prepared as described in EXAMPLE 3C, substituting EXAMPLE 316C for EXAMPLE 3B.

EXAMPLE 316E

N-(3-(5-(2-((3-(4-isopropylpiperazin-1-yl)phenyl)amino)pyrimidin-4-yl)imidazo[2,1-b][1,3]thiazol-6-yl)phenyl)-2-phenylacetamide The title compound was prepared as described in EXAMPLE 3D, substituting EXAMPLE 316D for EXAMPLE 3C and phenylacetyl)-chloride for 2,6-difluorobenzoyl chloride. MS (ESI(+)) m/e 629 (M+H)$^+$, (ESI(−)) m/e 627 (M−H)$^−$; $^1$H-NMR (300 MHz, DMSO-d$_6$) □ 10.29 (s, 1H), 9.62 (s, 1H), 9.29 (br s, 1H), 8.82 (m, 1H), 8.26 (d, 1H), 7.92 (m, 1H), 7.67 (m, 1H), 7.50 (d, 1H), 7.40 (m, 2H), 7.34-7.18 (m, 7H), 6.68 (m, 1H), 6.61 (d, 1H), 3.80 (m, 2H), 3.65 (s, 2H), 3.53 (m, 3H), 3.15 (m, 2H), 2.98 (m, 2H), 1.30 (d, 6H).

EXAMPLE 317

N-(3-(5-(2-((3-(4-isopropylpiperazin-1-yl)phenyl)amino)pyrimidin-4-yl)imidazo[2,1-b][1,3]thiazol-6-yl)phenyl)benzamide The title compound was prepared as described in EXAMPLE 3D, substituting EXAMPLE 316D for EXAMPLE 3C and benzoyl chloride for 2,6-difluorobenzoyl chloride. MS (ESI(+)) m/e 615 (M+H)$^+$, (ESI(−)) m/e 613 (M−H)$^−$; $^1$H-NMR (300 MHz, DMSO-d$_6$) □ 10.38 (s, 1H), 9.64 (s, 1H), 9.28 (br s, 1H), 8.84 (m, 1H), 8.29 (d, 1H), 8.13 (m, 1H), 7.96 (m, 2H), 7.90 (m, 1H), 7.60-7.44 (m, 5H), 7.35 (m, 1H), 7.28 (d, 1H), 7.21 (t, 1H), 6.69 (m, 1H), 6.67 (d, 1H), 3.80 (m, 2H), 3.53 (m, 3H), 3.15 (m, 2H), 2.98 (m, 2H), 1.30 (d, 6H).

EXAMPLE 318

2-(2-chlorophenyl)-N-(3-(5-(2-((3-(4-isopropylpiperazin-1-yl)phenyl)amino)pyrimidin-4-yl)imidazo[2,1-b][1,3]thiazol-6-yl)phenyl)acetamide The title compound was prepared as described in EXAMPLE 291, substituting EXAMPLE 316D for EXAMPLE 12E. MS (ESI(+)) m/e 663 (M+H)$^+$, (ESI(−)) m/e 661 (M−H)$^−$; $^1$H-NMR (300 MHz, DMSO-d$_6$) □ 10.35 (s, 1H), 9.62 (s, 1H), 9.28 (br s, 1H), 8.82 (m, 1H), 8.27 (d, 1H), 7.92 (m, 1H), 7.67 (m, 1H), 7.50 (d, 1H), 7.46-7.39 (m, 4H), 7.34-7.18 (m, 4H), 6.68 (m, 1H), 6.62 (d, 1H), 3.85 (s, 2H), 3.82 (m, 2H), 3.53 (m, 3H), 3.15 (m, 2H), 2.97 (m, 2H), 1.30 (d, 6H).

EXAMPLE 319

2-chloro-N-(3-(5-(2-((3-(4-isopropylpiperazin-1-yl)
phenyl)amino)pyrimidin-4-yl)imidazo[2,1-b][1,3]
thiazol-6-yl)phenyl)benzamide The title compound was prepared as described in EXAMPLE 3D, substituting EXAMPLE 316D for EXAMPLE 3C and 2-chlorobenzoyl chloride for 2,6-difluorobenzoyl chloride. MS (ESI(+)) m/e 649 (M+H)$^+$, (ESI(−)) m/e 647 (M−H)$^-$; $^1$H-NMR (300 MHz, DMSO-d$_6$) □ 10.62 (s, 1H), 9.62 (s, 1H), 9.28 (br s, 1H), 8.82 (m, 1H), 8.29 (d, 1H), 8.06 (m, 1H), 7.78 (m, 1H), 7.61-7.43 (m, 6H), 7.38 (m, 1H), 7.28 (d, 1H), 7.21 (t, 1H), 6.69 (m, 1H), 6.66 (d, 1H), 3.80 (m, 2H), 3.53 (m, 3H), 3.15 (m, 2H), 2.98 (m, 2H), 1.30 (d, 6H).

EXAMPLE 320

2,6-difluoro-N-(3-(5-(2-((3-(4-isopropylpiperazin-1-yl)phenyl)amino)pyrimidin-4-yl)imidazo[2,1-b][1,3]
thiazol-6-yl)phenyl)benzamide The title compound was prepared as described in EXAMPLE 3D, substituting EXAMPLE 316D for EXAMPLE 3C. MS (ESI(+)) m/e 651 (M+H)$^+$, (ESI(−)) m/e 649 (M−H)$^-$; $^1$H-NMR (300 MHz, DMSO-d$_6$) □ 10.92 (s, 1H), 9.63 (s, 1H), 9.27 (br s, 1H), 8.82 (m, 1H), 8.29 (d, 1H), 8.03 (m, 1H), 7.75 (m, 1H), 7.65-7.46 (m, 5H), 7.30-7.19 (m, 3H), 6.69 (m, 1H), 6.66 (d, 1H), 3.80 (m, 2H), 3.53 (m, 3H), 3.15 (m, 2H), 2.97 (m, 2H), 1.30 (d, 6H).

EXAMPLE 321

N-(3-(5-(2-((3-(4-ethylpiperazin-1-yl)phenyl)amino)
pyrimidin-4-yl)imidazo[2,1-b][1,3]thiazol-6-yl)phenyl)-2-phenylacetamide

EXAMPLE 321A

A solution of iodoethane (1.28 g) in N,N-dimethylformamide (5 mL) was added dropwise to a mixture of 1-(3-nitrophenyl)piperazine hydrochloride (1.90 g) and K$_2$CO$_3$ (2.69 g) in N,N-dimethylformamide (40 mL) with stirring. After stirring overnight at room temperature, the mixture was concentrated to dryness and the residue was dissolved in water/CH$_2$Cl$_2$. The layers were separated and the aqueous layer was extracted with CH$_2$Cl$_2$. The combined organic solution was dried (MgSO$_4$), filtered and concentrated. The residue was purified on a silica gel column eluting with 5% methanol in CH$_2$Cl$_2$, to afford the title compound.

EXAMPLE 321B

The title compound was prepared as described in EXAMPLE 1F, substituting EXAMPLE 321B for EXAMPLE 1E.

EXAMPLE 321C

The title compound was prepared as described in EXAMPLE 42A, substituting EXAMPLE 321B for 4-(1H-imidazol-1-yl)aniline.

EXAMPLE 321D

The title compound was prepared as described in EXAMPLE 1E, substituting EXAMPLE 321C for phenyl guanidine.

EXAMPLE 321E

The title compound was prepared as described in EXAMPLE 1F, substituting EXAMPLE for EXAMPLE 1E.

EXAMPLE 321F

N-(3-(5-(2-((3-(4-ethylpiperazin-1-yl)phenyl)amino)
pyrimidin-4-yl)imidazo[2,1-b][1,3]thiazol-6-yl)phenyl)-2-phenylacetamide The title compound was prepared as described in EXAMPLE 36D, substituting EXAMPLE 321F for EXAMPLE 36C. MS (ESI), m/e 615.3 (M+H)$^+$; (ESI), m/e 613.0 (M−H)$^-$; $^1$H-NMR (300 MHz, DMSO-d$_6$) □ ppm 10.31 (s, 1 H), 9.63 (s, 1H), 9.48 (bs, 1 H), 8.82 (s, 1 H), 8.26 (d, 1 H), 7.92 (s, 1 H), 7.78 (d, 1 H), 7.50 (d, 1H), 7.42 (d, 1 H), 7.40 (d, 1 H), 7.20-7.33 (m, 9 H), 6.69 (dd, 1 H), 6.60 (d, 1 H), 3.80 (bd, 2H), 3.65 (s, 2 H), 3.58 (bd, 2 H), 3.18-3.22 (m, 2 H), 3.11 (q, 2 H), 2.94-2.99 (m, 2 H), 1.26 (t, 3 H).

EXAMPLE 322

N-(3-(5-(2-((3-(4-ethylpiperazin-1-yl)phenyl)amino)
pyrimidin-4-yl)imidazo[2,1-b][1,3]thiazol-6-yl)phenyl)benzamide The title compound was prepared as described in EXAMPLE 36D, substituting EXAMPLE 321E for EXAMPLE 36C and benzoyl chloride for phenylacetyl chloride. MS (ESI), m/e 601.3 (M+H)$^+$; (ESI), m/e 599.0 (M−H)$^-$; $^1$H-NMR (300 MHz, DMSO-d$_6$) □ ppm 10.38 (s, 1 H), 10.00 (bs, 1 H), 9.62 (s, 1H), 8.85 (s, 1 H), 8.12 (s, 1 H), 7.97 (d, 2 H), 7.90 (d, 1 H), 7.67-7.72 (m, 1 H), 7.58-7.62 (m, 1 H), 7.52-7.55 (m, 3 H), 7.41-7.50 (m, 2 H), 7.36 (d, 1 H), 7.35 (d, 1 H), 7.28 (t, 1 H), 6.64-6.68 (m, 2 H), 3.78 (m, 2 H), 3.56 (m, 2 H), 3.19 (m, 2 H), 3.03-3.09 (m, 4 H), 1.27 (t, 3 H).

EXAMPLE 323

N-(3-(5-(2-((3-(4-ethylpiperazin-1-yl)phenyl)amino)
pyrimidin-4-yl)imidazo[2,1-b][1,3]thiazol-6-yl)phenyl)-2,6-difluorobenzamide The title compound was prepared as described in EXAMPLE 36D, substituting EXAMPLE 321E for EXAMPLE 36C and 2,6-difluoro-benzoyl chloride for phenylacetyl chloride. MS (ESI), m/e 637.2 (M+H)$^+$; (ESI), m/e 634.9 (M−H)$^-$; $^1$H-NMR (300 MHz, DMSO-d$_6$) □ ppm 10.93 (s, 1 H), 9.64 (s, 1H), 9.46 (bs, 1 H), 8.83 (s, 1 H), 8.29 (d, 1 H), 8.03 (s, 1 H), 7.76 (d, 1 H), 7.58-7.63 (m, 3 H), 7.46-7.52 (m, 3 H), 7.44 (s, 1 H), 7.39 (d, 1 H), 7.19-7.29 (m, 4 H), 6.69 (dd, 1 H), 6.65 (d, 1 H), 3.80 (m, 2 H), 3.60 (m, 2 H), 3.22 (m, 2 H), 3.12 (q, 2 H), 2.97 (m, 2 H), 1.26 (t, 3H).

EXAMPLE 324

2-phenyl-N-(3-(5-(2-(pyridin-4-ylamino)pyrimidin-4-yl)imidazo[2,1-b][1,3]thiazol-6-yl)phenyl)acetamide

EXAMPLE 324A

To a 5 mL microwave mixture vessel was charged 5-(2-chloropyrimidin-4-yl)-6-(3-nitrophenyl)imidazo[2,1-b]thiazole (150 mg), 4-aminopyridine (39.5 mg), palladium(II) acetate (1.88 mg), Xantphos (9,9-dimethyl-9H-xanthene-4,5-diyl)bis(diphenylphosphine) (7.28 mg), cesium carbonate (273 mg) and 1,4-dioxane (2.5 mL). The vessel was sealed and the mixture heated in a in a Biotage Initiator 2 monomode microwave reactor at 160° C. for 1 hour. The mixture was concentrated. The concentrate was sonicated with 30 mL $CH_2Cl_2$/methanol (2:1, v/v) and the suspension was filtered. The filtrate was concentrated and the residue was purified by flash chromatography on silica gel ($CH_2Cl_2$:methanol) to afford the title compound. MS (ESI(+)) m/e 415.9 $(M+H)^+$.

EXAMPLE 324B

The title compound was prepared as described in EXAMPLE 297E, substituting EXAMPLE 324A for EXAMPLE 297D. MS (ESI(+)) m/e 386.0 $(M+H)^+$.

EXAMPLE 324C

To a 4 mL vial was charged EXAMPLE 324B (41 mg) and N-methyl-2-pyrrolidinone (1 mL). The resulting solution was treated with 2-phenylacetyl chloride (16.44 mg) and the mixture was stirred for 40 minutes at room temperature. Two drops of methanol and 0.5 mL of DMSO were added and the resulting solution was purified by preparative HPLC on a Waters Nova-Pakâ HR C18 6 um 60 Å Prep-Pakâ cartridge column (25 mm×100 mm). A gradient of acetonitrile (A) and 0.1% trifluoroacetic acid in water (B) was used, at a flow rate of 40 mL/min (0-0.5 min 10% A, 0.5-7.0 min linear gradient 10-95% A, 7.0-10.0 min 95% A, 10.0-12.0 min linear gradient 95-10% A). to afford the bis-trifluoroacetic acid salt of the title compound. MS (ESI(+)) m/e 504.1 $(M+H)^+$; $^1$H NMR (300 MHz, DMSO-$d_6$) □ ppm 11.30 (s, 1 H); 10.29 (s, 1 H); 8.81 (d, 1 H); 8.58 (d, 2 H); 8.54 (d, 1 H); 8.20 (d, 2 H); 7.95 (bs, 1H); 7.67 (d, 1 H); 7.59 (d, 1 H); 7.42 (t, 1 H); 7.21-7.34 (m, 7 H); 6.98 (d, 1 H); 3.64 (s, 2H).

EXAMPLE 325

N-(3-(5-(2-((4-(4-ethyl-2-oxopiperazin-1-yl)phenyl)amino)pyrimidin-4-yl)imidazo[2,1-b][1,3]thiazol-6-yl)phenyl)-2-phenylacetamide

EXAMPLE 325A

A mixture of 1-iodo-4-nitrobenzene (3.74 g), tert-butyl 3-oxopiperazine-1-carboxylate (3.60 g), $K_3PO_4$ (30 mmole) and N,N'-dimethylethane-1,2-diamine (0.13 g) in anhydrous toluene (100 mL) was purged with argon, and copper (I) iodide (0.14 g) was added. The mixture was stirred under nitrogen at 100° C. for about 72 hours, cooled to room temperature, quenched with water (50 mL) and extracted with $CH_2Cl_2$. The organic solution was dried, filtered and concentrated. The residue was purified on a silica gel column eluting with 60% ethyl acetate-hexane, to afford the title compound.

EXAMPLE 325B

EXAMPLE 325A was treated with 4:1 trifluoroacetic acid/dichloromethane at room temperature overnight. Evaporation of solvent followed by trituration with diethyl ether gave a solid.

EXAMPLE 325C

The title compound was prepared as described in EXAMPLE 321A, substituting EXAMPLE 325B for 1-(3-nitrophenyl)piperazine.

EXAMPLE 325D

The title compound was prepared as described in EXAMPLE 1F, substituting. EXAMPLE 325C for EXAMPLE 1E.

EXAMPLE 325E

The title compound was prepared as described in EXAMPLE 42A, substituting EXAMPLE 325D for 4-(1H-imidazol-1-yl)aniline.

EXAMPLE 325F

The title compound was prepared as described in EXAMPLE 1E, substituting EXAMPLE 325E for phenyl guanidine.

EXAMPLE 325G

The title compound was prepared as described in EXAMPLE 1F, substituting EXAMPLE 325F for EXAMPLE E.

EXAMPLE 325H

N-(3-(5-(2-((4-(4-ethyl-2-oxopiperazin-1-yl)phenyl)amino)pyrimidin-4-yl)imidazo[2,1-b][1,3]thiazol-6-yl)phenyl)-2-phenylacetamide The title compound was prepared as described in EXAMPLE 36D, substituting EXAMPLE 325G for EXAMPLE 36C. MS (ESI), m/e 629.2 $(M+H)^+$; (ESI), m/e 627.1 $(M-H)^-$; 1H-NMR (300 MHz, DMSO-$d_6$) □ ppm 10.30 (s, 1 H), 9.83 (s, 1H), 8.83 (s, 1 H), 8.29 (d, 1 H), 7.90 (s, 1 H), 7.80 (d, 2 H), 7.70 (d, 1 H), 7.50 (d, 1 H), 7.41 (t, 1 H), 7.23-7.34 (m, 8 H), 6.63 (d, 1 H), 4.07 (m, 2H), 3.89 (m, 2H), 3.85 (m, 2H), 3.65 (s, 2 H), 3.31 (q, 2H), 1.29 (t, 3H).

EXAMPLE 326

N-(3-(5-(2-((4-(4-ethyl-2-oxopiperazin-1-yl)phenyl)amino)pyrimidin-4-yl)imidazo[2,1-b][1,3]thiazol-6-yl)phenyl)benzamide The title compound was prepared as described in EXAMPLE 36D, substituting EXAMPLE 325G for EXAMPLE 36C and benzoyl chloride for phenylacetyl chloride. MS (ESI), m/e 615.2 $(M+H)^+$; (ESI), m/e 613.0 $(M-H)^-$; $^1$H-NMR (300 MHz, DMSO-$d_6$) □ ppm 10.38 (s, 1 H), 9.85 (s, 1H), 8.66 (s, 1 H), 8.31 (d, 1 H), 8.11 (s, 1 H), 7.96 (d, 2 H), 7.91 (d, 1 H), 7.80 (d, 2 H), 7.59-7.64 (m, 1 H), 7.46-7.55 (m, 4 H), 7.36 (d, 1 H), 7.28 (d, 2 H), 6.69 (d, 1 H), 4.07 (m, 2H), 3.90 (m, 2H), 3.85 (m, 2H), 3.31 (q, 2H), 1.29 (t, 3H).

EXAMPLE 327

2-chloro-N-(3-(5-(2-((4-(4-ethyl-2-oxopiperazin-1-yl)phenyl)amino)pyrimidin-4-yl)imidazo[2,1-b][1,3]thiazol-6-yl)phenyl)benzamide The title compound was prepared as described in EXAMPLE 36D, substituting EXAMPLE 325G for EXAMPLE 36C and 2-chloro-benzoyl chloride for phenylacetyl chloride. MS (ESI), m/e 649.2 (M+H)+; (ESI), m/e 646.9 (M−H)−; 1H-NMR (300 MHz, DMSO-d6) ☐ ppm 10.63 (s, 1 H), 9.84 (s, 1H), 8.84 (s, 1 H), 8.31 (d, 1 H), 8.04 (s, 1 H), 7.78-7.81 (m, 3 H), 7.50-7.60 (m, 2 H), 7.45-7.54 (m, 4 H), 7.36 (d, 1H), 7.29 (d, 2 H), 6.68 (d, 1 H), 4.07 (m, 2H), 3.89 (m, 2H), 3.85 (m, 2H), 3.31 (q, 2H), 1.29 (t, 3H).

EXAMPLE 328

N-(3-(5-(2-((4-(4-ethyl-2-oxopiperazin-1-yl)phenyl)amino)pyrimidin-4-yl)imidazo[2,1-b][1,3]thiazol-6-yl)phenyl)-2,6-difluorobenzamide The title compound was prepared as described in EXAMPLE 36D, substituting EXAMPLE 325G for EXAMPLE 36C and 2,6-difluoro-benzoyl chloride for phenylacetyl chloride. MS (ESI), m/e 651.2 (M+H)+; (ESI), m/e 649.0 (M−H)−; 1H-NMR (300 MHz, DMSO-d6) ☐ ppm 10.92 (s, 1 H), 9.84 (s, 1H), 8.83 (s, 1 H), 8.31 (d, 1 H), 8.01 (s, 1 H), 7.80 (d, 2 H), 7.77 (d, 1 H), 7.58-7.63 (m, 2H), 7.47-7.54 (m, 2H), 7.39 (d, 1 H), 7.19-7.30 (m, 3 H), 6.67 (d, 1 H), 4.07 (m, 2H), 3.89 (m, 2H), 3.85 (m, 2H), 3.30 (q, 2H), 1.29 (t, 3H).

EXAMPLE 329

2-chloro-N-(3-(5-(2-((4-(4-ethyl-2-oxopiperazin-1-yl)phenyl)amino)pyrimidin-4-yl)imidazo[2,1-b][1,3]thiazol-6-yl)phenyl)-4-fluorobenzamide The title compound was prepared as described in EXAMPLE 36D, substituting EXAMPLE 325G for EXAMPLE 36C and 2-chloro-4-fluoro-benzoyl chloride for phenylacetyl chloride. MS (ESI), m/e 667.1 (M+H)+; (ESI), m/e 664.9 (M−H)−; 1H-NMR (300 MHz, DMSO-d6) ☐ ppm 10.63 (s, 1 H), 9.84 (s, 1H), 8.83 (s, 1 H), 8.31 (d, 1 H), 8.02 (s, 1 H), 7.78-7.81 (m, 3 H), 7.69 (dd, 1 H), 7.60 (dd, 1 H), 7.51 (d, 1H), 7.47 (t, 1H), 7.30-7.38 (m, 2 H), 7.28 (d, 2 H), 6.67 (d, 1 H), 4.07 (m, 2H), 3.89 (m, 2H), 3.85 (m, 2H), 3.30 (q, 2H), 1.29 (t, 3H).

EXAMPLE 330

N-(3-(5-(2-((3-(4-ethyl-2-oxopiperazin-1-yl)phenyl)amino)pyrimidin-4-yl)imidazo[2,1-b][1,3]thiazol-6-yl)phenyl)-2-phenylacetamide

EXAMPLE 330A

The title compound was prepared as described in EXAMPLE 325A, substituting substituting 1-iodo-3-nitrobenzene for 1-iodo-4-nitrobenezene.

EXAMPLE 330B

The title compound was prepared as described in EXAMPLE 325B, substituting EXAMPLE 330A for EXAMPLE 325A.

EXAMPLE 330C

The title compound was prepared as described in EXAMPLE 321A, substituting EXAMPLE 330B for 1-(3-nitrophenyl)piperazine.

EXAMPLE 330D

The title compound was prepared as described in EXAMPLE 1F, substituting EXAMPLE 330C for EXAMPLE 1E.

EXAMPLE 330E

The title compound was prepared as described in EXAMPLE 42A, substituting EXAMPLE 330D for 4-(1H-imidazol-1-yl)aniline.

EXAMPLE 330F

The title compound was prepared as described in EXAMPLE 1E, substituting EXAMPLE 330E for phenyl guanidine.

EXAMPLE 330G

The title compound was prepared as described in EXAMPLE 1F, substituting EXAMPLE 330F for EXAMPLE 1E.

EXAMPLE 330H

N-(3-(5-(2-((3-(4-ethyl-2-oxopiperazin-1-yl)phenyl)amino)pyrimidin-4-yl)imidazo[2,1-b][1,3]thiazol-6-yl)phenyl)-2-phenylacetamide The title compound was prepared as described in EXAMPLE 36D, substituting EXAMPLE 330G for EXAMPLE 36C. MS (ESI), m/e 629.3 (M+H)+; 1H-NMR (300 MHz, DMSO-d6) ☐ ppm 10.31 (s, 1 H), 9.88 (s, 1H), 8.84 (s, 1 H), 8.28 (d, 1 H), 7.90 (s, 1 H), 7.87 (s, 1 H), 7.69 (d, 1 H), 7.61 (d, 1 H), 7.50 (d, 1H), 7.39-7.43 (m, 2 H), 7.23-7.33 (m, 6 H), 6.94-6.96 (dd, 1 H), 6.62 (d, 1 H), 4.07 (m, 2H), 3.96 (m, 2H), 3.85 (m, 2H), 3.65 (s, 2 H), 3.30 (q, 2H), 2.54 (s, 2H), 1.27 (t, 3H).

EXAMPLE 331

N-(3-(5-(2-((3-(4-ethyl-2-oxopiperazin-1-yl)phenyl)amino)pyrimidin-4-yl)imidazo[2,1-b][1,3]thiazol-6-yl)phenyl)benzamide The title compound was prepared as described in EXAMPLE 36D, substituting EXAMPLE 330G for EXAMPLE 36C and benzoyl chloride for phenylacetyl chloride. MS (ESI), m/e 615.2 (M+H)+; (ESI), m/e 613.1 (M−H)−; 1H-NMR (300 MHz, DMSO-d6) ☐ ppm 10.38 (s, 1 H), 9.90 (s, 1H), 8.87 (s, 1 H), 8.30 (d, 1 H), 8.11 (s, 1 H), 7.96 (d, 2 H), 7.88-7.92 (m, 2 H), 7.58-7.64 (m, 2 H), 7.46-7.55 (m, 4 H), 7.35-7.43 (m, 2 H), 6.92-6.97 (dd, 1 H), 6.69 (d, 1 H), 4.07 (m, 2H), 3.96 (m, 2H), 3.85 (m, 2H), 3.30 (q, 2H), 1.27 (t, 3H).

EXAMPLE 332

2-chloro-N-(3-(5-(2-((3-(4-ethyl-2-oxopiperazin-1-yl)phenyl)amino)pyrimidin-4-yl)imidazo[2,1-b][1,3]thiazol-6-yl)phenyl)benzamide The title compound was prepared as described in EXAMPLE 36D, substituting EXAMPLE 330G for EXAMPLE 36C and 2-chloro-benzoyl chloride for phenylacetyl chloride. MS (ESI), m/e 649.2.1 (M+H)+; (ESI), m/e 647.0 (M−H)−; 1H-NMR (300 MHz, DMSO-d6) ☐ ppm 10.63 (s, 1 H), 9.89 (s, 1H), 8.84 (s, 1 H), 8.30 (d, 1 H), 8.05 (s, 1 H), 7.88 (s, 1 H), 7.79 (d, 1 H), 7.57-7.63 (m, 3 H), 7.47-7.54 (m, 4 H), 7.36-7.42 (m, 2 H), 6.94-6.96 (dd, 1 H), 6.68 (d, 1 H), 4.41 (m, 2H), 3.90 (m, 2H), 3.85 (m, 2H), 3.30 (q, 2H), 1.27 (t, 3H).

EXAMPLE 333

N-(3-(5-(2-((3-(4-ethyl-2-oxopiperazin-1-yl)phenyl) amino)pyrimidin-4-yl)imidazo[2,1-b][1,3]thiazol-6-yl)phenyl)-2,6-difluorobenzamide The title compound was prepared as described in EXAMPLE 36, substituting EXAMPLE 330G for EXAMPLE 36C and 2,4-difluoro-benzoyl chloride for phenylacetyl chloride. MS (ESI), m/e 651.2 (M+H)$^+$; (ESI), m/e 648.9 (M−H)$^−$; $^1$H-NMR (300 MHz, DMSO-d$_6$) ☐ ppm 10.93 (s, 1 H), 9.89 (s, 1H), 8.84 (s, 1 H), 8.30 (d, 1 H), 8.01 (s, 1 H), 7.88 (s, 1 H), 7.76 (d, 1 H), 7.57-7.62 (m, 3 H), 7.45-7.53 (m, 2 H), 7.38-7.42 (m, 2 H), 7.19-7.28 (m, 3h), 6.95 (d, 1 H), 6.68 (d, 1 H), 4.41 (m, 2H), 3.90 (m, 2H), 3.85 (m, 2H), 3.30 (q, 2H), 1.27 (t, 3H).

EXAMPLE 334

2-chloro-N-(3-(5-(2-((3-(4-ethyl-2-oxopiperazin-1-yl)phenyl)amino)pyrimidin-4-yl)imidazo[2,1-b][1,3]thiazol-6-yl)phenyl)-4-fluorobenzamide The title compound was prepared as described in EXAMPLE 36, substituting EXAMPLE 330G for EXAMPLE 36C and 2-chloro-4-fluoro-benzoyl chloride for phenylacetyl chloride. MS (ESI), m/e 667.1 (M+H)$^+$; (ESI), m/e 664.9 (M−H)$^−$; $^1$H-NMR (300 MHz, DMSO-d$_6$) ☐ ppm 10.64 (s, 1 H), 9.89 (s, 1H), 8.84 (s, 1 H), 8.30 (d, 1 H), 8.03 (s, 1 H), 7.87 (s, 1 H), 7.78 (d, 1 H), 7.69 (dd, 1 H), 7.57-7.65 (m, 2 H), 7.45-7.53 (m, 2 H), 7.34-7.42 (m, 3 H), 6.92-6.97 (dd, 1 H), 6.68 (d, 1 H), 4.41 (m, 2H), 3.90 (m, 2H), 3.85 (m, 2H), 3.30 (q, 2H), 1.27 (t, 3H).

EXAMPLE 335

2-chloro-4-fluoro-N-(3-(5-(2-((3-(2-oxopyrrolidin-1-yl)phenyl)amino)pyrimidin-4-yl)imidazo[2,1-b][1,3]thiazol-6-yl)phenyl)benzamide The title compound was prepared as described in EXAMPLE 36D, substituting EXAMPLE 286C for EXAMPLE 36C and 2-chloro-4-fluoro-benzoyl chloride for phenylacetyl chloride. MS (ESI), m/e 624.1 (M+H)$^+$; (ESI), m/e 621.9 (M−H)$^−$; $^1$H-NMR (300 MHz, DMSO-d$_6$) ☐ ppm 10.64 (s, 1 H), 9.80 (s, 1 H), 8.86 (s, 1 H), 8.29 (d, 1 H), 7.99-8.07 (m, 2 H), 7.81 (d, 1 H), 7.70 (dd, 1 H), 7.59 (dd, 2 H), 7.45-7.53 (m, 2 H), 7.34-7.39 (m, 2 H), 7.25-7.32 (m, 2 H), 6.65 (d, 1 H), 3.82 (t, 2 H), 2.47-2.54 (m, 6 H), 2.03-2.11 (m, 2 H).

EXAMPLE 336

N-(3-(5-(2-((3-methyl-1H-pyrazol-5-yl)amino)pyrimidin-4-yl)imidazo[2,1-b][1,3]thiazol-6-yl)phenyl)-2-phenylacetamide

EXAMPLE 336A

A 20 mL microwave mixture vessel equipped with a stir bar was charged with EXAMPLE 12C (0.507 g), 3-methyl-1H-pyrazol-5-amine (0.252 g) and HCl in dioxane (0.17 ml) in N-methylpyrrolidone (10 ml). The mixture was heated to 200° C. for 20 minutes in a Biotage Initiator 2 monomode microwave reactor, then cooled to ambient temperature. The mixture was diluted with 25 mL saturated NaHCO$_3$ and 25 mL water, and the precipitate was collected by filtration, washed with water, then vacuum dried to afford the title compound which was used in the next step without further purification.

EXAMPLE 336B

The title compound was prepared as described in EXAMPLE 1F, substituting EXAMPLE 336A for EXAMPLE 1E.

EXAMPLE 336C

A 50 mL roundbottom flask with stir bar was charged with EXAMPLE 336B (0.143 g), 2-phenylacetyl chloride (0.05 ml), pyridine (0.060 ml) and catalytic N,N-dimethylacetamide in CH$_2$Cl$_2$ (3 ml)/N-methylpyrrolidone (0.75 ml). The mixture was stirred at ambient temperature. After 3 hours, 2 mL of methanol was added and the vial was left to stir open to the air overnight. The mixture was concentrated and the resulting residue was purified by preparative HPLC on a Waters Nova-Pak® HR C18 6 um 60 A Prep-Pak® cartridge column (40 mm×100 mm) eluting with a gradient of 10-95% acetonitrile and 0.1% trifluoroacetic acid in water at a flow rate of 70 mL/min to afford the title compound as a TFA salt. MS (ESI(+)) m/e 507 (M+H)$^+$; (ESI(−)) m/e 505 (M−H)$^−$; $^1$H NMR (300 MHz, DMSO-d$_6$) δ 10.30 (s, 1H), 9.10 (d, 1H), 8.23 (d, 1H), 7.88 (s, 1H), 7.70 (d, 1H), 7.50 (m, 1H), 7.42 (t, 1H), 7.36-7.21 (m, 6H), 6.60 (d, 1H), 6.20 (s, 1H), 3.65 (s, 2H), 2.25 (s, 3H).

EXAMPLE 337

N-(3-(5-(2-((3-methyl-1H-pyrazol-5-yl)amino)pyrimidin-4-yl)imidazo[2,1-b][1,3]thiazol-6-yl)phenyl)benzamide The title compound was prepared as described in EXAMPLE 336C, substituting benzoyl chloride for 2-phenylacetyl chloride. MS (ESI(+)) m/e 493 (M+H)$^+$; (ESI(−)) m/e 491 (M−H)$^−$; $^1$H NMR (300 MHz, DMSO-d$_6$) δ 10.39 (s, 1H), 9.09 (d, 1H), 8.28 (d, 1H), 8.10 (s, 1H), 7.95 (m, 3H), 7.63 (m, 2H), 7.56-7.47 (m, 3H), 7.34 (d, 1H), 6.60 (d, 1H), 6.19 (s, 1H), 2.27 (s, 3H).

EXAMPLE 338

N-(3-(2-methyl-5-(2-((3-morpholin-4-ylphenyl) amino)pyrimidin-4-yl)imidazo[2,1-b][1,3]thiazol-6-yl)phenyl)benzamide

EXAMPLE 338A

The title compound was prepared as described in EXAMPLE 42A, substituting 3-morpholinoaniline for 4-(1H-imidazol-1-yl)aniline.

EXAMPLE 338B

The title compound was prepared as described in EXAMPLE 1, substituting 2-amino-5-methylthiazole for 2-aminothiazole in EXAMPLE 1A, EXAMPLE 338A for phenylguanidine in EXAMPLE 1E, and benzoyl chloride for 2-chlorobenzoyl chloride in EXAMPLE 1G. (ESI(+)) m/e 588 (M+H)+; $^1$H-NMR (300 MHz, DMSO-d$_6$) ☐ 10.35 (s, 1H); 9.50 (s, 1H); 8.53 (s, 1H); 8.27 (d, 1H); 8.08 (s, 1H); 7.96 (d, 2H); 7.70 (d, 1H); 7.60-7.43 (m, 4H); 7.34 (m, 2H); 7.21 (m, 2H); 6.64 (m, 2H); 3.73 (m, 4H); 3.09 (m, 4H); 2.48 (s, 3H).

EXAMPLE 339

N-(3-(2-methyl-5-(2-((3-morpholin-4-ylphenyl)amino)pyrimidin-4-yl)imidazo[2,1-b][1,3]thiazol-6-yl)phenyl)-2-phenylacetamide The title compound was prepared as described in EXAMPLE 1, substituting 2-amino-5-methylthiazole for 2-aminothiazole in EXAMPLE 1A, EXAMPLE 338A for phenylguanidine in EXAMPLE 1E, and phenylacetyl chloride for 2-chlorobenzoyl chloride in EXAMPLE 1G. (ESI(+)) m/e 602 (M+H)+; $^1$H-NMR (300 MHz, DMSO-d$_6$) ☐ 10.27 (s, 1H); 9.53 (s, 1H); 8.49 (s, 1H); 8.24 (d, 1H); 7.87 (s, 1H); 7.69 (d, 1H); 7.39 (t, 1H); 7.33-7.19 (m, 9H); 6.67 (m, 1H); 6.58 (d, 1H); 3.74 (m, 4H); 3.64 (s, 2H); 3.09 (m, 4H); 2.48 (s, 3H).

EXAMPLE 340

N-(3-(2-methyl-5-(2-((4-morpholin-4-ylphenyl)amino)pyrimidin-4-yl)imidazo[2,1-b][1,3]thiazol-6-yl)phenyl)benzamide The title compound was prepared as described in EXAMPLE 1, substituting 2-amino-5-methylthiazole for 2-aminothiazole in EXAMPLE 1A, EXAMPLE 3A for phenylguanidine in EXAMPLE 1E, and benzoyl chloride for 2-chlorobenzoyl chloride in EXAMPLE 1G. MS (ESI(+)) m/e 588 (M+H)+; $^1$H-NMR (300 MHz, DMSO-d$_6$) ☐ 10.34 (s, 1H); 9.38 (s, 1H); 8.42 (bs, 1H); 8.22 (d, 1H); 8.08 (s, 1H); 7.96 (d, 2H); 7.90 (d, 1H); 7.59-7.42 (m, 6H); 7.31 (d, 1H); 6.97 (d, 2H); 6.58 (d, 1H); 3.75 (m, 4H); 3.08 (m, 4H); 2.46 (s, 3H).

EXAMPLE 341

2-phenyl-N-(3-(5-(2-(1H-pyrazol-5-ylamino)pyrimidin-4-yl)imidazo[2,1-b][1,3]thiazol-6-yl)phenyl)acetamide The title compound was prepared as described in EXAMPLE 336, substituting 1H-pyrazol-3-amine for 3-methyl-1H-pyrazol-5-amine in EXAMPLE 336A. MS (ESI(+)) m/e 493 (M+H)+; (ESI(−)) m/e 491 (M−H)−; $^1$H NMR (300 MHz, CD$_3$OD) δ 8.98 (d, 1H), 8.11 (d, 1H), 7.98 (s, 1H), 7.77 (d, 1H), 7.64 (m, 1H), 7.53-7.46 (m, 2H), 7.43-7.21 (m, 6H), 6.86 (d, 1H), 6.35 (d, 1H), 6.25 (d, 1H), 3.65 (s, 2H).

EXAMPLE 342

N-(3-(5-(2-((4-(methylsulfonyl)phenyl)amino)pyrimidin-4-yl)imidazo[2,1-b][1,3]thiazol-6-yl)phenyl)benzamide The title compound was prepared as described in EXAMPLE 12, substituting 4-methylsulfonylaniline for 3-morpholinoaniline in EXAMPLE 12D and benzoyl chloride for phenylacetyl chloride in EXAMPLE 12F. (ESI(+)) m/e 567 (M+H)+; $^1$H-NMR (300 MHz, DMSO-d$_6$) ☐ 10.37 (s, 1H); 10.22 (s, 1H); 8.90 (d, 1H); 8.40 (d, 1H); 8.10 (s, 1H); 8.03-7.91 (m, 5H); 7.85 (d, 2H); 7.63-7.45 (m, 5H); 7.37 (d, 1H); 6.79 (d, 1H); 3.16 (s, 3H).

EXAMPLE 343

2,6-difluoro-N-(3-(5-(2-((4-(methylsulfonyl)phenyl)amino)pyrimidin-4-yl)imidazo[2,1-b][1,3]thiazol-6-yl)phenyl)benzamide The title compound was prepared as described in EXAMPLE 12, substituting 4-methylsulfonylaniline for 3-morpholinoaniline in EXAMPLE 12D and 2,6-difluorobenzoyl chloride for phenylacetyl chloride in EXAMPLE 12F. (ESI(+)) m/e 603 (M+H)+; $^1$H-NMR (300 MHz, DMSO-d$_6$) ☐ 10.92 (s, 1H); 10.23 (s, 1H); 8.87 (d, 1H); 8.40 (d, 1H); 8.03-8.00 (m, 3H); 7.85 (d, 2H); 7.79 (d, 1H); 7.63-7.52 (m, 2H); 7.49 (t, 1H); 7.40 (d, 1H); 7.26 (t, 2H); 6.77 (d, 1H); 3.16 (s, 3H).

EXAMPLE 344

N-(3-(5-(2-((4-(methylsulfonyl)phenyl)amino)pyrimidin-4-yl)imidazo[2,1-b][1,3]thiazol-6-yl)phenyl)-2-phenylacetamide The title compound was prepared as described in EXAMPLE 12, substituting 4-methylsulfonylaniline for 3-morpholinoaniline in EXAMPLE 12D. (ESI(+)) m/e 581 (M+H)+; $^1$H-NMR (300 MHz, DMSO-d$_6$) ☐ 10.29 (s, 1H); 10.22 (s, 1H); 8.87 (d, 1H); 8.37 (d, 1H); 8.01 (d, 2H); 7.89 (s, 1H); 7.84 (d, 2H); 7.72 (d, 1H); 7.56 (d, 1H); 7.41 (t, 1H); 7.33-7.24 (m, 6H); 6.73 (d, 1H); 3.65 (s, 2H); 3.16 (s, 3H).

EXAMPLE 345

N-(3-(5-(2-((3-tert-butyl-1H-pyrazol-5-yl)amino)pyrimidin-4-yl)imidazo[2,1-b][1,3]thiazol-6-yl)phenyl)-N'-phenylurea

EXAMPLE 345A

The title compound was prepared as described in EXAMPLE 336 by substituting 3-tert-butyl-1H-pyrazol-5-amine for 3-methyl-1H-pyrazol-5-amine in EXAMPLE 336A.

EXAMPLE 345B

A 50 mL round bottom flask with stir bar and reflux condenser was charged with EXAMPLE 345A (0.266 g) and isocyanatobenzene (0.070 ml) in CH$_2$Cl$_2$ (4 ml)/N-methylpyrrolidone (1 ml). The mixture was stirred in a 50° C. oil bath for 3 hours, then concentrated and the resulting residue was purified by preparative HPLC on a Waters Nova-Pak® HR C18 6 um 60 Å Prep-Pak® cartridge column (40 mm×100 mm) eluting with a gradient of 10-95% acetonitrile and 0.1% trifluoroacetic acid in water at a flow rate of 70 mL/min to afford the title compound as a TFA salt. MS (ESI(+)) m/e 550 (M+H)+; (ESI(−)) m/e 548 (M−H)−; $^1$H NMR (300 MHz, DMSO-d$_6$) δ 9.07 (bs, 1H), 8.85 (s, 1H), 8.71 (s, 1H), 8.25 (d, 1H), 7.76 (s, 1H), 7.55 (d, 1H), 7.47 (m, 1H), 7.46-7.38 (m, 4H), 7.30-7.19 (m, 4H), 6.97 (t, 1H), 6.63 (d, 1H), 6.22 (s, 1H), 1.30 (s, 9H).

EXAMPLE 346

N-(3-(5-(2-((3-tert-butyl-1H-pyrazol-5-yl)amino)
pyrimidin-4-yl)imidazo[2,1-b][1,3]thiazol-6-yl)phenyl)-2-phenylacetamide The title compound was prepared as described in EXAMPLE 336, substituting substituting 3-tert-butyl-1H-pyrazol-5-amine for 3-methyl-1H-pyrazol-5-amine in EXAMPLE 336A. MS (ESI(+)) m/e 549 (M+H)$^+$; (ESI(−)) m/e 547 (M−H)$^−$; $^1$H NMR (300 MHz, DMSO-d$_6$) δ 10.30 (s, 1H), 9.05 (bs, 1H), 8.23 (d, 1H), 7.88 (s, 1H), 7.72 (d, 1H), 7.46-7.25 (m, 8H), 6.56 (d, 1H), 6.22 (s, 1H), 3.67 (s, 2H), 1.30 (s, 9H).

EXAMPLE 347

N-(3-(5-(2-((3-(((2-(methylsulfonyl)ethyl)amino)
methyl)phenyl)amino)pyrimidin-4-yl)imidazo[2,1-b]
[1,3]thiazol-6-yl)phenyl)benzamide

EXAMPLE 347A

3-Nitrobenaldehyde (1.0 g) and 2-(methylthio)ethanamine (0.6 g) in methanol (10 ml) and acetic acid (1 ml) was stirred at room temperature for 5 minutes. Then sodium cyanoborohydride (1.25 g) was added. After stirring at room temperature overnight, the solvent was concentrated. The resulting residue was partitioned between ethyl acetate and NaHCO$_3$, the layers were separated, and the organic layer was washed with brine. The organic layer was passed through a silica gel plug eluting with 5% methanol in ethyl acetate to afford the title compound.

EXAMPLE 347B

To EXAMPLE 347A (1.02 g) in CH$_2$Cl$_2$ 10 ml was added di-tert-butyl carbonate (0.78 g) and the mixture stirred at room temperature overnight. The concentrated mixture was loaded onto a silica gel plug eluting 10% ethyl acetate/hexane to afford the title compound.

EXAMPLE 347C

To EXAMPLE 347B (1.3 g) in CH$_2$Cl$_2$ (10 ml) was added meta-chloroperbenzoic acid (1.96 g) and the mixture stirred at room temperature overnight. The solid was filtered. The filtrate was washed with NaHCO$_3$, and then brine. The solvent was concentrated to afford the title compound.

EXAMPLE 347D

The title compound was prepared as described in EXAMPLE 1F, substituting EXAMPLE 347C for EXAMPLE 1E.

EXAMPLE 347E

The title compound was prepared as described in EXAMPLE 12D, substituting EXAMPLE 347D for 3-morpholinoaniline.

EXAMPLE 347F

The title compound was prepared as described in EXAMPLE 347B, substituting EXAMPLE 347E for EXAMPLE 347A.

EXAMPLE 347G

The title compound was prepared as described in EXAMPLE 1F, substituting EXAMPLE 347F for EXAMPLE 1E.

EXAMPLE 347H

To EXAMPLE 347G (0.06 g) in tetrahydrofuran (3 ml) was added benzoyl chloride (0.011 ml). After stirring at room temperature for 1 hour, the mixture was partitioned between ethyl acetate and NaHCO$_3$. The organic layer was washed with brine, dried over Na$_2$SO$_4$ and concentrated. The crude material was treated with CH$_2$Cl$_2$ containing trifluoroacetic acid (25%) for 1 hour. The solvent was concentrated and the crude material was purified by reverse phase HPLC on a Shimadzu LC10 HPLC system with a Phenominex Luna 10 micron C18(2) 100 150×30 mm column, eluting with CH$_3$CN/water/0.1% TFA to afford the title compound as a TFA salt. MS (ESI(+)) m/e 624 (M+H)$^+$; $^1$H-NMR (300 MHz, DMSO-d$_6$) □ 10.37 (s, 1H); 9.86 (s, 1H); 8.99 (bs, 2H); 8.87 (d, 1H); 8.32 (d, 1H); 8.14 (s, 1H); 7.97-7.94 (m, 3H); 7.88 (d, 1H); 7.69 (d, 1H); 7.61-7.34 (m, 7H); 7.13 (d, 1H); 6.71 (d, 1H); 4.21 (m, 2H); 3.53 (m, 2H); 3.43 (m, 2H); 3.13 (s, 3H).

EXAMPLE 348

2,6-difluoro-N-(3-(5-(2-((3-(((2-(methylsulfonyl)
ethyl)amino)methyl)phenyl)amino)pyrimidin-4-yl)
imidazo[2,1-b][1,3]thiazol-6-yl)phenyl)benzamide The title compound was prepared as described in EXAMPLE 347, substituting 2,6-difluorobenzoyl chloride for benzoyl chloride in EXAMPLE 347H. MS (ESI(+)) m/e 660 (M+H)$^+$; $^1$H-NMR (300 MHz, DMSO-d$_6$) □ 10.92 (s, 1H); 9.87 (s, 1H); 8.99 (bs, 2H); 8.84 (d, 1H); 8.32 (d, 1H); 8.05 (s, 1H); 7.98 (s, 1H); 7.74-7.38 (m, 7H); 7.26 (t, 2H); 7.13 (d, 1H); 6.69 (d, 1H); 4.21 (m, 2H); 3.53 (m, 2H); 3.43 (m, 2H); 3.13 (s, 3H).

EXAMPLE 349

N-(3-(5-(2-((3-(((2-(methylsulfonyl)ethyl)amino)
methyl)phenyl)amino)pyrimidin-4-yl)imidazo[2,1-b]
[1,3]thiazol-6-yl)phenyl)-2-phenylacetamide The title compound was prepared as described in EXAMPLE 347, substituting phenylacetyl chloride for benzoyl chloride in EXAMPLE 347H. MS (ESI(+)) m/e 638 (M+H)$^+$; $^1$H-NMR (300 MHz, DMSO-d$_6$) □ 10.30 (s, 1H); 9.86 (s, 1H); 8.99 (bs, 2H); 8.84 (d, 1H); 8.29 (d, 1H); 7.95 (d, 2H); 7.67 (t, 2H); 7.52 (d, 1H); 7.43 (t, 2H); 7.34-7.23 (m, 6H); 7.13 (d, 1H); 6.64 (d, 1H); 4.21 (m, 2H); 3.53 (m, 2H); 3.43 (m, 2H); 3.13 (s, 3H).

EXAMPLE 350

N-(3-(5-(2-((3-tert-butyl-1H-pyrazol-5-yl)amino)
pyrimidin-4-yl)imidazo[2,1-b][1,3]thiazol-6-yl)phenyl)benzamide The title compound was prepared as described in EXAMPLE 336C, substituting EXAMPLE 345A for EXAMPLE 336B and benzoyl chloride for 2-phenylacetyl chloride in EXAMPLE 336C. MS (ESI(+)) m/e 535 (M+H)$^+$; (ESI(−)) m/e 533 (M−H)$^−$; $^1$H NMR (300 MHz, DMSO-d$_6$) δ

10.39 (s, 1H), 9.05 (d, 1H), 8.28 (d, 1H), 8.12 (s, 1H), 7.98-7.92 (m, 2H), 7.63-7.45 (m, 6H), 7.36 (d, 1H), 6.68 (d, 1H), 6.20 (s, 1H), 1.31 (s, 9H).

EXAMPLE 351

2-phenyl-N-(3-(5-(2-((3-pyridin-3-yl-1H-pyrazol-5-yl)amino)pyrimidin-4-yl)imidazo[2,1-b][1,3]thiazol-6-yl)phenyl)acetamide The title compound was prepared as described in EXAMPLE 336, substituting 3-(pyridin-3-yl)-1H-pyrazol-5-amine for 3-methyl-1H-pyrazol-5-amine in EXAMPLE 336A. MS (ESI(+)) m/e 570 (M+H)$^+$; (ESI(−)) m/e 568 (M−H)$^-$; $^1$H NMR (300 MHz, DMSO-d$_6$) δ 10.30 (s, 1H), 8.98 (d, 1H), 8.53 (dd, 1H), 8.27 (d, 1H), 8.13 (dt, 1H), 7.88 (s, 1H), 7.72 (d, 1H), 7.49-7.20 (m, 8H), 7.11 (m, 1H), 6.79 (s, 1H), 6.60 (d, 1H), 6.27 (s, 1H), 3.63 (s, 2H).

EXAMPLE 352

N-(3-(5-(2-((3-pyridin-3-yl-1H-pyrazol-5-yl)amino)pyrimidin-4-yl)imidazo[2,1-b][1,3]thiazol-6-yl)phenyl)benzamide The title compound was prepared as described in EXAMPLE 336, substituting 3-(pyridin-3-yl)-1H-pyrazol-5-amine for 3-methyl-1H-pyrazol-5-amine in EXAMPLE 336A and benzoyl chloride for 2-phenylacetyl chloride in EXAMPLE 336C. MS (ESI(+)) m/e 556 (M+H)$^+$; (ESI(−)) m/e 554 (M−H)$^-$; $^1$H NMR (300 MHz, DMSO-d$_6$) δ 10.30 (s, 1H), 9.08 (d, 1H), 8.62 (m, 1H), 8.31 (d, 1H), 8.11 (m, 1H), 7.98-7.91 (m, 4H), 7.69-7.45 (m, 7H), 7.36 (m, 1H), 6.92 (s, 1H), 6.69 (d, 1H), 6.27 (s, 1H).

EXAMPLE 353

4-(6-(3-(benzyloxy)phenyl)imidazo[2,1-b][1,3]thiazol-5-yl)-N-(4-morpholin-4-ylphenyl)pyrimidin-2-amine

EXAMPLE 353A

The title compound was prepared as described in EXAMPLE 1A, substituting 2-bromo-1-(3-hydroxyphenyl)ethanone for 2-bromo-1-(3-nitrophenyl)ethanone. MS (ESI(+)) m/e 217 (M+H)$^+$.

EXAMPLE 353B

A 0° C. soln of EXAMPLE 353A (2.0 g, 9.25 mmol) in DMF (60 mL) was treated portionwise with NaH (0.493 g, 18.5 mmol), stirred 5 min, then stirred at ambient temperature for 45 min. The reaction mixture was recooled to 0° C. and treated with benzyl bromide (1.898 g, 11.1 mmol), then allowed to warm to ambient temperature. After 2 h, the reaction was cooled to 0° C. and poured into water (150 mL). The mixture was extracted with 1:1 EtOAc/Et$_2$O (2×250 mL). The combined organic layers were washed with water (3×100 mL) and brine (100 mL), dried over Na$_2$SO$_4$, filtered and concentrated to provide 3.18 g brown oily residue which was purified by flash chromatography on a 115 g silica gel column using an AnaLogix IntelliFlash 280 system eluting with a gradient of 5% to 35% EtOAc/hexanes to provide 2.33 g of an orange solid. MS (ESI(+)) m/e 307 (M+H)$^+$.

EXAMPLE 353C

The title compound was prepared as described in EXAMPLE 1B, substituting EXAMPLE 353B for EXAMPLE 1A. MS (ESI(+)) m/e 433 (M+H)$^+$.

EXAMPLE 353D

The title compound was prepared as described in EXAMPLE 1C, substituting EXAMPLE 353C for EXAMPLE 1B. MS (ESI(+)) m/e 349 (M+H)$^+$.

EXAMPLE 353E

The title compound was prepared as described in EXAMPLE 1D, substituting EXAMPLE 353D for EXAMPLE 1C. MS (ESI(+)) m/e 404 (M+H)$^+$.

EXAMPLE 353F

The title compound was prepared as described in EXAMPLE 3B, substituting EXAMPLE 353E for EXAMPLE 1D. MS (ESI(+)) m/e 561.2 (M+H)$^+$; $^1$H NMR (300 MHz, DMSO-d$_6$) □ ppm 9.43 (s, 1 H) 8.75 (brs, 1 H) 8.19 (d, 1 H) 7.54 (m, 2 H) 7.30-7.48 (m, 7 H) 7.16-7.25 (m, 2 H) 7.11 (m, 1 H) 6.92 (m, 2 H) 6.49 (d, 1 H) 5.14 (s, 2 H) 3.74 (m, 4 H) 3.06 (m, 4 H).

EXAMPLE 354

4-(6-(3-(benzylamino)phenyl)imidazo[2,1-b][1,3]thiazol-5-yl)-N-(3-(3-morpholin-4-ylpropoxy)phenyl)pyrimidin-2-amine The title compound was prepared as described in EXAMPLE 355, substituting benzaldehyde for thiophene-2-carbaldehyde and EXAMPLE 238A for EXAMPLE 3C. MS (ESI(+)) m/e 618.3 (M+H)$^+$; $^1$H NMR (300 MHz, DMSO-d$_6$) □ ppm 9.67 (s, 1 H) 9.56 (br.s, 1 H) 8.86 (d, 1 H) 8.22 (d, 1 H) 7.56 (m, 1 H) 7.48 (d, 1 H) 7.13-7.37 (m, 9 H) 6.66-6.81 (m, 3 H) 6.58 (m, 2 H) 4.28 (s, 2 H) 3.47-4.07 (m, 8 H) 3.29 (m, 2 H) 3.13 (m, 2 H) 2.14 (m, 2 H).

EXAMPLE 355

N-(4-morpholin-4-ylphenyl)-4-(6-(3-((thien-2-ylmethyl)amino)phenyl)imidazo[2,1-b][1,3]thiazol-5-yl)pyrimidin-2-amine A 3 mL vial was charged with EXAMPLE 3C (30 mg, 0.064 mmol) and thiophene-2-carbaldehyde (7.17 mg. 0.067 mmol). 1,2-dichloroethane (0.6 mL) and AcOH (0.3 mL) were added and the solution was heated at 50° C. for 30 min. The rxn soln was cooled to RT and treated with MP-CNBH$_3$ resin (54.2 mg, 0.128 mmol) (Argonaut, 2.36 mmol/g). The mixture was stirred at RT for 2 h. The reaction mixture was filtered and the filtrate was concentrated and treated with MeOH (~200 uL) and conc. HCl (80 uL) and the rxn stirred at 50° C. for 30 min. The mixture was concentrated, then diluted with 1.5 mL DMSO/MeOH (1:1) and purified by preparative HPLC on a Waters Nova-Pak HR C18 6 um 60 Å Prep-Pak cartridge column (25 mm×100 mm). A gradient of acetonitrile and 0.1% trifluoroacetic acid in water was used at a flow rate of 40 mL/min (0-0.5 min 10% acetonitrile, 0.5-7.0 min linear gradient 10-95% acetonitrile, 7.0-10.0 min 95% acetonitrile, 10.0-12.0 min linear gradient 95-10% acetonitrile) allowed isolation of the title compound as the TFA salt, 27 mg. MS (ESI(+)) m/e 566.2 (M+H)+; 1H NMR (300 MHz, DMSO-d6) □ ppm 9.52 (s, 1 H) 8.76 (brs, 1 H) 8.14 (d, 1 H) 7.55 (m, 2 H) 7.46 (d 1 H) 7.35 (m, 1 H) 7.18 (t, 1 H) 6.90-7.03 (m, 5 H) 6.85 (m, 1 H) 6.74 (m, 2 H) 6.52 (d, 1 H) 4.46 (s, 2 H) 3.75 (m, 4 H) 3.10 (m, 4 H).

EXAMPLE 356

4-(6-(3-((2-chlorobenzyl)amino)phenyl)imidazo[2,1-b][1,3]thiazol-5-yl)-N-(4-morpholin-4-ylphenyl)pyrimidin-2-amine The title compound was prepared as described in EXAMPLE 355, substituting 2-chlorobenzaldehyde for thiophene-2-carbaldehyde. MS (ESI(+)) m/e 594.3 (M+H)+; 1H NMR (300 MHz, DMSO-d6) □ ppm 9.49 (s, 1 H) 8.74 (brs, 1 H) 8.13 (d, 1 H) 7.55 (m, 2 H) 7.43 (m, 4 H) 7.29 (m, 2 H) 7.18 (t, 1 H) 6.98 (m, 2 H) 6.76 (m, 2 H) 6.66 (m, 1 H) 6.52 (d, 1 H) 4.34 (s, 2 H) 3.76 (m, 4 H) 3.09 (m, 4 H).

EXAMPLE 357

4-(6-(3-((3-methylbenzyl)amino)phenyl)imidazo[2,1-b][1,3]thiazol-5-yl)-N-(4-morpholin-4-ylphenyl)pyrimidin-2-amine The title compound was prepared as described in EXAMPLE 355, substituting 3-methylbenzaldehyde for thiophene-2-carbaldehyde. MS (ESI(+)) m/e 574.3 (M+H)+; 1H NMR (300 MHz, DMSO-d6) □ ppm 9.50 (s, 1 H) 8.74 (br.s, 1 H) 8.13 (d, 1 H) 7.55 (m, 2 H) 7.45 (d, 1 H) 7.07-7.22 (m, 4 H) 6.99 (m, 3 H) 6.67-6.80 (m, 4 H) 6.52 (d, 1 H) 4.23 (s, 2 H) 3.76 (m, 4 H) 3.10 (m, 4 H) 2.26 (s, 3 H).

EXAMPLE 358

4-(6-(3-((4-methylbenzyl)amino)phenyl)imidazo[2,1-b][1,3]thiazol-5-yl)-N-(4-morpholin-4-ylphenyl)pyrimidin-2-amine The title compound was prepared as described in EXAMPLE 355, substituting 4-methylbenzaldehyde for thiophene-2-carbaldehyde. MS (ESI(+)) m/e 574.2 (M+H)+; 1H NMR (300 MHz, DMSO-d6) □ ppm 9.48 (s, 1 H) 8.75 (br.s, 1 H) 8.13 (d, 1 H) 7.55 (m, 2 H) 7.44 (d, 1 H) 7.06-7.24 (m, 6 H) 6.97 (m, 2 H) 6.64-6.79 (m, 3 H) 6.49 (d, 1 H) 4.22 (s, 2 H) 3.76 (m, 4 H) 3.09 (m, 4 H) 2.25 (s, 3 H).

EXAMPLE 359

4-(6-(3-((4-chlorobenzyl)amino)phenyl)imidazo[2,1-b][1,3]thiazol-5-yl)-N-(4-morpholin-4-ylphenyl)pyrimidin-2-amine The title compound was prepared as described in EXAMPLE 355, substituting 4-chlorobenzaldehyde for thiophene-2-carbaldehyde. MS (ESI(+)) m/e 594.2 (M+H)+; 1H NMR (300 MHz, DMSO-d6) □ ppm 9.50 (s, 1 H) 8.74 (br.s, 1 H) 8.13 (d, 1 H) 7.55 (m, 2 H) 7.45 (d, 1 H) 7.35 (m, 5 H) 7.16 (t, 1 H) 6.98 (m, 2 H) 6.64-6.78 (m, 3 H) 6.49 (d, 1 H) 4.28 (s, 2 H) 3.77 (m, 4 H) 3.10 (m, 4 H).

EXAMPLE 360

4-(6-(3-((3-chlorobenzyl)amino)phenyl)imidazo[2,1-b][1,3]thiazol-5-yl)-N-(4-morpholin-4-ylphenyl)pyrimidin-2-amine The title compound was prepared as described in EXAMPLE 355, substituting 3-chlorobenzaldehyde for thiophene-2-carbaldehyde. MS (ESI(+)) m/e 594.1 (M+H)+; 1H NMR (300 MHz, DMSO-d6) □ ppm 9.48 (s, 1 H) 8.75 (br.s, 1 H) 8.12 (d, 1 H) 7.55 (m, 2 H) 7.45 (d, 1 H) 7.24-7.39 (m, 5 H) 7.17 (t, 1 H) 6.97 (m, 2 H) 6.65-6.79 (m, 3 H) 6.48 (d, 1 H) 4.30 (s, 2 H) 3.77 (m, 4 H) 3.10 (m, 4 H).

EXAMPLE 361

4-(6-(3-((3-methoxybenzyl)amino)phenyl)imidazo[2,1-b][1,3]thiazol-5-yl)-N-(4-morpholin-4-ylphenyl)pyrimidin-2-amine The title compound was prepared as described in EXAMPLE 355, substituting 3-methoxybenzaldehyde for thiophene-2-carbaldehyde. MS (ESI(+)) m/e 590.3 (M+H)+; 1H NMR (300 MHz, DMSO-d6) □ ppm 9.48 (s, 1 H) 8.76 (br.s, 1 H) 8.12 (d, 1 H) 7.55 (m, 2 H) 7.45 (d, 1 H) 7.12-7.25 (m, 2 H) 6.88-7.00 (m, 5 H) 6.64-6.79 (m, 4 H) 6.50 (d, 1 H) 4.25 (s, 2 H) 3.73 (m, 7 H) 3.10 (m, 4 H).

EXAMPLE 362

2-(((3-(5-(2-((4-morpholin-4-ylphenyl)amino)pyrimidin-4-yl)imidazo[2,1-b][1,3]thiazol-6-yl)phenyl)amino)methyl)benzonitrile The title compound was prepared as described in EXAMPLE 355, substituting 2-cyanobenzaldehyde for thiophene-2-carbaldehyde. MS (ESI(+)) m/e 585.3 (M+H)+; 1H NMR (300 MHz, DMSO-d6) □ ppm 9.00 (br.s, 1 H) 8.56 (d, 1 H) 8.31 (d, 1 H) 8.24 (d, 1 H) 7.94 (m, 1 H) 7.66-7.88 (m, 7 H) 7.50 (m, 2 H) 7.36 (d, 1 H) 6.90 (m, 2 H) 6.75 (d, 1 H) 5.26 (s, 2 H) 3.76 (m, 4 H) 3.09 (m, 4 H).

EXAMPLE 363

N-(3-(5-(2-((4-morpholin-4-ylphenyl)amino)pyridin-4-yl)imidazo[2,1-b][1,3]thiazol-6-yl)phenyl)-2-phenylacetamide

EXAMPLE 363A

In a 25 mL round bottom flask was charged EXAMPLE 1B (0.50 g, 1.35 mmol), 2-fluoropyridin-4-ylboronic acid (0.266 g, 1.89 mmol), bis(triphenylphosphine) palladium(II) chloride (0.095 g, 0.135 mmol) in NMP (9 mL). The reaction was stirred at ambient temperature for 5 minutes and 1.7 mL of 2 M aq. sodium carbonate was added. The reaction was heated at 98° C. for 16 h, then poured into 75 mL water and the resulting yellow suspension stirred for 20 min. The suspension was filtered and the solids were washed with water then ether. The solids were dissolved in acetone and adsorbed on 15 g silica gel, then purified by flash chromatography on an 80 g silica gel column using an AnaLogix IntelliFlash 280 system eluting with a gradient of 0% to 2.5% MeOH in dichloromethane to provide the title compound as a yellow solid. MS (ESI(+)) m/e 341 (M+H)+.

EXAMPLE 363B

A suspension of EXAMPLE 363A (280 mg, 0.823 mmol) and 4-morpholinoaniline (147 mg, 0.823 mmol) in NMP (4 mL) was treated with conc HCl (0.274 mL, 3.29 mmol) and solution was heated in a microwave reactor at 155° C. for 2 h. The reaction mixture was poured into 25 mL saturated aq. NaHCO3. The resulting suspension was stirred 5 min, 30 mL water was added and the mixture was filtered. The solids were washed with water followed by ether and were air dried under vacuum on the filter to provide 285 mg of a gold solid. The solid was dissolved in $CH_2Cl_2$/MeOH and adsorbed onto silica gel. The residue was purified by flash chromatography on a 12 g silica gel column using an AnaLogix IntelliFlash 280 system eluting with a gradient of 0% to 3% MeOH in $CH_2Cl_2$ to provide the title compound as a yellow solid (117 mg). MS (ESI(+)) m/e 499 (M+H)$^+$.

EXAMPLE 363C

The title compound was prepared as described in EXAMPLE 3C, substituting EXAMPLE 363B for EXAMPLE 3B. MS (ESI(+)) m/e 469 (M+H)$^+$.

EXAMPLE 363D

The title compound was prepared as described in EXAMPLE 3D, substituting EXAMPLE 363C for EXAMPLE 3C and phenylacetyl chloride for 2,6-difluorobenzoyl chloride. MS (ESI(+)) m/e 587.2 (M+H)$^+$; $^1$H NMR (300 MHz, DMSO-d$_6$) □ ppm 10.22 (s, 1 H) 8.81 (s, 1 H) 8.16 (d, 1 H) 7.89 (m, 2 H) 7.65 (m, 1 H) 7.39 (m, 3 H) 7.22-7.32 (m, 6 H) 7.14 (m, 1 H) 6.83 (m, 2 H) 6.72 (m, 2 H) 3.73 (m, 4 H) 3.62 (s, 2 H) 3.05 (m, 4 H).

EXAMPLE 364

N-(3-(5-(2-((4-morpholin-4-ylphenyl)amino)pyridin-4-yl)imidazo[2,1-b][1,3]thiazol-6-yl)phenyl)benzamide The title compound was prepared as described in EXAMPLE 3D, substituting EXAMPLE 363C for EXAMPLE 3C and benzoyl chloride for 2,6-difluorobenzoyl chloride. MS (ESI(+)) m/e 573.2 (M+H)$^+$; $^1$H NMR (300 MHz, DMSO-d$_6$) □ ppm 10.34 (s, 1 H) 9.72 (br.s, 1 H) 8.12 (m, 1 H) 8.05 (m, 1 H) 7.92-8.02 (m, 3 H) 7.86 (m, 1 H) 7.47-7.64 (m, 5 H) 7.39 (t, 1 H) 7.18-7.29 (m, 3 H) 6.94 (m, 4 H) 3.74 (m, 4 H) 3.09 (m, 4 H).

EXAMPLE 365

N-(3-(4-isopropylpiperazin-1-yl)phenyl)-4-(6-(3-((5-phenyl-1,3,4-oxadiazol-2-yl)amino)phenyl)imidazo[2,1-b][1,3]thiazol-5-yl)pyrimidin-2-amine The title compound was prepared as described in EXAMPLE 137, substituting EXAMPLE 316D for EXAMPLE 65C. MS (ESI(+)) m/e 655 (M+H)$^+$, (ESI(−)) m/e 653 (M−H)$^−$; $^1$H NMR (300 MHz, DMSO-D6) □ ppm 10.84 (s, 1H), 9.54 (s, 1H), 8.85 (d, 1H), 8.27 (d, 1H), 7.84-7.95 (m, 3H), 7.73 (dd, 1H), 7.54-7.61 (m, 3H), 7.44-7.52 (m, 2H), 7.19-7.35 (m, 3H), 7.13 (t, 1H), 6.55-6.66 (m, 2H), 3.06-3.16 (m, 4H), 2.61-2.69 (m, 1H), 2.53-2.60 (m, 4H), 1.00 (d, 6H).

EXAMPLE 366

N-(3-(5-(2-((1-benzoyl-3-tert-butyl-1H-pyrazol-5-yl)amino)pyrimidin-4-yl)imidazo[2,1-b][1,3]thiazol-6-yl)phenyl)benzamide A 50 mL roundbottom flask with stir bar was charged with EXAMPLE 345A (0.15 g), benzoyl chloride (0.045 ml), pyridine (0.060 ml) and catalytic N,N-dimethylacetamide in $CH_2Cl_2$ (3 ml)/N-methylpyrrolidone (0.75 ml). The mixture was stirred at ambient temperature. After 3 hours, 2 mL of methanol was added and the vial was left to stir open to the air overnight. The remaining NMP solution was dried in vacuo, and the residues taken up in 2.5 mL 1:1 DMSO/methanol. A precipitate formed, which was filtered, washed with methanol and vacuum dried to give the title compound. MS (ESI(+)) m/e 640 (M+H)$^+$; (ESI(−)) m/e 638 (M−H)$^−$; $^1$H NMR (300 MHz, DMSO-d$_6$) δ 10.42 (s, 1H), 9.42 (d, 1H), 8.78 (d, 1H), 8.09 (m, 1H), 7.98-7.92 (m, 4H), 7.63-7.45 (m, 8H), 7.42 (m, 1H), 7.21 (d, 1H), 6.95 (s, 1H), 1.41 (s, 9H).

EXAMPLE 367

N-(3-morpholin-4-ylphenyl)-4-(6-(3-(3-phenoxyprop-1-ynyl)phenyl)imidazo[2,1-b][1,3]thiazol-5-yl)pyrimidin-2-amine

EXAMPLE 367A

The title compound was prepared as described in EXAMPLE 1A, substituting 2-bromo-1-(3-bromophenyl)ethanone for 2-bromo-1-(3-nitrophenyl)ethanone. MS (ESI(+)) m/e 278, 280 (M+H)$^+$.

EXAMPLE 367B

A microwave reactor vessel was charged with EXAMPLE 367A (1.67 g), sulfuric acid (0.1 ml) and acetic anhydride (12 ml) to give a yellow suspension which was heated for 10 min at 170° C. in a microwave reactor. The reaction volume was reduced under vacuum, and the residues partitioned between saturated NaHCO$_3$ and EtOAc. The organic layer was dried over MgSO$_4$, filtered and adsorbed onto silica gel. The title compound was purified by flash chromatography using an Argonaut Flashmaster Solo, 20 g column (10% EtOAc:hexanes for 10 min, then to 50% EtOAc:hexanes over 40 min). providing a pale yellow solid. MS (ESI(+)) m/e 320, 322 (M+H)$^+$.

EXAMPLE 367C

The title compound was prepared as described in EXAMPLE 1D, substituting EXAMPLE 367B for EXAMPLE 1C. MS (ESI(+)) m/e 376, 378 (M+H)$^+$.

EXAMPLE 367D

The title compound was prepared as described in EXAMPLE 1E, substituting EXAMPLE 367C for EXAMPLE 1D and EXAMPLE 338A for phenylguanidine. MS (ESI(+)) m/e 533, 535 (M+H)$^+$.

EXAMPLE 367E

A 2 mL Microwave Tube was charged with EXAMPLE 367D (0.0500 g, 0.094 mmol), (prop-2-ynyloxy)benzene (0.013 ml, 0.103 mmol), PdCl$_2$(PPh$_3$)$_2$ (3.29 mg, 4.69 μmol), triphenylphosphine (4.92 mg, 0.019 mmol), copper(I) iodide (0.893 mg, 4.69 μmol) and triethylamine (0.196 ml, 1.406 mmol) in DMF (0.469 ml) to give a yellow solution. The mixture was heated in a Biotage Initiator Microwave reactor for 25 min at 120° C. The mixture was cooled and partitioned between EtOAc and water, extracted with EtOAc, and the organics concentrated to absorb the crude product onto silica gel. The product was purified by flash chromatography using an Argonaut Flashmaster Solo, 10 g column (30% EtOAc: hexanes for 20 min, then to 100% EtOAc over 30 min), followed by further purification using a Shimadzu SIL-10 HPLC system (2 mL injections, run on a 150×30 mm Phenominex Gemini 10 micron C18 column with 110 Angstrom pore size, flow rate of 20 mL/min, mobile phase gradient from 50% to 90% acetonitrile/water with 0.1% NH$_4$OH over 25 min). The title compound was isolated as a light yellow solid. MS (ESI(+)) m/e 585 (M+H)$^+$; $^1$H NMR (300 MHz, DMSO-D6) ☐ ppm 9.56 (s, 1H), 8.79 (d, 1H), 8.27 (d, 1H), 7.66 (m, 2H), 7.50 (m, 3H), 7.33 (m, 3H), 7.23 (d, 1H), 7.16 (t, 1H), 7.04 (d, 2H), 6.97 (t, 1H), 6.61 (d, 1H), 6.51 (d, 1H), 5.05 (s, 2H), 3.73 (m, 4H), 3.08 (m, 4H).

EXAMPLE 368

4-(6-(3-(5-methyl-1,3,4-thiadiazol-2-yl)phenyl)imidazo[2,1-b][1,3]thiazol-5-yl)-N-(3-morpholin-4-ylphenyl)pyrimidin-2-amine

EXAMPLE 368A

A 5 mL Microwave Tube was charged with EXAMPLE 367D (0.3401 g, 0.638 mmol), bis(pinacolato)diboron (0.324 g, 1.275 mmol), potassium acetate (0.313 g, 3.19 mmol), and PdCl$_2$(PPh$_3$)$_2$ (0.045 g, 0.064 mmol) in DMF (2.125 ml). The mixture was heated in a microwave reactor at 150° C. for 10 min. The mixture was poured into water and the mixture filtered, saving the solids. The filtrate was extracted with EtOAc, the organics dried over MgSO$_4$, then filtered and concentrated. The residues were combined with the isolated solids and adsorbed onto silica gel. The product was purified by flash chromatography using an Argonaut Flashmaster Solo, 20 g column (30% EtOAc:hexanes for 20 min, then to 100% EtOAc over 30 min). The title compound was isolated as a pale yellow solid. MS (ESI(+)) m/e 581 (M+H)$^+$.

EXAMPLE 368B

A 2 mL Microwave Tube was charged with EXAMPLE 368A (31.8 mg, 0.055 mmol), 2-bromo-5-methyl-1,3,4-thiadiazole (10.79 mg, 0.060 mmol), sodium carbonate (8.71 mg, 0.082 mmol) and PdCl$_2$(PPh$_3$)$_2$ (1.922 mg, 2.74 µmol) in DME (365 µl) and water (183 µl). The mixture was heated in a Biotage Initiator microwave reactor at 130° C. for 20 min. The mixture was diluted with 0.5 mL MeOH and filtered through a syringe filter. The material was purified using a Shimadzu SIL-10 HPLC system (2 mL injections, run on a 150×30 mm Phenominex Gemini 10 micron C18 column with 110 Angstrom pore size, flow rate of 20 mL/min, mobile phase gradient from 30% to 70% acetonitrile/water with 0.1% NH$_4$OH over 25 min). The title compound was isolated as a light yellow solid. MS (ESI(+)) m/e 553 (M+H)$^+$; $^1$H NMR (300 MHz, DMSO-D6) ☐ ppm 9.58 (s, 1H), 8.79 (d, 1H), 8.29 (d, 1H), 8.19 (m, 1H), 8.01 (m, 1H), 7.82 (m, 1H), 7.66 (t, 1H), 7.52 (d, 1H), 7.36 (t, 1H), 7.23 (d, 1H), 7.15 (t, 1H), 6.64 (d, 1H), 6.61 (m, 1H), 3.73 (m, 4H), 3.08 (m, 4H), 2.78 (s, 3H).

EXAMPLE 369

N-(3-morpholin-4-ylphenyl)-4-(6-(3-(1,3-thiazol-2-yl)phenyl)imidazo[2,1-b][1,3]thiazol-5-yl)pyrimidin-2-amine The title compound was prepared as described in EXAMPLE 368B, substituting 2-bromothiazole for 2-bromo-5-methyl-1,3,4-thiadiazole. MS (ESI(+)) m/e 538 (M+H)$^+$; $^1$H NMR (300 MHz, DMSO-D6) ☐ ppm 9.59 (s, 1H), 8.80 (d, 1H), 8.29 (d, 1H), 8.03 (m, 1H), 7.95 (d, 1H), 7.82 (d, 3H), 7.75 (dt, 1H), 7.62 (t, 1H), 7.52 (d, 1H), 7.36 (t, 1H), 7.23 (d, 1H), 7.16 (t, 1H), 6.64 (d, 1H), 6.61 (m, 1H), 3.73 (m, 4H), 3.08 (m, 4H).

EXAMPLE 370

4-(6-(3-(1-methyl-1H-imidazol-2-yl)phenyl)imidazo[2,1-b][1,3]thiazol-5-yl)-N-(3-morpholin-4-ylphenyl)pyrimidin-2-amine The title compound was prepared as described in EXAMPLE 368B, substituting 2-bromo-1-methylimidazole for 2-bromo-5-methyl-1,3,4-thiadiazole. MS (ESI(+)) m/e 535 (M+H)$^+$; $^1$H NMR (300 MHz, DMSO-D6) ☐ ppm 9.57 (s, 1H), 8.84 (d, 1H), 8.28 (d, 1H), 7.92 (m, 1H), 7.78 (dt, 1H), 7.67 (dt, 1H), 7.59 (t, 1H), 7.51 (d, 1H), 7.35 (m, 1H), 7.26 (d, 1H), 7.23 (d, 1H), 7.16 (t, 1H), 6.98 (d, 1H), 6.61 (m, 2H), 3.76 (s, 3H), 3.74 (m, 4H), 3.08 (m, 4H).

EXAMPLE 371

N-(2-chloro-3-(5-(2-((3-morpholin-4-ylphenyl)amino)pyrimidin-4-yl)imidazo[2,1-b][1,3]thiazol-6-yl)phenyl)-2,6-difluorobenzamide

EXAMPLE 371A

The title compound was prepared as described in EXAMPLE 1A, substituting 2-bromo-1-(2-chloro-3-nitrophenyl)ethanone for 2-bromo-1-(3-nitrophenyl)ethanone. MS (ESI(+)) m/e 280 (M+H)$^+$.

EXAMPLE 371B

The title compound was prepared as described in EXAMPLE 367B, substituting EXAMPLE 371A for EXAMPLE 367A. MS (ESI(+)) m/e 322 (M+H)$^+$.

EXAMPLE 371C

The title compound was prepared as described in EXAMPLE 1D, substituting EXAMPLE 371B for EXAMPLE 1C. MS (ESI(+)) m/e 377 (M+H)$^+$.

EXAMPLE 371D

The title compound was prepared as described in EXAMPLE 1E, substituting EXAMPLE 371C for EXAMPLE 1D and EXAMPLE 338A for phenylguanidine. The title compound was purified by flash chromatography using an Argonaut Flashmaster Solo, 50 g column (30% EtOAc:hexanes for 20 min, then to 100% EtOAc over 30 min). MS (ESI(+)) m/e 534 (M+H)$^+$.

EXAMPLE 371E

The title compound was prepared as described in EXAMPLE 3C, substituting EXAMPLE 371D for EXAMPLE 3B. MS (ESI(+)) m/e 505 (M+H)$^+$.

EXAMPLE 371F

The title compound was prepared as described in EXAMPLE 3D, substituting EXAMPLE 371E for EXAMPLE 3C. MS (ESI(+)) m/e 644 (M+H)$^+$; $^1$H NMR (300 MHz, DMSO-D6) ☐ ppm 10.64 (s, 1H), 9.54 (s, 1H), 9.02 (d, 1H), 8.22 (d, 1H), 7.89 (dd, 1H), 7.57 (m, 3H), 7.48 (d, 1H), 7.21 (m, 4H), 6.62 (d, 1H), 6.12 (d, 1H), 3.74 (m, 4H), 3.09 (m, 4H).

EXAMPLE 372

N-(2-chloro-3-(5-(2-((3-morpholin-4-ylphenyl) amino)pyrimidin-4-yl)imidazo[2,1-b][1,3]thiazol-6-yl)phenyl)-2-fluorobenzamide The title compound was prepared as described in EXAMPLE 3D, substituting EXAMPLE 371E for EXAMPLE 3C and 2-fluorobenzoyl chloride for 2,6-difluorobenzoyl chloride. MS (ESI(+)) m/e 626 (M+H)$^+$; $^1$H NMR (300 MHz, DMSO-D6) □ ppm 10.08 (s, 1H), 9.53 (s, 1H), 9.02 (d, 1H), 8.22 (d, 1H), 8.00 (d, 1H), 7.81 (dt, 1H), 7.62 (m, 1H), 7.55 (m, 2H), 7.45 (dd, 1H), 7.36 (m, 2H), 7.25 (m, 2H), 7.17 (t, 1H), 6.62 (d, 1H), 6.13 (d, 1H), 3.75 (m, 4H), 3.10 (m, 4H).

EXAMPLE 373

N-(2-chloro-3-(5-(2-((3-morpholin-4-ylphenyl) amino)pyrimidin-4-yl)imidazo[2,1-b][1,3]thiazol-6-yl)phenyl)-2-phenylacetamide The title compound was prepared as described in EXAMPLE 3D, substituting EXAMPLE 371E for EXAMPLE 3C and phenylacetyl chloride for 2,6-difluorobenzoyl chloride. MS (ESI(+)) m/e 622 (M+H)$^+$; $^1$H NMR (300 MHz, DMSO-D6) □ ppm 9.80 (s, 1H), 9.53 (s, 1H), 9.02 (d, 1H), 8.20 (d, 1H), 7.90 (dd, 1H), 7.56 (d, 1H), 7.47 (t, 1H), 7.35 (m, 5H), 7.25 (m, 3H), 7.17 (t, 1H), 6.62 (d, 1H), 6.06 (d, 1H), 3.77 (s, 2H), 3.75 (m, 4H), 3.10 (m, 4H).

EXAMPLE 374

N-(2-(dimethylamino)-3-(5-(2-((3-morpholin-4-ylphenyl)amino)pyrimidin-4-yl)imidazo[2,1-b][1,3]thiazol-6-yl)phenyl)-2,6-difluorobenzamide

EXAMPLE 374A

The title compound was isolated as a byproduct when EXAMPLE 371D is prepared as described in EXAMPLE 1E, substituting EXAMPLE 371C for EXAMPLE 1D and EXAMPLE 338A for phenylguanidine by flash chromatography using an Argonaut Flashmaster Solo, 50 g column (30% EtOAc:hexanes for 20 min, then to 100% EtOAc over 30 min). MS (ESI(+)) m/e 543 (M+H)$^+$.

EXAMPLE 374B

The title compound was prepared as described in EXAMPLE 3C, substituting EXAMPLE 374A for EXAMPLE 3B. MS (ESI(+)) m/e 513 (M+H)$^+$.

EXAMPLE 374C

The title compound was prepared as described in EXAMPLE 3D, substituting EXAMPLE 374B for EXAMPLE 3C. MS (ESI(+)) m/e 653 (M+H)$^+$; $^1$H NMR (300 MHz, DMSO-D6) □ ppm 10.05 (s, 1H), 9.51 (s, 1H), 9.03 (d, 1H), 8.21 (d, 2H), 7.58 (m, 1H), 7.53 (d, 1H), 7.24 (m, 5H), 7.17 (t, 1H), 7.09 (dd, 1H), 6.62 (d, 1H), 6.22 (d, 1H), 3.74 (m, 4H), 3.09 (m, 4H), 2.39 (s, 6H).

EXAMPLE 375

N-(2-(dimethylamino)-3-(5-(2-((3-morpholin-4-ylphenyl)amino)pyrimidin-4-yl)imidazo[2,1-b][1,3]thiazol-6-yl)phenyl)-2-phenylacetamide The title compound was prepared as described in EXAMPLE 3D, substituting EXAMPLE 374B for EXAMPLE 3C and 2-fluorobenzoyl chloride for 2,6-difluorobenzoyl chloride. MS (ESI(+)) m/e 631 (M+H)$^+$; $^1$H NMR (300 MHz, DMSO-D6) □ ppm 9.49 (s, 1H), 9.09 (s, 1H), 9.02 (d, 1H), 8.29 (dd, 1H), 8.16 (d, 1H), 7.51 (d, 1H), 7.40 (m, 4H), 7.31 (m, 1H), 7.26 (m, 1H), 7.18 (m, 3H), 6.93 (dd, 1H), 6.62 (d, 1H), 6.10 (d, 1H), 3.81 (s, 2H), 3.74 (m, 4H), 3.09 (m, 4H), 2.18 (s, 6H).

EXAMPLE 376

2,6-difluoro-N-(3-(5-(2-((3-((4-methylpiperazin-1-yl)methyl)phenyl)amino)pyrimidin-4-yl)imidazo[2,1-b][1,3]thiazol-6-yl)phenyl)benzamide

EXAMPLE 376A

A 20 mL vial was charged with 1-(bromomethyl)-3-nitrobenzene (4.63 ml, 4.63 mmol) in acetonitrile to give a tan solution. N-Methylpiperazine (1.39 g, 13.89 mmol) and triethylamine (1.936 ml, 13.89 mmol) were added. The mixture was stirred at ambient temperature overnight, diluted with EtOAc, washed with aqueous sodium bicarbonate and brine, and the organic phase dried over MgSO$_4$, filtered and adsorbed onto silica gel. The product was purified by flash chromatography using an Argonaut Flashmaster Solo, 10 g column (90% CH$_2$Cl$_2$: 9% MeOH: 1% NH$_4$OH for 20 min). The title compound was isolated as a light yellow oil. MS (ESI(+)) m/e 236 (M+H)$^+$.

EXAMPLE 376B

The title compound was prepared as described in EXAMPLE 1F, substituting EXAMPLE 376A for EXAMPLE 1E. MS (ESI(+)) m/e 206 (M+H)$^+$.

EXAMPLE 376C

The title compound was prepared as described in EXAMPLE 12D, substituting EXAMPLE 376B for 3-morpholinoaniline. MS (ESI(+)) m/e 527 (M+H)$^+$.

EXAMPLE 376D

The title compound was prepared as described in EXAMPLE 1F, substituting EXAMPLE 376C for EXAMPLE 1E. MS (ESI(+)) m/e 497 (M+H)$^+$.

EXAMPLE 376E

The title compound was prepared as described in EXAMPLE 3D, substituting EXAMPLE 376D for EXAMPLE 3C. MS (ESI(+)) m/e 637 (M+H)$^+$; $^1$H NMR (300 MHz, DMSO-D6) □ ppm 10.91 (s, 1H), 9.66 (s, 1H), 8.83 (d, 1H), 8.29 (d, 1H), 7.99 (m, 1H), 7.79 (m, 1H), 7.70 (m, 1H), 7.61 (m, 2H), 7.48 (m, 2H), 7.39 (dt, 1H), 7.25 (m, 3H), 6.91 (d, 1H), 6.63 (d, 1H), 3.43 (s, 2H), 2.33 (m, 8H), 2.13 (s, 3H).

EXAMPLE 377

2-fluoro-N-(3-(5-(2-((3-((4-methylpiperazin-1-yl)methyl)phenyl)amino)pyrimidin-4-yl)imidazo[2,1-b][1,3]thiazol-6-yl)phenyl)benzamide The title compound was prepared as described in EXAMPLE 3D, substituting EXAMPLE 376D for EXAMPLE 3C and 2-fluorobenzoyl chloride for 2,6-difluorobenzoyl chloride. MS (ESI(+)) m/e 619 (M+H)$^+$; $^1$H NMR (300 MHz, DMSO-D6) □ ppm 10.54 (s, 1H), 9.67 (s, 1H), 8.86 (d, 1H), 8.29 (d, 1H), 8.02 (m, 1H), 7.84 (m, 1H), 7.67 (m, 3H), 7.58 (m, 1H), 7.50 (d, 1H), 7.47 (t, 1H), 7.35 (m, 3H), 7.25 (t, 1H), 6.91 (d, 1H), 6.63 (d, 1H), 3.43 (s, 2H), 2.37 (m, 8H), 2.16 (s, 3H).

EXAMPLE 378

N-(3-(5-(2-((3-((4-methylpiperazin-1-yl)methyl)phenyl)amino)pyrimidin-4-yl)imidazo[2,1-b][1,3]thiazol-6-yl)phenyl)-2-phenylacetamide The title compound was prepared as described in EXAMPLE 3D, substituting EXAMPLE 376D for EXAMPLE 3C and phenylacetyl chloride for 2,6-difluorobenzoyl chloride. MS (ESI(+)) m/e 615 (M+H)$^+$; $^1$H NMR (300 MHz, DMSO-D6) □ ppm 10.29 (s, 1H), 9.67 (s, 1H), 8.84 (d, 1H), 8.26 (d, 1H), 8.02 (m, 1H), 7.88 (m, 1H), 7.71 (m, 2H), 7.62 (m, 1H), 7.49 (d, 1H), 7.40 (t, 1H), 7.29 (m, 7H), 6.91 (d, 1H), 6.58 (d, 1H), 3.65 (s, 2H), 3.43 (s, 2H), 2.33 (m, 8H), 2.13 (s, 3H).

EXAMPLE 379

N-(3-(5-(2-((3-((dimethylamino)methyl)phenyl)amino)pyrimidin-4-yl)imidazo[2,1-b][1,3]thiazol-6-yl)phenyl)-2,6-difluorobenzamide

EXAMPLE 379A

The title compound was prepared as described in EXAMPLE 376A, substituting dimethylamine for N-methylpiperazine. MS (ESI(+)) m/e 181 (M+H)$^+$.

EXAMPLE 379B

The title compound was prepared as described in EXAMPLE 1F, substituting EXAMPLE 379A for EXAMPLE 1E. MS (ESI(+)) m/e 206 (M+H)$^+$.

EXAMPLE 379C

The title compound was prepared as described in EXAMPLE 12D, substituting EXAMPLE 379B for 3-morpholinoaniline. MS (ESI(+)) m/e 472 (M+H)$^+$.

EXAMPLE 379D

The title compound was prepared as described in EXAMPLE 1F, substituting EXAMPLE 379C for EXAMPLE 1E. MS (ESI(+)) m/e 442 (M+H)$^+$.

EXAMPLE 379E

The title compound was prepared as described in EXAMPLE 3D, substituting EXAMPLE 379D for EXAMPLE 3C. MS (ESI(+)) m/e 582 (M+H)$^+$; $^1$H NMR (300 MHz, DMSO-D6) □ ppm 10.92 (s, 1H), 9.68 (s, 1H), 8.84 (d, 1H), 8.29 (d, 1H), 7.99 (m, 1H), 7.78 (m, 1H), 7.67 (m, 2H), 7.60 (m, 2H), 7.50 (d, 1H), 7.48 (t, 1H), 7.39 (m, 1H), 7.26 (m, 3H), 6.91 (d, 1H), 6.63 (d, 1H), 3.38 (s, 2H), 2.17 (s, 6H).

EXAMPLE 380

N-(3-(5-(2-((3-((dimethylamino)methyl)phenyl)amino)pyrimidin-4-yl)imidazo[2,1-b][1,3]thiazol-6-yl)phenyl)-2-fluorobenzamide The title compound was prepared as described in EXAMPLE 3D, substituting EXAMPLE 379D for EXAMPLE 3C and 2-fluorobenzoyl chloride for 2,6-difluorobenzoyl chloride. MS (ESI(+)) m/e 564 (M+H)$^+$; $^1$H NMR (300 MHz, DMSO-D6) □ ppm 10.54 (s, 1H), 9.67 (s, 1H), 8.87 (d, 1H), 8.29 (d, 1H), 8.02 (m, 1H), 7.85 (m, 1H), 7.68 (m, 3H), 7.58 (m, 1H), 7.50 (d, 1H), 7.47 (t, 1H), 7.36 (m, 3H), 7.25 (m, 1H), 6.90 (d, 1H), 6.62 (d, 1H), 3.37 (s, 2H), 2.15 (s, 6H).

EXAMPLE 381

N-(3-(5-(2-((3-((dimethylamino)methyl)phenyl)amino)pyrimidin-4-yl)imidazo[2,1-b][1,3]thiazol-6-yl)phenyl)-2-phenylacetamide The title compound was prepared as described in EXAMPLE 3D, substituting EXAMPLE 379D for EXAMPLE 3C and phenylacetyl chloride for 2,6-difluorobenzoyl chloride. MS (ESI(+)) m/e 560 (M+H)$^+$; $^1$H NMR (300 MHz, DMSO-D6) □ ppm 10.29 (s, 1H), 9.66 (s, 1H), 8.85 (d, 1H), 8.26 (d, 1H), 7.87 (m, 1H), 7.70 (m, 2H), 7.65 (m, 1H), 7.49 (d, 1H), 7.40 (t, 1H), 7.29 (m, 7H), 6.90 (d, 1H), 6.58 (d, 1H), 3.65 (s, 2H), 3.36 (s, 2H), 2.15 (s, 6H).

EXAMPLE 382

2-chloro-N-(3-(5-(2-((3-((dimethylamino)methyl)phenyl)amino)pyrimidin-4-yl)imidazo[2,1-b][1,3]thiazol-6-yl)phenyl)benzamide The title compound was prepared as described in EXAMPLE 3D, substituting EXAMPLE 379D for EXAMPLE 3C and 2-chlorobenzoyl chloride for 2,6-difluorobenzoyl chloride. MS (ESI(+)) m/e 580 (M+H)$^+$; $^1$H NMR (300 MHz, DMSO-D6) □ ppm 10.62 (s, 1H), 9.67 (s, 1H), 8.86 (d, 1H), 8.29 (d, 1H), 8.02 (m, 1H), 7.81 (m, 1H), 7.69 (m, 1H), 7.65 (m, 1H), 7.57 (m, 2H), 7.47 (m, 4H), 7.37 (m, 1H), 7.25 (t, 1H), 6.90 (d, 1H), 6.63 (d, 1H), 3.36 (s, 2H), 2.15 (s, 6H).

EXAMPLE 383

N-(3-(5-(2-((3-((dimethylamino)methyl)phenyl)amino)pyrimidin-4-yl)imidazo[2,1-b][1,3]thiazol-6-yl)phenyl)-N'-phenylurea The title compound was prepared as described in EXAMPLE 13, substituting EXAMPLE 379D for EXAMPLE 3C. MS (ESI(+)) m/e 561 (M+H)$^+$; $^1$H NMR (300 MHz, DMSO-D6) □ ppm 9.67 (s, 1H), 8.88 (d, 1H), 8.83 (s, 1H), 8.69 (s, 1H), 8.29 (d, 1H), 7.73 (m, 1H), 7.69 (m, 1H), 7.65 (m, 1H), 7.54 (m, 1H), 7.50 (d, 1H), 7.44 (m, 2H), 7.39 (t, 1H), 7.25 (m, 4H), 6.96 (m, 1H), 6.90 (d, 1H), 6.62 (d, 1H), 3.37 (s, 2H), 2.15 (s, 6H).

EXAMPLE 384

2,6-difluoro-N-(3-(5-(2-((3-(morpholin-4-ylmethyl) phenyl)amino)pyrimidin-4-yl)imidazo[2,1-b][1,3] thiazol-6-yl)phenyl)benzamide

EXAMPLE 384A

The title compound was prepared as described in EXAMPLE 376A, substituting morpholine for N-methylpiperazine. MS (ESI(+)) m/e 223 (M+H)$^+$.

EXAMPLE 384B

The title compound was prepared as described in EXAMPLE 1F, substituting EXAMPLE 384A for EXAMPLE 1E. MS (ESI(+)) m/e 193 (M+H)$^+$.

EXAMPLE 384C

The title compound was prepared as described in EXAMPLE 12D, substituting EXAMPLE 384B for 3-morpholinoaniline. MS (ESI(+)) m/e 514 (M+H)$^+$.

EXAMPLE 384D

The title compound was prepared as described in EXAMPLE 1F, substituting EXAMPLE 384C for EXAMPLE 1E. MS (ESI(+)) m/e 484 (M+H)$^+$.

EXAMPLE 384E

The title compound was prepared as described in EXAMPLE 3D, substituting EXAMPLE 384D for EXAMPLE 3C. MS (ESI(+)) m/e 624 (M+H)$^+$; $^1$H NMR (300 MHz, DMSO-D6) □ ppm 10.91 (s, 1H), 9.68 (s, 1H), 8.84 (d, 1H), 8.29 (d, 1H), 7.99 (m, 1H), 7.78 (m, 1H), 7.70 (m, 1H), 7.64 (m, 1H), 7.60 (m, 1H), 7.51 (d, 1H), 7.48 (t, 1H), 7.40 (m, 1H), 7.26 (m, 3H), 6.93 (d, 1H), 6.63 (d, 1H), 3.56 (m, 4H), 3.44 (s, 2H), 2.36 (m, 4H).

EXAMPLE 385

2-fluoro-N-(3-(5-(2-((3-(morpholin-4-ylmethyl)phenyl)amino)pyrimidin-4-yl)imidazo[2,1-b][1,3]thiazol-6-yl)phenyl)benzamide The title compound was prepared as described in EXAMPLE 3D, substituting EXAMPLE 384D for EXAMPLE 3C and 2-fluorobenzoyl chloride for 2,6-difluorobenzoyl chloride. MS (ESI(+)) m/e 606 (M+H)$^+$; $^1$H NMR (300 MHz, DMSO-D6) □ ppm 10.54 (s, 1H), 9.68 (s, 1H), 8.86 (d, 1H), 8.29 (d, 1H), 8.02 (m, 1H), 7.84 (m, 1H), 7.68 (m, 3H), 7.58 (m, 1H), 7.50 (d, 1H), 7.47 (t, 1H), 7.36 (m, 3H), 7.26 (t, 1H), 6.93 (d, 1H), 6.63 (d, 1H), 3.56 (m, 4H), 3.44 (s, 2H), 2.36 (m, 4H).

EXAMPLE 386

N-(3-(5-(2-((3-(morpholin-4-ylmethyl)phenyl) amino)pyrimidin-4-yl)imidazo[2,1-b][1,3]thiazol-6-yl)phenyl)-2-phenylacetamide The title compound was prepared as described in EXAMPLE 3D, substituting EXAMPLE 384D for EXAMPLE 3C and phenylacetyl chloride for 2,6-difluorobenzoyl chloride. MS (ESI(+)) m/e 602 (M+H)$^+$; $^1$H NMR (300 MHz, DMSO-D6) □ ppm 10.29 (s, 1H), 9.67 (s, 1H), 8.85 (d, 1H), 8.26 (d, 1H), 7.88 (m, 2H), 7.71 (m, 1H), 7.64 (m, 1H), 7.49 (d, 1H), 7.41 (t, 1H), 7.29 (m, 7H), 6.93 (d, 1H), 6.59 (d, 1H), 3.65 (s, 2H), 3.56 (m, 4H), 3.44 (s, 2H), 2.36 (m, 4H).

EXAMPLE 387

2-chloro-N-(3-(5-(2-((3-(morpholin-4-ylmethyl)phenyl)amino)pyrimidin-4-yl)imidazo[2,1-b][1,3]thiazol-6-yl)phenyl)benzamide The title compound was prepared as described in EXAMPLE 3D, substituting EXAMPLE 384D for EXAMPLE 3C and 2-chlorobenzoyl chloride for 2,6-difluorobenzoyl chloride. MS (ESI(+)) m/e 622 (M+H)$^+$; $^1$H NMR (300 MHz, DMSO-D6) □ ppm 10.62 (s, 1H), 9.68 (s, 1H), 8.85 (d, 1H), 8.29 (d, 1H), 8.02 (m, 1H), 7.81 (m, 1H), 7.70 (m, 1H), 7.64 (m, 1H), 7.57 (m, 2H), 7.47 (m, 4H), 7.37 (m, 1H), 7.25 (t, 1H), 6.93 (d, 1H), 6.64 (d, 1H), 3.56 (m, 4H), 3.44 (s, 2H), 2.36 (m, 4H).

EXAMPLE 388

N-(3-(5-(2-((3-(morpholin-4-ylmethyl)phenyl) amino)pyrimidin-4-yl)imidazo[2,1-b][1,3]thiazol-6-yl)phenyl)-N'-phenylurea The title compound was prepared as described in EXAMPLE 13, substituting EXAMPLE 384D for EXAMPLE 3C. MS (ESI(+)) m/e 603 (M+H)$^+$; $^1$H NMR (300 MHz, DMSO-D6) □ ppm 9.67 (s, 1H), 8.87 (d, 1H), 8.85 (s, 1H), 8.71 (s, 1H), 8.28 (d, 1H), 7.71 (m, 2H), 7.64 (m, 1H), 7.55 (m, 1H), 7.50 (d, 1H), 7.44 (m, 2H), 7.39 (t, 1H), 7.25 (m, 4H), 6.95 (m, 2H), 6.63 (d, 1H), 3.56 (m, 4H), 3.45 (s, 2H), 2.37 (m, 4H).

EXAMPLE 389 methyl 4-((3-(5-(2-((3-morpholin-4-ylphenyl)amino) pyrimidin-4-yl)imidazo[2,1-b][1,3]thiazol-6-yl)phenyl)amino)-2-phenylbutanoate

EXAMPLE 389A

A 100 ml flask was charged with methyl 2-phenylacetate (4.75 g, 31.6 mmol) and DMF (56 ml). The solution was cooled to 0° C. and sodium hydride (60% mineral oil dispersion) (1.392 g, 34.8 mmol) was added in small portions over ca. 20 min. The mixture was allowed to warm to ambient temperature while stirring for 1.5 hr. A 200 ml flask was charged with 3-bromoprop-1-ene (8.21 ml, 95 mmol) and DMF (34 ml). This solution was cooled to −42° C. (acetonitrile/CO$_2$) and the cloudy brownish enolate mixture was canulated slowly dropwise into this solution over ca. 30 min. The cooling bath was then removed and the mixture was allowed to warm to ambient temperature. The reaction was stirred at ambient temperature for 2 hr then quenched by dropwise addition of water (12 ml). The majority of the DMF was removed under reduced pressure and the residue was partitioned between water (90 ml) and EtOAc (120 ml). The layers were separated and the aqueous layer was further extracted with EtOAc (3×50 ml). The combined organic layers were dried over sodium sulfate, filtered and concentrated to provide a yellow-brown oil. The material was purified on an ISCO chromatography system on a silica gel cartridge (150 g) eluted with a gradient 0-10% EtOAc/hexane to provide the title compound. MS (ESI(+)) m/e 191 (M+H)+.

EXAMPLE 389B

A 50 ml flask was charged with EXAMPLE 389A (0.5 g, 2.63 mmol), dioxane (15 ml), and water (5 ml). To the colorless solution was added osmium(VIII) oxide, solution in 2-propanol (0.330 ml, 0.026 mmol). The mixture was stirred for 5 min at ambient temperature, then sodium periodate (1.181 g, 5.52 mmol) was added slowly portionwise over ca. 22 min. The mixture was stirred under nitrogen for 1.5 hr, then diluted with water (35 ml) and filtered. The precipitate was washed with water and discarded. The filtrate was extracted with $CH_2Cl_2$ (75 ml, 2×50 ml) and the combined organic layers were dried over sodium sulfate, filtered and concentrated. The crude material was dissolved in $CH_2Cl_2$ and purified on an Alltech silica gel cartridge (10 g) eluted with $CH_2Cl_2$, then isolated and re-chromatographed on a new Alltech cartridge eluting with 50% $CH_2Cl_2$/hexane to provide the title compound. MS (ESI(+)) m/e 193 (M+H)+.

EXAMPLE 389C

The title compound was prepared as described in EXAMPLE 355, substituting EXAMPLE 12E for EXAMPLE 3C and EXAMPLE 389B for thiophene-2-carbaldehyde. MS (ESI(+)) m/e 646 (M+H)+; $^1$H NMR (300 MHz, DMSO-D6) □ ppm 9.58 (s, 1H), 8.85 (d, 1H), 8.20 (d, 1H), 7.48 (d, 1H), 7.13-7.38 (m, 10H), 6.70-6.80 (m, 2H), 6.58-6.67 (m, 3H), 3.81 (t, 1H), 3.71-3.77 (m, 4H), 3.57 (s, 3H), 3.06-3.14 (m, 4H), 2.88-2.96 (m, 2H), 2.26 (td, 1H), 1.92 (td, 1H).

EXAMPLE 390

4-(6-(3-((5-methyl-1,3,4-thiadiazol-2-yl)amino)phenyl)imidazo[2,1-b][1,3]thiazol-5-yl)-N-(4-morpholin-4-ylphenyl)pyrimidin-2-amine The title compound was prepared as described in EXAMPLE 137, substituting EXAMPLE 3C for EXAMPLE 65C and 2-bromo-5-methyl-1,3,4-thiadiazole for 2-bromo-5-phenyloxadiazole. MS (ESI(+)) m/e 568 (M+H)+, (ESI(−)) m/e 566 (M−H)−; $^1$H NMR (300 MHz, DMSO-D6) □ ppm 10.35 (s, 1H), 9.57 (s, 1H), 8.75 (s, 1H), 8.21 (d, 1H), 7.86-7.93 (m, 1H), 7.62-7.71 (m, 1H), 7.39-7.60 (m, 4H), 7.20 (d, 1H), 6.99 (d, 2H), 6.57 (d, 1H), 3.70-3.81 (m, 4H), 3.04-3.17 (m, 4H), 2.55 (s, 3H).

EXAMPLE 391

4-(6-(3-((5-methyl-1,3,4-thiadiazol-2-yl)amino)phenyl)imidazo[2,1-b][1,3]thiazol-5-yl)-N-(3-morpholin-4-ylphenyl)pyrimidin-2-amine The title compound was prepared as described in EXAMPLE 137, substituting EXAMPLE 12E for EXAMPLE 65C and 2-bromo-5-methyl-1,3,4-thiadiazole for 2-bromo-5-phenyloxadiazole. MS (ESI(+)) m/e 568 (M+H)+; $^1$H NMR (300 MHz, DMSO-D6) □ ppm 10.35 (s, 1H), 9.62 (s, 1H), 8.83 (d, 1H), 8.26 (d, 1H), 7.87-7.93 (m, 1H), 7.62-7.72 (m, 1H), 7.51 (d, 1H), 7.44 (t, 1H), 7.34-7.38 (m, 1H), 7.13-7.27 (m, 3H), 6.58-6.68 (m, 2H), 3.68-3.78 (m, 4H), 3.07-3.16 (m, 4H), 2.52-2.56 (m, 3H).

EXAMPLE 392

4-(6-(3-((5-methyl-1,3,4-thiadiazol-2-yl)amino)phenyl)imidazo[2,1-b][1,3]thiazol-5-yl)-N-(4-pyrrolidin-1-ylphenyl)pyrimidin-2-amine The title compound was prepared as described in EXAMPLE 137, substituting EXAMPLE 253C for EXAMPLE 65C and 2-bromo-5-methyl-1,3,4-thiadiazole for 2-bromo-5-phenyloxadiazole. MS (ESI(+)) m/e 552 (M+H)+; $^1$H NMR (300 MHz, DMSO-D6) □ ppm 10.36 (s, 1H), 9.55-9.74 (m, 1H), 8.73 (s, 1H), 8.16 (t, 1H), 7.85-7.96 (m, 1H), 7.67 (dd, 1H), 7.37-7.53 (m, 4H), 7.20 (d, 1H), 6.68 (d, 2H), 6.54 (d, 1H), 3.21-3.37 (m, 4H), 2.52-2.57 (m, 3H), 1.92-2.06 (m, 4H).

EXAMPLE 393

3-(5-(2-((3-morpholin-4-ylphenyl)amino)pyrimidin-4-yl)imidazo[2,1-b][1,3]thiazol-6-yl)benzaldehyde O-phenyloxime

EXAMPLE 393A

The title compound was prepared as described in EXAMPLE 1A, substituting 2-bromo-1-(3-cyanophenyl)ethanone for 2-bromo-1-(3-nitrophenyl)ethanone. MS (ESI(+)) m/e 226 (M+H)+.

EXAMPLE 393B

The title compound was prepared as described in EXAMPLE 367B, substituting EXAMPLE 393A for EXAMPLE 367A. MS (ESI(+)) m/e 268 (M+H)+.

EXAMPLE 393C

The title compound was prepared as described in EXAMPLE 1D, substituting EXAMPLE 393B for EXAMPLE 1C. MS (ESI(+)) m/e 323 (M+H)+.

EXAMPLE 393D

The title compound was prepared as described in EXAMPLE 3B, substituting EXAMPLE 393C for EXAMPLE 1D. MS (ESI(+)) m/e 480 (M+H)+.

EXAMPLE 393E

A 10 mL round bottom flask was charged with EXAMPLE 393D (0.030 g, 0.063 mmol) in THF (1 mL). The solution was cooled to −78° C. DIBAL-H (1M in THF) (0.44 mL, 0.44 mmol) was added dropwise and the solution stirred at −78° C. for 40 min and was then warmed to 0° C. The mixture was stirred at 0° C. for 3 h, then recooled to −78° C. and 2 eq more DIBAL was added. After 15 min, the mixture was warmed and stirred at 0° C. for 1 h. The reaction was quenched with 2.5 mL 1N HCl and the resulting solution was stirred at 0° C. for 15 min, then diluted with 5 mL water and extracted with 2×25 mL 10% MeOH/DCM. The combined organic layers were washed with brine, dried (Na$_2$SO$_4$), filtered, and concentrated to give the title compound. MS (ESI(+)) m/e 483 (M+H)+.

EXAMPLE 393F

A 4 mL vial was charged with EXAMPLE 393E (38 mg, 0.079 mmol) in DMSO (0.8 mL). O-Phenylhydroxylamine hydrochloride (11.46 mg, 0.079 mmol) was added and the resulting solution was stirred at room temperature for 8 h. The crude reaction mixture was purified by preparative HPLC on a Waters Nova-Pak HR C18 6 um 60 Å Prep-Pak cartridge column (25 mm×100 mm). A gradient of acetonitrile (A) and 0.1% trifluoroacetic acid in water (B) was used, at a flow rate of 40 mL/min (0-0.5 min 10% A, 0.5-7.0 min linear gradient 10-95% A, 7.0-10.0 min 95% A, 10.0-12.0 min linear gradient 95-10% A) to give the title compound as the TFA salt. MS (ESI(+)) m/e 574.2 (M+H)$^+$; $^1$H NMR (300 MHz, DMSO-d$_6$) □ ppm 9.59 (s, 1 H) 8.77 (m, 2 H) 8.30 (d, 1 H) 8.07 (m, 1 H) 7.88 (m, 1 H) 7.77 (m, 1 H) 7.60 (m, 1 H) 7.52 (d, 1 H) 7.36 (m, 3 H) 7.23 (m, 3 H) 7.16 (m, 1 H) 7.04 (m, 1 H) 6.61 (m, 2 H) 3.73 (m, 4 H) 3.08 (m, 4 H).

EXAMPLE 394

3-(5-(2-((3-morpholin-4-ylphenyl)amino)pyrimidin-4-yl)imidazo[2,1-b][1,3]thiazol-6-yl)benzaldehyde O-benzyloxime The title compound was prepared as described in EXAMPLE 393F, substituting O-benzylhydroxylamine hydrochloride for O-phenylhydroxylamine hydrochloride. MS (ESI(+)) m/e 588.2 (M+H)$^+$; $^1$H NMR (300 MHz, DMSO-d$_6$) □ ppm 9.61 (s, 1 H) 8.80 (m, 1 H) 8.37 (s, 1 H) 8.26 (d, 1 H) 7.89 (m, 1 H) 7.65 (m, 2 H) 7.51 (m, 2 H) 7.37 (m, 6 H) 7.19 (m, 2 H) 6.63 (m, 1 H) 6.55 (d, 1 H) 5.17 (s, 2 H) 3.74 (m, 4 H) 3.09 (m, 4 H).

EXAMPLE 395

3-(5-(2-((3-morpholin-4-ylphenyl)amino)pyrimidin-4-yl)imidazo[2,1-b][1,3]thiazol-6-yl)benzaldehyde O-ethyloxime The title compound was prepared as described in EXAMPLE 393F, substituting O-ethylhydroxylamine hydrochloride for O-phenylhydroxylamine hydrochloride. MS (ESI(+)) m/e 526.1 (M+H)$^+$; $^1$H NMR (300 MHz, DMSO-d$_6$) □ ppm 9.60 (s, 1 H) 8.80 (m, 1 H) 8.29 (s, 1 H) 8.27 (d, 1 H) 7.90 (m, 1 H) 7.67 (m, 2 H) 7.52 (m, 2 H) 7.36 (m, 1 H) 7.20 (m, 2 H) 6.63 (m, 1 H) 6.56 (d, 1 H) 4.16 (q, 2 H) 3.74 (m, 4 H) 3.09 (m, 4 H) 1.25 (t, 3 H).

EXAMPLE 396

N'-(benzoyloxy)-3-(5-(2-((3-morpholin-4-ylphenyl)amino)pyrimidin-4-yl)imidazo[2,1-b][1,3]thiazol-6-yl)benzenecarboximidamide

EXAMPLE 396A

A 10 mL screw-top pressure vessel was charged with EXAMPLE 393D (0.030 g, 0.063 mmol), hydroxylamine hydrochloride (0.015 g, 0.219 mmol), NMP (0.5 mL), EtOH (0.5 mL) and Et$_3$N (0.039 mL, 0.282 mmol). The mixture was heated at 85° C. for 40 min, then concentrated by rotovap. The mixture was diluted with water and filtered. The precipitate was washed with water then ether and dried to give the title compound as an off-white solid. MS (ESI(+)) m/e 513 (M+H)$^+$.

EXAMPLE 396B

A 4 mL vial was charged with EXAMPLE 396A (0.065 g, 0.127 mmol) and benzoyl chloride (0.027 g, 0.190 mmol) in THF (2 mL). The mixture was stirred at room temperature for 3.5 h. 1 mL NMP was added, and the mixture stirred an additional 35 min., then concentrated to remove THF. The residual oil was treated with ether (3 mL) and the suspension was stirred and sonicated for 10 min. The ether was decanted from the suspension and the precipitate was dried to in vacuo to give a yellow solid. The crude product was dissolved in 0.5 mL 15% MeOH/DCM and purified by flash chromatography on a 2 g silica gel column eluting with a gradient of 0% to 10% MeOH/CH$_2$Cl$_2$ to give the title compound as a white solid. MS (ESI(+)) m/e 617.2 (M+H)$^+$; $^1$H NMR (300 MHz, DMSO-d$_6$) □ ppm 9.57 (s, 1 H) 8.84 (m, 1 H) 8.29 (d, 1 H) 8.20 (m, 2 H) 8.09 (m, 1 H) 7.88 (m, 1 H) 7.77 (m, 1 H) 7.52-7.69 (m, 5 H) 7.36 (m, 1 H) 7.13-7.24 (m, 2 H) 7.04 (s, 2 H) 6.61 (m, 1 H) 6.57 (d, 1 H) 3.74 (m, 4 H) 3.09 (m, 4 H).

EXAMPLE 397

N-(3-(5-(2-((3-(methylsulfonyl)phenyl)amino)pyrimidin-4-yl)imidazo[2,1-b][1,3]thiazol-6-yl)phenyl)benzamide

EXAMPLE 397A

The title compound was prepared as described in EXAMPLE 12D, substituting 3-methylsulfonylaniline for 3-morpholinoaniline. MS (ESI(+)) m/e 493 (M+H)$^+$.

EXAMPLE 397B

The title compound was prepared as described in EXAMPLE 3C, substituting EXAMPLE 397A for EXAMPLE 3B. MS (ESI(+)) m/e 463 (M+H)$^+$.

EXAMPLE 397C

The title compound was prepared as described in EXAMPLE 3D, substituting EXAMPLE 397B for EXAMPLE 3C and benzoyl chloride for 2,6-difluorobenzoyl chloride. MS (ESI(+)) m/e 567 (M+H)$^+$; $^1$H-NMR (300 MHz, DMSO-d$_6$) □ 10.37 (s, 1H); 10.10 (s, 1H); 8.90 (d, 1H); 8.36 (m, 2H); 8.12 (m, 2H); 7.95 (m, 3H); 7.62-7.45 (m, 7H); 7.37 (d, 1H); 6.74 (d, 1H); 3.20 (s, 3H).

EXAMPLE 398

2,6-difluoro-N-(3-(5-(2-((3-(methylsulfonyl)phenyl)amino)pyrimidin-4-yl)imidazo[2,1-b][1,3]thiazol-6-yl)phenyl)benzamide The title compound was prepared as described in EXAMPLE 3D, substituting EXAMPLE 397B for EXAMPLE 3C. MS (ESI(+)) m/e 603 (M+H)$^+$; $^1$H-NMR (300 MHz, DMSO-d$_6$) □ 10.91 (s, 1H); 10.10 (s, 1H); 8.87 (d, 1H); 8.36 (m, 2H); 8.12 (d, 1H); 8.00 (s, 1H); 7.79 (d, 1H); 7.62-7.46 (m, 5H); 7.40 (d, 1H); 7.26 (t, 2H); 6.72 (d, 1H); 3.20 (s, 3H).

EXAMPLE 399

N-(3-(5-(2-((3-(methylsulfonyl)phenyl)amino)pyrimidin-4-yl)imidazo[2,1-b][1,3]thiazol-6-yl)phenyl)-2-phenylacetamide The title compound was prepared as described in EXAMPLE 3D, substituting EXAMPLE 397B for EXAMPLE 3C and phenylacetyl chloride for 2,6-difluorobenzoyl chloride. MS (ESI(+)) m/e 581 (M+H)+; ¹H-NMR (300 MHz, DMSO-d₆) □ 10.29 (s, 1H); 10.09 (s, 1H); 8.88 (d, 1H); 8.34 (m, 2H); 8.12 (d, 1H); 7.89 (s, 1H); 7.71 (d, 1H); 7.59 (t, 1H); 7.51 (m, 2H); 7.41 (t, 1H); 7.34-7.24 (m, 6H); 6.68 (d, 1H); 3.20 (s, 3H).

EXAMPLE 400

N-(3-morpholin-4-ylphenyl)-4-(6-(3-(5-phenyl-1,2,4-oxadiazol-3-yl)phenyl)imidazo[2,1-b][1,3]thiazol-5-yl)pyrimidin-2-amine A 2 mL vial was charged with EXAMPLE 396B (0.035 g, 0.057 mmol) in N-Methyl-2-pyrrolidinone (700 uL) and the mixture was heated at 98° C. for 10 h. The reaction mixture was cooled to room temperature, diluted with 1 mL 1:1 DMSO/MeOH and purified by reverse-phase HPLC on a Phenomenex C18 column (3×15 cm, 10 □m particle size) using a gradient of 50% to 100% acetonitrile:0.1% aqueous NH₄OH to give the title compound as an off white solid. MS (ESI(+)) m/e 599.2 (M+H)+; ¹H-NMR (300 MHz, DMSO-d₆) □ ppm 9.59 (s, 1 H) 8.78 (m, 1 H) 8.39 (m, 1 H) 8.31 (d, 1 H) 8.20 (m, 3 H) 7.88 (m, 1 H) 7.64-7.75 (m, 4 H) 7.53 (d, 1 H) 7.36 (m, 1 H) 7.18 (m, 2H) 6.65 (d, 1 H) 6.61 (m, 1 H) 3.73 (m, 4 H) 3.08 (m, 4 H).

EXAMPLE 401

N-(3-(5-(2-((3-(4-acetylpiperazin-1-yl)phenyl)amino)pyrimidin-4-yl)imidazo[2,1-b][1,3]thiazol-6-yl)phenyl)-2-phenylacetamide

EXAMPLE 401A

A 100 ml flask was charged with 1-(3-nitrophenyl)piperazine (1 g, 4.83 mmol) and dichloromethane (25 ml) under nitrogen. Pyridine (0.976 ml, 12.06 mmol) was added followed by N-methyl-2-pyrrolidinone (5 ml). Acetic anhydride (0.547 ml, 5.79 mmol) was added dropwise. After ca. 30 min additional N-methyl-2-pyrrolidinone (5 ml) was added and the mixture stirred for 1 h. The mixture was concentrated on high vacuum and the residue was taken up in ca. 10% MeOH/CH₂Cl₂ (100 ml) and washed with brine (100 ml). The layers were separated and the aqueous layer was extracted with CH₂Cl₂ (100 ml). The combined organic layers were dried over sodium sulfate, filtered and concentrated, and the crude was purified on an ISCO chromatography system using a silica gel cartridge (115 g) eluting with a step gradient of 0, 25, 50, 75% EtOAc/CH₂Cl₂ to give the title compound as an oil. MS (ESI(+)) m/e 581 (M+H)+.

EXAMPLE 401B

The title compound was prepared as described in EXAMPLE 1F, substituting EXAMPLE 401A for EXAMPLE 1E. MS (ESI(+)) m/e 220 (M+H)+.

EXAMPLE 401C

The title compound was prepared as described in EXAMPLE 12D, substituting EXAMPLE 401B for 3-morpholinoaniline. MS (ESI(+)) m/e 541 (M+H)+.

EXAMPLE 401D

The title compound was prepared as described in EXAMPLE 3C, substituting EXAMPLE 401C for EXAMPLE 3B. MS (ESI(+)) m/e 511 (M+H)+.

EXAMPLE 401E

The title compound was prepared as described in EXAMPLE 3D, substituting EXAMPLE 401D for EXAMPLE 3C and phenylacetyl chloride for 2,6-difluorobenzoyl chloride. MS (ESI(+)) m/e 629 (M+H)+, (ESI(−)) m/e 627 (M−H)⁻; ¹H NMR (300 MHz, DMSO-D6) □ ppm 10.29 (s, 1H), 9.59 (s, 1H), 8.81 (d, 1H), 8.26 (d, 1H), 7.84-7.92 (m, 1H), 7.71 (d, 1H), 7.50 (d, 1H), 7.13-7.44 (m, 9H), 6.64 (d, 1H), 6.58 (d, 1H), 3.64-3.69 (m, 4H), 3.59 (d, 3H), 3.03-3.20 (m, 4H), 2.04 (s, 3H).

EXAMPLE 402

N-(3-(5-(2-((3-(4-acetylpiperazin-1-yl)phenyl)amino)pyrimidin-4-yl)imidazo[2,1-b][1,3]thiazol-6-yl)phenyl)benzamide The title compound was prepared as described in EXAMPLE 3D, substituting EXAMPLE 401D for EXAMPLE 3C and benzoyl chloride for 2,6-difluorobenzoyl chloride. MS (ESI(+)) m/e 615 (M+H)+, (ESI(−)) m/e 613 (M−H)⁻; ¹H NMR (300 MHz, DMSO-D6) □ ppm 10.37 (s, 1H), 9.62 (s, 1H), 8.84 (d, 1H), 8.28 (d, 1H), 8.10 (t, 1H), 7.88-8.00 (m, 3H), 7.43-7.64 (m, 5H), 7.32-7.41 (m, 2H), 7.22-7.29 (m, 1H), 7.18 (t, 1H), 6.61-6.69 (m, 2H), 3.53-3.63 (m, 4H), 3.04-3.20 (m, 4H), 2.04 (s, 3H).

EXAMPLE 403

N-(3-(5-(2-((3-(4-acetylpiperazin-1-yl)phenyl)amino)pyrimidin-4-yl)imidazo[2,1-b][1,3]thiazol-6-yl)phenyl)-2-chlorobenzamide The title compound was prepared as described in EXAMPLE 3D, substituting EXAMPLE 401D for EXAMPLE 3C and 2-chlorobenzoyl chloride for 2,6-difluorobenzoyl chloride. MS (ESI(+)) m/e 649 (M+H)+, (ESI(−)) m/e 647 (M−H)⁻; 1H NMR (300 MHz, DMSO-D6) □ ppm 10.61 (s, 1H), 9.60 (s, 1H), 8.82 (d, 1H), 8.28 (d, 1H), 7.99-8.08 (m, 1H), 7.81 (d, 1H), 7.42-7.63 (m, 6H), 7.34-7.41 (m, 2H), 7.12-7.28 (m, 2H), 6.64 (d, 2H), 3.51-3.63 (m, 4H), 3.03-3.21 (m, 4H), 2.04 (s, 3H).

EXAMPLE 404

N-(3-(5-(2-((3-(4-acetylpiperazin-1-yl)phenyl)amino)pyrimidin-4-yl)imidazo[2,1-b][1,3]thiazol-6-yl)phenyl)-2,6-difluorobenzamide The title compound was prepared as described in EXAMPLE 3D, substituting EXAMPLE 401D for EXAMPLE 3C. MS (ESI(+)) m/e 651 (M+H)+, (ESI(−)) m/e 649 (M−H)⁻; ¹H NMR (300 MHz, DMSO-D6) □ ppm 10.91 (s, 1H), 9.61 (s, 1H), 8.81 (d, 1H), 8.28 (d, 1H), 7.96-8.03 (m, 1H), 7.78 (d, 1H), 7.53-7.67 (m, 1H), 7.44-7.53 (m, 2H), 7.40

(d, 2H), 7.12-7.30 (m, 4H), 6.58-6.72 (m, 2H), 3.51-3.64 (m, 4H), 3.03-3.22 (m, 4H), 2.04 (s, 3H).

EXAMPLE 405

4-(6-(3-(5-isobutyl-1,2,4-oxadiazol-3-yl)phenyl)imidazo[2,1-b][1,3]thiazol-5-yl)-N-(3-morpholin-4-ylphenyl)pyrimidin-2-amine

EXAMPLE 405A

The title compound was prepared as described in EXAMPLE 396B, substituting 3-methylbutanoyl chloride for benzoyl chloride. MS (ESI(+)) m/e 597 (M+H)$^+$.

EXAMPLE 405B

The title compound was prepared as described in EXAMPLE 400, substituting EXAMPLE 405A for EXAMPLE 396B. MS (ESI(+)) m/e 579.2 (M+H)$^+$; $^1$H-NMR (300 MHz, DMSO-d$_6$) □ ppm 9.59 (s, 1 H) 8.79 (m, 1 H) 8.28 (m, 2 H) 8.08 (m, 1 H) 7.85 (m, 1 H) 7.67 (m, 1 H) 7.52 (d, 1 H) 7.36 (m, 1 H) 7.13-7.24 (m, 2 H) 6.61 (m, 2 H) 3.73 (m, 4 H) 3.08 (m, 4 H) 2.91 (d, 2 H) 2.18 (m, 1 H) 0.99 (d, 6 H).

EXAMPLE 406

4-(6-(3-(5-ethyl-1,2,4-oxadiazol-3-yl)phenyl)imidazo[2,1-b][1,3]thiazol-5-yl)-N-(3-morpholin-4-ylphenyl)pyrimidin-2-amine

EXAMPLE 406A

The title compound was prepared as described in EXAMPLE 396B, substituting propionyl chloride for benzoyl chloride. MS (ESI(+)) m/e 569 (M+H)$^+$.

EXAMPLE 406B

The title compound was prepared as described in EXAMPLE 400, substituting EXAMPLE 406A for EXAMPLE 396B. MS (ESI(+)) m/e 551.1 (M+H)$^+$; $^1$H-NMR (300 MHz, DMSO-d$_6$) □ ppm 9.59 (s, 1 H) 8.78 (m, 1 H) 8.29 (m, 2 H) 8.07 (m, 1 H) 7.85 (m, 1 H) 7.67 (m, 1 H) 7.52 (d, 1 H) 7.36 (m, 1 H) 7.13-7.25 (m, 2 H) 6.61 (m, 2 H) 3.73 (m, 4 H) 2.98-3.10 (m, 6 H) 1.34 (t, 3 H).

EXAMPLE 407

(3R)-1-(3-(5-(2-((3-morpholin-4-ylphenyl)amino)pyrimidin-4-yl)imidazo[2,1-b][1,3]thiazol-6-yl)phenyl)-3-phenylpyrrolidin-2-one A 5 ml microwave vial was charged with EXAMPLE 389C (70 mg, 0.108 mmol), acetonitrile (4 ml) and water (0.5 ml). 2,2,2-Trifluoroacetic acid (0.042 ml, 0.542 mmol) was and the vial purged with argon, sealed and heated in a Biotage Initiator microwave at 150° C. for 10 min. The reaction mixture was concentrated by rotovap and the residue dissolved in methanol and purified by reverse phase HPLC on a Shimadzu LC10 HPLC system with a Phenominex Luna 10 micron C18(2) 100 150×30 mm column, eluting with CH$_3$CN/water/0.1% TFA to afford the title compound as a TFA salt. MS (DCI(+)) m/e 614 (M+H)$^+$; $^1$H NMR (300 MHz, DMSO-D6) □ ppm 9.56 (s, 1H), 8.84 (d, 1H), 8.27 (d, 1H), 7.95-8.04 (m, 1H), 7.75-7.86 (m, 1H), 7.46-7.55 (m, 2H), 7.12-7.45 (m, 9H), 6.56-6.65 (m, 2H), 3.91-4.01 (m, 3H), 3.69-3.78 (m, 4H), 3.03-3.12 (m, 4H), 2.52-2.64 (m, 1), 2.10-2.31 (m, 1H).

EXAMPLE 408

2,6-difluoro-N-(3-(5-(2-((3-((4-(2-hydroxyethyl)piperazin-1-yl)methyl)phenyl)amino)pyrimidin-4-yl)imidazo[2,1-b][1,3]thiazol-6-yl)phenyl)benzamide

EXAMPLE 408A

The title compound was prepared as described in EXAMPLE 376A, substituting N-(2-hydroxyethyl)piperazine for N-methylpiperazine. MS (ESI(+)) m/e 266 (M+H)$^+$.

EXAMPLE 408B

The title compound was prepared as described in EXAMPLE 1F, substituting EXAMPLE 408A for EXAMPLE 1E. MS (ESI(+)) m/e 236 (M+H)$^+$.

EXAMPLE 408C

The title compound was prepared as described in EXAMPLE 12D, substituting EXAMPLE 408B for 3-morpholinoaniline. MS (ESI(+)) m/e 557 (M+H)$^+$.

EXAMPLE 408D

The title compound was prepared as described in EXAMPLE 1F, substituting EXAMPLE 408C for EXAMPLE 1E. MS (ESI(+)) m/e 527 (M+H)$^+$.

EXAMPLE 408E

The title compound was prepared as described in EXAMPLE 3D, substituting EXAMPLE 408D for EXAMPLE 3C. MS (ESI(+)) m/e 667 (M+H)$^+$, (ESI(–)) m/e 665 (M–H)$^-$; $^1$H NMR (300 MHz, DMSO-D6) □ 10.92 (s, 1 H), 9.74 (s, 1 H), 8.84 (d, 1 H), 8.30 (d, 1H), 8.04 (t, 1 H), 7.71-7.81 (m, 2 H), 7.67 (dt, 1 H), 7.56-7.64 (m, 1 H), 7.45-7.53 (m, 2H), 7.36-7.42 (m, 1 H), 7.33 (t, 1 H), 7.20-7.29 (m, 2 H), 6.97-7.03 (m, 1 H), 6.66 (d, 1 H), 3.67-3.82 (m, 5 H), 3.20-2.93 (m, 9 H).

EXAMPLE 409

N-(3-(5-(2-((3-((4-(2-hydroxyethyl)piperazin-1-yl)methyl)phenyl)amino)pyrimidin-4-yl)imidazo[2,1-b][1,3]thiazol-6-yl)phenyl)-2-phenylacetamide The title compound was prepared as described in EXAMPLE 3D, substituting EXAMPLE 408D for EXAMPLE 3C and phenylacetyl chloride for 2,6-difluorobenzoyl chloride. MS (ESI(+)) m/e 645 (M+H)$^+$, (ESI(–)) m/e 643 (M–H)$^-$; $^1$H NMR (300 MHz, DMSO-D6) □ 10.29 (s, 1 H), 9.73 (s, 1 H), 8.84 (d, 1 H), 8.27 (d, 1 H), 7.92 (t, 1 H), 7.76 (s, 1 H), 7.68 (dd, 1 H), 7.51 (d, 1 H), 7.41 (t, 1 H), 7.20-7.36 (m, 11 H), 7.00 (d, 1 H), 6.62 (d, 1 H), 3.68-3.72 (m, 4 H), 3.65 (s, 3 H), 3.56 (s, 3 H), 3.20-2.93 (m, 7 H).

EXAMPLE 410

2,6-difluoro-N-(3-(5-(2-((3-((4-(3-methoxypropyl)piperazin-1-yl)methyl)phenyl)amino)pyrimidin-4-yl)imidazo[2,1-b][1,3]thiazol-6-yl)phenyl)benzamide

EXAMPLE 410A

The title compound was prepared as described in EXAMPLE 376A, substituting N-(3-methoxypropyl)piperazine for N-methylpiperazine. MS (ESI(+)) m/e 294 (M+H)$^+$.

EXAMPLE 410B

The title compound was prepared as described in EXAMPLE 1F, substituting EXAMPLE 410A for EXAMPLE 1E. MS (ESI(+)) m/e 264 (M+H)$^+$.

EXAMPLE 410C

The title compound was prepared as described in EXAMPLE 12D, substituting EXAMPLE 410B for 3-morpholinoaniline. MS (ESI(+)) m/e 585 (M+H)$^+$.

EXAMPLE 410D

The title compound was prepared as described in EXAMPLE 1F, substituting EXAMPLE 410C for EXAMPLE 1E. MS (ESI(+)) m/e 555 (M+H)$^+$.

EXAMPLE 410E

The title compound was prepared as described in EXAMPLE 3D, substituting EXAMPLE 410D for EXAMPLE 3C. MS (ESI(+)) m/e 695 (M+H)$^+$, (ESI(−)) m/e 693 (M−H)$^-$; $^1$H NMR (300 MHz, DMSO-D6) ☐ 10.93 (s, 1 H), 9.76 (s, 1 H), 8.83 (d, 1 H), 8.31 (d, 1 H), 8.04 (t, 1 H), 7.77 (s, 1 H), 7.74 (ddd, 1 H), 7.64-7.70 (m, 1 H), 7.60 (ddd, 1 H), 7.52 (d, 1 H), 7.44-7.50 (m, 1 H), 7.39 (ddd, 1 H), 7.33 (t, 1 H), 7.23-7.29 (m, 2 H), 6.99 (d, 1 H), 6.66 (d, 1 H), 3.36 (t, 4 H), 3.23 (s, 3 H), 2.99-3.13 (m, 4 H).

EXAMPLE 411

2-fluoro-N-(3-(5-(2-((3-((4-(3-methoxypropyl)piperazin-1-yl)methyl)phenyl)amino)pyrimidin-4-yl)imidazo[2,1-b][1,3]thiazol-6-yl)phenyl)benzamide The title compound was prepared as described in EXAMPLE 3D, substituting EXAMPLE 410D for EXAMPLE 3C and 2-fluorobenzoyl chloride for 2,6-difluorobenzoyl chloride. MS (ESI(+)) m/e 677 (M+H)$^+$, (ESI(−)) m/e 675 (M−H)$^-$; $^1$H NMR (300 MHz, DMSO-D6) ☐ 10.55 (s, 1 H), 9.75 (s, 1 H), 8.85 (d, 1 H), 8.30 (d, 1 H), 8.04-8.10 (m, 1 H), 7.73-7.84 (m, 2 H), 7.63-7.72 (m, 2 H), 7.54-7.64 (m, 1 H), 7.52 (d, 1 H), 7.47 (t, 1 H), 7.28-7.40 (m, 4 H), 6.99 (d, 1 H), 6.66 (d, 1 H), 3.36 (t, 4 H), 3.23 (s, 3 H), 2.96-3.15 (m, 5H), 1.76-1.89 (m, 2 H).

EXAMPLE 412

2-chloro-N-(3-(5-(2-((3-((4-(3-methoxypropyl)piperazin-1-yl)methyl)phenyl)amino)pyrimidin-4-yl)imidazo[2,1-b][1,3]thiazol-6-yl)phenyl)benzamide The title compound was prepared as described in EXAMPLE 3D, substituting EXAMPLE 410D for EXAMPLE 3C and 2-chlorobenzoyl chloride for 2,6-difluorobenzoyl chloride. MS (ESI(+)) m/e 693 (M+H)$^+$, (ESI(−)) m/e 691 (M−H)$^-$; $^1$H NMR (300 MHz, DMSO-D6) ☐ 10.63 (s, 1 H), 9.75 (s, 1 H), 8.84 (d, 1 H), 8.30 (d, 1 H), 8.07 (t, 1 H), 7.74-7.81 (m, 1 H), 7.64-7.70 (m, 1 H), 7.39-7.62 (m, 8 H), 7.29-7.39 (m, 2 H), 6.99 (d, 1 H), 6.67 (d, 1 H), 3.67-3.84 (m, 3 H), 3.34-3.39 (m, 4 H), 3.23 (s, 3 H), 2.97-3.13 (m, 4 H), 1.83 (dt, 2 H).

EXAMPLE 413

N-(3-(5-(2-((3-((4-(3-methoxypropyl)piperazin-1-yl)methyl)phenyl)amino)pyrimidin-4-yl)imidazo[2,1-b][1,3]thiazol-6-yl)phenyl)-2-phenylacetamide The title compound was prepared as described in EXAMPLE 3D, substituting EXAMPLE 410D for EXAMPLE 3C and phenylacetyl chloride for 2,6-difluorobenzoyl chloride. MS (ESI(+)) m/e 673 (M+H)$^+$, (ESI(−)) m/e 671 (M−H)$^-$; $^1$H NMR (300 MHz, DMSO-D6) ☐ 10.31 (s, 1 H), 9.76 (s, 1 H), 8.84 (d, 1 H), 8.27 (d, 1 H), 7.93 (t, 1 H), 7.78 (s, 1 H), 7.64-7.72 (m, 2 H), 7.51 (d, 1 H), 7.35-7.45 (m, 1 H), 7.19-7.35 (m, 10 H), 7.01 (d, 1 H), 6.62 (d, 1 H), 3.75-3.86 (m, 2 H), 3.65 (s, 2 H), 3.56 (s, 3 H), 3.36 (t, 3 H), 3.23 (s, 3 H), 3.00-3.13 (m, 4 H), 1.76-1.90 (m, 2 H).

EXAMPLE 414

N-(3-(5-(2-((3-((4-(3-methoxypropyl)piperazin-1-yl)methyl)phenyl)amino)pyrimidin-4-yl)imidazo[2,1-b][1,3]thiazol-6-yl)phenyl)-N'-phenylurea The title compound was prepared as described in EXAMPLE 13, substituting EXAMPLE 410D for EXAMPLE 3C. MS (ESI(+)) m/e 674 (M+H)$^+$, (ESI(−)) m/e 672 (M−H)$^-$; $^1$H NMR (300 MHz, DMSO-D6) ☐ 9.74 (s, 1 H), 8.86 (s, 2 H), 8.72 (s, 1 H), 8.30 (d, 1 H), 7.73-7.82 (m, 2 H), 7.63-7.71 (m, 1 H), 7.50 (ddd, 2 H), 7.41-7.47 (m, 2 H), 7.18-7.41 (m, 5 H), 6.90-7.03 (m, 2 H), 6.66 (d, 1 H), 3.56 (s, 2 H), 3.36 (t, 4 H), 3.23 (s, 3 H), 2.98-3.14 (m, 5 H), 1.77-1.89 (m, 1 H).

EXAMPLE 415

N-(3-(5-(2-(1H-indazol-5-ylamino)pyrimidin-4-yl)imidazo[2,1-b][1,3]thiazol-6-yl)phenyl)-2-phenylacetamide

EXAMPLE 415A

The title compound was prepared as described in EXAMPLE 12D, substituting 5-aminoindazole for 3-morpholinoaniline. MS (ESI(+)) m/e 455 (M+H)$^+$.

EXAMPLE 415B

The title compound was prepared as described in EXAMPLE 1F, substituting EXAMPLE 415A for EXAMPLE 1E. MS (ESI(+)) m/e 425 (M+H)$^+$.

EXAMPLE 415C

The title compound was prepared as described in EXAMPLE 3D, substituting EXAMPLE 415B for EXAMPLE 3C and phenylacetyl chloride for 2,6-difluorobenzoyl chloride. MS (ESI+), m/e 543.1; $^1$H-NMR (500 MHz, DMSO-d$_6$) ☐ ppm 10.30 (s, 1 H), 9.72 (s, 1 H), 8.75

(bs, 1 H), 8.24 (d, 1 H), 8.17 (s, 1 H), 8.01 (s, 1 H), 7.89 (s, 1 H), 7.71 (d, 1 H), 7.51-7.56 (m, 2 H), 7.40-7.44 (m, 2 H), 7.23-7.35 (m, 6 H), 6.56 (d, 1 H), 3.65 (s, 2 H).

EXAMPLE 416

N-(3-(5-(2-(1H-indazol-5-ylamino)pyrimidin-4-yl)imidazo[2,1-b][1,3]thiazol-6-yl)phenyl)benzamide The title compound was prepared as described in EXAMPLE 3D, substituting EXAMPLE 415B for EXAMPLE 3C and benzoyl chloride for 2,6-difluorobenzoyl chloride. MS (ESI+), m/e 529.1; $^1$H-NMR (500 MHz, DMSO-$d_6$) ppm 10.38 (s, 1 H), 9.71 (s, 1 H), 8.80 (bs, 1 H), 8.27 (d, 1 H), 8.18 (s, 1 H), 8.11 (s, 1 H), 8.01 (s, 1 H), 7.95 (d, 2 H), 7.92 (d, 1 H), 7.46-7.61 (m, 7 H), 7.36 (d, 1 H), 6.62 (d, 1 H).

EXAMPLE 417

2,6-difluoro-N-(3-(5-(2-(1H-indazol-5-ylamino)pyrimidin-4-yl)imidazo[2,1-b][1,3]thiazol-6-yl)phenyl)benzamide The title compound was prepared as described in EXAMPLE 3D, substituting EXAMPLE 415B for EXAMPLE 3C. MS (ESI+), m/e 565.1; $^1$H-NMR (500 MHz, DMSO-$d_6$) ppm 10.93 (s, 1 H), 9.73 (s, 1 H), 8.75 (bs, 1 H), 8.27 (d, 1 H), 8.17 (s, 1 H), 8.01 (d, 2 H), 7.78 (d, 1 H), 7.45-7.63 (m, 5 H), 7.40 (d, 1 H), 7.26 (t, 2 H), 6.60 (d, 1 H).

EXAMPLE 418

2-chloro-6-fluoro-N-(3-(5-(2-(1H-indazol-5-ylamino)pyrimidin-4-yl)imidazo[2,1-b][1,3]thiazol-6-yl)phenyl)benzamide The title compound was prepared as described in EXAMPLE 3D, substituting EXAMPLE 415B for EXAMPLE 3C and 2-chloro-6-fluorobenzoyl chloride for 2,6-difluorobenzoyl chloride. MS (ESI+), m/e 581.1; $^1$H-NMR (500 MHz, DMSO-$d_6$) ppm 10.91 (s, 1 H), 9.70 (s, 1 H), 8.75 (bs, 1 H), 8.27 (d, 1 H), 8.18 (s, 1 H), 8.00 (s, 2 H), 7.76 (d, 1 H), 7.38-7.58 (m, 8 H), 6.61 (d, 1 H).

EXAMPLE 419

5-fluoro-N-(3-(5-(2-(1H-indazol-5-ylamino)pyrimidin-4-yl)imidazo[2,1-b][1,3]thiazol-6-yl)phenyl)-2-methylbenzamide The title compound was prepared as described in EXAMPLE 3D, substituting EXAMPLE 415B for EXAMPLE 3C and 2-methyl-5-fluorobenzoyl chloride for 2,6-difluorobenzoyl chloride. MS (ESI+), m/e 561.1; $^1$H-NMR (500 MHz, DMSO-$d_6$) ppm 10.48 (s, 1 H), 9.69 (s, 1 H), 8.75 (bs, 1 H), 8.28 (d, 1 H), 8.17 (s, 1 H), 8.06 (s, 1 H), 8.00 (s, 1 H), 7.82 (d, 1 H), 7.40-7.56 (m, 4 H), 7.31-7.36 (m, 3 H), 7.22-7.26 (m, 1 H), 6.62 (d, 1 H), 2.35 (s, 3 H).

EXAMPLE 420

2-phenyl-N-(3-(5-(2-((2-(trifluoromethyl)-1H-benzimidazol-5-yl)amino)pyrimidin-4-yl)imidazo[2,1-b][1,3]thiazol-6-yl)phenyl)acetamide

EXAMPLE 420A

The title compound was prepared as described in EXAMPLE 12D, substituting 5-amino-2-trifluoromethylbenzimidazole for 3-morpholinoaniline. MS (ESI(+)) m/e 523 (M+H)$^+$.

EXAMPLE 420B

The title compound was prepared as described in EXAMPLE 1F, substituting EXAMPLE 420A for EXAMPLE 1E. MS (ESI(+)) m/e 493 (M+H)$^+$.

EXAMPLE 420C

The title compound was prepared as described in EXAMPLE 3D, substituting EXAMPLE 420B for EXAMPLE 3C and phenylacetyl chloride for 2,6-difluorobenzoyl chloride. MS (ESI+), m/e 611.1; $^1$H-NMR (500 MHz, DMSO-$d_6$) ppm 10.29 (s, 1 H), 9.89 (s, 1 H), 8.86 (bs, 1 H), 8.35 (s, 1 H), 8.31 (d, 1 H), 7.89 (s, 1 H), 7.67-7.64 (m, 2 H), 7.57-7.62 (m, 1 H), 7.50 (d, 1 H), 7.41 (t, 1 H), 7.29-7.35 (m, 5 H), 7.23-7.26 (m, 1 H), 6.61 (d, 1 H), 3.65 (s, 2 H).

EXAMPLE 421

N-(3-(5-(2-((2-(trifluoromethyl)-1H-benzimidazol-5-yl)amino)pyrimidin-4-yl)imidazo[2,1-b][1,3]thiazol-6-yl)phenyl)benzamide The title compound was prepared as described in EXAMPLE 3D, substituting EXAMPLE 420B for EXAMPLE 3C and benzoyl chloride for 2,6-difluorobenzoyl chloride. MS (ESI+), m/e 597.2; $^1$H-NMR (500 MHz, DMSO-$d_6$) ppm 10.38 (s, 1 H), 9.90 (s, 1 H), 8.88 (bs, 1 H), 8.34 (s, 1 H), 8.33 (d, 1 H), 8.10 (s, 1 H), 7.96 (d, 2 H), 7.94 (d, 1 H), 7.69 (d, 1 H), 7.46-7.61 (m, 6 H), 7.37 (d, 1 H), 6.67 (d, 1 H).

EXAMPLE 422

2,6-difluoro-N-(3-(5-(2-((2-(trifluoromethyl)-1H-benzimidazol-5-yl)amino)pyrimidin-4-yl)imidazo[2,1-b][1,3]thiazol-6-yl)phenyl)benzamide The title compound was prepared as described in EXAMPLE 3D, substituting EXAMPLE 420B for EXAMPLE 3C. MS (ESI+), m/e 633.1; $^1$H-NMR (500 MHz, DMSO-$d_6$) ppm 10.92 (s, 1 H), 9.90 (s, 1 H), 8.86 (bs, 1 H), 8.34 (d, 2 H), 7.99 (s, 1 H), 7.80 (d, 1 H), 7.70 (d, 1 H), 7.57-7.63 (m, 2 H), 7.48-7.52 (m, 2 H), 7.41 (d, 1 H), 7.26 (t, 2 H), 6.66 (d, 1 H).

EXAMPLE 423

2-chloro-6-fluoro-N-(3-(5-(2-((2-(trifluoromethyl)-1H-benzimidazol-5-yl)amino)pyrimidin-4-yl)imidazo[2,1-b][1,3]thiazol-6-yl)phenyl)benzamide The title compound was prepared as described in EXAMPLE 3D, substituting EXAMPLE 420B for EXAMPLE 3C and 2-chloro-6-fluorobenzoyl chloride for 2,6-difluorobenzoyl chloride. MS (ESI+), m/e 649.1; $^1$H-NMR (500 MHz, DMSO-d$_6$) ☐ ppm 10.91 (s, 1 H), 9.91 (s, 1 H), 8.86 (bs, 1 H), 8.34 (d, 2 H), 8.01 (s, 1 H), 7.78 (d, 1 H), 7.69 (d, 1 H), 7.38-7.60 (m, 7 H), 6.67 (d, 1 H).

EXAMPLE 424

5-fluoro-2-methyl-N-(3-(5-(2-((2-(trifluoromethyl)-1H-benzimidazol-5-yl)amino)pyrimidin-4-yl)imidazo[2,1-b][1,3]thiazol-6-yl)phenyl)benzamide The title compound was prepared as described in EXAMPLE 3D, substituting EXAMPLE 420B for EXAMPLE 3C and 2-methyl-5-fluorobenzoyl chloride for 2,6-difluorobenzoyl chloride. MS (ESI+), m/e 629.2; $^1$H-NMR (500 MHz, DMSO-d$_6$) ☐ ppm 10.48 (s, 1 H), 9.90 (s, 1 H), 8.87 (bs, 1 H), 8.34 (d, 2 H), 8.06 (s, 1 H), 7.84 (d, 1 H), 7.69 (d, 1 H), 7.59 (d, 1 H), 7.51 (d, 1 H), 7.47 (t, 1 H), 7.34-7.38 (m, 3 H), 7.24 (d.t, 1 H), 6.67 (d, 1 H).

EXAMPLE 425

1-(3-(5-(2-((4-morpholin-4-ylphenyl)amino)pyrimidin-4-yl)imidazo[2,1-b][1,3]thiazol-6-yl)phenyl)-3-phenylpyrrolidin-2-one

EXAMPLE 425A

The title compound was prepared as described in EXAMPLE 355, substituting EXAMPLE 389B for thiophene-2-carbaldehyde. MS (ESI(+)) m/e 646 (M+H)$^+$.

EXAMPLE 425B

The title compound was prepared as described in EXAMPLE 407, substituting EXAMPLE 425A for EXAMPLE 389C. MS (ESI(+)) m/e 614 (M+H)$^+$; $^1$H NMR (300 MHz, DMSO-D6) ☐ ppm 9.43 (s, 1H), 8.77 (s, 1H), 8.21 (d, 1H), 7.92-8.05 (m, 1H), 7.76-7.86 (m, 1H), 7.44-7.59 (m, 4H), 7.22-7.43 (m, 6H), 6.92 (d, 2H), 6.55 (d, 1H), 3.89-4.02 (m, 3H), 3.68-3.78 (m, 4H), 3.00-3.11 (m, 4H), 2.52-2.65 (m, 1H), 2.11-2.29 (m, 1H).

EXAMPLE 426

3-(5-(2-((3-morpholin-4-ylphenyl)amino)pyrimidin-4-yl)imidazo[2,1-b][1,3]thiazol-6-yl)-N'-(propionyloxy)benzenecarboximidamide The title compound was prepared as described in EXAMPLE 396B, substituting propionyl chloride for benzoyl chloride. MS (ESI(+)) m/e 569.2 (M+H)$^+$; $^1$H-NMR (300 MHz, DMSO-d$_6$) ☐ ppm 9.57 (s, 1 H) 8.83 (m, 1 H) 8.27 (d, 1 H) 8.02 (m, 1 H) 7.81 (m, 1 H) 7.74 (m, 1 H) 7.53 (m, 2 H) 7.36 (m, 1 H) 7.13-7.25 (m, 2 H) 6.84 (br.s, 2 H) 6.61 (m, 1 H) 6.54 (d, 1 H) 3.74 (m, 4 H) 3.08 (m, 4 H) 2.49 (q, 2 H) 1.09 (t, 3 H).

EXAMPLE 427

N'-((3-methylbutanoyl)oxy)-3-(5-(2-((3-morpholin-4-ylphenyl)amino)pyrimidin-4-yl)imidazo[2,1-b][1,3]thiazol-6-yl)benzenecarboximidamide The title compound was prepared as described in EXAMPLE 396B, substituting 3-methylbutyryl chloride for benzoyl chloride. MS (ESI(+)) m/e 597.3 (M+H)$^+$; $^1$H-NMR (300 MHz, DMSO-d$_6$) ☐ ppm 9.57 (s, 1 H) 8.83 (m, 1 H) 8.27 (d, 1 H) 8.02 (m, 1 H) 7.81 (m, 1 H) 7.74 (m, 1 H) 7.53 (m, 2 H) 7.35 (m, 1 H) 7.13-7.25 (m, 2 H) 6.83 (br.s, 2 H) 6.61 (m, 1 H) 6.54 (d, 1 H) 3.74 (m, 4 H) 3.08 (m, 4 H) 2.34 (d, 2 H) 2.07 (m, 1 H) 0.94 (d, 6 H).

EXAMPLE 428

3-(5-(2-((3-morpholin-4-ylphenyl)amino)pyrimidin-4-yl)imidazo[2,1-b][1,3]thiazol-6-yl)-N'-((phenylacetyl)oxy)benzenecarboximidamide The title compound was prepared as described in EXAMPLE 396B, substituting phenylacetyl chloride for benzoyl chloride. MS (ESI(+)) m/e 631.2 (M+H)$^+$; $^1$H-NMR (300 MHz, DMSO-d$_6$) ☐ ppm 9.56 (s, 1 H) 8.83 (m, 1 H) 8.26 (d, 1 H) 8.02 (m, 1 H) 7.80 (m, 1 H) 7.73 (m, 1 H) 7.53 (m, 2 H) 7.34 (m, 5 H) 7.12-7.29 (m, 3 H) 6.93 (br.s, 2 H) 6.61 (m, 1 H) 6.53 (d, 1 H) 3.82 (s, 2 H) 3.74 (m, 4 H) 3.08 (m, 4 H).

EXAMPLE 429

3-methoxy-N-(3-(5-(2-((4-morpholin-4-ylphenyl)amino)pyrimidin-4-yl)imidazo[2,1-b][1,3]thiazol-6-yl)phenyl)benzamide The title compound was prepared as described in EXAMPLE 3D, substituting 3-methoxybenzoyl chloride for 2,6-difluorobenzoyl chloride. MS (ESI(+)) m/e 604.3 (M+H)$^+$; $^1$H-NMR (300 MHz, CHLOROFORM-D) ☐ ppm 11.94 (br.s, 1 H) 8.09 (d, 1 H) 8.00 (m, 1 H) 7.94 (s, 1 H) 7.81 (d, 1 H) 7.68 (m, 1 H) 7.54 (t, 1 H) 7.44 (m, 6 H) 7.08 (m, 3 H) 6.87 (m, 2 H) 3.95 (m, 4 H) 3.89 (s, 3 H) 3.26 (m, 4 H).

EXAMPLE 430

2-chloro-6-fluoro-N-(3-(5-(2-((2-pyridin-3-yl-1,3-benzoxazol-5-yl)amino)pyrimidin-4-yl)imidazo[2,1-b][1,3]thiazol-6-yl)phenyl)benzamide

EXAMPLE 430A

The title compound was prepared as described in EXAMPLE 12D, substituting 2-(pyridin-3-yl)benzo[d]oxazol-5-amine for 3-morpholinoaniline. MS (ESI(+)) m/e 533 (M+H)$^+$.

EXAMPLE 430B

The title compound was prepared as described in EXAMPLE 1F, substituting EXAMPLE 430A for EXAMPLE 1E. MS (ESI(+)) m/e 503 (M+H)$^+$.

EXAMPLE 430C

The title compound was prepared as described in EXAMPLE 3D, substituting EXAMPLE 430B for EXAMPLE 3C and 2-chloro-6-fluorobenzoyl chloride for 2,6-difluorobenzoyl chloride. MS (ESI+), m/e 659.1; $^1$H-NMR (500 MHz, DMSO-d$_6$) ☐ ppm 10.90 (s, 1 H), 9.90

(s, 1 H), 9.36 (s, 1 H), 8.81 (d, 2 H), 8.55 (dd, 1 H), 8.34 (d, 2 H), 8.02 (s, 1 H), 7.78 (d, 2 H), 7.66-7.73 (m, 2 H), 7.37-7.58 (m, 6 H), 6.69 (d, 1 H).

EXAMPLE 431

N-(3-(5-(2-((2-methyl-1,3-benzothiazol-5-yl)amino)pyrimidin-4-yl)imidazo[2,1-b][1,3]thiazol-6-yl)phenyl)-2-phenylacetamide

EXAMPLE 431A

The title compound was prepared as described in EXAMPLE 12D, substituting 5-amino-2-methylbenzothiazole for 3-morpholinoaniline. MS (ESI(+)) m/e 486 (M+H)+.

EXAMPLE 431B

The title compound was prepared as described in EXAMPLE 2A, substituting EXAMPLE 431A for EXAMPLE 1A. MS (ESI(+)) m/e 456 (M+H)+.

EXAMPLE 431C

The title compound was prepared as described in EXAMPLE 3D, substituting EXAMPLE 431B for EXAMPLE 3C and phenylacetyl chloride for 2,6-difluorobenzoyl chloride. MS (ESI+), m/e 574.1; $^1$H-NMR (500 MHz, DMSO-$d_6$) ☐ ppm 10.28 (s, 1 H), 9.87 (s, 1 H), 8.84 (bs, 1 H), 8.44 (s, 1 H), 8.31 (d, 1 H), 7.92 (d, 1 H), 7.89 (s, 1 H), 7.70-7.72 (m, 2 H), 7.48 (d, 1 H), 7.41 (t, 1 H), 7.30-7.36 (m, 5 H), 7.22-7.28 (m, 1 H), 6.62 (d, 1 H), 3.65 (s, 2 H), 2.78 (s, 3 H).

EXAMPLE 432

N-(3-(5-(2-((2-methyl-1,3-benzothiazol-5-yl)amino)pyrimidin-4-yl)imidazo[2,1-b][1,3]thiazol-6-yl)phenyl)benzamide The title compound was prepared as described in EXAMPLE 3D, substituting EXAMPLE 431B for EXAMPLE 3C and benzoyl chloride for 2,6-difluorobenzoyl chloride. MS (ESI+), m/e 560.1; $^1$H-NMR (500 MHz, DMSO-$d_6$) ☐ ppm 10.36 (s, 1 H), 9.88 (s, 1 H), 8.87 (bs, 1 H), 8.44 (s, 1 H), 8.34 (d, 1 H), 8.10 (s, 1 H), 7.91-7.97 (m, 4 H), 7.72 (dd, 1 H), 7.46-7.60 (m, 5 H), 7.37 (d, 1 H), 6.68 (d, 1 H), 2.78 (s, 3 H).

EXAMPLE 433

2,6-difluoro-N-(3-(5-(2-((2-methyl-1,3-benzothiazol-5-yl)amino)pyrimidin-4-yl)imidazo[2,1-b][1,3]thiazol-6-yl)phenyl)benzamide The title compound was prepared as described in EXAMPLE 3D, substituting EXAMPLE 431B for EXAMPLE 3C. MS (ESI+), m/e 596.1; $^1$H-NMR (500 MHz, DMSO-$d_6$) ☐ ppm 10.90 (s, 1 H), 9.87 (s, 1 H), 8.85 (bs, 1 H), 8.44 (s, 1 H), 8.34 (d, 1 H), 7.99 (s, 1 H), 7.91 (d, 1 H), 7.98 (d, 1 H), 7.71 (dd, 1 H), 7.58 (t, 1 H), 7.44-7.50 (m, 2 H), 7.41 (d, 1 H), 7.23-7.27 (m, 2 H), 6.68 (d, 1 H), 2.78 (s, 3 H).

EXAMPLE 434

5-fluoro-2-methyl-N-(3-(5-(2-((2-methyl-1,3-benzothiazol-5-yl)amino)pyrimidin-4-yl)imidazo[2,1-b][1,3]thiazol-6-yl)phenyl)benzamide The title compound was prepared as described in EXAMPLE 3D, substituting EXAMPLE 431B for EXAMPLE 3C and 2-methyl-5-fluorobenzoyl chloride for 2,6-difluorobenzoyl chloride. MS (ESI+), m/e 592.1; $^1$H-NMR (500 MHz, DMSO-$d_6$) ☐ ppm 10.46 (s, 1 H), 9.87 (s, 1 H), 8.85 (bs, 1 H), 8.44 (s, 1 H), 8.34 (d, 1 H), 8.06 (s, 1 H), 7.91 (d, 1 H), 7.83 (d, 1 H), 7.71 (dd, 1 H), 7.49 (d, 1 H), 7.47 (t, 1 H), 7.33-7.38 (m, 3 H), 7.23 (dt, 1 H), 6.68 (d, 1 H), 2.78 (s, 3 H), 2.36 (s, 3 H).

EXAMPLE 435

N-(3-(5-(2-((2-oxo-2,3-dihydro-1H-indol-5-yl)amino)pyrimidin-4-yl)imidazo[2,1-b][1,3]thiazol-6-yl)phenyl)benzamide

EXAMPLE 435A

The title compound was prepared as described in EXAMPLE 1F, substituting 5-nitroindolin-2-one for EXAMPLE 1E. MS (ESI(+)) m/e 149 (M+H)+.

EXAMPLE 435B

The title compound was prepared as described in EXAMPLE 12D, substituting EXAMPLE 435A for 3-morpholinoaniline. MS (ESI(+)) m/e 470 (M+H)+.

EXAMPLE 435C

The title compound was prepared as described in EXAMPLE 1F, substituting EXAMPLE 435B for EXAMPLE 1E. MS (ESI(+)) m/e 440 (M+H)+.

EXAMPLE 435D

The title compound was prepared as described in EXAMPLE 3D, substituting EXAMPLE 435C for EXAMPLE 3C and benzoyl chloride for 2,6-difluorobenzoyl chloride. MS (ESI+), m/e 544.1; $^1$H-NMR (500 MHz, DMSO-$d_6$) ☐ ppm 10.35 (s, 1 H), 10.26 (s, 1 H), 9.54 (s, 1 H), 8.76 (bs, 1 H), 8.23 (s, 1 H), 8.09 (s, 1 H), 7.96 (d, 2 H), 7.92 (d, 1 H), 7.33-7.63 (m, 8 H), 6.78 (d, 1 H), 6.59 (d, 1 H), 2.47 (s, 2 H).

EXAMPLE 436

2-chloro-6-fluoro-N-(3-(5-(2-((2-oxo-2,3-dihydro-1H-indol-5-yl)amino)pyrimidin-4-yl)imidazo[2,1-b][1,3]thiazol-6-yl)phenyl)benzamide The title compound was prepared as described in EXAMPLE 3D, substituting EXAMPLE 435C for EXAMPLE 3C and 2-chloro-6-fluorobenzoyl chloride for 2,6-difluorobenzoyl chloride. MS (ESI+), m/e 596.1; $^1$H-NMR (500 MHz, DMSO-$d_6$) ☐ ppm 10.88 (s, 1 H), 10.26 (s, 1 H), 9.54 (s, 1 H), 8.73 (bs, 1 H), 8.23 (d, 1 H), 7.99 (s, 1 H), 7.77 (d, 1 H), 7.65 (s, 1 H), 7.36-7.58 (m, 8 H), 6.78 (d, 1 H), 6.59 (d, 1 H), 2.47 (s, 2 H).

EXAMPLE 437

N-(3-(5-(2-((3-(3-oxomorpholin-4-yl)phenyl)amino)pyrimidin-4-yl)imidazo[2,1-b][1,3]thiazol-6-yl)phenyl)-2-phenylacetamide

EXAMPLE 437A

A 100 ml flask was charged with 1-iodo-3-nitrobenzene (2.490 g, 10.000 mmol), morpholin-3-one (1.213 g, 12.00 mmol), potassium phosphate (4.25 g, 20.00 mmol), toluene (65 ml) and $N^1,N^2$-dimethylethane-1,2-diamine (0.108 ml, 1.000 mmol). The flask was placed under an argon atmosphere and copper(I) iodide (0.095 g, 0.500 mmol) was added. The mixture was heated to 100° C. under nitrogen for 62 h. The reaction mixture was cooled and diluted with water (75 ml) and $CH_2Cl_2$ (75 ml) which formed an emulsion. This was diluted further with $CH_2Cl_2$ (100 ml) and brine (100 ml), filtered through celite and the layers separated. The aqueous layer extracted again with $CH_2Cl_2$ (100 ml). The layers separated and the aqueous layer extracted again with $CH_2Cl_2$ (100 ml). The combined organic layers were dried over sodium sulfate, filtered and concentrated to provide the crude product which was purified on an ISCO chromatography system on a silica gel cartridge (150 g) eluted with a step gradient 0, 10, 20, 40% EtOAc/$CH_2Cl_2$ to provide the title compound. MS (DCI(+)) m/e 223 (M+H)$^+$.

EXAMPLE 437B

The title compound was prepared as described in EXAMPLE 1F, substituting EXAMPLE 437A for EXAMPLE 1E. MS (DCI(+)) m/e 193 (M+H)$^+$.

EXAMPLE 437C

The title compound was prepared as described in EXAMPLE 12D, substituting EXAMPLE 437B for 3-morpholinoaniline. MS (ESI(+)) m/e 514 (M+H)$^+$.

EXAMPLE 437D

The title compound was prepared as described in EXAMPLE 1F, substituting EXAMPLE 437C for EXAMPLE 1E. MS (ESI(+)) m/e 484 (M+H)$^+$.

EXAMPLE 437E

The title compound was prepared as described in EXAMPLE 3D, substituting EXAMPLE 437D for EXAMPLE 3C and phenylacetyl chloride for 2,6-difluorobenzoyl chloride. MS (ESI(+)) m/e 602 (M+H)$^+$, (ESI(−)) m/e 600 (M−H)$^-$; 1H NMR (300 MHz, DMSO-D6) □ ppm 10.29 (s, 1H), 9.81 (s, 1H), 8.81 (d, 1H), 8.29 (d, 1H), 7.79-7.91 (m, 2H), 7.67 (dd, 2H), 7.49 (d, 1H), 7.18-7.44 (m, 8H), 6.93-7.07 (m, 1H), 6.62 (d, 1H), 4.21 (s, 2H), 3.92-4.01 (m, 2H), 3.70-3.78 (m, 2H), 3.65 (s, 2H).

EXAMPLE 438

N-(3-(5-(2-((3-(3-oxomorpholin-4-yl)phenyl)amino)pyrimidin-4-yl)imidazo[2,1-b][1,3]thiazol-6-yl)phenyl)benzamide The title compound was prepared as described in EXAMPLE 3D, substituting EXAMPLE 437D for EXAMPLE 3C and benzoyl chloride for 2,6-difluorobenzoyl chloride. MS (ESI(+)) m/e 588 (M+H)$^+$, (ESI(−)) m/e 586 (M−H)$^-$; 1H NMR (300 MHz, DMSO-D6) □ ppm 10.37 (s, 1H), 9.81 (s, 1H), 8.84 (d, 1H), 8.31 (d, 1H), 8.06-8.12 (m, 1H), 7.89-8.01 (m, 3H), 7.84 (t, 1H), 7.42-7.67 (m, 6H), 7.31-7.40 (m, 2H), 7.00 (d, 1H), 6.67 (d, 1H), 4.21 (s, 2H), 3.97 (dd, 2H), 3.68-3.78 (m, 2H).

EXAMPLE 439

2,6-difluoro-N-(3-(5-(2-((3-(3-oxomorpholin-4-yl)phenyl)amino)pyrimidin-4-yl)imidazo[2,1-b][1,3]thiazol-6-yl)phenyl)benzamide The title compound was prepared as described in EXAMPLE 3D, substituting EXAMPLE 437D for EXAMPLE 3C. MS (ESI(+)) m/e 624 (M+H)$^+$, (ESI(−)) m/e 622 (M−H)$^-$; $^1$H NMR (300 MHz, DMSO-D6) □ ppm 10.91 (s, 1H), 9.82 (s, 1H), 8.81 (d, 1H), 8.32 (d, 1H), 7.99 (t, 1H), 7.74-7.87 (m, 2H), 7.53-7.68 (m, 2H), 7.44-7.52 (m, 2H), 7.31-7.43 (m, 2H), 7.21-7.30 (m, 2H), 6.95-7.04 (m, 1H), 6.66 (d, 1H), 4.21 (s, 2H), 3.91-4.06 (m, 2H), 3.68-3.79 (m, 2H).

EXAMPLE 440

2-chloro-6-fluoro-N-(3-(5-(2-((3-(3-oxomorpholin-4-yl)phenyl)amino)pyrimidin-4-yl)imidazo[2,1-b][1,3]thiazol-6-yl)phenyl)benzamide The title compound was prepared as described in EXAMPLE 3D, substituting EXAMPLE 437D for EXAMPLE 3C and 2-chloro-6-fluorobenzoyl chloride for 2,6-difluorobenzoyl chloride. MS (ESI(+)) m/e 640 (M+H)$^+$; 1H NMR (300 MHz, DMSO-D6) □ ppm 10.90 (s, 1H), 9.82 (s, 1H), 8.80 (d, 1H), 8.31 (d, 1H), 7.95-8.04 (m, 1H), 7.81-7.87 (m, 1H), 7.77 (d, 1H), 7.29-7.63 (m, 8H), 6.93-7.05 (m, 1H), 6.68 (d, 1H), 4.21 (s, 2H), 3.97 (dd, 2H), 3.69-3.76 (m, 2H).

EXAMPLE 441

2,6-dichloro-N-(3-(5-(2-((3-(3-oxomorpholin-4-yl)phenyl)amino)pyrimidin-4-yl)imidazo[2,1-b][1,3]thiazol-6-yl)phenyl)benzamide The title compound was prepared as described in EXAMPLE 3D, substituting EXAMPLE 437D for EXAMPLE 3C and 2,6-dichlorobenzoyl chloride for 2,6-difluorobenzoyl chloride. MS (ESI(+)) m/e 656 (M+H)$^+$, (ESI(−)) m/e 654 (M−H)$^-$; 1H NMR (300 MHz, DMSO-D6) □ ppm 10.86 (s, 1H), 9.82 (s, 1H), 8.80 (d, 1H), 8.31 (d, 1H), 7.96-8.04 (m, 1H), 7.83 (t, 1H), 7.75 (d, 1H), 7.30-7.67 (m, 8H), 7.00 (d, 1H), 6.69 (d, 1H), 4.21 (s, 2H), 3.97 (dd, 2H), 3.68-3.79 (m, 2H).

EXAMPLE 442

5-fluoro-2-methyl-N-(3-(5-(2-((3-(3-oxomorpholin-4-yl)phenyl)amino)pyrimidin-4-yl)imidazo[2,1-b][1,3]thiazol-6-yl)phenyl)benzamide The title compound was prepared as described in EXAMPLE 3D, substituting EXAMPLE 437D for EXAMPLE 3C and 2-methyl-5-fluorobenzoyl chloride for 2,6-difluorobenzoyl chloride. MS (ESI(+)) m/e 620 (M+H)$^+$, (ESI(−)) m/e 618 (M−H)$^-$; 1H NMR (300 MHz, DMSO-D6) □ ppm 10.47 (s, 1H), 9.82 (s, 1H), 8.82 (d, 1H), 8.31 (d, 1H), 8.05 (s, 1H), 7.76-7.86 (m, 2H), 7.63 (d, 1H), 7.41-7.52 (m, 2H), 7.29-7.41 (m, 4H), 7.18-7.29 (m, 1H), 6.91-7.10 (m, 1H), 6.67 (d, 1H), 4.15-4.28 (m, 2H), 3.97 (dd, 2H), 3.66-3.80 (m, 2H), 2.35 (s, 3H).

EXAMPLE 443

2-fluoro-N-(3-(5-(2-((3-(3-oxomorpholin-4-yl)phenyl)amino)pyrimidin-4-yl)imidazo[2,1-b][1,3]thiazol-6-yl)phenyl)benzamide The title compound was prepared as described in EXAMPLE 3D, substituting EXAMPLE 437D for EXAMPLE 3C and 2-fluorobenzoyl chloride for 2,6-difluorobenzoyl chloride. MS (ESI(+)) m/e 606 (M+H)+; $^1$H NMR (300 MHz, DMSO-D6) □ ppm 10.54 (s, 1H), 9.82 (s, 1H), 8.82 (d, 1H), 8.31 (d, 1H), 8.02 (s, 1H), 7.79-7.90 (m, 2H), 7.54-7.73 (m, 3H), 7.42-7.52 (m, 2H), 7.29-7.40 (m, 4H), 6.93-7.08 (m, 1H), 6.66 (d, 1H), 4.21 (s, 2H), 3.90-4.04 (m, 2H), 3.65-3.82 (m, 2H).

EXAMPLE 444

N-(3-(5-(2-((4-(3-oxomorpholin-4-yl)phenyl)amino)pyrimidin-4-yl)imidazo[2,1-b][1,3]thiazol-6-yl)phenyl)-2-phenylacetamide

EXAMPLE 444A

The title compound was prepared as described in EXAMPLE 437A, substituting 1-iodo-4-nitrobenzene for 1-iodo-3-nitrobenzene. MS (DCI(+)) m/e 223 (M+H)+.

EXAMPLE 444B

The title compound was prepared as described in EXAMPLE 1F, substituting EXAMPLE 444A for EXAMPLE 1E. MS (DCI(+)) m/e 193 (M+H)+.

EXAMPLE 444C

The title compound was prepared as described in EXAMPLE 12D, substituting EXAMPLE 444B for 3-morpholinoaniline. MS (ESI(+)) m/e 514 (M+H)+.

EXAMPLE 444D

The title compound was prepared as described in EXAMPLE 1F, substituting EXAMPLE 444C for EXAMPLE 1E. MS (ESI(+)) m/e 484 (M+H)+.

EXAMPLE 444E

The title compound was prepared as described in EXAMPLE 3D, substituting EXAMPLE 444D for EXAMPLE 3C and phenylacetyl chloride for 2,6-difluorobenzoyl chloride. MS (ESI(+)) m/e 602 (M+H)+, (ESI(−)) m/e 600 (M−H)−; 1H NMR (300 MHz, DMSO-D6) □ ppm 10.29 (s, 1H), 9.78 (s, 1H), 8.81 (d, 1H), 8.27 (d, 1H), 7.84-7.92 (m, 1H), 7.68-7.78 (m, 3H), 7.51 (d, 1H), 7.15-7.45 (m, 9H), 6.61 (d, 1H), 4.20 (s, 2H), 3.98 (dd, 2H), 3.70-3.80 (m, 2H), 3.65 (s, 2H).

EXAMPLE 445

2,6-difluoro-N-(3-(5-(2-((4-(3-oxomorpholin-4-yl)phenyl)amino)pyrimidin-4-yl)imidazo[2,1-b][1,3]thiazol-6-yl)phenyl)benzamide The title compound was prepared as described in EXAMPLE 3D, substituting EXAMPLE 444D for EXAMPLE 3C. MS (ESI(+)) m/e 624 (M+H)+, (ESI(−)) m/e 622 (M−H)−; 1H NMR (300 MHz, DMSO-D6) □ ppm 10.92 (s, 1H), 9.78 (s, 1H), 8.81 (d, 1H), 8.31 (d, 1H), 7.95-8.02 (m, 1H), 7.70-7.83 (m, 3H), 7.44-7.67 (m, 3H), 7.36-7.42 (m, 1H), 7.22-7.34 (m, 4H), 6.66 (d, 1H), 4.20 (s, 2H), 3.90-4.05 (m, 2H), 3.66-3.84 (m, 2H).

EXAMPLE 446

2-chloro-6-fluoro-N-(3-(5-(2-((4-(3-oxomorpholin-4-yl)phenyl)amino)pyrimidin-4-yl)imidazo[2,1-b][1,3]thiazol-6-yl)phenyl)benzamide The title compound was prepared as described in EXAMPLE 3D, substituting EXAMPLE 444D for EXAMPLE 3C and 2-chloro-6-fluorobenzoyl chloride for 2,6-difluorobenzoyl chloride. MS (ESI(+)) m/e 640 (M+H)+, (ESI(−)) m/e 638 (M−H)−; 1H NMR (300 MHz, DMSO-D6) □ ppm 10.90 (s, 1H), 9.78 (s, 1H), 8.80 (d, 1H), 8.30 (d, 1H), 7.98-8.01 (m, 1H), 7.70-7.82 (m, 3H), 7.27-7.62 (m, 8H), 6.67 (d, 1H), 4.20 (s, 2H), 3.92-4.02 (m, 2H), 3.69-3.84 (m, 2H).

EXAMPLE 447

2,6-dichloro-N-(3-(5-(2-((4-(3-oxomorpholin-4-yl)phenyl)amino)pyrimidin-4-yl)imidazo[2,1-b][1,3]thiazol-6-yl)phenyl)benzamide The title compound was prepared as described in EXAMPLE 3D, substituting EXAMPLE 444D for EXAMPLE 3C and 2,6-dichlorobenzoyl chloride for 2,6-difluorobenzoyl chloride. MS (ESI(+)) m/e 656 (M+H)+, (ESI(−)) m/e 654 (M−H)−; 1H NMR (300 MHz, DMSO-D6) □ ppm 10.85 (s, 1H), 9.78 (s, 1H), 8.80 (d, 1H), 8.30 (d, 1H), 8.00 (t, 1H), 7.69-7.81 (m, 3H), 7.55-7.64 (m, 2H), 7.44-7.55 (m, 3H), 7.37-7.43 (m, 1H), 7.27-7.35 (m, 2H), 6.68 (d, 1H), 4.20 (s, 2H), 3.93-4.03 (m, 2H), 3.68-3.76 (m, 2H).

EXAMPLE 448

5-fluoro-2-methyl-N-(3-(5-(2-((4-(3-oxomorpholin-4-yl)phenyl)amino)pyrimidin-4-yl)imidazo[2,1-b][1,3]thiazol-6-yl)phenyl)benzamide The title compound was prepared as described in EXAMPLE 3D, substituting EXAMPLE 444D for EXAMPLE 3C and 2-methyl-5-fluorobenzoyl chloride for 2,6-difluorobenzoyl chloride. MS (ESI(+)) m/e 620 (M+H)+, (ESI(−)) m/e 618 (M−H)−; 1H NMR (300 MHz, DMSO-D6) □ ppm 10.48 (s, 1H), 9.82 (s, 1H), 8.81 (d, 1H), 8.30 (d, 1H), 8.05 (s, 1H), 7.84 (d, 2H), 7.52 (d, 1H), 7.47 (t, 1H), 7.29-7.39 (m, 5H), 7.24 (td, 1H), 6.67 (d, 1H), 4.20 (s, 2H), 3.98 (dd, 2H), 3.69-3.77 (m, 2H), 2.35 (s, 3H).

EXAMPLE 449

2-fluoro-N-(3-(5-(2-((4-(3-oxomorpholin-4-yl)phenyl)amino)pyrimidin-4-yl)imidazo[2,1-b][1,3]thiazol-6-yl)phenyl)benzamide The title compound was prepared as described in EXAMPLE 3D, substituting EXAMPLE 444D for EXAMPLE 3C and 2-fluorobenzoyl chloride for 2,6-difluorobenzoyl chloride. MS (ESI(+)) m/e 606 (M+H)$^+$, (ESI(−)) m/e 604 (M−H)$^−$; 1H NMR (300 MHz, DMSO-D6) ☐ ppm 10.53 (s, 1H), 9.78 (s, 1H), 8.82 (d, 1H), 8.30 (d, 1H), 8.02 (s, 1H), 7.85 (d, 1H), 7.71-7.78 (m, 2H), 7.64-7.71 (m, 1H), 7.43-7.63 (m, 3H), 7.27-7.40 (m, 5H), 6.66 (d, 1H), 4.20 (s, 2H), 3.98 (dd, 2H), 3.71-3.83 (m, 2H).

EXAMPLE 450

N-(3-(5-(2-((3-fluoro-5-morpholin-4-ylphenyl)amino)pyrimidin-4-yl)imidazo[2,1-b][1,3]thiazol-6-yl)phenyl)-2-phenylacetamide

EXAMPLE 450A

A 20 mL vial was charged with 1,3-difluoro-5-nitrobenzene (1 g, 6.29 mmol) and morpholine (0.602 ml, 6.91 mmol) in anhydrous DMSO (10 ml). The mixture was stirred at ambient temperature for 72 h, then diluted with water and EtOAc and the layers separated. The organic layer was washed with H$_2$O (2×) and saturated NaCl, dried over Na$_2$SO$_4$, decanted, and concentrated. The crude product was purified on an Analogix normal phase HPLC using a SF25-40 g silica gel column eluting with 10% to 20% EtOAc/hex. To give the title compound as a yellow solid. MS (DCI(+)) m/e 227 (M+H)$^+$.

EXAMPLE 450B

The title compound was prepared as described in EXAMPLE 1F, substituting EXAMPLE 450A for EXAMPLE 1E. MS (DCI(+)) m/e 197 (M+H)$^+$.

EXAMPLE 450C

The title compound was prepared as described in EXAMPLE 12D, substituting EXAMPLE 450B for 3-morpholinoaniline. MS (ESI(+)) m/e 518 (M+H)$^+$.

EXAMPLE 450D

The title compound was prepared as described in EXAMPLE 1F, substituting EXAMPLE 450C for EXAMPLE 1E. MS (ESI(+)) m/e 488 (M+H)$^+$.

EXAMPLE 450E

The title compound was prepared as described in EXAMPLE 3D, substituting EXAMPLE 450D for EXAMPLE 3C and phenylacetyl chloride for 2,6-difluorobenzoyl chloride. MS (ESI(+)) m/e 606 (M+H)$^+$, $^1$H NMR (400 MHz, DMSO-D$_6$) ☐ ppm 10.28 (s, 1 H) 9.73 (s, 1 H) 8.83 (d, 1 H) 8.30 (s, 1 H) 7.89 (s, 1 H) 7.71 (d, 1 H) 7.51 (d, 1 H) 7.40 (t, 1 H) 7.33 (m, 4 H) 7.22-7.31 (m, 3 H) 7.07 (s, 1 H) 6.63 (d, 1 H) 6.41 (d, 1 H) 3.74 (m, 4 H) 3.65 (s, 2 H) 3.12 (m, 4 H).

EXAMPLE 451

2,6-difluoro-N-(3-(5-(2-((3-fluoro-5-morpholin-4-ylphenyl)amino)pyrimidin-4-yl)imidazo[2,1-b][1,3]thiazol-6-yl)phenyl)benzamide The title compound was prepared as described in EXAMPLE 3D, substituting EXAMPLE 450D for EXAMPLE 3C. MS (ESI(+)) m/e 628 (M+H)$^+$, $^1$H NMR (400 MHz, DMSO-D$_6$) ☐ ppm 10.90 (s, 1 H) 9.72 (s, 1 H) 8.82 (d, 1 H) 8.33 (d, 1 H) 8.00 (s, 1 H) 7.78 (d, 1 H) 7.59 (m, 1 H) 7.52 (d, 1 H) 7.48 (t, 1 H) 7.40 (m, 1 H) 7.25 (m, 3 H) 7.08 (s, 1 H) 6.68 (d, 1 H) 6.41 (d, 1 H) 3.73 (m, 4 H) 3.11 (m, 4 H).

EXAMPLE 452

N-(3-(5-(2-((3-fluoro-5-morpholin-4-ylphenyl)amino)pyrimidin-4-yl)imidazo[2,1-b][1,3]thiazol-6-yl)phenyl)-N'-phenylurea The title compound was prepared as described in EXAMPLE 13, substituting EXAMPLE 450D for EXAMPLE 3C. MS (ESI(+)) m/e 607 (M+H)$^+$, $^1$H NMR (400 MHz, DMSO-D$_6$) ☐ ppm 9.72 (s, 1 H) 8.86 (d, 1 H) 8.79 (s, 1 H) 8.65 (s, 1 H) 8.32 (d, 1 H) 7.75 (s, 1 H) 7.53 (m, 2 H) 7.45 (d, 2 H) 7.39 (t, 1 H) 7.20-7.30 (m, 4 H) 7.07 (s, 1 H) 6.98 (t, 1 H) 6.67 (d, 1 H) 6.42 (d, 1 H) 3.73 (m, 4 H) 3.12 (m, 4 H).

EXAMPLE 453

2-chloro-N-(3-(5-(2-((3-fluoro-5-morpholin-4-ylphenyl)amino)pyrimidin-4-yl)imidazo[2,1-b][1,3]thiazol-6-yl)phenyl)benzamide The title compound was prepared as described in EXAMPLE 3D, substituting EXAMPLE 450D for EXAMPLE 3C and 2-chlorobenzoyl chloride for 2,6-difluorobenzoyl chloride. MS (ESI(+)) m/e 627 (M+H)$^+$, $^1$H NMR (400 MHz, DMSO-D$_6$) ☐ ppm 10.60 (s, 1 H) 9.72 (s, 1 H) 8.83 (d, 1 H) 8.33 (d, 1 H) 8.03 (s, 1 H) 7.81 (d, 1 H) 7.58 (m, 2 H) 7.52 (m, 2 H) 7.46 (m, 2 H) 7.37 (d, 1 H) 7.25 (d, 1 H) 7.08 (s, 1 H) 6.69 (d, 1 H) 6.41 (d, 1 H) 3.73 (m, 4 H) 3.11 (m, 4 H).

EXAMPLE 454

N-(3-(5-(2-((3-fluoro-4-morpholin-4-ylphenyl)amino)pyrimidin-4-yl)imidazo[2,1-b][1,3]thiazol-6-yl)phenyl)-2-phenylacetamide

EXAMPLE 454A

To a 0° C. solution of morpholine (0.602 ml, 6.91 mmol) and Hunig's Base (1.208 ml, 6.91 mmol) in ethyl acetate (6 ml) under N$_2$ was added dropwise via an addition funnel 1,2-difluoro-4-nitrobenzene (1 g, 6.29 mmol). The reaction mixture was allowed to warm to ambient temperature over 16 h, then heated at 50° C. for 24 h. The reaction mixture was diluted with ethyl acetate and water, and the layers separated. The organic layer was washed with H$_2$O, and saturated NaCl, dried (Na$_2$SO$_4$), decanted, and concentrated. The crude product was purified on an Analogix normal phase HPLC using a SF25-40 g silica gel column eluting with 10% to 20% EtOAc/hex. To give the title compound as a yellow solid. MS (DCI(+)) m/e 227 (M+H)$^+$.

EXAMPLE 454B

The title compound was prepared as described in EXAMPLE 1F, substituting EXAMPLE 454A for EXAMPLE 1E. MS (DCI(+)) m/e 197 (M+H)$^+$.

EXAMPLE 454C

The title compound was prepared as described in EXAMPLE 12D, substituting EXAMPLE 454B for 3-morpholinoaniline. MS (ESI(+)) m/e 518 (M+H)$^+$.

EXAMPLE 454D

The title compound was prepared as described in EXAMPLE 1F, substituting EXAMPLE 454C for EXAMPLE 1E. MS (ESI(+)) m/e 488 (M+H)$^+$.

EXAMPLE 454E

The title compound was prepared as described in EXAMPLE 3D, substituting EXAMPLE 454D for EXAMPLE 3C and phenylacetyl chloride for 2,6-difluorobenzoyl chloride. MS (ESI(+)) m/e 606 (M+H)$^+$, $^1$H NMR (400 MHz, DMSO-D$_6$) □ ppm 10.27 (s, 1 H) 9.70 (s, 1 H) 8.80 (bs, 1 H) 8.27 (d, 1 H) 7.88 (s, 1 H) 7.73 (m, 2 H) 7.50 (d, 1 H) 7.40 (t, 1 H) 7.22-7.37 (m, 7 H) 7.01 (t, 1 H) 6.60 (d, 1 H) 3.74 (m, 4 H) 3.65 (s, 2 H) 2.96 (m, 4 H).

EXAMPLE 455

2,6-difluoro-N-(3-(5-(2-((3-fluoro-4-morpholin-4-ylphenyl)amino)pyrimidin-4-yl)imidazo[2,1-b][1,3]thiazol-6-yl)phenyl)benzamide The title compound was prepared as described in EXAMPLE 3D, substituting EXAMPLE 454D for EXAMPLE 3C. MS (ESI(+)) m/e 628 (M+H)$^+$, $^1$H NMR (400 MHz, DMSO-D6) □ ppm 10.90 (s, 1 H) 9.70 (s, 1 H) 8.79 (bs, 1 H) 8.31 (s, 1 H) 7.99 (s, 1 H) 7.79 (d, 1 H) 7.72 (dd, 1 H) 7.59 (m, 1 H) 7.50 (m, 2 H) 7.36 (m, 2 H) 7.25 (t, 2 H) 7.00 (t, 1 H) 6.65 (d, 1 H) 3.74 (m, 4 H) 2.96 (m, 4 H).

EXAMPLE 456

2-chloro-N-(3-(5-(2-((3-fluoro-4-morpholin-4-ylphenyl)amino)pyrimidin-4-yl)imidazo[2,1-b][1,3]thiazol-6-yl)phenyl)benzamide The title compound was prepared as described in EXAMPLE 3D, substituting EXAMPLE 454D for EXAMPLE 3C and 2-chlorobenzoyl chloride for 2,6-difluorobenzoyl chloride. MS (ESI(+)) m/e 627 (M+H)$^+$, $^1$H NMR (400 MHz, DMSO-D6) □ ppm 10.60 (s, 1 H) 9.70 (s, 1 H) 8.80 (bs, 1 H) 8.30 (d, 1 H) 8.02 (s, 1 H) 7.81 (d, 1 H) 7.72 (dd, 1 H) 7.58 (m, 2 H) 7.51 (m, 2 H) 7.46 (m, 2 H) 7.36 (d, 2 H) 7.01 (t, 1 H) 6.65 (d, 1 H) 3.74 (m, 4 H) 2.96 (m, 4 H).

EXAMPLE 457

N-(3-(5-(2-((3-fluoro-4-morpholin-4-ylphenyl)amino)pyrimidin-4-yl)imidazo[2,1-b][1,3]thiazol-6-yl)phenyl)-N'-phenylurea The title compound was prepared as described in EXAMPLE 13, substituting EXAMPLE 454D for EXAMPLE 3C. MS (ESI(+)) m/e 607 (M+H)$^+$, $^1$H NMR (400 MHz, DMSO-D6) □ ppm 9.70 (s, 1 H) 8.80 (m, 2 H) 8.65 (s, 1 H) 8.29 (d, 1 H) 7.73 (m, 2 H) 7.53 (m, 2 H) 7.45 (d, 2 H) 7.37 (m, 2 H) 7.27 (t, 2 H) 7.21 (d, 1 H) 6.99 (m, 2 H) 6.64 (d, 1 H) 3.74 (m, 4 H) 2.96 (m, 4 H).

EXAMPLE 458

N-(3-(5-(2-((3-fluoro-5-(2-oxopyrrolidin-1-yl)phenyl)amino)pyrimidin-4-yl)imidazo[2,1-b][1,3]thiazol-6-yl)phenyl)-2-phenylacetamide

EXAMPLE 458A

To a 0° C. solution of pyrrolidin-2-one (0.530 ml, 6.91 mmol) in anhydrous DMF (10 ml) under N$_2$ was added 60% NaH (0.277 g, 6.91 mmol). The mixture was stirred 30 minutes at 0° C. and 30 minutes at r.t. 1,2-difluoro-4-nitrobenzene (0.696 ml, 6.29 mmol) was added and the mixture stirred for 16 h at ambient temperature. The reaction mixture was diluted with ethyl acetate and 1 N HCl, and the layers separated. The organic layer was washed with saturated NaHCO$_3$, and saturated NaCl, dried (Na$_2$SO$_4$), decanted, and concentrated. The crude product was purified on an Analogix normal phase HPLC using a SF25-40 g silica gel column eluting with 10% to 20% EtOAc/hex. To give the title compound as a yellow solid. MS (DCI(+)) m/e 225 (M+H)$^+$.

EXAMPLE 458B

The title compound was prepared as described in EXAMPLE 1F, substituting EXAMPLE 458A for EXAMPLE 1E. MS (DCI(+)) m/e 195 (M+H)$^+$.

EXAMPLE 458C

The title compound was prepared as described in EXAMPLE 12D, substituting EXAMPLE 458B for 3-morpholinoaniline. MS (ESI(+)) m/e 516 (M+H)$^+$.

EXAMPLE 458D

The title compound was prepared as described in EXAMPLE 1F, substituting EXAMPLE 458C for EXAMPLE 1E. MS (ESI(+)) m/e 486 (M+H)$^+$.

EXAMPLE 458E

The title compound was prepared as described in EXAMPLE 3D, substituting EXAMPLE 458D for EXAMPLE 3C and phenylacetyl chloride for 2,6-difluorobenzoyl chloride. MS (ESI(+)) m/e 604 (M+H)$^+$, $^1$H NMR (400 MHz, DMSO-D$_6$) □ ppm 10.27 (s, 1 H) 9.94 (s, 1 H) 8.83 (d, 1 H) 8.32 (d, 1 H) 7.87 (m, 2 H) 7.72 (d, 1 H) 7.52 (d, 1 H) 7.46 (dd, 1 H) 7.39 (t, 1 H) 7.27-7.36 (m, 6 H) 7.25 (m, 1 H) 6.66 (d, 1 H) 3.72 (t, 2 H) 3.65 (s, 2 H) 2.42 (t, 2 H) 2.12 (m, 2 H).

EXAMPLE 459

2,6-difluoro-N-(3-(5-(2-((3-fluoro-5-(2-oxopyrrolidin-1-yl)phenyl)amino)pyrimidin-4-yl)imidazo[2,1-b][1,3]thiazol-6-yl)phenyl)benzamide The title compound was prepared as described in EXAMPLE 3D, substituting EXAMPLE 458D for EXAMPLE 3C. MS (ESI(+)) m/e 626 (M+H)$^+$, $^1$H NMR (400 MHz, DMSO-D$_6$) □ ppm 10.90 (s, 1 H) 9.95 (s, 1 H)

8.83 (d, 1 H) 8.35 (d, 1 H) 7.99 (s, 1 H) 7.87 (dd, 1 H) 7.80 (d, 1 H) 7.59 (m, 1 H) 7.54 (d, 1 H) 7.47 (m, 2 H) 7.40 (m, 1 H) 7.33 (t, 1 H) 7.25 (m, 2 H) 6.71 (d, 1 H) 3.72 (t, 2 H) 2.42 (t, 2 H) 2.12 (m, 2 H).

EXAMPLE 460

2-chloro-N-(3-(5-(2-((3-fluoro-5-(2-oxopyrrolidin-1-yl)phenyl)amino)pyrimidin-4-yl)imidazo[2,1-b][1,3]thiazol-6-yl)phenyl)benzamide The title compound was prepared as described in EXAMPLE 3D, substituting EXAMPLE 458D for EXAMPLE 3C and 2-chlorobenzoyl chloride for 2,6-difluorobenzoyl chloride. MS (ESI(+)) m/e 625 (M+H)$^+$, $^1$H NMR (400 MHz, DMSO-D$_6$) □ ppm 10.60 (s, 1 H) 9.94 (s, 1 H) 8.83 (d, 1 H) 8.35 (d, 1 H) 8.03 (s, 1 H) 7.87 (dd, 1 H) 7.82 (d, 1 H) 7.59 (m, 1 H) 7.52 (m, 2 H) 7.47 (m, 3 H) 7.35 (m, 2 H) 6.72 (d, 1 H) 3.72 (t, 2 H) 2.42 (t, 2 H) 2.12 (m, 2 H).

EXAMPLE 461

N-(3-(5-(2-((4-fluoro-3-(2-oxopyrrolidin-1-yl)phenyl)amino)pyrimidin-4-yl)imidazo[2,1-b][1,3]thiazol-6-yl)phenyl)-2-phenylacetamide

EXAMPLE 461A

To a solution of 2-fluoro-5-nitroaniline (1.00 g, 6.41 mmol) in anhydrous CH$_2$Cl$_2$ (50 ml) was added 4-chlorobutanoyl chloride (0.719 ml, 6.41 mmol) and triethylamine (1.786 ml, 12.81 mmol). The mixture was allowed to stir 16 h at ambient temperature. Another 0.5 equiv. of the acid chloride was added, and the mixture stirred one hour. The reaction mixture was washed succesively with H$_2$O, 1M HCl, and saturated NaCl. The organic layer was dried with Na$_2$SO$_4$, filtered, and concentrated. The crude product was purified on an Analogix normal phase HPLC using a SF25-40 g silica gel column eluting with 20% to 30% EtOAc/hexanes to give the title compound. MS (DCI(+)) m/e 261 (M+H)$^+$.

EXAMPLE 461B

To a suspension of 60% NaH (165 mg, 4.14 mmol) in anhydrous THF (6 ml) was added a solution of EXAMPLE 461A (719 mg, 2.76 mmol) in anhydrous THF (3 ml). The mixture was stirred at ambient temperature for 16 h. The reaction mixture was diluted with EtOAc and washed with saturated NH$_4$Cl (2x), and saturated NaCl. The organic layer was dried with (Na$_2$SO$_4$), filtered, and concentrated. The crude product was purified on an Analogix normal phase HPLC using a SF25-40 g silica gel column eluting with 50% EtOAc/hexanes to give the title compound as a yellow solid. MS (DCI(+)) m/e 225 (M+H)$^+$.

EXAMPLE 461C

The title compound was prepared as described in EXAMPLE 1F, substituting EXAMPLE 461B for EXAMPLE 1E. MS (DCI(+)) m/e 195 (M+H)$^+$.

EXAMPLE 461D

The title compound was prepared as described in EXAMPLE 12D, substituting EXAMPLE 461C for 3-morpholinoaniline. MS (ESI(+)) m/e 516 (M+H)$^+$.

EXAMPLE 461E

The title compound was prepared as described in EXAMPLE 1F, substituting EXAMPLE 461D for EXAMPLE 1E. MS (ESI(+)) m/e 486 (M+H)$^+$.

EXAMPLE 461F

The title compound was prepared as described in EXAMPLE 3D, substituting EXAMPLE 461E for EXAMPLE 3C and phenylacetyl chloride for 2,6-difluorobenzoyl chloride. MS (ESI(+)) m/e 604 (M+H)$^+$, $^1$H NMR (400 MHz, DMSO-D$_6$) □ ppm 10.16 (s, 1 H) 9.57 (s, 1 H) 8.56 (bs, 1 H) 8.09 (d, 1 H) 7.71 (s, 1 H) 7.65 (dd, 1 H) 7.52 (d, 1 H) 7.43 (m, 1 H) 7.26 (m, 2 H) 7.17 (m, 4 H) 7.09 (m, 3 H) 6.44 (d, 1 H) 3.58 (t, 2 H) 3.65 (s, 2 H) 2.28 (t, 2 H) 1.96 (m, 2 H).

EXAMPLE 462

2,6-difluoro-N-(3-(5-(2-((4-fluoro-3-(2-oxopyrrolidin-1-yl)phenyl)amino)pyrimidin-4-yl)imidazo[2,1-b][1,3]thiazol-6-yl)phenyl)benzamide The title compound was prepared as described in EXAMPLE 3D, substituting EXAMPLE 461E for EXAMPLE 3C. MS (ESI(+)) m/e 626 (M+H)$^+$, $^1$H NMR (400 MHz, DMSO-D$_6$) □ ppm 10.90 (s, 1 H) 9.77 (s, 1 H) 8.75 (bs, 1 H) 8.30 (d, 1 H) 7.99 (s, 1 H) 7.84 (dd, 1 H) 7.79 (d, 1 H) 7.60 (m, 2 H) 7.48 (m, 2 H) 7.39 (m, 1 H) 7.25 (m, 3 H) 6.66 (d, 1 H) 3.75 (t, 2 H) 2.44 (t, 2 H) 2.12 (m, 2 H).

EXAMPLE 463

2-chloro-N-(3-(5-(2-((4-fluoro-3-(2-oxopyrrolidin-1-yl)phenyl)amino)pyrimidin-4-yl)imidazo[2,1-b][1,3]thiazol-6-yl)phenyl)benzamide The title compound was prepared as described in EXAMPLE 3D, substituting EXAMPLE 461E for EXAMPLE 3C and 2-chlorobenzoyl chloride for 2,6-difluorobenzoyl chloride. MS (ESI(+)) m/e 625 (M+H)$^+$, $^1$H NMR (400 MHz, DMSO-D$_6$) □ ppm 10.58-10.63 (m, 1 H) 9.77 (s, 1 H) 8.76 (s, 1 H) 8.30 (d, 1 H) 8.02 (s, 1 H) 7.82 (m, 2 H) 7.55-7.65 (m, 3 H) 7.42-7.53 (m, 4 H) 7.37 (d, 1 H) 7.24 (m, 1 H) 6.67 (d, 1 H) 3.75 (t, 2 H) 2.44 (t, 2 H) 2.12 (m, 2 H).

EXAMPLE 464

N-(3-(5-(2-((6-morpholin-4-ylpyridin-3-yl)amino)pyrimidin-4-yl)imidazo[2,1-b][1,3]thiazol-6-yl)phenyl)-2-phenylacetamide

EXAMPLE 464A

To a mixture of 2-chloro-5-nitropyridine (1.00 g, 6.31 mmol) in anhydrous MeOH (10 ml) was added morpholine (1.099 ml, 12.61 mmol). The mixture was stirred for 17 h at ambient temperature under N$_2$. The reaction mixture was diluted with EtOAc and CH$_2$Cl$_2$ then washed with H$_2$O and saturated NaCl, dried (Na$_2$SO$_4$), filtered, and concentrated. The crude product was purified on an Analogix normal phase HPLC using a SF25-40 g silica gel column eluting with 10%-20%-100% EtOAc/hexanes to give the title compound as a yellow solid. MS (DCI(+)) m/e 210 (M+H)$^+$.

EXAMPLE 464B

The title compound was prepared as described in EXAMPLE 1F, substituting EXAMPLE 464A for EXAMPLE 1E. MS (DCI(+)) m/e 180 (M+H)+.

EXAMPLE 464C

The title compound was prepared as described in EXAMPLE 12D, substituting EXAMPLE 464B for 3-morpholinoaniline. MS (ESI(+)) m/e 501 (M+H)+.

EXAMPLE 464D

The title compound was prepared as described in EXAMPLE 1F, substituting EXAMPLE 464C for EXAMPLE 1E. MS (ESI(+)) m/e 471 (M+H)+.

EXAMPLE 464E

The title compound was prepared as described in EXAMPLE 3D, substituting EXAMPLE 464D for EXAMPLE 3C and phenylacetyl chloride for 2,6-difluorobenzoyl chloride. MS (ESI(+)) m/e 589 (M+H)+, $^1$H NMR (400 MHz, DMSO-D$_6$) □ ppm 10.26 (s, 1 H) 9.44 (s, 1 H) 8.69 (bs, 1 H) 8.39 (d, 1 H) 8.19 (d, 1 H) 7.89 (m, 2 H) 7.71 (d, 1 H) 7.46 (d, 1 H) 7.39 (t, 1 H) 7.33 (m, 4 H) 7.26 (m, 2 H) 6.85 (d, 1 H) 6.54 (d, 1 H) 3.72 (m, 4 H) 3.65 (s, 2 H) 3.38 (m, 4 H).

EXAMPLE 465

2,6-difluoro-N-(3-(5-(2-((6-morpholin-4-ylpyridin-3-yl)amino)pyrimidin-4-yl)imidazo[2,1-b][1,3]thiazol-6-yl)phenyl)benzamide The title compound was prepared as described in EXAMPLE 3D, substituting EXAMPLE 464D for EXAMPLE 3C. MS (ESI(+)) m/e 611 (M+H)+, $^1$H NMR (400 MHz, DMSO-D$_6$) □ ppm 10.89 (s, 1 H) 9.44 (s, 1 H) 8.70 (bs, 1 H) 8.39 (d, 1 H) 8.23 (d, 1 H) 7.98 (s, 1 H) 7.89 (dd, 1 H) 7.78 (d, 1 H) 7.59 (m, 1 H) 7.47 (m, 2 H) 7.38 (d, 1 H) 7.25 (m, 2 H) 6.84 (d, 1 H) 6.59 (d, 1 H) 3.72 (m, 4 H) 3.38 (m, 4 H).

EXAMPLE 466

2-chloro-N-(3-(5-(2-((6-morpholin-4-ylpyridin-3-yl)amino)pyrimidin-4-yl)imidazo[2,1-b][1,3]thiazol-6-yl)phenyl)benzamide The title compound was prepared as described in EXAMPLE 3D, substituting EXAMPLE 464D for EXAMPLE 3C and 2-chlorobenzoyl chloride for 2,6-difluorobenzoyl chloride. MS (ESI(+)) m/e 610 (M+H)+, $^1$H NMR (400 MHz, DMSO-D$_6$) □ ppm 10.60 (s, 1 H) 9.44 (s, 1 H) 8.71 (bs, 1 H) 8.39 (d, 1 H) 8.22 (d, 1 H) 8.01 (s, 1 H) 7.90 (dd, 1 H) 7.81 (d, 1 H) 7.59 (m, 2 H) 7.51 (m, 1 H) 7.46 (m, 3 H) 7.35 (d, 1 H) 6.84 (d, 1 H) 6.59 (d, 1 H) 3.72 (m, 4 H) 3.38 (m, 4 H).

EXAMPLE 467

N-(3-(5-(2-((6-morpholin-4-ylpyridin-3-yl)amino)pyrimidin-4-yl)imidazo[2,1-b][1,3]thiazol-6-yl)phenyl)-N'-phenylurea The title compound was prepared as described in EXAMPLE 13, substituting EXAMPLE 464D for EXAMPLE 3C. MS (ESI(+)) m/e 590 (M+H)+, $^1$H NMR (400 MHz, DMSO-D$_6$) □ ppm 9.44 (s, 1 H) 8.79 (s, 1 H) 8.72 (m, 1 H) 8.65 (s, 1 H) 8.39 (d, 1 H) 8.22 (d, 1 H) 7.89 (dd, 1 H) 7.73 (s, 1 H) 7.54 (d, 1 H) 7.46 (m, 3 H) 7.39 (t, 1 H) 7.27 (m, 2 H) 7.20 (d, 1 H) 6.97 (t, 1 H) 6.84 (d, 1 H) 6.59 (d, 1 H) 3.71 (m, 4 H) 3.38 (m, 4 H).

EXAMPLE 468

4-(6-(3-(benzylamino)phenyl)imidazo[2,1-b][1,3]thiazol-5-yl)-N-(4-morpholin-4-ylphenyl)pyrimidin-2-amine The title compound was prepared as described in EXAMPLE 355, substituting benzaldehyde for thiophene-2-carbaldehyde. MS (ESI(+)) m/e 560.2 (M+H)+; $^1$H-NMR (300 MHz, DMSO-d$_6$) □ ppm 9.49 (s, 1 H) 8.75 (br.s, 1 H) 8.13 (d, 1 H) 7.54 (m, 2 H) 7.44 (d, 1 H) 7.31 (m, 5 H) 7.18 (m, 2 H) 6.97 (m, 2 H) 6.80 (m, 1 H) 6.71 (m, 2 H) 6.51 (d, 1 H) 4.28 (s, 2 H) 3.76 (m, 4 H) 3.09 (m, 4 H).

EXAMPLE 469

N-(4-morpholin-4-ylphenyl)-4-(6-(3-((2-phenylethyl)amino)phenyl)imidazo[2,1-b][1,3]thiazol-5-yl)pyrimidin-2-amine The title compound was prepared as described in EXAMPLE 355, substituting 2-phenylacetaldehyde for thiophene-2-carbaldehyde. MS (ESI(+)) m/e 574.2 (M+H)+; $^1$H-NMR (300 MHz, DMSO-d$_6$) □ ppm 9.52 (s, 1 H) 8.76 (br.s, 1 H) 8.19 (d, 1 H) 7.55 (m, 2 H) 7.46 (d, 1 H) 7.23 (m, 7 H) 6.98 (m, 2 H) 6.76 (m, 3 H) 6.59 (d, 1 H) 3.76 (m, 4 H) 3.26 (m, 2 H) 3.10 (m, 4 H) 2.83 (m, 2 H).

EXAMPLE 470

2-((3-(5-(2-((4-morpholin-4-ylphenyl)amino)pyrimidin-4-yl)imidazo[2,1-b][1,3]thiazol-6-yl)phenyl)amino)-1-phenylethanone Into a 4 mL vial was charged EXAMPLE 3C (45 mg, 0.098 mmol), 2-bromo-1-phenylethanone (21.45 mg, 0.108 mmol) and NMP (1 mL). The mixture was allowed to stir for 3 min. Hunig's base (0.019 mL, 0.108 mmol) was added and the mixture was stirred at ambient temperature for 18 h. The reaction mixture was treated with 5 mL water and suspension was stirred for 30 min. The precipitate was filtered and washed with ether and dried. The crude product was purified by flash chromatography on an 12 g silica gel column using an AnaLogix IntelliFlash 280 system eluting with a step gradient of CH$_2$Cl$_2$ followed by 98:1:1 CH$_2$Cl$_2$/MeOH/NH$_4$OH to give the title compound. MS (ESI(+)) m/e 588.2 (M+H)+; $^1$H-NMR (300 MHz, DMSO-d$_6$) □ ppm 9.38 (s, 1 H) 8.78 (br.s, 1 H) 8.16 (d, 1 H) 8.05 (m, 2 H) 7.66 (m, 1 H) 7.53 (m, 4 H) 7.44 (d, 1 H) 7.19 (m, 1 H) 6.91 (m, 3 H) 6.78 (m, 2 H) 6.54 (d, 1 H) 6.07 (t, 1 H) 4.70 (d, 2 H) 3.77 (m, 4 H) 3.06 (m, 4 H).

EXAMPLE 471

2-((3-(5-(2-((4-morpholin-4-ylphenyl)amino)pyrimidin-4-yl)imidazo[2,1-b][1,3]thiazol-6-yl)phenyl)amino)-1-phenylethanol Into a 4 mL vial was charged EXAMPLE 470 (0.015 g, 0.026 mmol), 300 uL MeOH and 200 uL THF. To the stirring soln was added 1 mg NaBH$_4$ at 0° C. The mixture was stirred at ambient temperature for 2 h. The reaction mixture was treated with one drop saturated aqueous ammonium chloride and diluted with 1 mL DMSO and purified by preparative HPLC on a Waters Nova-Pak HR C18 6 um 60 Å Prep-Pak cartridge column (25 mm×100 mm). A gradient of acetonitrile and 0.1% ammonium acetate in water was used at a flow rate of 40 mL/min (0-0.5 min 10% acetonitrile, 0.5-7.0 min linear gradient 10-95% acetonitrile, 7.0-10.0 min 95% acetonitrile, 10.0-12.0 min linear gradient 95-10% acetonitrile) allowing isolation of the title compound. MS (ESI(+)) m/e 590.3 (M+H)$^+$; $^1$H-NMR (300 MHz, DMSO-d$_6$) ☐ ppm 9.40 (s, 1 H) 8.78 (br.s, 1 H) 8.18 (d, 1 H) 7.54 (m, 2 H) 7.45 (d, 1 H) 7.33 (m, 4 H) 7.19 (m, 2 H) 6.94 (m, 2 H) 6.82 (m, 1 H) 6.72 (m, 2 H) 6.58 (d, 1 H) 5.80 (m, 1 H) 5.45 (d, 1 H) 4.73 (m, 1 H) 3.76 (m, 4 H) 3.19 (m, 2 H) 3.06 (m, 4 H).

EXAMPLE 472

N-(4-(4-isopropylpiperazin-1-yl)phenyl)-4-(6-(3-((5-phenyl-1,3,4-oxadiazol-2-yl)amino)phenyl)imidazo[2,1-b][1,3]thiazol-5-yl)pyrimidin-2-amine The title compound was prepared as described in EXAMPLE 137, substituting EXAMPLE 257C for EXAMPLE 65C. MS (ESI+), m/e 596.1; $^1$H-NMR (500 MHz, DMSO-d$_6$) ☐ ppm 10.87 (s, 1 H), (s, 1 H), 9.56 (s, 1 H), 9.37 (bs, 1 H), 8.81 (bs, 1 H), 8.23 (d, 1 H), 7.89-7.91 (m, 3 H), 7.72 (d, 1 H), 7.56-7.61 (m, 5 H), 7.47-7.51 (m, 2 H), 7.26 (d, 1 H), 7.01 (d, 2 H), 6.59 (d, 1 H), 3.78-3.80 (m, 2 H), 3.50 (m, 1 H), 3.30 (m, 2 H), 3.15-3.22 (m, 2 H), 2.92-2.97 (m, 2 H), 1.30 (d, 6 H).

EXAMPLE 473

N-(4-morpholin-4-ylphenyl)-4-(6-(3-((pyridin-2-ylmethyl)amino)phenyl)imidazo[2,1-b][1,3]thiazol-5-yl)pyrimidin-2-amine The title compound was prepared as described in EXAMPLE 355, substituting 2-pyridinecarboxaldehyde for thiophene-2-carbaldehyde. MS (ESI(+)) m/e 561.2 (M+H)$^+$; $^1$H-NMR (300 MHz, DMSO-d$_6$) ☐ ppm 9.49 (s, 1 H) 8.75 (br.s, 1 H) 8.62 (d, 1 H) 8.13 (d, 1 H) 8.06 (m, 1 H) 7.44-7.63 (m, 6 H) 7.16-7.23 (m, 1 H) 6.97 (m, 2 H) 6.79 (m, 2 H) 6.71 (m, 1 H) 6.47 (d, 1 H) 4.51 (s, 2 H) 3.77 (s, 4 H) 3.08 (m, 4 H).

EXAMPLE 474

4-(6-(3-((2,6-difluorobenzyl)amino)phenyl)imidazo[2,1-b][1,3]thiazol-5-yl)-N-(4-morpholin-4-ylphenyl)pyrimidin-2-amine The title compound was prepared as described in EXAMPLE 355, substituting 2,6-difluorobenzaldehyde for thiophene-2-carbaldehyde. MS (ESI(+)) m/e 596.2 (M+H)$^+$; $^1$H-NMR (300 MHz, DMSO-d$_6$) ☐ ppm 9.53 (s, 1 H) 8.77 (br.s, 1 H) 8.13 (d, 1 H) 7.55 (m, 2 H) 7.47 (d, 1 H) 7.39 (m, 1 H) 7.19 (m, 1 H) 7.08 (m, 2 H) 6.99 (m, 2 H) 6.89 (m, 1 H) 6.75 (m, 2 H) 6.52 (d, 1 H) 4.27 (s, 2 H) 3.77 (m, 4 H) 3.09 (m, 4 H).

EXAMPLE 475

4-(6-(3-((2-methoxybenzyl)amino)phenyl)imidazo[2,1-b][1,3]thiazol-5-yl)-N-(4-morpholin-4-ylphenyl)pyrimidin-2-amine The title compound was prepared as described in EXAMPLE 355, substituting 3-methoxybenzaldehyde for thiophene-2-carbaldehyde. MS (ESI(+)) m/e 590.3 (M+H)$^+$; $^1$H-NMR (300 MHz, DMSO-d$_6$) ☐ ppm 9.53 (s, 1 H) 8.75 (br.s, 1 H) 8.13 (d, 1 H) 7.54 (m, 2 H) 7.45 (d, 1 H) 7.21 (m, 4 H) 6.97 (m, 3 H) 6.88 (m, 1 H) 6.76 (m, 2 H) 6.68 (m, 1 H) 6.53 (d, 1 H) 4.23 (s, 2 H) 3.77 (m, 7 H) 3.09 (m, 4 H).

The foregoing is meant to illustrate the invention but not to limit it. Variations and changes obvious to one skilled in the art are intended to be within the scope of the invention as defined in the claims.

We claim:
1. A compound having Formula I

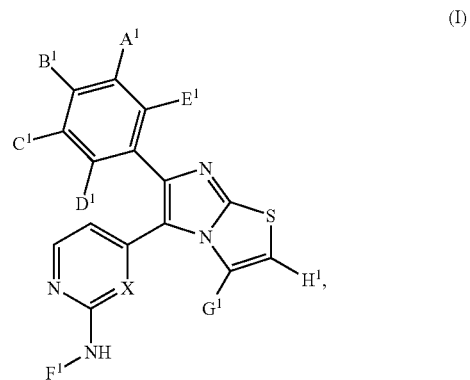

(I)

or a therapeutically acceptable salt thereof, wherein
X is N;
A$^1$ is NHR$^1$, NHC(O)R$^1$, NHC(O)NHR$^1$, NHC(O)OR$^1$, C=NOR$^1$, or C(NH$_2$)NOC(O)R$^1$;
B$^1$, C$^1$, D$^1$, and E$^1$, are each independently H, OR$^1$, NHR$^1$, N(R$^1$)$_2$, OH, CN, N$_3$, NO$_2$, CF$_3$, CF$_2$CF$_3$, OCF$_3$, OCF$_2$CF$_3$, F, Cl, Br, or I;
G$^1$ and H$^1$ are H;
R$^1$ is R$^2$, R$^3$, R$^4$ or R$^5$;
R$^2$ is phenyl which is unfused or fused with benzene, heteroarene or R$^{2A}$; R$^{2A}$ is cycloalkane, cycloalkene, heterocycloalkane or heterocycloalkene;
R$^3$ is heteroaryl which is unfused or fused with benzene, heteroarene or R$^{3A}$; R$^{3A}$ is cycloalkane, cycloalkene, heterocycloalkane or heterocycloalkene;
R$^4$ is cycloalkyl, cycloalkenyl, heterocycloalkyl or heterocycloalkenyl, each of which is unfused or fused with benzene, heteroarene or R$^{4A}$; R$^{4A}$ is cycloalkane, cycloalkene, heterocycloalkane or heterocycloalkene;
R$^5$ is alkyl, alkenyl, or alkynyl, each of which is unsubstituted or substituted with one, two, three, four or five of independently selected spiroalkyl, R$^6$,
R$^6$ is R$^7$, R$^8$, or R$^9$;
R$^7$ is phenyl which is unfused or fused with benzene, heteroarene or R$^{7A}$; R$^{7A}$ is cycloalkane, cycloalkene, heterocycloalkane or heterocycloalkene;
R$^8$ is heteroaryl which is unfused or fused with benzene, heteroarene or R$^{8A}$; R$^{8A}$ is cycloalkane, cycloalkene, heterocycloalkane or heterocycloalkene;
R$^9$ is cycloalkyl, cycloalkenyl, heterocycloalkyl or heterocycloalkenyl, each of which is unfused or fused with benzene, heteroarene or R$^{9A}$; R$^{9A}$ is cycloalkane, cycloalkene, heterocycloalkane or heterocycloalkene;
F$^1$ is H, R$^{10}$, C(O)R$^{10}$, R$^{11}$ or R$^{110}$;
R$^{10}$ is phenyl which is unfused or fused with R$^{10A}$; R$^{10A}$ is benzene, heteroarene, cycloalkane, cycloalkene, heterocycloalkane, or heterocycloalkene;

$R^{11}$ is heteroaryl which is unfused or fused with $R^{11A}$; $R^{11A}$ is benzene, heteroarene, cycloalkane, cycloalkene, heterocycloalkane, or heterocycloalkene;

$R^{110}$ is alkyl which is unsubstituted or substituted with $R^{111}$;

$R^{111}$ is $R^{112}$;

$R^{112}$ is phenyl which is unfused or fused with benzene or heteroarene;

wherein each foregoing variable cyclic moiety is independently unsubstituted or substituted with one or two or three or four or five of independently selected $R^{12}$, $OR^{12}$, $SR^{12}$, $S(O)R^{12}$, $SO_2R^{12}$, $C(O)R^{12}$, $CO(O)R^{12}$, $OC(O)R^{12}$, $OC(O)OR^{12}$, $NH_2$, $NHR^{12}$, $N(R^{12})_2$, $NHC(O)R^{12}$, $NR^{12}C(O)R^{12}$, $NHS(O)_2R^{12}$, $NR^{12}S(O)_2R^{12}$, $NHC(O)OR^{12}$, $NR^{12}C(O)OR^{12}$, $NHC(O)NH_2$, $NHC(O)NHR^{12}$, $NHC(O)N(R^{12})_2$, $NR^{12}C(O)NHR^{12}$, $NR^{12}C(O)N(R^{12})_2$, $NHSO_2R^{12}$, $C(O)NH_2$, $C(O)NHR^{12}$, $C(O)N(R^{12})_2$, $C(O)NHOH$, $C(O)NHOR^{12}$, $C(O)NHSO_2R^{12}$, $C(O)NR^{12}SO_2R^{12}$, $SO_2NH_2$, $SO_2NHR^{12}$, $SO_2N(R^{12})_2$, $C(O)H$, $C(O)OH$, $C(N)NH_2$, $C(N)NHR^{12}$, $C(N)N(R^{12})_2$, $CNOH$, $CNOCH_3$, $OH$, $(O)$, $CN$, $N_3$, $NO_2$, $CF_3$, $CF_2CF_3$, $OCF_3$, $OCF_2CF_3$, F, Cl, Br or I;

$R^{12}$ is $R^{13}$, $R^{14}$, $R^{15}$, or $R^{16}$;

$R^{13}$ is phenyl which is unfused or fused with benzene, heteroarene or $R^{13A}$; $R^{13A}$ is cycloalkane, cycloalkene, heterocycloalkane or heterocycloalkene;

$R^{14}$ is heteroaryl which is unfused or fused with benzene, heteroarene or $R^{14A}$; $R^{14A}$ is cycloalkane, cycloalkene, heterocycloalkane or heterocycloalkene;

$R^{15}$ is cycloalkyl, cycloalkenyl, heterocycloalkyl or heterocycloalkenyl, each of which is unfused or fused with benzene, heteroarene or $R^{15A}$; $R^{15A}$ is cycloalkane, cycloalkene, heterocycloalkane or heterocycloalkene;

$R^{16}$ is alkyl, alkenyl, or alkenyl, each of which is unsubstituted or substituted with one, two, three, four or five of independently selected $R^{17}$, $OR^{17}$, $SR^{17}$, $S(O)R^{17}$, $SO_2R^{17}$, $C(O)R^{17}$, $CO(O)R^{17}$, $OC(O)R^{17}$, $OC(O)OR^{17}$, $NH_2$, $NHR^{17}$, $N(R^{17})_2$, $NHC(O)R^{17}$, $NR^{17}C(O)R^{17}$, $NHS(O)_2R^{17}$, $NR^{17}S(O)_2R^{17}$, $NHC(O)OR^{17}$, $NR^{17}C(O)OR^{17}$, $NHC(O)NH_2$, $NHC(O)NHR^{17}$, $NHC(O)N(R^{17})_2$, $NR^{17}C(O)NHR^{17}$, $NR^{17}C(O)N(R^{17})_2$, $C(O)NH_2$, $C(O)NHR^{17}$, $C(O)N(R^{17})_2$, $C(O)NHOH$, $C(O)NHOR^{17}$, $C(O)NHSO_2R^{17}$, $C(O)NR^{17}SO_2R^{17}$, $SO_2NH_2$, $SO_2NHR^{17}$, $SO_2N(R^7)_2$, $C(O)H$, $C(O)OH$, $C(N)NH_2$, $C(N)NHR^{17}$, $C(N)N(R^{17})_2$, $CNOH$, $CNOCH_3$, $OH$, $(O)$, $CN$, $N_3$, $NO_2$, $CF_3$, $CF_2CF_3$, $OCF_3$, $OCF_2CF_3$, F, Cl, Br or I;

$R^{17}$ is $R^{18}$, $R^{19}$, $R^{20}$ or $R^{21}$;

$R^{18}$ is phenyl which is unfused or fused with benzene, heteroarene or $R^{18A}$; $R^{18A}$ is cycloalkane, cycloalkene, heterocycloalkane or heterocycloalkene;

$R^{19}$ is heteroaryl which is unfused or fused with benzene, heteroarene or $R^{19A}$; $R^{19A}$ is cycloalkane, cycloalkene, heterocycloalkane or heterocycloalkene;

$R^{20}$ is cycloalkyl, cycloalkenyl, heterocycloalkyl or heterocycloalkenyl, each of which is unfused or fused with benzene, heteroarene or $R^{20A}$; $R^{20A}$ is cycloalkane, cycloalkene, heterocycloalkane or heterocycloalkene;

$R^{21}$ is alkyl, alkenyl, or alkenyl, each of which is unsubstituted or substituted with one, two, three, four or five of independently selected $R^{22}$, $OR^{22}$, $SR^{22}$, $S(O)R^{22}$, $SO_2R^{22}$, $C(O)R^{22}$, $CO(O)R^{22}$, $OC(O)R^{22}$, $OC(O)OR^{22}$, $NH_2$, $NHR^{22}$, $N(R^{22})_2$, $NHC(O)R^{22}$, $NR^{22}C(O)R^{22}$, $NHS(O)_2R^{22}$, $NR^{22}S(O)_2R^{22}$, $NHC(O)OR^{22}$, $NR^{22}C(O)OR^{22}$, $NHC(O)NH_2$, $NHC(O)NHR^{22}$, $NHC(O)N(R^{22})_2$, $NR^{22}C(O)NHR^{22}$, $NR^{22}C(O)N(R^{22})_2$, $C(O)NH_2$, $C(O)NHR^{22}$, $C(O)N(R^{22})_2$, $C(O)NHOH$, $C(O)NHOR^{22}$, $C(O)NHSO_2R^{22}$, $C(O)NR^{22}SO_2R^{22}$, $SO_2NH_2$, $SO_2NHR^{22}$, $SO_2N(R^{22})_2$, $C(O)H$, $C(O)OH$, $C(N)NH_2$, $C(N)NHR^{22}$, $C(N)N(R^{22})_2$, $CNOH$, $CNOCH_3$, $OH$, $(O)$, $CN$, $N_3$, $NO_2$, $CF_3$, $CF_2CF_3$, $OCF_3$, $OCF_2CF_3$, F, Cl, Br or I;

$R^{22}$ is alkyl, alkenylalkenyl, heteroaryl, cycloalkenyl or heterocycloalkyl;

wherein the moieties represented by $R^{13}$, $R^{14}$, $R^{15}$, $R^{18}$, $R^{19}$, $R^{20}$, and $R^{22}$ are independently unsubstituted or substituted with one or two or three or four or five of independently selected $R^{23}$, $OR^{23}$, $SR^{23}$, $S(O)R^{23}$, $SO_2R^{23}$, $C(O)R^{23}$, $CO(O)R^{23}$, $OC(O)R^{23}$, $OC(O)R^{23}$, $NH_2$, $NHR^{23}$, $N(R^{23})_2$, $NHC(O)R^{23}$, $NR^{23}C(O)R^{23}$, $NHS(O)_2R^{23}$, $NR^{23}S(O)_2R^{23}$, $NHC(O)OR^{23}$, $NR^{23}C(O)OR^{23}$, $NHC(O)NH_2$, $NHC(O)NHR^{23}$, $NHC(O)N(R^{23})_2$, $NR^{23}C(O)NHR^{23}$, $NR^{23}C(O)N(R^{23})_2$, $C(O)NH_2$, $C(O)NHR^{23}$, $C(O)N(R^{23})_2$, $C(O)NHOH$, $C(O)NHOR^{23}$, $C(O)NHSO_2R^{23}$, $C(O)NR^{23}SO_2R^{23}SO_2NH_2$, $SO_2NHR^{23}$, $SO_2N(R^{23})_2$, $C(O)H$, $C(O)OH$, $C(N)NH_2$, $C(N)NHR^{23}$, $C(N)N(R^{23})_2$, $CNOH$, $CNOCH_3$, $OH$, $(O)$, $CN$, $N_3$, $NO_2$, $CF_3$, $CF_2CF_3$, $OCF_3$, $OCF_2CF_3$, F, Cl, Br or I;

$R^{23}$ is alkyl which is unsubstituted or substituted with one or two of independently selected $OR^{24}$; and $R^{24}$ is hydrogen or alkyl which is unsubstituted or substituted with OH.

2. The compound having Formula I of claim 1 wherein $B^1$ is H, $OR^1$, $NHR^1$ or $N(R^1)_2$; and
$C^1$, $D^1$, and $E^1$ are H.

3. The compound having Formula I of claim 2 wherein $A^1$ is $NHC(O)R^1$.

4. The compound having Formula I of claim 3 wherein
$R^1$ is $R^2$ or $R^3$;
$R^2$ is phenyl;
$R^3$ is heteroaryl; wherein each foregoing variable cyclic moiety is unsubstituted or substituted with one or two or three or four or five of independently selected $R^{12}$, $OR^{12}$, $C(O)R^{12}$, $CO(O)R^{12}$, $N(R^{12})_2$, $NHS(O)_2R^{12}$, $C(O)NHR^{12}$, $C(O)N(R^{12})_2$, $SO_2NH_2$, $SO_2N(R^{12})_2$, $C(O)OH$, CN, $NO_2$, $CF_3$, $OCF_3$, F, Cl, Br or I.

5. The compound having Formula I of claim 3 wherein
$R^1$ is $R^5$;
$R^5$ is alkyl, which is substituted with one $R^6$;
$R^6$ is $R^7$, $R^8$ or $R^9$;
$R^7$ is phenyl which is unfused or fused with benzene or heterocycloalkane;
$R^8$ is heteroaryl; and
$R^9$ is cycloalkyl or heterocycloalkyl; wherein each foregoing variable cyclic moiety is independently unsubstituted or substituted with one or two or three or four or five of independently selected $R^{12}$, $OR^{12}$, $C(O)R^{12}$, $CO(O)R^{12}$, $N(R^{12})_2$, $NHS(O)_2R^{12}$, $C(O)NHR^{12}$, $C(O)N(R^{12})_2$, $SO_2NH_2$, $SO_2N(R^{12})_2$, $C(O)OH$, $(O)$, CN, $NO_2$, $CF_3$, $OCF_3$, F, Cl, Br or I.

6. The compound having Formula I of claim 2 wherein $A^1$ is $NHC(O)NHR^1$.

7. The compound having Formula I of claim 6 wherein
$R^1$ is $R^2$ or $R^3$;
$R^2$ is phenyl;
$R^3$ is heteroaryl; wherein each foregoing variable cyclic moiety is unsubstituted or substituted with one or two or three or four or five of independently selected $R^{12}$, $OR^{12}$, $C(O)R^{12}$, $CO(O)R^{12}$, $N(R^{12})_2$, $NHS(O)_2R^{12}$, $C(O)NHR^{12}$, $C(O)N(R^{12})_2$, $SO_2NH_2$, $SO_2N(R^{12})_2$, $C(O)OH$, CN, $NO_2$, $CF_3$, $OCF_3$, F, Cl, Br or I.

8. The compound having Formula I of claim 2 wherein
F¹ is phenyl which is unsubstituted or substituted with one or two or three or four or five of independently selected $R^{12}$, $OR^{12}$, $C(O)R^{12}$, $CO(O)R^{12}$, $N(R^{12})_2$, $NHS(O)_2R^{12}$, $C(O)NHR^{12}$, $C(O)N(R^{12})_2$, $SO_2NH_2$, $SO_2N(R^{12})_2$, $C(O)OH$, (O), CN, $NO_2$, $CF_3$, $OCF_3$, F, Cl, Br or I.

9. The compound having Formula I of claim 8 wherein the phenyl is substituted with $R^{12}$,
$R^{12}$ is $R^{15}$; and
$R^{15}$ is heterocycloalkyl.

10. The compound having Formula I of claim 2 wherein
F¹ is $R^{110}$;
$R^{110}$ is alkyl which is unsubstituted or substituted with phenyl; wherein the phenyl is unsubstituted or substituted with one or two or three or four or five of independently selected $R^{12}$, $OR^{12}$, $C(O)R^{12}$, $CO(O)R^{12}$, $N(R^{12})_2$, $NHS(O)_2R^{12}$, $C(O)NHR^{12}$, $C(O)N(R^{12})_2$, $SO_2NH_2$, $SO_2N(R^{12})_2$, $C(O)OH$, (O), CN, $NO_2$, $CF_3$, $OCF_3$, F, Cl, Br or I.

11. The compound having Formula I of claim 1 selected from the group consisting of
N-(3-(5-(2-anilinopyrimidin-4-yl)imidazo[2,1-b][1,3]thiazol-6-yl)phenyl)-2-chlorobenzamide,
N-(3-(5-(2-anilinopyrimidin-4-yl)imidazo[2,1-b][1,3]thiazol-6-yl)phenyl)benzamide,
2,6-difluoro-N-(3-(5-(2((4-morpholin-4-ylphenyl)amino)pyrimidin-4-yl)imidazo[2,1-b][1,3]thiazol-6-yl)phenyl)benzamide,
N-(3-(5-(2((4-morpholin-4-ylphenyl)amino)pyrimidin-4-yl)imidazo[2,1-b][1,3]thiazol-6-yl)phenyl)benzamide,
N-(3-(5-(2((4-morpholin-4-ylphenyl)amino)pyrimidin-4-yl)imidazo[2,1-b][1,3]thiazol-6-yl)phenyl)-2-phenylacetamide,
N-(3-(5-(2-((3-fluoro-4-methoxyphenyl)amino)pyrimidin-4-yl)imidazo[2,1-b][1,3]thiazol-6-yl)phenyl)benzamide,
N-(3-(5-(2-((3-fluoro-4-methoxyphenyl)amino)pyrimidin-4-yl)imidazo[2,1-b][1,3]thiazol-6-yl)phenyl)-2-phenylacetamide,
N-(3-(5-(2-anilinopyrimidin-4-yl)imidazo[2,1-b][1,3]thiazol-6-yl)phenyl)-2-phenylacetamide,
N-(3-(5-(2-anilinopyrimidin-4-yl)imidazo[2,1-b][1,3]thiazol-6-yl)phenyl)acetamide,
N-(3-(5-(2-((3-fluorophenyl)amino)pyrimidin-4-yl)imidazo[2,1-b][1,3]thiazol-6-yl)phenyl)-2-phenylacetamide,
N-(3-(5-(2-((3-fluorophenyl)amino)pyrimidin-4-yl)imidazo[2,1-b][1,3]thiazol-6-yl)phenyl)benzamide,
N-(3-(5-(2-((3-morpholin-4-ylphenyl)amino)pyrimidin-4-yl)imidazo[2,1-b][1,3]thiazol-6-yl)phenyl)-2-phenylacetamide,
N-(3-(5-(2((4-morpholin-4-ylphenyl)amino)pyrimidin-4-yl)imidazo[2,1-b][1,3]thiazol-6-yl)phenyl)-N'-phenylurea,
N-(3-(5-(2-((4-(4-(3-methoxypropyl)piperazin-1-yl)phenyl)amino)pyrimidin-4-yl)imidazo[2,1-b][1,3]thiazol-6-yl)phenyl)-2-phenylacetamide,
2-(2,6-difluorophenyl)-N-(3-(5-(2((4-(4-(3-methoxypropyl)piperazin-1-yl)phenyl)amino)pyrimidin-4-yl)imidazo[2,1-b][1,3]thiazol-6-yl)phenyl)acetamide,
N-(3-(5-(2-((4-(4-(3-methoxypropyl)piperazin-1-yl)phenyl)amino)pyrimidin-4-yl)imidazo[2,1-b][1,3]thiazol-6-yl)phenyl)acetamide,
2-(2-methoxyphenyl)-N-(3-(5-(2-((4-(4-(3-methoxypropyl)piperazin-1-yl )phenyl)amino)pyrimidin-4-yl)imidazo[2,1-b][1,3]thiazol-6-yl)phenyl)acetamide,
N-(2-methoxyphenyl)-N'-(3-(5-(2-((4-morpholin-4-ylphenyl)amino)pyrimidin-4-yl)imidazo[2,1-b][1,3]thiazol-6-yl)phenyl)urea,
N-(2-methylphenyl)-N'-(3-(5-(2-((4-morpholin-4-ylphenyl)amino)pyrimidin-4-yl)imidazo[2,1-b][1,3]thiazol-6-yl)phenyl)urea,
N-(3-methylphenyl)-N'-(3-(5-(2-((4-morpholin-4-ylphenyl)amino)pyrimidin-4-yl)imidazo[2,1-b][1,3]thiazol-6-yl)phenyl)urea,
N-(4-methylphenyl)-N'-(3-(5-(2-((4-morpholin-4-ylphenyl)amino)pyrimidin-4-yl)imidazo[2,1-b][1,3]thiazol-6-yl)phenyl)urea,
N-(2-fluorophenyl)-N'-(3-(5-(2-((4-morpholin-4-ylphenyl)amino)pyrimidin-4-yl)imidazo[2,1-b][1,3]thiazol-6-yl)phenyl)urea,
N-(3-fluorophenyl)-N'-(3-(5-(2-((4-morpholin-4-ylphenyl)amino)pyrimidin-4-yl)imidazo[2,1-b][1,3]thiazol-6-yl)phenyl)urea,
N-(4-fluorophenyl)-N'-(3-(5-(2-((4-morpholin-4-ylphenyl)amino)pyrimidin-4-yl)imidazo[2,1-b][1,3]thiazol-6-yl)phenyl)urea,
N-(2-chlorophenyl)-N'-(3-(5-(2-((4-morpholin-4-ylphenyl)amino)pyrimidin-4-yl)imidazo[2,1-b][1,3]thiazol-6-yl)phenyl)urea,
N-(3-chlorophenyl)-N'-(3-(5-(2-((4-morpholin-4-ylphenyl)amino)pyrimidin-4-yl)imidazo[2,1-b][1,3]thiazol-6-yl)phenyl)urea,
N-(4-chlorophenyl)-N'-(3-(5-(2-((4-morpholin-4-ylphenyl)amino)pyrimidin-4-yl)imidazo[2,1-b][1,3]thiazol-6-yl)phenyl)urea,
N-(3-methoxyphenyl)-N'-(3-(5-(2-((4-morpholin-4-ylphenyl)amino)pyrimidin-4-yl)imidazo[2,1-b][1,3]thiazol-6-yl)phenyl)urea,
N-(4-methoxyphenyl)-N'-(3-(5-(2-((4-morpholin-4-ylphenyl)amino)pyrimidin-4-yl)imidazo[2,1-b][1,3]thiazol-6-yl)phenyl)urea,
N-(3-(5-(2-((4-morpholin-4-ylphenyl)amino)pyrimidin-4-yl)imidazo[2,1-b][1,3]thiazol-6-yl)phenyl)-N'-(2-(trifluoromethyl)phenyl)urea,
N-(3-(5-(2-((4-morpholin-4-ylphenyl)amino)pyrimidin-4-yl)imidazo[2,1-b][1,3]thiazol-6-yl)phenyl)-N'-(3-(trifluoromethyl)phenyl)urea,
N-(3-(5-(2-((4-morpholin-4-ylphenyl)amino)pyrimidin-4-yl)imidazo[2,1-b][1,3]thiazol-6-yl)phenyl)-N'-(4-(trifluoromethyl)phenyl)urea,
N-(3-(5-(2-aminopyrimidin-4-yl)imidazo[2,1-b][1,3]thiazol-6-yl)phenyl)benzamide,
N-(3-(5-(2-((3-(acetylamino)phenyl)amino)pyrimidin-4-yl)imidazo[2,1-b][1,3]thiazol-6-yl)phenyl)benzamide,
N-(3-(5-(2-((3-(acetylamino)phenyl)amino)pyrimidin-4-yl)imidazo[2,1-b][1,3]thiazol-6-yl)phenyl)-2-phenylacetamide,
N-(3-(5-(2-((4-(4-methylpiperazin-1-yl)phenyl)amino)pyrimidin-4-yl)imidazo[2,1-b][1,3]thiazol-6-yl)phenyl)-2-phenylacetamide,
N-(3-(5-(2-((3-chlorophenyl)amino)pyrimidin-4-yl)imidazo[2,1-b][1,3]thiazol-6-yl)phenyl)-2-phenylacetamide,
N-(3-(5-(2-((3-methylphenyl)amino)pyrimidin-4-yl)imidazo[2,1-b][1,3]thiazol-6-yl)phenyl)-2-phenylacetamide,
N-(3-(5-(2-((3-methoxyphenyl)amino)pyrimidin-4-yl)imidazo[2,1-b][1,3]thiazol-6-yl)phenyl)-2-phenylacetamide,
N-(3-(5-(2-((4-(1H-imidazol-1-yl)phenyl)amino)pyrimidin-4-yl)imidazo[2,1-b][1,3]thiazol-6-yl)phenyl)-2-phenylacetamide, N-(3-(5-(2-((4-(1H-imidazol-1-yl)phenyl)amino)pyrimidin-4-yl)imidazo[2,1-b][1,3]thiazol-6-yl)phenyl)-2-phenylbutanamide,
N-(3-(5-(2-((4-(1,1-dioxidothiomorpholin-4-yl)phenyl)amino)pyrimidin-4-yl)imidazo[2,1-b][1,3]thiazol-6-yl)phenyl)-2-phenylacetamide,
N-(3-(5-(2-((4-(1,1-dioxidothiomorpholin-4-yl)phenyl)amino)pyrimidin-4-yl)imidazo[2,1-b][1,3]thiazol-6-yl)phenyl)-2-(3-methoxyphenyl)acetamide,
N-(3-(5-(2-((4-(1,1-dioxidothiomorpholin-4-yl)phenyl)amino)pyrimidin-4-yl)imidazo[2,1-b][1,3]thiazol-6-yl)phenyl)-2-(4-methoxyphenyl)acetamide,
N-benzyl-N'-(3-(5-(2-((4-morpholin-4-ylphenyl)amino)pyrimidin-4-yl)imidazo[2,1-b][1,3]thiazol-6-yl)phenyl)urea,
N-(3-(5-(2-((4-morpholin-4-ylphenyl)amino)pyrimidin-4-yl)imidazo[2,1-b][1,3]thiazol-6-yl)phenyl)-2-thien-2-ylacetamide,
phenyl 3-(5-(2-((4-morpholin-4-ylphenyl)amino)pyrimidin-4-yl)imidazo[2,1-b][1,3]thiazol-6-yl)phenylcarbamate,
N-(3-(5-(2-((3-((methylsulfonyl)amino)phenyl)amino)pyrimidin-4-yl)imidazo[2,1-b][1,3]thiazol-6-yl)phenyl)-2-phenylacetamide,
3-(1H-imidazol-4-yl)-N-(3-(5-(2-((4-morpholin-4-ylphenyl)amino)pyrimidin-4-yl)imidazo[2,1-b][1,3]thiazol-6-yl)phenyl)propanamide,
ethyl 3-((4-(6-(3-((phenylacetyl)amino)phenyl)imidazo[2,1-b][1,3]thiazol-5-yl)pyrimidin-2-yl)amino)benzoate,
benzyl 3-(5-(2-((4-morpholin-4-ylphenyl)amino)pyrimidin-4-yl)imidazo [2,1 -b][1,3]thiazol-6-yl)phenylcarbamate,
4-methoxyphenyl 3-(5-(2-((4-morpholin-4-ylphenyl)amino)pyrimidin-4-yl)imidazo [2,1-b][1,3 ]thiazol-6-yl)phenylcarbamate,
N-(3-(5-(2-((3-methylphenyl)amino)pyrimidin-4-yl)imidazo[2, 1-b][1,3 ]thiazol-6-yl)phenyl)benzamide,
N-(3-(5-(2-((4-methylphenyl)amino)pyrimidin-4-yl)imidazo[2, 1-b][1,3 ]thiazol-6-yl)phenyl)benzamide,
N-(3-(5-(2-((4-methylphenyl)amino)pyrimidin-4-yl)imidazo[2, 1-b][1,3 ]thiazol-6-yl)phenyl)-2-phenylacetamide,
N-(3-(5-(2-((4-methylphenyl)amino)pyrimidin-4-yl)imidazo[2, 1-b][1,3 ]thiazol-6-yl)phenyl)benzamide,
N-(3-(5-(2-((2-chlorophenyl)amino)pyrimidin-4-yl)imidazo [2,1-b][1,3 ]thiazol-6-yl)phenyl)benzamide,
N-(3-(5-(2-((4-chlorophenyl)amino)pyrimidin-4-yl)imidazo [2,1-b][1,3 ]thiazol-6-yl)phenyl)benzamide,
N-(3-(5-(2-((4-chlorophenyl)amino)pyrimidin-4-yl)imidazo [2,1-b][1,3 ]thiazol-6-yl)phenyl)-2-phenylacetamide,
3-((4-(6-(3-((phenylacetyl)amino)phenyl)imidazo [2,1-b][1,3 ]thiazol-5-yl)pyrimidin-2-yl)amino)benzoic acid,
N-(3-(5-(2-((2-methylphenyl)amino)pyrimidin-4-yl)imidazo[2, 1-b][1,3 ]thiazol-6-yl)phenyl)-2-phenylacetamide,
N-(3-(5-(2-((2-chlorophenyl)amino)pyrimidin-4-yl)imidazo [2,1-b][1,3 ]thiazol-6-yl)phenyl)-2-phenylacetamide,
N-(3-(5-(2-((4-(4-acetylpiperazin-1-yl)phenyl)amino)pyrimidin-4-yl)imidazo [2,1-b][1,3]thiazol-6-yl)phenyl)-2-phenylacetamide,
benzyl 3-(5-(2-((4-(4-acetylpiperazin-1-yl)phenyl)amino)pyrimidin-4-yl)imidazo[2,1-b][1,3]thiazol-6-yl)phenylcarbamate,
N-(3-(5-(2-((4-(2-oxopyrrolidin-1-yl)phenyl)amino)pyrimidin-4-yl)imidazo [2,1 -b][1,3]thiazol-6-yl)phenyl)-2-phenylacetamide,
benzyl 3-(5-(2-((4-(2-oxopyrrolidin-1-yl)phenyl)amino)pyrimidin-4-yl)imidazo [2,1 -b][1,3]thiazol-6-yl)phenylcarbamate,
2-(2-methylphenyl)-N-(3-(5-(2-((4-morpholin-4-ylphenyl)amino)pyrimidin-4-yl)imidazo[2,1-b][1,3]thiazol-6-yl)phenyl)acetamide,
2-(3-methylphenyl)-N-(3-(5-(2-((4-morpholin-4-ylphenyl)amino)pyrimidin-4-yl)imidazo[2,1-b][1,3]thiazol-6-yl)phenyl)acetamide,
2-(4-methylphenyl)-N-(3-(5-(2-((4-morpholin-4-ylphenyl)amino)pyrimidin-4-yl)imidazo[2,1-b][1,3]thiazol-6-yl)phenyl)acetamide,
N-(3-(5-(2-((4-morpholin-4-ylphenyl)amino)pyrimidin-4-yl)imidazo[2,1-b][1,3]thiazol-6-yl)phenyl)-2-(2-nitrophenyl)acetamide,
2-(2-fluorophenyl)-N-(3-(5-(2-((4-morpholin-4-ylphenyl)amino)pyrimidin-4-yl)imidazo[2,1-b][1,3]thiazol-6-yl)phenyl)acetamide,
2-(2-chlorophenyl)-N-(3-(5-(2-((4-morpholin-4-ylphenyl)amino)pyrimidin-4-yl)imidazo[2,1-b][1,3]thiazol-6-yl)phenyl)acetamide,
2-(3-chlorophenyl)-N-(3-(5-(2-((4-morpholin-4-ylphenyl)amino)pyrimidin-4-yl)imidazo[2,1-b][1,3]thiazol-6-yl)phenyl)acetamide,
2-(4-chlorophenyl)-N-(3-(5-(2-((4-morpholin-4-ylphenyl)amino)pyrimidin-4-yl)imidazo[2,1-b][1,3]thiazol-6-yl)phenyl)acetamide,
2-(2-bromophenyl)-N-(3-(5-(2-((4-morpholin-4-ylphenyl)amino)pyrimidin-4-yl)imidazo[2,1-b][1,3]thiazol-6-yl)phenyl)acetamide,
2-(3-bromophenyl)-N-(3-(5-(2-((4-morpholin-4-ylphenyl)amino)pyrimidin-4-yl)imidazo[2,1-b][1,3]thiazol-6-yl)phenyl)acetamide,
2-(4-bromophenyl)-N-(3-(5-(2-((4-morpholin-4-ylphenyl)amino)pyrimidin-4-yl)imidazo[2,1-b][1,3]thiazol-6-yl)phenyl)acetamide,
N-(3-(5-(2-((4-morpholin-4-ylphenyl)amino)pyrimidin-4-yl)imidazo[2,1-b][1,3]thiazol-6-yl)phenyl)-2-(3-nitrophenyl)acetamide,
N-(3-(5-(2-((4-morpholin-4-ylphenyl)amino)pyrimidin-4-yl)imidazo[2,1-b][1,3]thiazol-6-yl)phenyl)-2-(4-nitrophenyl)acetamide,
2-(1,1'-biphenyl-4-yl)-N-(3-(5-(2-((4-morpholin-4-ylphenyl)amino)pyrimidin-4-yl)imidazo[2,1-b][1,3]thiazol-6-yl)phenyl)acetamide,
2-(4-(dimethylamino)phenyl)-N-(3-(5-(2-((4-morpholin-4-ylphenyl)amino)pyrimidin-4-yl)imidazo[2,1-b][1,3]thiazol-6-yl)phenyl)acetamide,
N-(3-(5-(2-((4-morpholin-4-ylphenyl)amino)pyrimidin-4-yl)imidazo[2,1-b][1,3]thiazol-6-yl)phenyl)-2-(3-(trifluoromethyl)phenyl)acetamide,
N-(3-(5-(2-((4-morpholin-4-ylphenyl)amino)pyrimidin-4-yl)imidazo[2,1-b][1,3]thiazol-6-yl)phenyl)-2-(4-(trifluoromethyl)phenyl)acetamide,
N-(3-(5-(2-((4-morpholin-4-ylphenyl)amino)pyrimidin-4-yl)imidazo[2,1-b][1,3]thiazol-6-yl)phenyl)-2-(3-(trifluoromethoxy)phenyl)acetamide,
N-(3-(5-(2-((4-morpholin-4-ylphenyl)amino)pyrimidin-4-yl)imidazo[2,1-b][1,3]thiazol-6-yl)phenyl)-2-(4-phenoxyphenyl)acetamide,
2-(4-(benzyloxy)phenyl)-N-(3-(5-(2-((4-morpholin-4-ylphenyl)amino)pyrimidin-4-yl)imidazo[2,1-b][1,3]thiazol-6-yl)phenyl)acetamide, N-(3-(5-(2-((4-morpholin-4-ylphenyl)amino)pyrimidin-4-yl)imidazo[2,1-b][1,3]thiazol-6-yl)phenyl)-2-(1-naphthyl)acetamide,
N-(3-(5-(2-((4-morpholin-4-ylphenyl)amino)pyrimidin-4-yl)imidazo[2,1-b][1,3]thiazol-6-yl)phenyl)-2-(2-naphthyl)acetamide,
2-(2,5-dimethylphenyl)-N-(3-(5-(2-((4-morpholin-4-ylphenyl)amino)pyrimidin-4-yl)imidazo[2,1-b][1,3]thiazol-6-yl)phenyl)acetamide,
2-mesityl-N-(3-(5-(2-((4-morpholin-4-ylphenyl)amino)pyrimidin-4-yl)imidazo[2,1-b][1,3]thiazol-6-yl)phenyl)acetamide,
2-(3,5-dimethylphenyl)-N-(3-(5-(2-((4-morpholin-4-ylphenyl)amino)pyrimidin-4-yl)imidazo[2,1-b][1,3]thiazol-6-yl)phenyl)acetamide,
2-(2,3-dimethoxyphenyl)-N-(3-(5-(2-((4-morpholin-4-ylphenyl)amino)pyrimidin-4-yl)imidazo[2,1-b][1,3]thiazol-6-yl)phenyl)acetamide,
2-(2,4-dimethoxyphenyl)-N-(3-(5-(2-((4-morpholin-4-ylphenyl)amino)pyrimidin-4-yl)imidazo[2,1-b][1,3]thiazol-6-yl)phenyl)acetamide,
2-(2,5-dimethoxyphenyl)-N-(3-(5-(2-((4-morpholin-4-ylphenyl)amino)pyrimidin-4-yl)imidazo[2,1-b][1,3]thiazol-6-yl)phenyl)acetamide,
2-(3,4-dimethoxyphenyl)-N-(3-(5-(2-((4-morpholin-4-ylphenyl)amino)pyrimidin-4-yl)imidazo[2,1-b][1,3]thiazol-6-yl)phenyl)acetamide,
2-(3,5-dimethoxyphenyl)-N-(3-(5-(2-((4-morpholin-4-ylphenyl)amino)pyrimidin-4-yl)imidazo[2,1-b][1,3]thiazol-6-yl)phenyl)acetamide,
2-(1,3-benzodioxol-5-yl)-N-(3-(5-(2-((4-morpholin-4-ylphenyl)amino)pyrimidin-4-yl)imidazo[2,1-b][1,3]thiazol-6-yl)phenyl)acetamide,
N-(3-(5-(2-((4-morpholin-4-ylphenyl)amino)pyrimidin-4-yl)imidazo[2,1-b][1,3]thiazol-6-yl)phenyl)-2-(3,4,5-trimethoxyphenyl)acetamide,
2-(2,3-difluorophenyl)-N-(3-(5-(2-((4-morpholin-4-ylphenyl)amino)pyrimidin-4-yl)imidazo[2,1-b][1,3]thiazol-6-yl)phenyl)acetamide,
2-(2,4-dichlorophenyl)-N-(3-(5-(2-((4-morpholin-4-ylphenyl)amino)pyrimidin-4-yl)imidazo[2,1-b][1,3]thiazol-6-yl)phenyl)acetamide,
2-(2,5-difluorophenyl)-N-(3-(5-(2-((4-morpholin-4-ylphenyl)amino)pyrimidin-4-yl)imidazo[2,1-b][1,3]thiazol-6-yl)phenyl)acetamide,
2-(3,4-dichlorophenyl)-N-(3-(5-(2-((4-morpholin-4-ylphenyl)amino)pyrimidin-4-yl)imidazo[2,1-b][1,3]thiazol-6-yl)phenyl)acetamide,
2-(2,6-dichlorophenyl)-N-(3-(5-(2-((4-morpholin-4-ylphenyl)amino)pyrimidin-4-yl)imidazo[2,1-b][1,3]thiazol-6-yl)phenyl)acetamide,
N-(3-(5-(2-((4-morpholin-4-ylphenyl)amino)pyrimidin-4-yl)imidazo[2,1-b][1,3]thiazol-6-yl)phenyl)-2-furamide,
N-(3-(5-(2-((4-morpholin-4-ylphenyl)amino)pyrimidin-4-yl)imidazo[2,1-b][1,3]thiazol-6-yl)phenyl)-3-furamide,
2,5-dimethyl-N-(3-(5-(2-((4-morpholin-4-ylphenyl)amino)pyrimidin-4-yl)imidazo[2,1-b][1,3]thiazol-6-yl)phenyl)-3-furamide,
N-(3-(5-(2-((4-morpholin-4-ylphenyl)amino)pyrimidin-4-yl)imidazo[2,1-b][1,3]thiazol-6-yl)phenyl)thiophene-2-carboxamide,
N-(3-(5-(2-((4-morpholin-4-ylphenyl)amino)pyrimidin-4-yl)imidazo[2,1-b][1,3]thiazol-6-yl)phenyl)thiophene-3-carboxamide,
3-methyl-N-(3-(5-(2-((4-morpholin-4-ylphenyl)amino)pyrimidin-4-yl)imidazo[2,1-b][1,3]thiazol-6-yl)phenyl)thiophene-2-carboxamide,
5-methyl-N-(3-(5-(2-((4-morpholin-4-ylphenyl)amino)pyrimidin-4-yl)imidazo[2,1-b][1,3]thiazol-6-yl)phenyl)thiophene-2-carboxamide,
N-(3-(5-(2-((4-morpholin-4-ylphenyl)amino)pyrimidin-4-yl)imidazo[2,1-b][1,3]thiazol-6-yl)phenyl)-1H-pyrrole-2-carboxamide,
1-methyl-N-(3-(5-(2-((4-morpholin-4-ylphenyl)amino)pyrimidin-4-yl)imidazo[2,1-b][1,3]thiazol-6-yl)phenyl)-1H-pyrrole-2-carboxamide,
N-(3-(5-(2-((4-morpholin-4-ylphenyl)amino)pyrimidin-4-yl)imidazo[2,1-b][1,3]thiazol-6-yl)phenyl)-1,3-thiazole-4-carboxamide,
N-(3-(5-(2-((4-morpholin-4-ylphenyl)amino)pyrimidin-4-yl)imidazo[2,1-b][1,3]thiazol-6-yl)phenyl)-1,3-thiazole-5-carboxamide,
N-(3-(5-(2-((4-morpholin-4-ylphenyl)amino)pyrimidin-4-yl)imidazo[2,1-b][1,3]thiazol-6-yl)phenyl)-1H-pyrazole-4-carboxamide,
3,5-dimethyl-N-(3-(5-(2-((4-morpholin-4-ylphenyl)amino)pyrimidin-4-yl)imidazo[2,1-b][1,3]thiazol-6-yl)phenyl)isoxazole-4-carboxamide,
5-methyl-N-(3-(5-(2-((4-morpholin-4-ylphenyl)amino)pyrimidin-4-yl)imidazo[2,1-b][1,3]thiazol-6-yl)phenyl)-3-phenylisoxazole-4-carboxamide,
N-(3-(5-(2-((4-morpholin-4-ylphenyl)amino)pyrimidin-4-yl)imidazo[2,1-b][1,3]thiazol-6-yl)phenyl)pyridine-2-carboxamide,
N-(3-(5-(2-((4-morpholin-4-ylphenyl)amino)pyrimidin-4-yl)imidazo[2,1-b][1,3]thiazol-6-yl)phenyl)nicotinamide,
N-(3-(5-(2-((4-morpholin-4-ylphenyl)amino)pyrimidin-4-yl)imidazo[2,1-b][1,3]thiazol-6-yl)phenyl)isonicotinamide,
N-(3-(5-(2-((4-morpholin-4-ylphenyl)amino)pyrimidin-4-yl)imidazo[2,1-b][1,3]thiazol-6-yl)phenyl)-2-pyridin-2-ylacetamide,
N-(3-(5-(2-((4-morpholin-4-ylphenyl)amino)pyrimidin-4-yl)imidazo[2,1-b][1,3]thiazol-6-yl)phenyl)-2-pyridin-3-ylacetamide,
N-(3-(5-(2-((4-morpholin-4-ylphenyl)amino)pyrimidin-4-yl)imidazo[2,1-b][1,3]thiazol-6-yl)phenyl)-2-pyridin-4-ylacetamide,
N-(3-(5-(2-((4-morpholin-4-ylphenyl)amino)pyrimidin-4-yl)imidazo[2,1-b][1,3]thiazol-6-yl)phenyl)pyrazine-2-carboxamide,
N-(3-(5-(2-((4-morpholin-4-ylphenyl)amino)pyrimidin-4-yl)imidazo[2,1-b][1,3]thiazol-6-yl)phenyl)pyrimidine-4-carboxamide,
5-methyl-N-(3-(5-(2-((4-morpholin-4-ylphenyl)amino)pyrimidin-4-yl)imidazo[2,1-b][1,3]thiazol-6-yl)phenyl)pyrazine-2-carboxamide,
N-(3-(5-(2-((4-morpholin-4-ylphenyl)amino)pyrimidin-4-yl)imidazo[2,1-b][1,3]thiazol-6-yl)phenyl)-1H-indole-3-carboxamide,
5-methyl-N-(3-(5-(2-((4-morpholin-4-ylphenyl)amino)pyrimidin-4-yl)imidazo[2,1-b][1,3]thiazol-6-yl)phenyl)-1-phenyl-1H-pyrazole-4-carboxamide,
N-(3-(5-(2-((4-morpholin-4-ylphenyl)amino)pyrimidin-4-yl)imidazo[2,1-b][1,3]thiazol-6-yl)phenyl)-4-oxo-4,5,6,7-tetrahydro-1-benzofuran-3-carboxamide,
N-(3-(5-(2-((4-morpholin-4-ylphenyl)amino)pyrimidin-4-yl)imidazo[2,1-b][1,3]thiazol-6-yl)phenyl)-2-pyrrolidin-1-ylacetamide, N-(3-(5-(2-((4-morpholin-4-ylphenyl)amino)pyrimidin-4-yl)imidazo[2,1-b][1,3]thiazol-6-yl)phenyl)-3-piperidin-1-ylpropanamide, 2-(4-methylpiperazin-1-yl)-N-(3-(5-(2-((4-morpholin-4-ylphenyl)amino)pyrimidin-4-yl)imidazo[2,1-b][1,3]thiazol-6-yl)phenyl)acetamide, 2-cyclopentyl-N-(3-(5-(2-((4-morpholin-4-ylphenyl)amino)pyrimidin-4-yl)imidazo[2,1-b][1,3]thiazol-6-yl)phenyl)acetamide, N-(4-(4-acetylpiperazin-1-yl)phenyl)-4-(6-(3-((5-phenyl-1,3,4-oxadiazol-2-yl)amino)phenyl)imidazo[2,1-b][1,3]thiazol-5-yl)pyrimidin-2-amine, N-(3-(5-(2-((4-(4-acetylpiperazin-1-yl)phenyl)amino)pyrimidin-4-yl)imidazo[2,1-b][1,3]thiazol-6-yl)phenyl)benzamide, N-(3-(5-(2-((4-(2-oxopyrrolidin-1-yl)phenyl)amino)pyrimidin-4-yl)imidazo[2,1-b][1,3]thiazol-6-yl)phenyl)benzamide, 2-cyclohexyl-N-(3-(5-(2-((4-morpholin-4-ylphenyl)amino)pyrimidin-4-yl)imidazo[2,1-b][1,3]thiazol-6-yl)phenyl)acetamide, 2-chlorobenzyl 3-(5-(2-((4-morpholin-4-ylphenyl)amino)pyrimidin-4-yl)imidazo[2,1-b][1,3]thiazol-6-yl)phenylcarbamate, N-(3-(5-(2-((4-morpholin-4-ylphenyl)amino)pyrimidin-4-yl)imidazo[2,1-b][1,3]thiazol-6-yl)phenyl)-1,3-benzoxazol-2-amine, 5-methyl-N-(3-(5-(2-((4-morpholin-4-ylphenyl)amino)pyrimidin-4-yl)imidazo[2,1-b][1,3]thiazol-6-yl)phenyl)-1,3-benzoxazol-2-amine, 6-chloro-N-(3-(5-(2-((4-morpholin-4-ylphenyl)amino)pyrimidin-4-yl)imidazo[2,1-b][1,3]thiazol-6-yl)phenyl)-1,3-benzoxazol-2-amine, N-(3-(5-(2-((4-morpholin-4-ylphenyl)amino)pyrimidin-4-yl)imidazo[2,1-b][1,3]thiazol-6-yl)phenyl)-1H-indazol-3-amine, N-(3-(5-(2-((4-((dimethylamino)sulfonyl)phenyl)amino)pyrimidin-4-yl)imidazo[2,1-b][1,3]thiazol-6-yl)phenyl)-2-phenylacetamide, N-(3-(5-(2-((3-(2-morpholin-4-ylethoxy)phenyl)amino)pyrimidin-4-yl)imidazo[2,1-b][1,3]thiazol-6-yl)phenyl)benzamide, N-(3-(5-(2-((3-(2-morpholin-4-ylethoxy)phenyl)amino)pyrimidin-4-yl)imidazo[2,1-b][1,3]thiazol-6-yl)phenyl)-2-phenylacetamide, 2-(2-methoxyphenyl)-N-(3-(5-(2-((4-morpholin-4-ylphenyl)amino)pyrimidin-4-yl)imidazo[2,1-b][1,3]thiazol-6-yl)phenyl)acetamide, N-(3-(5-(2-((4-morpholin-4-ylphenyl)amino)pyrimidin-4-yl)imidazo[2,1-b][1,3]thiazol-6-yl)phenyl)-2-(2-(trifluoromethyl)phenyl)acetamide, N-(3-(5-(2-((4-morpholin-4-ylphenyl)amino)pyrimidin-4-yl)imidazo[2,1-b][1,3]thiazol-6-yl)phenyl)-2-(2-(trifluoromethoxy)phenyl)acetamide, 2-(2-fluoro-3-(trifluoromethyl)phenyl)-N-(3-(5-(2-((4-morpholin-4-ylphenyl)amino)pyrimidin-4-yl)imidazo[2,1-b][1,3]thiazol-6-yl)phenyl)acetamide, 2-(2,6-difluorophenyl)-N-(3-(5-(2-((4-morpholin-4-ylphenyl)amino)pyrimidin-4-yl)imidazo[2,1-b][1,3]thiazol-6-yl)phenyl)acetamide, N-(3-(5-(2-((3-(3-(4-methylpiperazin-1-yl)propoxy)phenyl)amino)pyrimidin-4-yl)imidazo[2,1-b][1,3]thiazol-6-yl)phenyl)benzamide, N-(3-(5-(2-((3-(3-(4-methylpiperazin-1-yl)propoxy)phenyl)amino)pyrimidin-4-yl)imidazo[2,1-b][1,3]thiazol-6-yl)phenyl)-2-phenylacetamide, N-(3-(5-(2-((3-(3-morpholin-4-ylpropoxy)phenyl)amino)pyrimidin-4-yl)imidazo[2,1-b][1,3]thiazol-6-yl)phenyl)benzamide, N-(3-(5-(2-((3-(3-morpholin-4-ylpropoxy)phenyl)amino)pyrimidin-4-yl)imidazo[2,1-b][1,3]thiazol-6-yl)phenyl)-2-phenylacetamide, N-(3-(5-(2-((4-(4-(3-methoxypropyl)piperazin-1-yl)phenyl)amino)pyrimidin-4-yl)imidazo[2,1-b][1,3]thiazol-6-yl)phenyl)benzamide, 2,6-difluoro-N-(3-(5-(2-((4-(4-(3-methoxypropyl)piperazin-1-yl)phenyl)amino)pyrimidin-4-yl)imidazo[2,1-b][1,3]thiazol-6-yl)phenyl)benzamide, N-(2-morpholin-4-ylethyl)-3-((4-(6-(3-((phenylacetyl)amino)phenyl)imidazo[2,1-b][1,3]thiazol-5-yl)pyrimidin-2-yl)amino)benzamide, N-(2-isopropoxyethyl)-3-((4-(6-(3-((phenylacetyl)amino)phenyl)imidazo[2,1-b][1,3]thiazol-5-yl)pyrimidin-2-yl)amino)benzamide, 3-((4-(6-(3-((phenylacetyl)amino)phenyl)imidazo[2,1-b][1,3]thiazol-5-yl)pyrimidin-2-yl)amino)-N-(3-propoxypropyl)benzamide, N-(3-methoxypropyl)-3-((4-(6-(3-((phenylacetyl)amino)phenyl)imidazo[2,1-b][1,3]thiazol-5-yl)pyrimidin-2-yl)amino)benzamide, 3-((4-(6-(3-((phenylacetyl)amino)phenyl)imidazo[2,1-b][1,3]thiazol-5-yl)pyrimidin-2-yl)amino)-N-((2S)-tetrahydrofuran-2-ylmethyl)benzamide, N,N-bis(2-ethoxyethyl)-3-((4-(6-(3-((phenylacetyl)amino)phenyl)imidazo[2,1-b][1,3]thiazol-5-yl)pyrimidin-2-yl)amino)benzamide, N-(2-methoxyethyl)-N-methyl-3-((4-(6-(3-((phenylacetyl)amino)phenyl)imidazo[2,1-b][1,3]thiazol-5-yl)pyrimidin-2-yl)amino)benzamide, N-ethyl-N-(2-methoxyethyl)-3-((4-(6-(3-((phenylacetyl)amino)phenyl)imidazo[2,1-b][1,3]thiazol-5-yl)pyrimidin-2-yl)amino)benzamide, N,N-bis(2-methoxyethyl)-3-((4-(6-(3-((phenylacetyl)amino)phenyl)imidazo[2,1-b][1,3]thiazol-5-yl)pyrimidin-2-yl)amino)benzamide, N-(3-(5-(2-((3-(morpholin-4-ylcarbonyl)phenyl)amino)pyrimidin-4-yl)imidazo[2,1-b][1,3]thiazol-6-yl)phenyl)-2-phenylacetamide, 2-phenyl-N-(3-(5-(2-((3-(thiomorpholin-4-ylcarbonyl)phenyl)amino)pyrimidin-4-yl)imidazo[2,1-b][1,3]thiazol-6-yl)phenyl)acetamide, N-(2-(dimethylamino)ethyl)-3-((4-(6-(3-((phenylacetyl)amino)phenyl)imidazo[2,1-b][1,3]thiazol-5-yl)pyrimidin-2-yl)amino)benzamide, 3-((4-(6-(3-((phenylacetyl)amino)phenyl)imidazo[2,1-b][1,3]thiazol-5-yl)pyrimidin-2-yl)amino)-N-(2-pyrrolidin-1-ylethyl)benzamide, 3-((4-(6-(3-((phenylacetyl)amino)phenyl)imidazo[2,1-b][1,3]thiazol-5-yl)pyrimidin-2-yl)amino)-N-(2-piperidin-1-ylethyl)benzamide, N-(3-morpholin-4-ylpropyl)-3-((4-(6-(3-((phenylacetyl)amino)phenyl)imidazo[2,1-b][1,3]thiazol-5-yl)pyrimidin-2-yl)amino)benzamide, N-(2-(4-methylpiperazin-1-yl)ethyl)-3-((4-(6-(3-((phenylacetyl)amino)phenyl)imidazo[2,1-b][1,3]thiazol-5-yl)pyrimidin-2-yl)amino)benzamide, N-methyl-3-((4-(6-(3-((phenylacetyl)amino)phenyl)imidazo[2,1-b][1,3]thiazol-5-yl)pyrimidin-2-yl)amino)-N-(tetrahydrofuran-2-ylmethyl)benzamide, N-(3-(dimethylamino)propyl)-N-methyl-3-((4-(6-(3-((phenylacetyl)amino)phenyl)imidazo[2,1-b][1,3]thiazol-5-yl)pyrimidin-2-yl)amino)benzamide, N-(2-(dimethylamino)ethyl)-N-ethyl-3-((4-(6-(3-((phenylacetyl)amino)phenyl)imidazo[2,1-b][1,3]thiazol-5-yl)pyrimidin-2-yl)amino)benzamide,
N-methyl-3-((4-(6-(3-((phenylacetyl)amino)phenyl)imidazo[2,1-b][1,3]thiazol-5-yl)pyrimidin-2-yl)amino)-N-(2-pyridin-2-ylethyl)benzamide,
N-(3-(5-(2-((3-((2,6-dimethylmorpholin-4-yl)carbonyl)phenyl)amino)pyrimidin-4-yl)imidazo[2,1-b][1,3]thiazol-6-yl)phenyl)-2-phenylacetamide,
N-(3-(5-(2-((3-((4-methylpiperazin-1-yl)carbonyl)phenyl)amino)pyrimidin-4-yl)imidazo[2,1-b][1,3]thiazol-6-yl)phenyl)-2-phenylacetamide,
N-(3-(5-(2-((3-((4-ethylpiperazin-1-yl)carbonyl)phenyl)amino)pyrimidin-4-yl)imidazo[2,1-b][1,3]thiazol-6-yl)phenyl)-2-phenylacetamide,
N-(3-(5-(2-((3-((4-(2-hydroxyethyl)piperazin-1-yl)carbonyl)phenyl)amino)pyrimidin-4-yl)imidazo[2,1-b][1,3]thiazol-6-yl)phenyl)-2-phenylacetamide,
N-(3-(5-(2-((3-((4-(2-(2-hydroxyethoxy)ethyl)piperazin-1-yl)carbonyl)phenyl)amino)pyrimidin-4-yl)imidazo[2,1-b][1,3]thiazol-6-yl)phenyl)-2-phenylacetamide,
N-(4-(dimethylamino)butyl)-3-((4-(6-(3-((phenylacetyl)amino)phenyl)imidazo[2,1-b][1,3]thiazol-5-yl)pyrimidin-2-yl)amino)benzamide,
N-(3-(1H-imidazol-1-yl)propyl)-3-((4-(6-(3-((phenylacetyl)amino)phenyl)imidazo[2,1-b][1,3]thiazol-5-yl)pyrimidin-2-y1)amino)benzamide,
2-fluoro-N-(3-(5-(2-((4-morpholin-4-ylphenyl)amino)pyrimidin-4-yl)imidazo[2,1-b][1,3]thiazol-6-yl)phenyl)benzamide,
2-methyl-N-(3-(5-(2-((4-morpholin-4-ylphenyl)amino)pyrimidin-4-yl)imidazo[2,1-b][1,3]thiazol-6-yl)phenyl)benzamide,
4-(6-(3-((5-(4-methoxyphenyl)-1,3-oxazol-2-yl)amino)phenyl)imidazo[2,1-b][1,3]thiazol-5-yl)-N-(4-morpholin-4-ylphenyl)pyrimidin-2-amine,
N-(4-morpholin-4-ylphenyl)-4-(6-(3-((5-phenyl-1,3-oxazol-2-yl)amino)phenyl)imidazo[2,1-b][1,3]thiazol-5-yl)pyrimidin-2-amine,
N-(3-(2-bromo-5-(2-((3-morpholin-4-ylphenyl)amino)pyrimidin-4-yl)imidazo[2,1-b][1,3]thiazol-6-yl)phenyl)benzamide,
N-(3-(2-bromo-5-(2-((3-morpholin-4-ylphenyl)amino)pyrimidin-4-yl)imidazo[2,1-b][1,3]thiazol-6-yl)phenyl)-2-phenylacetamide,
2-methoxy-N-(3-(5-(2-((4-morpholin-4-ylphenyl)amino)pyrimidin-4-yl)imidazo[2,1-b][1,3]thiazol-6-yl)phenyl)benzamide,
2-chloro-N-(3-(5-(2-((4-morpholin-4-ylphenyl)amino)pyrimidin-4-yl)imidazo[2,1-b][1,3]thiazol-6-yl)phenyl)benzamide,
2,6-dimethoxy-N-(3-(5-(2-((4-morpholin-4-ylphenyl)amino)pyrimidin-4-yl)imidazo[2,1-b][1,3]thiazol-6-yl)phenyl)benzamide,
2-chloro-6-fluoro-N-(3-(5-(2-((4-morpholin-4-ylphenyl)amino)pyrimidin-4-yl)imidazo[2,1-b][1,3]thiazol-6-yl)phenyl)benzamide,
2,6-dichloro-N-(3-(5-(2-((4-morpholin-4-ylphenyl)amino)pyrimidin-4-yl)imidazo[2,1-b][1,3]thiazol-6-yl)phenyl)benzamide,
N-(3-(5-(2-((4-morpholin-4-ylphenyl)amino)pyrimidin-4-yl)imidazo[2,1-b][1,3]thiazol-6-yl)phenyl)-2-nitrobenzamide,
N-(3-(5-(2-((4-morpholin-4-ylphenyl)amino)pyrimidin-4-yl)imidazo[2,1-b][1,3]thiazol-6-yl)phenyl)-2-(trifluoromethyl)benzamide,
2,5-dichloro-N-(3-(5-(2-((4-morpholin-4-ylphenyl)amino)pyrimidin-4-yl)imidazo[2,1-b][1,3]thiazol-6-yl)phenyl)thiophene-3-carboxamide,
N-(3-(5-(2-((4-(4-ethylpiperazin-1-yl)phenyl)amino)pyrimidin-4-yl)imidazo[2,1-b][1,3]thiazol-6-yl)phenyl)-2-phenylacetamide,
2-(2-chlorophenyl)-N-(3-(5-(2-((4-(4-ethylpiperazin-1-yl)phenyl)amino)pyrimidin-4-yl)imidazo[2,1-b][1,3]thiazol-6-yl)phenyl)acetamide,
N-(3-(5-(2-((4-(4-ethylpiperazin-1-yl)phenyl)amino)pyrimidin-4-yl)imidazo[2,1-b][1,3]thiazol-6-yl)phenyl)-2-(2-methylphenyl)acetamide,
N-(3-(5-(2-((4-(4-ethylpiperazin-1-yl)phenyl)amino)pyrimidin-4-yl)imidazo[2,1-b][1,3]thiazol-6-yl)phenyl)-2-(2-(trifluoromethyl)phenyl)acetamide,
N-(3-(5-(2-((4-(4-ethylpiperazin-1-yl)phenyl)amino)pyrimidin-4-yl)imidazo[2,1-b][1,3]thiazol-6-yl)phenyl)benzamide,
N-(3-(5-(2-((4-(4-ethylpiperazin-1-yl)phenyl)amino)pyrimidin-4-yl)imidazo[2,1-b][1,3]thiazol-6-yl)phenyl)-2,6-difluorobenzamide,
2-chloro-N-(3-(5-(2-((4-(4-ethylpiperazin-1-yl)phenyl)amino)pyrimidin-4-yl)imidazo[2,1-b][1,3]thiazol-6-yl)phenyl)-6-fluorobenzamide,
2-chloro-N-(3-(5-(2-((4-(4-ethylpiperazin-1-yl)phenyl)amino)pyrimidin-4-yl)imidazo[2,1-b][1,3]thiazol-6-yl)phenyl)benzamide,
2,6-dichloro-N-(3-(5-(2-((4-(4-ethylpiperazin-1-yl)phenyl)amino)pyrimidin-4-yl)imidazo[2,1-b][1,3]thiazol-6-yl)phenyl)benzamide,
N-(4-(4-ethylpiperazin-1-yl)phenyl)-4-(6-(3-((5-phenyl-1,3,4-oxadiazol-2-yl)amino)phenyl)imidazo[2,1-b][1,3]thiazol-5-yl)pyrimidin-2-amine,
N-(4-(4-ethylpiperazin-1-yl)phenyl)-4-(6-(3-((5-phenyl-1,3-oxazol-2-yl)amino)phenyl)imidazo[2,1-b][1,3]thiazol-5-yl)pyrimidin-2-amine,
N-(3-(2-bromo-5-(2-((4-morpholin-4-ylphenyl)amino)pyrimidin-4-yl)imidazo[2,1-b][1,3]thiazol-6-yl)phenyl)benzamide,
N-(3-(2-bromo-5-(2-((4-morpholin-4-ylphenyl)amino)pyrimidin-4-yl)imidazo[2,1-b][1,3]thiazol-6-yl)phenyl)-2-phenylacetamide,
2-phenyl-N-(3-(5-(2-((3-(3-pyrrolidin-1-ylpropoxy)phenyl)amino)pyrimidin-4-yl)imidazo[2,1-b][1,3]thiazol-6-yl)phenyl)acetamide,
N-(3-(5-(2-((3-(morpholin-4-ylsulfonyl)phenyl)amino)pyrimidin-4-yl)imidazo[2,1-b][1,3]thiazol-6-yl)phenyl)-2-phenylacetamide,
N-(3-(5-(2-((4-morpholin-4-ylphenyl)amino)pyrimidin-4-yl)imidazo[2,1-b][1,3]thiazol-6-yl)phenyl)-1-phenylcyclopropanecarboxamide,
2-methyl-N-(3-(5-(2-((4-morpholin-4-ylphenyl)amino)pyrimidin-4-yl)imidazo[2,1-b][1,3]thiazol-6-yl)phenyl)-2-phenylpropanamide,
N-(2-morpholin-4-ylethyl)-4-(4-(6-(3-((phenylacetyl)amino)phenyl)imidazo[2,1-b][1,3]thiazol-5-yl)pyrimidin-2-yl)amino)benzamide,
3-cyanobenzyl 3-(5-(2-((4-morpholin-4-ylphenyl)amino)pyrimidin-4-yl)imidazo[2,1-b][1,3]thiazol-6-yl)phenylcarbamate,
3-methylbenzyl 3-(5-(2-((4-morpholin-4-ylphenyl)amino)pyrimidin-4-yl)imidazo[2,1-b][1,3]thiazol-6-yl)phenylcarbamate,
3-chlorobenzyl 3-(5-(2-((4-morpholin-4-ylphenyl)amino)pyrimidin-4-yl)imidazo[2,1-b][1,3]thiazol-6-yl)phenylcarbamate, 3-methoxybenzyl 3-(5-(2-((4-morpholin-4-ylphenyl)amino)pyrimidin-4-yl)imidazo[2,1-b][1,3]thiazol-6-yl)phenylcarbamate,
3-fluorobenzyl 3-(5-(2-((4-morpholin-4-ylphenyl)amino)pyrimidin-4-yl)imidazo[2,1-b][1,3]thiazol-6-yl)phenylcarbamate,
4-fluorobenzyl 3-(5-(2-((4-morpholin-4-ylphenyl)amino)pyrimidin-4-yl)imidazo[2,1-b][1,3]thiazol-6-yl)phenylcarbamate,
4-methylbenzyl 3-(5-(2-((4-morpholin-4-ylphenyl)amino)pyrimidin-4-yl)imidazo[2,1-b][1,3]thiazol-6-yl)phenylcarbamate,
3,5-difluorobenzyl 3-(5-(2-((4-morpholin-4-ylphenyl)amino)pyrimidin-4-yl)imidazo[2,1-b][1,3]thiazol-6-yl)phenylcarbamate,
3-(benzyloxy)benzyl 3-(5-(2-((4-morpholin-4-ylphenyl)amino)pyrimidin-4-yl)imidazo[2,1-b][1,3]thiazol-6-yl)phenylcarbamate,
1,3-benzodioxol-5-ylmethyl 3-(5-(2-((4-morpholin-4-ylphenyl)amino)pyrimidin-4-yl)imidazo[2,1-b][1,3]thiazol-6-yl)phenylcarbamate,
N-(3-(5-(2-((3-((dimethylamino)sulfonyl)phenyl)amino)pyrimidin-4-yl)imidazo[2,1-b][1,3]thiazol-6-yl)phenyl)-2-phenylacetamide,
N-(3-(5-(2-((3-morpholin-4-ylphenyl)amino)pyrimidin-4-yl)imidazo[2,1-b][1,3]thiazol-6-yl)phenyl)-N'-phenylurea,
N-(2-methylphenyl)-N'-(3-(5-(2-((3-morpholin-4-ylphenyl)amino)pyrimidin-4-yl)imidazo[2,1-b][1,3]thiazol-6-yl)phenyl)urea,
N-(2-fluorophenyl)-N'-(3-(5-(2-((3-morpholin-4-ylphenyl)amino)pyrimidin-4-yl)imidazo[2,1-b][1,3]thiazol-6-yl)phenyl)urea,
N-(3-(5-(2-((4-(4-ethylpiperazin-1-yl)phenyl)amino)pyrimidin-4-yl)imidazo[2,1-b][1,3]thiazol-6-yl)phenyl)-1-phenylcyclopropanecarboxamide,
N-(3-(5-(2-((3-(3-morpholin-4-ylpropoxy)phenyl)amino)pyrimidin-4-yl)imidazo[2,1-b][1,3]thiazol-6-yl)phenyl)-N'-phenylurea,
N-(2-methylphenyl)-N'-(3-(5-(2-((3-(3-morpholin-4-ylpropoxy)phenyl)amino)pyrimidin-4-yl)imidazo[2,1-b][1,3]thiazol-6-yl)phenyl)urea,
N-(2-fluorophenyl)-N'-(3-(5-(2-((3-(3-morpholin-4-ylpropoxy)phenyl)amino)pyrimidin-4-yl)imidazo[2,1-b][1,3]thiazol-6-yl)phenyl)urea,
N-(3-(5-(2-((3-(3-(4-methylpiperazin-1-yl)propoxy)phenyl)amino)pyrimidin-4-yl)imidazo[2,1-b][1,3]thiazol-6-yl)phenyl)-N'-phenylurea,
N-(2-methylphenyl)-N'-(3-(5-(2-((3-(3-(4-methylpiperazin-1-yl)propoxy)phenyl)amino)pyrimidin-4-yl)imidazo[2,1-b][1,3]thiazol-6-yl)phenyl)urea,
N-(2-fluorophenyl)-N'-(3-(5-(2-((3-(3-(4-methylpiperazin-1-yl)propoxy)phenyl)amino)pyrimidin-4-yl)imidazo[2,1-b][1,3]thiazol-6-yl)phenyl)urea,
N-(3-(5-(2-((3-(aminosulfonyl)phenyl)amino)pyrimidin-4-yl)imidazo[2,1-b][1,3]thiazol-6-yl)phenyl)-2-phenylacetamide,
N-(3-(5-(2-((4-(aminosulfonyl)phenyl)amino)pyrimidin-4-yl)imidazo[2,1-b][1,3]thiazol-6-yl)phenyl)-2-phenylacetamide,
N-(3-(5-(2-((3-(((2-morpholin-4-ylethyl)amino)sulfonyl)phenyl)amino)pyrimidin-4-yl)imidazo[2,1-b][1,3]thiazol-6-yl)phenyl)-2-phenylacetamide,
trans-2-phenyl-N-(3-(5-(2-((4-piperidin-1-ylphenyl)amino)pyrimidin-4-yl)imidazo[2,1-b][1,3]thiazol-6-yl)phenyl)cyclopropanecarboxamide,
3-phenyl-N-(3-(5-(2-((4-piperidin-1-ylphenyl)amino)pyrimidin-4-yl)imidazo[2,1-b][1,3]thiazol-6-yl)phenyl)propanamide,
2-phenyl-N-(3-(5-(2-((4-piperidin-1-ylphenyl)amino)pyrimidin-4-yl)imidazo[2,1-b][1,3]thiazol-6-yl)phenyl)acetamide,
N-(3-(5-(2-((4-piperidin-1-ylphenyl)amino)pyrimidin-4-yl)imidazo[2,1-b][1,3]thiazol-6-yl)phenyl)benzamide,
N-(3-(5-(2-((4-(4-(2-hydroxyethyl)piperazin-1-yl)phenyl)amino)pyrimidin-4-yl)imidazo[2,1-b][1,3]thiazol-6-yl)phenyl)-2-phenylacetamide,
N-(3-(5-(2-((4-(4-(2-hydroxyethyl)piperazin-1-yl)phenyl)amino)pyrimidin-4-yl)imidazo[2,1-b][1,3]thiazol-6-yl)phenyl)benzamide,
trans-2-phenyl-N-(3-(5-(2-((4-pyrrolidin-1-ylphenyl)amino)pyrimidin-4-yl)imidazo[2,1-b][1,3]thiazol-6-yl)phenyl)cyclopropanecarboxamide,
N-(3-(5-(2-((4-(4-(2-hydroxyethyl)piperazin-1-yl)phenyl)amino)pyrimidin-4-yl)imidazo[2,1-b][1,3]thiazol-6-yl)phenyl)-3-phenylpropanamide,
3-phenyl-N-(3-(5-(2-((4-pyrrolidin-1-ylphenyl)amino)pyrimidin-4-yl)imidazo[2,1-b][1,3]thiazol-6-yl)phenyl)propanamide,
trans-N-(3-(5-(2-((4-(4-(2-hydroxyethyl)piperazin-1-yl)phenyl)amino)pyrimidin-4-yl)imidazo[2,1-b][1,3]thiazol-6-yl)phenyl)-2-phenylcyclopropanecarboxamide,
N-(3-(5-(2-((4-(4-isopropylpiperazin-1-yl)phenyl)amino)pyrimidin-4-yl)imidazo[2,1-b][1,3]thiazol-6-yl)phenyl)-2-phenylacetamide,
2-phenyl-N-(3-(5-(2-((4-pyrrolidin-1-ylphenyl)amino)pyrimidin-4-yl)imidazo[2,1-b][1,3]thiazol-6-yl)phenyl)acetamide,
N-(3-(5-(2-((4-(4-isopropylpiperazin-1-yl)phenyl)amino)pyrimidin-4-yl)imidazo[2,1-b][1,3]thiazol-6-yl)phenyl)benzamide,
N-(3-(5-(2-((4-(4-isopropylpiperazin-1-yl)phenyl)amino)pyrimidin-4-yl)imidazo[2,1-b][1,3]thiazol-6-yl)phenyl)-3-phenylpropanamide,
N-(3-(5-(2-((4-pyrrolidin-1-ylphenyl)amino)pyrimidin-4-yl)imidazo[2,1-b][1,3]thiazol-6-yl)phenyl)benzamide,
trans-N-(3-(5-(2-((4-(4-isopropylpiperazin-1-yl)phenyl)amino)pyrimidin-4-yl)imidazo[2,1-b][1,3]thiazol-6-yl)phenyl)-2-phenylcyclopropanecarboxamide,
2-(2-chlorophenyl)-N-(3-(5-(2-((4-(4-isopropylpiperazin-1-yl)phenyl)amino)pyrimidin-4-yl)imidazo[2,1-b][1,3]thiazol-6-yl)phenyl)acetamide,
2-chloro-N-(3-(5-(2-((4-(4-isopropylpiperazin-1-yl)phenyl)amino)pyrimidin-4-yl)imidazo[2,1-b][1,3]thiazol-6-yl)phenyl)benzamide,
N-(3-(5-(2-((3-(acetylamino)phenyl)amino)pyrimidin-4-yl)imidazo[2,1-b][1,3]thiazol-6-yl)phenyl)-2,6-difluorobenzamide,
N-(3-(5-(2-((4-(4-(3-methoxypropyl)piperazin-1-yl)phenyl)amino)pyrimidin-4-yl)imidazo[2,1-b][1,3]thiazol-6-yl)phenyl)-N'-phenylurea,
N-(2-chlorophenyl)-N'-(3-(5-(2-((4-(4-(3-methoxypropyl)piperazin-1-yl)phenyl)amino)pyrimidin-4-yl)imidazo[2,1-b][1,3]thiazol-6-yl)phenyl)urea,
N-(3-((4-(6-(3-((anilinocarbonyl)amino)phenyl)imidazo[2,1-b][1,3]thiazol-5-yl)pyrimidin-2-yl)amino)phenyl)acetamide,
N-(3-((4-(6-(3-((((2-chlorophenyl)amino)carbonyl)amino)phenyl)imidazo[2,1-b][1,3]thiazol-5-yl)pyrimidin-2-yl)amino)phenyl)acetamide,
N-(3-(5-(2-((3-(acetylamino)phenyl)amino)pyrimidin-4-yl)imidazo[2,1-b][1,3]thiazol-6-yl)phenyl)-2-(2-chlorophenyl)acetamide, 2-(2-chlorophenyl)-N-(3-(5-(2-((4-(4-(3-methoxypropyl)piperazin-1-yl)phenyl)amino)pyrimidin-4-yl)imidazo[2,1-b][1,3]thiazol-6-yl)phenyl)acetamide, N-(3-(5-(2-((4-(4-acetylpiperazin-1-yl)phenyl)amino)pyrimidin-4-yl)imidazo[2,1-b][1,3]thiazol-6-yl)phenyl)-2-(2-chlorophenyl)acetamide, N-(3-(5-(2-((4-(4-acetylpiperazin-1-yl)phenyl)amino)pyrimidin-4-yl)imidazo[2,1-b][1,3]thiazol-6-yl)phenyl)-2,6-difluorobenzamide, N-(3-(5-(2-((4-(4-acetylpiperazin-1-yl)phenyl)amino)pyrimidin-4-yl)imidazo[2,1-b][1,3]thiazol-6-yl)phenyl)-2-chlorobenzamide, N-(3-(5-(2-((4-(4-acetylpiperazin-1-yl)phenyl)amino)pyrimidin-4-yl)imidazo[2,1-b][1,3]thiazol-6-yl)phenyl)-N'-phenylurea, N-(3-(5-(2-((4-(4-acetylpiperazin-1-yl)phenyl)amino)pyrimidin-4-yl)imidazo[2,1-b][1,3]thiazol-6-yl)phenyl)-N'-(2-chlorophenyl)urea, 2,6-difluoro-N-(3-(5-(2-((4-(4-isopropylpiperazin-1-yl)phenyl)amino)pyrimidin-4-yl)imidazo[2,1-b][1,3]thiazol-6-yl)phenyl)benzamide, N-(3-(5-(2-((4-(4-isopropylpiperazin-1-yl)phenyl)amino)pyrimidin-4-yl)imidazo[2,1-b][1,3]thiazol-6-yl)phenyl)-N'-phenylurea, N-(2-chlorophenyl)-N'-(3-(5-(2-((4-(4-isopropylpiperazin-1-yl)phenyl)amino)pyrimidin-4-yl)imidazo[2,1-b][1,3]thiazol-6-yl)phenyl)urea, 2-(5-acetylthien-3-yl)-N-(3-(5-(2-((4-morpholin-4-ylphenyl)amino)pyrimidin-4-yl)imidazo[2,1-b][1,3]thiazol-6-yl)phenyl)acetamide, 2-methyl-N-(3-(5-(2-((3-(2-morpholin-4-ylethyl)phenyl)amino)pyrimidin-4-yl)imidazo[2,1-b][1,3]thiazol-6-yl)phenyl)benzamide, 2-fluoro-N-(3-(5-(2-((3-(2-morpholin-4-ylethyl)phenyl)amino)pyrimidin-4-yl)imidazo[2,1-b][1,3]thiazol-6-yl)phenyl)benzamide, 2,6-difluoro-N-(3-(5-(2-((3-(2-morpholin-4-ylethyl)phenyl)amino)pyrimidin-4-yl)imidazo[2,1-b][1,3]thiazol-6-yl)phenyl)benzamide, N-(3-(5-(2-((3-(2-morpholin-4-ylethyl)phenyl)amino)pyrimidin-4-yl)imidazo[2,1-b][1,3]thiazol-6-yl)phenyl)-N'-phenylurea, N-(3-(5-(2-((3-(2-morpholin-4-ylethyl)phenyl)amino)pyrimidin-4-yl)imidazo[2,1-b][1,3]thiazol-6-yl)phenyl)-2-phenylacetamide, N-(3-(5-(2-((3-(2-oxopyrrolidin-1-yl)phenyl)amino)pyrimidin-4-yl)imidazo[2,1-b][1,3]thiazol-6-yl)phenyl)-2-phenylacetamide, 2-(2-chlorophenyl)-N-(3-(5-(2-((3-(2-oxopyrrolidin-1-yl)phenyl)amino)pyrimidin-4-yl)imidazo[2,1-b][1,3]thiazol-6-yl)phenyl)acetamide, N-(3-(5-(2-((3-(2-oxopyrrolidin-1-yl)phenyl)amino)pyrimidin-4-yl)imidazo[2,1-b][1,3]thiazol-6-yl)phenyl)benzamide, 2-chloro-N-(3-(5-(2-((3-(2-oxopyrrolidin-1-yl)phenyl)amino)pyrimidin-4-yl)imidazo[2,1-b][1,3]thiazol-6-yl)phenyl)benzamide, 2,6-difluoro-N-(3-(5-(2-((3-(2-oxopyrrolidin-1-yl)phenyl)amino)pyrimidin-4-yl)imidazo[2,1-b][1,3]thiazol-6-yl)phenyl)benzamide, 2-(2-chlorophenyl)-N-(3-(5-(2-((3-morpholin-4-ylphenyl)amino)pyrimidin-4-yl)imidazo[2,1-b][1,3]thiazol-6-yl)phenyl)acetamide, N-(3-(5-(2-((3-morpholin-4-ylphenyl)amino)pyrimidin-4-yl)imidazo[2,1-b][1,3]thiazol-6-yl)phenyl)benzamide, 2,6-difluoro-N-(3-(5-(2-((3-morpholin-4-ylphenyl)amino)pyrimidin-4-yl)imidazo[2,1-b][1,3]thiazol-6-yl)phenyl)benzamide, N-(2-chlorophenyl)-N'-(3-(5-(2-((3-morpholin-4-ylphenyl)amino)pyrimidin-4-yl)imidazo[2,1-b][1,3]thiazol-6-yl)phenyl)urea, N-(3-(5-(2-((3-(2-pyrrolidin-1-ylethoxy)phenyl)amino)pyrimidin-4-yl)imidazo[2,1-b][1,3]thiazol-6-yl)phenyl)benzamide, 2-phenyl-N-(3-(5-(2-((3-(2-pyrrolidin-1-ylethoxy)phenyl)amino)pyrimidin-4-yl)imidazo[2,1-b][1,3]thiazol-6-yl)phenyl)acetamide, 2,6-difluoro-N-(3-(5-(2-((3-(3-morpholin-4-ylpropoxy)phenyl)amino)pyrimidin-4-yl)imidazo[2,1-b][1,3]thiazol-6-yl)phenyl)benzamide, N-(2-chlorophenyl)-N'-(3-(5-(2-((3-(3-morpholin-4-ylpropoxy)phenyl)amino)pyrimidin-4-yl)imidazo[2,1-b][1,3]thiazol-6-yl)phenyl)urea, 2-(2-chlorophenyl)-N-(3-(5-(2-((3-(3-morpholin-4-ylpropoxy)phenyl)amino)pyrimidin-4-yl)imidazo[2,1-b][1,3]thiazol-6-yl)phenyl)acetamide, 3-((4-(6-(3-(benzoylamino)phenyl)imidazo[2,1-b][1,3]thiazol-5-yl)pyrimidin-2-yl)amino)-N-(2-(dimethylamino)ethyl)benzamide, N-(3-(5-(2-((3-(((2-(dimethylamino)ethyl)amino)carbonyl)phenyl)amino)pyrimidin-4-yl)imidazo[2,1-b][1,3]thiazol-6-yl)phenyl)-2,6-difluorobenzamide, 3-((4-(6-(3-((anilinocarbonyl)amino)phenyl)imidazo[2,1-b][1,3]thiazol-5-yl)pyrimidin-2-yl)amino)-N-(2-(dimethylamino)ethyl)benzamide, 3-((4-(6-(3-((((2-chlorophenyl)amino)carbonyl)amino)phenyl)imidazo[2,1-b][1,3]thiazol-5-yl)pyrimidin-2-yl)amino)-N-(2-(dimethylamino)ethyl)benzamide, N-(2-chloro-5-(5-(2-((3-morpholin-4-ylphenyl)amino)pyrimidin-4-yl)imidazo[2,1-b][1,3]thiazol-6-yl)phenyl)benzamide, N-(2-(dimethylamino)-5-(5-(2-((3-morpholin-4-ylphenyl)amino)pyrimidin-4-yl)imidazo[2,1-b][1,3]thiazol-6-yl)phenyl)benzamide, N-(2-chloro-5-(5-(2-((3-morpholin-4-ylphenyl)amino)pyrimidin-4-yl)imidazo[2,1-b][1,3]thiazol-6-yl)phenyl)-2-phenylacetamide, N-(2-(dimethylamino)-5-(5-(2-((3-morpholin-4-ylphenyl)amino)pyrimidin-4-yl)imidazo[2,1-b][1,3]thiazol-6-yl)phenyl)-2-phenylacetamide, N-(2-ethoxy-5-(5-(2-((3-morpholin-4-ylphenyl)amino)pyrimidin-4-yl)imidazo[2,1-b][1,3]thiazol-6-yl)phenyl)-2-phenylacetamide, N-(3-(5-(2-((4-(4-(3-hydroxypropyl)piperazin-1-yl)phenyl)amino)pyrimidin-4-yl)imidazo[2,1-b][1,3]thiazol-6-yl)phenyl)benzamide, N-(3-(5-(2-((4-(4-(3-hydroxypropyl)piperazin-1-yl)phenyl)amino)pyrimidin-4-yl)imidazo[2,1-b][1,3]thiazol-6-yl)phenyl)-2-phenylacetamide, 3-((4-(6-(3-(((2-chlorophenyl)acetyl)amino)phenyl)imidazo[2,1-b][1,3]thiazol-5-yl)pyrimidin-2-yl)amino)-N-(2-(dimethylamino)ethyl)benzamide, N-(2-ethoxy-5-(5-(2-((3-morpholin-4-ylphenyl)amino)pyrimidin-4-yl)imidazo[2,1-b][1,3]thiazol-6-yl)phenyl)benzamide, 2,6-difluoro-N-(3-(5-(2-((3-(3-(4-methylpiperazin-1-yl)propoxy)phenyl)amino)pyrimidin-4-yl)imidazo[2,1-b][1,3]thiazol-6-yl)phenyl)benzamide, N-(2-chlorophenyl)-N'-(3-(5-(2-((3-(3-(4-methylpiperazin-1-yl)propoxy)phenyl)amino)pyrimidin-4-yl)imidazo[2,1-b][1,3]thiazol-6-yl)phenyl)urea, 2-(2-chlorophenyl)-N-(3-(5-(2-((3-(3-(4-methylpiperazin-1-yl)propoxy)phenyl)amino)pyrimidin-4-yl)imidazo[2,1-b][1,3]thiazol-6-yl)phenyl)acetamide, N-(3-(5-(2-((3-(4-isopropylpiperazin-1-yl)phenyl)amino)pyrimidin-4-yl)imidazo[2,1-b][1,3]thiazol-6-yl)phenyl)-2-phenylacetamide, N-(3-(5-(2-((3-(4-isopropylpiperazin-1-yl)phenyl)amino)pyrimidin-4-yl)imidazo[2,1-b][1,3]thiazol-6-yl)phenyl)benzamide, 2-(2-chlorophenyl)-N-(3-(5-(2-((3-(4-isopropylpiperazin-1-yl)phenyl)amino)pyrimidin-4-yl)imidazo[2,1-b][1,3]thiazol-6-yl)phenyl)acetamide, 2-chloro-N-(3-(5-(2-((3-(4-isopropylpiperazin-1-yl)phenyl)amino)pyrimidin-4-yl)imidazo[2,1-b][1,3]thiazol-6-yl)phenyl)benzamide, 2,6-difluoro-N-(3-(5-(2-((3-(4-isopropylpiperazin-1-yl)phenyl)amino)pyrimidin-4-yl)imidazo[2,1-b][1,3]thiazol-6-yl)phenyl)benzamide, N-(3-(5-(2-((3-(4-ethylpiperazin-1-yl)phenyl)amino)pyrimidin-4-yl)imidazo[2,1-b][1,3]thiazol-6-yl)phenyl)-2-phenylacetamide, N-(3-(5-(2-((3-(4-ethylpiperazin-1-yl)phenyl)amino)pyrimidin-4-yl)imidazo[2,1-b][1,3]thiazol-6-yl)phenyl)benzamide, N-(3-(5-(2-((3-(4-ethylpiperazin-1-yl)phenyl)amino)pyrimidin-4-yl)imidazo[2,1-b][1,3]thiazol-6-yl)phenyl)-2,6-difluorobenzamide, 2-phenyl-N-(3-(5-(2-(pyridin-4-ylamino)pyrimidin-4-yl)imidazo[2,1-b][1,3]thiazol-6-y1)phenyl)acetamide, N-(3-(5-(2-((4-(4-ethyl-2-oxopiperazin-1-yl)phenyl)amino)pyrimidin-4-yl)imidazo[2,1-b][1,3]thiazol-6-yl)phenyl)-2-phenylacetamide, N-(3-(5-(2-((4-(4-ethyl-2-oxopiperazin-1-yl)phenyl)amino)pyrimidin-4-yl)imidazo[2,1-b][1,3]thiazol-6-yl)phenyl)benzamide, 2-chloro-N-(3-(5-(2-((4-(4-ethyl-2-oxopiperazin-1-yl)phenyl)amino)pyrimidin-4-yl)imidazo[2,1-b][1,3]thiazol-6-yl)phenyl)benzamide, N-(3-(5-(2-((4-(4-ethyl-2-oxopiperazin-1-yl)phenyl)amino)pyrimidin-4-yl)imidazo [2,1-b][1,3]thiazol-6-yl)phenyl)-2,6-difluorobenzamide, 2-chloro-N-(3-(5-(2-((4-(4-ethyl-2-oxopiperazin-1-yl)phenyl)amino)pyrimidin-4-yl)imidazo [2,1-b][1,3]thiazol-6-yl)phenyl)-4-fluorobenzamide, N-(3-(5-(2-((3-(4-ethyl-2-oxopiperazin-1-yl)phenyl)amino)pyrimidin-4-yl)imidazo [2,1-b][1,3]thiazol-6-yl)phenyl)-2-phenylacetamide, N-(3-(5-(2-((3-(4-ethyl-2-oxopiperazin-1-yl)phenyl)amino)pyrimidin-4-yl)imidazo [2,1-b][1,3]thiazol-6-yl)phenyl)benzamide, 2-chloro-N-(3-(5-(2-((3-(4-ethyl-2-oxopiperazin-1-yl)phenyl)amino)pyrimidin-4-yl)imidazo [2,1-b][1,3]thiazol-6-yl)phenyl)benzamide, N-(3-(5-(2-((3-(4-ethyl-2-oxopiperazin-1-yl)phenyl)amino)pyrimidin-4-yl)imidazo [2,1-b][1,3]thiazol-6-yl)phenyl)-2,6-difluorobenzamide, 2-chloro-N-(3-(5-(2-((3-(4-ethyl-2-oxopiperazin-1-yl)phenyl)amino)pyrimidin-4-yl)imidazo [2,1-b][1,3]thiazol-6-yl)phenyl)-4-fluorobenzamide, 2-chloro-4-fluoro-N-(3-(5-(243-(2-oxopyrrolidin-1-yl)phenyl)amino)pyrimidin-4-yl)imidazo [2,1-b][1,3]thiazol-6-yl)phenyl)benzamide, N-(3-(5-(2-((3-methyl-1H-pyrazol-5-yl)amino)pyrimidin-4-yl)imidazo [2,1-b][1,3]thiazol-6-yl)phenyl)-2-phenylacetamide, N-(3-(5-(2-((3-methyl-1H-pyrazol-5-yl)amino)pyrimidin-4-yl)imidazo [2,1-b][1,3]thiazol-6-yl)phenyl)benzamide, N-(3-(2-methyl-5-(243-morpholin-4-ylphenyl)amino)pyrimidin-4-yl)imidazo[2,1-b][1,3]thiazol-6-yl)phenyl)benzamide, N-(3-(2-methyl-5-(243-morpholin-4-ylphenyl)amino)pyrimidin-4-yl)imidazo[2,1-b][1,3]thiazol-6-yl)phenyl)-2-phenylacetamide, N-(3-(2-methyl-5-(2-((4-morpholin-4-ylphenyl)amino)pyrimidin-4-yl)imidazo[2,1-b][1,3]thiazol-6-yl)phenyl)benzamide, 2-phenyl-N-(3-(5-(2-(1H-pyrazol-5-ylamino)pyrimidin-4-yl)imidazo [2,1-b][1,3]thiazol-6-yl)phenyl)acetamide, N-(3-(5-(2-((4-(methylsulfonyl)phenyl)amino)pyrimidin-4-yl)imidazo [2,1-b][1,3]thiazol-6-yl)phenyl)benzamide, 2,6-difluoro-N-(3-(5-(2-((4-(methylsulfonyl)phenyl)amino)pyrimidin-4-yl)imidazo [2,1-b][1,3]thiazol-6-yl)phenyl)benzamide, N-(3-(5-(2-((4-(methylsulfonyl)phenyl)amino)pyrimidin-4-yl)imidazo [2,1-b][1,3]thiazol-6-yl)phenyl)-2-phenylacetamide, N-(3-(5-(2-((3-tert-butyl-1H-pyrazol-5-yl)amino)pyrimidin-4-yl)imidazo [2,1-b][1,3]thiazol-6-yl)phenyl)-N'-phenylurea, N-(3-(5-(2-((3-tert-butyl-1H-pyrazol-5-yl)amino)pyrimidin-4-yl)imidazo [2,1-b][1,3]thiazol-6-yl)phenyl)-2-phenylacetamide, N-(3-(5-(2-((3-(((2-(methylsulfonyl)ethyl)amino)methyl)phenyl)amino)pyrimidin-4-yl)imidazo [2,1-b][1,3]thiazol-6-yl)phenyl)benzamide, 2,6-difluoro-N-(3-(5-(2-((3-(((2-(methylsulfonyl)ethyl)amino)methyl)phenyl)amino)pyrimidin-4-yl)imidazo [2,1-b][1,3]thiazol-6-yl)phenyl)benzamide, N-(3-(5-(2-((3-(((2-(methylsulfonyl)ethyl)amino)methyl)phenyl)amino)pyrimidin-4-yl)imidazo [2,1-b][1,3]thiazol-6-yl)phenyl)-2-phenylacetamide, N-(3-(5-(2-((3-tert-butyl-1H-pyrazol-5-yl)amino)pyrimidin-4-yl)imidazo [2,1-b][1,3]thiazol-6-yl)phenyl)benzamide, 2-phenyl-N-(3-(5-(2-((3-pyridin-3-yl-1H-pyrazol-5-yl)amino)pyrimidin-4-yl)imidazo [2,1-b][1,3]thiazol-6-yl)phenyl)acetamide, 4-(6-(3-(benzylamino)phenyl)imidazo[2,1-b][1,3]thiazol-5-yl)-N-(3-(3-morpholin-4-ylpropoxy)phenyl)pyrimidin-2-amine, N-(4-morpholin-4-ylphenyl)-4-(6-(3-((thien-2-ylmethyl)amino)phenyl)imidazo [2,1-b][1,3]thiazol-5-yl)pyrimidin-2-amine, 4-(6-(3-((2-chlorobenzyl)amino)phenyl)imidazo [2,1-b][1,3]thiazol-5-yl)-N-(4-morpholin-4-ylphenyl)pyrimidin-2-amine, 4-(6-(3-((3-methylbenzyl)amino)phenyl)imidazo [2,1-b][1,3]thiazol-5-yl)-N-(4-morpholin-4-ylphenyl)pyrimidin-2-amine, 4-(6-(3-((4-methylbenzyl)amino)phenyl)imidazo [2,1-b][1,3]thiazol-5-yl)-N-(4-morpholin-4-ylphenyl)pyrimidin-2-amine, 4-(6-(3-((4-chlorobenzyl)amino)phenyl)imidazo [2,1-b][1,3]thiazol-5-yl)-N-(4-morpholin-4-ylphenyl)pyrimidin-2-amine, 4-(6-(3-((3-chlorobenzyl)amino)phenyl)imidazo [2,1-b][1,3]thiazol-5-yl)-N-(4-morpholin-4-ylphenyl)pyrimidin-2-amine, 4-(6-(3-((3-methoxybenzyl)amino)phenyl)imidazo [2,1-b][1,3 ]thiazol-5-yl)-N-(4-morpholin-4-ylphenyl)pyrimidin-2-amine, 2-(((3-(5-(2-((4-morpholin-4-ylphenyl)amino)pyrimidin-4-yl)imidazo[2,1-b][1,3]thiazol-6-yl)phenyl)amino) methyl)benzonitrile, N-(3-(5-(2-((4-morpholin-4-ylphenyl)amino)pyridin-4-yl)imidazo[2,1-b][1,3]thiazol-6-yl)phenyl)-2-phenylacetamide, N-(3-(5-(2-((4-morpholin-4-ylphenyl)amino)pyridin-4-yl)imidazo[2,1-b][1,3]thiazol-6-yl)phenyl)benzamide, N-(3-(4-isopropylpiperazin-1-yl)phenyl)-4-(6-(3-((5-phenyl-1,3,4-oxadiazol-2-yl)amino)phenyl)imidazo[2,1-b][1,3]thiazol-5-yl)pyrimidin-2-amine, N-(3-(5-(2-((1-benzoyl-3-tert-butyl-1H-pyrazol-5-yl) amino)pyrimidin-4-yl)imidazo[2,1-b][1,3]thiazol-6-yl) phenyl)benzamide, 4-(6-(3-(1-methyl-1H-imidazol-2-yl)phenyl)imidazo[2,1-b][1,3]thiazol-5-yl)-N-(3-morpholin-4-ylphenyl)pyrimidin-2-amine, N-(2-chloro-3-(5-(2-((3-morpholin-4-ylphenyl)amino) pyrimidin-4-yl)imidazo[2,1-b][1,3]thiazol-6-yl)phenyl)-2,6-difluorobenzamide, N-(2-chloro-3-(5-(2-((3-morpholin-4-ylphenyl)amino) pyrimidin-4-yl)imidazo[2,1-b][1,3]thiazol-6-yl)phenyl)-2-fluorobenzamide, N-(2-chloro-3-(5-(2-((3-morpholin-4-ylphenyl)amino) pyrimidin-4-yl)imidazo[2,1-b][1,3]thiazol-6-yl)phenyl)-2-phenylacetamide, N-(2-(dimethylamino)-3-(5-(2-((3-morpholin-4-ylphenyl)amino)pyrimidin-4-yl)imidazo[2,1-b][1,3]thiazol-6-yl)phenyl)-2,6-difluorobenzamide, N-(2-(dimethylamino)-3-(5-(2-((3-morpholin-4-ylphenyl)amino)pyrimidin-4-yl)imidazo[2,1-b][1,3]thiazol-6-yl)phenyl)-2-phenylacetamide, 2,6-difluoro-N-(3-(5-(2-((3-((4-methylpiperazin-1-yl) methyl)phenyl)amino)pyrimidin-4-yl)imidazo[2,1-b][1,3]thiazol-6-yl)phenyl)benzamide, 2-fluoro-N-(3-(5-(2-((3-((4-methylpiperazin-1-yl)methyl)phenyl)amino)pyrimidin-4-yl)imidazo[2,1-b][1,3]thiazol-6-yl)phenyl)benzamide, N-(3-(5-(2-((3-((4-methylpiperazin-1-yl)methyl)phenyl) amino)pyrimidin-4-yl)imidazo[2,1-b][1,3]thiazol-6-yl) phenyl)-2-phenylacetamide, N-(3-(5-(2-((3-((dimethylamino)methyl)phenyl)amino) pyrimidin-4-yl)imidazo[2,1-b][1,3]thiazol-6-yl)phenyl)-2,6-difluorobenzamide, N-(3-(5-(2-((3-((dimethylamino)methyl)phenyl)amino) pyrimidin-4-yl)imidazo[2,1-b][1,3]thiazol-6-yl)phenyl)-2-fluorobenzamide, N-(3-(5-(2-((3-((dimethylamino)methyl)phenyl)amino) pyrimidin-4-yl)imidazo[2,1-b][1,3]thiazol-6-yl)phenyl)-2-phenylacetamide, 2-chloro-N-(3-(5-(2-((3-((dimethylamino)methyl)phenyl) amino)pyrimidin-4-yl)imidazo[2,1-b][1,3]thiazol-6-yl) phenyl)benzamide, N-(3-(5-(2-((3-((dimethylamino)methyl)phenyl)amino) pyrimidin-4-yl)imidazo[2,1-b][1,3]thiazol-6-yl)phenyl)-N'-phenylurea, 2,6-difluoro-N-(3-(5-(2-((3-(morpholin-4-ylmethyl)phenyl)amino)pyrimidin-4-yl)imidazo[2,1-b][1,3]thiazol-6-yl)phenyl)benzamide, 2-fluoro-N-(3-(5-(2-((3-(morpholin-4-ylmethyl)phenyl) amino)pyrimidin-4-yl)imidazo[2,1-b][1,3]thiazol-6-yl) phenyl)benzamide, N-(3-(5-(2-((3-(morpholin-4-ylmethyl)phenyl)amino)pyrimidin-4-yl)imidazo[2,1-b][1,3]thiazol-6-yl)phenyl)-2-phenylacetamide, 2-chloro-N-(3-(5-(2-((3-(morpholin-4-ylmethyl)phenyl) amino)pyrimidin-4-yl)imidazo[2,1-b][1,3]thiazol-6-yl) phenyl)benzamide, N-(3-(5-(2-((3-(morpholin-4-ylmethyl)phenyl)amino)pyrimidin-4-yl)imidazo[2,1-b][1,3]thiazol-6-yl)phenyl)-N'-phenylurea, 4-(6-(3-((5-methyl-1,3,4-thiadiazol-2-yl)amino)phenyl) imidazo[2,1-b][1,3]thiazol-5-y1)-N-(4-morpholin-4-ylphenyl)pyrimidin-2-amine, 4-(6-(3-((5-methyl-1,3,4-thiadiazol-2-yl)amino)phenyl) imidazo[2,1-b][1,3]thiazol-5-yl)-N-(3-morpholin-4-ylphenyl)pyrimidin-2-amine, 4-(6-(3-((5-methyl-1,3,4-thiadiazol-2-yl)amino)phenyl) imidazo[2,1-b][1,3]thiazol-5-y1)-N-(4-pyrrolidin-1-ylphenyl)pyrimidin-2-amine, 3-(5-(2-((3-morpholin-4-ylphenyl)amino)pyrimidin-4-yl) imidazo[2,1-b][1,3]thiazol-6-yl)benzaldehyde 0-phenyloxime, 3-(5-(2-((3-morpholin-4-ylphenyl)amino)pyrimidin-4-yl) imidazo[2,1-b][1,3]thiazol-6-yl)benzaldehyde O-benzyloxime, 3-(5-(2-((3-morpholin-4-ylphenyl)amino)pyrimidin-4-yl) imidazo[2,1-b][1,3]thiazol-6-yl)benzaldehyde 0-ethyloxime, N'-(benzoyloxy)-3-(5-(2-((3-morpholin-4-ylphenyl) amino)pyrimidin-4-yl)imidazo[2,1-b][1,3]thiazol-6-yl) benzenecarboximidamide, N-(3-(5-(2-((3-(methylsulfonyl)phenyl)amino)pyrimidin-4-yl)imidazo[2,1-b][1,3]thiazol-6-yl)phenyl)benzamide, 2,6-difluoro-N-(3-(5-(2-((3-(methylsulfonyl)phenyl) amino)pyrimidin-4-yl)imidazo[2,1-b][1,3]thiazol-6-yl) phenyl)benzamide, N-(3-(5-(2-((3-(methylsulfonyl)phenyl)amino)pyrimidin-4-yl)imidazo[2,1-b][1,3]thiazol-6-yl)phenyl)-2-phenylacetamide, N-(3-(5-(2-((3-(4-acetylpiperazin-1-yl)phenyl)amino)pyrimidin-4-yl)imidazo[2,1-b][1,3]thiazol-6-yl)phenyl)-2-phenylacetamide, N-(3-(5-(2-((3-(4-acetylpiperazin-1-yl)phenyl)amino)pyrimidin-4-yl)imidazo[2,1-b][1,3]thiazol-6-yl)phenyl) benzamide, N-(3-(5-(2-((3-(4-acetylpiperazin-1-yl)phenyl)amino)pyrimidin-4-yl)imidazo[2,1-b][1,3]thiazol-6-yl)phenyl)-2-chlorobenzamide, N-(3-(5-(2-((3-(4-acetylpiperazin-1-yl)phenyl)amino)pyrimidin-4-yl)imidazo[2,1-b][1,3]thiazol-6-yl)phenyl)-2,6-difluorobenzamide, 2,6-difluoro-N-(3-(5-(2-((3-((4-(2-hydroxyethyl)piperazin-1-yl)methyl)phenyl)amino)pyrimidin-4-yl)imidazo[2,1-b][1,3]thiazol-6-yl)phenyl)benzamide, N-(3-(5-(2-((3-((4-(2-hydroxyethyl)piperazin-1-yl)methyl)phenyl)amino)pyrimidin-4-yl)imidazo[2,1-b][1,3] thiazol-6-yl)phenyl)-2-phenylacetamide, 2,6-difluoro-N-(3-(5-(2-((3-((4-(3-methoxypropyl)piperazin-1-yl)methyl)phenyl)amino)pyrimidin-4-yl)imidazo[2,1-b][1,3]thiazol-6-yl)phenyl)benzamide, 2-fluoro-N-(3-(5-(2-((3-((4-(3-methoxypropyl)piperazin-1-yl)methyl)phenyl)amino)pyrimidin-4-yl)imidazo[2,1-b][1,3]thiazol-6-yl)phenyl)benzamide, 2-chloro-N-(3-(5-(2-((3-((4-(3-methoxypropyl)piperazin-1-yl)methyl)phenyl)amino)pyrimidin-4-yl)imidazo[2,1-b][1,3]thiazol-6-yl)phenyl)benzamide, N-(3-(5-(2-((3-((4-(3-methoxypropyl)piperazin-1-yl)methyl)phenyl)amino)pyrimidin-4-yl)imidazo[2,1-b][1,3]thiazol-6-yl)phenyl)-2-phenylacetamide, N-(3-(5-(2-((3-((4-(3-methoxypropyl)piperazin-1-yl)methyl)phenyl)amino)pyrimidin-4-yl)imidazo[2,1-b][1,3]thiazol-6-yl)phenyl)-N'-phenylurea, N-(3-(5-(2-(1H-indazol-5-ylamino)pyrimidin-4-yl)imidazo[2,1-b][1,3]thiazol-6-yl)phenyl)-2-phenylacetamide, N-(3-(5-(2-(1H-indazol-5-ylamino)pyrimidin-4-yl)imidazo[2,1-b][1,3]thiazol-6-yl)phenyl)benzamide, 2,6-difluoro-N-(3-(5-(2-(1H-indazol-5-ylamino)pyrimidin-4-yl)imidazo[2,1-b][1,3]thiazol-6-yl)phenyl)benzamide, 2-chloro-6-fluoro-N-(3-(5-(2-(1H-indazol-5-ylamino)pyrimidin-4-yl)imidazo[2, 1-b][1,3 ]thiazol-6-yl)phenyl)benzamide, 5-fluoro-N-(3-(5-(2-(1H-indazol-5-ylamino)pyrimidin-4-yl)imidazo [2,1 -b][1,3 ]thiazol-6-yl)phenyl)-2-methylbenzamide, 2-phenyl-N-(3-(5-(2-((2-(trifluoromethyl)-1H-benzimidazol-5-yl)amino)pyrimidin-4-yl)imidazo [2,1-b][1,3 ]thiazol-6-yl)phenyl)acetamide, N-(3-(5-(2-((2-(trifluoromethyl)-1H-benzimidazol-5-yl) amino)pyrimidin-4-yl)imidazo [2,1-b][1,3 ]thiazol-6-yl)phenyl)benzamide, 2,6-difluoro-N-(3-(5-(2-((2-(trifluoromethyl)- 1H-benzimidazol-5 -yl)amino)pyrimidin-4-yl)imidazo [2,1-b][1,3 ]thiazol-6-yl)phenyl)benzamide, 2-chloro-6-fluoro-N-(3-(5-(2-((2-(trifluoromethyl)-1H-benzimidazol-5 -yl)amino)pyrimidin-4-yl)imidazo [2,1-b][1,3 ]thiazol-6-yl)phenyl)benzamide, 5-fluoro-2-methyl-N-(3-(5-(2-((2-(trifluoromethyl)-1H-benzimidazol-5-yl)amino)pyrimidin-4-yl)imidazo [2,1-b][1,3 ]thiazol-6-yl)phenyl)benzamide, 3-(5-(2-((3-morpholin-4-ylphenyl)amino)pyrimidin-4-yl)imidazo[2, 1-b][1,3 ]thiazol-6-yl)-N'-(propionyloxy)benzenecarboximidamide, N'-((3-methylbutanoyl)oxy)-3-(5-(2-((3-morpholin-4-ylphenyl)amino)pyrimidin-4-yl)imidazo [2,1-b][1,3 ]thiazol-6-yl)benzenecarboximidamide, 3-(5-(2-((3-morpholin-4-ylphenyl)amino)pyrimidin-4-yl)imidazo[2, 1-b][1,3 ]thiazol-6-yl)-N'-((phenylacetyl)oxy)benzenecarboximidamide, 3-methoxy-N-(3-(5-(2-((4-morpholin-4-ylphenyl)amino)pyrimidin-4-yl)imidazo[2, 1-b][1,3 ]thiazol-6-yl)phenyl)benzamide, 2-chloro-6-fluoro-N-(3-(5-(2-((2-pyridin-3-yl-1,3 -benzoxazol-5-yl)amino)pyrimidin-4-yl)imidazo[2, 1-b][1,3 ]thiazol-6-yl)phenyl)benzamide, N-(3-(5-(2-((2-methyl- 1,3 -benzothiazol-5-yl)amino)pyrimidin-4-yl)imidazo [2,1-b][1,3 ]thiazol-6-yl)phenyl)-2-phenylacetamide, N-(3-(5-(2-((2-methyl- 1,3 -benzothiazol-5-yl)amino)pyrimidin-4-yl)imidazo [2,1-b][1,3 ]thiazol-6-yl)phenyl)benzamide, 2,6-difluoro-N-(3-(5-(2-((2-methyl- 1,3 -benzothiazol-5-yl)amino)pyrimidin-4-yl)imidazo [2,1-b][1,3 ]thiazol-6-yl)phenyl)benzamide, 5-fluoro-2-methyl-N-(3-(5-(2-((2-methyl- 1,3 -benzothiazol-5-yl)amino)pyrimidin-4-yl)imidazo [2,1-b][1,3 ]thiazol-6-yl)phenyl)benzamide, N-(3-(5-(2-((2-oxo-2,3-dihydro-1H-indol-5-yl)amino)pyrimidin-4-yl)imidazo[2,1-b][1,3]thiazol-6-yl)phenyl)benzamide, 2-chloro-6-fluoro-N-(3-(5-(2-((2-oxo-2,3-dihydro-1H-indol-5-yl)amino)pyrimidin-4-yl)imidazo[2,1-b][1,3]thiazol-6-yl)phenyl)benzamide, N-(3-(5-(2-((3-(3-oxomorpholin-4-yl)phenyl)amino)pyrimidin-4-yl)imidazo[2,1-b][1,3]thiazol-6-yl)phenyl)-2-phenylacetamide, N-(3-(5-(2-((3-(3-oxomorpholin-4-yl)phenyl)amino)pyrimidin-4-yl)imidazo[2,1-b][1,3]thiazol-6-yl)phenyl)benzamide, 2,6-difluoro-N-(3-(5-(2-((3-(3-oxomorpholin-4-yl)phenyl)amino)pyrimidin-4-yl)imidazo[2,1-b][1,3]thiazol-6-yl)phenyl)benzamide, 2-chloro-6-fluoro-N-(3-(5-(2-((3-(3-oxomorpholin-4-yl)phenyl)amino)pyrimidin-4-yl)imidazo[2,1-b][1,3]thiazol-6-yl)phenyl)benzamide, 2,6-dichloro-N-(3-(5-(2-((3-(3-oxomorpholin-4-yl)phenyl)amino)pyrimidin-4-yl)imidazo[2,1-b][1,3]thiazol-6-yl)phenyl)benzamide, 5-fluoro-2-methyl-N-(3-(5-(2-((3-(3-oxomorpholin-4-yl)phenyl)amino)pyrimidin-4-yl)imidazo[2,1-b][1,3]thiazol-6-yl)phenyl)benzamide, 2-fluoro-N-(3-(5-(2-((3-(3-oxomorpholin-4-yl)phenyl)amino)pyrimidin-4-yl)imidazo[2,1-b][1,3]thiazol-6-yl)phenyl)benzamide, N-(3-(5-(2-((4-(3-oxomorpholin-4-yl)phenyl)amino)pyrimidin-4-yl)imidazo[2,1-b][1,3]thiazol-6-yl)phenyl)-2-phenylacetamide, 2,6-difluoro-N-(3-(5-(2-((4-(3-oxomorpholin-4-yl)phenyl)amino)pyrimidin-4-yl)imidazo[2,1-b][1,3]thiazol-6-yl)phenyl)benzamide, 2-chloro-6-fluoro-N-(3-(5-(2-((4-(3-oxomorpholin-4-yl)phenyl)amino)pyrimidin-4-yl)imidazo[2,1-b][1,3]thiazol-6-yl)phenyl)benzamide, 2,6-dichloro-N-(3-(5-(2-((4-(3-oxomorpholin-4-yl)phenyl)amino)pyrimidin-4-yl)imidazo[2,1-b][1,3]thiazol-6-yl)phenyl)benzamide, 5-fluoro-2-methyl-N-(3-(5-(2-((4-(3-oxomorpholin-4-yl)phenyl)amino)pyrimidin-4-yl)imidazo[2,1-b][1,3]thiazol-6-yl)phenyl)benzamide, 2-fluoro-N-(3-(5-(2-((4-(3-oxomorpholin-4-yl)phenyl)amino)pyrimidin-4-yl)imidazo[2,1-b][1,3]thiazol-6-yl)phenyl)benzamide, N-(3-(5-(2-((3-fluoro-5-morpholin-4-ylphenyl)amino)pyrimidin-4-yl)imidazo[2,1-b][1,3]thiazol-6-yl)phenyl)-2-phenylacetamide, 2,6-difluoro-N-(3-(5-(2-((3-fluoro-5-morpholin-4-ylphenyl)amino)pyrimidin-4-yl)imidazo[2,1-b][1,3]thiazol-6-yl)phenyl)benzamide, N-(3-(5-(2-((3-fluoro-5-morpholin-4-ylphenyl)amino)pyrimidin-4-yl)imidazo[2,1-b][1,3]thiazol-6-yl)phenyl)-N'-phenylurea, 2-chloro-N-(3-(5-(2-((3-fluoro-5-morpholin-4-ylphenyl)amino)pyrimidin-4-yl)imidazo[2,1-b][1,3]thiazol-6-yl)phenyl)benzamide, N-(3-(5-(2-((3-fluoro-4-morpholin-4-ylphenyl)amino)pyrimidin-4-yl)imidazo[2,1-b][1,3]thiazol-6-yl)phenyl)-2-phenylacetamide, 2,6-difluoro-N-(3-(5-(2-((3-fluoro-4-morpholin-4-ylphenyl)amino)pyrimidin-4-yl)imidazo[2,1-b][1,3]thiazol-6-yl)phenyl)benzamide, 2-chloro-N-(3-(5-(2-((3-fluoro-4-morpholin-4-ylphenyl)amino)pyrimidin-4-yl)imidazo[2,1-b][1,3]thiazol-6-yl)phenyl)benzamide, N-(3-(5-(2-((3-fluoro-4-morpholin-4-ylphenyl)amino)pyrimidin-4-yl)imidazo[2,1-b][1,3]thiazol-6-yl)phenyl)-N'-phenylurea, N-(3-(5-(2-((3-fluoro-5-(2-oxopyrrolidin-1-yl)phenyl) amino)pyrimidin-4-yl)imidazo[2,1-b][1,3]thiazol-6-yl) phenyl)-2-phenylacetamide, 2,6-difluoro-N-(3-(5-(2-((3-fluoro-5-(2-oxopyrrolidin-1-yl)phenyl)amino)pyrimidin-4-yl)imidazo[2,1-b][1,3] thiazol-6-yl)phenyl)benzamide, 2-chloro-N-(3-(5-(2-((3-fluoro-5-(2-oxopyrrolidin-1-yl) phenyl)amino)pyrimidin-4-yl)imidazo[2,1-b][1,3]thiazol-6-yl)phenyl)benzamide, N-(3-(5-(2-((4-fluoro-3-(2-oxopyrrolidin-1-yl)phenyl) amino)pyrimidin-4-yl)imidazo[2,1-b][1,3]thiazol-6-yl) phenyl)-2-phenylacetamide, 2,6-difluoro-N-(3-(5-(2-((4-fluoro-3-(2-oxopyrrolidin-1-yl)phenyl)amino)pyrimidin-4-yl)imidazo[2,1-b][1,3] thiazol-6-yl)phenyl)benzamide, 2-chloro-N-(3-(5-(2-((4-fluoro-3-(2-oxopyrrolidin-1-yl) phenyl)amino)pyrimidin-4-yl)imidazo[2,1-b][1,3]thiazol-6-yl)phenyl)benzamide, N-(3-(5-(2-((6-morpholin-4-ylpyridin-3-yl)amino)pyrimidin-4-yl)imidazo[2,1-b][1,3]thiazol-6-yl)phenyl)-2-phenylacetamide, 2,6-difluoro-N-(3-(5-(2-((6-morpholin-4-ylpyridin-3-yl) amino)pyrimidin-4-yl)imidazo[2,1-b][1,3]thiazol-6-yl) phenyl)benzamide, 2-chloro-N-(3-(5-(2-((6-morpholin-4-ylpyridin-3-yl) amino)pyrimidin-4-yl)imidazo[2,1-b][1,3]thiazol-6-yl) phenyl)benzamide, N-(3-(5-(2-((6-morpholin-4-ylpyridin-3-yl)amino)pyrimidin-4-yl)imidazo[2,1-b][1,3]thiazol-6-yl)phenyl)-N'-phenylurea, 4-(6-(3-(benzylamino)phenyl)imidazo[2,1-b][1,3]thiazol-5-yl)-N-(4-morpholin-4-ylphenyl)pyrimidin-2-amine, N-(4-morpholin-4-ylphenyl)-4-(6-(3-((2-phenylethyl) amino)phenyl)imidazo[2,1-b][1,3]thiazol-5-yl)pyrimidin-2-amine, N-(4-(4-isopropylpiperazin-1-yl)phenyl)-4-(6-(3-((5-phenyl-1,3,4-oxadiazol-2-yl)amino)phenyl)imidazo[2,1-b] [1,3]thiazol-5-yl)pyrimidin-2-amine, N-(4-morpholin-4-ylphenyl)-4-(6-(3-((pyridin-2-ylmethyl)amino)phenyl)imidazo[2,1-b][1,3]thiazol-5-yl) pyrimidin-2-amine, 4-(6-(3-((2,6-difluorobenzyl)amino)phenyl)imidazo[2,1-b][1,3]thiazol-5-yl)-N-(4-morpholin-4-ylphenyl)pyrimidin-2-amine, and 4-(6-(3-((2-methoxybenzyl)amino)phenyl)imidazo[2,1-b] [1,3]thiazol-5-yl)-N-(4-morpholin-4-ylphenyl)pyrimidin-2-amine.

12. A composition comprising an excipient and a therapeutically effective amount of a compound of claim 1.

\* \* \* \* \*

UNITED STATES PATENT AND TRADEMARK OFFICE
CERTIFICATE OF CORRECTION

PATENT NO. : 8,067,409 B2
APPLICATION NO. : 12/274834
DATED : November 29, 2011
INVENTOR(S) : Ba-Maung et al.

Page 1 of 2

It is certified that error appears in the above-identified patent and that said Letters Patent is hereby corrected as shown below:

In the Claims:

Column 202, line 35, claim 1: "$E^1$," to read as --$E^1$--

Column 203, line 44, claim 1: "$SO_2N(R^7)_2$" to read as -- $SO_2N(R^{17})_2$--

Column 204, line 06, claim 1: "$R^{22}$ is alkyl, alkenylalkenyl" to read as --$R^{22}$ is alkyl, alkenyl, alkynyl,--

Column 204, line 06, claim 1: "heteroaryl, cycloalkenyl" to read as --phenyl, heteroaryl, cycloalkyl, cycloalkenyl--

Column 204, line 12, claim 1: "$OC(O)R^{23}$, $OC(O)R^{23}$" to read as --$OC(O)R^{23}$, $OC(O)OR^{23}$--

Column 204, line 19, claim 1: "$C(O)NR^{23}SO_2R^{23}SO_2NH_2$," to read as --$C(O)NR^{23}SO_2R^{23}$, $SO_2NH_2$,--

Column 204, line 31, claim 3: "$A^l$" to read as --$A^1$--

Column 205, line 08, claim 9: "with $R^{12}$," to read as --with $R^{12}$;--

Column 205, line 27, claim 11: "(2(" to read as --(2-(--

Column 205, line 30, claim 11: "(2(" to read as --(2-(--

Column 205, line 32, claim 11: "(2(" to read as --(2-(--

Column 205, line 53, claim 11: "(2(" to read as --(2-(--

Column 205, line 59, claim 11: "(2(" to read as --(2-(--

Column 209, line 32, claim 11: "benzodioxo1" to read as --benzodioxol--

Column 212, line 67, claim 11: "y1" to read as --yl--

Column 213, line 28, claim 11: "y1" to read as --yl--

Column 215, line 20, claim 11: "benzodioxo1" to read as --benzodioxol--

Column 215, line 51, claim 11: "y1" to read as --yl--

Signed and Sealed this
Sixth Day of August, 2013

Teresa Stanek Rea
*Acting Director of the United States Patent and Trademark Office*

CERTIFICATE OF CORRECTION (continued)
U.S. Pat. No. 8,067,409 B2

Column 215, line 54, claim 11: "y1" to read as --yl--

Column 218, line 66, claim 11: "y1" to read as --yl--

Column 219, line 02, claim 11: "y1" to read as --yl--

Column 219, line 31, claim 11: "y1" to read as --yl--

Column 219, line 62, claim 11: "5-243 -" to read as --5-(2-((3---

Column 220, line 04, claim 11: "243-morpholin" to read as --2-((3-morpholin--

Column 220, line 07, claim 11: "243-morpholin" to read as --2-((3-morpholin--

Column 220, line 26, claim 11: "butyl- 1 H-pyrazol" to read as --butyl-1H-pyrazol--

Column 220, line 29, claim 11: "butyl- 1 H-pyrazol" to read as --butyl-1H-pyrazol--

Column 220, line 41, claim 11: "butyl- 1 H-pyrazol" to read as --butyl-1H-pyrazol--

Column 220, line 44, claim 11: "(3-pyridin-3-yl-1 H-pyrazol-5-yl)" to read as --(3-pyridin-3-yl-1H-pyrazol-5-yl)--

Column 222, line 11, claim 11: "y1" to read as --yl--

Column 222, line 18, claim 11: "y1" to read as --yl--

Column 222, line 21, claim 11: "0-phenyloxime" to read as --O-phenyloxime--

Column 222, line 27, claim 11: "0-ethyloxime" to read as --O-ethyloxime--

Column 223, line 08, claim 11: "y1" to read as --yl--

Column 223, line 11, claim 11: "y1" to read as --yl--

Column 223, line 17, claim 11: "[2, I-b]" to read as --[2, 1-b]--

Column 223, line 28, claim 11: "((2-(trifluromethyl)- 1H-benzimidazol-5 -yl)amino" to read as --((2-(trifluromethyl)-1H-benzimidazol-5-yl)amino--

Column 223, line 31, claim 11: "((2-(trifluromethyl)- 1H-benzimidazol-5 -yl)amino" to read as --((2-(trifluromethyl)-1H-benzimidazol-5-yl)amino--

Column 223, line 34, claim 11: "((2-(trifluromethyl)- 1H-benzimidazol-5-yl)amino" to read as --((2-(trifluromethyl)-1H-benzimidazol-5-yl)amino--

Column 223, line 65, claim 11: "indo1" to read as --indole--

Column 224, line 02, claim 11: "indo1" to read as --indole--